United States Patent
Ikegami et al.

(10) Patent No.: US 7,867,949 B2
(45) Date of Patent: Jan. 11, 2011

(54) HYDRAZIDE COMPOUND AND PESTICIDAL USE OF THE SAME

(75) Inventors: Hiroshi Ikegami, Ikeda (JP); Markus Jachmann, Kobe (JP); Yoshihiko Nokura, Toyonaka (JP); Chiemi Iwata, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 341 days.

(21) Appl. No.: 11/992,490

(22) PCT Filed: Oct. 10, 2006

(86) PCT No.: PCT/JP2006/320522

§ 371 (c)(1),
(2), (4) Date: Mar. 24, 2008

(87) PCT Pub. No.: WO2007/043677

PCT Pub. Date: Apr. 19, 2007

(65) Prior Publication Data

US 2009/0181956 A1    Jul. 16, 2009

(30) Foreign Application Priority Data

Oct. 14, 2005  (JP) .............................. 2005-299843
May 25, 2006  (JP) .............................. 2006-144829

(51) Int. Cl.
A01N 43/40  (2006.01)
A01N 43/56  (2006.01)
A61K 31/5355  (2006.01)
C07D 265/14  (2006.01)
C07D 401/00  (2006.01)
C07D 231/10  (2006.01)

(52) U.S. Cl. ...................... 504/130; 504/139; 504/140; 544/88; 544/90; 546/275.4; 548/356.1

(58) Field of Classification Search .................. 544/88, 544/90; 546/275.4; 548/356.1; 504/130, 504/139, 140
See application file for complete search history.

(56) References Cited

U.S. PATENT DOCUMENTS 5,270,343 A    12/1993    Robinson et al.

FOREIGN PATENT DOCUMENTS

| EP | 0 524 041 A2 | 1/1993 |
|---|---|---|
| WO | WO-95/25723 A1 | 9/1995 |
| WO | WO-01/70671 A2 | 9/2001 |
| WO | WO-03/015518 A1 | 2/2003 |
| WO | WO-03/015519 A1 | 2/2003 |
| WO | WO-03/016284 A1 | 2/2003 |
| WO | WO-03/016300 A1 | 2/2003 |
| WO | WO-03/024222 A1 | 3/2003 |
| WO | WO-2005/085234 A2 | 9/2005 |

OTHER PUBLICATIONS

Chen et al., "Synthesis and Insecticidal Evaluation of Propesticides of Benzoylphenylureas," J. Agrc. Food Chem., vol. 53, 2005, pp. 38-41.
EP Office Action issued on Jan. 15, 2010 in corresponding European Patent Application No. 06 811 793.6.
Abdel-Hamid et al., Phosphorus, Sulfur, and Silicon, vol. 72, pp. 237-247, (1992).

*Primary Examiner*—Kamal A Saeed
*Assistant Examiner*—Samantha L Shterengarts
(74) *Attorney, Agent, or Firm*—Birch, Stewart, Kolasch & Birch, LLP

(57) ABSTRACT

A hydrazide compound represented by the formula (1):

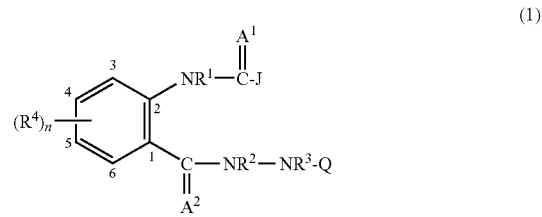

has excellent pesticidal activity.

21 Claims, No Drawings

US 7,867,949 B2

HYDRAZIDE COMPOUND AND PESTICIDAL USE OF THE SAME

TECHNICAL FIELD

The present invention relates to a hydrazide compound and pesticidal use of the same.

BACKGROUND ART

In WO 01/70671, WO 03/015518, WO 03/016284, WO 03/016300 and WO 03/024222, certain amide compounds are known to be compounds having pesticidal activity.

DISCLOSURE OF THE INVENTION

The present invention is intended to provide a compound having excellent efficacy of controlling pests.

The present inventors have intensively studied in order to find out a compound having excellent efficacy of controlling pests and, as a result, found out that a hydrazide compound represented by the following formula (1) has excellent controlling efficacy. Thus, the present invention has been completed.

According to the present invention, there is provided:

(1) A hydrazide compound represented by the formula (1):

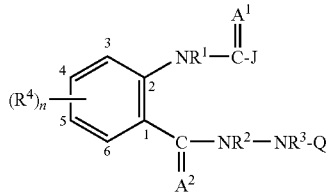

(1)

wherein $R^1$ represents a hydrogen atom, a C1-C6 alkyl group optionally substituted with at least one halogen atom, a C2-C6 cyanoalkyl group, a C2-C6 alkoxyalkyl group optionally substituted with at least one halogen atom, a C2-C6 alkenyl group optionally substituted with at least one halogen atom, a C3-C6 alkynyl group optionally substituted with at least one halogen atom, or a C7-C9 phenyl alkyl group whose benzene ring moiety may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^2$ and $R^3$ independently represent a hydrogen atom, a C1-C6 alkyl group optionally substituted with at least one halogen atom, a C1-C6 acyl group, a C2-C6 alkoxycarbonyl group, a C3-C7 N,N-dialkylcarbamoyl group, or a phenyl group optionally substituted with 1 to 5 independent substituents selected from the group consisting of (1) a halogen atom, (2) a cyano group, (3) a nitro group and (4) a C1-C6 alkyl group optionally substituted with at least one halogen atom, $R^4$ represents a halogen atom, a cyano group, a nitro group, a C1-C6 alkyl group optionally substituted with at least one halogen atom, a C1-C6 alkoxy group optionally substituted with at least one halogen atom, a phenyl group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, or two $R^4$ groups which are bound to the adjacent carbon atoms are bound at their terminal ends to each other to form a group T1 or T2

T1: —$CR^{41}$=$CR^{42}$—$CR^{43}$=$CR^{44}$—

T2: —$(CR^{45}R^{46})_h$—

(wherein $R^{41}$, $R^{42}$, $R^{43}$ and $R^{44}$ independently, represent a hydrogen atom, a halogen atom, a cyano group, a nitro group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, $R^{45}$ and $R^{46}$ independently represent a hydrogen atom, or a C1-C6 alkyl group optionally substituted with at least one halogen atom, and h represents an integer of 3 or 4), n represents an integer of 0 to 4 (provided that, when n is an integer of 2 or more, $R^4$'s may be the same or different), Q represents a group selected from Q1 to Q6:

Q1: —$C(=A^{31})$-$R^5$
Q2: —$C(=A^{32})$-$OR^6$
Q3: —$C(=A^{33})$-$SR^7$
Q4: —$C(=A^{34})$-$NR^8R^9$
Q5: —$S(O)_2$—$R^{10}$
Q6: —$S(O)_2$—$NR^{11}R^{12}$ (wherein $A^{31}$, $A^{32}$, $A^{33}$ and $A^{34}$ represent an oxygen atom or a sulfur atom, $R^5$ represents a hydrogen atom; a C2-C6 alkenyl group optionally substituted with at least one halogen atom; a C2-C6 alkynyl group optionally substituted with at least one halogen atom; a C1-C6 alkyl group optionally substituted with one or more independent substituents selected from the group consisting of (1) a halogen atom, (2) a C1-C6 alkoxy group, (3) a C1-C6 alkylthio group, (4) a C1-C6 alkylsulfinyl group, (5) a C1-C6 alkylsulfonyl group, (6) a C2-C6 dialkylamino group and (7) a C3-C6 cycloalkyl group; a C3-C6 cycloalkyl group optionally substituted with one or more independent substituents selected from the group consisting of (1) a halogen atom, (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom; a naphthyl group optionally substituted with 1 to 9 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; a 5- to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; a 3- to 8-membered non-aromatic heterocyclic group optionally substituted with one or more independent substituents selected from the group consisting of (1) a halogen atom and (2) a C1-C6 alkyl group; a C7-C9 phenylalkyl group whose benzene ring moiety may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or a C7-C9 phenoxyalkyl group whose benzene ring moiety may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^6$ and $R^7$ represent a C1-C6 alkyl group optionally substituted with at least one halogen atom; a C3-C6 alkoxyalkyl group optionally substituted with at least one halogen atom; a C2-C6 alkenyl group optionally substituted with at least one halogen atom; a C3-C6 alkynyl group optionally substituted with at least one halogen atom; a C3-C6 cycloalkyl group optionally substituted with one or more independent substituents selected from the group consisting of (1) a halogen atom and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom; a 5- to 6-membered heteroaryl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or a C7-C9 phenylalkyl group whose benzene ring moiety may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^8$ and $R^9$ independently represent a hydrogen atom; a C1-C6 alkyl group optionally substituted with at least one halogen atom; a C2-C6 alkoxyalkyl group optionally substituted with at least one halogen atom; a C2-C6 alkenyl group optionally substituted with at least one halogen atom; a C3-C6 alkynyl group optionally substituted with at least one halogen atom; a C3-C6 cycloalkyl group optionally substituted with one or more independent substituents selected from the group consisting of (1) a halogen atom and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom; a 5- to 6-membered heteroaryl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or a C7-C9 phenylalkyl group whose benzene ring moiety may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or $R^8$ and $R^9$ are taken together with the nitrogen atom to which they are bound to form a 3- to 8-membered non-aromatic heterocyclic group, the 3- to 8-membered non-aromatic heterocyclic group may contain, in the ring, one or more independent groups selected from the group consisting of (1) an oxygen atom, (2) a sulfur group and (3) a —$NR^a$— group (wherein $R^a$ represents a C1-C6 alkyl group optionally substituted with at least one halogen atom, a C2-C6 alkoxycarbonyl group optionally substituted with at least one halogen atom, or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom), and carbon atom(s) in the ring may be substituted with one or more independent substituents selected from the group consisting of (1) a halogen atom, (2) a C1-C6 alkyl group optionally substituted with at least one halogen atom and (3) a C2-C6 alkoxycarbonyl group optionally substituted with at least one halogen atom, $R^{10}$ represents a C1-C6 alkyl group optionally substituted with at least one halogen atom; a C3-C6 cycloalkyl group optionally substituted with one or more independent substituents selected from the group consisting of (1) a halogen atom and (2) a C1-C6 alkyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, and $R^{11}$ and $R^{12}$ independently represent a C1-C6 alkyl group optionally substituted with at least one halogen atom; a C3-C6 cycloalkyl group optionally substituted with one or more independent substituents selected from the group consisting of (1) a halogen atom and (2) a C1-C6 alkyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or $R^{11}$ and $R^{12}$ are taken together with the nitrogen atom to which they are bound to form a 3- to 8-membered non-aromatic heterocyclic group, the 3- to 8-membered non-aromatic heterocyclic group may contain, in the ring, one or more independent groups selected from the group consisting of (1) an oxygen atom, (2) a sulfur atom and (3) a —$NR^b$-group (wherein $R^b$ represents a C1-C6 alkyl group optionally substituted with at least one halogen atom, a C2-C6 alkoxycarbonyl group optionally substituted with at least one halogen atom, or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom), and carbon atom(s) in the ring may be substituted with one or more independent substituents selected from the group consisting of (1) a halogen atom, (2) a C1-C6 alkyl group optionally substituted with at least one halogen atom and (3) a C2-C6 alkoxycarbonyl group optionally substituted with at least one halogen atom), J represents a group represented by J1 or J2:

J1:

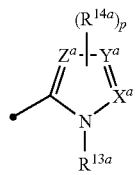

J2:

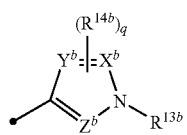

(wherein $X^a$, $Y^a$, $Z^a$, $X^b$, $Y^b$ and $Z^b$ independently represent CH or a nitrogen atom, $R^{13a}$ and $R^{13b}$ represent a C1-C6 alkyl group optionally substituted with at least one halogen atom; a C2-C6 cyanoalkyl group; a C2-C6 alkoxyalkyl group optionally substituted with at least one halogen atom; a C2-C6 alkenyl group optionally substituted with at least one halogen atom; a C2-C6 alkynyl group optionally substituted with at least one halogen atom; a C3-C6 cycloalkyl group optionally substituted with one or more independent substituents selected from the group consisting of (1) a halogen atom and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom and (8) a C1-C6 alkylsulfonyl group optionally substituted with at least one halogen atom; a 5- to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; a C7-C9 phenylalkyl group whose benzene ring moiety may be substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or a C7-C9 pyridinylalkyl group whose pyridine ring moiety may be substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^{14a}$ and $R^{14b}$ represent a halogen atom; a cyano group; a nitro group; a C1-C6 alkyl group optionally substituted with at least one halogen atom; a C1-C6 alkoxy group optionally substituted with at least one halogen atom; a C2-C6 cyanoalkyloxy group; a C3-C6 alkoxyalkyloxy group optionally substituted with at least one halogen atom; a C3-C6 alkenyloxy group optionally substituted with at least one halogen atom; a C3-C6 alkynyloxy group optionally substituted with at least one halogen atom; a C1-C6 alkylthio group optionally substituted with at least one halogen atom; a C1-C6 alkylsulfinyl group optionally substituted with at least one halogen atom; a C1-C6 alkylsulfonyl group optionally substituted with at least one halogen atom; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; a 5- to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or a phenoxy group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, p represents an integer of 0 to 3, and q represents an integer of 0 to 3 (provided that, when p is an integer of 2 or 3, two or more $R^{14}$'s may be the same or different and, when q is an integer of 2 or 3, two or more $R^{14b}$'s may be the same or different), and $A^1$ and $A^2$ independently represent an oxygen atom or a sulfur atom (hereinafter referred to as the present compound).

(2) The compound according to the above (1), wherein n is an integer of 0 to 3.

(3) The compound according to the above (2), wherein $R^4$ is a halogen atom, a cyano group, a C1-C6 alkyl group optionally substituted with at least one halogen atom, a C1-C6 alkoxy group optionally substituted with at least one halogen atom, a phenyl group optionally substituted with at least one halogen atom, or two $R^4$ groups which are bound to the adjacent carbon atoms are bound at their terminal ends to form a group T1: —$CR^{41}$=$CR^{42}$—$CR^{43}$=$CR^{44}$—

(wherein $R^{41}$, $R^{42}$, $R^{43}$ and $R^{44}$ represent a hydrogen atom).

(4) The compound according to the above (3), wherein $R^4$ is a fluorine atom, a chlorine atom, a bromine atom, an iodine atom, a cyano group, a methyl group, an ethyl group, a trifluoromethyl group, a methoxy group, a phenyl group, or two $R^4$ groups which are bound to the adjacent carbon atoms are bound at their terminal ends to form a group T1: —$CR^{41}$=$CR^{42}$—$CR^{43}$=$CR^{44}$—

(wherein $R^{41}$, $R^{42}$, $R^{43}$ and $R^{44}$ represent a hydrogen atom).

(5) The compound according to any one of the above (1) to (4), wherein

J is J1, $Y^a$ is CH, $R^{13a}$ is a C1-C6 alkyl group optionally substituted with at least one halogen atom; a C3-C6 cycloalkyl group optionally substituted with one or more independent substituents selected from the group consisting of (1) a halogen atom and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom and (8) a C1-C6 alkylsulfonyl group optionally substituted with at least one halogen atom; or a 5- to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^{14a}$ is a halogen atom; a cyano group; a C1-C6 alkyl group optionally substituted with at least one halogen atom; a C1-C6 alkylthio group optionally substituted with at least one halogen atom; a C1-C6 alkylsulfinyl group optionally substituted with at least one halogen atom; a C1-C6 alkylsulfonyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, and p is an integer of 0 to 2.

(6) The compound according to any one of the above (1) to (4), wherein

J is J2, $Y^b$ is CH, $R^{13b}$ is a C1-C6 alkyl group optionally substituted with at least one halogen atom, $R^{14b}$ is a C1-C6 alkyl group optionally substituted with at least one halogen atom, or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, and q is 1.

(7) The compound according to any one of the above (1) to (6), wherein $A^1$ and $A^2$ are an oxygen atom, and $R^1$ is a hydrogen atom or a methyl group.

(8) The compound according to any one of the above (1) to (7), wherein

Q is Q1, $A^{31}$ is an oxygen atom, and $R^5$ is a hydrogen atom; a C1-C6 alkyl group optionally substituted with one or more independent substituents selected from the group consisting of (1) a halogen atom, (2) a C1-C6 alkoxy group, (3) a C1-C6 alkylthio group, (4) a C1-C6 alkylsulfinyl group, (5) a C1-C6 alkylsulfonyl group, (6) a C2-C6 dialkylamino group and (7) a C3-C6 cycloalkyl group; a C3-C6 cycloalkyl group optionally substituted with one or more independent substituents selected from the group consisting of (1) a halogen and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom; a 5- to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or a 3 to 8-membered non-aromatic heterocyclic group optionally substituted with one or more independent groups selected from the group consisting of (1) a halogen atom and (2) a C1-C6 alkyl group.

(9) The compound according to the above (8), wherein $R^5$ is a hydrogen atom, a methyl group, an ethyl group, a tert-butyl group, a cyclopropyl group, a phenyl group, a 3-methylphenyl group, a 4-methoxyphenyl group, a 2-pyridinyl group, or a morpholino group.

(10) The compound according to any one of the above (1) to (7), wherein

Q is Q2, $A^{32}$ is an oxygen atom, and $R^6$ is a C1-C6 alkyl group optionally substituted with at least one halogen atom; a C2-C6 alkenyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxy carbonyl group optionally substituted with at least one halogen atom.

(11) The compound according to the above (10), wherein $R^6$ is a methyl group, an ethyl group, a propyl group, an isopropyl group, a butyl group, a sec-butyl group, a 2-propenyl group, or a phenyl group.

(12) The compound according to any one of the above (1) to (7), wherein

Q is Q4, $A^{34}$ is an oxygen atom, and $R^8$ and $R^9$ independently represent a hydrogen atom; a C1-C6 alkyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxy carbonyl group optionally substituted with at least one halogen atom.

(13) The compound according to the above (12), wherein $R^8$ and $R^9$, each, independently, represent a hydrogen atom, a methyl group, an ethyl group, or a phenyl group.

(14) The compound according to any one of the above (1) to (13), wherein $R^2$ is a hydrogen atom or a methyl group, and $R^3$ is a hydrogen atom, a methyl group, an isopropyl group, or a methoxycarbonyl group.

(15) The compound according to the above (1), wherein $R^1$ is a hydrogen atom, or a C1-C6 alkyl group optionally substituted with at least one halogen atom, $R^2$ is a hydrogen atom, or a C1-C6 alkyl group optionally substituted with at least one halogen atom, $R^3$ is a hydrogen atom, a C1-C6 alkyl group optionally substituted with at least one halogen atom, or a C2-C6 alkoxycarbonyl group, $R^4$ is a halogen atom, a cyano group, a C1-C6 alkyl group optionally substituted with at least one halogen atom, a C1-C6 alkoxy group optionally substituted with at least one halogen atom, or a phenyl group optionally substituted with at least one halogen atom, or two $R^4$ groups which are bound to the adjacent carbon atoms are bound at their terminal ends to form T1: —CR$^{41}$=CR$^{42}$—CR$^{43}$=CR$^{44}$—

(wherein $R^{41}$, $R^{42}$, $R^{43}$ and $R^{44}$ represent a hydrogen atom), n is an integer of 0 to 3, Q is a group represented by Q1 to Q6:
Q1: —C(=A$^{31}$)-R$^5$
Q2: —C(=A$^{32}$)-OR$^6$
Q3: —C(=A$^{33}$)-SR$^7$
Q4: —C(=A$^{34}$)-NR$^8$R$^9$
Q5: —S(O)$_2$—R$^{10}$
Q6: —S(O)$_2$—NR$^{11}$R$^{12}$ (wherein $A^{31}$, $A^{32}$ and $A^{33}$ are an oxygen atom, $A^{34}$ is an oxygen atom or a sulfur atom, $R^5$ is a hydrogen atom; a C1-C6 alkyl group optionally substituted with one or more independent substituents selected from the group consisting of (1) a halogen atom, (2) a C1-C6 alkoxy group, (3) a C1-C6 alkylthio group, (4) a C1-C6 alkylsulfinyl group, (5) a C1-C6 alkylsulfonyl group, (6) a C2-C6 dialkylamino group and (7) a C3-C6 cycloalkyl group; a C3-C6 cycloalkyl group optionally substituted with one or more independent substituents selected from the group consisting of (1) a halogen atom and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom; a 5- to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or a 3- to 8-membered non-aromatic heterocyclic group optionally substituted with one or more independent substituents selected from the group consisting of (1) a halogen atom and (2) a C1-C6 alkyl group, $R^6$ is a C1-C6 alkyl group optionally substituted with at least one halogen atom; a C2-C6 alkenyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom, $R^7$ is a C1-C6 alkyl group optionally substituted with at least one halogen atom, $R^8$ and $R^9$ independently represent a hydrogen atom; a C1-C6 alkyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom, $R^{10}$ is a C1-C6 alkyl group optionally substituted with at least one halogen atom, and $R^{11}$ and $R^{12}$ independently represent a C1-C6 alkyl group optionally substituted with at least one halogen atom), J is a group represented by J1 or J2:

J1:

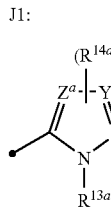

J2:

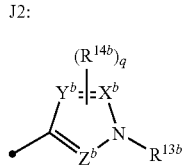

(wherein $X^a$ is CH or a nitrogen atom, $Y^a$ is CH, $Z^a$ is CH or a nitrogen atom, $X^b$ is CH or a nitrogen atom, $Y^b$ is CH, and $Z^b$ is CH or a nitrogen atom, $R^{13a}$ is a C1-C6 alkyl group optionally substituted with at least one halogen atom; a C3-C6 cycloalkyl group optionally substituted with one or more independent substituents selected from the group consisting of (1) a halogen atom and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom and (8) a C1-C6 alkylsulfonyl group optionally substituted with at least one halogen atom; or a 5- to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^{13b}$ is a C1-C6 alkyl group optionally substituted with at least one halogen atom, $R^{14a}$ is a halogen atom; a cyano group; a C1-C6 alkyl group optionally substituted with at least one halogen atom; a C1-C6 alkylthio group optionally substituted with at least one halogen atom; a C1-C6 alkylsulfinyl group optionally substituted with at least one halogen atom; a C1-C6 alkylsulfonyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^{14b}$ is a C1-C6 alkyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, p is an integer of 0 to 2, q is 1, (provided that, when p is 2, two $R^{14a}$'s may be the same or different)), and $A^1$ and $A^2$ are an oxygen atom.

(16) A hydrazide compound represented by the formula (1-1):

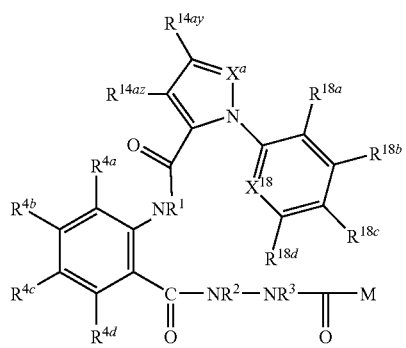

(1-1)

wherein $R^1$ is a hydrogen atom, or a C1-C6 alkyl group optionally substituted with at least one halogen atom, $R^2$ is a C1-C6 alkyl group optionally substituted with at least one halogen atom, $R^3$ is a hydrogen atom, a C1-C6 alkyl group optionally substituted with at least one halogen atom, or a C2-C6 alkoxycarbonyl group, $R^{4a}$ is a hydrogen atom, a halogen atom, a C1-C6 alkyl group optionally substituted with at least one halogen atom, a C1-C6 alkoxy group optionally substituted with at least one halogen atom, or a phenyl group optionally substituted with at least one halogen atom, $R^{4b}$, $R^{4c}$ and $R^{4d}$ are independently a hydrogen atom, a halogen atom, a cyano group, a C1-C6 alkyl group optionally substituted with at least one halogen atom, or $R^{4b}$ and $R^{4c}$ are bound to each other at their terminal ends to form a group: —$CR^{41}$=$CR^{42}$—$CR^{43}$=$CR^{44}$—

(wherein $R^{41}$, $R^{42}$, $R^{43}$ and $R^{44}$ represent a hydrogen atom),

M is $OR^6$, $SR^7$ or $NR^8R^9$ (wherein $R^6$ and $R^7$ are a C1-C6 alkyl group optionally substituted with at least one halogen atom, a C3-C6 alkoxyalkyl group optionally substituted with at least one halogen atom, a C2-C6 alkenyl group optionally substituted with at least one halogen atom, or a C3-C6 alkynyl group optionally substituted with at least one halogen atom, $R^8$ and $R^9$ are independently a hydrogen atom, a C1-C6 alkyl group optionally substituted with at least one halogen atom, a C2-C6 alkenyl group optionally substituted with at least one halogen atom, a C3-C6 alkynyl group optionally substituted with at least one halogen atom, or $R^8$ and $R^9$ are taken together with the nitrogen atom to which they are bound to form a pyrrolidin-1-yl group, a piperidino group, a hexamethyleneimin-1-yl group, a heptamethyleneimin-1-yl group, a morpholino group, a thiomorpholin-4-yl group, or a 4-phenylpiperazin-1-yl group), $X^a$ is a nitrogen atom or $CR^{14ax}$ (wherein $R^{14ax}$ represents a hydrogen atom, a halogen atom, a cyano group, a C1-C6 alkyl group optionally substituted with at least one halogen atom, a C1-C6 alkylthio group optionally substituted with at least one halogen atom, or a C1-C6 alkylsulfinyl group optionally substituted with at least one halogen atom), $R^{14ay}$ is a hydrogen atom, a halogen atom, a cyano group, a C1-C6 alkyl group optionally substituted with at least one halogen atom, a C1-C6 alkylthio group optionally substituted with at least one halogen atom, a C1-C6 alkylsulfinyl group optionally substituted with at least one halogen atom, a C1-C6 alkylsulfonyl group optionally substituted with at least one halogen atom, or a phenyl group, $R^{14az}$ is a hydrogen atom, $X^{18}$ is a nitrogen atom or $CR^{18e}$ (wherein $R^{18e}$ is a hydrogen atom or a halogen atom), and $R^{18a}$, $R^{18b}$, $R^{18c}$ and $R^{18d}$ are independently a hydrogen atom or a halogen atom.

(17) A hydrazide compound represented by the formula (1-1):

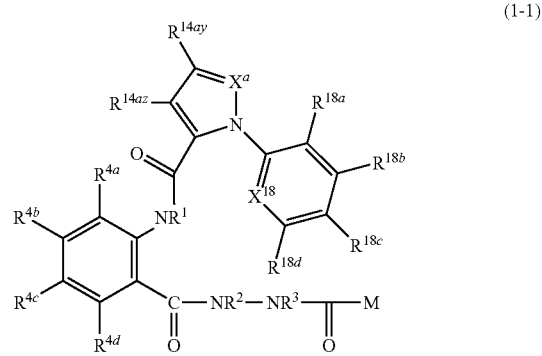

(1-1)

wherein $R^1$ is a hydrogen atom, or a C1-C6 alkyl group optionally substituted with at least one halogen atom, $R^2$ is a hydrogen atom, or a C1-C6 alkyl group optionally substituted with at least one halogen atom, $R^3$ is a hydrogen atom, a C1-C6 alkyl group optionally substituted with at least one halogen atom, or a C2-C6 alkoxycarbonyl group, $R^{4a}$ is a hydrogen atom, a halogen atom, a C1-C6 alkyl group optionally substituted with at least one halogen atom, a C1-C6 alkoxy group optionally substituted with at least one halogen atom, or a phenyl group optionally substituted with at least one halogen atom, $R^{4b}$, $R^{4c}$ and $R^{4d}$ are independently a hydrogen atom, a halogen atom, a cyano group, a C1-C6 alkyl group optionally substituted with at least one halogen atom, or $R^{4b}$ and $R^{4c}$ are bound to each other at their terminal ends to form a group: —$CR^{41}$=$CR^{42}$—$CR^{43}$=$CR^{44}$—

(wherein $R^{41}$, $R^{42}$, $R^{43}$ and $R^{44}$ represent a hydrogen atom),

M is a hydrogen atom, $X^a$ is a nitrogen atom or $CR^{14ax}$ (wherein $R^{14ax}$ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom), $R^{14ay}$ is a hydrogen atom, a halogen atom, a cyano group, a C1-C6 alkyl group optionally substituted with at least one halogen atom, a C1-C6 alkylthio group optionally substituted with at least one halogen atom, a C1-C6 alkylsulfinyl group optionally substituted with at least one halogen atom, a C1-C6 alkylsulfonyl group optionally substituted with at least one halogen atom, or a phenyl group, $R^{14az}$ is a hydrogen atom, $X^{18}$ is a nitrogen atom or $CR^{18e}$ (wherein $R^{18e}$ is a hydrogen atom or a halogen atom), and $R^{18a}$, $R^{18b}$, $R^{18c}$ and $R^{18d}$ are independently a hydrogen atom or a halogen atom.

(18) A hydrazide compound represented by the formula (II):

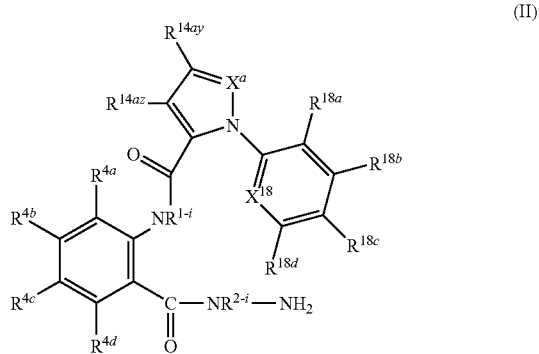

wherein $R^{1-i}$ represents a hydrogen atom, or a C1-C6 alkyl group optionally substituted with at least one halogen atom, $R^{2-i}$ represents a hydrogen atom or a methyl group, $R^{4a}$ represents a halogen atom, or a C1-C6 alkyl group optionally substituted with at least one halogen atom, $R^{4b}$, $R^{4c}$ and $R^{4d}$ independently, represent a hydrogen atom, a halogen atom, a cyano group, a C1-C6 alkyl group optionally substituted with at least one halogen atom, or $R^{4b}$ and $R^{4c}$ are bound at an end to form a group T1: —$CR^{41}$=$CR^{42}$—$CR^{43}$=$CR^{44}$—

(wherein $R^{41}$, $R^{42}$, $R^{43}$ and $R^{44}$, each, independently, represent a hydrogen atom, a halogen atom, a cyano group, or a C1-C6 alkyl group optionally substituted with at least one halogen atom), $X^a$ represents a nitrogen atom or $CR^{14ax}$ (wherein $R^{14ax}$ represents a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom), $R^{14ay}$ and $R^{14az}$ independently represent a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, $X^{18}$ represents a nitrogen atom or $CR^{18e}$, (wherein $R^{18e}$ represents a hydrogen atom, a halogen atom, or a C1-C6 alkyl group optionally substituted with at least one halogen atom)

$R^{18a}$ represents a halogen atom, or a C1-C6 alkyl group optionally substituted with at least one halogen atom, and $R^{18b}$, $R^{18c}$ and $R^{18d}$ independently represent a hydrogen atom, a halogen atom, or a C1-C6 alkyl group optionally substituted with at least one halogen atom.

(19) The compound according to the above (18), wherein $R^{2-i}$ is a methyl group.

(20) A pesticide comprising the compound according to any one of the above (1) to (17) as an active ingredient.

(21) A method of controlling a pest which comprises applying the compound according to any one of the above (1) to (17) directly to a pest or to a place where a pest inhabits.

(22) Use of the compound according to any one of the above (1) to (17) for controlling a pest.

(23) Use of the compound according to any one of the above (1) to (17) for manufacturing a pesticidal preparation.

Hereinafter, preferred embodiments of the present invention will be illustrated.

$R^{14a}$ used herein represents a group which can substitute for a hydrogen atom of a ring constituting CH of a group represented by J1, and $R^{14b}$ represents a group which can substitute for a hydrogen atom of a ring constituting CH of a group represented by J2.

In the present invention, examples of a halogen atom include a fluorine atom, a chlorine atom, a bromine atom and an iodine atom.

In $R^1$, $R^2$ and $R^3$, examples of the "C1-C6 alkyl group optionally substituted with at least one halogen atom" include a methyl group, an ethyl group, a 2,2,2-trifluoroethyl group, a propyl group, an isopropyl group, a butyl group, an isobutyl group, a sec-butyl group, a tert-butyl group, a pentyl group and a hexyl group.

In $R^1$, examples of the "C2-C6 cyanoalkyl group" include a cyanomethyl group and a 2-cyanoethyl group;

examples of the "C2-C6 alkoxyalkyl group optionally substituted with at least one halogen atom" include a 2-methoxyethyl group, a 2-ethoxyethyl group and a 2-isopropyloxyethyl group;

examples of the "C2-C6 alkenyl group optionally substituted with at least one halogen atom" include a 2-propenyl group, a 3-chloro-2-propenyl group, a 2-chloro-2-propenyl group, a 3,3-dichloro-2-propenyl group, a 2-butenyl group, a 3-butenyl group, a 2-methyl-2-propenyl group, a 3-methyl-2-butenyl group, a 2-pentenyl group and a 2-hexenyl group;

example of the "C3-C6 alkynyl group optionally substituted with at least one halogen atom" include a 2-propynyl group, a 3-chloro-2-propynyl group, a 3-bromo-2-propynyl group, a 2-butynyl group and a 3-butynyl group; and examples of the "C7-C9 phenylalkyl group whose benzene ring moiety may be substituted with 1 to 5 independent groups selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a benzyl group, a 1-phenylethyl group, a 2-phenylethyl group, a 2-chlorobenzyl group, a 3-chlorobenzyl group, a 4-chlorobenzyl group, a 2-cyanobenzyl group, a 3-cyanobenzyl group, a 4-cyanobenzyl group, a 2-nitrobenzyl group, a 3-nitrobenzyl group, a 4-nitrobenzyl group, a 2-methylbenzyl group, a 3-methylbenzyl group, a 4-methylbenzyl group, a 2-(trifluoromethyl)benzyl group, a 3-(trifluoromethyl)benzyl group, a 4-(trifluoromethyl)benzyl group, a 2-methoxybenzyl group, a 3-methoxybenzyl group and a 4-methoxybenzyl group.

In $R^2$ and $R^3$, examples of the "C1-C6 acyl group" include a formyl group, an acetyl group, a propionyl group, an isobutyryl group and a trimethylacetyl group;

examples of the "C2-C6 alkoxycarbonyl group" include a methoxycarbonyl group, an ethoxycarbonyl group, an isopropoxycarbonyl group and a tert-butoxycarbonyl group;

examples of the "C3-C7 N,N-dialkylcarbamoyl group" include a N,N-dimethylcarbamoyl group and a N,N-diethylcarbamoyl group; and examples of the "phenyl group optionally substituted with 1 to 5 independent groups selected from the group consisting of (1) a halogen atom, (2) a cyano group, (3) a nitro group, (4) a C1-C6 alkyl group optionally substituted with at least one halogen atom and (5) a C1-C6 alkyl group optionally substituted with at least one halogen atom" include a phenyl group, a 2-chlorophenyl group, a 3-chlorophenyl group, a 4-chlorophenyl group, a 2-cyanophenyl group, a 3-cyanophenyl group, a 4-cyanophenyl group, a 2-nitrophenyl group, a 3-nitrophenyl group, a 4-nitrophenyl group, a 2-methylphenyl group, a 3-methylphenyl group, a 4-methylphenyl group, a 2-(trifluoromethyl)phenyl group, a 3-(trifluoromethyl)phenyl group and a 4-(trifluoromethyl)phenyl group.

In $R^4$, $R^{41}$, $R^{42}$, $R^{43}$ and $R^{44}$, examples of the "C1-C6 alkyl group optionally substituted with at least one halogen atom" include a methyl group, a trifluoromethyl group, an ethyl group, a propyl group, an isopropyl group, a butyl group, an isobutyl group, a sec-butyl group, a tert-butyl group, a pentyl group and a hexyl group.

In $R^4$, $R^{41}$, $R^{42}$, $R^{43}$ and $R^{44}$, examples of the "C1-C6 alkoxy group optionally substituted with at least one halogen atom" include a methoxy group, a trifluoromethoxy group, an ethoxy group, a 2,2,2-trifluoroethoxy group, a propyloxy group, an isopropyloxy group, a butoxy group, an isobutyloxy group, a sec-butoxy group, a tert-butoxy group, a pentyloxy group and a hexyloxy group.

In $R^4$, $R^{41}$, $R^{42}$, $R^{43}$ and $R^{44}$, examples of the "C1-C6 alkylthio group optionally substituted with at least one halogen atom" include a methylthio group, a trifluoromethylthio group and an ethylthio group.

In $R^4$, $R^{41}$, $R^{42}$, $R^{43}$ and $R^{44}$, examples of the "C1-C6 alkylsulfinyl group optionally substituted with at least one halogen atom" include a methylsulfinyl group, a trifluoromethylsulfinyl group and an ethylsulfinyl group.

In $R^4$, $R^{41}$, $R^{42}$, $R^{43}$ and $R^{44}$, examples of the "C1-C6 alkylsulfonyl group optionally substituted with at least one halogen atom" include a methylsulfonyl group, a trifluoromethylsulfonyl group and an ethylsulfonyl group.

In $R^4$, examples of the "phenyl group optionally substituted with at least one halogen atom" include a phenyl group, a 2-chlorophenyl group, a 3-chlorophenyl group and a 4-chlorophenyl group.

In $R^{45}$ and $R^{46}$, examples of the "C1-C6 alkyl group optionally substituted with at least one halogen atom" include a methyl group, a trifluoromethyl group, and an ethyl group.

In $R^5$, examples of the "C2-C6 alkenyl group optionally substituted with at least one halogen atom" include a vinyl group, a 1-propenyl group, a 2-propenyl group, a 1-methylvinyl group, a 2-chlorovinyl group and a 2-methyl-1-propenyl group;

examples of the "C2-C6 alkynyl group optionally substituted with at least one halogen atom" include an ethynyl group;

examples of the "C1-C6 alkyl group optionally substituted with one or more independent substituents selected from the group consisting of (1) a halogen atom, (2) a C1-C6 alkoxy group, (3) a C1-C6 alkylthio group, (4) a C1-C6 alkylsulfinyl group, (5) a C1-C6 alkylsulfonyl group, (6) a C2-C6 dialkylamino group and (7) a C3-C6 cycloalkyl group" include a methyl group, a trifluoromethyl group, a trichloromethyl group, a chloromethyl group, a dichloromethyl group, a fluoromethyl group, a difluoromethyl group, a methoxymethyl group, an ethoxymethyl group, a methylthiomethyl group, an ethylthiomethyl group, a methylsulfinylmethyl group, a methylsulfonylmethyl group, a dimethylaminomethyl group, a cyclopropylmethyl group, a cyclopentylmethyl group, a cyclohexylmethyl group, an ethyl group, a pentafluoroethyl group, a propyl group, an isopropyl group, a butyl group, an isobutyl group, a sec-butyl group, a tert-butyl group, a pentyl group and a hexyl group;

examples of the "C3-C6 cycloalkyl group optionally substituted with one or more independent substituents selected from the group consisting of (1) a halogen atom and (2) a C1-C6 alkyl group" include a cyclopropyl group, a 2-methylcyclopropyl group, a cyclobutyl group, a cyclopentyl group and a cyclohexyl group;

examples of the "phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom" include a phenyl group, a 2-chlorophenyl group, a 3-chlorophenyl group, a 4-chlorophenyl group, a 4-fluorophenyl group, a 4-bromophenyl group, a 4-iodophenyl group, a 2-cyanophenyl group, a 3-cyanophenyl group, a 4-cyanophenyl group, a 2-nitrophenyl group, a 3-nitrophenyl group, a 4-nitrophenyl group, a 2-methylphenyl group, a 3-methylphenyl group, a 4-methylphenyl group, a 2-(trifluoromethyl)phenyl group, a 3-(trifluoromethyl)phenyl group, a 4-(trifluoromethyl)phenyl group, a 2-methoxyphenyl group, a 3-methoxyphenyl group, a 4-methoxyphenyl group, a 4-(trifluoromethoxy)phenyl group, a 4-(methylthio)phenyl group, a 4-(methylsulfinyl)phenyl group, a 4-(methylsulfonyl)phenyl group and a 4-(methoxycarbonyl)phenyl group;

examples of the "naphthyl group optionally substituted with 1 to 9 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a 1-naphthyl and a 2-naphthyl group;

examples of the "5- to 6-membered heteroaryl group optionally substituted with one or more independent substituents selected from the group (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a 1-methyl-2-pyrrolyl group, a 2-furyl group, a 3-furyl group, a 5-bromo-2-furyl group, a 5-nitro-2-furyl group, a 2-methyl-3-furyl group, a 2,5-dimethyl-3-furyl group, a 2,4-dimethyl-3-furyl group, a 2-thienyl group, a 3-thienyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a 2-pyridinyl group, a 3-pyridinyl group, a 4-pyridinyl group, a 2-methyl-3-pyridinyl group, a 6-methyl-3-pyridinyl group, a 2-chloro-3-pyridinyl group, a 6-chloro-3-pyridinyl group and a pyrazinyl group;

examples of the "3- to 8-membered non-aromatic heterocyclic group optionally substituted with one or more independent substituents selected from a group consisting of (1) a halogen atom and (2) a C1-C6 alkyl group" include a tetrahydro-2-furyl group, a tetrahydro-3-furyl group, and a morpholino group;

examples of the "C7-C9 phenylalkyl group whose benzene ring moiety may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a benzyl group, a 1-phenylethyl group, a 2-phenylethyl group, a 2-chlorobenzyl group, a 3-chlorobenzyl group, a 4-chlorobenzyl group, a 2-cyanobenzyl group, a 3-cyanobenzyl group, a 4-cyanobenzyl group, a 2-nitrobenzyl group, a 3-nitrobenzyl group, a 4-nitrobenzyl group, a 2-methylbenzyl group, a 3-methylbenzyl group, a 4-methylbenzyl group, a 2-(trifluoromethyl)benzyl group, a 3-(trifluoromethyl)benzyl group, a 4-(trifluoromethyl)benzyl group, a 2-methoxybenzyl group, a 3-methoxybenzyl group and a 4-methoxybenzyl group; and examples of the "C7-C9 phenoxyalkyl group whose benzene ring moiety may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a phenoxymethyl group, a 2-phenoxyethyl group and a 1-phenoxyethyl group.

In $R^6$ and $R^7$, examples of the "C1-C6 alkyl group optionally substituted with at least one halogen atom" include a methyl group, an ethyl group, a 2,2,2-trifluoroethyl group, a 2,2,2-trichloroethyl group, a propyl group, an isopropyl group, a butyl group, an isobutyl group, a sec-butyl group, a tert-butyl group, a pentyl group and a hexyl group;

examples of the "C3-C6 alkoxyalkyl group optionally substituted with at least one halogen atom" include a 2-methoxyethyl group, 2-ethoxyethyl group and a 2-isopropyloxyethyl group;

examples of the "C2-C6 alkenyl group optionally substituted with at least one halogen atom" include a 1-propenyl group, a 2-propenyl group, a 3-chloro-2-propenyl group, a 2-chloro-2-propenyl group, a 3,3-dichloro-2-propenyl group, a 2-butenyl group, a 3-butenyl group, a 2-methyl-2-propenyl group, a 3-methyl-2-butenyl group, a 2-pentenyl group and a 2-hexenyl group;

examples of the "C3-C6 alkynyl group optionally substituted with at least one halogen atom" include a 2-propynyl group, a 3-chloro-2-propynyl group, a 3-bromo-2-propynyl group, a 2-butynyl group and a 3-butynyl group;

examples of the "C3-C6 cycloalkyl group optionally substituted with one or more independent substituents selected from the group consisting of (1) a halogen atom and (2) a C1-C6 alkyl group" include a cyclopropyl group, a cyclobutyl group, a cyclopentyl group and a cyclohexyl group;

examples of the "phenyl group optionally substituted with 1 to 5 independent substituents selected from the group consisting of the (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom" include a phenyl group, a 2-chlorophenyl group, a 3-chlorophenyl group, a 4-chlorophenyl group, a 4-fluorophenyl group, a 4-bromophenyl group, a 4-iodophenyl group, a 2-cyanophenyl group, a 3-cyanophenyl group, a 4-cyanophenyl group, a 2-nitrophenyl group, a 3-nitrophenyl group, a 4-nitrophenyl group, a 2-methylphenyl group, a 3-methylphenyl group, a 4-methylphenyl group, a 2-(trifluoromethyl)phenyl group, a 3-(trifluoromethyl)phenyl group, a 4-(trifluoromethyl)phenyl group, a 2-methoxyphenyl group, a 3-methoxyphenyl group, a 4-methoxyphenyl group, a 4-(trifluoromethoxy)phenyl group, a 4-(methylthio)phenyl group, a 4-(methylsulfinyl)phenyl group, a 4-(methylsulfonyl)phenyl group and a 4-(methoxycarbonyl)phenyl group;

examples of the "5- to 6-membered heteroaryl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a 2-pyridinyl group; and examples of the "C7-C9 phenylalkyl group whose benzene ring moiety may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a benzyl group, a 1-phenylethyl group, a 2-phenylethyl group, a 2-chlorobenzyl group, a 3-chlorobenzyl group, a 4-chlorobenzyl group, a 2-cyanobenzyl group, a 3-cyanobenzyl group, a 4-cyanobenzyl group, a 2-nitrobenzyl group, a 3-nitrobenzyl group, a 4-nitrobenzyl group, a 2-methylbenzyl group, a 3-methylbenzyl group, a 4-methylbenzyl group, a 2-(trifluoromethyl)benzyl group, a 3-(trifluoromethyl)benzyl group, a 4-(trifluoromethyl)benzyl group, a 2-methoxybenzyl group, a 3-methoxybenzyl group and a 4-methoxybenzyl group.

In $R^8$ and $R^9$, examples of the "C1-C6 alkyl group optionally substituted with at least one halogen atom" include a methyl group, an ethyl group, a 2,2,2-trifluoroethyl group, a 2,2,2-trichloroethyl group, a propyl group, an isopropyl group, a butyl group, an isobutyl group, a sec-butyl group, a tert-butyl group, a pentyl group and a hexyl group;

examples of the "C2-C6 alkoxyalkyl group optionally substituted with at least one halogen atom" include a 2-methoxyethyl group, a 2-ethoxyethyl group and a 2-isopropyloxyethyl group;

examples of the "C2-C6 alkenyl group optionally substituted with at least one halogen atom" include a 2-propenyl group, a 3-chloro-2-propenyl group, a 2-chloro-2-propenyl group, a 3,3-dichloro-2-propenyl group, a 2-butenyl group, a 3-butenyl group, a 2-methyl-2-propenyl group, a 3-methyl-2-butenyl group, a 2-pentenyl group and a 2-hexenyl group;

examples of the "C3-C6 alkynyl group optionally substituted with at least one halogen atom" include a 2-propynyl group, a 3-chloro-2-propynyl group, a 3-bromo-2-propynyl group, a 2-butynyl group and a 3-butynyl group;

examples of the "C3-C6 cycloalkyl group optionally substituted with one or more independent substituents selected from the group consisting of (1) a halogen atom and (2) a C1-C6 alkyl group include a cyclopropyl group, a cyclobutyl group, a cyclopentyl group and a cyclohexyl group;

examples of the "phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom" include a phenyl group, a 2-chlorophenyl group, a 3-chlorophenyl group, a 4-chlorophenyl group, a 4-fluorophenyl group, a 4-bromophenyl group, a 4-iodophenyl group, a 2-cyanophenyl group, a 3-cyanophenyl group, a 4-cyanophenyl group, a 2-nitrophenyl group, a 3-nitrophenyl group, a 4-nitrophenyl group, a 2-methylphenyl group, a 3-methylphenyl group, a 4-methylphenyl group, a 2-(trifluoromethyl)phenyl group, a 3-(trifluoromethyl)phenyl group, a 4-(trifluoromethyl)phenyl group, a 2-methoxyphenyl group, a 3-methoxyphenyl group, a 4-methoxyphenyl group, a 4-(trifluoromethoxy)phenyl group, a 4-(methylthio)phenyl group, a 4-(methylsulfinyl)phenyl group, a 4-(methylsulfonyl)phenyl group and a 4-(methoxycarbonyl)phenyl group;

examples of the "5- to 6-membered heteroaryl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a 3-pyridinyl group;

examples of the "C7-C9 phenylalkyl group whose benzene ring moiety may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a benzyl group, a 1-phenylethyl group, a 2-phenylethyl group, a 2-chlorobenzyl group, a 3-chlorobenzyl group, a 4-chlorobenzyl group, a 2-cyanobenzyl group, a 3-cyanobenzyl group, a 4-cyanobenzyl group, a 2-nitrobenzyl group, a 3-nitrobenzyl group, a 4-nitrobenzyl group, a 2-methylbenzyl group, a 3-methylbenzyl group, a 4-methylbenzyl group, a 2-(trifluoromethyl)benzyl group, a 3-(trifluoromethyl)benzyl group, a 4-(trifluoromethyl)benzyl group, a 2-methoxybenzyl group, a 3-methoxybenzyl group and a 4-methoxybenzyl group; and examples of the "3- to 8-membered non-aromatic heterocyclic group" when "$R^8$ and $R^9$ are taken together with the nitrogen atom to which they are bound to form a 3- to 8-membered non-aromatic heterocyclic group" include a pyrrolidin-1-yl group, piperidino group, a 3,5-dimethylpiperidino group, a hexamethyleneimin-1-yl group, a heptamethyleneimin-1-yl group, a morpholino group, a 2,6-dimethylmorpholino group, a thiomorpholin-4-yl group, a 4-methylpiperazin-1-yl group, a 4-(ethoxycarbonyl)piperazin-1-yl group and a 4-phenylpiperazin-1-yl group.

In $R^{10}$, examples of the "C1-C6 alkyl group optionally substituted with at least one halogen atom" include a methyl group, a trifluoromethyl group, a trichloromethyl group, an ethyl group, a 2-chloroethyl group, a 2,2,2-trifluoroethyl group, a propyl group, an isopropyl group, a butyl group, an isobutyl group, a sec-butyl group, a tert-butyl group, a pentyl group and a hexyl group;

examples of the "C3-C6 cycloalkyl group optionally substituted with one or more independent substituents selected from the group consisting of (1) a halogen atom and (2) a C1-C6 alkyl group optionally substituted with at least one halogen atom" include a cyclopropyl group, a cyclobutyl group, a cyclopentyl group and a cyclohexyl group; and examples of the "phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a phenyl group, a 4-chlorophenyl group, a 4-nitrophenyl group and a 4-methylphenyl group.

In $R^{11}$ and $R^{12}$, examples of the "C1-C6 alkyl group optionally substituted with at least one halogen atom" include a methyl group, an ethyl group, a 2,2,2-trifluoroethyl group, a 2,2,2-trichloroethyl group, a propyl group, an isopropyl group, a butyl group, an isobutyl group, a sec-butyl group, a tert-butyl group, a pentyl group and a hexyl group;

examples of the "C3-C6 cycloalkyl group optionally substituted with one or more independent substituents selected from the group consisting of (1) a halogen atom and (2) a C1-C6 alkyl group optionally substituted with at least one halogen atom" include a cyclopropyl group, a cyclobutyl group, a cyclopentyl group and a cyclohexyl group;

examples of the "phenyl group optionally substituted with 1 to 5 independent groups selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a phenyl group and a 4-methylphenyl group; and examples of the "3- to 8-membered non-aromatic heterocyclic group" when "$R^{11}$ and $R^{12}$ are taken together with the nitrogen atom to which they are bound to form a 3- to 8-membered non-aromatic heterocyclic group" include a pyrrolidin-1-yl group, a piperidino group, a 3,5-dimethylpiperidino group, a morpholino group, a 2,6-dimethylmorpholino group, a thiomorpholin-4-yl group, a 4-methylpiperazin-1-yl group, a 4-(ethoxycarbonyl)piperazin-1-yl group and a 4-phenylpiperazin-1-yl group.

In $R^{13a}$ and $R^{13b}$, examples of the "C1-C6 alkyl group optionally substituted with at least one halogen atom" include a methyl group, a fluoromethyl group, a difluoromethyl group, a trifluoromethyl group, an ethyl group, a 2,2,2-trifluoroethyl group, a 1,1,2,2-tetrafluoroethyl group, a propyl group, an isopropyl group, a butyl group, an isobutyl group, a sec-butyl group, a tert-butyl group, a pentyl group and a hexyl group;

examples of the "C2-C6 cyanoalkyl group" include a cyanomethyl group and a 2-cyanoethyl group;

examples of the "C2-C6 alkoxyalkyl group optionally substituted with at least one halogen atom" include a methoxymethyl group, an ethoxymethyl group, a 2-methoxyethyl group, a 2-ethoxyethyl group and a 2-isopropyloxyethyl group;

examples of the "C2-C6 alkenyl group optionally substituted with at least one halogen atom" include a 2-propenyl group, a 3-chloro-2-propenyl group, a 2-chloro-2-propenyl group, a 3,3-dichloro-2-propenyl group, a 2-butenyl group, a 3-butenyl group, a 2-methyl-2-propenyl group, a 3-methyl-2-butenyl group, a 2-pentenyl group and a 2-hexenyl group;

examples of the "C2-C6 alkynyl group optionally substituted with at least one halogen atom" include a 2-propynyl group, a 3-chloro-2-propynyl group, a 3-bromo-2-propynyl group, a 2-butynyl group and a 3-butynyl group;

examples of the "C3-C6 cycloalkyl group optionally substituted with one or more independent substituents selected from the group consisting of (1) a halogen atom and (2) a C1-C6 alkyl group" include a cyclopropyl group, a cyclobutyl group, a cyclopentyl group and a cyclohexyl group;

examples of the "phenyl group optionally substituted with 1 to 5 independent substituents selected from a group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom and (8) a C1-C6 alkylsulfonyl group optionally substituted with at least one halogen atom" include a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 2-iodophenyl group, a 2,6-difluorophenyl group, a 2,6-dichlorophenyl group, a 2-chloro-6-fluorophenyl group, a 2-chloro-4-fluorophenyl group, a 2-cyanophenyl group, a 3-cyanophenyl group, a 4-cyanophenyl group, a 2-nitrophenyl group, a 3-nitrophenyl group, a 4-nitrophenyl group, a 2-methylphenyl group, a 3-methylphenyl group, a 4-methylphenyl group, a 2-ethylphenyl group, a 2-isopropylphenyl group, a 2-tert-butylphenyl group, a 2-(trifluoromethyl)phenyl group, a 3-(trifluoromethyl)phenyl group, a 4-(trifluoromethyl)phenyl group, a 2-methoxyphenyl group, a 3-methoxyphenyl group, a 4-methoxyphenyl group, a 2-ethoxyphenyl group, a 2-(trifluoromethoxy)phenyl group, a 2-(methylthio)phenyl group, a 2-(methylsulfinyl)phenyl group and a 2-(methylsulfonyl)phenyl group;

examples of the "5- to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a 2-pyridinyl group, a 3-fluoro-2-pyridinyl group, a 3-chloro-2-pyridinyl group, a 3-bromo-2-pyridinyl group, a 3-iodo-2-pyridinyl group, a 3-methyl-2-pyridinyl group, a 3-trifluoromethyl-2-pyridinyl group, a 3-methoxy-2-pyridinyl group, a 3-cyano-2-pyridinyl group, a 3-nitro-2-pyridinyl group, a 3-pyridinyl group, a 2-chloro-3-pyridinyl group, a 4-chloro-3-pyridinyl group, a 4-pyridinyl group, a 3-chloro-4-pyridinyl group, a 3,5-dichloro-4-pyridinyl group, a 2-pyrimidinyl group, a 4-methyl-2-pyrimidinyl group, a 4,6-dimethyl-2-pyrimidinyl group, a 4-pyrimidinyl group, a 5-chloro-4-pyrimidinyl group, a pyrazinyl group, a 3-methyl-2-pyrazinyl group, a 2-thiazolyl group, a 1-methyl-5-pyrazolyl group, a 4-chloro-1-methyl-5-pyrazolyl group, a 4-chloro-1,3-dimethyl-5-pyrazolyl group and a 4-chloro-5-methyl-3-isooxazolyl group;

examples of the "C7-C9 phenylalkyl group whose benzene ring moiety may be substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a benzyl group, a 1-phenylethyl group, a 2-phenylethyl group, a 2-chlorobenzyl group, a 3-chlorobenzyl group, a 4-chlorobenzyl group, a 2-cyanobenzyl group, a 3-cyanobenzyl group, a 4-cyanobenzyl group, a 2-nitrobenzyl group, a 3-nitrobenzyl group, a 4-nitrobenzyl group, a 2-methylbenzyl group, a 3-methylbenzyl group, a 4-methylbenzyl group, a 2-(trifluoromethyl)benzyl group, a 3-(trifluoromethyl)benzyl group, a 4-(trifluoromethyl)benzyl group, a 2-methoxybenzyl group, a 3-methoxybenzyl group and a 4-methoxybenzyl group; and examples of the "C7-C9 pyridinylalkyl group whose pyridine ring moiety may be substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a 2-pyridinylmethyl group, a 3-pyridinylmethyl group, a 4-pyridinylmethyl group, a 3-chloro-2-pyridinylmethyl group, and a 2-chloro-3-pyridinylmethyl group.

In $R^{14a}$ and $R^{14b}$, examples of the "C1-C6 alkyl group optionally substituted with at least one halogen atom" include a methyl group, a trifluoromethyl group, a trichloromethyl group, a chloromethyl group, a dichloromethyl group, a fluoromethyl group, a difluoromethyl group, an ethyl group, a pentafluoroethyl group, a propyl group, an isopropyl group, a butyl group, an isobutyl group, a sec-butyl group, a tert-butyl group, a pentyl group and a hexyl group;

examples of the "C1-C6 alkoxy group optionally substituted with at least one halogen atom" include a methoxy group, an ethoxy group, a 2,2,2-trifluoroethoxy group, a propoxy group, an isopropyloxy group, a butoxy group, an isobutyloxy group, a sec-butoxy group and a tert-butoxy group;

examples of the "C2-C6 cyanoalkyloxy group" include a cyanomethoxy group and a 2-cyanoethoxy group;

examples of the "C3-C6 alkoxyalkyloxy group optionally substituted with at least one halogen atom" include a 2-(methoxy)ethoxy group;

examples of the "C3-C6 alkenyloxy group optionally substituted with at least one halogen atom" include a 2-propenyloxy group and a 2-methyl-2-propenyloxy group;

examples of the "C3-C6 alkynyloxy group optionally substituted with at least one halogen atom" include a 2-propynyloxy group and a 2-butynyloxy group;

examples of the "C1-C6 alkylthio group optionally substituted with at least one halogen atom" include a methylthio group, a trifluoromethylthio group, an ethylthio group, a propylthio group, an isopropylthio group, a butylthio group, an isobutylthio group, a sec-butylthio group, a tert-butylthio group, a pentylthio group and a hexylthio group;

examples of the "C1-C6 alkylsulfinyl group optionally substituted with at least one halogen atom" include a methylsulfinyl group, a trifluoromethylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a pentylsulfinyl group and a hexylsulfinyl group;

examples of the "C1-C6 alkylsulfonyl group optionally substituted with at least one halogen atom" include a methylsulfonyl group, a trifluoromethylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group and a hexylsulfonyl group;

examples of the "phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a phenyl group, a 2-chlorophenyl group, a 3-chlorophenyl group, a 4-chlorophenyl group, a 4-fluorophenyl group, a 4-bromophenyl group, a 4-iodophenyl group, a 2-cyanophenyl group, a 3-cyanophenyl group, a 4-cyanophenyl group, a 2-nitrophenyl group, a 3-nitrophenyl group, a 4-nitrophenyl group, a 2-methylphenyl group, a 3-methylphenyl group, a 4-methylphenyl group, a 2-(trifluoromethyl)phenyl group, a 3-(trifluoromethyl)phenyl group, a 4-(trifluoromethyl)phenyl group, a 2-methoxyphenyl group, a 3-methoxyphenyl group, a 4-methoxyphenyl group and a 4-(trifluoromethoxy)phenyl group;

examples of the "5- to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a 2-furyl group, a 3-furyl group, a 2-pyridinyl group, a 3-pyridinyl group, a 4-pyridinyl group and a pyrazinyl group; and examples of the "phenoxy group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom" include a phenoxy group, a 2-chlorophenoxy group, a 3-chlorophenoxy group, a 4-chlorophenoxy group, a 2-cyanophenoxy group, a 3-cyanophenoxy group, a 4-cyanophenoxy group, a 2-nitrophenoxy group, a 3-nitrophenoxy group, a 4-nitrophenoxy group, a 2-methylphenoxy group, a 3-methylphenoxy group, a 4-methylphenoxy group, a 2-(trifluoromethyl)phenoxy group, a 3-(trifluoromethyl)phenoxy group, a 4-(trifluoromethyl)phenoxy group, a 2-methoxyphenoxy group, a 3-methoxyphenoxy group, a 4-methoxyphenoxy group and a 4-(trifluoromethoxy)phenoxy group.

Examples of the group represented by J1 include a 1-phenylpyrazol-5-yl group, a 1-(2-chlorophenyl)pyrazol-5-yl group, a 1-(2-pyridinyl)pyrazol-5-yl group, a 1-(3-chloro-2-pyridinyl)pyrazol-5-yl, a 3-fluoro-1-phenylpyrazol-5-yl group, a 1-(2-chlorophenyl)-3-fluoropyrazol-5-yl group, a 3-fluoro-1-(2-pyridinyl)pyrazol-5-yl group, a 3-fluoro-1-(3-chloro-2-pyridinyl)pyrazol-5-yl group, a 3-chloro-1-phenylpyrazol-5-yl group, a 3-chloro-1-(2-chlorophenyl)pyrazol-5-yl group, a 3-chloro-1-(2-pyridinyl)pyrazol-5-yl group, a 3-chloro-1-(3-chloro-2-pyridinyl)pyrazol-5-yl group, a 3-bromo-1-phenylpyrazol-5-yl group, a 3-bromo-1-(2-chlorophenyl)pyrazol-5-yl group, a 3-bromo-1-(2-pyridinyl)pyrazol-5-yl group, a 3-bromo-1-(3-chloro-2-pyridinyl)pyrazol-5-yl group, a 3-iodo-1-phenylpyrazol-5-yl group, a 3-iodo-1-(2-chlorophenyl)pyrazol-5-yl group, a 3-iodo-1-(2-pyridinyl)pyrazol-5-yl group, a 3-iodo-1-(3-chloro-2-pyridinyl)pyrazol-5-yl group, a 3-methyl-1-phenylpyrazol-5-yl group, a 1-(2-chlorophenyl)-3-methylpyrazol-5-yl group, a 3-methyl-1-(2-pyridinyl)pyrazol-5-yl group, a 1-(3-chloro-2-pyridinyl)-3-methylpyrazol-5-yl group, a 1-phenyl-3-(trifluoromethyl)pyrazol-5-yl group, a 1-(2-chlorophenyl)-3-(trifluoromethyl)pyrazol-5-yl group, a 1-(2-pyridinyl)-3-(trifluoromethyl)pyrazol-5-yl group, a 1-(3-chloro-2-pyridinyl)-3-(trifluoromethyl)pyrazol-5-yl group, a 3-chloro-1-methylpyrazol-5-yl group, a 3-chloro-1-ethylpyrazol-5-yl group, a 3-chloro-1-isopropylpyrazol-5-yl group, a 1-tert-butyl-3-chloropyrazol-5-yl group, a 3-chloro-1-(3-fluoro-2-pyridinyl)pyrazol-5-yl group, a 1-(3-bromo-2-pyridinyl)-3-chloropyrazol-5-yl group, a 3-chloro-1-(3-iodo-2-pyridinyl)pyrazol-5-yl group, a 3-chloro-1-(3-methyl-2-pyridinyl)pyrazol-5-yl group, a 3-chloro-1-(3-trifluoromethyl-2-pyridinyl)pyrazol-5-yl group, a 3-chloro-1-(3-methoxy-2-pyridinyl)pyrazol-5-yl group, a 3-chloro-1-(3-cyano-2-pyridinyl)pyrazol-5-yl group, a 3-chloro-1-(3-nitro-2-pyridinyl)pyrazol-5-yl group, a 3-bromo-1-methylpyrazol-5-yl group, a 3-bromo-1-ethylpyrazol-5-yl group, a 3-bromo-1-isopropylpyrazol-5-yl group, a 3-bromo-1-tert-butylpyrazol-5-yl group, a 3-bromo-1-(3-fluoro-2-pyridinyl)pyrazol-5-yl group, a 3-bromo-1-(3-bromo-2-pyridinyl)pyrazol-5-yl group, a 3-bromo-1-(3-iodo-2-pyridinyl)pyrazol-5-yl group, a 3-bromo-1-(3-methyl-2-pyridinyl)pyrazol-5-yl group, a 3-bromo-1-(3-trifluoromethyl-2-pyridinyl)pyrazol-5-yl group, a 3-bromo-1-(3-methoxy-2-pyridinyl)pyrazol-5-yl group, a 3-bromo-1-(3-cyano-2-pyridinyl)pyrazol-5-yl group, a 3-bromo-1-(3-nitro-2-pyridinyl)pyrazol-5-yl group, a 1-methyl-3-(trifluoromethyl)pyrazol-5-yl group, a 1-ethyl-3-(trifluoromethyl)pyrazol-5-yl group, a 1-isopropyl-3-(trifluoromethyl)pyrazol-5-yl group, a 1-tert-butyl-3-(trifluoromethyl)pyrazol-5-yl group, a 1-(3-fluoro-2-pyridinyl)-3-(trifluoromethyl)pyrazol-5-yl group, a 1-(3-bromo-2-pyridinyl)-3-(trifluoromethyl)pyrazol-5-yl group, a 1-(3-iodo-2-pyridinyl)-3-(trifluoromethyl)pyrazol-5-yl group, a 1-(3-methyl-2-pyridinyl)-3-(trifluoromethyl)pyrazol-5-yl group, a 1-(3-trifluoromethyl-2-pyridinyl)-3-(trifluoromethyl)pyrazol-5-yl group, a 1-(3-methoxy-2-pyridinyl)-3-(trifluoromethyl)pyrazol-5-yl group, a 1-(3-cyano-2-pyridinyl)-3-(trifluoromethyl)pyrazol-5-yl group, a 1-(3-nitro-2-pyridinyl)-3-(trifluoromethyl)pyrazol-5-yl group, a 1-(3-chloro-2-pyridinyl)-3-ethylpyrazol-5-yl group, a 1-(3-chloro-2-pyridinyl)-3-isopropylpyrazol-5-yl group, a 3-tert-butyl-1-(3-chloro-2-pyridinyl)pyrazol-5-yl group, a 1-(3-chloro-2-pyridinyl)-3-(methylthio)pyrazol-5-yl group, a 1-(3-chloro-2-pyridinyl)-3-(ethylthio)pyrazol-5-yl group, a 1-(3-chloro-2-pyridinyl)-3-(isopropylthio)pyrazol-5-yl group, a 3-tert-butylthio-1-(3-chloro-2-pyridinyl)pyrazol-5-yl group, a 1-(3-chloro-2-pyridinyl)-3-(methylsulfinyl)pyrazol-5-yl group, a 1-(3-chloro-2-pyridinyl)-3-(ethylsulfinyl)pyrazol-5-yl group, a 1-(3-chloro-2-pyridinyl)-3-(isopropylsulfinyl)pyrazol-5-yl group, a 3-tert-butylsulfinyl-1-(3-chloro-2-pyridinyl)pyrazol-5-yl group, a 1-(3-chloro-2-pyridinyl)-3-(methylsulfonyl)pyrazol-5-yl group, a 1-(3-chloro-2-pyridinyl)-3-(ethylsulfonyl)pyrazol-5-yl group, a 1-(3-chloro-2-pyridinyl)-3-(isopropylsulfonyl)pyrazol-5-yl group, a 3-tert-butylsulfonyl-1-(3-chloro-2-pyridinyl)pyrazol-5-yl group, a 1-(3-chloro-2-pyridinyl)-3-(2,2,2-trifluoroethoxy)pyrazol-5-yl group, a 1-(3-chloro-2-pyridinyl)-3-cyanopyrazol-5-yl group, a 1-(2-chlorophenyl)pyrrol-2-yl group, a 1-(3-chloro-2-pyridinyl)pyrrol-2-yl group, a 4-chloro-1-(2-chlorophenyl)pyrrol-2-yl group, a 4-chloro-1-(3-chloro-2-pyridinyl)pyrrol-2-yl group, a 5-chloro-1-(2-chlorophenyl)pyrrol-2-yl group, a 5-chloro-1-(3-chloro-2-pyridinyl)pyrrol-2-yl group, a 1-(2-chlorophenyl)-4,5-dichloropyrrol-2-yl group, a 1-(3-chloro-2-pyridinyl)-4,5-dichloropyrrol-2-yl group, a 4-bromo-1-(2-chlorophenyl)pyrrol-2-yl group, a 4-bromo-1-(3-chloro-2-pyridinyl)pyrrol-2-yl group, a 5-bromo-1-(2-chlorophenyl)pyrrol-2-yl group, a 5-bromo-1-(3-chloro-2-pyridinyl)pyrrol-2-yl group, a 1-(2-chlorophenyl)-4,5-dibromopyrrol-2-yl group, a 1-(3-chloro-2-pyridinyl)-4,5-dibromopyrrol-2-yl group, a 1-(2-chlorophenyl)-4-iodopyrrol-2-yl group, a 1-(3-chloro-2-pyridinyl)-4-iodopyrrol-2-yl group, a 1-(2-chlorophenyl)-5-iodopyrrol-2-yl group, a 1-(3-chloro-2-pyridinyl)-5-iodopyrrol-2-yl group, a 1-(2-chlorophenyl)-4,5-diiodopyrrol-2-yl group, a 1-(3-chloro-2-pyridinyl)-4,5-diiodopyrrol-2-yl group, a 1-(2-chlorophenyl)-4-(trifluoromethyl)pyrrol-2-yl group, a 1-(3-chloro-2-pyridinyl)-4-(trifluoromethyl)pyrrol-2-yl group, a 1-(2-chlorophenyl)-5-(trifluoromethyl)pyrrol-2-yl group, a 1-(3-chloro-2-pyridinyl)-5-(trifluoromethyl)pyrrol-2-yl group, a 1-(2-chlorophenyl)imidazol-2-yl group, a 1-(3-chloro-2-pyridinyl)imidazol-2-yl group, a 4-chloro-1-(2-chlorophenyl)imidazol-2-yl group, a 4-chloro-1-(3-chloro-2-pyridinyl)imidazol-2-yl group, a 4-bromo-1-(2-chlorophenyl)imidazol-2-yl group, a 4-bromo-1-(3-chloro-2-pyridinyl)imidazol-2-yl group, a 1-(2-chlorophenyl)-4-(trifluoromethyl)imdazol-2-yl group, a 1-(3-chloro-2-pyridinyl)-4-(trifluoromethyl)imidazol-2-yl group, a 1-(2-chlorophenyl)-1,2,4-triazol-5-yl group, a 1-(3-chloro-2-pyridinyl)-1,2,4-triazol-5-yl group, a 3-chloro-1-(2-chlorophenyl)-1,2,4-triazol-5-yl group, a 3-chloro-1-(3-chloro-2-pyridinyl)-1,2,4-triazol-5-yl group, a 3-bromo-1-(2-chlorophenyl)-1,2,4-triazol-5-yl group, a 3-bromo-1-(3-chloro-2-pyridinyl)-1,2,4-triazol-5-yl group, a 1-(2-chlorophenyl)-3-(trifluoromethyl)-1,2,4-triazol-5-yl group and a 1-(3-chloro-2-pyridinyl)-3-(trifluoromethyl)-1,2,4-triazol-5-yl group.

Examples of the group represented by J2 include a 1-methyl-3-phenylpyrazol-4-yl group, a 3-(2-chlorophenyl)-1-methylpyrazol-4-yl group, a 1-methyl-3-(2-pyridinyl)pyrazol-4-yl group, a 3-(3-chloro-2-pyridinyl)-1-methylpyrazol-4-yl group, a 1-methyl-5-phenylpyrazol-4-yl group, a 5-(2-chlorophenyl)-1-methylpyrazol-4-yl group, a 1-methyl-5-(2-pyridinyl)pyrazol-4-yl group, a 5-(3-chloro-2-pyridinyl)-1-methylpyrazol-4-yl group, a 3-phenyl-1-(2,2,2-trifluoroethyl)pyrazol-4-yl group, a 3-(2-chlorophenyl)-1-(2,2,2-trifluoroethyl)pyrazol-4-yl group, a 3-(2-pyridinyl)-1-(2,2,2-trifluoroethyl)pyrazol-4-yl group, a 3-(3-chloro-2-pyridinyl)-1-(2,2,2-trifluoroethyl)pyrazol-4-yl group, a 5-phenyl-1-(2,2,2-trifluoroethyl)pyrazol-4-yl group, a 5-(2-chlorophenyl)-1-(2,2,2-trifluoroethyl)pyrazol-4-yl group, a 5-(2-pyridinyl)-1-(2,2,2-trifluoroethyl)pyrazol-4-yl group, a 5-(3-chloro-2-pyridinyl)-1-(2,2,2-trifluoroethyl)pyrazol-4-yl group, a 1-(difluoromethyl)-3-phenylpyrazol-4-yl group, a 3-(2-chlorophenyl)-1-(difluoromethyl)pyrazol-4-yl group, a 1-(difluoromethyl)-3-(2-pyridinyl)pyrazol-4-yl group, a 3-(3-chloro-2-pyridinyl)-1-(difluoromethyl)pyrazol-4-yl group, a 1-(difluoromethyl)-5-phenylpyrazol-4-yl group, a 5-(2-chlorophenyl)-1-(difluoromethyl)pyrazol-4-yl group, a 1-(difluoromethyl)-5-(2-pyridinyl)pyrazol-4-yl group, a 5-(3-chloro-2-pyridinyl)-1-(difluoromethyl)pyrazol-4-yl group, a 3-(2-chlorophenyl)-1-ethylpyrazol-4-yl group, a 3-(3-chloro-2-pyridinyl)-1-ethylpyrazol-4-yl group, a 5-(2-chlorophenyl)-1-ethylpyrazol-4-yl group, a 5-(3-chloro-2-pyridinyl)-1-ethylpyrazol-4-yl group, a 3-(2-chlorophenyl)-1-isopropylpyrazol-4-yl group, a 3-(3-chloro-2-pyridinyl)-1-isopropylpyrazol-4-yl group, a 5-(2-chlorophenyl)-1-isopropylpyrazol-4-yl group, a 5-(3-chloro-2-pyridinyl)-1-isopropylpyrazol-4-yl group, a 3-(2-chlorophenyl)-1-tert-butylpyrazol-4-yl group, a 3-(3-chloro-2-pyridinyl)-1-tert-butylpyrazol-4-yl group, a 5-(2-chlorophenyl)-1-tert-butylpyrazol-4-yl group and a 5-(3-chloro-2-pyridinyl)-1-tert-butylpyrazol-4-yl group.

As an example of the compound represented by the formula (1), the following compound is mentioned:

A compound of the formula (1), wherein $R^1$ is a hydrogen atom, or a C1-C6 alkyl group optionally substituted with at least one halogen atom, $R^2$ is a hydrogen atom, or a C1-C6 alkyl group optionally substituted with at least one halogen atom, $R^3$ is a hydrogen atom, a C1-C6 alkyl group optionally substituted with at least one halogen atom, or a C2-C6 alkoxycarbonyl group, $R^4$ is a halogen atom, a cyano group, a C1-C6 alkyl group optionally substituted with at least one halogen atom, a C1-C6 alkoxy group optionally substituted with at least one halogen atom, a phenyl group optionally substituted with at least one halogen atom, or two $R^4$ groups which are bound to the adjacent carbon atoms are bound to each other at their terminal ends to form a group T1: —$CR^{41}$=$CR^{42}$—$CR^{43}$=$CR^{44}$—

(wherein $R^{41}$, $R^{42}$, $R^{43}$ and $R^{44}$ represent a hydrogen atom), n is an integer of 0 to 3, Q is a group represented by Q1 to Q6:

Q1: —$C(=A^{31})$-$R^5$
Q2: —$C(=A^{32})$-$OR^6$
Q3: —$C(=A^{33})$-$SR^7$
Q4: —$C(=A^{34})$-$NR^8R^9$
Q5: —$S(O)_2$—$R^{10}$
Q6: —$S(O)_2$—$NR^{11}R^{12}$ (wherein $A^{31}$, $A^{32}$ and $A^{33}$ are an oxygen atom, $A^{34}$ is an oxygen atom or a sulfur atom, $R^5$ is a hydrogen atom; a C1-C6 alkyl group optionally substituted with one or more independent substituents selected from the group consisting of (1) a halogen atom, (2) a C1-C6 alkoxy group, (3) a C1-C6 alkylthio group, (4) a C1-C6 alkylsulfinyl group, (5) a C1-C6 alkylsulfonyl group, (6) a C2-C6 dialkylamino group and (7) a C3-C6 cycloalkyl group; a C3-C6 cycloalkyl group optionally substituted with one or more independent substituents selected from the group consisting of (1) a halogen atom and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom; a 5 to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or a 3- to 8-membered non-aromatic heterocyclic group optionally substituted with one or more independent substituents selected from the group consisting of (1) a halogen atom and (2) a C1-C6 alkyl group, $R^6$ is a C1-C6 alkyl group optionally substituted with at least one halogen atom; a C2-C6 alkenyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom, $R^7$ is a C1-C6 alkyl group optionally substituted with at least one halogen atom, $R^8$ and $R^9$ are independently a hydrogen atom; a C1-C6 alkyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom, $R^{10}$ is a C1-C6 alkyl group optionally substituted with at least one halogen atom, $R^{11}$ and $R^{12}$ are independently a C1-C6 alkyl group optionally substituted with at least one halogen atom, J is a group represented by J1 or J2:

J1:

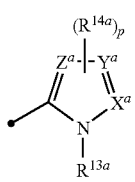

J2:

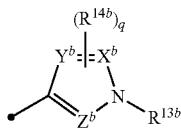

(wherein $X^a$ is CH or a nitrogen atom, $Y^a$ is CH, $Z^a$ is CH or a nitrogen atom, $X^b$ is CH or a nitrogen atom, $Y^b$ is CH, and $Z^b$ is CH or a nitrogen atom, $R^{13a}$ is a C1-C6 alkyl group optionally substituted with at least one halogen atom; a C3-C6 cycloalkyl group optionally substituted with one or more independent substituents selected from the group consisting of (1) a halogen atom and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom and (8) a C1-C6 alkylsulfonyl group optionally substituted with at least one halogen atom; or a 5- to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^{13b}$ is a C1-C6 alkyl group optionally substituted with at least one halogen atom, $R^{14a}$ is a halogen atom; a cyano group; a C1-C6 alkyl group optionally substituted with at least one halogen atom; a C1-C6 alkylthio group optionally substituted with at least one halogen atom; a C1-C6 alkylsulfinyl group optionally substituted with at least one halogen atom; a C1-C6 alkylsulfonyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^{14b}$ is a C1-C6 alkyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, p is an integer of 0 to 2, q is 1, (provided that when p is 2, two $R^{14a}$'s may be the same or different)), and $A^1$ and $A^2$ are an oxygen atom.

Examples of the specific aspects of the present compound include the following "Aspects 1 to 32":

"Aspect 1"

A compound of the formula (1-1):

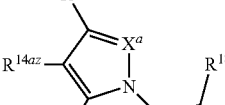

wherein
R$^1$ is a hydrogen atom, or a C1-C6 alkyl group optionally substituted with at least one halogen atom,
R$^2$ is a hydrogen atom, or a C1-C6 alkyl group optionally substituted with at least one halogen atom,
R$^3$ is a hydrogen atom, a C1-C6 alkyl group optionally substituted with at least one halogen atom, or a C2-C6 alkoxycarbonyl group,
R$^{4a}$ is a hydrogen atom, a halogen atom, a C1-C6 alkyl group optionally substituted with at least one halogen atom, a C1-C6 alkoxy group optionally substituted with at least one halogen atom, or a phenyl group optionally substituted with at least one halogen atom,
R$^{4b}$, R$^{4c}$ and R$^{4d}$ are independently a hydrogen atom, a halogen atom, a cyano group, or a C1-C6 alkyl group optionally substituted with at least one halogen atom, or R$^{4b}$ and R$^{4c}$ are bound to each other at their terminal ends to form a group: —CR$^{41}$=CR$^{42}$—CR$^{43}$=CR$^{44}$—

(wherein R$^{41}$, R$^{42}$, R$^{43}$ and R$^{44}$ are a hydrogen atom),
M is R$^5$, OR$^6$, SR$^7$, or NR$^8$R$^9$ (wherein
R$^5$ is a hydrogen atom; a C1-C6 alkyl group optionally substituted with at least one halogen atom; a C3-C6 cycloalkyl group; a phenyl group optionally substituted with one substituent selected from the group consisting of (1) a C1-C6 alkyl group optionally substituted with at least one halogen atom and (2) a C1-C6 alkoxy group optionally substituted with at least one halogen atom; a 5 to 6-membered heteroaryl group; or a 3- to 8-membered non-aromatic heterocyclic group,
R$^6$ is a C1-C6 alkyl group optionally substituted with at least one halogen atom, a C2-C6 alkenyl group optionally substituted with at least one halogen atom, or a phenyl group,
R$^7$ is a C1-C6 alkyl group optionally substituted with at least one halogen atom,
R$^8$ and R$^9$ are independently a hydrogen atom, a C1-C6 alkyl group optionally substituted with at least one halogen atom, or a phenyl group, or R$^8$ and R$^9$ are taken together with the nitrogen atom to which they are bound to form a morpholino group),
X$^a$ is a nitrogen atom,
R$^{14ay}$ is a hydrogen atom, a halogen atom, a cyano group, a C1-C6 alkyl group optionally substituted with at least one halogen atom, a C1-C6 alkylthio group optionally substituted with at least one halogen atom, a C1-C6 alkylsulfinyl group optionally substituted with at least one halogen atom, a C1-C6 alkylsulfonyl group optionally substituted with at least one halogen atom, or a phenyl group,
R$^{14az}$ is a hydrogen atom,
X$^{18}$ is a nitrogen atom or CR$^{18e}$ (wherein R$^{18e}$ is a hydrogen atom or a halogen atom), and
R$^{18a}$, R$^{18b}$, R$^{18c}$ and R$^{18d}$ are independently a hydrogen atom or a halogen atom.

"Aspect 2"
A compound of the formula (1-1), wherein
R$^1$ is a hydrogen atom, or a C1-C6 alkyl group optionally substituted with at least one halogen atom,
R$^2$ is a hydrogen atom, or a C1-C6 alkyl group optionally substituted with at least one halogen atom,
R$^3$ is a hydrogen atom, a C1-C6 alkyl group optionally substituted with at least one halogen atom, or a C2-C6 alkoxycarbonyl group,
R$^{4a}$ is a hydrogen atom, a halogen atom, a C1-C6 alkyl group optionally substituted with at least one halogen atom, a C1-C6 alkoxy group optionally substituted with at least one halogen atom, or a phenyl group optionally substituted with at least one halogen atom,
R$^{4b}$, R$^{4c}$ and R$^{4d}$ are independently a hydrogen atom, a halogen atom, a cyano group, or a C1-C6 alkyl group optionally substituted with at least one halogen atom,
or R$^{4b}$ and R$^{4c}$ are bound to each other at their terminal ends to form a group; —CR$^{41}$=CR$^{42}$—CR$^{43}$=CR$^{44}$—

(wherein R$^{41}$, R$^{42}$, R$^{43}$ and R$^{44}$ are a hydrogen atom),
M is R$^5$, OR$^6$, SR$^7$, or NR$^8$R$^9$ (wherein R$^5$ is a hydrogen atom; a C1-C6 alkyl group optionally substituted with at least one halogen atom; a C3-C6 cycloalkyl group; a phenyl group optionally substituted with one substituent selected from the group consisting of (1) a C1-C6 alkyl group optionally substituted with at least one halogen atom and (2) a C1-C6 alkoxy group optionally substituted with at least one halogen atom; a 5 to 6-membered heteroaryl group; or a 3- to 8-membered non-aromatic heterocyclic group,
R$^6$ is a C1-C6 alkyl group optionally substituted with at least one halogen atom, a C2-C6 alkenyl group optionally substituted with at least one halogen atom, or a phenyl group,
R$^7$ is a C1-C6 alkyl group optionally substituted with at least one halogen atom,
R$^8$ and R$^9$ are independently a hydrogen atom, a C1-C6 alkyl group optionally substituted with at least one halogen atom, or a phenyl group,
or R$^8$ and R$^9$ are taken together with the nitrogen atom to which they are bound to form a morpholino group),
X$^a$ is CR$^{14ax}$ (wherein R$^{14ax}$ is a hydrogen atom; a halogen atom; a cyano group; a C1-C6 alkyl group optionally substituted with at least one halogen atom; a C1-C6 alkylthio group optionally substituted with at least one halogen atom; or a C1-C6 alkylsulfinyl group optionally substituted with at least one halogen atom, a C1-C6 alkylsulfonyl group optionally substituted with at least one halogen atom, or a phenyl group),
R$^{14ay}$ is a hydrogen atom; a halogen atom; a cyano group; a C1-C6 alkyl group optionally substituted with at least one halogen atom; a C1-C6 alkylthio group optionally substituted with at least one halogen atom; a C1-C6 alkylsulfinyl group optionally substituted with at least one halogen atom; a C1-C6 alkylsulfonyl group optionally substituted with at least one halogen atom; or a phenyl group,
R$^{14az}$ is a hydrogen atom,
X$^{18}$ is a nitrogen atom or CR$^{18e}$ (wherein R$^{18e}$ is a hydrogen atom or a halogen atom), and
R$^{18a}$, R$^{18b}$, R$^{18c}$ and R$^{18d}$ are independently a hydrogen atom or a halogen atom.

"Aspect 3"
A compound of the formula (1-1), wherein
R$^1$ is a hydrogen atom, or a C1-C6 alkyl group optionally substituted with at least one halogen atom,
R$^2$ is a hydrogen atom, or a C1-C6 alkyl group optionally substituted with at least one halogen atom,
R$^3$ is a hydrogen atom, a C1-C6 alkyl group optionally substituted with at least one halogen atom, or a C2-C6 alkoxycarbonyl group,
R$^{4a}$ is a halogen atom, or a C1-C6 alkyl group optionally substituted with at least one halogen atom,
R$^{4b}$ is a hydrogen atom,
R$^{4c}$ is a hydrogen atom, a halogen atom, a cyano group, or a C1-C6 alkyl group optionally substituted with at least one halogen atom, $R^{4d}$ is a hydrogen atom, a halogen atom, or a C1-C6 alkyl group optionally substituted with at least one halogen atom, M is $OR^6$ (wherein $R^6$ is a C1-C6 alkyl group optionally substituted with at least one halogen atom), $X^a$ is a nitrogen atom, $R^{14ay}$ is a hydrogen atom, a halogen atom, a C1-C6 alkyl group optionally substituted with at least one halogen atom, $R^{14az}$ is a hydrogen atom, $X^{18}$ is a nitrogen atom, $R^{18a}$ is a halogen atom, or a C1-C6 alkyl group optionally substituted with at least one halogen atom, and $R^{18b}$, $R^{18c}$ and $R^{18d}$ are a hydrogen atom.

"Aspect 4"

A compound of the formula (1-1), wherein $R^1$ is a hydrogen atom, or a C1-C6 alkyl group optionally substituted with at least one halogen atom, $R^2$ is a hydrogen atom, or a C1-C6 alkyl group optionally substituted with at least one halogen atom, $R^3$ is a hydrogen atom, a C1-C6 alkyl group optionally substituted with at least one halogen atom, or a C2-C6 alkoxycarbonyl group, $R^{4a}$ is a halogen atom, or a C1-C6 alkyl group optionally substituted with at least one halogen atom, $R^{4b}$ is a hydrogen atom, $R^{4c}$ is a hydrogen atom, a halogen atom, a cyano group, or a C1-C6 alkyl group optionally substituted with at least one halogen atom, $R^{4d}$ is a hydrogen atom, a halogen atom, or a C1-C6 alkyl group optionally substituted with at least one halogen atom, M is $OR^6$ (wherein $R^6$ is a C1-C6 alkyl group optionally substituted with at least one halogen atom), $X^a$ is $CR^{14ax}$ (wherein $R^{14ax}$ is a hydrogen atom, a halogen atom, or a C1-C6 alkyl group optionally substituted with at least one halogen atom), $R^{14ay}$ is a hydrogen atom, a halogen atom, a C1-C6 alkyl group optionally substituted with at least one halogen atom, $R^{14az}$ is a hydrogen atom, $X^{18}$ is a nitrogen atom, $X^{18a}$ is a halogen atom, or a C1-C6 alkyl group optionally substituted with at least one halogen atom, and $R^{18b}$, $R^{18c}$ and $R^{18d}$ are a hydrogen atom.

"Aspect 5"

A compound of the formula (1-1), wherein $R^1$ is a hydrogen atom or a methyl group, $R^2$ is a hydrogen atom or a methyl group, $R^3$ is a hydrogen atom, a methyl group, or a methoxycarbonyl group, $R^{4a}$ is a hydrogen atom, a chlorine atom, a bromine atom, an iodine atom, a methyl group, an ethyl group, a trifluoromethyl group, a methoxy group, or a phenyl group, $R^{4c}$ is a hydrogen atom, a fluorine atom, a chlorine atom, a bromine atom, an iodine atom, a methyl group, or a cyano group, $R^{4b}$ and $R^{4d}$ are a hydrogen atom, a chlorine atom, or a methyl group, M is $OR^6$ (wherein $R^6$ is a methyl group), $X^a$ is a nitrogen atom, $R^{14ay}$ is a hydrogen atom, a chlorine atom, a bromine atom, a cyano group, a methyl group, an isopropyl group, a trifluoromethyl group, a methylthio group, a methylsulfinyl group, a methylsulfonyl group, or a phenyl group, $R^{14az}$ is a hydrogen atom or a bromine atom, $X^{18}$ is a nitrogen atom, $R^{18a}$ is a chlorine atom, and $R^{18b}$, $R^{18c}$ and $R^{18d}$ are a hydrogen atom.

"Aspect 6"

A compound of the formula (1-1), wherein $R^1$ is a hydrogen atom or a methyl group, $R^2$ is a hydrogen atom or a methyl group, $R^3$ is a hydrogen atom, a methyl group, or a methoxycarbonyl group $R^{4a}$ is a hydrogen atom, a chlorine atom, a bromine atom, an iodine atom, a methyl group, an ethyl group, a trifluoromethyl group, a methoxy group, or a phenyl group, $R^{4c}$ is a hydrogen atom, a fluorine atom, a chlorine atom, a bromine atom, an iodine atom, a methyl group, or a cyano group, $R^{4b}$ and $R^{4d}$ are a hydrogen atom, a chlorine atom, or a methyl group, M is $OR^6$ (wherein $R^6$ is a methyl group), $X^a$ is $CR^{14ax}$ (wherein $R^{14ax}$ is a hydrogen atom or a halogen atom), $R^{14ay}$ is a hydrogen atom, a chlorine atom, a bromine atom, a cyano group, a methyl group, an isopropypl group, a trifluoromethyl group, a methylthio group, a methylsulfinyl group, a methylsulfonyl group, or a phenyl group, $R^{14az}$ is a hydrogen atom or a bromine atom, $X^{18}$ is a nitrogen atom, $R^{18a}$ is a chlorine atom, and $R^{18b}$, $R^{18c}$ and $R^{18d}$ are a hydrogen atom.

"Aspect 7"

A compound of the formula (1-1), wherein $R^1$ is a hydrogen atom, or a C1-C6 alkyl group optionally substituted with at least one halogen atom, $R^2$ is a C1-C6 alkyl group optionally substituted with at least one halogen atom.

$R^3$ is a hydrogen atom, a C1-C6 alkyl group optionally substituted with at least one halogen atom, or a C2-C6 alkoxycarbonyl group, $R^{4a}$ is a hydrogen atom, a halogen atom, a C1-C6 alkyl group optionally substituted with at least one halogen atom, a C1-C6 alkoxy group optionally substituted with at least one halogen atom, or a phenyl group optionally substituted with at least one halogen atom, $R^{4b}$, $R^{4c}$ and $R^{4d}$ are independently a hydrogen atom, a halogen atom, a cyano group, a C1-C6 alkyl group optionally substituted with at least one halogen atom, or $R^{4b}$ and $R^{4c}$ are bound to each other at their terminal ends to form a group: $-CR^{41}=CR^{42}-CR^{43}=CR^{44}-$ (wherein $R^{41}$, $R^{42}$, $R^{43}$ and $R^{44}$ are a hydrogen atom), M is $OR^6$, $SR^7$ or $NR^8R^9$ (wherein $R^6$ and $R^7$ are a C1-C6 alkyl group optionally substituted with at least one halogen atom, a C3-C6 alkoxyalkyl group optionally substituted with at least one halogen atom, a C2-C6 alkenyl group optionally substituted with at least one halogen atom, or a C3-C6 alkynyl group optionally substituted with at least one halogen atom, $R^8$ and $R^9$ are independently a hydrogen atom, a C1-C6 alkyl group optionally substituted with at least one halogen atom, a C2-C6 alkenyl group optionally substituted with at least one halogen atom, a C3-C6 alkynyl group optionally substituted with at least one halogen atom, or $R^8$ and $R^9$ are taken together with the nitrogen atom to which they are bound to form a pyrrolidin-1-yl group, a piperidino group, a hexamethyleneimin-1-yl group, a heptamethyleneimin-1-yl group, a morpholino group, a thiomorpholin-4-yl group, or a 4-phenylpiperazin-1-yl group), $X^a$ is a nitrogen atom or $CR^{14ax}$ (wherein $X^{14ax}$ is a hydrogen atom, a halogen atom, a cyano group, a C1-C6 alkyl group optionally substituted with at least one halogen atom, a C1-C6 alkylthio group optionally substituted with at least one halogen atom, or a C1-C6 alkylsulfinyl group optionally substituted with at least one halogen atom), $R^{14ay}$ is a hydrogen atom, a halogen atom, a cyano group, a C1-C6 alkyl group optionally substituted with at least one halogen atom, a C1-C6 alkylthio group optionally substituted with at least one halogen atom, or a C1-C6 alkylsulfinyl group optionally substituted with at least one halogen atom, a C1-C6 alkylsulfonyl group optionally substituted with at least one halogen atom, or a phenyl group, $R^{14az}$ is a hydrogen atom, $X^{18}$ is a nitrogen atom or a $CR^{18e}$ (wherein $R^{18e}$ is a hydrogen atom or a halogen atom), and $R^{18a}$, $R^{18b}$, $R^{18c}$ and $R^{18d}$ are independently a hydrogen atom or a halogen atom.

"Aspect 8"

A compound of the formula (1-1), wherein $R^1$ is a hydrogen atom, or a C1-C6 alkyl group optionally substituted with at least one halogen atom, $R^2$ is a hydrogen, or a C1-C6 alkyl group optionally substituted with at least one halogen atom, $R^3$ is a hydrogen, a C1-C6 alkyl group optionally substituted with at least one halogen atom, or a C2-C6 alkoxycarbonyl group, $R^{4a}$ is a hydrogen atom, a halogen atom, a C1-C6 alkyl group optionally substituted with at least one halogen atom, a C1-C6 alkoxy group optionally substituted with at least one halogen atom, or a phenyl group optionally substituted with at least one halogen atom.

$R^{4b}$, $R^{4c}$ and $R^{4d}$ are independently a hydrogen atom, a halogen atom, a cyano group, a C1-C6 alkyl group optionally substituted with at least one halogen atom, or $R^{4b}$ and $R^{4c}$ are bound to each other at their terminal ends to form a group: —$CR^{41}$=$CR^{42}$—$CR^{43}$=$CR^{44}$—

(wherein $R^{41}$, $R^{42}$, $R^{43}$ and $R^{44}$ are a hydrogen atom),

M is a hydrogen atom, $X^a$ is a nitrogen atom or $CR^{14ax}$ (wherein $R^{14ax}$ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfony group optionally substituted with at least one halogen atom), $R^{14ay}$ is a hydrogen atom, a halogen atom, a cyano group, a C1-C6 alkyl group optionally substituted with at least one halogen atom, a C1-C6 alkylthio group optionally substituted with at least one halogen atom, a C1-C6 alkylsulfinyl group optionally substituted with at least one halogen atom, a C1-C6 alkylsulfonyl group optionally substituted with at least one halogen atom, or a phenyl group, $R^{14az}$ is a hydrogen atom, $X^{18}$ is a nitrogen atom or $CR^{18e}$ (wherein $R^{18e}$ is a hydrogen atom or a halogen atom), and $R^{18a}$, $R^{18b}$, $R^{18c}$ and $R^{18d}$ are independently a hydrogen atom or a halogen atom.

"Aspect 9"

A compound of the formula (1-1), wherein $R^1$ is a hydrogen atom, or a C1-C6 alkyl group optionally substituted with at least one halogen atom, $R^2$ is a hydrogen atom, or a C1-C6 alkyl group optionally substituted with at least one halogen atom, $R^3$ is a hydrogen atom, a C1-C6 alkyl group optionally substituted with at least one halogen atom, or a C2-C6 alkoxycarbonyl group, $R^{4a}$ is a halogen atom, or a C1-C6 alkyl group optionally substituted with at least one halogen atom, $R^{4b}$, $R^{4c}$ and $R^{4d}$ are independently a hydrogen atom, a halogen atom, a cyano group, or a C1-C6 alkyl group optionally substituted with at least one halogen atom, or $R^{4b}$ and $R^{4c}$ are bound to each other at their terminal ends to form a group: —$CR^{41}$=$CR^{42}$—$CR^{43}$=$CR^{44}$—

(wherein $R^{41}$, $R^{42}$, $R^{43}$ and $R^{44}$ are independently a hydrogen atom, a halogen atom, a cyano group or a C1-C6 alkyl group optionally substituted with at least one halogen atom), M is $R^5$, $OR^6$, $SR^7$ or $NR^8R^9$, (wherein $R^5$ is a hydrogen atom, or a C1-C6 alkyl group optionally substituted with at least one halogen atom, $R^6$ and $R^7$ are a C1-C6 alkyl group optionally substituted with at least one halogen atom, a C3-C6 alkoxyalkyl group optionally substituted with at least one halogen atom, a C2-C6 alkenyl group optionally substituted with at least one halogen atom or a C3-C6 alkynyl group optionally substituted with at least one halogen atom, $R^8$ and $R^9$ are independently a hydrogen atom, a C1-C6 alkyl group optionally substituted with at least one halogen atom, a C2-C6 alkenyl group optionally substituted with at least one halogen atom, a C3-C6 alkynyl group optionally substituted with at least one halogen atom, or $R^8$ and $R^9$ are taken together with the nitrogen atom to which they are bound to form a pyrrolidin-1-yl group, a piperidino group, a hexamethyleneimin-1-yl group, a heptamethyleneimin-1-yl group, a morpholino group or a thiomorfolin-4-yl group), $X^a$ is a nitrogen atom or $CR^{14ax}$ (wherein $R^{14ax}$ is a hydrogen atom, a halogen atom, a cyano group, a C1-C6 alkyl group optionally substituted with a halogen atom, a C1-C6 alkoxy group optionally substituted with a halogen atom, a C1-C6 alkylthio group optionally substituted with a halogen atom, a C1-C6 alkylsulfinyl group optionally substituted with a halogen atom, or a C1-C6 alkylsulfonyl group optionally substituted with a halogen atom), $R^{14ay}$ and $R^{14az}$ are independently a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, $X^{18}$ is a nitrogen atom or $CR^{18e}$, (wherein $R^{18e}$ is a hydrogen atom, a halogen atom, or C1-C6 alkyl group optionally substituted with at least one halogen atom), and $R^{18a}$, $R^{18b}$, $R^{18c}$ and $R^{18d}$ are independently a hydrogen atom, a halogen atom, or a C1-C6 alkyl group optionally substituted with at least one halogen atom.

"Aspect 10"

A compound of the formula (1-1), wherein $R^1$ is a hydrogen atom, or a C1-C6 alkyl group optionally substituted with at least one halogen atom, $R^2$ is a hydrogen atom, or a C1-C6 alkyl group optionally substituted with at least one halogen atom, $R^3$ is a hydrogen atom, a C1-C6 alkyl group optionally substituted with at least one halogen atom, or a C2-C6 alkoxycarbonyl group, $R^{4a}$ is a halogen atom, or a C1-C6 alkyl group optionally substituted with at least one halogen atom, $R^{4b}$, $R^{4c}$ and $R^{4d}$ are independently a hydrogen atom, a halogen atom, a cyano group, or a C1-C6 alkyl group optionally substituted with at least one halogen atom, or $R^{4b}$ and $R^{4c}$ are bound to each other at their terminal ends to form a group: —$CR^{41}$=$CR^{42}$—$CR^{43}$=$CR^{44}$—

(wherein $R^{41}$, $R^{42}$, $R^{43}$ and $R^{44}$ are independently a hydrogen atom, a halogen atom, a cyano group, or a C1-C6 alkyl group optionally substituted with at least one halogen atom), M is $R^5$, $OR^6$, $SR^7$ or $NR^8R^9$, (wherein $R^5$ is a hydrogen atom, or a C1-C6 alkyl group optionally substituted with at least one halogen atom, $R^6$ and $R^7$ are a C1-C6 alkyl group optionally substituted with at least one halogen atom, a C3-C6 alkoxyalkyl group optionally substituted with at least one halogen atom, a C2-C6 alkenyl group optionally substituted with at least one halogen atom, or a C3-C6 alkynyl group optionally substituted with at least one halogen atom, $R^8$ and $R^9$ are independently a hydrogen atom, a C1-C6 alkyl group optionally substituted with at least one halogen atom, a C2-C6 alkenyl group optionally substituted with at least one halogen atom, a C3-C6 alkynyl group optionally substituted with at least one halogen atom, or $R^8$ and $R^9$ are taken together with a nitrogen atom to which they are bound to represent a pyrrolidin-1-yl group, a piperidino group, a hexamethyleneimin-1-yl group, a heptamethyleneimin-1-yl group, a morpholino or a thiomorpholin-4-yl group), $X^a$ is a nitrogen atom, $R^{14ay}$ and $R^{14az}$ are independently a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, $X^{18}$ is a nitrogen atom or $CR^{18e}$, (wherein $R^{18e}$ is a hydrogen atom, a halogen atom, or a C1-C6 alkyl group optionally substituted with at least one halogen atom), and $R^{18a}$, $R^{18b}$, $R^{18c}$ and $R^{18d}$ are independently a hydrogen atom, a halogen atom or a C1-C6 alkyl group optionally substituted with at least one halogen atom.

"Aspect 11"

A compound of the formula (1-1), wherein $R^1$ is a hydrogen atom, or a C1-C6 alkyl group optionally substituted with at least one halogen atom, $R^2$ is a hydrogen atom, or a C1-C6 alkyl group optionally substituted with at least one halogen atom, $R^3$ is a hydrogen atom, a C1-C6 alkyl group optionally substituted with at least one halogen atom, or a C2-C6 alkoxycarbonyl group, $R^{4a}$ is a halogen atom, or a C1-C6 alkyl group optionally substituted with at least one halogen atom, $R^{4b}$, $R^{4c}$ and $R^{4d}$ are independently a hydrogen atom, a halogen atom, a cyano group, or a C1-C6 alkyl group optionally substituted with at least one halogen atom, or $R^{4b}$ and $R^{4c}$ are bound to each other at their terminal ends to for a group: —$CR^{41}$=$CR^{42}$—$CR^{43}$=$CR^{44}$—

(wherein $R^{41}$, $R^{42}$, $R^{43}$ and $R^{44}$ are independently a hydrogen atom, a halogen atom, a cyano group, or a C1-C6 alkyl group optionally substituted with at least one halogen atom), M is $R^5$, $OR^6$, $SR^7$ or $NR^8R^9$, (wherein $R^5$ is a hydrogen atom, or a C1-C6 alkyl group optionally substituted with at least one halogen atom, $R^6$ and $R^7$ are a C1-C6 alkyl group optionally substituted with at least one halogen atom, a C3-C6 alkoxyalkyl group optionally substituted with at least one halogen atom, a C2-C6 alkenyl group optionally substituted with at least one halogen atom, or a C3-C6 alkynyl group optionally substituted with at least one halogen atom, $R^8$ and $R^9$ are independently a hydrogen atom, a C1-C6 alkyl group optionally substituted with at least one halogen atom, a C2-C6 alkenyl group optionally substituted with at least one halogen atom, a C3-C6 alkynyl group optionally substituted with at least one halogen atom, or $R^8$ and $R^9$ are taken together with the nitrogen atom to which they are bound to form a pyrroridin-1-yl group, a piperidino group, a hexamethyleneimin-1-yl group, a heptamethyleneimin-1-yl group, a morpholino group or a thiomorpholin-4-yl group), $X^a$ is $CR^{14ax}$ (wherein $R^{14ax}$ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom), $R^{14ay}$ and $R^{14az}$ are independently a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, $X^{18}$ is a nitrogen atom, or $CR^{18e}$, (wherein $R^{18e}$ is a hydrogen atom, a halogen atom, or a C1-C6 alkyl group optionally substituted with at least one halogen atom), and $R^{18a}$, $R^{18b}$, $R^{18c}$ and $R^{18d}$ are independently a hydrogen atom, a halogen atom, or a C1-C6 alkyl group optionally substituted with at least one halogen atom.

"Aspect 12"

A compound of the formula (1-1), wherein $R^1$ is a hydrogen atom, or a C1-C6 alkyl group optionally substituted with at least one halogen atom, $R^2$ is a hydrogen atom, or a C1-C6 alkyl group optionally substituted with at least one halogen atom, $R^3$ is a hydrogen atom, a C1-C6 alkyl group optionally substituted with at least one halogen atom, or a C2-C6 alkoxycarbonyl group, $R^{4a}$ is a halogen atom, or a C1-C6 alkyl group optionally substituted with at least one halogen atom, $R^{4b}$, $R^{4c}$ and $R^{4d}$ are independently a hydrogen atom, a halogen atom, a cyano group, or a C1-C6 alkyl group optionally substituted with at least one halogen atom, or $R^{4b}$ and $R^{4c}$ are bound to each other at their terminal ends to form a group: —$CR^{41}$=$CR^{42}$—$CR^{43}$=$CR^{44}$—

(wherein $R^{41}$, $R^{42}$, $R^{43}$ and $R^{44}$ are independently a hydrogen atom, a halogen atom, a cyano group, or a C1-C6 alkyl group optionally substituted with at least one halogen atom), M is $R^5$, $OR^6$, $SR^7$ or $NR^8R^9$, (wherein $R^5$ is a hydrogen atom, or a C1-C6 alkyl group optionally substituted with at least one halogen atom, $R^6$ and $R^7$ are a C1-C6 alkyl group optionally substituted with at least one halogen atom, a C3-C6 alkoxyalkyl group optionally substituted with at least one halogen atom, a C2-C6 alkenyl group optionally substituted with at least one halogen atom, or a C3-C6 alkynyl group optionally substituted with at least one halogen atom, $R^8$ and $R^9$ are independently a hydrogen atom, a C1-C6 alkyl group optionally substituted with at least one halogen atom, a C2-C6 alkenyl group optionally substituted with at least one halogen atom, a C3-C6 alkynyl group optionally substituted with at least one halogen atom, or $R^8$ and $R^9$ are taken together with the nitrogen atom to which they are bound to form a pyrroridin-1-yl group, a piperidino group, a hexamethyleneimin-1-yl group, a heptamethyleneimin-1-yl group, a morpholino group or a thiomorpholin-4-yl group), $X^a$ is $CR^{14ax}$ (wherein $R^{14ax}$ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom), $R^{14ay}$ and $R^{14az}$ are independently a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, $X^{18}$ is a nitrogen atom, or $CR^{18e}$, (wherein $R^{18e}$ is a halogen atom, or a C1-C6 alkyl group optionally substituted with at least one halogen atom), and $R^{18a}$, $R^{18b}$, $R^{18c}$ and $R^{18d}$ are independently a hydrogen atom, a halogen atom, or a C1-C6 alkyl group optionally substituted with at least one halogen atom.

"Aspect 13"

A compound of the formula (1-1), wherein $R^1$ is a hydrogen atom, or a C1-C6 alkyl group optionally substituted with at least one halogen atom, $R^2$ is a hydrogen atom, or a C1-C6 alkyl group optionally substituted with at least one halogen atom, $R^3$ is a hydrogen atom, a C1-C6 alkyl group optionally substituted with at least one halogen atom, or a C2-C6 alkoxycarbonyl group, $R^{4a}$ is a hydrogen atom, a halogen atom, or a C1-C6 alkyl group optionally substituted with at least one halogen atom, $R^{4b}$ is a hydrogen atom, $R^{4c}$ is a hydrogen atom, a halogen atom, a cyano group, or a C1-C6 alkyl group optionally substituted with at least one halogen atom, $R^{4d}$ is a hydrogen atom, M is $OR^6$, $R^6$ is a C1-C6 alkyl group optionally substituted with at least one halogen atom, $X^a$ is a nitrogen atom, $R^{14ay}$ is a hydrogen atom, a halogen atom, or a C1-C6 alkyl group optionally substituted with at least one halogen atom, $R^{14az}$ is a hydrogen atom, $X^{18}$ is a nitrogen atom, $R^{18a}$ is a halogen atom, or a C1-C6 alkyl group optionally substituted with at least one halogen atom, and $R^{18b}$, $R^{18c}$, $R^{18d}$ are a hydrogen atom.

"Aspect 14"

A compound of the formula (1-1), wherein $R^1$ is a hydrogen atom, or a C1-C6 alkyl group optionally substituted with at least one halogen atom, $R^2$ is a hydrogen atom, or a C1-C6 alkyl group optionally substituted with at least one halogen atom, $R^3$ is a hydrogen atom, a C1-C6 alkyl group optionally substituted with at least one halogen atom, or a C2-C6 alkoxycarbonyl group, $R^{4a}$ is a hydrogen atom, a halogen atom or a C1-C6 alkyl group optionally substituted with at least one halogen atom, $R^{4b}$ is a hydrogen atom, $R^{4c}$ is a hydrogen atom, a halogen atom, a cyano group, or a C1-C6 alkyl group optionally substituted with at least one halogen atom, $R^{4d}$ is a hydrogen atom, M is $OR^6$, $R^6$ is a C1-C6 alkyl group optionally substituted with at least one halogen atom, $X^a$ is a $CR^{14ax}$ (wherein $R^{14ax}$ represents a hydrogen atom, a halogen atom, or a C1-C6 alkyl group optionally substituted with at least one halogen atom), $R^{14ay}$ is a hydrogen atom, a halogen atom, or a C1-C6 alkyl group optionally substituted with at least one halogen atom, $R^{14az}$ is a hydrogen atom, $X^{18}$ is a nitrogen atom, $R^{18a}$ is a halogen atom, or a C1-C6 alkyl group optionally substituted with at least one halogen atom, and $R^{18b}$, $R^{18c}$ and $R^{18d}$ are a hydrogen atom.

"Aspect 15"

A compound of the formula (1-1), wherein $R^1$ is a hydrogen atom or a methyl group, $R^2$ is a hydrogen atom or a methyl group, $R^3$ is a hydrogen atom, a methyl group, or a methoxycarbonyl group, $R^{4a}$ is a chlorine atom, a bromine atom, an iodide atom, or a methyl group, $R^{4c}$ is a chlorine atom, a bromine atom, an iodine atom, a methyl group or a cyano group, $R^{4b}$ and $R^{4d}$ are a hydrogen atom, M is a $OR^6$, (wherein $R^6$ is a methyl group), $X^a$ is a nitrogen atom, $R^{14ay}$ is a chlorine atom, a bromine atom, or a trifluoromethyl group, $R^{14az}$ is a hydrogen atom, $X^{18}$ is a nitrogen atom, $R^{18a}$ is a chlorine atom or a bromine atom, and $R^{18b}$, $R^{18c}$ and $R^{18d}$ are a hydrogen atom.

"Aspect 16"

A compound of the formula (1-1), wherein
$R^1$ is a hydrogen atom or a methyl group,
$R^2$ is a hydrogen atom or a methyl group,
$R^3$ is a hydrogen atom, a methyl group, or a methoxycarbonyl group,
$R^{4a}$ is a chlorine atom, a bromine atom, or an iodine atom, or a methyl group,
$R^{4c}$ is a chlorine atom, a bromine atom, an iodine atom, a methyl group or a cyano group,
$R^{4b}$ and $R^{4d}$ are a hydrogen atom,
M is $OR^6$ (wherein $R^6$ is a methyl group),
$X^a$ is $CR^{14ax}$ (wherein $R^{14ax}$ is a hydrogen atom, a chlorine atom or a bromine atom),
$R^{14ay}$ is a chlorine atom, a bromine atom or a trifluoromethyl group,
$R^{14az}$ is a hydrogen atom,
$X^{18}$ is a nitrogen atom,
$R^{18a}$ is a chlorine atom or a bromine atom, and
$R^{18b}$, $R^{18c}$ and $R^{18d}$ are a hydrogen atom.

"Aspect 17"

A compound of the formula (1-1), wherein
$R^1$ is a hydrogen atom, or a C1-C6 alkyl group optionally substituted with at least one halogen atom,
$R^2$ is a C1-C6 alkyl group optionally substituted with at least one halogen atom,
$R^3$ is a hydrogen atom, a C1-C6 alkyl group optionally substituted with at least one halogen atom, or a C2-C6 alkoxycarbonyl group,
$R^{4a}$ is a halogen atom, or a C1-C6 alkyl group optionally substituted with at least one halogen atom,
$R^{4b}$, $R^{4c}$ and $R^{4d}$ are independently a hydrogen atom, a halogen atom, a cyano group, or a C1-C6 alkyl group optionally substituted with at least one halogen atom,
or $R^{4b}$ and $R^{4c}$ are bound to each other at their terminal ends to form a group: —$CR^{41}$=$CR^{42}$—$CR^{43}$=$CR^{44}$—

(wherein $R^{41}$, $R^{42}$, $R^{43}$ and $R^{44}$ are independently a hydrogen atom, a halogen atom, a cyano group, or a C1-C6 alkyl group optionally substituted with at least one halogen atom),
M is $OR^6$, $SR^7$ or $NR^8R^9$, (wherein $R^6$ and $R^7$ are a C1-C6 alkyl group optionally substituted with at least one halogen atom, a C3-C6 alkoxyalkyl group optionally substituted with at least one halogen atom, or a C2-C6 alkenyl group optionally substituted with at least one halogen atom, or a C3-C6 alkynyl group optionally substituted with at least one halogen atom,
$R^8$ and $R^9$, each, independently, are a hydrogen atom, a C1-C6 alkyl group optionally substituted with at least one halogen atom, a C2-C6 alkenyl group optionally substituted with at least one halogen atom, a C3-C6 alkynyl group optionally substituted with at least one halogen atom,
or $R^8$ and $R^9$ are taken together with the nitrogen atom to which they are bound to form a pyrrolidin-1-yl group, a piperidino group, a hexamethyleneimin-1-yl group, a heptamethyleneimin-1-yl group, a morpholino group, or a thiomorpholino-4-yl group),
$X^a$ is a nitrogen atom or $CR^{14ax}$ (wherein $R^{14ax}$ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom),
$R^{14ay}$ and $R^{14az}$ are independently a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom,
$X^{18}$ is a nitrogen atom, or $CR^{18e}$, (wherein $R^{18e}$ is a hydrogen atom, a halogen atom, or a C1-C6 alkyl group optionally substituted with at least one halogen atom), and
$R^{18a}$, $R^{18b}$, $R^{18c}$ and $R^{18d}$ are independently a hydrogen atom, a halogen atom or a C1-C6 alkyl group optionally substituted with at least one halogen atom.

"Aspect 18"

A compound of the formula (1-1), wherein
$R^1$ is a hydrogen atom, or a C1-C6 alkyl group optionally substituted with at least one halogen atom,
$R^2$ is a hydrogen atom, or a C1-C6 alkyl group optionally substituted with at least one halogen atom,
$R^3$ is a hydrogen atom, a C1-C6 alkyl group optionally substituted with at least one halogen atom, or a C2-C6 alkoxycarbonyl group,
$R^{4a}$ is a halogen atom, or a C1-C6 alkyl group optionally substituted with at least one halogen atom,
$R^{4b}$, $R^{4c}$ and $R^{4d}$ are independently a hydrogen atom, a halogen atom, a cyano group, or a C1-C6 alkyl group optionally substituted with at least one halogen atom,
or $R^{4b}$ and $R^{4c}$ are bound at end to be —$CR^{41}$=$CR^{42}$—$CR^{43}$=$CR^{44}$—

(wherein $R^{41}$, $R^{42}$, $R^{43}$, and $R^{44}$, each, independently, are a hydrogen atom, a halogen atom, a cyano group, or a C1-C6 alkyl group optionally substituted with at least one halogen atom,
M is a hydrogen atom,
$X^a$ is a nitrogen atom or $CR^{14ax}$ (wherein $R^{14ax}$ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom),
$R^{14ay}$ and $R^{14az}$, each, independently, are a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom,
$X^{18}$ is a nitrogen atom or $CR^{18e}$, (wherein $R^{18e}$ is a hydrogen atom, a halogen atom, or a C1-C6 alkyl group optionally substituted with at least one halogen atom), and
$R^{18a}$, $R^{18b}$, $R^{18c}$ and $R^{18d}$ are independently a hydrogen atom, a halogen atom, or a C1-C6 alkyl group optionally substituted with at least one halogen atom.

"Aspect 19"

A compound of the formula (1-1), wherein
$R^1$ is a hydrogen atom, or a C1-C6 alkyl group optionally substituted with at least one halogen atom,
$R^2$ is a hydrogen atom, or a C1-C6 alkyl group optionally substituted with at least one halogen atom,
$R^3$ is a hydrogen atom, a C1-C6 alkyl group optionally substituted with at least one halogen atom, or a C2-C6 alkoxycarbonyl group,
$R^{4a}$ is a hydrogen atom, a halogen atom, a cyano group, or a nitro group or a C1-C6 alkyl group optionally substituted with at least one halogen atom,
$R^{4b}$ and $R^{4c}$ are bound to each other at their terminal ends to form a group: —CR$^{41}$=CR$^{42}$—CR$^{43}$=CR$^{44}$—
(wherein $R^{41}$, $R^{42}$, $R^{43}$ and $R^{44}$ are independently a hydrogen atom, a halogen atom, a cyano group, a nitro group, or a C1-C6 alkyl group optionally substituted with at least one halogen atom),
$R^{4d}$ is a hydrogen atom, a halogen atom, a cyano group, a nitro group, or a C1-C6 alkyl group optionally substituted with at least one halogen atom,
M is $R^5$, $OR^6$, $SR^7$ or $NR^8R^9$,
(wherein $R^5$ is a hydrogen atom, a C1-C6 alkyl group optionally substituted with at least one halogen atom, or a C3-C6 cycloalkyl group,
$R^6$ and $R^7$ are a C1-C6 alkyl group optionally substituted with at least one halogen atom, a C3-C6 alkoxyalkyl group optionally substituted with at least one halogen atom, a C2-C6 alkenyl group optionally substituted with at least one halogen atom, or a C3-C6 alkynyl group optionally substituted with at least one halogen atom,
$R^8$ and $R^9$ are independently a hydrogen atom, a C1-C6 alkyl group optionally substituted with at least one halogen atom, a C2-C6 alkenyl group optionally substituted with at least one halogen atom, or a C3-C6 alkynyl group optionally substituted with at least one halogen atom,
or $R^8$ and $R^9$ are taken together with the nitrogen atom to which they are bound to form a pyrroridin-1-yl group, a piperidino group, a hexamethyleneimin-1-yl group, a heptamethyleneimin-1-yl group, a morpholino group, a thiomorphorin-4-yl group, or a 4-methylpiperazin-1-yl group),
$X^a$ is a nitrogen atom or $CR^{14ax}$,
$R^{14ax}$, $R^{14ay}$ and $R^{14az}$ are independently a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkyl sulfonyl group optionally substituted with at least one halogen atom,
$X^{18}$ is a nitrogen atom, or a $CR^{18e}$, and
$R^{18a}$, $R^{18b}$, $R^{18c}$, $R^{18d}$ and $R^{18e}$ are independently a hydrogen atom, a halogen atom, or a C1-C6 alkyl group optionally substituted with at least one halogen atom.

"Aspect 20"

A compound of the formula (1-1), wherein
$R^1$ is a hydrogen atom, or a C1-C6 alkyl group optionally substituted with at least one halogen atom,
$R^2$ is a hydrogen atom, or a C1-C6 alkyl group optionally substituted with at least one halogen atom,
$R^3$ is a hydrogen atom, a C1-C6 alkyl group optionally substituted with at least one halogen atom, or a C2-C6 alkoxycarbonyl group,
$R^{4a}$ is a hydrogen atom or a halogen atom,
$R^{4b}$ and $R^{4c}$ are bound to each other at their terminal ends to form a group: —CR$^{41}$=CR$^{42}$—CR$^{43}$=CR$^{44}$—
(wherein $R^{41}$, $R^{42}$, $R^{43}$ and $R^{44}$ are independently a hydrogen atom, or a halogen atom),
$R^{4d}$ is a hydrogen atom,
M is $R^5$, $OR^6$, $SR^7$ or $NR^8R^9$,
(wherein $R^5$ is a hydrogen atom, a C1-C6 alkyl group optionally substituted with at least one halogen atom, or a C3-C6 cycloalkyl group,
$R^6$ and $R^7$ are a C1-C6 alkyl group optionally substituted with at least one halogen atom, a C3-C6 alkoxyalkyl group optionally substituted with at least one halogen atom, a C2-C6 alkenyl group optionally substituted with at least one halogen atom, or a C3-C6 alkynyl group optionally substituted with at least one halogen atom,
$R^8$ and $R^9$ are independently a hydrogen atom, a C1-C6 alkyl group optionally substituted with at least one halogen atom, a C2-C6 alkenyl group optionally substituted with at least one halogen atom, or a C3-C6 alkynyl group optionally substituted with at least one halogen atom,
or $R^8$ and $R^9$ are taken together with the nitrogen atom to which they are bound to form a pyrroridin-1-yl group, a piperidino group, a hexamethyleneimin-1-yl group, a heptamethyleneimin-1-yl group, a morpholino group, a thiomorphorin-4-yl group, or a 4-methylpiperazin-1-yl group),
$X^a$ is a nitrogen atom or $CR^{14ax}$,
$R^{14ax}$, $R^{14ay}$ and $R^{14az}$ are independently a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom,
$X^{18}$ is a nitrogen atom, or a $CR^{18e}$, and
$R^{18a}$, $R^{18b}$, $R^{18c}$, $R^{18d}$ and $R^{18e}$ are independently a hydrogen atom, a halogen atom, or a C1-C6 alkyl group optionally substituted with at least one halogen atom.

"Aspect 21"

A compound represented by the formula (1-2):

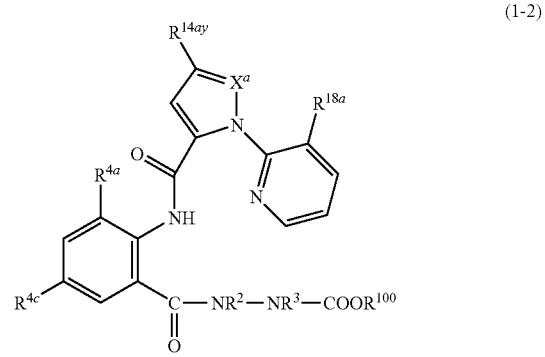

(1-2)

wherein,
$R^2$ represents a hydrogen atom or a C1-C6 alkyl group,
$R^3$ represents a hydrogen atom or a methyl group,
$R^{4a}$ represents a halogen atom or a methyl group,
$R^{4c}$ represents a halogen atom,
$R^{14ay}$ represents a halogen atom or a trifluoromethyl group,
$X^a$ represents a nitrogen atom or CH,
$R^{18a}$ represents a halogen atom, and
$R^{100}$ represents a C1-C6 alkyl group.

"Aspect 22"

A compound of the formula (1-2), wherein
R² is a C1-C6 alkyl group,
R³ is a hydrogen atom or a methyl group,
R⁴ᵃ is a halogen atom, or a methyl group,
R⁴ᶜ is a halogen atom,
R¹⁴ᵃʸ is a halogen atom or a trifluoromethyl group,
Xᵃ is a nitrogen atom or CH, and
R¹⁸ᵃ is a halogen atom.

"Aspect 23"

A compound represented by the formula (1-3):

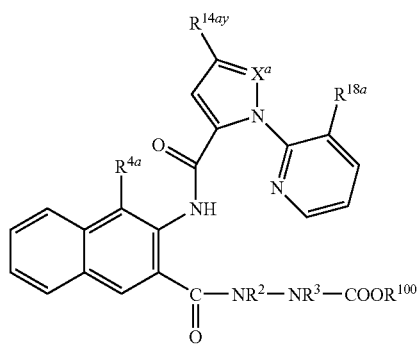

(1-3)

wherein
R² represents a hydrogen atom or a C1-C6 alkyl group,
R³ represents a hydrogen atom or a methyl group,
R⁴ᵃ represents a halogen atom or a methyl group,
R¹⁴ᵃʸ represents a halogen atom or a trifluoromethyl group,
Xᵃ represents a nitrogen atom or CH,
R¹⁸ᵃ represents a halogen atom, and
R¹⁰⁰ represents a C1-C6 alkyl group.

"Aspect 24"

A compound of the formula (1-1), wherein
R¹ is a hydrogen atom, or a C1-C6 alkyl group optionally substituted with at least one halogen atom,
R² is a hydrogen atom, or a C1-C6 alkyl group optionally substituted with at least one halogen atom,
R³ is a hydrogen atom, a C1-C6 alkyl group optionally substituted with at least one halogen atom, or a C2-C6 alkoxycarbonyl group,
R⁴ᵃ is a halogen atom, or a C1-C6 alkyl group optionally substituted with at least one halogen atom,
R⁴ᵇ is a hydrogen atom,
R⁴ᶜ is a hydrogen atom, a halogen atom, a cyano group, or a C1-C6 alkyl group optionally substituted with at least one halogen atom,
R⁴ᵈ is a hydrogen atom,
M is OR⁶
(wherein R⁶ is a C1-C6 alkyl group optionally substituted with at least one halogen atom, a C3-C6 alkoxyalkyl group optionally substituted with at least one halogen atom, a C2-C6 alkenyl group optionally substituted with at least one halogen atom, or a C3-C6 alkynyl group optionally substituted with at least one halogen atom),
Xᵃ is a nitrogen atom or CR¹⁴ᵃˣ
(wherein R¹⁴ᵃˣ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom),
R¹⁴ᵃʸ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom,
R¹⁴ᵃᶻ is a hydrogen atom,
X¹⁸ is a nitrogen atom
R¹⁸ᵃ is a halogen atom, or a C1-C6 alkyl group optionally substituted with at least one halogen atom, and
R¹⁸ᵇ, R¹⁸ᶜ, R¹⁸ᵈ are a hydrogen atom.

"Aspect 25"

A compound of the formula (1-1), wherein
R¹ is a hydrogen atom, or a C1-C6 alkyl group optionally substituted with at least one halogen atom,
R² is a hydrogen atom, or a C1-C6 alkyl group optionally substituted with at least one halogen atom,
R³ is a hydrogen atom, a C1-C6 alkyl group optionally substituted with at least one halogen atom, or a C2-C6 alkoxycarbonyl group,
R⁴ᵃ is a halogen atom, or a C1-C6 alkyl group optionally substituted with at least one halogen atom,
R⁴ᵇ is a hydrogen atom,
R⁴ᶜ is a hydrogen atom, a halogen atom, a cyano group, or a C1-C6 alkyl group optionally substituted with at least one halogen atom,
R⁴ᵈ is a hydrogen atom,
M is OR⁶,
(wherein R⁶ is a C1-C6 alkyl group optionally substituted with at least one halogen atom, a C3-C6 alkoxyalkyl group optionally substituted with at least one halogen atom, a C2-C6 alkenyl group optionally substituted with at least one halogen atom, or a C3-C6 alkynyl group optionally substituted with at least one halogen atom),
Xᵃ is a nitrogen atom,
R¹⁴ᵃʸ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom,
R¹⁴ᵃᶻ is a hydrogen atom,
X¹⁸ is a nitrogen atom,
R¹⁸ᵃ is a halogen atom, or a C1-C6 alkyl group optionally substituted with at least one halogen atom, and
R¹⁸ᵇ, R¹⁸ᶜ, R¹⁸ᵈ are a hydrogen atom.

"Aspect 26"

A compound of the formula (1-1), wherein
R¹ is a hydrogen atom, or a C1-C6 alkyl group optionally substituted with at least one halogen atom,
R² is a hydrogen atom, or a C1-C6 alkyl group optionally substituted with at least one halogen atom,
R³ is a hydrogen atom, a C1-C6 alkyl group optionally substituted with at least one halogen atom, or a C2-C6 alkoxycarbonyl group, $R^{4a}$ is a halogen atom or a C1-C6 alkyl group optionally substituted with at least one halogen atom, $R^{4b}$ is a hydrogen atom, $R^{4c}$ is a hydrogen atom, a halogen atom, a cyano group, or a C1-C6 alkyl group optionally substituted with at least one halogen atom, $R^{4d}$ is a hydrogen atom, M is $OR^6$, (wherein $R^6$ is a C1-C6 alkyl group optionally substituted with at least one halogen atom, a C3-C6 alkoxyalkyl group optionally substituted with at least one halogen atom, a C2-C6 alkenyl group optionally substituted with at least one halogen atom, or a C3-C6 alkynyl group optionally substituted with at least one halogen atom), $X^a$ is a $CR^{14ax}$ (wherein $R^{14ax}$ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom), $R^{14ay}$ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, $R^{14az}$ is a hydrogen atom, $X^{18}$ is a nitrogen atom, $R^{18a}$ is a halogen atom, or a C1-C6 alkyl group optionally substituted with at least one halogen atom, and $R^{18b}$, $R^{18c}$ and $R^{18d}$ are a hydrogen atom.

"Aspect 27"

A compound of the formula (1-1), wherein $R^1$ is a hydrogen atom, or a C1-C6 alkyl group optionally substituted with at least one halogen atom, $R^2$ is a C1-C6 alkyl group optionally substituted with at least one halogen atom, $R^3$ is a hydrogen atom, a C1-C6 alkyl group optionally substituted with at least one halogen atom, or a C2-C6 alkoxycarbonyl group, $R^{4a}$ is a halogen atom, or a C1-C6 alkyl group optionally substituted with at least one halogen atom, $R^{4b}$ is a hydrogen atom, $R^{4c}$ is a hydrogen atom, a halogen atom, a cyano group, or a C1-C6 alkyl group optionally substituted with at least one halogen atom, $R^{4d}$ is a hydrogen atom, M is $OR^6$, (wherein $R^6$ is a C1-C6 alkyl group optionally substituted with at least one halogen atom, a C3-C6 alkoxyalkyl group optionally substituted with at least one halogen atom, a C2-C6 alkenyl group optionally substituted with at least one halogen atom, or a C3-C6 alkynyl group optionally substituted with at least one halogen atom), $X^a$ is a nitrogen atom or $CR^{14ax}$ (wherein $R^{14ax}$ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom), $R^{14ay}$ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom), $R^{14az}$ is a hydrogen atom, $X^{18}$ is a nitrogen atom, $R^{18a}$ is a halogen atom, or a C1-C6 alkyl group optionally substituted with at least one halogen atom, and $R^{18b}$, $R^{18c}$, $R^{18d}$ are a hydrogen atom.

"Aspect 28"

A compound of the formula (1-1), wherein $R^1$ is a hydrogen atom, or a C1-C6 alkyl group optionally substituted with at least one halogen atom, $R^2$ is a hydrogen atom, or a C1-C6 alkyl group optionally substituted with at least one halogen atom, $R^3$ is a hydrogen atom, a C1-C6 alkyl group optionally substituted with at least one halogen atom, or a C2-C6 alkoxycarbonyl group, $R^{4a}$ is a halogen atom, a cyano group, a nitro group, or a C1-C6 alkyl group optionally substituted with at least one halogen atom, $R^{4b}$ and $R^{4c}$ are bound to each other at their terminal ends to form a group: —$CR^{41}$=$CR^{42}$—$CR^{43}$=$CR^{44}$—

(wherein $R^{41}$, $R^{42}$, $R^{43}$ and $R^{44}$ are independently a hydrogen atom, a halogen atom, a cyano group, a nitro group, or a C1-C6 alkyl group optionally substituted with at least one halogen atom), $R^{4d}$ is a hydrogen atom, M is $OR^6$, (wherein $R^6$ is a C1-C6 alkyl group optionally substituted with at least one halogen atom, a C3-C6 alkoxyalkyl group optionally substituted with at least one halogen atom, a C2-C6 alkenyl group optionally substituted with at least one halogen atom, or a C3-C6 alkynyl group optionally substituted with at least one halogen atom), $X^a$ is a nitrogen atom or $CR^{14ax}$ (wherein $R^{14ax}$ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom), $R^{14ay}$ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, $R^{14az}$ is a hydrogen atom, $X^{18}$ is a nitrogen atom, $R^{18a}$ is a halogen atom, or a C1-C6 alkyl group optionally substituted with at least one halogen atom, and $R^{18b}$, $R^{18c}$, $R^{18d}$ are a hydrogen atom.

"Aspect 29"
A compound represented by the formula (1-2), wherein
$R^2$ represents a hydrogen atom or a C1-C6 alkyl group,
$R^3$ represents a hydrogen atom or a C1-C6 alkyl group,
$R^{4a}$ represents a halogen atom or a methyl group,
$R^{4c}$ represents a halogen atom,
$R^{14ay}$ represents a halogen atom or a trifluoromethyl group,
$X^a$ represents a nitrogen atom or $CR^{14ax}$ (wherein $R^{14ax}$ is a hydrogen atom or a halogen atom),
$R^{18a}$ represents a halogen atom, and
$R^{100}$ represents a C1-C6 alkyl group.

"Aspect 30"
A compound of the formula (1-2), wherein
$R^2$ is a C1-C6 alkyl group,
$R^3$ is a hydrogen atom or a C1-C6 alkyl group,
$R^{4a}$ is a halogen atom, or a methyl group,
$R^{4c}$ is a halogen atom,
$R^{14ay}$ is a halogen atom or a trifluoromethyl group,
$X^a$ is a nitrogen atom or $CR^{14ax}$ (wherein $R^{14ax}$ is a hydrogen atom or a halogen atom),
$R^{18a}$ is a halogen atom, and
$R^{100}$ is a C1-C6 alkyl group.

"Aspect 31"
A compound of the formula (1-2), wherein
$R^2$ is a C1-C6 alkyl group,
$R^3$ is a C1-C6 alkyl group,
$R^{4a}$ is a halogen atom, or a methyl group,
$R^{4c}$ is a halogen atom,
$R^{14ay}$ is a halogen atom or a trifluoromethyl group,
$X^a$ is a nitrogen atom or $CR^{14ax}$ (wherein $R^{14ax}$ represents a hydrogen atom or a halogen atom),
$R^{18a}$ is a halogen atom, and
$R^{100}$ is a C1-C6 alkyl group.

"Aspect 32"
A compound represented by the formula (1-3), wherein
$R^2$ represents a hydrogen atom or a C1-C6 alkyl group,
$R^3$ represents a hydrogen atom or a C1-C6 alkyl group,
$R^{4a}$ represents a halogen atom or a methyl group,
$R^{14ay}$ represents a halogen atom or a trifluoromethyl group,
$X^a$ represents a nitrogen atom or $CR^{14ax}$ (wherein $R^{14ax}$ represents a hydrogen atom or a halogen atom),
$R^{18a}$ represents a halogen atom, and
$R^{100}$ represents a C1-C6 alkyl group.

Hereinafter, a process for producing the present compound will be explained.

The present compound can be produced, for example, by the following Process A-1 to Process C-1.

Process A-1
Among the present compounds, a compound represented by the formula (1-i):

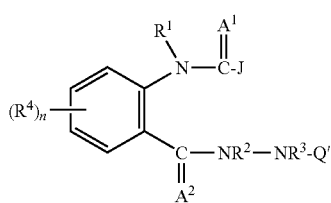

(1-i)

wherein $R^1$, $R^2$, $R^3$, $R^4$, $A^1$, $A^2$, J and n are as defined above, Q' represents a group selected from the group consisting of Q1 to Q6 (provided that the compound wherein Q' is Q4, and $R^8$ and $R^9$ are a hydrogen atom is excluded) (hereinafter, referred to as the compound (1-i)) can be produced by reacting a compound represented by the formula (2):

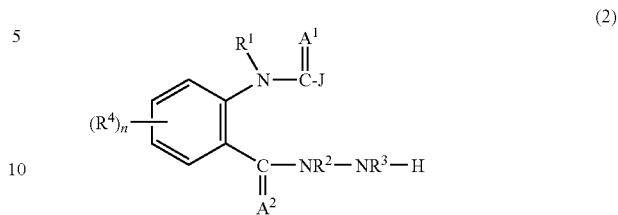

(2)

wherein $R^1$, $R^2$, $R^3$, $R^4$, $A^1$, $A^2$, J and n are as defined above (hereinafter, referred to as the compound (2)), and a compound represented by the formula (3):

$L^1$-Q' (3)

wherein Q' is as defined above, and $L^1$ represents a halogen atom or a Q'-O-group (provided that the case where Q' is Q4, and $R^8$ and $R^9$ are a hydrogen atom is excluded) (hereinafter, referred to as the compound (3)).

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitriles such as acetonitrile and the like, aprotic polar solvents such as N,N-dimethylformamide, N-methlpyrrolidone, 1,3-dimethyl-2-imidadzolidinone, dimethyl sulfoxide, and the like, and a mixture thereof.

The amount of the compound (3) to be used in the reaction is usually 1 to 2 mols per 1 mol of the compound (2).

The reaction is performed in the presence of a base, if necessary. Examples of the base include nitrogen-containing heterocyclic compounds such as pyridine, picoline, 2,6-lutidine, 1,8-diazabicyclo[5,4,0]7-undecene (DBU), 1,5-diazabicyclo[4,3,0]5-nonene (DBN), and the like, tertiary amines such as triethylamine, N,N-diisopropylethylamine, and the like, and inorganic bases such as potassium carbonate, sodium hydride, and the like. The amount of the base when the reaction is performed in the presence of the base is usually 1 to 2 mols per 1 mol of the compound (2), while the base may be used in an excess amount in case that the base used is liquid under the reaction conditions such as pyridine, and the like.

The reaction temperature is usually in a range of 0 to 100° C., and the reaction time is usually in a range of 0.1 to 24 hours.

After completion of the reaction, the compound (1-i) can be isolated by pouring the reaction mixture into water and extracting the mixture with an organic solvent, or collecting a deposited precipitate by filtration. The isolated compound (1-i) may be further purified by recrystallization, chromatography, or the like.

Process A-2
Among the present compounds, a compound represented by the formula (1-ii):

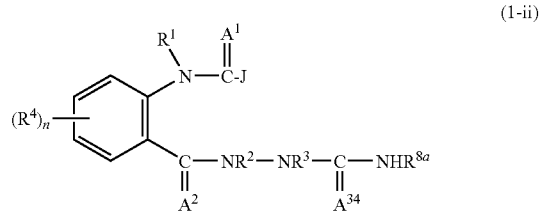

(1-ii)

wherein $R^1$, $R^2$, $R^3$, $R^4$, $A^1$, $A^2$, $A^{34}$, J and n are as defined above, and $R^{8a}$ represents a C1-C6 alkyl group optionally substituted with at least one halogen atom; a C2-C6 alkoxyalkyl group optionally substituted with at least one halogen atom; a C2-C6 alkenyl group optionally substituted with at least one halogen atom; a C3-C6 alkynyl group optionally substituted with at least one halogen atom; a C3-C6 cycloalkyl group optionally substituted with one or more independent substituents selected from the group consisting of (1) a halogen atom and (2) a C1-C6 alkyl group; a phenyl group optionally substituted with a 1 to 5 independent substituents selected from the group consisting of (1) a halogen atom (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom; a 5- to 6-membered heteroaryl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or a C7-C9 phenylalkyl group whose benzene ring moiety may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom (hereinafter, referred to as the compound (1-ii)) can be produced by reacting the compound (2) with a compound represented by the formula (4):

$$A^{34}=C=N-R^{8a} \tag{4}$$

wherein $A^{34}$ and $R^{8a}$ are as defined above (hereinafter, referred to as the compound (4)).

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitriles such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The amount of the compound (4) used in the reaction is usually 1 to 2 mols per 1 mol of the compound (2).

The reaction temperature is usually in a range of 0 to 100° C., and the reaction time is a usually a range of 0.1 to 24 hours.

After completion of the reaction, the compound (1-ii) can be isolated by pouring the reaction mixture into water, and extracting the mixture with an organic solvent, or collecting a deposited precipitate by filtration. The isolated compound (1-ii) may be further purified by recrystallization, chromatography, or the like.

Process A-3

Among the present compounds, a compound represented by the formula (1-iii):

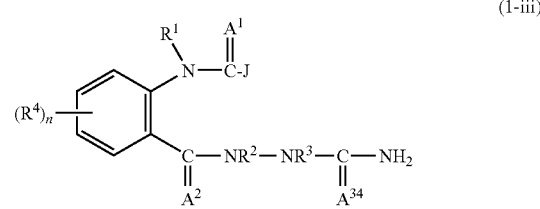

wherein $R^1$, $R^2$, $R^3$, $R^4$, $A^1$, $A^2$, $A^{34}$, J and n are as defined above (hereinafter, referred to as the compound (I-iii)) can be produced by reacting the compound (2) and a cyanate or a thiocyanate.

The reaction is performed in the presence of a solvent. Examples of the solvent used in the reaction include acids such as organic acids such as acetic acids, and the like and mineral acids such as hydrochloric acid, and the like, as well as a mixture of these acids and water, chloroform, or the like.

The amount of the cyanate or the thiocyanate used in the reaction is usually 1 to 2 mols per 1 mol of the compound (2).

The reaction temperature is usually in a range of 0 to 100° C., and the reaction time is usually in a range of 0.1 to 24 hours.

Examples of the cyanate or the thiocyanate include potassium cyanate, sodium cyanate, ammonium cyanate, potassium thiocyanate, sodium thiocyanate and ammonium thiocyanate.

After completion of the reaction, the compound (I-iii) can be isolated by pouring the reaction mixture into water and extracting the mixture with an organic solvent, or collecting a deposited precipitate by filtration. The isolated Compound (I-iii) may be further purified by recrystallization, chromatography, or the like.

Process B-1

The present compound can be produced by reacting a compound represented by the formula (6):

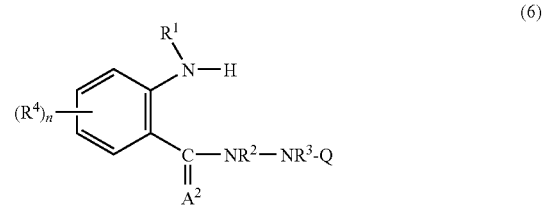

wherein $R^1$, $R^2$, $R^3$, $R^4$, $A^2$, Q and n are as defined above (hereinafter, referred to as Compound (6)) and a compound represented by the formula (7):

wherein $A^1$ and J are as define above, and $L^2$ represents a halogen atom (hereinafter, referred to as the compound (7)).

The reaction is performed in the presence or the absence of a solvent. Examples of the solvent used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitrites such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The amount of the compound (7) used in the reaction is usually 1 to 2 mols per 1 mol of the compound (6).

The reaction is performed in the presence of a base, if necessary. Examples of the base include nitrogen-containing heterocyclic compounds such as pyridine, picoline, 2,6-lutidine, 1,8-diazabicyclo[5,4,0]7-undecene (DBU), 1,5-diazadicyclo[4,3,0]5-nonene (DBN), and the like, tertiary amines such as triethylamine, N,N-diisopropylethylamine, and the like, and inorganic bases such as potassium carbonate, sodium hydride, and the like. The amount of the base when the reaction is performed in the presence of the base is usually 1 to 2 mole per 1 mol of the compound (6), while the base may be used in an excess amount in case that the base used is liquid under the reaction conditions such as pyridine, and the like.

The reaction temperature is usually in a range of 0 to 100° C., and the reaction time is usually in a range of 0.1 to 24 hours.

After completion of the reaction, the present compound can be isolated by pouring the reaction mixture into water, and extracting the mixture with an organic solvent, or collecting a deposited precipitation by filtration. The isolated present compound may be further purified by recrystallization, chromatography, or the like.

Process B-2

Among the present compounds, a compound represented by the formula (I-iv):

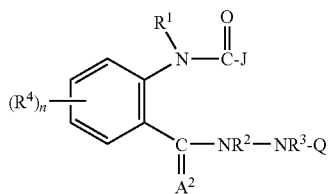

(1-iv)

wherein $R^1$, $R^2$, $R^3$, $R^4$, $A^2$, J, Q and n are as defined above (hereinafter referred to as the compound (I-iv)) can be produced by reacting the compound (6) and a compound represented by the formula (8):

(8)

wherein J is as defined above (hereinafter, referred to as the compound (8)) in the presence of a dehydrating agent.

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitrites such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The amount of the compound (8) used in the reaction is usually 1 to 2 mols per 1 mol of the compound (6).

Examples of the dehydrating agent to be used in the reaction include carbodiimides such as dicyclohexylcarbodiimide (DCC), 1-ethyl-3-(3-dimethylaminopropyl)carbodiimide hydrochloride (WSC), and the like. The amount of the dehydrating agent to be used is usually 1 to 2 mols per 1 mol of the compound (6).

The reaction temperature is usually in a range of 0 to 100° C., and the reaction time is usually in a range of 0.1 to 24 hours.

After completion of the reaction, the compound (I-iv) can be isolated by pouring the reaction mixture into water, and extracting the mixture with an organic solvent, or collecting a deposited precipitate by filtration. The isolated compound (I-iv) may be further purified by recrystallization, chromatography, or the like.

Process C-1

Among the present compounds, a compound represented by the formula (1-v):

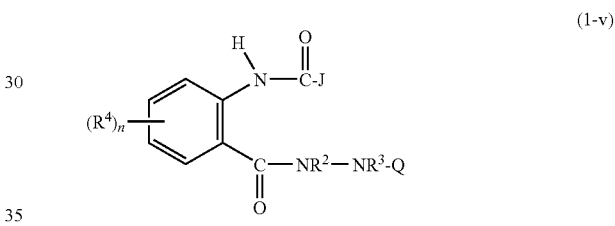

(1-v)

wherein $R^2$, $R^3$, $R^4$, J, Q and n are as defined above (hereinafter, referred to as the compound (1-v)) can be produced by reacting a compound represented by the formula (9):

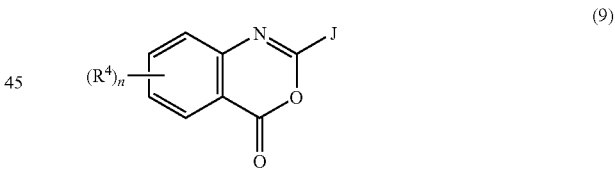

(9)

wherein $R^4$, J and n are as defined above (hereinafter, referred to as the compound (9)) and a compound represented by the formula (10):

(10)

wherein $R^2$, $R^3$ and Q are as defined above (hereinafter, referred to as the compound (10)).

The reaction is performed in the presence or the absence of a solvent. Examples of the solvent used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitrites such as acetonitrile, and the like, aprotic polar solvents such as N,N-dimethylformamide, N-methylpyrrolidone, 1,3-dimethyl-2-imidaozolidinone, dimethyl sulfoxide, and the like, and a mixture thereof.

The amount of the compound (10) to be used in the reaction is usually 1 to 20 mols per 1 mol of the compound (9).

The reaction temperature is usually in a range of 0 to 100° C., and the reaction time is usually in a range of 0.1 to 48 hours.

After completion of the reaction, the compound (1-v) can be isolated by pouring the reaction mixture into water, and extracting the mixture with an organic solvent, or collecting a deposited precipitate by filtration. The isolated compound (1-v) may be further purified by recrystallization, chromatography, or the like.

Process C-2

Among the present compounds, a compound represented by the formula (1-vi):

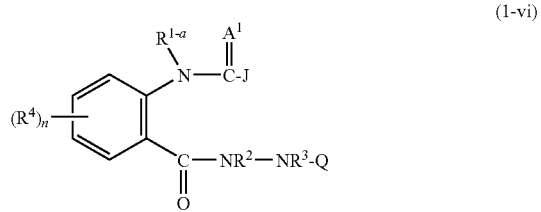

(1-vi)

wherein $R^2$, $R^3$, $R^4$, $A^1$, J, Q and n are as defined above, $R^{1-a}$ represents a C1-C6 alkyl group optionally substituted with at least one halogen atom; a C2-C6 cyanoalkyl group; a C2-C6 alkoxyalkyl group optionally substituted with at least one halogen atom; a C2-C6 alkenyl group optionally substituted with at least one halogen atom; a C3-C6 alkynyl group optionally substituted with at least one halogen atom; or a C7-C9 phenylalkyl group in which a benzene ring part may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom (hereinafter, referred to as the compound (1-vi)) can be produced by reacting a compound represented by the formula (11):

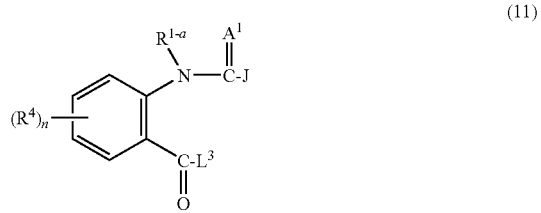

(11)

wherein $R^{1-a}$, $R^4$, $A^1$, J and n are as defined above, and $L^3$ represents a halogen atom (hereinafter, referred to as the compound (11)) and the compound (10).

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichlorethane, chlorobenzene, and the like, hydrocarbons such as toluene, benzene, xylene, and the like, nitrites such as acetonitrile, and the like, aprotic polar solvents such as N,N-diethylformamide, N-methylpyrrolidone, 1,3-dimethyl-2-imidazolidinone, dimethyl sulfoxide, and the like, and a mixture thereof.

The amount of the compound (10) to be used in the reaction is usually 1 to 2 mols per 1 mol of the compound (11).

The reaction is performed in the presence of a base, if necessary. Examples of the base include nitrogen-containing heterocyclic compounds such as pyridine, picoline, 2,6-lutidine, 1,8-diazabicyclo[5,4,0]7-undecene (DBU), 1,5-diazabicyclo[4,3,0]5-nonene (DBN), and the like, tertiary amines such as triethylamine, N,N-diisopropylethylamine, and the like, and inorganic bases such as potassium carbonate, sodium hydride, and the like. The amount of the base to be used when the reaction is performed in the presence of the base is usually 1 to 2 mols per 1 mol of the compound (11), while the base may be used in an excess amount in the case that the base used is liquid under the reaction conditions such as pyridine and the like.

The reaction temperature is usually in a range of 0 to 100° C., and the reaction time is usually in a range of 0.1 to 24 hours.

After completion of the reaction, the compound (1-vi) can be isolated after pouring the reaction mixture into water, and extracting the mixture with an organic solvent, or collecting a deposited precipitate by filtration. The isolated compound (1-vi) may be further purified by recrystallization, chromatography or the like.

Process C-3

The compound (1-vi) can also be produced by reacting a compound represented by the formula (12):

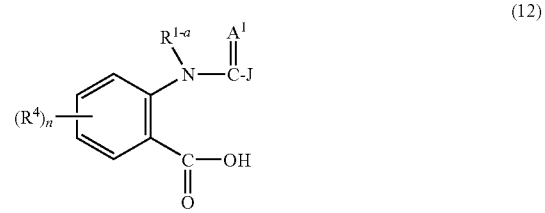

(12)

wherein $R^4$, $R^{1-a}$, $A^1$, J and n are as defined above (hereinafter, referred to as Compound (12)) and the compound (10) in the presence of a dehydrating agent.

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichlroethane, chlorobenzene, and the like, hydrocarbons such as toluene, benzene, xylene, and the like, nitrites such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The amount of the compound (10) used in the reaction is usually 1 to 2 mols per 1 mol of the compound (12).

Examples of the dehydrating agent used in the reaction include carbodiimides such as dicyclohexylcarbodiimide (DCC), 1-ethyl-3-(3-dimethylaminopropyl)carbodiimide hydrochloride (WSC), and the like. The amount of the dehydrating agent to be used is usually 1 to 2 mols per 1 mol of the compound (12).

The reaction temperature is usually in a range of 0 to 100° C., and the reaction time is usually in a range of 0.1 to 24 hours.

After completion of the reaction, the compound (1-vi) can be isolated by pouring the reaction mixture into water and extracting the mixture with an organic solvent, or collecting a deposited precipitate by filtration. The isolated compound (1-vi) may be further purified by recrystallization, chromatography, or the like.

Then, a process for producing intermediates for producing the present compound will be explained.

Reference Process 1

Among the compound (2), a compound represented by the formula (2-i):

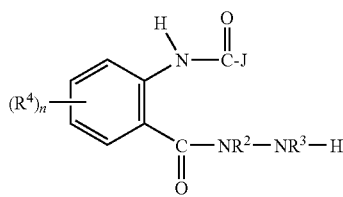

wherein $R^2$, $R^3$, $R^4$, J and n are as defined above (hereinafter, referred to as the compound (2-i)) can be produced by reacting the compound (9) and a compound represented by the formula (13):

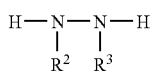

wherein $R^2$ and $R^3$ are as defined above (hereinafter, referred to as the compound (13)).

The reaction is performed in the presence or the absence of a solvent. Examples of the solvent used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene and the like, hydrocarbons such as toluene, benzene, xylene and the like, nitrites such as acetonitrile, and the like, aprotic polar solvents such as N,N-dimethylformamide, N-methylpyrrolidone, 1,3-dimethyl-2-imidazolidinone, dimethyl sulfoxide, and the like, alcohols such as methanol, ethanol, 2-propanol, and the like, and a mixture thereof.

The amount of the compound (13) to be used in the reaction is usually 1 to 5 mols per 1 mol of the compound (9).

The reaction temperature is usually in a range of −50 to 100° C., and the reaction time is usually in a range of 0.1 to 24 hours.

After completion of the reaction, the compound (2-i) can be isolated by pouring the reaction mixture into water, and extracting the mixture with an organic solvent, or collecting a deposited precipitate by filtration. The isolated compound (2-i) may be further purified by recrystallization, chromatography, or the like.

Reference Process 2

Among the compound (2), a compound represented by the formula (2-ii):

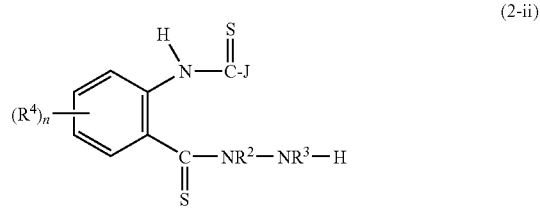

wherein $R^2$, $R^3$, $R^4$, J and n are as defined above (hereinafter, referred to as Compound (2-ii)) can be produced by reacting a compound represented by the formula (14):

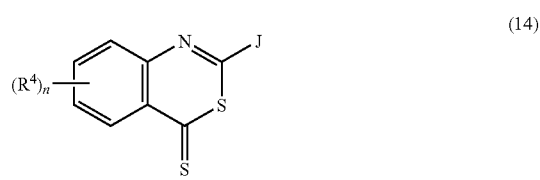

wherein $R^4$, J and n are as defined above (hereinafter, referred to as the compound (14)) and the compound (13).

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene and the like, hydrocarbons such as toluene, benzene, xylene, and the like, nitrites such as acetonitrile, and the like, aprotic polar solvents such as N,N-dimethylformamide, N-methylpyrrolidone, 1,3-dimethyl-2-imidazolidinone, dimethyl sulfoxide, and the like, alcohols such as methanol, ethanol, 2-propanol, and the like, and a mixture thereof.

The amount of the compound (13) to be used in the reaction is usually 1 to 5 mols per 1 mol of the compound (14).

The reaction temperature is usually in a range of −50 to 100° C., and the reaction time is usually in a range of 0.1 to 24 hours.

After completion of the reaction, the compound (2-ii) can be isolated by pouring the reaction mixture into water, and extracting the mixture with an organic solvent, or collecting a deposited precipitate by filtration. The isolated compound (2-ii) may be further purified by recrystallization, chromatography, or the like.

Reference Process 3

Among the compound (2), a compound represented by the formula (2-iii):

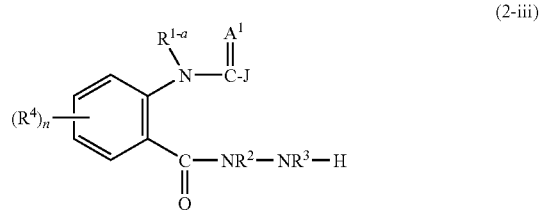

wherein $R^{1-a}$, $R^2$, $R^3$, $R^4$, $A^1$, J and n are as defined above (hereinafter, referred to as the compound (2-iii)) can be produced by reacting the compound (11) and the compound (13).

The reaction is performed in the presence or the absence of a solvent. Examples of the solvent used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitrites such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The amount of Compound (13) used in the reaction is usually 2 to 10 mols per 1 mol of the compound (11).

The reaction temperature is usually in a range of –50 to 100° C., and the reaction time is in a range of 0.1 to 24 hours.

After completion of the reaction, the compound (2-iii) can be isolated by pouring the reaction mixture into water, and extracting the mixture with an organic solvent, or collecting a deposited precipitate by filtration. The isolated compound (2-iii) may be further purified by recrystallization, chromatography, or the like.

Reference Process 4

The compound (9) can be produced by reacting a compound represented by the formula (16).

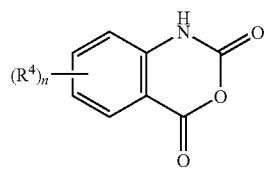
(16)

wherein $R^4$ and n are as defined above (hereinafter, referred to as the compound (16)) and a compound represented by the formula (7'):

(7')

wherein J and $L^2$ are as defined above (hereinafter, referred to as Compound (7')).

The reaction is performed in the presence or the absence of a solvent in the presence of a base. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitrites such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The amount of the compound (7') used in the reaction is usually 0.5 to 2 mols per 1 mol of the compound (16).

Examples of the base to be used in the reaction include nitrogen-containing heterocyclic compounds such as pyridine, picoline, 2,6-lutidine, 1,8-diazabicyclo[5,4,0]7-undecene(DBU), 1,5-diazabicyclo[4,3,0]5-nonene (DBN), and the like, tertiary amines such as triethylamine, N,N-diisopropylethylamine, and the like, and inorganic bases such as potassium carbonate, sodium hydride, and the like. The amount of the base to be used is usually 1 to 2 mols per 1 mol of the compound (16), while the base may be used in an excess amount in case that the base is liquid under the reaction conditions such as pyridine, and the like.

The reaction temperature is usually in a range of 50 to 150° C., and the reaction time is usually in a range of 1 to 24 hours.

After completion of the reaction, the compound (9) can be isolated by pouring the reaction mixture into water, and extracting the mixture with an organic solvent, or collecting a deposited precipitates by filtration. The isolated compound (9) may be further purified by recrystallization, chromatography, or the like.

Reference Process 5

The compound (9) can be produced by reacting a compound represented by the formula (17):

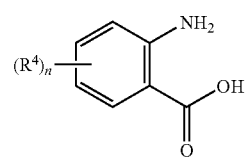
(17)

wherein $R^4$ and n are as defined above (hereinafter, referred to as Compound (17)) and the compound (7').

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitrites such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The process comprises the following step 5-1 and step 5-2.

Step 5-1

This step is performed by reacting the compound (17) and the compound (7') in the presence of a base.

The amount of the compound (7') to be used in this step is usually 1 to 2 mols per 1 mol of the compound (17). Examples of the base include nitrogen-containing heterocyclic compounds such as pyridine, picoline, 2,6-lutidine, 1,8-diazabicyclo[5,4,0]7-undecene (DBU), 1,5-diazabicyclo[4,3,0]5-nonene (DBN), and the like, tertiary amines such as triethylamine, N,N-diisopropylethylamine, and the like, and inorganic bases such as potassium carbonate, sodium hydride, and the like. The amount of the base to be used is usually 1 to 2 mols per 1 mol of the compound (17).

The reaction temperature of this step is usually in a range of 0 to 50° C., and the reaction time is usually in a range of 0.1 to 24 hours.

After completion of this step, usually, the reaction mixture is used as it is in the next step 5-2.

Step 5-2

This step is performed by reacting the reaction mixture in the step 5-1 and a sulfonyl halide in the presence of a base.

Examples of the sulfonyl halide used in this step include methanesulfonyl chloride, p-toluenesulfonyl chloride, and trifluoromethanesulfonyl chloride. The amount of the sulfonyl halide to be used in this step is usually 1 to 2 mols per 1 mol of the compound (17) used in the step 5-1.

Examples of the base include the same bases as those described with respect to the step 5-1. The amount of the base is usually 2 to 4 mols per 1 mol of the compound (17) used in the step 5-1.

The reaction temperature of this step is usually in a range of 0 to 50° C., and the reaction time is usually in a range of 0.1 to 24 hours.

After completion of this step, the compound (9) can be isolated by pouring the reaction mixture into water, followed by conventional extraction with an organic solvent. The isolated compound (9) may be further purified by recrystallization, chromatography, or the like.

Reference Process 6

The compound (14) can be produced by reacting the compound (9) with a thiocarbonylation agent.

The reaction is performed in the presence or the absence of a solvent. Examples of the solvent to be used in the reaction include ethers such as 1,4-dioxane, diethyl ether, tetrahydrofuran, methyl tert-butyl ether, diglyme, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitrites such as acetonitrile, and the like, pyridines such as pyridine, picoline, lutidine, and the like, and a mixture thereof.

Examples of the thiocarbonylation agent to be used in the reaction include diphosphorus pentasulfide, a Lawesson's reagent (2,4-bis-(4-methoxyphenyl)-1,3-dithia-2,4-diphosphetane 2,4-disulfide), and the like.

The amount of the thiocarbonylation agent to be used in the reaction is usually 1 to 3 mols per 1 mol of the compound (9).

The reaction temperature is usually in a range of 0° C. to 200° C., and the reaction time is usually in a range of 1 to 24 hours.

After completion of the reaction, the compound (14) can be isolated by collecting a precipitate deposited in the reaction mixture by filtration, or extracting the reaction mixture with an organic solvent. The isolated compound (14) may be further purified by recrystallization, chromatography, or the like.

Reference Process 7

The compound (11) can be produced by reacting the compound (12) with a halogenating agent.

The reaction is performed in the presence or the absence of a solvent. Examples of the solvent to be used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitrites such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

Examples of the halogenating agent to be used in the reaction include thionyl chloride, thionyl bromide, phosphorus oxychloride, phosphorus oxybromide, phosphorus pentachloride, oxalyl chloride, and phosgene.

The amount of the halogenating agent to be used in the reaction is usually 1 to 2 mols per 1 mol of the compound (12) and, in some cases, the halogenating agent may be used in an excess amount.

The reaction temperature is usually in a range of 0° C. to 150° C., and the reaction time is usually in a range of 0.1 to 24 hours.

After completion of the reaction, the compound (11) can be isolated by collecting a precipitate deposited in the reaction mixture, or concentrating the reaction mixture. The isolated compound (11) is usually used as it is in the next step and, if necessary, may be further purified by recrystallization, or the like.

Reference Process 8

The compound (12) can be produced by reacting a compound represented by the formula (18'):

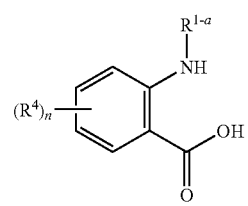

(18')

wherein $R^{1-a}$, $R^4$ and n are as defined above (hereinafter, referred to as the compound (18')) and the compound (7).

The reaction is performed in the presence or the absence of a solvent. Examples of the solvent used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitrites such as acetonitrile, and the like, aprotic polar solvents such as N,N-dimethylformamide, N-methylpyrrolidone, 1,3-dimethyl-2-imidazolidinone, dimethyl sulfoxide, and the like, and a mixture thereof.

The amount of the compound (7) to be used in the reaction is usually 1 to 2 mols per 1 mol of the compound (18').

The reaction is performed in the presence of a base. Examples of the base to be used include nitrogen-containing heterocyclic compounds such as pyridine, picoline, 2,6-lutidine, 1,8-diazabicyclo[5,4,0]7-undecene (DBU), 1,5-diazabicyclo[4,3,0]5-nonene (DBN), and the like, tertiary amines such as triethylamine, N,N-diisopropylethylamine, and the like, inorganic bases such as potassium carbonate, sodium hydride, and the like. The amount of the base to be used is usually 1 to 2 mols per 1 mol of the compound (18').

The reaction temperature is usually in a range of 0 to 50° C., and the reaction time is usually in range of 0.1 to 24 hours.

After completion of the reaction, the compound (12) can be isolated by pouring the reaction mixture into water, followed by conventional extraction with an organic solvent, or collecting a deposited precipitate by filtration. The isolated compound (12) may be further purified by recrystallization, chromatography, or the like.

Reference Process 9

The compound (6) can be produced by reacting a compound represented by the formula (20):

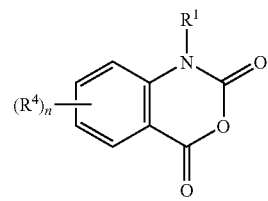

(20)

wherein $R^1$, $R^4$ and n are as defined above (hereinafter, referred to as the compound (20)) and the compound (10).

The reaction is performed in the presence or the absence of a solvent. Examples of the solvent used in the reaction include ethers such as 1,4-dioxane, diethyl ether, tetrahydrofuran, methyl tert-butyl ether, and the like, halogenated hydrocarbons such as dichloromethane, chloroform, carbon tetrachloride, 1,2-dichloroethane, chlorobenzene, and the like, hydrocarbons such as toluene, benzene, xylene, and the like, nitriles such as acetonitrile, and the like, aprotic polar solvents such as N,N-dimethylformamide, N-methylpyrrolidone, 1,3-dimethyl-2-imidazolidinone, dimethyl sulfoxide, and the like, alcohols such as methanol, ethanol, isopropyl alcohol, and the like, and a mixture thereof.

The amount of the compound (10) to be used in the reaction is usually 1 to 2 mols per 1 mol of the compound (20).

The reaction temperature is usually in a range of −20 to 150° C., and the reaction time is usually in a range of 0.1 to 24 hours.

After completion of the reaction, the compound (20) can be isolated by pouring the reaction mixture into water, and extracting the mixture with an organic solvent, or collecting a deposited precipitate by filtration. The isolated Compound (20) may be further purified by recrystallization, chromatography, or the like.

The compounds (3), (4) and (13) are known compounds, or can be produced from known compounds according to known processes (e.g. see Organic Functional Group Preparations, 2nd edition, Vol. 1, chapter 12, p. 359-376 (Stanley R. Sandler, Wolf Karo.) or Organic Functional Group Preparations, 2nd edition, Vol. 1, chapter 14, p. 434-465 (Stanley R. Sandler, Wolf Karo.)).

As an aspect of the compound (2), the following compound is mentioned:

A hydrazide compound of the formula (II):

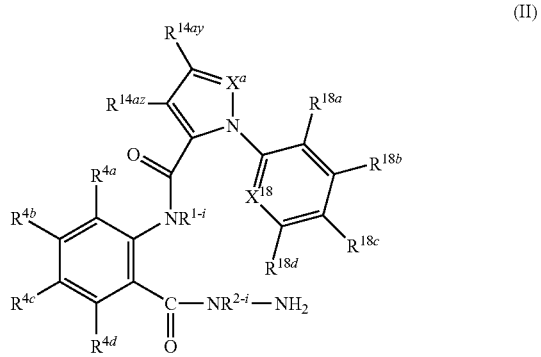

(II)

wherein $R^{1-i}$ represents a hydrogen atom, or a C1-C6 alkyl group optionally substituted with at least one halogen atom, $R^{2-i}$ represents a hydrogen atom, or a methyl group, $R^{4a}$ represents a halogen atom, or a C1-C6 alkyl group optionally substituted with at least one halogen atom, $R^{4b}$, $R^{4c}$ and $R^{4d}$ independently represent a hydrogen atom, a halogen atom, a cyano group, or a C1-C6 alkyl group optionally substituted with at least one halogen atom, or $R^{4b}$ and $R^{4c}$ are bound to each other at their terminal ends to form a group T1: —$CR^{41}$=$CR^{42}$—$CR^{43}$=$CR^{44}$—

(wherein $R^{41}$, $R^{42}$, $R^{43}$ and $R^{44}$ independently represent a hydrogen atom, a halogen atom, a cyano group, or a C1-C6 alkyl group optionally substituted with at least one halogen atom), $X^a$ represents a nitrogen atom or $CR^{14ax}$ (wherein $R^{14ax}$ represents a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom), $R^{14ay}$ and $R^{14az}$ independently represent a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, $X^{18}$ represents a nitrogen atom or $CR^{18e}$ (wherein $R^{18e}$ represents a hydrogen atom, a halogen atom, or a C1-C6 alkyl group optionally substituted with at least one halogen atom), $R^{18a}$ represents a halogen atom, or a C1-C6 alkyl group optionally substituted with at least one halogen atom, and $R^{18b}$, $R^{18c}$ and $R^{18d}$ independently represent a hydrogen atom, a halogen atom, or a C1-C6 alkyl group optionally substituted with at least one halogen atom.

The compound (10) can be produced, for example, according to the following scheme (1).

Scheme (1)

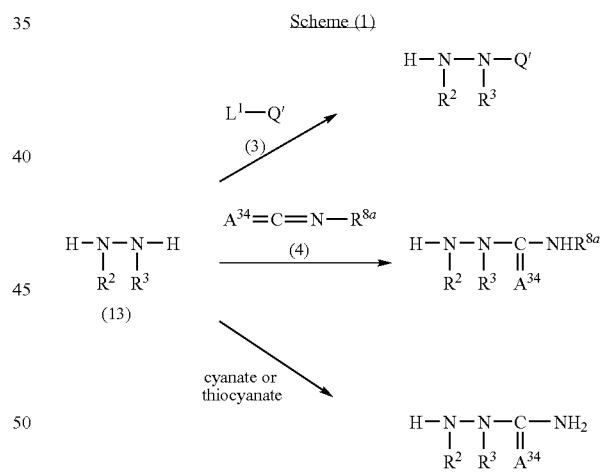

In Scheme (I), $A^{34}$, $L^1$, Q', $R^2$, $R^3$ and $R^{8a}$ are as defined above.

Among the compound (10), a compound represented by the formula (10-i):

(10-i)

wherein $R^2$, $R^3$ and $R^6$ are as defined above, can be produced, for example, according to the following scheme (2).

Scheme (2)

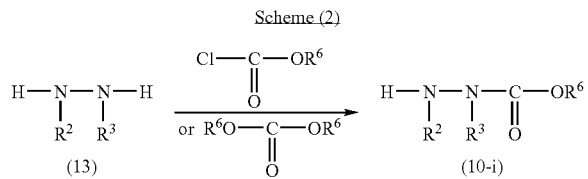

In Scheme (2), $R^2$, $R^3$ and $R^6$ are as defined above.

The compound (17) can be produced, for example, according to the following Scheme (3).

Scheme (3)

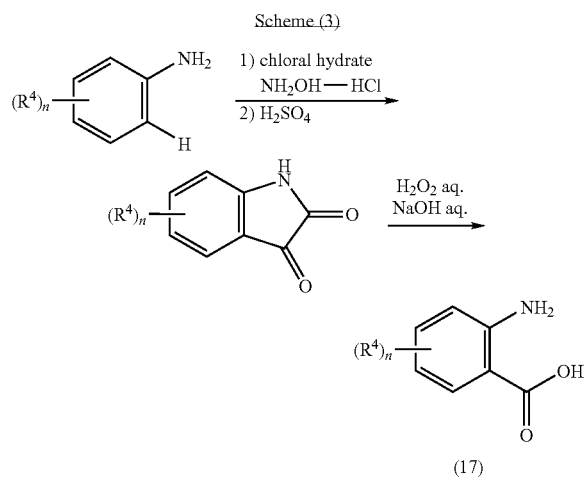

In Scheme (3), $R^4$ and n are as defined above.

The compounds (16), (18') and (20) can be produced, for example, according to the following Scheme (4).

Scheme (4)

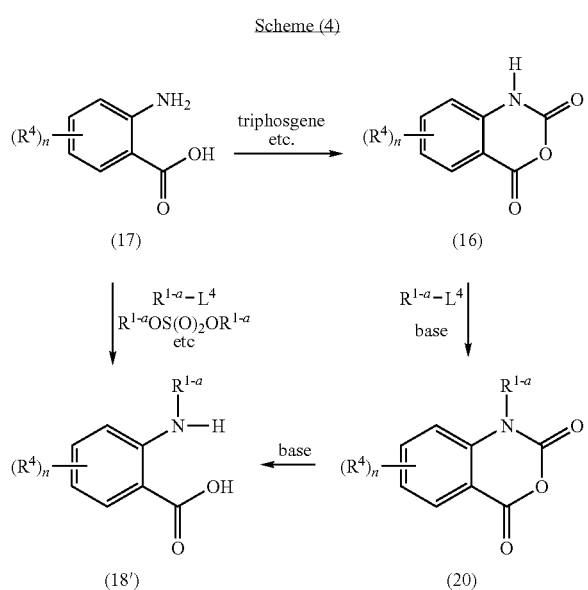

In Scheme (4), $R^{1-a}$, $R^4$ and n are as defined above, and $L^4$ represents a leaving group (e.g. a halogen atom, a methanesulfonyloxy group, a p-toluenesulfonyloxy group etc.).

Among the compounds (17) and (18), a compound represented by the formula (17-i):

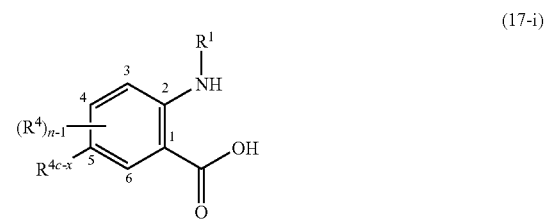

(17-i)

wherein $R^1$ and $R^4$ are as defined above, $R^{4c-x}$ represents a halogen atom or a cyano group, and n−1 represents an integer of 0 to 3, can be produced, for example, according to the following Scheme (5).

Scheme (5)

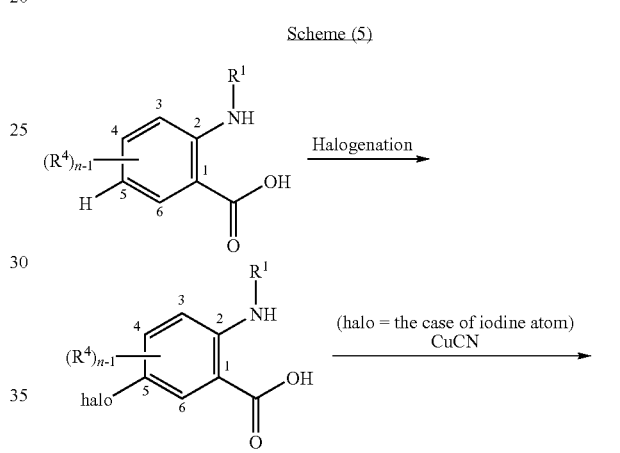

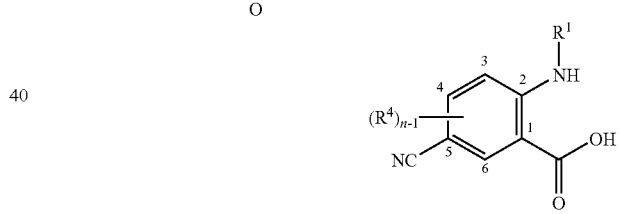

In Scheme (5), $R^1$, $R^4$ and n−1 are as defined above, and halo represents a halogen atom.

Among the compounds (17) and (18), a compound represented by the formula (17-ii):

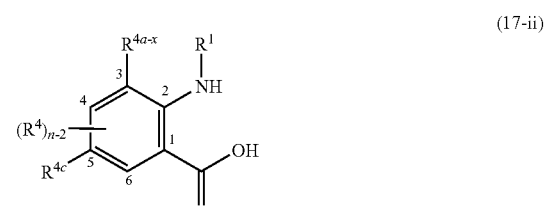

(17-ii)

wherein $R^1$ and $R^4$ are as defined above, $R^{4a-x}$ represents a halogen atom, $R^{4c}$ represents the same meaning as that of $R^4$, and n−2 represents an integer of 0 to 2, can be produced, for example, according to the following Scheme (6).

Scheme (6)

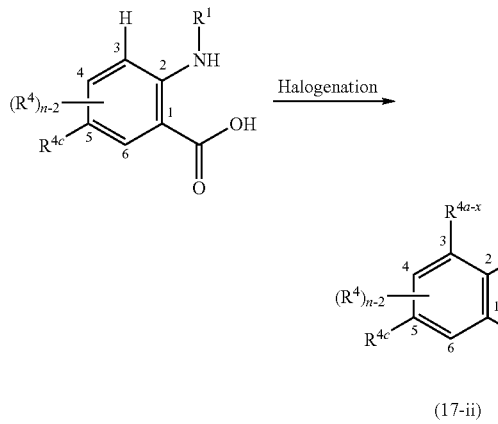

(17-ii)

In Scheme (6), $R^1$, $R^4$, $R^{4a-x}$, $R^{4c}$ and n−2 are as defined above.

The compound (8) can be produced, for example, according to the process shown in the following Scheme (7).

Scheme (7)

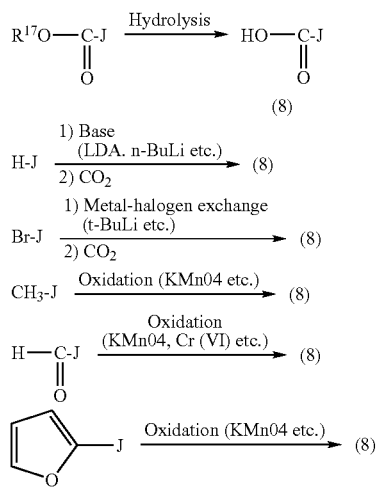

In Scheme (7), J is as defined above, $R^{17}$ represents a methyl group or an ethyl group, LDA represents lithium diisopropylamide, n-BuLi represents normal butyl lithium, and t-BuLi represents tertiary butyl lithium.

Among the compound (8), a compound represented by the formula (8-i)

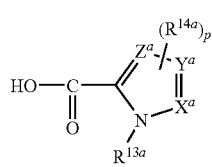

(8-i)

wherein $R^{13a}$, $R^{14a}$, $X^a$, $Y^a$, $Z^a$ and p are as defined above, can be produced, for example, according to the process shown in the following Scheme (8).

Scheme (8)

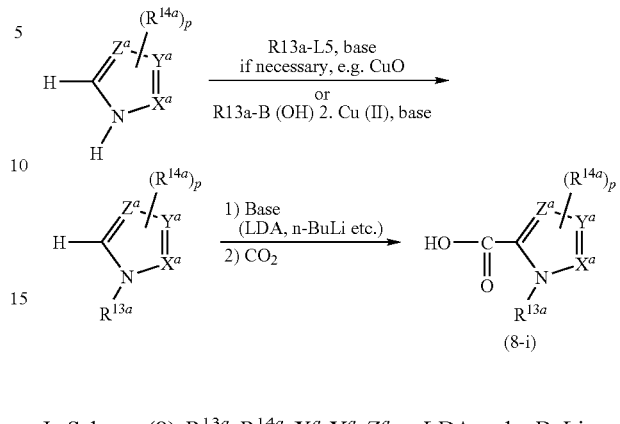

In Scheme (8), $R^{13a}$, $R^{14a}$, $X^a$, $Y^a$, $Z^a$, p, LDA and n-BuLi are as defined above, and $L^5$ represents a leaving group (e.g. a halogen atom, a methanesulfonyloxy group, a p-toluenesulfonyloxy group, a methylsulfonyl group etc.).

Among the compound (8), a compound represented by the formula (8-ii):

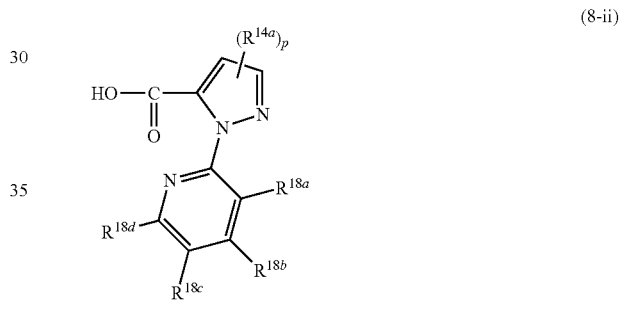

(8-ii)

wherein $R^{14a}$ and p are as defined above, $R^{18a}$, $R^{18b}$, $R^{18c}$ and $R^{18d}$, each, independently, represent a hydrogen atom, a halogen atom, a cyano group, a nitro group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, can be produced, for example, according to the process shown in the following Scheme (9).

Scheme (9)

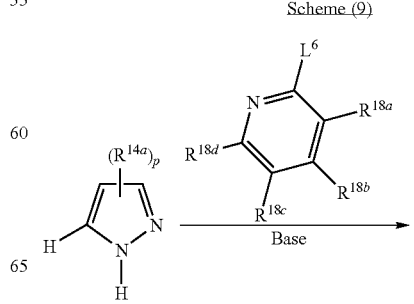

-continued

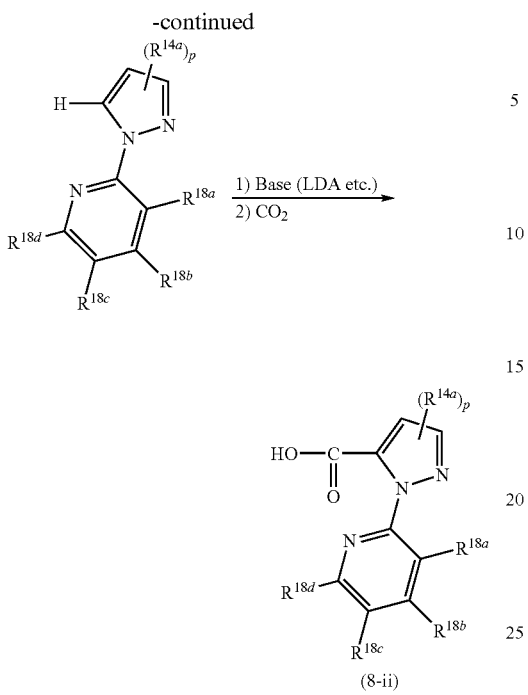

(8-ii)

In Scheme (9), $R^{14a}$, $R^{18a}$, $R^{18b}$, $R^{18c}$, $R^{18d}$, LDA and p are as defined above, and $L^6$ represents a leaving group (e.g. a halogen atom, a methylsulfonyl group etc.).

Among the compound (8), a compound represented by the formula (8-iii):

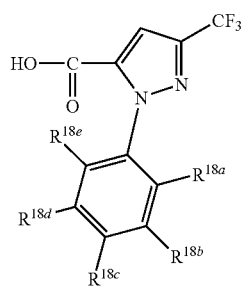

(8-iii)

wherein $R^{18a}$, $R^{18b}$, $R^{18c}$, $R^{18d}$ and $R^{18e}$ independently represent a hydrogen atom, a halogen atom, a cyano group, a nitro group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, can be produced, for example, according to the process shown in the following Scheme (10).

Scheme (10)

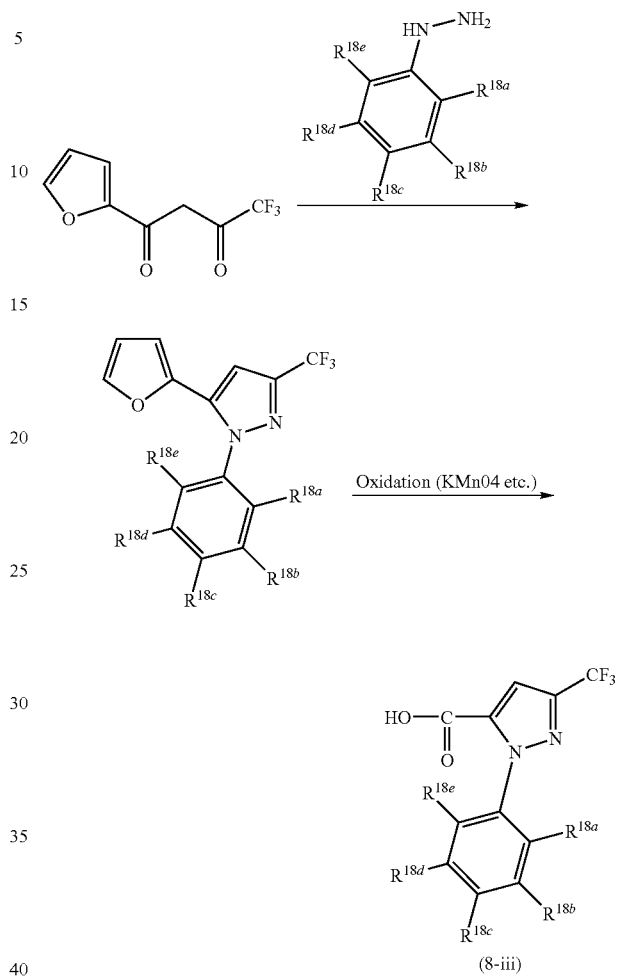

(8-iii)

In Scheme (10), $R^{18a}$, $R^{18b}$, $R^{18c}$, $R^{18d}$ and $R^{18e}$ are as defined above.

Among the compound (8), a compound represented by the formula (8-iv):

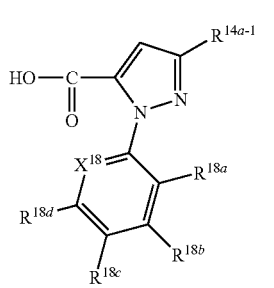

(8-iv)

wherein $X^{18}$ represents —N=, or —$CR^{18e}$=; $R^{18a}$, $R^{18b}$, $R^{18c}$, $R^{18d}$ and $R^{18e}$ are as defined above, and $R^{14a-1}$ represents a C1-C6 alkyl group optionally substituted with at least one halogen atom, can be produced, for example, according to the process shown in the following Scheme (11).

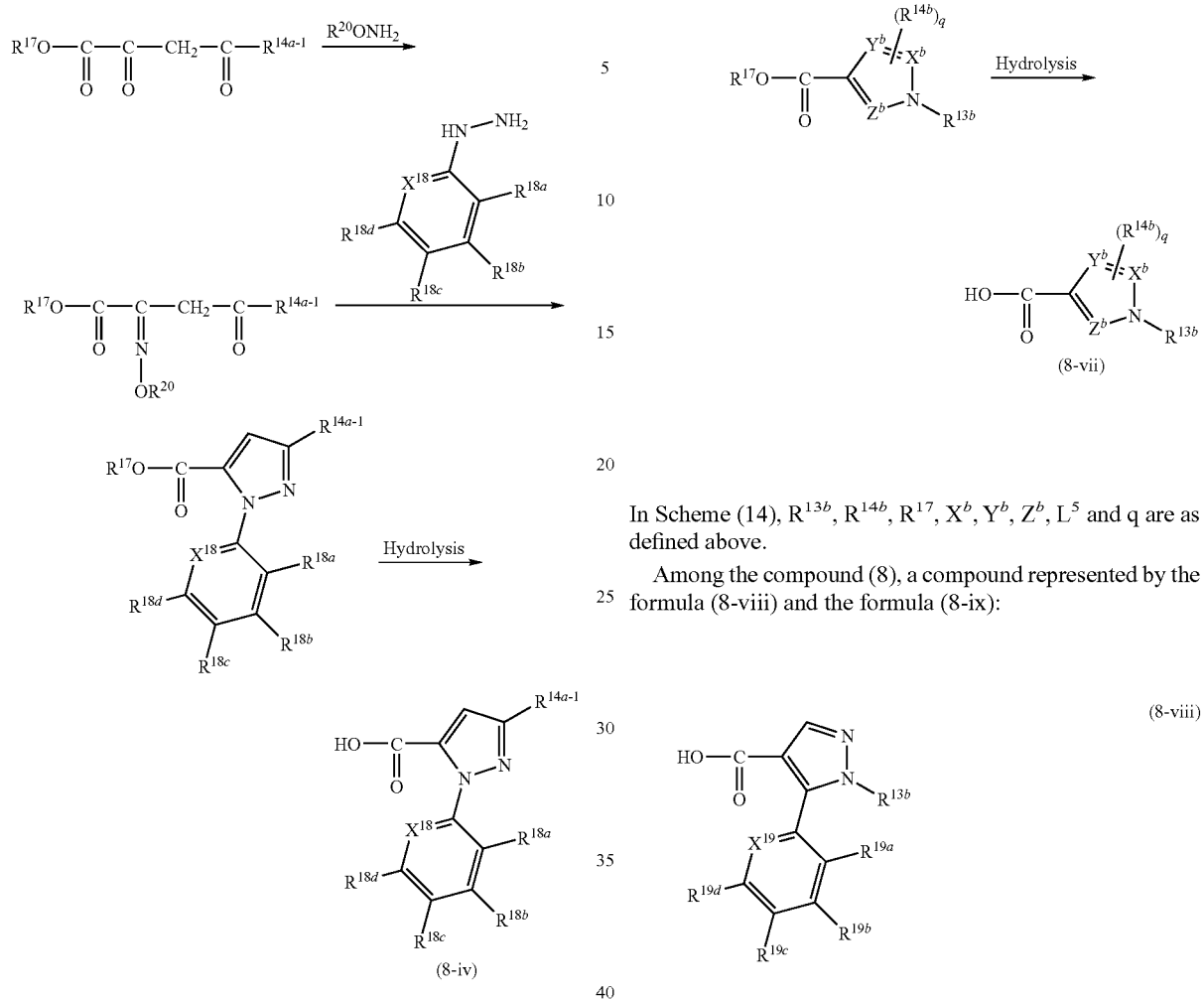

In Scheme (11), $R^{14a-1}$, $R^{17}$, $R^{18a}$, $R^{18b}$, $R^{18c}$, $R^{18d}$ and $X^{18}$ are as defined above, and $R^{20}$ represents a methyl group or an ethyl group.

Among the compound (8), a compound represented by the formula (8-vii):

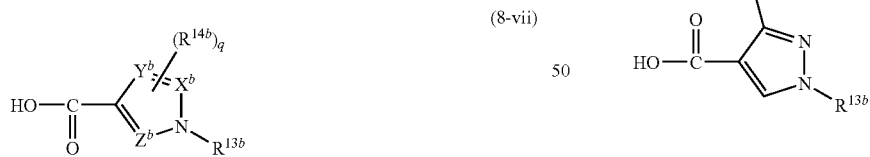

(8-vii)

wherein $R^{13b}$, $R^{14b}$, $X^b$, $Y^b$, $Z^b$ and q are as defined above, can be produced, for example, according to the process shown in the following Scheme (14).

Scheme (14)

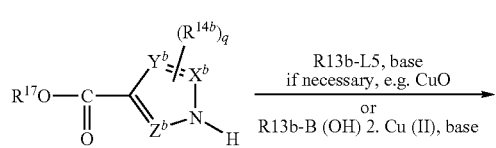

In Scheme (14), $R^{13b}$, $R^{14b}$, $R^{17}$, $X^b$, $Y^b$, $Z^b$, $L^5$ and q are as defined above.

Among the compound (8), a compound represented by the formula (8-viii) and the formula (8-ix):

(8-viii)

(8-ix)

[wherein $R^{13b}$ is as defined above, $X^{19}$ represents —N=, or —$CR^{19e}$=, $R^{19a}$, $R^{19b}$, $R^{19c}$, $R^{19d}$ and $R^{19e}$, each, independently, represent a hydrogen atom, a halogen atom, a cyano group, a nitro group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom]

can be produced, for example, according to the process shown in the following Scheme (15).

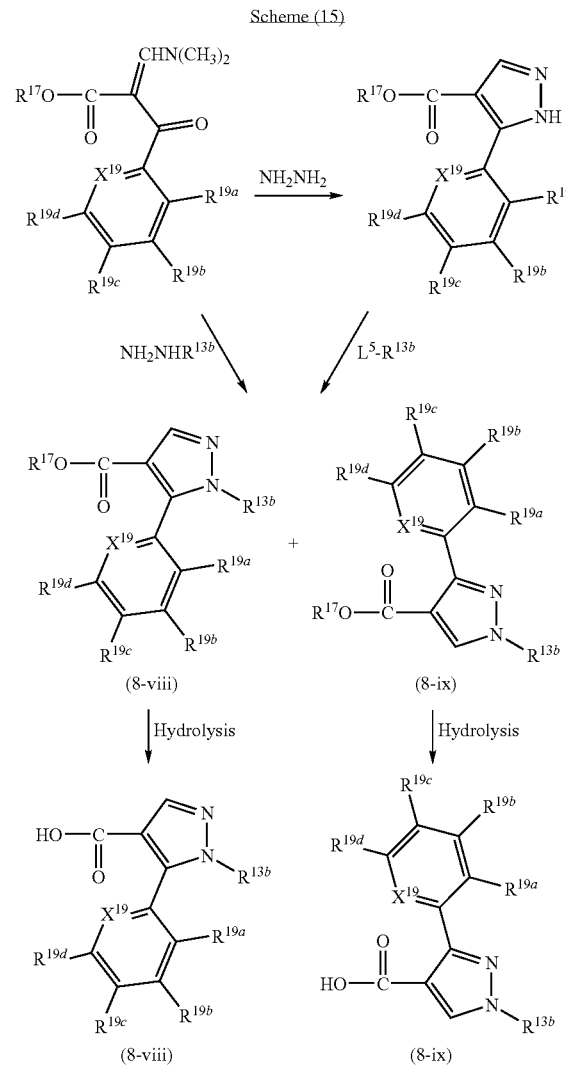

In Scheme (15), $R^{13b}$, $R^{17}$, $R^{19a}$, $R^{19b}$, $R^{19c}$, $R^{19d}$, $L^5$ and $X^{19}$ are as defined above.

Among the compound (7), a compound represented by the formula (7-i):

(7-i)

wherein $L^2$ and J are as defined above, can be produced, for example, according to the process shown in the following Scheme (16).

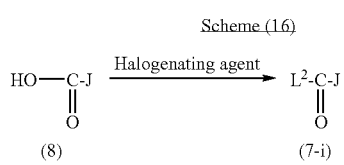

In Scheme (16), $L^2$ and J are as defined above.

Among the compound (7), a compound represented by the formula (7-ii):

(7-ii)

wherein $L^2$ and J are as defined above, can be produced, for example, according to the process shown in the following scheme (17).

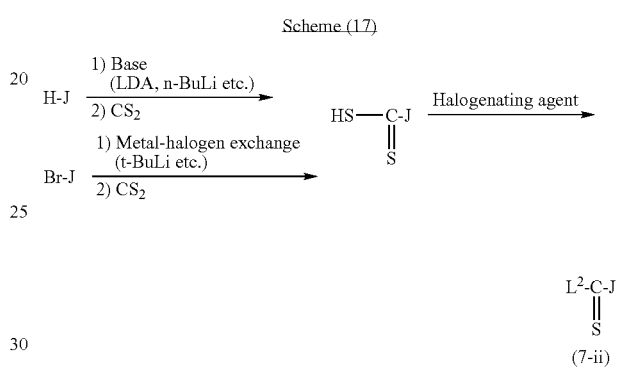

In Scheme (17), $L^2$ and J are as defined above, LDA represents lithium diisopropylamide, n-BuLi represents normal butyl lithium, and t-BuLi represents tertiary butyl lithium.

Among the compound (8), a compound represented by the formula (8-v):

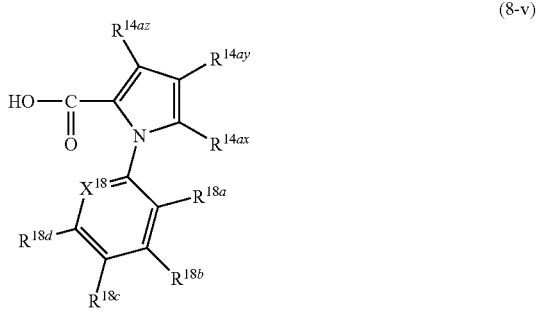

(8-v)

wherein $R^{18a}$, $R^{18b}$, $R^{18c}$, $R^{18d}$ and $X^{18}$ are as defined above, and $R^{14ax}$, $R^{14ay}$ and $X^{14az}$ independently represent a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, can be produced, for example, according to the process shown in the following Scheme (18).
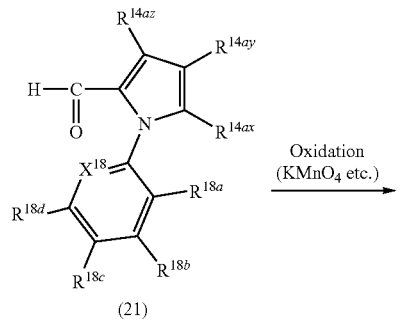
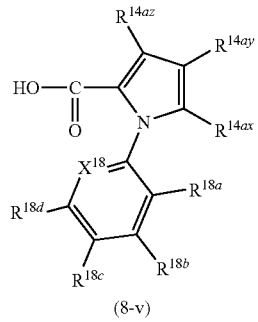
In Scheme (18), $R^{18a}$, $R^{18b}$, $R^{18c}$, $R^{18d}$, $X^{18}$, $R^{14ax}$, $R^{14ay}$ and $X^{14az}$ are as defined above.
The compounds (21) in scheme (18) can be produced, for example, according to the process shown in the following Scheme (19).
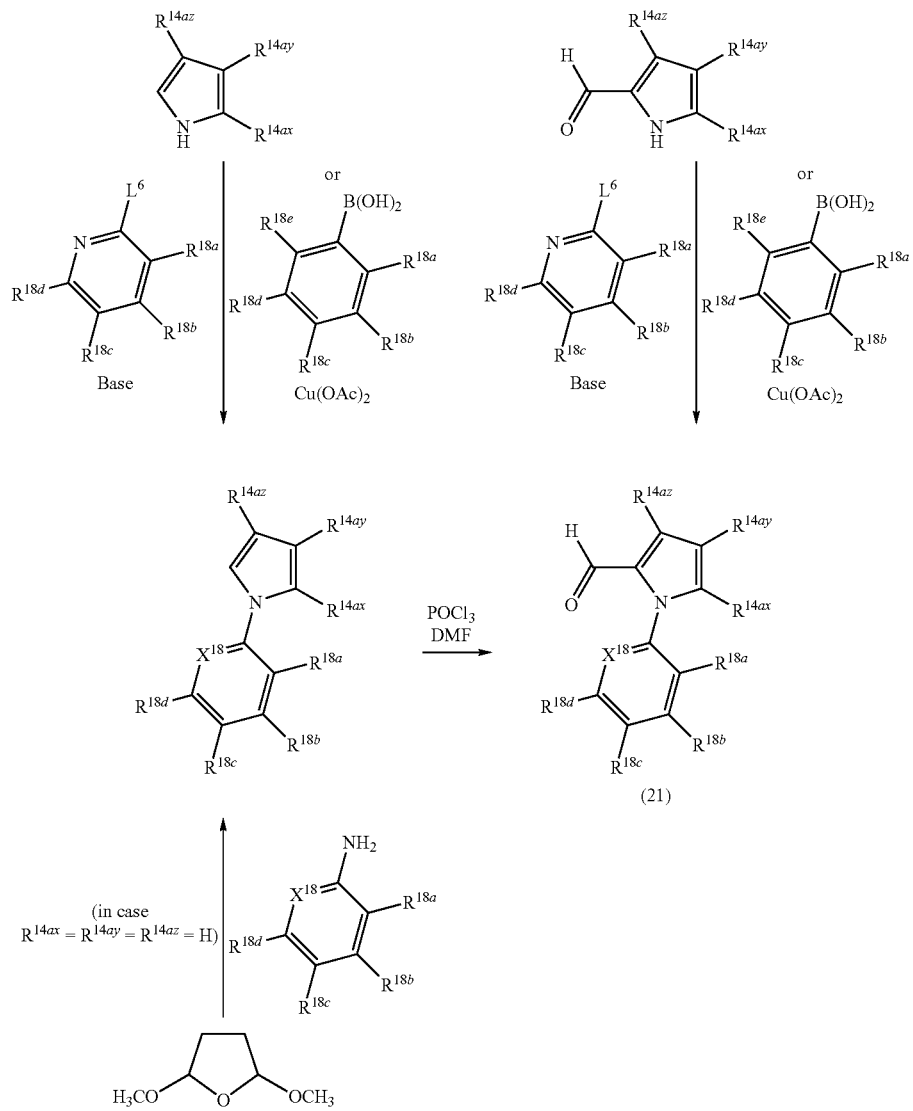

In Scheme (19), $R^{18a}$, $R^{18b}$, $R^{18c}$, $R^{18d}$, $R^{18e}$, $X^{18}$, $R^{14ax}$, $R^{14ay}$, $X^{14az}$ and $L^6$ are as defined above.

Among the compounds (21) in scheme (18), a compound represented by the formula (21-i), the formula (21-ii), and the formula (21-iii):

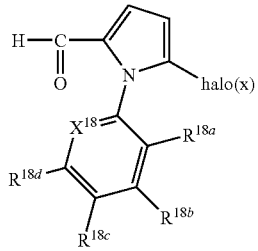

(21-i)

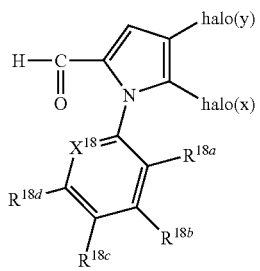

(21-iii)

wherein $R^{18a}$, $R^{18b}$, $R^{18c}$, $R^{18d}$ and $X^{18}$ are as defined above, and halo (x) and halo (y) independently represent a halogen atom, can be produced, for example, according to the process shown in the following Scheme (20).

Scheme (20)

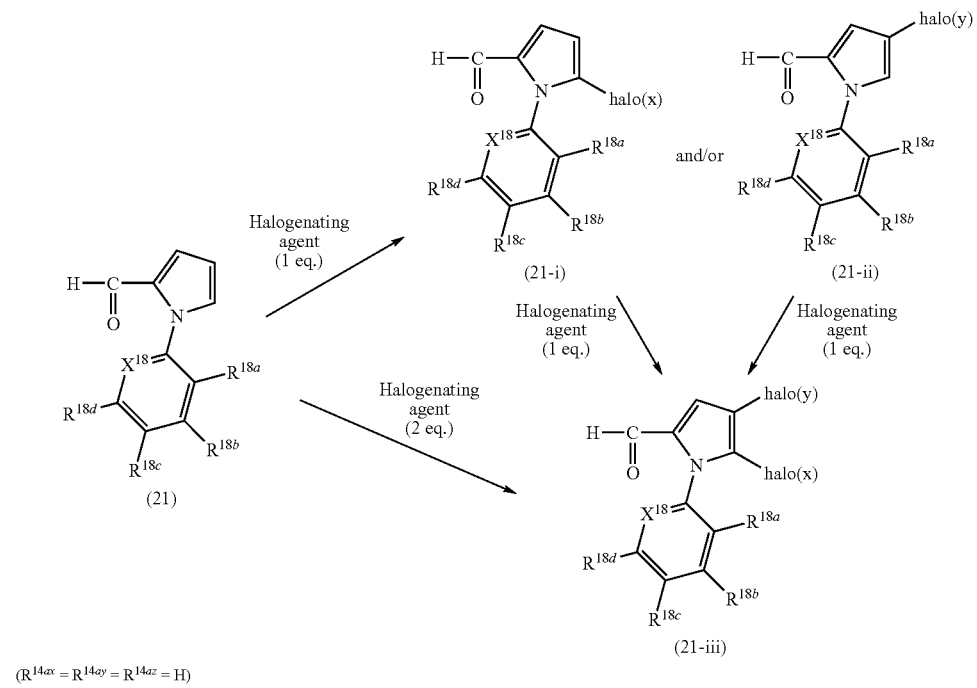

($R^{14ax} = R^{14ay} = R^{14az} = H$)

In Scheme (20), $R^{18a}$, $R^{18b}$, $R^{18c}$, $R^{18d}$, $X^{18}$, halo (x) and halo (y) are as defined above.

Among the compound (8), a compound represented by the formula (8-vi):

-continued

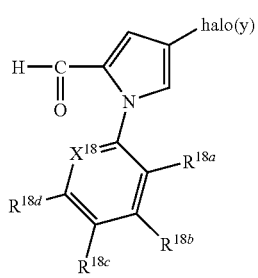

(21-ii)

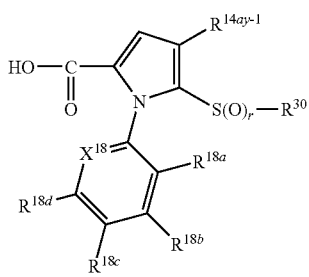

(8-vi)

wherein $R^{18a}$, $R^{18b}$, $R^{18c}$, $R^{18d}$ and $X^{18}$ are as defined above, $R^{14ay\text{-}1}$ represents a hydrogen atom or a halogen atom, $R^{30}$ represents a C1-C6 alkyl group optionally substituted with at least one halogen atom, and r represents an integer of 0 to 2, can be produced, for example, according to the process shown in the following Scheme (21).
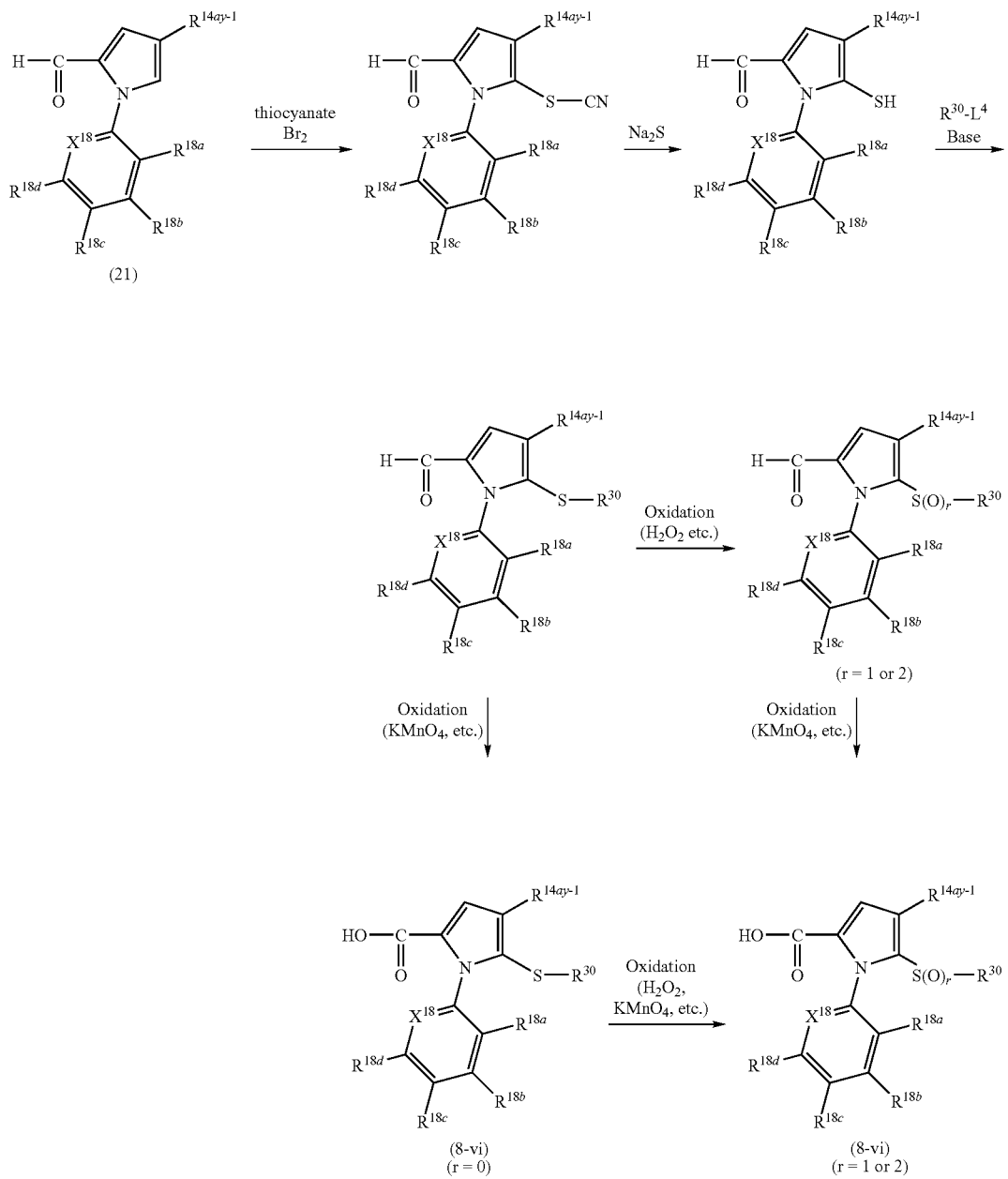

In Scheme (21), $R^{18a}$, $R^{18b}$, $R^{18c}$, $R^{18d}$, $X^{18}$, $R^{14ay-1}$, $R^{30}$, r and $L^4$ are as defined above.

The specific examples of the present compound are summarized in the following tables.

A compound represented by the formula (1-A):

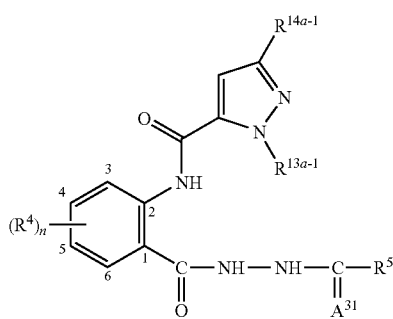

wherein $R^5$, $A^{31}$, $(R^4)_n$, $R^{13a-1}$ and $R^{14a-1}$ are combinations shown in Table 1 to Table 7.

TABLE 1

| $R^5$ | $A^{31}$ | $(R^4)_n$ | $R^{13a-1}$ | $R^{14a-1}$ |
|---|---|---|---|---|
| H | O | 3-CH₃, 5-Cl | 3-chloro-2-pyridinyl | H |
| H | O | 3-Br, 5-Cl | 3-chloro-2-pyridinyl | H |
| H | O | 3-Br, 5-Br | 3-chloro-2-pyridinyl | H |
| H | O | 3-CH₃, 5-CN | 3-chloro-2-pyridinyl | H |
| H | O | 3-CH₃, 5-Cl | 3-chloro-2-pyridinyl | Cl |
| H | O | 3-Br, 5-Cl | 3-chloro-2-pyridinyl | Cl |
| H | O | 3-Br, 5-Br | 3-chloro-2-pyridinyl | Cl |
| H | O | 3-CH₃, 5-CN | 3-chloro-2-pyridinyl | Cl |
| H | O | 3-CH₃, 5-Cl | 3-chloro-2-pyridinyl | Br |
| H | O | 3-Br, 5-Cl | 3-chloro-2-pyridinyl | Br |
| H | O | 3-Br, 5-Br | 3-chloro-2-pyridinyl | Br |
| H | O | 3-CH₃, 5-CN | 3-chloro-2-pyridinyl | Br |
| H | O | 3-CH₃, 5-Cl | 3-chloro-2-pyridinyl | CF₃ |
| H | O | 3-Br, 5-Cl | 3-chloro-2-pyridinyl | CF₃ |
| H | O | 3-Br, 5-Br | 3-chloro-2-pyridinyl | CF₃ |
| H | O | 3-CH₃, 5-CN | 3-chloro-2-pyridinyl | CF₃ |
| CH₃ | O | 3-CH₃, 5-Cl | 3-chloro-2-pyridinyl | H |
| CH₃ | O | 3-Br, 5-Cl | 3-chloro-2-pyridinyl | H |
| CH₃ | O | 3-Br, 5-Br | 3-chloro-2-pyridinyl | H |
| CH₃ | O | 3-CH₃, 5-CN | 3-chloro-2-pyridinyl | H |
| CH₃ | O | 3-CH₃, 5-Cl | 3-chloro-2-pyridinyl | Cl |
| CH₃ | O | 3-Br, 5-Cl | 3-chloro-2-pyridinyl | Cl |
| CH₃ | O | 3-Br, 5-Br | 3-chloro-2-pyridinyl | Cl |
| CH₃ | O | 3-CH₃, 5-CN | 3-chloro-2-pyridinyl | Cl |
| CH₃ | O | 3-CH₃, 5-Cl | 3-chloro-2-pyridinyl | Br |
| CH₃ | O | 3-Br, 5-Cl | 3-chloro-2-pyridinyl | Br |
| CH₃ | O | 3-Br, 5-Br | 3-chloro-2-pyridinyl | Br |
| CH₃ | O | 3-CH₃, 5-CN | 3-chloro-2-pyridinyl | Br |
| CH₃ | O | 3-CH₃, 5-Cl | 3-chloro-2-pyridinyl | CF₃ |
| CH₃ | O | 3-Br, 5-Cl | 3-chloro-2-pyridinyl | CF₃ |
| CH₃ | O | 3-Br, 5-Br | 3-chloro-2-pyridinyl | CF₃ |
| CH₃ | O | 3-CH₃, 5-CN | 3-chloro-2-pyridinyl | CF₃ |

TABLE 2

| $R^5$ | $A^{31}$ | $(R^4)_n$ | $R^{13a-1}$ | $R^{14a-1}$ |
|---|---|---|---|---|
| CH₂CH₃ | O | 3-CH₃, 5-Cl | 3-chloro-2-pyridinyl | H |
| CH₂CH₃ | O | 3-Br, 5-Cl | 3-chloro-2-pyridinyl | H |
| CH₂CH₃ | O | 3-Br, 5-Br | 3-chloro-2-pyridinyl | H |
| CH₂CH₃ | O | 3-CH₃, 5-CN | 3-chloro-2-pyridinyl | H |
| CH₂CH₃ | O | 3-CH₃, 5-Cl | 3-chloro-2-pyridinyl | Cl |
| CH₂CH₃ | O | 3-Br, 5-Cl | 3-chloro-2-pyridinyl | Cl |
| CH₂CH₃ | O | 3-Br, 5-Br | 3-chloro-2-pyridinyl | Cl |
| CH₂CH₃ | O | 3-CH₃, 5-CN | 3-chloro-2-pyridinyl | Cl |
| CH₂CH₃ | O | 3-CH₃, 5-Cl | 3-chloro-2-pyridinyl | Br |
| CH₂CH₃ | O | 3-Br, 5-Cl | 3-chloro-2-pyridinyl | Br |
| CH₂CH₃ | O | 3-Br, 5-Br | 3-chloro-2-pyridinyl | Br |

TABLE 2-continued

| $R^5$ | $A^{31}$ | $(R^4)_n$ | $R^{13a-1}$ | $R^{14a-1}$ |
|---|---|---|---|---|
| CH₂CH₃ | O | 3-CH₃, 5-CN | 3-chloro-2-pyridinyl | Br |
| CH₂CH₃ | O | 3-CH₃, 5-Cl | 3-chloro-2-pyridinyl | CF₃ |
| CH₂CH₃ | O | 3-Br, 5-Cl | 3-chloro-2-pyridinyl | CF₃ |
| CH₂CH₃ | O | 3-Br, 5-Br | 3-chloro-2-pyridinyl | CF₃ |
| CH₂CH₃ | O | 3-CH₃, 5-CN | 3-chloro-2-pyridinyl | CF₃ |
| CH(CH₃)₂ | O | 3-CH₃, 5-Cl | 3-chloro-2-pyridinyl | H |
| CH(CH₃)₂ | O | 3-Br, 5-Cl | 3-chloro-2-pyridinyl | H |
| CH(CH₃)₂ | O | 3-Br, 5-Br | 3-chloro-2-pyridinyl | H |
| CH(CH₃)₂ | O | 3-CH₃, 5-CN | 3-chloro-2-pyridinyl | H |
| CH(CH₃)₂ | O | 3-CH₃, 5-Cl | 3-chloro-2-pyridinyl | Cl |
| CH(CH₃)₂ | O | 3-Br, 5-Cl | 3-chloro-2-pyridinyl | Cl |
| CH(CH₃)₂ | O | 3-Br, 5-Br | 3-chloro-2-pyridinyl | Cl |
| CH(CH₃)₂ | O | 3-CH₃, 5-CN | 3-chloro-2-pyridinyl | Cl |
| CH(CH₃)₂ | O | 3-CH₃, 5-Cl | 3-chloro-2-pyridinyl | Br |
| CH(CH₃)₂ | O | 3-Br, 5-Cl | 3-chloro-2-pyridinyl | Br |
| CH(CH₃)₂ | O | 3-Br, 5-Br | 3-chloro-2-pyridinyl | Br |
| CH(CH₃)₂ | O | 3-CH₃, 5-CN | 3-chloro-2-pyridinyl | Br |
| CH(CH₃)₂ | O | 3-CH₃, 5-Cl | 3-chloro-2-pyridinyl | CF₃ |
| CH(CH₃)₂ | O | 3-Br, 5-Cl | 3-chloro-2-pyridinyl | CF₃ |
| CH(CH₃)₂ | O | 3-Br, 5-Br | 3-chloro-2-pyridinyl | CF₃ |
| CH(CH₃)₂ | O | 3-CH₃, 5-CN | 3-chloro-2-pyridinyl | CF₃ |

TABLE 3

| $R^5$ | $A^{31}$ | $(R^4)_n$ | $R^{13a-1}$ | $R^{14a-1}$ |
|---|---|---|---|---|
| C(CH₃)₃ | O | 3-CH₃, 5-Cl | 3-chloro-2-pyridinyl | H |
| C(CH₃)₃ | O | 3-Br, 5-Cl | 3-chloro-2-pyridinyl | H |
| C(CH₃)₃ | O | 3-Br, 5-Br | 3-chloro-2-pyridinyl | H |
| C(CH₃)₃ | O | 3-CH₃, 5-CN | 3-chloro-2-pyridinyl | H |
| C(CH₃)₃ | O | 3-CH₃, 5-Cl | 3-chloro-2-pyridinyl | Cl |
| C(CH₃)₃ | O | 3-Br, 5-Cl | 3-chloro-2-pyridinyl | Cl |
| C(CH₃)₃ | O | 3-Br, 5-Br | 3-chloro-2-pyridinyl | Cl |
| C(CH₃)₃ | O | 3-CH₃, 5-CN | 3-chloro-2-pyridinyl | Cl |
| C(CH₃)₃ | O | 3-CH₃, 5-Cl | 3-chloro-2-pyridinyl | Br |
| C(CH₃)₃ | O | 3-Br, 5-Cl | 3-chloro-2-pyridinyl | Br |
| C(CH₃)₃ | O | 3-Br, 5-Br | 3-chloro-2-pyridinyl | Br |
| C(CH₃)₃ | O | 3-CH₃, 5-CN | 3-chloro-2-pyridinyl | Br |
| C(CH₃)₃ | O | 3-CH₃, 5-Cl | 3-chloro-2-pyridinyl | CF₃ |
| C(CH₃)₃ | O | 3-Br, 5-Cl | 3-chloro-2-pyridinyl | CF₃ |
| C(CH₃)₃ | O | 3-Br, 5-Br | 3-chloro-2-pyridinyl | CF₃ |
| C(CH₃)₃ | O | 3-CH₃, 5-CN | 3-chloro-2-pyridinyl | CF₃ |
| CF₃ | O | 3-CH₃, 5-Cl | 3-chloro-2-pyridinyl | H |
| CF₃ | O | 3-Br, 5-Cl | 3-chloro-2-pyridinyl | H |
| CF₃ | O | 3-Br, 5-Br | 3-chloro-2-pyridinyl | H |
| CF₃ | O | 3-CH₃, 5-CN | 3-chloro-2-pyridinyl | H |
| CF₃ | O | 3-CH₃, 5-Cl | 3-chloro-2-pyridinyl | Cl |
| CF₃ | O | 3-Br, 5-Cl | 3-chloro-2-pyridinyl | Cl |
| CF₃ | O | 3-Br, 5-Br | 3-chloro-2-pyridinyl | Cl |
| CF₃ | O | 3-CH₃, 5-CN | 3-chloro-2-pyridinyl | Cl |
| CF₃ | O | 3-CH₃, 5-Cl | 3-chloro-2-pyridinyl | Br |
| CF₃ | O | 3-Br, 5-Cl | 3-chloro-2-pyridinyl | Br |
| CF₃ | O | 3-Br, 5-Br | 3-chloro-2-pyridinyl | Br |
| CF₃ | O | 3-CH₃, 5-CN | 3-chloro-2-pyridinyl | Br |
| CF₃ | O | 3-CH₃, 5-Cl | 3-chloro-2-pyridinyl | CF₃ |
| CF₃ | O | 3-Br, 5-Cl | 3-chloro-2-pyridinyl | CF₃ |
| CF₃ | O | 3-Br, 5-Br | 3-chloro-2-pyridinyl | CF₃ |
| CF₃ | O | 3-CH₃, 5-CN | 3-chloro-2-pyridinyl | CF₃ |

TABLE 4

| $R^5$ | $A^{31}$ | $(R^4)_n$ | $R^{13a-1}$ | $R^{14a-1}$ |
|---|---|---|---|---|
| CH₂OCH₃ | O | 3-CH₃, 5-Cl | 3-chloro-2-pyridinyl | H |
| CH₂OCH₃ | O | 3-Br, 5-Cl | 3-chloro-2-pyridinyl | H |
| CH₂OCH₃ | O | 3-Br, 5-Br | 3-chloro-2-pyridinyl | H |
| CH₂OCH₃ | O | 3-CH₃, 5-CN | 3-chloro-2-pyridinyl | H |
| CH₂OCH₃ | O | 3-CH₃, 5-Cl | 3-chloro-2-pyridinyl | Cl |
| CH₂OCH₃ | O | 3-Br, 5-Cl | 3-chloro-2-pyridinyl | Cl |
| CH₂OCH₃ | O | 3-Br, 5-Br | 3-chloro-2-pyridinyl | Cl |
| CH₂OCH₃ | O | 3-CH₃, 5-CN | 3-chloro-2-pyridinyl | Cl |
| CH₂OCH₃ | O | 3-CH₃, 5-Cl | 3-chloro-2-pyridinyl | Br |

TABLE 4-continued

| R⁵ | A³¹ | (R⁴)ₙ | R¹³ᵃ⁻¹ | R¹⁴ᵃ⁻¹ |
|---|---|---|---|---|
| CH₂OCH₃ | O | 3-Br, 5-Cl | 3-chloro-2-pyridinyl | Br |
| CH₂OCH₃ | O | 3-Br, 5-Br | 3-chloro-2-pyridinyl | Br |
| CH₂OCH₃ | O | 3-CH₃, 5-CN | 3-chloro-2-pyridinyl | Br |
| CH₂OCH₃ | O | 3-CH₃, 5-Cl | 3-chloro-2-pyridinyl | CF₃ |
| CH₂OCH₃ | O | 3-Br, 5-Cl | 3-chloro-2-pyridinyl | CF₃ |
| CH₂OCH₃ | O | 3-Br, 5-Br | 3-chloro-2-pyridinyl | CF₃ |
| CH₂OCH₃ | O | 3-CH₃, 5-CN | 3-chloro-2-pyridinyl | CF₃ |
| CH₂SCH₃ | O | 3-CH₃, 5-Cl | 3-chloro-2-pyridinyl | H |
| CH₂SCH₃ | O | 3-Br, 5-Cl | 3-chloro-2-pyridinyl | H |
| CH₂SCH₃ | O | 3-Br, 5-Br | 3-chloro-2-pyridinyl | H |
| CH₂SCH₃ | O | 3-CH₃, 5-CN | 3-chloro-2-pyridinyl | H |
| CH₂SCH₃ | O | 3-CH₃, 5-Cl | 3-chloro-2-pyridinyl | Cl |
| CH₂SCH₃ | O | 3-Br, 5-Cl | 3-chloro-2-pyridinyl | Cl |
| CH₂SCH₃ | O | 3-Br, 5-Br | 3-chloro-2-pyridinyl | Cl |
| CH₂SCH₃ | O | 3-CH₃, 5-CN | 3-chloro-2-pyridinyl | Cl |
| CH₂SCH₃ | O | 3-CH₃, 5-Cl | 3-chloro-2-pyridinyl | Br |
| CH₂SCH₃ | O | 3-Br, 5-Cl | 3-chloro-2-pyridinyl | Br |
| CH₂SCH₃ | O | 3-Br, 5-Br | 3-chloro-2-pyridinyl | Br |
| CH₂SCH₃ | O | 3-CH₃, 5-CN | 3-chloro-2-pyridinyl | Br |
| CH₂SCH₃ | O | 3-CH₃, 5-Cl | 3-chloro-2-pyridinyl | CF₃ |
| CH₂SCH₃ | O | 3-Br, 5-Cl | 3-chloro-2-pyridinyl | CF₃ |
| CH₂SCH₃ | O | 3-Br, 5-Br | 3-chloro-2-pyridinyl | CF₃ |
| CH₂SCH₃ | O | 3-CH₃, 5-CN | 3-chloro-2-pyridinyl | CF₃ |

TABLE 5

| R⁵ | A³¹ | (R⁴)ₙ | R¹³ᵃ⁻¹ | R¹⁴ᵃ⁻¹ |
|---|---|---|---|---|
| CH₂N(CH₃)₂ | O | 3-CH₃, 5-Cl | 3-chloro-2-pyridinyl | H |
| CH₂N(CH₃)₂ | O | 3-Br, 5-Cl | 3-chloro-2-pyridinyl | H |
| CH₂N(CH₃)₂ | O | 3-Br, 5-Br | 3-chloro-2-pyridinyl | H |
| CH₂N(CH₃)₂ | O | 3-CH₃, 5-CN | 3-chloro-2-pyridinyl | H |
| CH₂N(CH₃)₂ | O | 3-CH₃, 5-Cl | 3-chloro-2-pyridinyl | Cl |
| CH₂N(CH₃)₂ | O | 3-Br, 5-Cl | 3-chloro-2-pyridinyl | Cl |
| CH₂N(CH₃)₂ | O | 3-Br, 5-Br | 3-chloro-2-pyridinyl | Cl |
| CH₂N(CH₃)₂ | O | 3-CH₃, 5-CN | 3-chloro-2-pyridinyl | Cl |
| CH₂N(CH₃)₂ | O | 3-CH₃, 5-Cl | 3-chloro-2-pyridinyl | Br |
| CH₂N(CH₃)₂ | O | 3-Br, 5-Cl | 3-chloro-2-pyridinyl | Br |
| CH₂N(CH₃)₂ | O | 3-Br, 5-Br | 3-chloro-2-pyridinyl | Br |
| CH₂N(CH₃)₂ | O | 3-CH₃, 5-CN | 3-chloro-2-pyridinyl | Br |
| CH₂N(CH₃)₂ | O | 3-CH₃, 5-Cl | 3-chloro-2-pyridinyl | CF₃ |
| CH₂N(CH₃)₂ | O | 3-Br, 5-Cl | 3-chloro-2-pyridinyl | CF₃ |
| CH₂N(CH₃)₂ | O | 3-Br, 5-Br | 3-chloro-2-pyridinyl | CF₃ |
| CH₂N(CH₃)₂ | O | 3-CH₃, 5-CN | 3-chloro-2-pyridinyl | CF₃ |
| cyclopropyl | O | 3-CH₃, 5-Cl | 3-chloro-2-pyridinyl | H |
| cyclopropyl | O | 3-Br, 5-Cl | 3-chloro-2-pyridinyl | H |
| cyclopropyl | O | 3-Br, 5-Br | 3-chloro-2-pyridinyl | H |
| cyclopropyl | O | 3-CH₃, 5-CN | 3-chloro-2-pyridinyl | H |
| cyclopropyl | O | 3-CH₃, 5-Cl | 3-chloro-2-pyridinyl | Cl |
| cyclopropyl | O | 3-Br, 5-Cl | 3-chloro-2-pyridinyl | Cl |
| cyclopropyl | O | 3-Br, 5-Br | 3-chloro-2-pyridinyl | Cl |
| cyclopropyl | O | 3-CH₃, 5-CN | 3-chloro-2-pyridinyl | Cl |
| cyclopropyl | O | 3-CH₃, 5-Cl | 3-chloro-2-pyridinyl | Br |
| cyclopropyl | O | 3-Br, 5-Cl | 3-chloro-2-pyridinyl | Br |
| cyclopropyl | O | 3-Br, 5-Br | 3-chloro-2-pyridinyl | Br |
| cyclopropyl | O | 3-CH₃, 5-CN | 3-chloro-2-pyridinyl | Br |
| cyclopropyl | O | 3-CH₃, 5-Cl | 3-chloro-2-pyridinyl | CF₃ |
| cyclopropyl | O | 3-Br, 5-Cl | 3-chloro-2-pyridinyl | CF₃ |
| cyclopropyl | O | 3-Br, 5-Br | 3-chloro-2-pyridinyl | CF₃ |
| cyclopropyl | O | 3-CH₃, 5-CN | 3-chloro-2-pyridinyl | CF₃ |

TABLE 6

| R⁵ | A³¹ | (R⁴)ₙ | R¹³ᵃ⁻¹ | R¹⁴ᵃ⁻¹ |
|---|---|---|---|---|
| cyclobutyl | O | 3-CH₃, 5-Cl | 3-chloro-2-pyridinyl | H |
| cyclobutyl | O | 3-Br, 5-Cl | 3-chloro-2-pyridinyl | H |
| cyclobutyl | O | 3-Br, 5-Br | 3-chloro-2-pyridinyl | H |
| cyclobutyl | O | 3-CH₃, 5-CN | 3-chloro-2-pyridinyl | H |
| cyclobutyl | O | 3-CH₃, 5-Cl | 3-chloro-2-pyridinyl | Cl |
| cyclobutyl | O | 3-Br, 5-Cl | 3-chloro-2-pyridinyl | Cl |
| cyclobutyl | O | 3-Br, 5-Br | 3-chloro-2-pyridinyl | Cl |
| cyclobutyl | O | 3-CH₃, 5-CN | 3-chloro-2-pyridinyl | Cl |
| cyclobutyl | O | 3-CH₃, 5-Cl | 3-chloro-2-pyridinyl | Br |
| cyclobutyl | O | 3-Br, 5-Cl | 3-chloro-2-pyridinyl | Br |
| cyclobutyl | O | 3-Br, 5-Br | 3-chloro-2-pyridinyl | Br |
| cyclobutyl | O | 3-CH₃, 5-CN | 3-chloro-2-pyridinyl | Br |
| cyclobutyl | O | 3-CH₃, 5-Cl | 3-chloro-2-pyridinyl | CF₃ |
| cyclobutyl | O | 3-Br, 5-Cl | 3-chloro-2-pyridinyl | CF₃ |
| cyclobutyl | O | 3-Br, 5-Br | 3-chloro-2-pyridinyl | CF₃ |
| cyclobutyl | O | 3-CH₃, 5-CN | 3-chloro-2-pyridinyl | CF₃ |
| cyclopentyl | O | 3-CH₃, 5-Cl | 3-chloro-2-pyridinyl | H |
| cyclopentyl | O | 3-Br, 5-Cl | 3-chloro-2-pyridinyl | H |
| cyclopentyl | O | 3-Br, 5-Br | 3-chloro-2-pyridinyl | H |
| cyclopentyl | O | 3-CH₃, 5-CN | 3-chloro-2-pyridinyl | H |
| cyclopentyl | O | 3-CH₃, 5-Cl | 3-chloro-2-pyridinyl | Cl |
| cyclopentyl | O | 3-Br, 5-Cl | 3-chloro-2-pyridinyl | Cl |
| cyclopentyl | O | 3-Br, 5-Br | 3-chloro-2-pyridinyl | Cl |
| cyclopentyl | O | 3-CH₃, 5-CN | 3-chloro-2-pyridinyl | Cl |
| cyclopentyl | O | 3-CH₃, 5-Cl | 3-chloro-2-pyridinyl | Br |
| cyclopentyl | O | 3-Br, 5-Cl | 3-chloro-2-pyridinyl | Br |
| cyclopentyl | O | 3-Br, 5-Br | 3-chloro-2-pyridinyl | Br |
| cyclopentyl | O | 3-CH₃, 5-CN | 3-chloro-2-pyridinyl | Br |
| cyclopentyl | O | 3-CH₃, 5-Cl | 3-chloro-2-pyridinyl | CF₃ |
| cyclopentyl | O | 3-Br, 5-Cl | 3-chloro-2-pyridinyl | CF₃ |
| cyclopentyl | O | 3-Br, 5-Br | 3-chloro-2-pyridinyl | CF₃ |
| cyclopentyl | O | 3-CH₃, 5-CN | 3-chloro-2-pyridinyl | CF₃ |

TABLE 7

| R⁵ | A³¹ | (R⁴)ₙ | R¹³ᵃ⁻¹ | R¹⁴ᵃ⁻¹ |
|---|---|---|---|---|
| cyclohexyl | O | 3-CH₃, 5-Cl | 3-chloro-2-pyridinyl | H |
| cyclohexyl | O | 3-Br, 5-Cl | 3-chloro-2-pyridinyl | H |
| cyclohexyl | O | 3-Br, 5-Br | 3-chloro-2-pyridinyl | H |
| cyclohexyl | O | 3-CH₃, 5-CN | 3-chloro-2-pyridinyl | H |
| cyclohexyl | O | 3-CH₃, 5-Cl | 3-chloro-2-pyridinyl | Cl |
| cyclohexyl | O | 3-Br, 5-Cl | 3-chloro-2-pyridinyl | Cl |
| cyclohexyl | O | 3-Br, 5-Br | 3-chloro-2-pyridinyl | Cl |
| cyclohexyl | O | 3-CH₃, 5-CN | 3-chloro-2-pyridinyl | Cl |
| cyclohexyl | O | 3-CH₃, 5-Cl | 3-chloro-2-pyridinyl | Br |
| cyclohexyl | O | 3-Br, 5-Cl | 3-chloro-2-pyridinyl | Br |
| cyclohexyl | O | 3-Br, 5-Br | 3-chloro-2-pyridinyl | Br |
| cyclohexyl | O | 3-CH₃, 5-CN | 3-chloro-2-pyridinyl | Br |
| cyclohexyl | O | 3-CH₃, 5-Cl | 3-chloro-2-pyridinyl | CF₃ |
| cyclohexyl | O | 3-Br, 5-Cl | 3-chloro-2-pyridinyl | CF₃ |
| cyclohexyl | O | 3-Br, 5-Br | 3-chloro-2-pyridinyl | CF₃ |
| cyclohexyl | O | 3-CH₃, 5-CN | 3-chloro-2-pyridinyl | CF₃ |
| phenyl | O | 3-CH₃, 5-Cl | 3-chloro-2-pyridinyl | H |
| phenyl | O | 3-Br, 5-Cl | 3-chloro-2-pyridinyl | H |
| phenyl | O | 3-Br, 5-Br | 3-chloro-2-pyridinyl | H |
| phenyl | O | 3-CH₃, 5-CN | 3-chloro-2-pyridinyl | H |
| phenyl | O | 3-CH₃, 5-Cl | 3-chloro-2-pyridinyl | Cl |
| phenyl | O | 3-Br, 5-Cl | 3-chloro-2-pyridinyl | Cl |
| phenyl | O | 3-Br, 5-Br | 3-chloro-2-pyridinyl | Cl |
| phenyl | O | 3-CH₃, 5-CN | 3-chloro-2-pyridinyl | Cl |
| phenyl | O | 3-CH₃, 5-Cl | 3-chloro-2-pyridinyl | Br |
| phenyl | O | 3-Br, 5-Cl | 3-chloro-2-pyridinyl | Br |
| phenyl | O | 3-Br, 5-Br | 3-chloro-2-pyridinyl | Br |
| phenyl | O | 3-CH₃, 5-CN | 3-chloro-2-pyridinyl | Br |
| phenyl | O | 3-CH₃, 5-Cl | 3-chloro-2-pyridinyl | CF₃ |
| phenyl | O | 3-Br, 5-Cl | 3-chloro-2-pyridinyl | CF₃ |
| phenyl | O | 3-Br, 5-Br | 3-chloro-2-pyridinyl | CF₃ |
| phenyl | O | 3-CH₃, 5-CN | 3-chloro-2-pyridinyl | CF₃ |

A compound represented by the formula (1-B):

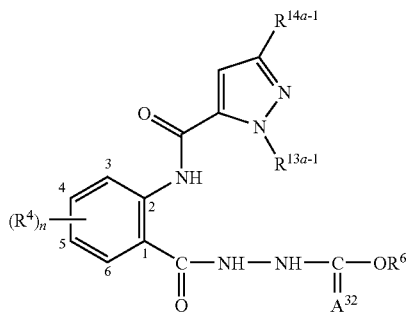

(1-B)

wherein $R^6$, $A^{32}$, $(R^4)_n$, $R^{13a-1}$ and $R^{14a-1}$ represent combinations shown in Table 8 to Table 31.

TABLE 8

| $R^6$ | $A^{32}$ | $(R^4)_n$ | $R^{13a-1}$ | $R^{14a-1}$ |
|---|---|---|---|---|
| CH₃ | O | 3-CH₃ | 3-chloro-2-pyridinyl | H |
| CH₃ | O | 3-CH₃, 5-Cl | 3-chloro-2-pyridinyl | H |
| CH₃ | O | 3-CH₃, 5-Br | 3-chloro-2-pyridinyl | H |
| CH₃ | O | 3-CH₃, 5-I | 3-chloro-2-pyridinyl | H |
| CH₃ | O | 3-CH₃, 5-CH₃ | 3-chloro-2-pyridinyl | H |
| CH₃ | O | 3-CH₃, 5-CN | 3-chloro-2-pyridinyl | H |
| CH₃ | O | 3-Cl | 3-chloro-2-pyridinyl | H |
| CH₃ | O | 3-Cl, 5-Cl | 3-chloro-2-pyridinyl | H |
| CH₃ | O | 3-Cl, 5-Br | 3-chloro-2-pyridinyl | H |
| CH₃ | O | 3-Cl, 5-I | 3-chloro-2-pyridinyl | H |
| CH₃ | O | 3-Cl, 5-CH₃ | 3-chloro-2-pyridinyl | H |
| CH₃ | O | 3-Cl, 5-CN | 3-chloro-2-pyridinyl | H |
| CH₃ | O | 3-Br | 3-chloro-2-pyridinyl | H |
| CH₃ | O | 3-Br, 5-Cl | 3-chloro-2-pyridinyl | H |
| CH₃ | O | 3-Br, 5-Br | 3-chloro-2-pyridinyl | H |
| CH₃ | O | 3-Br, 5-I | 3-chloro-2-pyridinyl | H |
| CH₃ | O | 3-Br, 5-CH₃ | 3-chloro-2-pyridinyl | H |
| CH₃ | O | 3-Br, 5-CN | 3-chloro-2-pyridinyl | H |
| CH₃ | O | 3-I | 3-chloro-2-pyridinyl | H |
| CH₃ | O | 3-I, 5-Cl | 3-chloro-2-pyridinyl | H |
| CH₃ | O | 3-I, 5-Br | 3-chloro-2-pyridinyl | H |
| CH₃ | O | 3-I, 5-I | 3-chloro-2-pyridinyl | H |
| CH₃ | O | 3-I, 5-CH₃ | 3-chloro-2-pyridinyl | H |
| CH₃ | O | 3-I, 5-CN | 3-chloro-2-pyridinyl | H |

TABLE 9

| $R^6$ | $A^{32}$ | $(R^4)_n$ | $R^{13a-1}$ | $R^{14a-1}$ |
|---|---|---|---|---|
| CH₃ | O | 3-CH₃ | 3-chloro-2-pyridinyl | F |
| CH₃ | O | 3-CH₃, 5-Cl | 3-chloro-2-pyridinyl | F |
| CH₃ | O | 3-CH₃, 5-Br | 3-chloro-2-pyridinyl | F |
| CH₃ | O | 3-CH₃, 5-I | 3-chloro-2-pyridinyl | F |
| CH₃ | O | 3-CH₃, 5-CH₃ | 3-chloro-2-pyridinyl | F |
| CH₃ | O | 3-CH₃, 5-CN | 3-chloro-2-pyridinyl | F |
| CH₃ | O | 3-Cl | 3-chloro-2-pyridinyl | F |
| CH₃ | O | 3-Cl, 5-Cl | 3-chloro-2-pyridinyl | F |
| CH₃ | O | 3-Cl, 5-Br | 3-chloro-2-pyridinyl | F |
| CH₃ | O | 3-Cl, 5-I | 3-chloro-2-pyridinyl | F |
| CH₃ | O | 3-Cl, 5-CH₃ | 3-chloro-2-pyridinyl | F |
| CH₃ | O | 3-Cl, 5-CN | 3-chloro-2-pyridinyl | F |
| CH₃ | O | 3-Br | 3-chloro-2-pyridinyl | F |
| CH₃ | O | 3-Br, 5-Cl | 3-chloro-2-pyridinyl | F |
| CH₃ | O | 3-Br, 5-Br | 3-chloro-2-pyridinyl | F |
| CH₃ | O | 3-Br, 5-I | 3-chloro-2-pyridinyl | F |
| CH₃ | O | 3-Br, 5-CH₃ | 3-chloro-2-pyridinyl | F |
| CH₃ | O | 3-Br, 5-CN | 3-chloro-2-pyridinyl | F |
| CH₃ | O | 3-I | 3-chloro-2-pyridinyl | F |
| CH₃ | O | 3-I, 5-Cl | 3-chloro-2-pyridinyl | F |
| CH₃ | O | 3-I, 5-Br | 3-chloro-2-pyridinyl | F |

TABLE 9-continued

| $R^6$ | $A^{32}$ | $(R^4)_n$ | $R^{13a-1}$ | $R^{14a-1}$ |
|---|---|---|---|---|
| CH₃ | O | 3-I, 5-I | 3-chloro-2-pyridinyl | F |
| CH₃ | O | 3-I, 5-CH₃ | 3-chloro-2-pyridinyl | F |
| CH₃ | O | 3-I, 5-CN | 3-chloro-2-pyridinyl | F |

TABLE 10

| $R^6$ | $A^{32}$ | $(R^4)_n$ | $R^{13a-1}$ | $R^{14a-1}$ |
|---|---|---|---|---|
| CH₃ | O | 3-CH₃ | 3-chloro-2-pyridinyl | Cl |
| CH₃ | O | 3-CH₃, 5-Cl | 3-chloro-2-pyridinyl | Cl |
| CH₃ | O | 3-CH₃, 5-Br | 3-chloro-2-pyridinyl | Cl |
| CH₃ | O | 3-CH₃, 5-I | 3-chloro-2-pyridinyl | Cl |
| CH₃ | O | 3-CH₃, 5-CH₃ | 3-chloro-2-pyridinyl | Cl |
| CH₃ | O | 3-CH₃, 5-CN | 3-chloro-2-pyridinyl | Cl |
| CH₃ | O | 3-Cl | 3-chloro-2-pyridinyl | Cl |
| CH₃ | O | 3-Cl, 5-Cl | 3-chloro-2-pyridinyl | Cl |
| CH₃ | O | 3-Cl, 5-Br | 3-chloro-2-pyridinyl | Cl |
| CH₃ | O | 3-Cl, 5-I | 3-chloro-2-pyridinyl | Cl |
| CH₃ | O | 3-Cl, 5-CH₃ | 3-chloro-2-pyridinyl | Cl |
| CH₃ | O | 3-Cl, 5-CN | 3-chloro-2-pyridinyl | Cl |
| CH₃ | O | 3-Br | 3-chloro-2-pyridinyl | Cl |
| CH₃ | O | 3-Br, 5-Cl | 3-chloro-2-pyridinyl | Cl |
| CH₃ | O | 3-Br, 5-Br | 3-chloro-2-pyridinyl | Cl |
| CH₃ | O | 3-Br, 5-I | 3-chloro-2-pyridinyl | Cl |
| CH₃ | O | 3-Br, 5-CH₃ | 3-chloro-2-pyridinyl | Cl |
| CH₃ | O | 3-Br, 5-CN | 3-chloro-2-pyridinyl | Cl |
| CH₃ | O | 3-I | 3-chloro-2-pyridinyl | Cl |
| CH₃ | O | 3-I, 5-Cl | 3-chloro-2-pyridinyl | Cl |
| CH₃ | O | 3-I, 5-Br | 3-chloro-2-pyridinyl | Cl |
| CH₃ | O | 3-I, 5-I | 3-chloro-2-pyridinyl | Cl |
| CH₃ | O | 3-I, 5-CH₃ | 3-chloro-2-pyridinyl | Cl |
| CH₃ | O | 3-I, 5-CN | 3-chloro-2-pyridinyl | Cl |

TABLE 11

| $R^6$ | $A^{32}$ | $(R^4)_n$ | $R^{13a-1}$ | $R^{14a-1}$ |
|---|---|---|---|---|
| CH₃ | O | 3-CH₂CH₃ | 3-chloro-2-pyridinyl | Cl |
| CH₃ | O | 3-CH(CH₃)₂ | 3-chloro-2-pyridinyl | Cl |
| CH₃ | O | 3-C(CH₃)₃ | 3-chloro-2-pyridinyl | Cl |
| CH₃ | O | 3-CF₃ | 3-chloro-2-pyridinyl | Cl |
| CH₃ | O | 3-OCH₃ | 3-chloro-2-pyridinyl | Cl |
| CH₃ | O | 3-phenyl | 3-chloro-2-pyridinyl | Cl |
| CH₃ | O | 3-CH₂CH₃, 5-Cl | 3-chloro-2-pyridinyl | Cl |
| CH₃ | O | 3-CH(CH₃)₂, 5-Cl | 3-chloro-2-pyridinyl | Cl |
| CH₃ | O | 3-C(CH₃)₃, 5-Cl | 3-chloro-2-pyridinyl | Cl |
| CH₃ | O | 3-CF₃, 5-Cl | 3-chloro-2-pyridinyl | Cl |
| CH₃ | O | 3-OCH₃, 5-Cl | 3-chloro-2-pyridinyl | Cl |
| CH₃ | O | 3-phenyl, 5-Cl | 3-chloro-2-pyridinyl | Cl |
| CH₃ | O | 3-CH₃, 4-Cl | 3-chloro-2-pyridinyl | Cl |
| CH₃ | O | 3-Cl, 4-Cl | 3-chloro-2-pyridinyl | Cl |
| CH₃ | O | 3-CH₃, 6-Cl | 3-chloro-2-pyridinyl | Cl |
| CH₃ | O | 3-Cl, 6-Cl | 3-chloro-2-pyridinyl | Cl |
| CH₃ | O | 3-CH₃, 4-Cl, 5-Cl | 3-chloro-2-pyridinyl | Cl |
| CH₃ | O | 3-Cl, 4-Cl, 5-Cl | 3-chloro-2-pyridinyl | Cl |
| CH₃ | O | 3-CH₃, 5-Cl, 6-Cl | 3-chloro-2-pyridinyl | Cl |
| CH₃ | O | 3-Cl, 5-Cl, 6-Cl | 3-chloro-2-pyridinyl | Cl |
| CH₃ | O | 3-CH₃, 5-F | 3-chloro-2-pyridinyl | Cl |
| CH₃ | O | 3-Cl, 5-F | 3-chloro-2-pyridinyl | Cl |
| CH₃ | O | 3-Br, 5-F | 3-chloro-2-pyridinyl | Cl |
| CH₃ | O | 3-I, 5-F | 3-chloro-2-pyridinyl | Cl |
| CH₃ | O | 3-Me,4,5-CH=CH—CH=CH— | 3-chloro-2-pyridinyl | Cl |
| CH₃ | O | 3-Cl,4,5-CH=CH—CH=CH— | 3-chloro-2-pyridinyl | Cl |
| CH₃ | O | 3-Br,4,5-CH=CH—CH=CH— | 3-chloro-2-pyridinyl | Cl |
| CH₃ | O | 3-I,4,5-CH=CH—CH=CH— | 3-chloro-2-pyridinyl | Cl |

TABLE 12

| $R^6$ | $A^{32}$ | $(R^4)_n$ | $R^{13a-1}$ | $R^{14a-1}$ |
|---|---|---|---|---|
| CH$_3$ | O | 3-CH$_3$ | 3-chloro-2-pyridinyl | Br |
| CH$_3$ | O | 3-CH$_3$, 5-Cl | 3-chloro-2-pyridinyl | Br |
| CH$_3$ | O | 3-CH$_3$, 5-Br | 3-chloro-2-pyridinyl | Br |
| CH$_3$ | O | 3-CH$_3$, 5-I | 3-chloro-2-pyridinyl | Br |
| CH$_3$ | O | 3-CH$_3$, 5-CH$_3$ | 3-chloro-2-pyridinyl | Br |
| CH$_3$ | O | 3-CH$_3$, 5-CN | 3-chloro-2-pyridinyl | Br |
| CH$_3$ | O | 3-Cl | 3-chloro-2-pyridinyl | Br |
| CH$_3$ | O | 3-Cl, 5-Cl | 3-chloro-2-pyridinyl | Br |
| CH$_3$ | O | 3-Cl, 5-Br | 3-chloro-2-pyridinyl | Br |
| CH$_3$ | O | 3-Cl, 5-I | 3-chloro-2-pyridinyl | Br |
| CH$_3$ | O | 3-Cl, 5-CH$_3$ | 3-chloro-2-pyridinyl | Br |
| CH$_3$ | O | 3-Cl, 5-CN | 3-chloro-2-pyridinyl | Br |
| CH$_3$ | O | 3-Br | 3-chloro-2-pyridinyl | Br |
| CH$_3$ | O | 3-Br, 5-Cl | 3-chloro-2-pyridinyl | Br |
| CH$_3$ | O | 3-Br, 5-Br | 3-chloro-2-pyridinyl | Br |
| CH$_3$ | O | 3-Br, 5-I | 3-chloro-2-pyridinyl | Br |
| CH$_3$ | O | 3-Br, 5-CH$_3$ | 3-chloro-2-pyridinyl | Br |
| CH$_3$ | O | 3-Br, 5-CN | 3-chloro-2-pyridinyl | Br |
| CH$_3$ | O | 3-I | 3-chloro-2-pyridinyl | Br |
| CH$_3$ | O | 3-I, 5-Cl | 3-chloro-2-pyridinyl | Br |
| CH$_3$ | O | 3-I, 5-Br | 3-chloro-2-pyridinyl | Br |
| CH$_3$ | O | 3-I, 5-I | 3-chloro-2-pyridinyl | Br |
| CH$_3$ | O | 3-I, 5-CH$_3$ | 3-chloro-2-pyridinyl | Br |
| CH$_3$ | O | 3-I, 5-CN | 3-chloro-2-pyridinyl | Br |

TABLE 13

| $R^6$ | $A^{32}$ | $(R^4)_n$ | $R^{13a-1}$ | $R^{14a-1}$ |
|---|---|---|---|---|
| CH$_3$ | O | 3-CH$_2$CH$_3$ | 3-chloro-2-pyridinyl | Br |
| CH$_3$ | O | 3-CH(CH$_3$)$_2$ | 3-chloro-2-pyridinyl | Br |
| CH$_3$ | O | 3-C(CH$_3$)$_3$ | 3-chloro-2-pyridinyl | Br |
| CH$_3$ | O | 3-CF$_3$ | 3-chloro-2-pyridinyl | Br |
| CH$_3$ | O | 3-OCH$_3$ | 3-chloro-2-pyridinyl | Br |
| CH$_3$ | O | 3-phenyl | 3-chloro-2-pyridinyl | Br |
| CH$_3$ | O | 3-CH$_2$CH$_3$, 5-Cl | 3-chloro-2-pyridinyl | Br |
| CH$_3$ | O | 3-CH(CH$_3$)$_2$, 5-Cl | 3-chloro-2-pyridinyl | Br |
| CH$_3$ | O | 3-C(CH$_3$)$_3$, 5-Cl | 3-chloro-2-pyridinyl | Br |
| CH$_3$ | O | 3-CF$_3$, 5-Cl | 3-chloro-2-pyridinyl | Br |
| CH$_3$ | O | 3-OCH$_3$, 5-Cl | 3-chloro-2-pyridinyl | Br |
| CH$_3$ | O | 3-phenyl, 5-Cl | 3-chloro-2-pyridinyl | Br |
| CH$_3$ | O | 3-CH$_3$, 4-Cl | 3-chloro-2-pyridinyl | Br |
| CH$_3$ | O | 3-Cl, 4-Cl | 3-chloro-2-pyridinyl | Br |
| CH$_3$ | O | 3-CH$_3$, 6-Cl | 3-chloro-2-pyridinyl | Br |
| CH$_3$ | O | 3-Cl, 6-Cl | 3-chloro-2-pyridinyl | Br |
| CH$_3$ | O | 3-CH$_3$, 4-Cl, 5-Cl | 3-chloro-2-pyridinyl | Br |
| CH$_3$ | O | 3-Cl, 4-Cl, 5-Cl | 3-chloro-2-pyridinyl | Br |
| CH$_3$ | O | 3-CH$_3$, 5-Cl, 6-Cl | 3-chloro-2-pyridinyl | Br |
| CH$_3$ | O | 3-Cl, 5-Cl, 6-Cl | 3-chloro-2-pyridinyl | Br |
| CH$_3$ | O | 3-CH$_3$, 5-F | 3-chloro-2-pyridinyl | Br |
| CH$_3$ | O | 3-Cl, 5-F | 3-chloro-2-pyridinyl | Br |
| CH$_3$ | O | 3-Br, 5-F | 3-chloro-2-pyridinyl | Br |
| CH$_3$ | O | 3-I, 5-F | 3-chloro-2-pyridinyl | Br |
| CH$_3$ | O | 3-Me,4,5-CH=CH—CH=CH— | 3-chloro-2-pyridinyl | Br |
| CH$_3$ | O | 3-Cl,4,5-CH=CH—CH=CH— | 3-chloro-2-pyridinyl | Br |
| CH$_3$ | O | 3-Br,4,5-CH=CH—CH=CH— | 3-chloro-2-pyridinyl | Br |
| CH$_3$ | O | 3-I,4,5-CH=CH—CH=CH— | 3-chloro-2-pyridinyl | Br |

TABLE 14

| $R^6$ | $A^{32}$ | $(R^4)_n$ | $R^{13a-1}$ | $R^{14a-1}$ |
|---|---|---|---|---|
| CH$_3$ | O | 3-CH$_3$ | 3-chloro-2-pyridinyl | I |
| CH$_3$ | O | 3-CH$_3$, 5-Cl | 3-chloro-2-pyridinyl | I |
| CH$_3$ | O | 3-CH$_3$, 5-Br | 3-chloro-2-pyridinyl | I |
| CH$_3$ | O | 3-CH$_3$, 5-I | 3-chloro-2-pyridinyl | I |
| CH$_3$ | O | 3-CH$_3$, 5-CH$_3$ | 3-chloro-2-pyridinyl | I |
| CH$_3$ | O | 3-CH$_3$, 5-CN | 3-chloro-2-pyridinyl | I |

TABLE 14-continued

| $R^6$ | $A^{32}$ | $(R^4)_n$ | $R^{13a-1}$ | $R^{14a-1}$ |
|---|---|---|---|---|
| CH$_3$ | O | 3-Cl | 3-chloro-2-pyridinyl | I |
| CH$_3$ | O | 3-Cl, 5-Cl | 3-chloro-2-pyridinyl | I |
| CH$_3$ | O | 3-Cl, 5-Br | 3-chloro-2-pyridinyl | I |
| CH$_3$ | O | 3-Cl, 5-I | 3-chloro-2-pyridinyl | I |
| CH$_3$ | O | 3-Cl, 5-CH$_3$ | 3-chloro-2-pyridinyl | I |
| CH$_3$ | O | 3-Cl, 5-CN | 3-chloro-2-pyridinyl | I |
| CH$_3$ | O | 3-Br | 3-chloro-2-pyridinyl | I |
| CH$_3$ | O | 3-Br, 5-Cl | 3-chloro-2-pyridinyl | I |
| CH$_3$ | O | 3-Br, 5-Br | 3-chloro-2-pyridinyl | I |
| CH$_3$ | O | 3-Br, 5-I | 3-chloro-2-pyridinyl | I |
| CH$_3$ | O | 3-Br, 5-CH$_3$ | 3-chloro-2-pyridinyl | I |
| CH$_3$ | O | 3-Br, 5-CN | 3-chloro-2-pyridinyl | I |
| CH$_3$ | O | 3-I | 3-chloro-2-pyridinyl | I |
| CH$_3$ | O | 3-I, 5-Cl | 3-chloro-2-pyridinyl | I |
| CH$_3$ | O | 3-I, 5-Br | 3-chloro-2-pyridinyl | I |
| CH$_3$ | O | 3-I, 5-I | 3-chloro-2-pyridinyl | I |
| CH$_3$ | O | 3-I, 5-CH$_3$ | 3-chloro-2-pyridinyl | I |
| CH$_3$ | O | 3-I, 5-CN | 3-chloro-2-pyridinyl | I |

TABLE 15

| $R^6$ | $A^{32}$ | $(R^4)_n$ | $R^{13a-1}$ | $R^{14a-1}$ |
|---|---|---|---|---|
| CH$_3$ | O | 3-CH$_3$ | 3-chloro-2-pyridinyl | CH$_3$ |
| CH$_3$ | O | 3-CH$_3$, 5-Cl | 3-chloro-2-pyridinyl | CH$_3$ |
| CH$_3$ | O | 3-CH$_3$, 5-Br | 3-chloro-2-pyridinyl | CH$_3$ |
| CH$_3$ | O | 3-CH$_3$, 5-I | 3-chloro-2-pyridinyl | CH$_3$ |
| CH$_3$ | O | 3-CH$_3$, 5-CH$_3$ | 3-chloro-2-pyridinyl | CH$_3$ |
| CH$_3$ | O | 3-CH$_3$, 5-CN | 3-chloro-2-pyridinyl | CH$_3$ |
| CH$_3$ | O | 3-Cl | 3-chloro-2-pyridinyl | CH$_3$ |
| CH$_3$ | O | 3-Cl, 5-Cl | 3-chloro-2-pyridinyl | CH$_3$ |
| CH$_3$ | O | 3-Cl, 5-Br | 3-chloro-2-pyridinyl | CH$_3$ |
| CH$_3$ | O | 3-Cl, 5-I | 3-chloro-2-pyridinyl | CH$_3$ |
| CH$_3$ | O | 3-Cl, 5-CH$_3$ | 3-chloro-2-pyridinyl | CH$_3$ |
| CH$_3$ | O | 3-Cl, 5-CN | 3-chloro-2-pyridinyl | CH$_3$ |
| CH$_3$ | O | 3-Br | 3-chloro-2-pyridinyl | CH$_3$ |
| CH$_3$ | O | 3-Br, 5-Cl | 3-chloro-2-pyridinyl | CH$_3$ |
| CH$_3$ | O | 3-Br, 5-Br | 3-chloro-2-pyridinyl | CH$_3$ |
| CH$_3$ | O | 3-Br, 5-I | 3-chloro-2-pyridinyl | CH$_3$ |
| CH$_3$ | O | 3-Br, 5-CH$_3$ | 3-chloro-2-pyridinyl | CH$_3$ |
| CH$_3$ | O | 3-Br, 5-CN | 3-chloro-2-pyridinyl | CH$_3$ |
| CH$_3$ | O | 3-I | 3-chloro-2-pyridinyl | CH$_3$ |
| CH$_3$ | O | 3-I, 5-Cl | 3-chloro-2-pyridinyl | CH$_3$ |
| CH$_3$ | O | 3-I, 5-Br | 3-chloro-2-pyridinyl | CH$_3$ |
| CH$_3$ | O | 3-I, 5-I | 3-chloro-2-pyridinyl | CH$_3$ |
| CH$_3$ | O | 3-I, 5-CH$_3$ | 3-chloro-2-pyridinyl | CH$_3$ |
| CH$_3$ | O | 3-I, 5-CN | 3-chloro-2-pyridinyl | CH$_3$ |

TABLE 16

| $R^6$ | $A^{32}$ | $(R^4)_n$ | $R^{13a-1}$ | $R^{14a-1}$ |
|---|---|---|---|---|
| CH$_3$ | O | 3-CH$_3$ | 3-chloro-2-pyridinyl | CF$_3$ |
| CH$_3$ | O | 3-CH$_3$, 5-Cl | 3-chloro-2-pyridinyl | CF$_3$ |
| CH$_3$ | O | 3-CH$_3$, 5-Br | 3-chloro-2-pyridinyl | CF$_3$ |
| CH$_3$ | O | 3-CH$_3$, 5-I | 3-chloro-2-pyridinyl | CF$_3$ |
| CH$_3$ | O | 3-CH$_3$, 5-CH$_3$ | 3-chloro-2-pyridinyl | CF$_3$ |
| CH$_3$ | O | 3-CH$_3$, 5-CN | 3-chloro-2-pyridinyl | CF$_3$ |
| CH$_3$ | O | 3-Cl | 3-chloro-2-pyridinyl | CF$_3$ |
| CH$_3$ | O | 3-Cl, 5-Cl | 3-chloro-2-pyridinyl | CF$_3$ |
| CH$_3$ | O | 3-Cl, 5-Br | 3-chloro-2-pyridinyl | CF$_3$ |
| CH$_3$ | O | 3-Cl, 5-I | 3-chloro-2-pyridinyl | CF$_3$ |
| CH$_3$ | O | 3-Cl, 5-CH$_3$ | 3-chloro-2-pyridinyl | CF$_3$ |
| CH$_3$ | O | 3-Cl, 5-CN | 3-chloro-2-pyridinyl | CF$_3$ |
| CH$_3$ | O | 3-Br | 3-chloro-2-pyridinyl | CF$_3$ |
| CH$_3$ | O | 3-Br, 5-Cl | 3-chloro-2-pyridinyl | CF$_3$ |
| CH$_3$ | O | 3-Br, 5-Br | 3-chloro-2-pyridinyl | CF$_3$ |
| CH$_3$ | O | 3-Br, 5-I | 3-chloro-2-pyridinyl | CF$_3$ |
| CH$_3$ | O | 3-Br, 5-CH$_3$ | 3-chloro-2-pyridinyl | CF$_3$ |
| CH$_3$ | O | 3-Br, 5-CN | 3-chloro-2-pyridinyl | CF$_3$ |
| CH$_3$ | O | 3-I | 3-chloro-2-pyridinyl | CF$_3$ |
| CH$_3$ | O | 3-I, 5-Cl | 3-chloro-2-pyridinyl | CF$_3$ |

TABLE 16-continued

| $R^6$ | $A^{32}$ | $(R^4)_n$ | $R^{13a\text{-}1}$ | $R^{14a\text{-}1}$ |
|---|---|---|---|---|
| $CH_3$ | O | 3-I, 5-Br | 3-chloro-2-pyridinyl | $CF_3$ |
| $CH_3$ | O | 3-I, 5-I | 3-chloro-2-pyridinyl | $CF_3$ |
| $CH_3$ | O | 3-I, 5-$CH_3$ | 3-chloro-2-pyridinyl | $CF_3$ |
| $CH_3$ | O | 3-I, 5-CN | 3-chloro-2-pyridinyl | $CF_3$ |

TABLE 17

| $R^6$ | $A^{32}$ | $(R^4)_n$ | $R^{13a\text{-}1}$ | $R^{14a\text{-}1}$ |
|---|---|---|---|---|
| $CH_3$ | O | 3-$CH_2CH_3$ | 3-chloro-2-pyridinyl | $CF_3$ |
| $CH_3$ | O | 3-$CH(CH_3)_2$ | 3-chloro-2-pyridinyl | $CF_3$ |
| $CH_3$ | O | 3-$C(CH_3)_3$ | 3-chloro-2-pyridinyl | $CF_3$ |
| $CH_3$ | O | 3-$CF_3$ | 3-chloro-2-pyridinyl | $CF_3$ |
| $CH_3$ | O | 3-$OCH_3$ | 3-chloro-2-pyridinyl | $CF_3$ |
| $CH_3$ | O | 3-phenyl | 3-chloro-2-pyridinyl | $CF_3$ |
| $CH_3$ | O | 3-$CH_2CH_3$, 5-Cl | 3-chloro-2-pyridinyl | $CF_3$ |
| $CH_3$ | O | 3-$CH(CH_3)_2$, 5-Cl | 3-chloro-2-pyridinyl | $CF_3$ |
| $CH_3$ | O | 3-$C(CH_3)_3$, 5-Cl | 3-chloro-2-pyridinyl | $CF_3$ |
| $CH_3$ | O | 3-$CF_3$, 5-Cl | 3-chloro-2-pyridinyl | $CF_3$ |
| $CH_3$ | O | 3-$OCH_3$, 5-Cl | 3-chloro-2-pyridinyl | $CF_3$ |
| $CH_3$ | O | 3-phenyl, 5-Cl | 3-chloro-2-pyridinyl | $CF_3$ |
| $CH_3$ | O | 3-$CH_3$, 4-Cl | 3-chloro-2-pyridinyl | $CF_3$ |
| $CH_3$ | O | 3-Cl, 4-Cl | 3-chloro-2-pyridinyl | $CF_3$ |
| $CH_3$ | O | 3-$CH_3$, 6-Cl | 3-chloro-2-pyridinyl | $CF_3$ |
| $CH_3$ | O | 3-Cl, 6-Cl | 3-chloro-2-pyridinyl | $CF_3$ |
| $CH_3$ | O | 3-$CH_3$, 4-Cl, 5-Cl | 3-chloro-2-pyridinyl | $CF_3$ |
| $CH_3$ | O | 3-Cl, 4-Cl, 5-Cl | 3-chloro-2-pyridinyl | $CF_3$ |
| $CH_3$ | O | 3-$CH_3$, 5-Cl, 6-Cl | 3-chloro-2-pyridinyl | $CF_3$ |
| $CH_3$ | O | 3-Cl, 5-Cl, 6-Cl | 3-chloro-2-pyridinyl | $CF_3$ |
| $CH_3$ | O | 3-$CH_3$, 5-F | 3-chloro-2-pyridinyl | $CF_3$ |
| $CH_3$ | O | 3-Cl, 5-F | 3-chloro-2-pyridinyl | $CF_3$ |
| $CH_3$ | O | 3-Br, 5-F | 3-chloro-2-pyridinyl | $CF_3$ |
| $CH_3$ | O | 3-I, 5-F | 3-chloro-2-pyridinyl | $CF_3$ |
| $CH_3$ | O | 3-Me,4,5-CH=CH—CH=CH— | 3-chloro-2-pyridinyl | $CF_3$ |
| $CH_3$ | O | 3-Cl,4,5-CH=CH—CH=CH— | 3-chloro-2-pyridinyl | $CF_3$ |
| $CH_3$ | O | 3-Br,4,5-CH=CH—CH=CH— | 3-chloro-2-pyridinyl | $CF_3$ |
| $CH_3$ | O | 3-I,4,5-CH=CH—CH=CH— | 3-chloro-2-pyridinyl | $CF_3$ |

TABLE 18

| $R^6$ | $A^{32}$ | $(R^4)_n$ | $R^{13a\text{-}1}$ | $R^{14a\text{-}1}$ |
|---|---|---|---|---|
| $CH_3$ | O | 3-$CH_3$ | 3-chloro-2-pyridinyl | $SCH_3$ |
| $CH_3$ | O | 3-$CH_3$, 5-Cl | 3-chloro-2-pyridinyl | $SCH_3$ |
| $CH_3$ | O | 3-$CH_3$, 5-Br | 3-chloro-2-pyridinyl | $SCH_3$ |
| $CH_3$ | O | 3-$CH_3$, 5-I | 3-chloro-2-pyridinyl | $SCH_3$ |
| $CH_3$ | O | 3-$CH_3$, 5-$CH_3$ | 3-chloro-2-pyridinyl | $SCH_3$ |
| $CH_3$ | O | 3-$CH_3$, 5-CN | 3-chloro-2-pyridinyl | $SCH_3$ |
| $CH_3$ | O | 3-Cl | 3-chloro-2-pyridinyl | $SCH_3$ |
| $CH_3$ | O | 3-Cl, 5-Cl | 3-chloro-2-pyridinyl | $SCH_3$ |
| $CH_3$ | O | 3-Cl, 5-Br | 3-chloro-2-pyridinyl | $SCH_3$ |
| $CH_3$ | O | 3-Cl, 5-I | 3-chloro-2-pyridinyl | $SCH_3$ |
| $CH_3$ | O | 3-Cl, 5-$CH_3$ | 3-chloro-2-pyridinyl | $SCH_3$ |
| $CH_3$ | O | 3-Cl, 5-CN | 3-chloro-2-pyridinyl | $SCH_3$ |
| $CH_3$ | O | 3-Br | 3-chloro-2-pyridinyl | $SCH_3$ |
| $CH_3$ | O | 3-Br, 5-Cl | 3-chloro-2-pyridinyl | $SCH_3$ |
| $CH_3$ | O | 3-Br, 5-Br | 3-chloro-2-pyridinyl | $SCH_3$ |
| $CH_3$ | O | 3-Br, 5-I | 3-chloro-2-pyridinyl | $SCH_3$ |
| $CH_3$ | O | 3-Br, 5-$CH_3$ | 3-chloro-2-pyridinyl | $SCH_3$ |
| $CH_3$ | O | 3-Br, 5-CN | 3-chloro-2-pyridinyl | $SCH_3$ |
| $CH_3$ | O | 3-I | 3-chloro-2-pyridinyl | $SCH_3$ |
| $CH_3$ | O | 3-I, 5-Cl | 3-chloro-2-pyridinyl | $SCH_3$ |
| $CH_3$ | O | 3-I, 5-Br | 3-chloro-2-pyridinyl | $SCH_3$ |
| $CH_3$ | O | 3-I, 5-I | 3-chloro-2-pyridinyl | $SCH_3$ |
| $CH_3$ | O | 3-I, 5-$CH_3$ | 3-chloro-2-pyridinyl | $SCH_3$ |
| $CH_3$ | O | 3-I, 5-CN | 3-chloro-2-pyridinyl | $SCH_3$ |

TABLE 19

| $R^6$ | $A^{32}$ | $(R^4)_n$ | $R^{13a\text{-}1}$ | $R^{14a\text{-}1}$ |
|---|---|---|---|---|
| $CH_3$ | O | 3-$CH_3$ | 3-chloro-2-pyridinyl | $S(=O)CH_3$ |
| $CH_3$ | O | 3-$CH_3$, 5-Cl | 3-chloro-2-pyridinyl | $S(=O)CH_3$ |
| $CH_3$ | O | 3-$CH_3$, 5-Br | 3-chloro-2-pyridinyl | $S(=O)CH_3$ |
| $CH_3$ | O | 3-$CH_3$, 5-I | 3-chloro-2-pyridinyl | $S(=O)CH_3$ |
| $CH_3$ | O | 3-$CH_3$, 5-$CH_3$ | 3-chloro-2-pyridinyl | $S(=O)CH_3$ |
| $CH_3$ | O | 3-$CH_3$, 5-CN | 3-chloro-2-pyridinyl | $S(=O)CH_3$ |
| $CH_3$ | O | 3-Cl | 3-chloro-2-pyridinyl | $S(=O)CH_3$ |
| $CH_3$ | O | 3-Cl, 5-Cl | 3-chloro-2-pyridinyl | $S(=O)CH_3$ |
| $CH_3$ | O | 3-Cl, 5-Br | 3-chloro-2-pyridinyl | $S(=O)CH_3$ |
| $CH_3$ | O | 3-Cl, 5-I | 3-chloro-2-pyridinyl | $S(=O)CH_3$ |
| $CH_3$ | O | 3-Cl, 5-$CH_3$ | 3-chloro-2-pyridinyl | $S(=O)CH_3$ |
| $CH_3$ | O | 3-Cl, 5-CN | 3-chloro-2-pyridinyl | $S(=O)CH_3$ |
| $CH_3$ | O | 3-Br | 3-chloro-2-pyridinyl | $S(=O)CH_3$ |
| $CH_3$ | O | 3-Br, 5-Cl | 3-chloro-2-pyridinyl | $S(=O)CH_3$ |
| $CH_3$ | O | 3-Br, 5-Br | 3-chloro-2-pyridinyl | $S(=O)CH_3$ |
| $CH_3$ | O | 3-Br, 5-I | 3-chloro-2-pyridinyl | $S(=O)CH_3$ |
| $CH_3$ | O | 3-Br, 5-$CH_3$ | 3-chloro-2-pyridinyl | $S(=O)CH_3$ |
| $CH_3$ | O | 3-Br, 5-CN | 3-chloro-2-pyridinyl | $S(=O)CH_3$ |
| $CH_3$ | O | 3-I | 3-chloro-2-pyridinyl | $S(=O)CH_3$ |
| $CH_3$ | O | 3-I, 5-Cl | 3-chloro-2-pyridinyl | $S(=O)CH_3$ |
| $CH_3$ | O | 3-I, 5-Br | 3-chloro-2-pyridinyl | $S(=O)CH_3$ |
| $CH_3$ | O | 3-I, 5-I | 3-chloro-2-pyridinyl | $S(=O)CH_3$ |
| $CH_3$ | O | 3-I, 5-$CH_3$ | 3-chloro-2-pyridinyl | $S(=O)CH_3$ |
| $CH_3$ | O | 3-I, 5-CN | 3-chloro-2-pyridinyl | $S(=O)CH_3$ |

TABLE 20

| $R^6$ | $A^{32}$ | $(R^4)_n$ | $R^{13a\text{-}1}$ | $R^{14a\text{-}1}$ |
|---|---|---|---|---|
| $CH_3$ | O | 3-$CH_3$ | 3-chloro-2-pyridinyl | $S(=O)_2CH_3$ |
| $CH_3$ | O | 3-$CH_3$, 5-Cl | 3-chloro-2-pyridinyl | $S(=O)_2CH_3$ |
| $CH_3$ | O | 3-$CH_3$, 5-Br | 3-chloro-2-pyridinyl | $S(=O)_2CH_3$ |
| $CH_3$ | O | 3-$CH_3$, 5-I | 3-chloro-2-pyridinyl | $S(=O)_2CH_3$ |
| $CH_3$ | O | 3-$CH_3$, 5-$CH_3$ | 3-chloro-2-pyridinyl | $S(=O)_2CH_3$ |
| $CH_3$ | O | 3-$CH_3$, 5-CN | 3-chloro-2-pyridinyl | $S(=O)_2CH_3$ |
| $CH_3$ | O | 3-Cl | 3-chloro-2-pyridinyl | $S(=O)_2CH_3$ |
| $CH_3$ | O | 3-Cl, 5-Cl | 3-chloro-2-pyridinyl | $S(=O)_2CH_3$ |
| $CH_3$ | O | 3-Cl, 5-Br | 3-chloro-2-pyridinyl | $S(=O)_2CH_3$ |
| $CH_3$ | O | 3-Cl, 5-I | 3-chloro-2-pyridinyl | $S(=O)_2CH_3$ |
| $CH_3$ | O | 3-Cl, 5-$CH_3$ | 3-chloro-2-pyridinyl | $S(=O)_2CH_3$ |
| $CH_3$ | O | 3-Cl, 5-CN | 3-chloro-2-pyridinyl | $S(=O)_2CH_3$ |
| $CH_3$ | O | 3-Br | 3-chloro-2-pyridinyl | $S(=O)_2CH_3$ |
| $CH_3$ | O | 3-Br, 5-Cl | 3-chloro-2-pyridinyl | $S(=O)_2CH_3$ |
| $CH_3$ | O | 3-Br, 5-Br | 3-chloro-2-pyridinyl | $S(=O)_2CH_3$ |
| $CH_3$ | O | 3-Br, 5-I | 3-chloro-2-pyridinyl | $S(=O)_2CH_3$ |
| $CH_3$ | O | 3-Br, 5-$CH_3$ | 3-chloro-2-pyridinyl | $S(=O)_2CH_3$ |
| $CH_3$ | O | 3-Br, 5-CN | 3-chloro-2-pyridinyl | $S(=O)_2CH_3$ |
| $CH_3$ | O | 3-I | 3-chloro-2-pyridinyl | $S(=O)_2CH_3$ |
| $CH_3$ | O | 3-I, 5-Cl | 3-chloro-2-pyridinyl | $S(=O)_2CH_3$ |
| $CH_3$ | O | 3-I, 5-Br | 3-chloro-2-pyridinyl | $S(=O)_2CH_3$ |
| $CH_3$ | O | 3-I, 5-I | 3-chloro-2-pyridinyl | $S(=O)_2CH_3$ |
| $CH_3$ | O | 3-I, 5-$CH_3$ | 3-chloro-2-pyridinyl | $S(=O)_2CH_3$ |
| $CH_3$ | O | 3-I, 5-CN | 3-chloro-2-pyridinyl | $S(=O)_2CH_3$ |

TABLE 21

| $R^6$ | $A^{32}$ | $(R^4)_n$ | $R^{13a\text{-}1}$ | $R^{14a\text{-}1}$ |
|---|---|---|---|---|
| $CH_3$ | O | 3-$CH_3$, 5-Cl | 3-chloro-2-pyridinyl | $SCH_2CH_3$ |
| $CH_3$ | O | 3-Br, 5-Cl | 3-chloro-2-pyridinyl | $SCH_2CH_3$ |
| $CH_3$ | O | 3-Br, 5-Br | 3-chloro-2-pyridinyl | $SCH_2CH_3$ |
| $CH_3$ | O | 3-$CH_3$, 5-CN | 3-chloro-2-pyridinyl | $SCH_2CH_3$ |
| $CH_3$ | O | 3-$CH_3$, 5-Cl | 3-chloro-2-pyridinyl | $SCH(CH_3)_2$ |
| $CH_3$ | O | 3-Br, 5-Cl | 3-chloro-2-pyridinyl | $SCH(CH_3)_2$ |
| $CH_3$ | O | 3-Br, 5-Br | 3-chloro-2-pyridinyl | $SCH(CH_3)_2$ |
| $CH_3$ | O | 3-$CH_3$, 5-CN | 3-chloro-2-pyridinyl | $SCH(CH_3)_2$ |
| $CH_3$ | O | 3-$CH_3$, 5-Cl | 3-chloro-2-pyridinyl | $OCH_3$ |
| $CH_3$ | O | 3-Br, 5-Cl | 3-chloro-2-pyridinyl | $OCH_3$ |
| $CH_3$ | O | 3-Br, 5-Br | 3-chloro-2-pyridinyl | $OCH_3$ |
| $CH_3$ | O | 3-$CH_3$, 5-CN | 3-chloro-2-pyridinyl | $OCH_3$ |
| $CH_3$ | O | 3-$CH_3$, 5-Cl | 3-chloro-2-pyridinyl | $OCH_2CF_3$ |
| $CH_3$ | O | 3-Br, 5-Cl | 3-chloro-2-pyridinyl | $OCH_2CF_3$ |

TABLE 21-continued

| R⁶ | A³² | (R⁴)ₙ | R¹³ᵃ⁻¹ | R¹⁴ᵃ⁻¹ |
|---|---|---|---|---|
| $CH_3$ | O | 3-Br, 5-Br | 3-chloro-2-pyridinyl | $OCH_2CF_3$ |
| $CH_3$ | O | 3-$CH_3$, 5-CN | 3-chloro-2-pyridinyl | $OCH_2CF_3$ |
| $CH_3$ | O | 3-$CH_3$, 5-Cl | 3-chloro-2-pyridinyl | $CH_2CH_3$ |
| $CH_3$ | O | 3-Br, 5-Cl | 3-chloro-2-pyridinyl | $CH_2CH_3$ |
| $CH_3$ | O | 3-Br, 5-Br | 3-chloro-2-pyridinyl | $CH_2CH_3$ |
| $CH_3$ | O | 3-$CH_3$, 5-CN | 3-chloro-2-pyridinyl | $CH_2CH_3$ |
| $CH_3$ | O | 3-$CH_3$, 5-Cl | 3-chloro-2-pyridinyl | $CH(CH_3)_2$ |
| $CH_3$ | O | 3-Br, 5-Cl | 3-chloro-2-pyridinyl | $CH(CH_3)_2$ |
| $CH_3$ | O | 3-Br, 5-Br | 3-chloro-2-pyridinyl | $CH(CH_3)_2$ |
| $CH_3$ | O | 3-$CH_3$, 5-CN | 3-chloro-2-pyridinyl | $CH(CH_3)_2$ |
| $CH_3$ | O | 3-$CH_3$, 5-Cl | 3-chloro-2-pyridinyl | $C(CH_3)_3$ |
| $CH_3$ | O | 3-Br, 5-Cl | 3-chloro-2-pyridinyl | $C(CH_3)_3$ |
| $CH_3$ | O | 3-Br, 5-Br | 3-chloro-2-pyridinyl | $C(CH_3)_3$ |
| $CH_3$ | O | 3-$CH_3$, 5-CN | 3-chloro-2-pyridinyl | $C(CH_3)_3$ |
| $CH_3$ | O | 3-$CH_3$, 5-Cl | 3-chloro-2-pyridinyl | CN |
| $CH_3$ | O | 3-Br, 5-Cl | 3-chloro-2-pyridinyl | CN |
| $CH_3$ | O | 3-Br, 5-Br | 3-chloro-2-pyridinyl | CN |
| $CH_3$ | O | 3-$CH_3$, 5-CN | 3-chloro-2-pyridinyl | CN |

TABLE 22

| R⁶ | A³² | (R⁴)ₙ | R¹³ᵃ⁻¹ | R¹⁴ᵃ⁻¹ |
|---|---|---|---|---|
| $CH_3$ | O | 3-$CH_3$, 5-Cl | 3-fluoro-2-pyridinyl | H |
| $CH_3$ | O | 3-Br, 5-Cl | 3-fluoro-2-pyridinyl | H |
| $CH_3$ | O | 3-Br, 5-Br | 3-fluoro-2-pyridinyl | H |
| $CH_3$ | O | 3-$CH_3$, 5-CN | 3-fluoro-2-pyridinyl | H |
| $CH_3$ | O | 3-$CH_3$, 5-Cl | 3-fluoro-2-pyridinyl | Cl |
| $CH_3$ | O | 3-Br, 5-Cl | 3-fluoro-2-pyridinyl | Cl |
| $CH_3$ | O | 3-Br, 5-Br | 3-fluoro-2-pyridinyl | Cl |
| $CH_3$ | O | 3-$CH_3$, 5-CN | 3-fluoro-2-pyridinyl | Cl |
| $CH_3$ | O | 3-$CH_3$, 5-Cl | 3-fluoro-2-pyridinyl | Br |
| $CH_3$ | O | 3-Br, 5-Cl | 3-fluoro-2-pyridinyl | Br |
| $CH_3$ | O | 3-Br, 5-Br | 3-fluoro-2-pyridinyl | Br |
| $CH_3$ | O | 3-$CH_3$, 5-CN | 3-fluoro-2-pyridinyl | Br |
| $CH_3$ | O | 3-$CH_3$, 5-Cl | 3-fluoro-2-pyridinyl | $CF_3$ |
| $CH_3$ | O | 3-Br, 5-Cl | 3-fluoro-2-pyridinyl | $CF_3$ |
| $CH_3$ | O | 3-Br, 5-Br | 3-fluoro-2-pyridinyl | $CF_3$ |
| $CH_3$ | O | 3-$CH_3$, 5-CN | 3-fluoro-2-pyridinyl | $CF_3$ |
| $CH_3$ | O | 3-$CH_3$, 5-Cl | 3-bromo-2-pyridinyl | H |
| $CH_3$ | O | 3-Br, 5-Cl | 3-bromo-2-pyridinyl | H |
| $CH_3$ | O | 3-Br, 5-Br | 3-bromo-2-pyridinyl | H |
| $CH_3$ | O | 3-$CH_3$, 5-CN | 3-bromo-2-pyridinyl | H |
| $CH_3$ | O | 3-$CH_3$, 5-Cl | 3-bromo-2-pyridinyl | Cl |
| $CH_3$ | O | 3-Br, 5-Cl | 3-bromo-2-pyridinyl | Cl |
| $CH_3$ | O | 3-Br, 5-Br | 3-bromo-2-pyridinyl | Cl |
| $CH_3$ | O | 3-$CH_3$, 5-CN | 3-bromo-2-pyridinyl | Cl |
| $CH_3$ | O | 3-$CH_3$, 5-Cl | 3-bromo-2-pyridinyl | Br |
| $CH_3$ | O | 3-Br, 5-Cl | 3-bromo-2-pyridinyl | Br |
| $CH_3$ | O | 3-Br, 5-Br | 3-bromo-2-pyridinyl | Br |
| $CH_3$ | O | 3-$CH_3$, 5-CN | 3-bromo-2-pyridinyl | Br |
| $CH_3$ | O | 3-$CH_3$, 5-Cl | 3-bromo-2-pyridinyl | $CF_3$ |
| $CH_3$ | O | 3-Br, 5-Cl | 3-bromo-2-pyridinyl | $CF_3$ |
| $CH_3$ | O | 3-Br, 5-Br | 3-bromo-2-pyridinyl | $CF_3$ |
| $CH_3$ | O | 3-$CH_3$, 5-CN | 3-bromo-2-pyridinyl | $CF_3$ |

TABLE 23

| R⁶ | A³² | (R⁴)ₙ | R¹³ᵃ⁻¹ | R¹⁴ᵃ⁻¹ |
|---|---|---|---|---|
| $CH_3$ | O | 3-$CH_3$, 5-Cl | 3-methyl-2-pyridinyl | H |
| $CH_3$ | O | 3-Br, 5-Cl | 3-methyl-2-pyridinyl | H |
| $CH_3$ | O | 3-Br, 5-Br | 3-methyl-2-pyridinyl | H |
| $CH_3$ | O | 3-$CH_3$, 5-CN | 3-methyl-2-pyridinyl | H |
| $CH_3$ | O | 3-$CH_3$, 5-Cl | 3-methyl-2-pyridinyl | Cl |
| $CH_3$ | O | 3-Br, 5-Cl | 3-methyl-2-pyridinyl | Cl |
| $CH_3$ | O | 3-Br, 5-Br | 3-methyl-2-pyridinyl | Cl |
| $CH_3$ | O | 3-$CH_3$, 5-CN | 3-methyl-2-pyridinyl | Cl |
| $CH_3$ | O | 3-$CH_3$, 5-Cl | 3-methyl-2-pyridinyl | Br |
| $CH_3$ | O | 3-Br, 5-Cl | 3-methyl-2-pyridinyl | Br |
| $CH_3$ | O | 3-Br, 5-Br | 3-methyl-2-pyridinyl | Br |
| $CH_3$ | O | 3-$CH_3$, 5-CN | 3-methyl-2-pyridinyl | Br |

TABLE 23-continued

| R⁶ | A³² | (R⁴)ₙ | R¹³ᵃ⁻¹ | R¹⁴ᵃ⁻¹ |
|---|---|---|---|---|
| $CH_3$ | O | 3-$CH_3$, 5-Cl | 3-methyl-2-pyridinyl | $CF_3$ |
| $CH_3$ | O | 3-Br, 5-Cl | 3-methyl-2-pyridinyl | $CF_3$ |
| $CH_3$ | O | 3-Br, 5-Br | 3-methyl-2-pyridinyl | $CF_3$ |
| $CH_3$ | O | 3-$CH_3$, 5-CN | 3-methyl-2-pyridinyl | $CF_3$ |
| $CH_3$ | O | 3-$CH_3$, 5-Cl | 3-trifluoromethyl-2-pyridinyl | H |
| $CH_3$ | O | 3-Br, 5-Cl | 3-trifluoromethyl-2-pyridinyl | H |
| $CH_3$ | O | 3-Br, 5-Br | 3-trifluoromethyl-2-pyridinyl | H |
| $CH_3$ | O | 3-$CH_3$, 5-CN | 3-trifluoromethyl-2-pyridinyl | H |
| $CH_3$ | O | 3-$CH_3$, 5-Cl | 3-trifluoromethyl-2-pyridinyl | Cl |
| $CH_3$ | O | 3-Br, 5-Cl | 3-trifluoromethyl-2-pyridinyl | Cl |
| $CH_3$ | O | 3-Br, 5-Br | 3-trifluoromethyl-2-pyridinyl | Cl |
| $CH_3$ | O | 3-$CH_3$, 5-CN | 3-trifluoromethyl-2-pyridinyl | Cl |
| $CH_3$ | O | 3-$CH_3$, 5-Cl | 3-trifluoromethyl-2-pyridinyl | Br |
| $CH_3$ | O | 3-Br, 5-Cl | 3-trifluoromethyl-2-pyridinyl | Br |
| $CH_3$ | O | 3-Br, 5-Br | 3-trifluoromethyl-2-pyridinyl | Br |
| $CH_3$ | O | 3-$CH_3$, 5-CN | 3-trifluoromethyl-2-pyridinyl | Br |
| $CH_3$ | O | 3-$CH_3$, 5-Cl | 3-trifluoromethyl-2-pyridinyl | $CF_3$ |
| $CH_3$ | O | 3-Br, 5-Cl | 3-trifluoromethyl-2-pyridinyl | $CF_3$ |
| $CH_3$ | O | 3-Br, 5-Br | 3-trifluoromethyl-2-pyridinyl | $CF_3$ |
| $CH_3$ | O | 3-$CH_3$, 5-CN | 3-trifluoromethyl-2-pyridinyl | $CF_3$ |

TABLE 24

| R⁶ | A³² | (R⁴)ₙ | R¹³ᵃ⁻¹ | R¹⁴ᵃ⁻¹ |
|---|---|---|---|---|
| $CH_3$ | O | 3-$CH_3$, 5-Cl | 3-cyano-2-pyridinyl | H |
| $CH_3$ | O | 3-Br, 5-Cl | 3-cyano-2-pyridinyl | H |
| $CH_3$ | O | 3-Br, 5-Br | 3-cyano-2-pyridinyl | H |
| $CH_3$ | O | 3-$CH_3$, 5-CN | 3-cyano-2-pyridinyl | H |
| $CH_3$ | O | 3-$CH_3$, 5-Cl | 3-cyano-2-pyridinyl | Cl |
| $CH_3$ | O | 3-Br, 5-Cl | 3-cyano-2-pyridinyl | Cl |
| $CH_3$ | O | 3-Br, 5-Br | 3-cyano-2-pyridinyl | Cl |
| $CH_3$ | O | 3-$CH_3$, 5-CN | 3-cyano-2-pyridinyl | Cl |
| $CH_3$ | O | 3-$CH_3$, 5-Cl | 3-cyano-2-pyridinyl | Br |
| $CH_3$ | O | 3-Br, 5-Cl | 3-cyano-2-pyridinyl | Br |
| $CH_3$ | O | 3-Br, 5-Br | 3-cyano-2-pyridinyl | Br |
| $CH_3$ | O | 3-$CH_3$, 5-CN | 3-cyano-2-pyridinyl | Br |
| $CH_3$ | O | 3-$CH_3$, 5-Cl | 3-cyano-2-pyridinyl | $CF_3$ |
| $CH_3$ | O | 3-Br, 5-Cl | 3-cyano-2-pyridinyl | $CF_3$ |
| $CH_3$ | O | 3-Br, 5-Br | 3-cyano-2-pyridinyl | $CF_3$ |
| $CH_3$ | O | 3-$CH_3$, 5-CN | 3-cyano-2-pyridinyl | $CF_3$ |
| $CH_3$ | O | 3-$CH_3$, 5-Cl | 3-nitro-2-pyridinyl | H |
| $CH_3$ | O | 3-Br, 5-Cl | 3-nitro-2-pyridinyl | H |
| $CH_3$ | O | 3-Br, 5-Br | 3-nitro-2-pyridinyl | H |
| $CH_3$ | O | 3-$CH_3$, 5-CN | 3-nitro-2-pyridinyl | H |
| $CH_3$ | O | 3-$CH_3$, 5-Cl | 3-nitro-2-pyridinyl | Cl |
| $CH_3$ | O | 3-Br, 5-Cl | 3-nitro-2-pyridinyl | Cl |
| $CH_3$ | O | 3-Br, 5-Br | 3-nitro-2-pyridinyl | Cl |
| $CH_3$ | O | 3-$CH_3$, 5-CN | 3-nitro-2-pyridinyl | Cl |
| $CH_3$ | O | 3-$CH_3$, 5-Cl | 3-nitro-2-pyridinyl | Br |
| $CH_3$ | O | 3-Br, 5-Cl | 3-nitro-2-pyridinyl | Br |
| $CH_3$ | O | 3-Br, 5-Br | 3-nitro-2-pyridinyl | Br |
| $CH_3$ | O | 3-$CH_3$, 5-CN | 3-nitro-2-pyridinyl | Br |
| $CH_3$ | O | 3-$CH_3$, 5-Cl | 3-nitro-2-pyridinyl | $CF_3$ |
| $CH_3$ | O | 3-Br, 5-Cl | 3-nitro-2-pyridinyl | $CF_3$ |
| $CH_3$ | O | 3-Br, 5-Br | 3-nitro-2-pyridinyl | $CF_3$ |
| $CH_3$ | O | 3-$CH_3$, 5-CN | 3-nitro-2-pyridinyl | $CF_3$ |

TABLE 25

| R⁶ | A³² | (R⁴)ₙ | R¹³ᵃ⁻¹ | R¹⁴ᵃ⁻¹ |
|---|---|---|---|---|
| $CH_3$ | O | 3-$CH_3$, 5-Cl | 2-chlorophenyl | H |
| $CH_3$ | O | 3-Br, 5-Cl | 2-chlorophenyl | H |
| $CH_3$ | O | 3-Br, 5-Br | 2-chlorophenyl | H |
| $CH_3$ | O | 3-$CH_3$, 5-CN | 2-chlorophenyl | H |
| $CH_3$ | O | 3-$CH_3$, 5-Cl | 2-chlorophenyl | Cl |
| $CH_3$ | O | 3-Br, 5-Cl | 2-chlorophenyl | Cl |
| $CH_3$ | O | 3-Br, 5-Br | 2-chlorophenyl | Cl |
| $CH_3$ | O | 3-$CH_3$, 5-CN | 2-chlorophenyl | Cl |
| $CH_3$ | O | 3-$CH_3$, 5-Cl | 2-chlorophenyl | Br |
| $CH_3$ | O | 3-Br, 5-Cl | 2-chlorophenyl | Br |

TABLE 25-continued

| R⁶ | A³² | (R⁴)ₙ | R¹³ᵃ⁻¹ | R¹⁴ᵃ⁻¹ |
|---|---|---|---|---|
| CH₃ | O | 3-Br, 5-Br | 2-chlorophenyl | Br |
| CH₃ | O | 3-CH₃, 5-CN | 2-chlorophenyl | Br |
| CH₃ | O | 3-CH₃, 5-Cl | 2-chlorophenyl | CF₃ |
| CH₃ | O | 3-Br, 5-Cl | 2-chlorophenyl | CF₃ |
| CH₃ | O | 3-Br, 5-Br | 2-chlorophenyl | CF₃ |
| CH₃ | O | 3-CH₃, 5-CN | 2-chlorophenyl | CF₃ |
| CH₃ | O | 3-CH₃, 5-Cl | 2,6-dichlorophenyl | H |
| CH₃ | O | 3-Br, 5-Cl | 2,6-dichlorophenyl | H |
| CH₃ | O | 3-Br, 5-Br | 2,6-dichlorophenyl | H |
| CH₃ | O | 3-CH₃, 5-CN | 2,6-dichlorophenyl | H |
| CH₃ | O | 3-CH₃, 5-Cl | 2,6-dichlorophenyl | Cl |
| CH₃ | O | 3-Br, 5-Cl | 2,6-dichlorophenyl | Cl |
| CH₃ | O | 3-Br, 5-Br | 2,6-dichlorophenyl | Cl |
| CH₃ | O | 3-CH₃, 5-CN | 2,6-dichlorophenyl | Cl |
| CH₃ | O | 3-CH₃, 5-Cl | 2,6-dichlorophenyl | Br |
| CH₃ | O | 3-Br, 5-Cl | 2,6-dichlorophenyl | Br |
| CH₃ | O | 3-Br, 5-Br | 2,6-dichlorophenyl | Br |
| CH₃ | O | 3-CH₃, 5-CN | 2,6-dichlorophenyl | Br |
| CH₃ | O | 3-CH₃, 5-Cl | 2,6-dichlorophenyl | CF₃ |
| CH₃ | O | 3-Br, 5-Cl | 2,6-dichlorophenyl | CF₃ |
| CH₃ | O | 3-Br, 5-Br | 2,6-dichlorophenyl | CF₃ |
| CH₃ | O | 3-CH₃, 5-CN | 2,6-dichlorophenyl | CF₃ |

TABLE 26

| R⁶ | A³² | (R⁴)ₙ | R¹³ᵃ⁻¹ | R¹⁴ᵃ⁻¹ |
|---|---|---|---|---|
| CH₂CH₃ | O | 3-CH₃, 5-Cl | 3-chloro-2-pyridinyl | H |
| CH₂CH₃ | O | 3-Br, 5-Cl | 3-chloro-2-pyridinyl | H |
| CH₂CH₃ | O | 3-Br, 5-Br | 3-chloro-2-pyridinyl | H |
| CH₂CH₃ | O | 3-CH₃, 5-CN | 3-chloro-2-pyridinyl | H |
| CH₂CH₃ | O | 3-CH₃, 5-Cl | 3-chloro-2-pyridinyl | Cl |
| CH₂CH₃ | O | 3-Br, 5-Cl | 3-chloro-2-pyridinyl | Cl |
| CH₂CH₃ | O | 3-Br, 5-Br | 3-chloro-2-pyridinyl | Cl |
| CH₂CH₃ | O | 3-CH₃, 5-CN | 3-chloro-2-pyridinyl | Cl |
| CH₂CH₃ | O | 3-CH₃, 5-Cl | 3-chloro-2-pyridinyl | Br |
| CH₂CH₃ | O | 3-Br, 5-Cl | 3-chloro-2-pyridinyl | Br |
| CH₂CH₃ | O | 3-Br, 5-Br | 3-chloro-2-pyridinyl | Br |
| CH₂CH₃ | O | 3-CH₃, 5-CN | 3-chloro-2-pyridinyl | Br |
| CH₂CH₃ | O | 3-CH₃, 5-Cl | 3-chloro-2-pyridinyl | CF₃ |
| CH₂CH₃ | O | 3-Br, 5-Cl | 3-chloro-2-pyridinyl | CF₃ |
| CH₂CH₃ | O | 3-Br, 5-Br | 3-chloro-2-pyridinyl | CF₃ |
| CH₂CH₃ | O | 3-CH₃, 5-CN | 3-chloro-2-pyridinyl | CF₃ |

TABLE 27

| R⁶ | A³² | (R⁴)ₙ | R¹³ᵃ⁻¹ | R¹⁴ᵃ⁻¹ |
|---|---|---|---|---|
| CH₂CH₂CH₃ | O | 3-CH₃, 5-Cl | 3-chloro-2-pyridinyl | H |
| CH₂CH₂CH₃ | O | 3-Br, 5-Cl | 3-chloro-2-pyridinyl | H |
| CH₂CH₂CH₃ | O | 3-Br, 5-Br | 3-chloro-2-pyridinyl | H |
| CH₂CH₂CH₃ | O | 3-CH₃, 5-CN | 3-chloro-2-pyridinyl | H |
| CH₂CH₂CH₃ | O | 3-CH₃, 5-Cl | 3-chloro-2-pyridinyl | Cl |
| CH₂CH₂CH₃ | O | 3-Br, 5-Cl | 3-chloro-2-pyridinyl | Cl |
| CH₂CH₂CH₃ | O | 3-Br, 5-Br | 3-chloro-2-pyridinyl | Cl |
| CH₂CH₂CH₃ | O | 3-CH₃, 5-CN | 3-chloro-2-pyridinyl | Cl |
| CH₂CH₂CH₃ | O | 3-CH₃, 5-Cl | 3-chloro-2-pyridinyl | Br |
| CH₂CH₂CH₃ | O | 3-Br, 5-Cl | 3-chloro-2-pyridinyl | Br |
| CH₂CH₂CH₃ | O | 3-Br, 5-Br | 3-chloro-2-pyridinyl | Br |
| CH₂CH₂CH₃ | O | 3-CH₃, 5-CN | 3-chloro-2-pyridinyl | Br |
| CH₂CH₂CH₃ | O | 3-CH₃, 5-Cl | 3-chloro-2-pyridinyl | CF₃ |
| CH₂CH₂CH₃ | O | 3-Br, 5-Cl | 3-chloro-2-pyridinyl | CF₃ |
| CH₂CH₂CH₃ | O | 3-Br, 5-Br | 3-chloro-2-pyridinyl | CF₃ |
| CH₂CH₂CH₃ | O | 3-CH₃, 5-CN | 3-chloro-2-pyridinyl | CF₃ |
| CH(CH₃)₂ | O | 3-CH₃, 5-Cl | 3-chloro-2-pyridinyl | H |
| CH(CH₃)₂ | O | 3-Br, 5-Cl | 3-chloro-2-pyridinyl | H |
| CH(CH₃)₂ | O | 3-Br, 5-Br | 3-chloro-2-pyridinyl | H |
| CH(CH₃)₂ | O | 3-CH₃, 5-CN | 3-chloro-2-pyridinyl | H |
| CH(CH₃)₂ | O | 3-CH₃, 5-Cl | 3-chloro-2-pyridinyl | Cl |
| CH(CH₃)₂ | O | 3-Br, 5-Cl | 3-chloro-2-pyridinyl | Cl |
| CH(CH₃)₂ | O | 3-Br, 5-Br | 3-chloro-2-pyridinyl | Cl |
| CH(CH₃)₂ | O | 3-CH₃, 5-CN | 3-chloro-2-pyridinyl | Cl |

TABLE 27-continued

| R⁶ | A³² | (R⁴)ₙ | R¹³ᵃ⁻¹ | R¹⁴ᵃ⁻¹ |
|---|---|---|---|---|
| CH(CH₃)₂ | O | 3-CH₃, 5-Cl | 3-chloro-2-pyridinyl | Br |
| CH(CH₃)₂ | O | 3-Br, 5-Cl | 3-chloro-2-pyridinyl | Br |
| CH(CH₃)₂ | O | 3-Br, 5-Br | 3-chloro-2-pyridinyl | Br |
| CH(CH₃)₂ | O | 3-CH₃, 5-CN | 3-chloro-2-pyridinyl | Br |
| CH(CH₃)₂ | O | 3-CH₃, 5-Cl | 3-chloro-2-pyridinyl | CF₃ |
| CH(CH₃)₂ | O | 3-Br, 5-Cl | 3-chloro-2-pyridinyl | CF₃ |
| CH(CH₃)₂ | O | 3-Br, 5-Br | 3-chloro-2-pyridinyl | CF₃ |
| CH(CH₃)₂ | O | 3-CH₃, 5-CN | 3-chloro-2-pyridinyl | CF₃ |

TABLE 28

| R⁶ | A³² | (R⁴)ₙ | R¹³ᵃ⁻¹ | R¹⁴ᵃ⁻¹ |
|---|---|---|---|---|
| C(CH₃)₃ | O | 3-CH₃, 5-Cl | 3-chloro-2-pyridinyl | H |
| C(CH₃)₃ | O | 3-Br, 5-Cl | 3-chloro-2-pyridinyl | H |
| C(CH₃)₃ | O | 3-Br, 5-Br | 3-chloro-2-pyridinyl | H |
| C(CH₃)₃ | O | 3-CH₃, 5-CN | 3-chloro-2-pyridinyl | H |
| C(CH₃)₃ | O | 3-CH₃, 5-Cl | 3-chloro-2-pyridinyl | Cl |
| C(CH₃)₃ | O | 3-Br, 5-Cl | 3-chloro-2-pyridinyl | Cl |
| C(CH₃)₃ | O | 3-Br, 5-Br | 3-chloro-2-pyridinyl | Cl |
| C(CH₃)₃ | O | 3-CH₃, 5-CN | 3-chloro-2-pyridinyl | Cl |
| C(CH₃)₃ | O | 3-CH₃, 5-Cl | 3-chloro-2-pyridinyl | Br |
| C(CH₃)₃ | O | 3-Br, 5-Cl | 3-chloro-2-pyridinyl | Br |
| C(CH₃)₃ | O | 3-Br, 5-Br | 3-chloro-2-pyridinyl | Br |
| C(CH₃)₃ | O | 3-CH₃, 5-CN | 3-chloro-2-pyridinyl | Br |
| C(CH₃)₃ | O | 3-CH₃, 5-Cl | 3-chloro-2-pyridinyl | CF₃ |
| C(CH₃)₃ | O | 3-Br, 5-Cl | 3-chloro-2-pyridinyl | CF₃ |
| C(CH₃)₃ | O | 3-Br, 5-Br | 3-chloro-2-pyridinyl | CF₃ |
| C(CH₃)₃ | O | 3-CH₃, 5-CN | 3-chloro-2-pyridinyl | CF₃ |
| CH₂CH=CH₂ | O | 3-CH₃, 5-Cl | 3-chloro-2-pyridinyl | H |
| CH₂CH=CH₂ | O | 3-Br, 5-Cl | 3-chloro-2-pyridinyl | H |
| CH₂CH=CH₂ | O | 3-Br, 5-Br | 3-chloro-2-pyridinyl | H |
| CH₂CH=CH₂ | O | 3-CH₃, 5-CN | 3-chloro-2-pyridinyl | H |
| CH₂CH=CH₂ | O | 3-CH₃, 5-Cl | 3-chloro-2-pyridinyl | Cl |
| CH₂CH=CH₂ | O | 3-Br, 5-Cl | 3-chloro-2-pyridinyl | Cl |
| CH₂CH=CH₂ | O | 3-Br, 5-Br | 3-chloro-2-pyridinyl | Cl |
| CH₂CH=CH₂ | O | 3-CH₃, 5-CN | 3-chloro-2-pyridinyl | Cl |
| CH₂CH=CH₂ | O | 3-CH₃, 5-Cl | 3-chloro-2-pyridinyl | Br |
| CH₂CH=CH₂ | O | 3-Br, 5-Cl | 3-chloro-2-pyridinyl | Br |
| CH₂CH=CH₂ | O | 3-Br, 5-Br | 3-chloro-2-pyridinyl | Br |
| CH₂CH=CH₂ | O | 3-CH₃, 5-CN | 3-chloro-2-pyridinyl | Br |
| CH₂CH=CH₂ | O | 3-CH₃, 5-Cl | 3-chloro-2-pyridinyl | CF₃ |
| CH₂CH=CH₂ | O | 3-Br, 5-Cl | 3-chloro-2-pyridinyl | CF₃ |
| CH₂CH=CH₂ | O | 3-Br, 5-Br | 3-chloro-2-pyridinyl | CF₃ |
| CH₂CH=CH₂ | O | 3-CH₃, 5-CN | 3-chloro-2-pyridinyl | CF₃ |

TABLE 29

| R⁶ | A³² | (R⁴)ₙ | R¹³ᵃ⁻¹ | R¹⁴ᵃ⁻¹ |
|---|---|---|---|---|
| CH₂CCH | O | 3-CH₃, 5-Cl | 3-chloro-2-pyridinyl | H |
| CH₂CCH | O | 3-Br, 5-Cl | 3-chloro-2-pyridinyl | H |
| CH₂CCH | O | 3-Br, 5-Br | 3-chloro-2-pyridinyl | H |
| CH₂CCH | O | 3-CH₃, 5-CN | 3-chloro-2-pyridinyl | H |
| CH₂CCH | O | 3-CH₃, 5-Cl | 3-chloro-2-pyridinyl | Cl |
| CH₂CCH | O | 3-Br, 5-Cl | 3-chloro-2-pyridinyl | Cl |
| CH₂CCH | O | 3-Br, 5-Br | 3-chloro-2-pyridinyl | Cl |
| CH₂CCH | O | 3-CH₃, 5-CN | 3-chloro-2-pyridinyl | Cl |
| CH₂CCH | O | 3-CH₃, 5-Cl | 3-chloro-2-pyridinyl | Br |
| CH₂CCH | O | 3-Br, 5-Cl | 3-chloro-2-pyridinyl | Br |
| CH₂CCH | O | 3-Br, 5-Br | 3-chloro-2-pyridinyl | Br |
| CH₂CCH | O | 3-CH₃, 5-CN | 3-chloro-2-pyridinyl | Br |
| CH₂CCH | O | 3-CH₃, 5-Cl | 3-chloro-2-pyridinyl | CF₃ |
| CH₂CCH | O | 3-Br, 5-Cl | 3-chloro-2-pyridinyl | CF₃ |
| CH₂CCH | O | 3-Br, 5-Br | 3-chloro-2-pyridinyl | CF₃ |
| CH₂CCH | O | 3-CH₃, 5-CN | 3-chloro-2-pyridinyl | CF₃ |
| phenyl | O | 3-CH₃, 5-Cl | 3-chloro-2-pyridinyl | H |
| phenyl | O | 3-Br, 5-Cl | 3-chloro-2-pyridinyl | H |
| phenyl | O | 3-Br, 5-Br | 3-chloro-2-pyridinyl | H |
| phenyl | O | 3-CH₃, 5-CN | 3-chloro-2-pyridinyl | H |
| phenyl | O | 3-CH₃, 5-Cl | 3-chloro-2-pyridinyl | Cl |
| phenyl | O | 3-Br, 5-Cl | 3-chloro-2-pyridinyl | Cl |

TABLE 29-continued

| R⁶ | A³² | (R⁴)ₙ | R¹³ᵃ⁻¹ | R¹⁴ᵃ⁻¹ |
|---|---|---|---|---|
| phenyl | O | 3-Br, 5-Br | 3-chloro-2-pyridinyl | Cl |
| phenyl | O | 3-CH₃, 5-CN | 3-chloro-2-pyridinyl | Cl |
| phenyl | O | 3-CH₃, 5-Cl | 3-chloro-2-pyridinyl | Br |
| phenyl | O | 3-Br, 5-Cl | 3-chloro-2-pyridinyl | Br |
| phenyl | O | 3-Br, 5-Br | 3-chloro-2-pyridinyl | Br |
| phenyl | O | 3-CH₃, 5-CN | 3-chloro-2-pyridinyl | Br |
| phenyl | O | 3-CH₃, 5-Cl | 3-chloro-2-pyridinyl | CF₃ |
| phenyl | O | 3-Br, 5-Cl | 3-chloro-2-pyridinyl | CF₃ |
| phenyl | O | 3-Br, 5-Br | 3-chloro-2-pyridinyl | CF₃ |
| phenyl | O | 3-CH₃, 5-CN | 3-chloro-2-pyridinyl | CF₃ |

TABLE 30

| R⁶ | A³² | (R⁴)ₙ | R¹³ᵃ⁻¹ | R¹⁴ᵃ⁻¹ |
|---|---|---|---|---|
| CH₃ | S | 3-CH₃, 5-Cl | 3-chloro-2-pyridinyl | H |
| CH₃ | S | 3-Br, 5-Cl | 3-chloro-2-pyridinyl | H |
| CH₃ | S | 3-Br, 5-Br | 3-chloro-2-pyridinyl | H |
| CH₃ | S | 3-CH₃, 5-CN | 3-chloro-2-pyridinyl | H |
| CH₃ | S | 3-CH₃, 5-Cl | 3-chloro-2-pyridinyl | Cl |
| CH₃ | S | 3-Br, 5-Cl | 3-chloro-2-pyridinyl | Cl |
| CH₃ | S | 3-Br, 5-Br | 3-chloro-2-pyridinyl | Cl |
| CH₃ | S | 3-CH₃, 5-CN | 3-chloro-2-pyridinyl | Cl |
| CH₃ | S | 3-CH₃, 5-Cl | 3-chloro-2-pyridinyl | Br |
| CH₃ | S | 3-Br, 5-Cl | 3-chloro-2-pyridinyl | Br |
| CH₃ | S | 3-Br, 5-Br | 3-chloro-2-pyridinyl | Br |
| CH₃ | S | 3-CH₃, 5-CN | 3-chloro-2-pyridinyl | Br |
| CH₃ | S | 3-CH₃, 5-Cl | 3-chloro-2-pyridinyl | CF₃ |
| CH₃ | S | 3-Br, 5-Cl | 3-chloro-2-pyridinyl | CF₃ |
| CH₃ | S | 3-Br, 5-Br | 3-chloro-2-pyridinyl | CF₃ |
| CH₃ | S | 3-CH₃, 5-CN | 3-chloro-2-pyridinyl | CF₃ |
| CH₂CH₃ | S | 3-CH₃, 5-Cl | 3-chloro-2-pyridinyl | H |
| CH₂CH₃ | S | 3-Br, 5-Cl | 3-chloro-2-pyridinyl | H |
| CH₂CH₃ | S | 3-Br, 5-Br | 3-chloro-2-pyridinyl | H |
| CH₂CH₃ | S | 3-CH₃, 5-CN | 3-chloro-2-pyridinyl | H |
| CH₂CH₃ | S | 3-CH₃, 5-Cl | 3-chloro-2-pyridinyl | Cl |
| CH₂CH₃ | S | 3-Br, 5-Cl | 3-chloro-2-pyridinyl | Cl |
| CH₂CH₃ | S | 3-Br, 5-Br | 3-chloro-2-pyridinyl | Cl |
| CH₂CH₃ | S | 3-CH₃, 5-CN | 3-chloro-2-pyridinyl | Cl |
| CH₂CH₃ | S | 3-CH₃, 5-Cl | 3-chloro-2-pyridinyl | Br |
| CH₂CH₃ | S | 3-Br, 5-Cl | 3-chloro-2-pyridinyl | Br |
| CH₂CH₃ | S | 3-Br, 5-Br | 3-chloro-2-pyridinyl | Br |
| CH₂CH₃ | S | 3-CH₃, 5-CN | 3-chloro-2-pyridinyl | Br |
| CH₂CH₃ | S | 3-CH₃, 5-Cl | 3-chloro-2-pyridinyl | CF₃ |
| CH₂CH₃ | S | 3-Br, 5-Cl | 3-chloro-2-pyridinyl | CF₃ |
| CH₂CH₃ | S | 3-Br, 5-Br | 3-chloro-2-pyridinyl | CF₃ |
| CH₂CH₃ | S | 3-CH₃, 5-CN | 3-chloro-2-pyridinyl | CF₃ |

TABLE 31

| R⁶ | A³² | (R⁴)ₙ | R¹³ᵃ⁻¹ | R¹⁴ᵃ⁻¹ |
|---|---|---|---|---|
| phenyl | S | 3-CH₃, 5-Cl | 3-chloro-2-pyridinyl | H |
| phenyl | S | 3-Br, 5-Cl | 3-chloro-2-pyridinyl | H |
| phenyl | S | 3-Br, 5-Br | 3-chloro-2-pyridinyl | H |
| phenyl | S | 3-CH₃, 5-CN | 3-chloro-2-pyridinyl | H |
| phenyl | S | 3-CH₃, 5-Cl | 3-chloro-2-pyridinyl | Cl |
| phenyl | S | 3-Br, 5-Cl | 3-chloro-2-pyridinyl | Cl |
| phenyl | S | 3-Br, 5-Br | 3-chloro-2-pyridinyl | Cl |
| phenyl | S | 3-CH₃, 5-CN | 3-chloro-2-pyridinyl | Cl |
| phenyl | S | 3-CH₃, 5-Cl | 3-chloro-2-pyridinyl | Br |
| phenyl | S | 3-Br, 5-Cl | 3-chloro-2-pyridinyl | Br |
| phenyl | S | 3-Br, 5-Br | 3-chloro-2-pyridinyl | Br |
| phenyl | S | 3-CH₃, 5-CN | 3-chloro-2-pyridinyl | Br |
| phenyl | S | 3-CH₃, 5-Cl | 3-chloro-2-pyridinyl | CF₃ |
| phenyl | S | 3-Br, 5-Cl | 3-chloro-2-pyridinyl | CF₃ |
| phenyl | S | 3-Br, 5-Br | 3-chloro-2-pyridinyl | CF₃ |
| phenyl | S | 3-CH₃, 5-CN | 3-chloro-2-pyridinyl | CF₃ |

A compound represented by the formula (1-R):

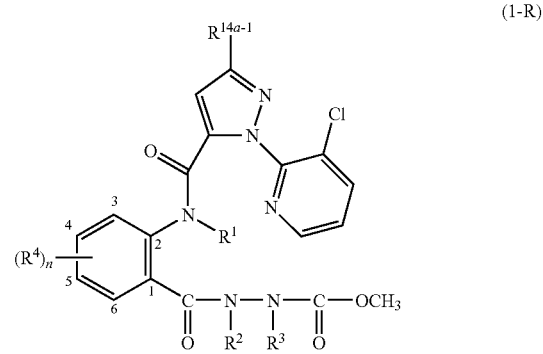

(1-R)

wherein $R^1$, $R^2$, $R^3$, $(R^4)_n$ and $R^{14a-1}$ represent combinations shown in Table 32 to Table 39.

TABLE 32

| R¹ | R² | R³ | (R⁴)ₙ | R¹⁴ᵃ⁻¹ |
|---|---|---|---|---|
| H | CH₃ | H | 3-CH₃, 5-Cl | H |
| H | CH₃ | H | 3-Br, 5-Cl | H |
| H | CH₃ | H | 3-Br, 5-Br | H |
| H | CH₃ | H | 3-CH₃, 5-CN | H |
| H | CH₃ | H | 3-CH₃, 5-Cl | Cl |
| H | CH₃ | H | 3-Br, 5-Cl | Cl |
| H | CH₃ | H | 3-Br, 5-Br | Cl |
| H | CH₃ | H | 3-CH₃, 5-CN | Cl |
| H | CH₃ | H | 3-CH₃, 5-Cl | Br |
| H | CH₃ | H | 3-Br, 5-Cl | Br |
| H | CH₃ | H | 3-Br, 5-Br | Br |
| H | CH₃ | H | 3-CH₃, 5-CN | Br |
| H | CH₃ | H | 3-CH₃, 5-Cl | CF₃ |
| H | CH₃ | H | 3-Br, 5-Cl | CF₃ |
| H | CH₃ | H | 3-Br, 5-Br | CF₃ |
| H | CH₃ | H | 3-CH₃, 5-CN | CF₃ |
| H | H | CH₃ | 3-CH₃, 5-Cl | H |
| H | H | CH₃ | 3-Br, 5-Cl | H |
| H | H | CH₃ | 3-Br, 5-Br | H |
| H | H | CH₃ | 3-CH₃, 5-CN | H |
| H | H | CH₃ | 3-CH₃, 5-Cl | Cl |
| H | H | CH₃ | 3-Br, 5-Cl | Cl |
| H | H | CH₃ | 3-Br, 5-Br | Cl |
| H | H | CH₃ | 3-CH₃, 5-CN | Cl |
| H | H | CH₃ | 3-CH₃, 5-Cl | Br |
| H | H | CH₃ | 3-Br, 5-Cl | Br |
| H | H | CH₃ | 3-Br, 5-Br | Br |
| H | H | CH₃ | 3-CH₃, 5-CN | Br |
| H | H | CH₃ | 3-CH₃, 5-Cl | CF₃ |
| H | H | CH₃ | 3-Br, 5-Cl | CF₃ |
| H | H | CH₃ | 3-Br, 5-Br | CF₃ |
| H | H | CH₃ | 3-CH₃, 5-CN | CF₃ |

TABLE 33

| R¹ | R² | R³ | (R⁴)ₙ | R¹⁴ᵃ⁻¹ |
|---|---|---|---|---|
| H | CH₃ | CH₃ | 3-CH₃, 5-Cl | H |
| H | CH₃ | CH₃ | 3-Br, 5-Cl | H |
| H | CH₃ | CH₃ | 3-Br, 5-Br | H |
| H | CH₃ | CH₃ | 3-CH₃, 5-CN | H |
| H | CH₃ | CH₃ | 3-CH₃, 5-Cl | Cl |
| H | CH₃ | CH₃ | 3-Br, 5-Cl | Cl |
| H | CH₃ | CH₃ | 3-Br, 5-Br | Cl |
| H | CH₃ | CH₃ | 3-CH₃, 5-CN | Cl |
| H | CH₃ | CH₃ | 3-CH₃, 5-Cl | Br |
| H | CH₃ | CH₃ | 3-Br, 5-Cl | Br |
| H | CH₃ | CH₃ | 3-Br, 5-Br | Br |
| H | CH₃ | CH₃ | 3-CH₃, 5-CN | Br |
| H | CH₃ | CH₃ | 3-CH₃, 5-Cl | CF₃ |

TABLE 33-continued

| R¹ | R² | R³ | (R⁴)ₙ | R¹⁴ᵃ⁻¹ |
|---|---|---|---|---|
| H | CH₃ | CH₃ | 3-Br, 5-Cl | CF₃ |
| H | CH₃ | CH₃ | 3-Br, 5-Br | CF₃ |
| H | CH₃ | CH₃ | 3-CH₃, 5-CN | CF₃ |
| H | H | CH₂CH₃ | 3-CH₃, 5-Cl | H |
| H | H | CH₂CH₃ | 3-Br, 5-Cl | H |
| H | H | CH₂CH₃ | 3-Br, 5-Br | H |
| H | H | CH₂CH₃ | 3-CH₃, 5-CN | H |
| H | H | CH₂CH₃ | 3-CH₃, 5-Cl | Cl |
| H | H | CH₂CH₃ | 3-Br, 5-Cl | Cl |
| H | H | CH₂CH₃ | 3-Br, 5-Br | Cl |
| H | H | CH₂CH₃ | 3-CH₃, 5-CN | Cl |
| H | H | CH₂CH₃ | 3-CH₃, 5-Cl | Br |
| H | H | CH₂CH₃ | 3-Br, 5-Cl | Br |
| H | H | CH₂CH₃ | 3-Br, 5-Br | Br |
| H | H | CH₂CH₃ | 3-CH₃, 5-CN | Br |
| H | H | CH₂CH₃ | 3-CH₃, 5-Cl | CF₃ |
| H | H | CH₂CH₃ | 3-Br, 5-Cl | CF₃ |
| H | H | CH₂CH₃ | 3-Br, 5-Br | CF₃ |
| H | H | CH₂CH₃ | 3-CH₃, 5-CN | CF₃ |

TABLE 34

| R¹ | R² | R³ | (R⁴)ₙ | R¹⁴ᵃ⁻¹ |
|---|---|---|---|---|
| H | H | CH(CH₃)₂ | 3-CH₃, 5-Cl | H |
| H | H | CH(CH₃)₂ | 3-Br, 5-Cl | H |
| H | H | CH(CH₃)₂ | 3-Br, 5-Br | H |
| H | H | CH(CH₃)₂ | 3-CH₃, 5-CN | H |
| H | H | CH(CH₃)₂ | 3-CH₃, 5-Cl | Cl |
| H | H | CH(CH₃)₂ | 3-Br, 5-Cl | Cl |
| H | H | CH(CH₃)₂ | 3-Br, 5-Br | Cl |
| H | H | CH(CH₃)₂ | 3-CH₃, 5-CN | Cl |
| H | H | CH(CH₃)₂ | 3-CH₃, 5-Cl | Br |
| H | H | CH(CH₃)₂ | 3-Br, 5-Cl | Br |
| H | H | CH(CH₃)₂ | 3-Br, 5-Br | Br |
| H | H | CH(CH₃)₂ | 3-CH₃, 5-CN | Br |
| H | H | CH(CH₃)₂ | 3-CH₃, 5-Cl | CF₃ |
| H | H | CH(CH₃)₂ | 3-Br, 5-Cl | CF₃ |
| H | H | CH(CH₃)₂ | 3-Br, 5-Br | CF₃ |
| H | H | CH(CH₃)₂ | 3-CH₃, 5-CN | CF₃ |
| H | H | C(CH₃)₃ | 3-CH₃, 5-Cl | H |
| H | H | C(CH₃)₃ | 3-Br, 5-Cl | H |
| H | H | C(CH₃)₃ | 3-Br, 5-Br | H |
| H | H | C(CH₃)₃ | 3-CH₃, 5-CN | H |
| H | H | C(CH₃)₃ | 3-CH₃, 5-Cl | Cl |
| H | H | C(CH₃)₃ | 3-Br, 5-Cl | Cl |
| H | H | C(CH₃)₃ | 3-Br, 5-Br | Cl |
| H | H | C(CH₃)₃ | 3-CH₃, 5-CN | Cl |
| H | H | C(CH₃)₃ | 3-CH₃, 5-Cl | Br |
| H | H | C(CH₃)₃ | 3-Br, 5-Cl | Br |
| H | H | C(CH₃)₃ | 3-Br, 5-Br | Br |
| H | H | C(CH₃)₃ | 3-CH₃, 5-CN | Br |
| H | H | C(CH₃)₃ | 3-CH₃, 5-Cl | CF₃ |
| H | H | C(CH₃)₃ | 3-Br, 5-Cl | CF₃ |
| H | H | C(CH₃)₃ | 3-Br, 5-Br | CF₃ |
| H | H | C(CH₃)₃ | 3-CH₃, 5-CN | CF₃ |

TABLE 35

| R¹ | R² | R³ | (R⁴)ₙ | R¹⁴ᵃ⁻¹ |
|---|---|---|---|---|
| H | H | C(=O)OCH₃ | 3-CH₃, 5-Cl | H |
| H | H | C(=O)OCH₃ | 3-Br, 5-Cl | H |
| H | H | C(=O)OCH₃ | 3-Br, 5-Br | H |
| H | H | C(=O)OCH₃ | 3-CH₃, 5-CN | H |
| H | H | C(=O)OCH₃ | 3-CH₃, 5-Cl | Cl |
| H | H | C(=O)OCH₃ | 3-Br, 5-Cl | Cl |
| H | H | C(=O)OCH₃ | 3-Br, 5-Br | Cl |
| H | H | C(=O)OCH₃ | 3-CH₃, 5-CN | Cl |
| H | H | C(=O)OCH₃ | 3-CH₃, 5-Cl | Br |
| H | H | C(=O)OCH₃ | 3-Br, 5-Cl | Br |
| H | H | C(=O)OCH₃ | 3-Br, 5-Br | Br |

TABLE 35-continued

| R¹ | R² | R³ | (R⁴)ₙ | R¹⁴ᵃ⁻¹ |
|---|---|---|---|---|
| H | H | C(=O)OCH₃ | 3-CH₃, 5-CN | Br |
| H | H | C(=O)OCH₃ | 3-CH₃, 5-Cl | CF₃ |
| H | H | C(=O)OCH₃ | 3-Br, 5-Cl | CF₃ |
| H | H | C(=O)OCH₃ | 3-Br, 5-Br | CF₃ |
| H | H | C(=O)OCH₃ | 3-CH₃, 5-CN | CF₃ |
| H | H | C(=O)N(CH₃)₂ | 3-CH₃, 5-Cl | H |
| H | H | C(=O)N(CH₃)₂ | 3-Br, 5-Cl | H |
| H | H | C(=O)N(CH₃)₂ | 3-Br, 5-Br | H |
| H | H | C(=O)N(CH₃)₂ | 3-CH₃, 5-CN | H |
| H | H | C(=O)N(CH₃)₂ | 3-CH₃, 5-Cl | Cl |
| H | H | C(=O)N(CH₃)₂ | 3-Br, 5-Cl | Cl |
| H | H | C(=O)N(CH₃)₂ | 3-Br, 5-Br | Cl |
| H | H | C(=O)N(CH₃)₂ | 3-CH₃, 5-CN | Cl |
| H | H | C(=O)N(CH₃)₂ | 3-CH₃, 5-Cl | Br |
| H | H | C(=O)N(CH₃)₂ | 3-Br, 5-Cl | Br |
| H | H | C(=O)N(CH₃)₂ | 3-Br, 5-Br | Br |
| H | H | C(=O)N(CH₃)₂ | 3-CH₃, 5-CN | Br |
| H | H | C(=O)N(CH₃)₂ | 3-CH₃, 5-Cl | CF₃ |
| H | H | C(=O)N(CH₃)₂ | 3-Br, 5-Cl | CF₃ |
| H | H | C(=O)N(CH₃)₂ | 3-Br, 5-Br | CF₃ |
| H | H | C(=O)N(CH₃)₂ | 3-CH₃, 5-CN | CF₃ |

TABLE 36

| R¹ | R² | R³ | (R⁴)ₙ | R¹⁴ᵃ⁻¹ |
|---|---|---|---|---|
| CH₃ | CH₃ | H | 3-CH₃, 5-Cl | H |
| CH₃ | CH₃ | H | 3-Br, 5-Cl | H |
| CH₃ | CH₃ | H | 3-Br, 5-Br | H |
| CH₃ | CH₃ | H | 3-CH₃, 5-CN | H |
| CH₃ | CH₃ | H | 3-CH₃, 5-Cl | Cl |
| CH₃ | CH₃ | H | 3-Br, 5-Cl | Cl |
| CH₃ | CH₃ | H | 3-Br, 5-Br | Cl |
| CH₃ | CH₃ | H | 3-CH₃, 5-CN | Cl |
| CH₃ | CH₃ | H | 3-CH₃, 5-Cl | Br |
| CH₃ | CH₃ | H | 3-Br, 5-Cl | Br |
| CH₃ | CH₃ | H | 3-Br, 5-Br | Br |
| CH₃ | CH₃ | H | 3-CH₃, 5-CN | Br |
| CH₃ | CH₃ | H | 3-CH₃, 5-Cl | CF₃ |
| CH₃ | CH₃ | H | 3-Br, 5-Cl | CF₃ |
| CH₃ | CH₃ | H | 3-Br, 5-Br | CF₃ |
| CH₃ | CH₃ | H | 3-CH₃, 5-CN | CF₃ |
| CH₃ | H | CH₃ | 3-CH₃, 5-Cl | H |
| CH₃ | H | CH₃ | 3-Br, 5-Cl | H |
| CH₃ | H | CH₃ | 3-Br, 5-Br | H |
| CH₃ | H | CH₃ | 3-CH₃, 5-CN | H |
| CH₃ | H | CH₃ | 3-CH₃, 5-Cl | Cl |
| CH₃ | H | CH₃ | 3-Br, 5-Cl | Cl |
| CH₃ | H | CH₃ | 3-Br, 5-Br | Cl |
| CH₃ | H | CH₃ | 3-CH₃, 5-CN | Cl |
| CH₃ | H | CH₃ | 3-CH₃, 5-Cl | Br |
| CH₃ | H | CH₃ | 3-Br, 5-Cl | Br |
| CH₃ | H | CH₃ | 3-Br, 5-Br | Br |
| CH₃ | H | CH₃ | 3-CH₃, 5-CN | Br |
| CH₃ | H | CH₃ | 3-CH₃, 5-Cl | CF₃ |
| CH₃ | H | CH₃ | 3-Br, 5-Cl | CF₃ |
| CH₃ | H | CH₃ | 3-Br, 5-Br | CF₃ |
| CH₃ | H | CH₃ | 3-CH₃, 5-CN | CF₃ |

TABLE 37

| R¹ | R² | R³ | (R⁴)ₙ | R¹⁴ᵃ⁻¹ |
|---|---|---|---|---|
| CH₃ | CH₃ | CH₃ | 3-CH₃, 5-Cl | H |
| CH₃ | CH₃ | CH₃ | 3-Br, 5-Cl | H |
| CH₃ | CH₃ | CH₃ | 3-Br, 5-Br | H |
| CH₃ | CH₃ | CH₃ | 3-CH₃, 5-CN | H |
| CH₃ | CH₃ | CH₃ | 3-CH₃, 5-Cl | Cl |
| CH₃ | CH₃ | CH₃ | 3-Br, 5-Cl | Cl |
| CH₃ | CH₃ | CH₃ | 3-Br, 5-Br | Cl |
| CH₃ | CH₃ | CH₃ | 3-CH₃, 5-CN | Cl |
| CH₃ | CH₃ | CH₃ | 3-CH₃, 5-Cl | Br |

TABLE 37-continued

| R¹ | R² | R³ | (R⁴)ₙ | R¹⁴ᵃ⁻¹ |
|---|---|---|---|---|
| CH₃ | CH₃ | CH₃ | 3-Br, 5-Cl | Br |
| CH₃ | CH₃ | CH₃ | 3-Br, 5-Br | Br |
| CH₃ | CH₃ | CH₃ | 3-CH₃, 5-CN | Br |
| CH₃ | CH₃ | CH₃ | 3-CH₃, 5-Cl | CF₃ |
| CH₃ | CH₃ | CH₃ | 3-Br, 5-Cl | CF₃ |
| CH₃ | CH₃ | CH₃ | 3-Br, 5-Br | CF₃ |
| CH₃ | CH₃ | CH₃ | 3-CH₃, 5-CN | CF₃ |
| CH₃ | H | CH₂CH₃ | 3-CH₃, 5-Cl | H |
| CH₃ | H | CH₂CH₃ | 3-Br, 5-Cl | H |
| CH₃ | H | CH₂CH₃ | 3-Br, 5-Br | H |
| CH₃ | H | CH₂CH₃ | 3-CH₃, 5-CN | H |
| CH₃ | H | CH₂CH₃ | 3-CH₃, 5-Cl | Cl |
| CH₃ | H | CH₂CH₃ | 3-Br, 5-Cl | Cl |
| CH₃ | H | CH₂CH₃ | 3-Br, 5-Br | Cl |
| CH₃ | H | CH₂CH₃ | 3-CH₃, 5-CN | Cl |
| CH₃ | H | CH₂CH₃ | 3-CH₃, 5-Cl | Br |
| CH₃ | H | CH₂CH₃ | 3-Br, 5-Cl | Br |
| CH₃ | H | CH₂CH₃ | 3-Br, 5-Br | Br |
| CH₃ | H | CH₂CH₃ | 3-CH₃, 5-CN | Br |
| CH₃ | H | CH₂CH₃ | 3-CH₃, 5-Cl | CF₃ |
| CH₃ | H | CH₂CH₃ | 3-Br, 5-Cl | CF₃ |
| CH₃ | H | CH₂CH₃ | 3-Br, 5-Br | CF₃ |
| CH₃ | H | CH₂CH₃ | 3-CH₃, 5-CN | CF₃ |

TABLE 38

| R¹ | R² | R³ | (R⁴)ₙ | R¹⁴ᵃ⁻¹ |
|---|---|---|---|---|
| CH₃ | H | CH(CH₃)₂ | 3-CH₃, 5-Cl | H |
| CH₃ | H | CH(CH₃)₂ | 3-Br, 5-Cl | H |
| CH₃ | H | CH(CH₃)₂ | 3-Br, 5-Br | H |
| CH₃ | H | CH(CH₃)₂ | 3-CH₃, 5-CN | H |
| CH₃ | H | CH(CH₃)₂ | 3-CH₃, 5-Cl | Cl |
| CH₃ | H | CH(CH₃)₂ | 3-Br, 5-Cl | Cl |
| CH₃ | H | CH(CH₃)₂ | 3-Br, 5-Br | Cl |
| CH₃ | H | CH(CH₃)₂ | 3-CH₃, 5-CN | Cl |
| CH₃ | H | CH(CH₃)₂ | 3-CH₃, 5-Cl | Br |
| CH₃ | H | CH(CH₃)₂ | 3-Br, 5-Cl | Br |
| CH₃ | H | CH(CH₃)₂ | 3-Br, 5-Br | Br |
| CH₃ | H | CH(CH₃)₂ | 3-CH₃, 5-CN | Br |
| CH₃ | H | CH(CH₃)₂ | 3-CH₃, 5-Cl | CF₃ |
| CH₃ | H | CH(CH₃)₂ | 3-Br, 5-Cl | CF₃ |
| CH₃ | H | CH(CH₃)₂ | 3-Br, 5-Br | CF₃ |
| CH₃ | H | CH(CH₃)₂ | 3-CH₃, 5-CN | CF₃ |
| CH₃ | H | C(CH₃)₃ | 3-CH₃, 5-Cl | H |
| CH₃ | H | C(CH₃)₃ | 3-Br, 5-Cl | H |
| CH₃ | H | C(CH₃)₃ | 3-Br, 5-Br | H |
| CH₃ | H | C(CH₃)₃ | 3-CH₃, 5-CN | H |
| CH₃ | H | C(CH₃)₃ | 3-CH₃, 5-Cl | Cl |
| CH₃ | H | C(CH₃)₃ | 3-Br, 5-Cl | Cl |
| CH₃ | H | C(CH₃)₃ | 3-Br, 5-Br | Cl |
| CH₃ | H | C(CH₃)₃ | 3-CH₃, 5-CN | Cl |
| CH₃ | H | C(CH₃)₃ | 3-CH₃, 5-Cl | Br |
| CH₃ | H | C(CH₃)₃ | 3-Br, 5-Cl | Br |
| CH₃ | H | C(CH₃)₃ | 3-Br, 5-Br | Br |
| CH₃ | H | C(CH₃)₃ | 3-CH₃, 5-CN | Br |
| CH₃ | H | C(CH₃)₃ | 3-CH₃, 5-Cl | CF₃ |
| CH₃ | H | C(CH₃)₃ | 3-Br, 5-Cl | CF₃ |
| CH₃ | H | C(CH₃)₃ | 3-Br, 5-Br | CF₃ |
| CH₃ | H | C(CH₃)₃ | 3-CH₃, 5-CN | CF₃ |

TABLE 39

| R¹ | R² | R³ | (R⁴)ₙ | R¹⁴ᵃ⁻¹ |
|---|---|---|---|---|
| CH₃ | H | C(=O)OCH₃ | 3-CH₃, 5-Cl | H |
| CH₃ | H | C(=O)OCH₃ | 3-Br, 5-Cl | H |
| CH₃ | H | C(=O)OCH₃ | 3-Br, 5-Br | H |
| CH₃ | H | C(=O)OCH₃ | 3-CH₃, 5-CN | H |
| CH₃ | H | C(=O)OCH₃ | 3-CH₃, 5-Cl | Cl |
| CH₃ | H | C(=O)OCH₃ | 3-Br, 5-Cl | Cl |
| CH₃ | H | C(=O)OCH₃ | 3-Br, 5-Br | Cl |
| CH₃ | H | C(=O)OCH₃ | 3-CH₃, 5-CN | Cl |
| CH₃ | H | C(=O)OCH₃ | 3-CH₃, 5-Cl | Br |
| CH₃ | H | C(=O)OCH₃ | 3-Br, 5-Cl | Br |
| CH₃ | H | C(=O)OCH₃ | 3-Br, 5-Br | Br |
| CH₃ | H | C(=O)OCH₃ | 3-CH₃, 5-CN | Br |
| CH₃ | H | C(=O)OCH₃ | 3-CH₃, 5-Cl | CF₃ |
| CH₃ | H | C(=O)OCH₃ | 3-Br, 5-Cl | CF₃ |
| CH₃ | H | C(=O)OCH₃ | 3-Br, 5-Br | CF₃ |
| CH₃ | H | C(=O)OCH₃ | 3-CH₃, 5-CN | CF₃ |
| CH₃ | H | C(=O)N(CH₃)₂ | 3-CH₃, 5-Cl | H |
| CH₃ | H | C(=O)N(CH₃)₂ | 3-Br, 5-Cl | H |
| CH₃ | H | C(=O)N(CH₃)₂ | 3-Br, 5-Br | H |
| CH₃ | H | C(=O)N(CH₃)₂ | 3-CH₃, 5-CN | H |
| CH₃ | H | C(=O)N(CH₃)₂ | 3-CH₃, 5-Cl | Cl |
| CH₃ | H | C(=O)N(CH₃)₂ | 3-Br, 5-Cl | Cl |
| CH₃ | H | C(=O)N(CH₃)₂ | 3-Br, 5-Br | Cl |
| CH₃ | H | C(=O)N(CH₃)₂ | 3-CH₃, 5-CN | Cl |
| CH₃ | H | C(=O)N(CH₃)₂ | 3-CH₃, 5-Cl | Br |
| CH₃ | H | C(=O)N(CH₃)₂ | 3-Br, 5-Cl | Br |
| CH₃ | H | C(=O)N(CH₃)₂ | 3-Br, 5-Br | Br |
| CH₃ | H | C(=O)N(CH₃)₂ | 3-CH₃, 5-CN | Br |
| CH₃ | H | C(=O)N(CH₃)₂ | 3-CH₃, 5-Cl | CF₃ |
| CH₃ | H | C(=O)N(CH₃)₂ | 3-Br, 5-Cl | CF₃ |
| CH₃ | H | C(=O)N(CH₃)₂ | 3-Br, 5-Br | CF₃ |
| CH₃ | H | C(=O)N(CH₃)₂ | 3-CH₃, 5-CN | CF₃ |
| H | CH₃ | H | 3-Cl, 5-Cl | H |
| H | CH₃ | H | 3-Cl, 5-Cl | Cl |
| H | CH₃ | H | 3-Cl, 5-Cl | Br |
| H | CH₃ | H | 3-Cl, 5-Cl | CF₃ |
| H | H | CH₃ | 3-Cl, 5-Cl | H |
| H | H | CH₃ | 3-Cl, 5-Cl | Cl |
| H | H | CH₃ | 3-Cl, 5-Cl | Br |
| H | H | CH₃ | 3-Cl, 5-Cl | CF₃ |
| H | CH₃ | CH₃ | 3-Cl, 5-Cl | H |
| H | CH₃ | CH₃ | 3-Cl, 5-Cl | Cl |
| H | CH₃ | CH₃ | 3-Cl, 5-Cl | Br |
| H | CH₃ | CH₃ | 3-Cl, 5-Cl | CF₃ |
| H | H | CH₂CH₃ | 3-Cl, 5-Cl | H |
| H | H | CH₂CH₃ | 3-Cl, 5-Cl | Cl |
| H | H | CH₂CH₃ | 3-Cl, 5-Cl | Br |
| H | H | CH₂CH₃ | 3-Cl, 5-Cl | CF₃ |
| H | H | CH(CH₃)₂ | 3-Cl, 5-Cl | H |
| H | H | CH(CH₃)₂ | 3-Cl, 5-Cl | Cl |
| H | H | CH(CH₃)₂ | 3-Cl, 5-Cl | Br |
| H | H | CH(CH₃)₂ | 3-Cl, 5-Cl | CF₃ |
| H | H | C(CH₃)₃ | 3-Cl, 5-Cl | H |
| H | H | C(CH₃)₃ | 3-Cl, 5-Cl | Cl |
| H | H | C(CH₃)₃ | 3-Cl, 5-Cl | Br |
| H | H | C(CH₃)₃ | 3-Cl, 5-Cl | CF₃ |
| H | H | C(=O)OCH₃ | 3-Cl, 5-Cl | H |
| H | H | C(=O)OCH₃ | 3-Cl, 5-Cl | Cl |
| H | H | C(=O)OCH₃ | 3-Cl, 5-Cl | Br |
| H | H | C(=O)OCH₃ | 3-Cl, 5-Cl | CF₃ |
| H | H | C(=O)N(CH₃)₂ | 3-Cl, 5-Cl | H |
| H | H | C(=O)N(CH₃)₂ | 3-Cl, 5-Cl | Cl |
| H | H | C(=O)N(CH₃)₂ | 3-Cl, 5-Cl | Br |
| H | H | C(=O)N(CH₃)₂ | 3-Cl, 5-Cl | CF₃ |
| CH₃ | CH₃ | H | 3-Cl, 5-Cl | H |
| CH₃ | CH₃ | H | 3-Cl, 5-Cl | Cl |
| CH₃ | CH₃ | H | 3-Cl, 5-Cl | Br |
| CH₃ | CH₃ | H | 3-Cl, 5-Cl | CF₃ |
| CH₃ | H | CH₃ | 3-Cl, 5-Cl | H |
| CH₃ | H | CH₃ | 3-Cl, 5-Cl | Cl |
| CH₃ | H | CH₃ | 3-Cl, 5-Cl | Br |
| CH₃ | H | CH₃ | 3-Cl, 5-Cl | CF₃ |
| CH₃ | CH₃ | CH₃ | 3-Cl, 5-Cl | H |
| CH₃ | CH₃ | CH₃ | 3-Cl, 5-Cl | Cl |
| CH₃ | CH₃ | CH₃ | 3-Cl, 5-Cl | Br |
| CH₃ | CH₃ | CH₃ | 3-Cl, 5-Cl | CF₃ |
| CH₃ | H | CH₂CH₃ | 3-Cl, 5-Cl | H |
| CH₃ | H | CH₂CH₃ | 3-Cl, 5-Cl | Cl |
| CH₃ | H | CH₂CH₃ | 3-Cl, 5-Cl | Br |
| CH₃ | H | CH₂CH₃ | 3-Cl, 5-Cl | CF₃ |
| CH₃ | H | CH(CH₃)₂ | 3-Cl, 5-Cl | H |
| CH₃ | H | CH(CH₃)₂ | 3-Cl, 5-Cl | Cl |
| CH₃ | H | CH(CH₃)₂ | 3-Cl, 5-Cl | Br |
| CH₃ | H | CH(CH₃)₂ | 3-Cl, 5-Cl | CF₃ |

TABLE 39-continued

| R¹ | R² | R³ | (R⁴)ₙ | R¹⁴ᵃ⁻¹ |
|---|---|---|---|---|
| CH₃ | H | C(CH₃)₃ | 3-Cl, 5-Cl | H |
| CH₃ | H | C(CH₃)₃ | 3-Cl, 5-Cl | Cl |
| CH₃ | H | C(CH₃)₃ | 3-Cl, 5-Cl | Br |
| CH₃ | H | C(CH₃)₃ | 3-Cl, 5-Cl | CF₃ |
| CH₃ | H | C(=O)OCH₃ | 3-Cl, 5-Cl | H |
| CH₃ | H | C(=O)OCH₃ | 3-Cl, 5-Cl | Cl |
| CH₃ | H | C(=O)OCH₃ | 3-Cl, 5-Cl | Br |
| CH₃ | H | C(=O)OCH₃ | 3-Cl, 5-Cl | CF₃ |
| CH₃ | H | C(=O)N(CH₃)₂ | 3-Cl, 5-Cl | H |
| CH₃ | H | C(=O)N(CH₃)₂ | 3-Cl, 5-Cl | Cl |
| CH₃ | H | C(=O)N(CH₃)₂ | 3-Cl, 5-Cl | Br |
| CH₃ | H | C(=O)N(CH₃)₂ | 3-Cl, 5-Cl | CF₃ |
| H | CH₃ | CH₂CH₃ | 3-CH₃, 5-Cl | H |
| H | CH₃ | CH₂CH₃ | 3-Br, 5-Cl | H |
| H | CH₃ | CH₂CH₃ | 3-Br, 5-Br | H |
| H | CH₃ | CH₂CH₃ | 3-CH₃, 5-CN | H |
| H | CH₃ | CH₂CH₃ | 3-Cl, 5-Cl | H |
| H | CH₃ | CH₂CH₃ | 3-CH₃, 5-Cl | Cl |
| H | CH₃ | CH₂CH₃ | 3-Br, 5-Cl | Cl |
| H | CH₃ | CH₂CH₃ | 3-Br, 5-Br | Cl |
| H | CH₃ | CH₂CH₃ | 3-CH₃, 5-CN | Cl |
| H | CH₃ | CH₂CH₃ | 3-Cl, 5-Cl | Cl |
| H | CH₃ | CH₂CH₃ | 3-CH₃, 5-Cl | Br |
| H | CH₃ | CH₂CH₃ | 3-Br, 5-Cl | Br |
| H | CH₃ | CH₂CH₃ | 3-Br, 5-Br | Br |
| H | CH₃ | CH₂CH₃ | 3-CH₃, 5-CN | Br |
| H | CH₃ | CH₂CH₃ | 3-Cl, 5-Cl | Br |
| H | CH₃ | CH₂CH₃ | 3-CH₃, 5-Cl | CF₃ |
| H | CH₃ | CH₂CH₃ | 3-Br, 5-Cl | CF₃ |
| H | CH₃ | CH₂CH₃ | 3-Br, 5-Br | CF₃ |
| H | CH₃ | CH₂CH₃ | 3-CH₃, 5-CN | CF₃ |
| H | CH₃ | CH₂CH₃ | 3-Cl, 5-Cl | CF₃ |
| H | CH₃ | CH(CH₃)₂ | 3-CH₃, 5-Cl | H |
| H | CH₃ | CH(CH₃)₂ | 3-Br, 5-Cl | H |
| H | CH₃ | CH(CH₃)₂ | 3-Br, 5-Br | H |
| H | CH₃ | CH(CH₃)₂ | 3-CH₃, 5-CN | H |
| H | CH₃ | CH(CH₃)₂ | 3-Cl, 5-Cl | H |
| H | CH₃ | CH(CH₃)₂ | 3-CH₃, 5-Cl | Cl |
| H | CH₃ | CH(CH₃)₂ | 3-Br, 5-Cl | Cl |
| H | CH₃ | CH(CH₃)₂ | 3-Br, 5-Br | Cl |
| H | CH₃ | CH(CH₃)₂ | 3-CH₃, 5-CN | Cl |
| H | CH₃ | CH(CH₃)₂ | 3-Cl, 5-Cl | Cl |
| H | CH₃ | CH(CH₃)₂ | 3-CH₃, 5-Cl | Br |
| H | CH₃ | CH(CH₃)₂ | 3-Br, 5-Cl | Br |
| H | CH₃ | CH(CH₃)₂ | 3-Br, 5-Br | Br |
| H | CH₃ | CH(CH₃)₂ | 3-CH₃, 5-CN | Br |
| H | CH₃ | CH(CH₃)₂ | 3-Cl, 5-Cl | Br |
| H | CH₃ | CH(CH₃)₂ | 3-CH₃, 5-Cl | CF₃ |
| H | CH₃ | CH(CH₃)₂ | 3-Br, 5-Cl | CF₃ |
| H | CH₃ | CH(CH₃)₂ | 3-Br, 5-Br | CF₃ |
| H | CH₃ | CH(CH₃)₂ | 3-CH₃, 5-CN | CF₃ |
| H | CH₂CH₃ | CH₃ | 3-CH₃, 5-Cl | H |
| H | CH₂CH₃ | CH₃ | 3-Br, 5-Cl | H |
| H | CH₂CH₃ | CH₃ | 3-Br, 5-Br | H |
| H | CH₂CH₃ | CH₃ | 3-CH₃, 5-CN | H |
| H | CH₂CH₃ | CH₃ | 3-Cl, 5-Cl | H |
| H | CH₂CH₃ | CH₃ | 3-CH₃, 5-Cl | Cl |
| H | CH₂CH₃ | CH₃ | 3-Br, 5-Cl | Cl |
| H | CH₂CH₃ | CH₃ | 3-Br, 5-Br | Cl |
| H | CH₂CH₃ | CH₃ | 3-CH₃, 5-CN | Cl |
| H | CH₂CH₃ | CH₃ | 3-Cl, 5-Cl | Cl |
| H | CH₂CH₃ | CH₃ | 3-CH₃, 5-Cl | Br |
| H | CH₂CH₃ | CH₃ | 3-Br, 5-Cl | Br |
| H | CH₂CH₃ | CH₃ | 3-Br, 5-Br | Br |
| H | CH₂CH₃ | CH₃ | 3-CH₃, 5-CN | Br |
| H | CH₂CH₃ | CH₃ | 3-Cl, 5-Cl | Br |
| H | CH₂CH₃ | CH₃ | 3-CH₃, 5-Cl | CF₃ |
| H | CH₂CH₃ | CH₃ | 3-Br, 5-Cl | CF₃ |
| H | CH₂CH₃ | CH₃ | 3-Br, 5-Br | CF₃ |
| H | CH₂CH₃ | CH₃ | 3-CH₃, 5-CN | CF₃ |
| H | CH₂CH₃ | CH₃ | 3-Cl, 5-Cl | CF₃ |
| H | CH(CH₃)₂ | CH₃ | 3-CH₃, 5-Cl | H |
| H | CH(CH₃)₂ | CH₃ | 3-Br, 5-Cl | H |
| H | CH(CH₃)₂ | CH₃ | 3-Br, 5-Br | H |
| H | CH(CH₃)₂ | CH₃ | 3-CH₃, 5-CN | H |
| H | CH(CH₃)₂ | CH₃ | 3-Cl, 5-Cl | H |
| H | CH(CH₃)₂ | CH₃ | 3-CH₃, 5-Cl | Cl |
| H | CH(CH₃)₂ | CH₃ | 3-Br, 5-Cl | Cl |
| H | CH(CH₃)₂ | CH₃ | 3-Br, 5-Br | Cl |
| H | CH(CH₃)₂ | CH₃ | 3-CH₃, 5-CN | Cl |
| H | CH(CH₃)₂ | CH₃ | 3-Cl, 5-Cl | Cl |
| H | CH(CH₃)₂ | CH₃ | 3-CH₃, 5-Cl | Br |
| H | CH(CH₃)₂ | CH₃ | 3-Br, 5-Cl | Br |
| H | CH(CH₃)₂ | CH₃ | 3-Br, 5-Br | Br |
| H | CH(CH₃)₂ | CH₃ | 3-CH₃, 5-CN | Br |
| H | CH(CH₃)₂ | CH₃ | 3-Cl, 5-Cl | Br |
| H | CH(CH₃)₂ | CH₃ | 3-CH₃, 5-Cl | CF₃ |
| H | CH(CH₃)₂ | CH₃ | 3-Br, 5-Cl | CF₃ |
| H | CH(CH₃)₂ | CH₃ | 3-Br, 5-Br | CF₃ |
| H | CH(CH₃)₂ | CH₃ | 3-CH₃, 5-CN | CF₃ |
| H | CH(CH₃)₂ | CH₃ | 3-Cl, 5-Cl | CF₃ |
| H | CH₂CH₃ | CH₂CH₃ | 3-CH₃, 5-Cl | H |
| H | CH₂CH₃ | CH₂CH₃ | 3-Br, 5-Cl | H |
| H | CH₂CH₃ | CH₂CH₃ | 3-Br, 5-Br | H |
| H | CH₂CH₃ | CH₂CH₃ | 3-CH₃, 5-CN | H |
| H | CH₂CH₃ | CH₂CH₃ | 3-Cl, 5-Cl | H |
| H | CH₂CH₃ | CH₂CH₃ | 3-CH₃, 5-Cl | Cl |
| H | CH₂CH₃ | CH₂CH₃ | 3-Br, 5-Cl | Cl |
| H | CH₂CH₃ | CH₂CH₃ | 3-Br, 5-Br | Cl |
| H | CH₂CH₃ | CH₂CH₃ | 3-CH₃, 5-CN | Cl |
| H | CH₂CH₃ | CH₂CH₃ | 3-Cl, 5-Cl | Cl |
| H | CH₂CH₃ | CH₂CH₃ | 3-CH₃, 5-Cl | Br |
| H | CH₂CH₃ | CH₂CH₃ | 3-Br, 5-Cl | Br |
| H | CH₂CH₃ | CH₂CH₃ | 3-Br, 5-Br | Br |
| H | CH₂CH₃ | CH₂CH₃ | 3-CH₃, 5-CN | Br |
| H | CH₂CH₃ | CH₂CH₃ | 3-Cl, 5-Cl | Br |
| H | CH₂CH₃ | CH₂CH₃ | 3-CH₃, 5-Cl | CF₃ |
| H | CH₂CH₃ | CH₂CH₃ | 3-Br, 5-Cl | CF₃ |
| H | CH₂CH₃ | CH₂CH₃ | 3-Br, 5-Br | CF₃ |
| H | CH₂CH₃ | CH₂CH₃ | 3-CH₃, 5-CN | CF₃ |
| H | CH₂CH₃ | CH₂CH₃ | 3-Cl, 5-Cl | CF₃ |

A compound represented by the formula (1-C):

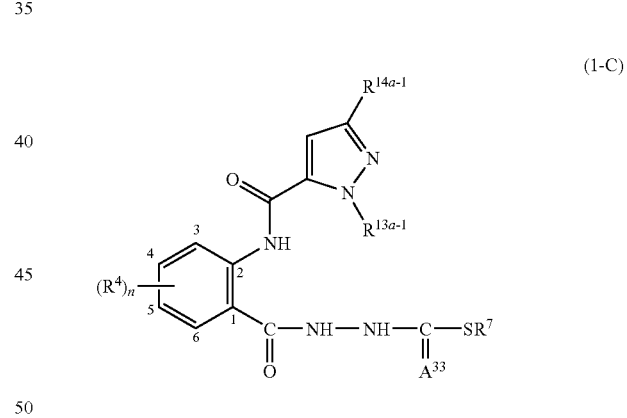

(1-C)

wherein R⁷, A³³, (R⁴)ₙ, R¹³ᵃ⁻¹ and R¹⁴ᵃ⁻¹ represent combinations shown in Table 40 to Table 41.

TABLE 40

| R⁷ | A³³ | (R⁴)ₙ | R¹³ᵃ⁻¹ | R¹⁴ᵃ⁻¹ |
|---|---|---|---|---|
| CH₃ | O | 3-CH₃, 5-Cl | 3-chloro-2-pyridinyl | H |
| CH₃ | O | 3-Br, 5-Cl | 3-chloro-2-pyridinyl | H |
| CH₃ | O | 3-Br, 5-Br | 3-chloro-2-pyridinyl | H |
| CH₃ | O | 3-CH₃, 5-CN | 3-chloro-2-pyridinyl | H |
| CH₃ | O | 3-CH₃, 5-Cl | 3-chloro-2-pyridinyl | Cl |
| CH₃ | O | 3-Br, 5-Cl | 3-chloro-2-pyridinyl | Cl |
| CH₃ | O | 3-Br, 5-Br | 3-chloro-2-pyridinyl | Cl |
| CH₃ | O | 3-CH₃, 5-CN | 3-chloro-2-pyridinyl | Cl |
| CH₃ | O | 3-CH₃, 5-Cl | 3-chloro-2-pyridinyl | Br |
| CH₃ | O | 3-Br, 5-Cl | 3-chloro-2-pyridinyl | Br |
| CH₃ | O | 3-Br, 5-Br | 3-chloro-2-pyridinyl | Br |

TABLE 40-continued

| $R^7$ | $A^{33}$ | $(R^4)_n$ | $R^{13a\text{-}1}$ | $R^{14a\text{-}1}$ |
|---|---|---|---|---|
| CH$_3$ | O | 3-CH$_3$, 5-CN | 3-chloro-2-pyridinyl | Br |
| CH$_3$ | O | 3-CH$_3$, 5-Cl | 3-chloro-2-pyridinyl | CF$_3$ |
| CH$_3$ | O | 3-Br, 5-Cl | 3-chloro-2-pyridinyl | CF$_3$ |
| CH$_3$ | O | 3-Br, 5-Br | 3-chloro-2-pyridinyl | CF$_3$ |
| CH$_3$ | O | 3-CH$_3$, 5-CN | 3-chloro-2-pyridinyl | CF$_3$ |
| CH$_2$CH$_3$ | O | 3-CH$_3$, 5-Cl | 3-chloro-2-pyridinyl | H |
| CH$_2$CH$_3$ | O | 3-Br, 5-Cl | 3-chloro-2-pyridinyl | H |
| CH$_2$CH$_3$ | O | 3-Br, 5-Br | 3-chloro-2-pyridinyl | H |
| CH$_2$CH$_3$ | O | 3-CH$_3$, 5-CN | 3-chloro-2-pyridinyl | H |
| CH$_2$CH$_3$ | O | 3-CH$_3$, 5-Cl | 3-chloro-2-pyridinyl | Cl |
| CH$_2$CH$_3$ | O | 3-Br, 5-Cl | 3-chloro-2-pyridinyl | Cl |
| CH$_2$CH$_3$ | O | 3-Br, 5-Br | 3-chloro-2-pyridinyl | Cl |
| CH$_2$CH$_3$ | O | 3-CH$_3$, 5-CN | 3-chloro-2-pyridinyl | Cl |
| CH$_2$CH$_3$ | O | 3-CH$_3$, 5-Cl | 3-chloro-2-pyridinyl | Br |
| CH$_2$CH$_3$ | O | 3-Br, 5-Cl | 3-chloro-2-pyridinyl | Br |
| CH$_2$CH$_3$ | O | 3-Br, 5-Br | 3-chloro-2-pyridinyl | Br |
| CH$_2$CH$_3$ | O | 3-CH$_3$, 5-CN | 3-chloro-2-pyridinyl | Br |
| CH$_2$CH$_3$ | O | 3-CH$_3$, 5-Cl | 3-chloro-2-pyridinyl | CF$_3$ |
| CH$_2$CH$_3$ | O | 3-Br, 5-Cl | 3-chloro-2-pyridinyl | CF$_3$ |
| CH$_2$CH$_3$ | O | 3-Br, 5-Br | 3-chloro-2-pyridinyl | CF$_3$ |
| CH$_2$CH$_3$ | O | 3-CH$_3$, 5-CN | 3-chloro-2-pyridinyl | CF$_3$ |

TABLE 41

| $R^7$ | $A^{33}$ | $(R^4)_n$ | $R^{13a\text{-}1}$ | $R^{14a\text{-}1}$ |
|---|---|---|---|---|
| phenyl | O | 3-CH$_3$, 5-Cl | 3-chloro-2-pyridinyl | H |
| phenyl | O | 3-Br, 5-Cl | 3-chloro-2-pyridinyl | H |
| phenyl | O | 3-Br, 5-Br | 3-chloro-2-pyridinyl | H |
| phenyl | O | 3-CH$_3$, 5-CN | 3-chloro-2-pyridinyl | H |
| phenyl | O | 3-CH$_3$, 5-Cl | 3-chloro-2-pyridinyl | Cl |
| phenyl | O | 3-Br, 5-Cl | 3-chloro-2-pyridinyl | Cl |
| phenyl | O | 3-Br, 5-Br | 3-chloro-2-pyridinyl | Cl |
| phenyl | O | 3-CH$_3$, 5-CN | 3-chloro-2-pyridinyl | Cl |
| phenyl | O | 3-CH$_3$, 5-Cl | 3-chloro-2-pyridinyl | Br |
| phenyl | O | 3-Br, 5-Cl | 3-chloro-2-pyridinyl | Br |
| phenyl | O | 3-Br, 5-Br | 3-chloro-2-pyridinyl | Br |
| phenyl | O | 3-CH$_3$, 5-CN | 3-chloro-2-pyridinyl | Br |
| phenyl | O | 3-CH$_3$, 5-Cl | 3-chloro-2-pyridinyl | CF$_3$ |
| phenyl | O | 3-Br, 5-Cl | 3-chloro-2-pyridinyl | CF$_3$ |
| phenyl | O | 3-Br, 5-Br | 3-chloro-2-pyridinyl | CF$_3$ |
| phenyl | O | 3-CH$_3$, 5-CN | 3-chloro-2-pyridinyl | CF$_3$ |
| phenyl | S | 3-CH$_3$, 5-Cl | 3-chloro-2-pyridinyl | H |
| phenyl | S | 3-Br, 5-Cl | 3-chloro-2-pyridinyl | H |
| phenyl | S | 3-Br, 5-Br | 3-chloro-2-pyridinyl | H |
| phenyl | S | 3-CH$_3$, 5-CN | 3-chloro-2-pyridinyl | H |
| phenyl | S | 3-CH$_3$, 5-Cl | 3-chloro-2-pyridinyl | Cl |
| phenyl | S | 3-Br, 5-Cl | 3-chloro-2-pyridinyl | Cl |
| phenyl | S | 3-Br, 5-Br | 3-chloro-2-pyridinyl | Cl |
| phenyl | S | 3-CH$_3$, 5-CN | 3-chloro-2-pyridinyl | Cl |
| phenyl | S | 3-CH$_3$, 5-Cl | 3-chloro-2-pyridinyl | Br |
| phenyl | S | 3-Br, 5-Cl | 3-chloro-2-pyridinyl | Br |
| phenyl | S | 3-Br, 5-Br | 3-chloro-2-pyridinyl | Br |
| phenyl | S | 3-CH$_3$, 5-CN | 3-chloro-2-pyridinyl | Br |
| phenyl | S | 3-CH$_3$, 5-Cl | 3-chloro-2-pyridinyl | CF$_3$ |
| phenyl | S | 3-Br, 5-Cl | 3-chloro-2-pyridinyl | CF$_3$ |
| phenyl | S | 3-Br, 5-Br | 3-chloro-2-pyridinyl | CF$_3$ |
| phenyl | S | 3-CH$_3$, 5-CN | 3-chloro-2-pyridinyl | CF$_3$ |

A compound represented by the formula (1-D):

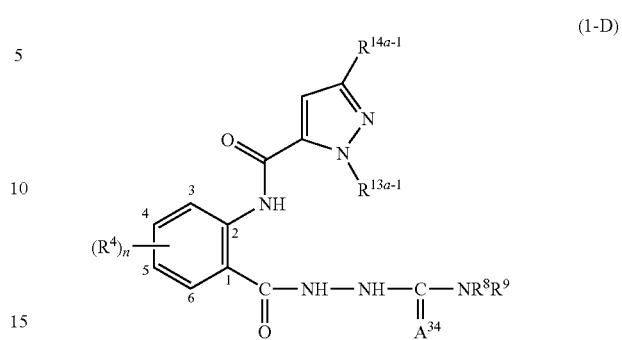

(1-D)

wherein NR$^8$R$^9$, A$^{34}$, $(R^4)_n$, $R^{13a\text{-}1}$ and $R^{14a\text{-}1}$ represent combinations shown in Table 42 to Table 57.

TABLE 42

| NR$^8$R$^9$ | A$^{34}$ | $(R^4)_n$ | $R^{13a\text{-}1}$ | $R^{14a\text{-}1}$ |
|---|---|---|---|---|
| NH$_2$ | O | 3-CH$_3$, 5-Cl | 3-chloro-2-pyridinyl | H |
| NH$_2$ | O | 3-Br, 5-Cl | 3-chloro-2-pyridinyl | H |
| NH$_2$ | O | 3-Br, 5-Br | 3-chloro-2-pyridinyl | H |
| NH$_2$ | O | 3-CH$_3$, 5-CN | 3-chloro-2-pyridinyl | H |
| NH$_2$ | O | 3-CH$_3$, 5-Cl | 3-chloro-2-pyridinyl | Cl |
| NH$_2$ | O | 3-Br, 5-Cl | 3-chloro-2-pyridinyl | Cl |
| NH$_2$ | O | 3-Br, 5-Br | 3-chloro-2-pyridinyl | Cl |
| NH$_2$ | O | 3-CH$_3$, 5-CN | 3-chloro-2-pyridinyl | Cl |
| NH$_2$ | O | 3-CH$_3$, 5-Cl | 3-chloro-2-pyridinyl | Br |
| NH$_2$ | O | 3-Br, 5-Cl | 3-chloro-2-pyridinyl | Br |
| NH$_2$ | O | 3-Br, 5-Br | 3-chloro-2-pyridinyl | Br |
| NH$_2$ | O | 3-CH$_3$, 5-CN | 3-chloro-2-pyridinyl | Br |
| NH$_2$ | O | 3-CH$_3$, 5-Cl | 3-chloro-2-pyridinyl | CF$_3$ |
| NH$_2$ | O | 3-Br, 5-Cl | 3-chloro-2-pyridinyl | CF$_3$ |
| NH$_2$ | O | 3-Br, 5-Br | 3-chloro-2-pyridinyl | CF$_3$ |
| NH$_2$ | O | 3-CH$_3$, 5-CN | 3-chloro-2-pyridinyl | CF$_3$ |
| NHCH$_3$ | O | 3-CH$_3$, 5-Cl | 3-chloro-2-pyridinyl | H |
| NHCH$_3$ | O | 3-Br, 5-Cl | 3-chloro-2-pyridinyl | H |
| NHCH$_3$ | O | 3-Br, 5-Br | 3-chloro-2-pyridinyl | H |
| NHCH$_3$ | O | 3-CH$_3$, 5-CN | 3-chloro-2-pyridinyl | H |
| NHCH$_3$ | O | 3-CH$_3$, 5-Cl | 3-chloro-2-pyridinyl | Cl |
| NHCH$_3$ | O | 3-Br, 5-Cl | 3-chloro-2-pyridinyl | Cl |
| NHCH$_3$ | O | 3-Br, 5-Br | 3-chloro-2-pyridinyl | Cl |
| NHCH$_3$ | O | 3-CH$_3$, 5-CN | 3-chloro-2-pyridinyl | Cl |
| NHCH$_3$ | O | 3-CH$_3$, 5-Cl | 3-chloro-2-pyridinyl | Br |
| NHCH$_3$ | O | 3-Br, 5-Cl | 3-chloro-2-pyridinyl | Br |
| NHCH$_3$ | O | 3-Br, 5-Br | 3-chloro-2-pyridinyl | Br |
| NHCH$_3$ | O | 3-CH$_3$, 5-CN | 3-chloro-2-pyridinyl | Br |
| NHCH$_3$ | O | 3-CH$_3$, 5-Cl | 3-chloro-2-pyridinyl | CF$_3$ |
| NHCH$_3$ | O | 3-Br, 5-Cl | 3-chloro-2-pyridinyl | CF$_3$ |
| NHCH$_3$ | O | 3-Br, 5-Br | 3-chloro-2-pyridinyl | CF$_3$ |
| NHCH$_3$ | O | 3-CH$_3$, 5-CN | 3-chloro-2-pyridinyl | CF$_3$ |

TABLE 43

| NR$^8$R$^9$ | A$^{34}$ | $(R^4)_n$ | $R^{13a\text{-}1}$ | $R^{14a\text{-}1}$ |
|---|---|---|---|---|
| NHCH$_2$CH$_3$ | O | 3-CH$_3$, 5-Cl | 3-chloro-2-pyridinyl | H |
| NHCH$_2$CH$_3$ | O | 3-Br, 5-Cl | 3-chloro-2-pyridinyl | H |
| NHCH$_2$CH$_3$ | O | 3-Br, 5-Br | 3-chloro-2-pyridinyl | H |
| NHCH$_2$CH$_3$ | O | 3-CH$_3$, 5-CN | 3-chloro-2-pyridinyl | H |
| NHCH$_2$CH$_3$ | O | 3-CH$_3$, 5-Cl | 3-chloro-2-pyridinyl | Cl |
| NHCH$_2$CH$_3$ | O | 3-Br, 5-Cl | 3-chloro-2-pyridinyl | Cl |
| NHCH$_2$CH$_3$ | O | 3-Br, 5-Br | 3-chloro-2-pyridinyl | Cl |
| NHCH$_2$CH$_3$ | O | 3-CH$_3$, 5-CN | 3-chloro-2-pyridinyl | Cl |
| NHCH$_2$CH$_3$ | O | 3-CH$_3$, 5-Cl | 3-chloro-2-pyridinyl | Br |
| NHCH$_2$CH$_3$ | O | 3-Br, 5-Cl | 3-chloro-2-pyridinyl | Br |
| NHCH$_2$CH$_3$ | O | 3-Br, 5-Br | 3-chloro-2-pyridinyl | Br |
| NHCH$_2$CH$_3$ | O | 3-CH$_3$, 5-CN | 3-chloro-2-pyridinyl | Br |
| NHCH$_2$CH$_3$ | O | 3-CH$_3$, 5-Cl | 3-chloro-2-pyridinyl | CF$_3$ |
| NHCH$_2$CH$_3$ | O | 3-Br, 5-Cl | 3-chloro-2-pyridinyl | CF$_3$ |

TABLE 43-continued

| NR⁸R⁹ | A³⁴ | (R⁴)ₙ | R¹³ᵃ⁻¹ | R¹⁴ᵃ⁻¹ |
|---|---|---|---|---|
| NHCH₂CH₃ | O | 3-Br, 5-Br | 3-chloro-2-pyridinyl | CF₃ |
| NHCH₂CH₃ | O | 3-CH₃, 5-CN | 3-chloro-2-pyridinyl | CF₃ |
| NHCH(CH₃)₂ | O | 3-CH₃, 5-Cl | 3-chloro-2-pyridinyl | H |
| NHCH(CH₃)₂ | O | 3-Br, 5-Cl | 3-chloro-2-pyridinyl | H |
| NHCH(CH₃)₂ | O | 3-Br, 5-Br | 3-chloro-2-pyridinyl | H |
| NHCH(CH₃)₂ | O | 3-CH₃, 5-CN | 3-chloro-2-pyridinyl | H |
| NHCH(CH₃)₂ | O | 3-CH₃, 5-Cl | 3-chloro-2-pyridinyl | Cl |
| NHCH(CH₃)₂ | O | 3-Br, 5-Cl | 3-chloro-2-pyridinyl | Cl |
| NHCH(CH₃)₂ | O | 3-Br, 5-Br | 3-chloro-2-pyridinyl | Cl |
| NHCH(CH₃)₂ | O | 3-CH₃, 5-CN | 3-chloro-2-pyridinyl | Cl |
| NHCH(CH₃)₂ | O | 3-CH₃, 5-Cl | 3-chloro-2-pyridinyl | Br |
| NHCH(CH₃)₂ | O | 3-Br, 5-Cl | 3-chloro-2-pyridinyl | Br |
| NHCH(CH₃)₂ | O | 3-Br, 5-Br | 3-chloro-2-pyridinyl | Br |
| NHCH(CH₃)₂ | O | 3-CH₃, 5-CN | 3-chloro-2-pyridinyl | Br |
| NHCH(CH₃)₂ | O | 3-CH₃, 5-Cl | 3-chloro-2-pyridinyl | CF₃ |
| NHCH(CH₃)₂ | O | 3-Br, 5-Cl | 3-chloro-2-pyridinyl | CF₃ |
| NHCH(CH₃)₂ | O | 3-Br, 5-Br | 3-chloro-2-pyridinyl | CF₃ |
| NHCH(CH₃)₂ | O | 3-CH₃, 5-CN | 3-chloro-2-pyridinyl | CF₃ |

TABLE 44

| NR⁸R⁹ | A³⁴ | (R⁴)ₙ | R¹³ᵃ⁻¹ | R¹⁴ᵃ⁻¹ |
|---|---|---|---|---|
| NHC(CH₃)₃ | O | 3-CH₃, 5-Cl | 3-chloro-2-pyridinyl | H |
| NHC(CH₃)₃ | O | 3-Br, 5-Cl | 3-chloro-2-pyridinyl | H |
| NHC(CH₃)₃ | O | 3-Br, 5-Br | 3-chloro-2-pyridinyl | H |
| NHC(CH₃)₃ | O | 3-CH₃, 5-CN | 3-chloro-2-pyridinyl | H |
| NHC(CH₃)₃ | O | 3-CH₃, 5-Cl | 3-chloro-2-pyridinyl | Cl |
| NHC(CH₃)₃ | O | 3-Br, 5-Cl | 3-chloro-2-pyridinyl | Cl |
| NHC(CH₃)₃ | O | 3-Br, 5-Br | 3-chloro-2-pyridinyl | Cl |
| NHC(CH₃)₃ | O | 3-CH₃, 5-CN | 3-chloro-2-pyridinyl | Cl |
| NHC(CH₃)₃ | O | 3-CH₃, 5-Cl | 3-chloro-2-pyridinyl | Br |
| NHC(CH₃)₃ | O | 3-Br, 5-Cl | 3-chloro-2-pyridinyl | Br |
| NHC(CH₃)₃ | O | 3-Br, 5-Br | 3-chloro-2-pyridinyl | Br |
| NHC(CH₃)₃ | O | 3-CH₃, 5-CN | 3-chloro-2-pyridinyl | Br |
| NHC(CH₃)₃ | O | 3-CH₃, 5-Cl | 3-chloro-2-pyridinyl | CF₃ |
| NHC(CH₃)₃ | O | 3-Br, 5-Cl | 3-chloro-2-pyridinyl | CF₃ |
| NHC(CH₃)₃ | O | 3-Br, 5-Br | 3-chloro-2-pyridinyl | CF₃ |
| NHC(CH₃)₃ | O | 3-CH₃, 5-CN | 3-chloro-2-pyridinyl | CF₃ |
| N(CH₃)₂ | O | 3-CH₃, 5-Cl | 3-chloro-2-pyridinyl | H |
| N(CH₃)₂ | O | 3-Br, 5-Cl | 3-chloro-2-pyridinyl | H |
| N(CH₃)₂ | O | 3-Br, 5-Br | 3-chloro-2-pyridinyl | H |
| N(CH₃)₂ | O | 3-CH₃, 5-CN | 3-chloro-2-pyridinyl | H |
| N(CH₃)₂ | O | 3-CH₃, 5-Cl | 3-chloro-2-pyridinyl | Cl |
| N(CH₃)₂ | O | 3-Br, 5-Cl | 3-chloro-2-pyridinyl | Cl |
| N(CH₃)₂ | O | 3-Br, 5-Br | 3-chloro-2-pyridinyl | Cl |
| N(CH₃)₂ | O | 3-CH₃, 5-CN | 3-chloro-2-pyridinyl | Cl |
| N(CH₃)₂ | O | 3-CH₃, 5-Cl | 3-chloro-2-pyridinyl | Br |
| N(CH₃)₂ | O | 3-Br, 5-Cl | 3-chloro-2-pyridinyl | Br |
| N(CH₃)₂ | O | 3-Br, 5-Br | 3-chloro-2-pyridinyl | Br |
| N(CH₃)₂ | O | 3-CH₃, 5-CN | 3-chloro-2-pyridinyl | Br |
| N(CH₃)₂ | O | 3-CH₃, 5-Cl | 3-chloro-2-pyridinyl | CF₃ |
| N(CH₃)₂ | O | 3-Br, 5-Cl | 3-chloro-2-pyridinyl | CF₃ |
| N(CH₃)₂ | O | 3-Br, 5-Br | 3-chloro-2-pyridinyl | CF₃ |
| N(CH₃)₂ | O | 3-CH₃, 5-CN | 3-chloro-2-pyridinyl | CF₃ |

TABLE 45

| NR⁸R⁹ | A³⁴ | (R⁴)ₙ | R¹³ᵃ⁻¹ | R¹⁴ᵃ⁻¹ |
|---|---|---|---|---|
| N(CH₂CH₃)₂ | O | 3-CH₃, 5-Cl | 3-chloro-2-pyridinyl | H |
| N(CH₂CH₃)₂ | O | 3-Br, 5-Cl | 3-chloro-2-pyridinyl | H |
| N(CH₂CH₃)₂ | O | 3-Br, 5-Br | 3-chloro-2-pyridinyl | H |
| N(CH₂CH₃)₂ | O | 3-CH₃, 5-CN | 3-chloro-2-pyridinyl | H |
| N(CH₂CH₃)₂ | O | 3-CH₃, 5-Cl | 3-chloro-2-pyridinyl | Cl |
| N(CH₂CH₃)₂ | O | 3-Br, 5-Cl | 3-chloro-2-pyridinyl | Cl |
| N(CH₂CH₃)₂ | O | 3-Br, 5-Br | 3-chloro-2-pyridinyl | Cl |
| N(CH₂CH₃)₂ | O | 3-CH₃, 5-CN | 3-chloro-2-pyridinyl | Cl |
| N(CH₂CH₃)₂ | O | 3-CH₃, 5-Cl | 3-chloro-2-pyridinyl | Br |
| N(CH₂CH₃)₂ | O | 3-Br, 5-Cl | 3-chloro-2-pyridinyl | Br |
| N(CH₂CH₃)₂ | O | 3-Br, 5-Br | 3-chloro-2-pyridinyl | Br |
| N(CH₂CH₃)₂ | O | 3-CH₃, 5-CN | 3-chloro-2-pyridinyl | Br |

TABLE 45-continued

| NR⁸R⁹ | A³⁴ | (R⁴)ₙ | R¹³ᵃ⁻¹ | R¹⁴ᵃ⁻¹ |
|---|---|---|---|---|
| N(CH₂CH₃)₂ | O | 3-CH₃, 5-Cl | 3-chloro-2-pyridinyl | CF₃ |
| N(CH₂CH₃)₂ | O | 3-Br, 5-Cl | 3-chloro-2-pyridinyl | CF₃ |
| N(CH₂CH₃)₂ | O | 3-Br, 5-Br | 3-chloro-2-pyridinyl | CF₃ |
| N(CH₂CH₃)₂ | O | 3-CH₃, 5-CN | 3-chloro-2-pyridinyl | CF₃ |
| N{CH(CH₃)₂}₂ | O | 3-CH₃, 5-Cl | 3-chloro-2-pyridinyl | H |
| N{CH(CH₃)₂}₂ | O | 3-Br, 5-Cl | 3-chloro-2-pyridinyl | H |
| N{CH(CH₃)₂}₂ | O | 3-Br, 5-Br | 3-chloro-2-pyridinyl | H |
| N{CH(CH₃)₂}₂ | O | 3-CH₃, 5-CN | 3-chloro-2-pyridinyl | H |
| N{CH(CH₃)₂}₂ | O | 3-CH₃, 5-Cl | 3-chloro-2-pyridinyl | Cl |
| N{CH(CH₃)₂}₂ | O | 3-Br, 5-Cl | 3-chloro-2-pyridinyl | Cl |
| N{CH(CH₃)₂}₂ | O | 3-Br, 5-Br | 3-chloro-2-pyridinyl | Cl |
| N{CH(CH₃)₂}₂ | O | 3-CH₃, 5-CN | 3-chloro-2-pyridinyl | Cl |
| N{CH(CH₃)₂}₂ | O | 3-CH₃, 5-Cl | 3-chloro-2-pyridinyl | Br |
| N{CH(CH₃)₂}₂ | O | 3-Br, 5-Cl | 3-chloro-2-pyridinyl | Br |
| N{CH(CH₃)₂}₂ | O | 3-Br, 5-Br | 3-chloro-2-pyridinyl | Br |
| N{CH(CH₃)₂}₂ | O | 3-CH₃, 5-CN | 3-chloro-2-pyridinyl | Br |
| N{CH(CH₃)₂}₂ | O | 3-CH₃, 5-Cl | 3-chloro-2-pyridinyl | CF₃ |
| N{CH(CH₃)₂}₂ | O | 3-Br, 5-Cl | 3-chloro-2-pyridinyl | CF₃ |
| N{CH(CH₃)₂}₂ | O | 3-Br, 5-Br | 3-chloro-2-pyridinyl | CF₃ |
| N{CH(CH₃)₂}₂ | O | 3-CH₃, 5-CN | 3-chloro-2-pyridinyl | CF₃ |

TABLE 46

| NR⁸R⁹ | A³⁴ | (R⁴)ₙ | R¹³ᵃ⁻¹ | R¹⁴ᵃ⁻¹ |
|---|---|---|---|---|
| cyclopropylamino | O | 3-CH₃, 5-Cl | 3-chloro-2-pyridinyl | H |
| cyclopropylamino | O | 3-Br, 5-Cl | 3-chloro-2-pyridinyl | H |
| cyclopropylamino | O | 3-Br, 5-Br | 3-chloro-2-pyridinyl | H |
| cyclopropylamino | O | 3-CH₃, 5-CN | 3-chloro-2-pyridinyl | H |
| cyclopropylamino | O | 3-CH₃, 5-Cl | 3-chloro-2-pyridinyl | Cl |
| cyclopropylamino | O | 3-Br, 5-Cl | 3-chloro-2-pyridinyl | Cl |
| cyclopropylamino | O | 3-Br, 5-Br | 3-chloro-2-pyridinyl | Cl |
| cyclopropylamino | O | 3-CH₃, 5-CN | 3-chloro-2-pyridinyl | Cl |
| cyclopropylamino | O | 3-CH₃, 5-Cl | 3-chloro-2-pyridinyl | Br |
| cyclopropylamino | O | 3-Br, 5-Cl | 3-chloro-2-pyridinyl | Br |
| cyclopropylamino | O | 3-Br, 5-Br | 3-chloro-2-pyridinyl | Br |
| cyclopropylamino | O | 3-CH₃, 5-CN | 3-chloro-2-pyridinyl | Br |
| cyclopropylamino | O | 3-CH₃, 5-Cl | 3-chloro-2-pyridinyl | CF₃ |
| cyclopropylamino | O | 3-Br, 5-Cl | 3-chloro-2-pyridinyl | CF₃ |
| cyclopropylamino | O | 3-Br, 5-Br | 3-chloro-2-pyridinyl | CF₃ |
| cyclopropylamino | O | 3-CH₃, 5-CN | 3-chloro-2-pyridinyl | CF₃ |
| cyclobutylamino | O | 3-CH₃, 5-Cl | 3-chloro-2-pyridinyl | H |
| cyclobutylamino | O | 3-Br, 5-Cl | 3-chloro-2-pyridinyl | H |
| cyclobutylamino | O | 3-Br, 5-Br | 3-chloro-2-pyridinyl | H |
| cyclobutylamino | O | 3-CH₃, 5-CN | 3-chloro-2-pyridinyl | H |
| cyclobutylamino | O | 3-CH₃, 5-Cl | 3-chloro-2-pyridinyl | Cl |
| cyclobutylamino | O | 3-Br, 5-Cl | 3-chloro-2-pyridinyl | Cl |
| cyclobutylamino | O | 3-Br, 5-Br | 3-chloro-2-pyridinyl | Cl |
| cyclobutylamino | O | 3-CH₃, 5-CN | 3-chloro-2-pyridinyl | Cl |
| cyclobutylamino | O | 3-CH₃, 5-Cl | 3-chloro-2-pyridinyl | Br |
| cyclobutylamino | O | 3-Br, 5-Cl | 3-chloro-2-pyridinyl | Br |
| cyclobutylamino | O | 3-Br, 5-Br | 3-chloro-2-pyridinyl | Br |
| cyclobutylamino | O | 3-CH₃, 5-CN | 3-chloro-2-pyridinyl | Br |
| cyclobutylamino | O | 3-CH₃, 5-Cl | 3-chloro-2-pyridinyl | CF₃ |
| cyclobutylamino | O | 3-Br, 5-Cl | 3-chloro-2-pyridinyl | CF₃ |
| cyclobutylamino | O | 3-Br, 5-Br | 3-chloro-2-pyridinyl | CF₃ |
| cyclobutylamino | O | 3-CH₃, 5-CN | 3-chloro-2-pyridinyl | CF₃ |

TABLE 47

| NR⁸R⁹ | A³⁴ | (R⁴)ₙ | R¹³ᵃ⁻¹ | R¹⁴ᵃ⁻¹ |
|---|---|---|---|---|
| cyclopentylamino | O | 3-CH₃, 5-Cl | 3-chloro-2-pyridinyl | H |
| cyclopentylamino | O | 3-Br, 5-Cl | 3-chloro-2-pyridinyl | H |
| cyclopentylamino | O | 3-Br, 5-Br | 3-chloro-2-pyridinyl | H |
| cyclopentylamino | O | 3-CH₃, 5-CN | 3-chloro-2-pyridinyl | H |
| cyclopentylamino | O | 3-CH₃, 5-Cl | 3-chloro-2-pyridinyl | Cl |
| cyclopentylamino | O | 3-Br, 5-Cl | 3-chloro-2-pyridinyl | Cl |
| cyclopentylamino | O | 3-Br, 5-Br | 3-chloro-2-pyridinyl | Cl |
| cyclopentylamino | O | 3-CH₃, 5-CN | 3-chloro-2-pyridinyl | Cl |
| cyclopentylamino | O | 3-CH₃, 5-Cl | 3-chloro-2-pyridinyl | Br |
| cyclopentylamino | O | 3-Br, 5-Cl | 3-chloro-2-pyridinyl | Br |

TABLE 47-continued

| NR8R9 | A34 | (R4)n | R13a-1 | R14a-1 |
|---|---|---|---|---|
| cyclopentylamino | O | 3-Br, 5-Br | 3-chloro-2-pyridinyl | Br |
| cyclopentylamino | O | 3-CH3, 5-CN | 3-chloro-2-pyridinyl | Br |
| cyclopentylamino | O | 3-CH3, 5-Cl | 3-chloro-2-pyridinyl | CF3 |
| cyclopentylamino | O | 3-Br, 5-Cl | 3-chloro-2-pyridinyl | CF3 |
| cyclopentylamino | O | 3-Br, 5-Br | 3-chloro-2-pyridinyl | CF3 |
| cyclopentylamino | O | 3-CH3, 5-CN | 3-chloro-2-pyridinyl | CF3 |
| cyclohexylamino | O | 3-CH3, 5-Cl | 3-chloro-2-pyridinyl | H |
| cyclohexylamino | O | 3-Br, 5-Cl | 3-chloro-2-pyridinyl | H |
| cyclohexylamino | O | 3-Br, 5-Br | 3-chloro-2-pyridinyl | H |
| cyclohexylamino | O | 3-CH3, 5-CN | 3-chloro-2-pyridinyl | H |
| cyclohexylamino | O | 3-CH3, 5-Cl | 3-chloro-2-pyridinyl | Cl |
| cyclohexylamino | O | 3-Br, 5-Cl | 3-chloro-2-pyridinyl | Cl |
| cyclohexylamino | O | 3-Br, 5-Br | 3-chloro-2-pyridinyl | Cl |
| cyclohexylamino | O | 3-CH3, 5-CN | 3-chloro-2-pyridinyl | Cl |
| cyclohexylamino | O | 3-CH3, 5-Cl | 3-chloro-2-pyridinyl | Br |
| cyclohexylamino | O | 3-Br, 5-Cl | 3-chloro-2-pyridinyl | Br |
| cyclohexylamino | O | 3-Br, 5-Br | 3-chloro-2-pyridinyl | Br |
| cyclohexylamino | O | 3-CH3, 5-CN | 3-chloro-2-pyridinyl | Br |
| cyclohexylamino | O | 3-CH3, 5-Cl | 3-chloro-2-pyridinyl | CF3 |
| cyclohexylamino | O | 3-Br, 5-Cl | 3-chloro-2-pyridinyl | CF3 |
| cyclohexylamino | O | 3-Br, 5-Br | 3-chloro-2-pyridinyl | CF3 |
| cyclohexylamino | O | 3-CH3, 5-CN | 3-chloro-2-pyridinyl | CF3 |

TABLE 48

| NR8R9 | A34 | (R4)n | R13a-1 | R14a-1 |
|---|---|---|---|---|
| anilino | O | 3-CH3, 5-Cl | 3-chloro-2-pyridinyl | H |
| anilino | O | 3-Br, 5-Cl | 3-chloro-2-pyridinyl | H |
| anilino | O | 3-Br, 5-Br | 3-chloro-2-pyridinyl | H |
| anilino | O | 3-CH3, 5-CN | 3-chloro-2-pyridinyl | H |
| anilino | O | 3-CH3, 5-Cl | 3-chloro-2-pyridinyl | Cl |
| anilino | O | 3-Br, 5-Cl | 3-chloro-2-pyridinyl | Cl |
| anilino | O | 3-Br, 5-Br | 3-chloro-2-pyridinyl | Cl |
| anilino | O | 3-CH3, 5-CN | 3-chloro-2-pyridinyl | Cl |
| anilino | O | 3-CH3, 5-Cl | 3-chloro-2-pyridinyl | Br |
| anilino | O | 3-Br, 5-Cl | 3-chloro-2-pyridinyl | Br |
| anilino | O | 3-Br, 5-Br | 3-chloro-2-pyridinyl | Br |
| anilino | O | 3-CH3, 5-CN | 3-chloro-2-pyridinyl | Br |
| anilino | O | 3-CH3, 5-Cl | 3-chloro-2-pyridinyl | CF3 |
| anilino | O | 3-Br, 5-Cl | 3-chloro-2-pyridinyl | CF3 |
| anilino | O | 3-Br, 5-Br | 3-chloro-2-pyridinyl | CF3 |
| anilino | O | 3-CH3, 5-CN | 3-chloro-2-pyridinyl | CF3 |
| pyrrolidin-1-yl | O | 3-CH3, 5-Cl | 3-chloro-2-pyridinyl | H |
| pyrrolidin-1-yl | O | 3-Br, 5-Cl | 3-chloro-2-pyridinyl | H |
| pyrrolidin-1-yl | O | 3-Br, 5-Br | 3-chloro-2-pyridinyl | H |
| pyrrolidin-1-yl | O | 3-CH3, 5-CN | 3-chloro-2-pyridinyl | H |
| pyrrolidin-1-yl | O | 3-CH3, 5-Cl | 3-chloro-2-pyridinyl | Cl |
| pyrrolidin-1-yl | O | 3-Br, 5-Cl | 3-chloro-2-pyridinyl | Cl |
| pyrrolidin-1-yl | O | 3-Br, 5-Br | 3-chloro-2-pyridinyl | Cl |
| pyrrolidin-1-yl | O | 3-CH3, 5-CN | 3-chloro-2-pyridinyl | Cl |
| pyrrolidin-1-yl | O | 3-CH3, 5-Cl | 3-chloro-2-pyridinyl | Br |
| pyrrolidin-1-yl | O | 3-Br, 5-Cl | 3-chloro-2-pyridinyl | Br |
| pyrrolidin-1-yl | O | 3-Br, 5-Br | 3-chloro-2-pyridinyl | Br |
| pyrrolidin-1-yl | O | 3-CH3, 5-CN | 3-chloro-2-pyridinyl | Br |
| pyrrolidin-1-yl | O | 3-CH3, 5-Cl | 3-chloro-2-pyridinyl | CF3 |
| pyrrolidin-1-yl | O | 3-Br, 5-Cl | 3-chloro-2-pyridinyl | CF3 |
| pyrrolidin-1-yl | O | 3-Br, 5-Br | 3-chloro-2-pyridinyl | CF3 |
| pyrrolidin-1-yl | O | 3-CH3, 5-CN | 3-chloro-2-pyridinyl | CF3 |

TABLE 49

| NR8R9 | A34 | (R4)n | R13a-1 | R14a-1 |
|---|---|---|---|---|
| piperidin-1-yl | O | 3-CH3, 5-Cl | 3-chloro-2-pyridinyl | H |
| piperidin-1-yl | O | 3-Br, 5-Cl | 3-chloro-2-pyridinyl | H |
| piperidin-1-yl | O | 3-Br, 5-Br | 3-chloro-2-pyridinyl | H |
| piperidin-1-yl | O | 3-CH3, 5-CN | 3-chloro-2-pyridinyl | H |
| piperidin-1-yl | O | 3-CH3, 5-Cl | 3-chloro-2-pyridinyl | Cl |
| piperidin-1-yl | O | 3-Br, 5-Cl | 3-chloro-2-pyridinyl | Cl |
| piperidin-1-yl | O | 3-Br, 5-Br | 3-chloro-2-pyridinyl | Cl |
| piperidin-1-yl | O | 3-CH3, 5-CN | 3-chloro-2-pyridinyl | Cl |

TABLE 49-continued

| NR8R9 | A34 | (R4)n | R13a-1 | R14a-1 |
|---|---|---|---|---|
| piperidin-1-yl | O | 3-CH3, 5-Cl | 3-chloro-2-pyridinyl | Br |
| piperidin-1-yl | O | 3-Br, 5-Cl | 3-chloro-2-pyridinyl | Br |
| piperidin-1-yl | O | 3-Br, 5-Br | 3-chloro-2-pyridinyl | Br |
| piperidin-1-yl | O | 3-CH3, 5-CN | 3-chloro-2-pyridinyl | Br |
| piperidin-1-yl | O | 3-CH3, 5-Cl | 3-chloro-2-pyridinyl | CF3 |
| piperidin-1-yl | O | 3-Br, 5-Cl | 3-chloro-2-pyridinyl | CF3 |
| piperidin-1-yl | O | 3-Br, 5-Br | 3-chloro-2-pyridinyl | CF3 |
| piperidin-1-yl | O | 3-CH3, 5-CN | 3-chloro-2-pyridinyl | CF3 |
| morpholin-4-yl | O | 3-CH3, 5-Cl | 3-chloro-2-pyridinyl | H |
| morpholin-4-yl | O | 3-Br, 5-Cl | 3-chloro-2-pyridinyl | H |
| morpholin-4-yl | O | 3-Br, 5-Br | 3-chloro-2-pyridinyl | H |
| morpholin-4-yl | O | 3-CH3, 5-CN | 3-chloro-2-pyridinyl | H |
| morpholin-4-yl | O | 3-CH3, 5-Cl | 3-chloro-2-pyridinyl | Cl |
| morpholin-4-yl | O | 3-Br, 5-Cl | 3-chloro-2-pyridinyl | Cl |
| morpholin-4-yl | O | 3-Br, 5-Br | 3-chloro-2-pyridinyl | Cl |
| morpholin-4-yl | O | 3-CH3, 5-CN | 3-chloro-2-pyridinyl | Cl |
| morpholin-4-yl | O | 3-CH3, 5-Cl | 3-chloro-2-pyridinyl | Br |
| morpholin-4-yl | O | 3-Br, 5-Cl | 3-chloro-2-pyridinyl | Br |
| morpholin-4-yl | O | 3-Br, 5-Br | 3-chloro-2-pyridinyl | Br |
| morpholin-4-yl | O | 3-CH3, 5-CN | 3-chloro-2-pyridinyl | Br |
| morpholin-4-yl | O | 3-CH3, 5-Cl | 3-chloro-2-pyridinyl | CF3 |
| morpholin-4-yl | O | 3-Br, 5-Cl | 3-chloro-2-pyridinyl | CF3 |
| morpholin-4-yl | O | 3-Br, 5-Br | 3-chloro-2-pyridinyl | CF3 |
| morpholin-4-yl | O | 3-CH3, 5-CN | 3-chloro-2-pyridinyl | CF3 |

TABLE 50

| NR8R9 | A34 | (R4)n | R13a-1 | R14a-1 |
|---|---|---|---|---|
| thiomorpholin-4-yl | O | 3-CH3, 5-Cl | 3-chloro-2-pyridinyl | H |
| thiomorpholin-4-yl | O | 3-Br, 5-Cl | 3-chloro-2-pyridinyl | H |
| thiomorpholin-4-yl | O | 3-Br, 5-Br | 3-chloro-2-pyridinyl | H |
| thiomorpholin-4-yl | O | 3-CH3, 5-CN | 3-chloro-2-pyridinyl | H |
| thiomorpholin-4-yl | O | 3-CH3, 5-Cl | 3-chloro-2-pyridinyl | Cl |
| thiomorpholin-4-yl | O | 3-Br, 5-Cl | 3-chloro-2-pyridinyl | Cl |
| thiomorpholin-4-yl | O | 3-Br, 5-Br | 3-chloro-2-pyridinyl | Cl |
| thiomorpholin-4-yl | O | 3-CH3, 5-CN | 3-chloro-2-pyridinyl | Cl |
| thiomorpholin-4-yl | O | 3-CH3, 5-Cl | 3-chloro-2-pyridinyl | Br |
| thiomorpholin-4-yl | O | 3-Br, 5-Cl | 3-chloro-2-pyridinyl | Br |
| thiomorpholin-4-yl | O | 3-Br, 5-Br | 3-chloro-2-pyridinyl | Br |
| thiomorpholin-4-yl | O | 3-CH3, 5-CN | 3-chloro-2-pyridinyl | Br |
| thiomorpholin-4-yl | O | 3-CH3, 5-Cl | 3-chloro-2-pyridinyl | CF3 |
| thiomorpholin-4-yl | O | 3-Br, 5-Cl | 3-chloro-2-pyridinyl | CF3 |
| thiomorpholin-4-yl | O | 3-Br, 5-Br | 3-chloro-2-pyridinyl | CF3 |
| thiomorpholin-4-yl | O | 3-CH3, 5-CN | 3-chloro-2-pyridinyl | CF3 |
| 1-methylpiperazin-4-yl | O | 3-CH3, 5-Cl | 3-chloro-2-pyridinyl | H |
| 1-methylpiperazin-4-yl | O | 3-Br, 5-Cl | 3-chloro-2-pyridinyl | H |
| 1-methylpiperazin-4-yl | O | 3-Br, 5-Br | 3-chloro-2-pyridinyl | H |
| 1-methylpiperazin-4-yl | O | 3-CH3, 5-CN | 3-chloro-2-pyridinyl | H |
| 1-methylpiperazin-4-yl | O | 3-CH3, 5-Cl | 3-chloro-2-pyridinyl | Cl |
| 1-methylpiperazin-4-yl | O | 3-Br, 5-Cl | 3-chloro-2-pyridinyl | Cl |
| 1-methylpiperazin-4-yl | O | 3-Br, 5-Br | 3-chloro-2-pyridinyl | Cl |
| 1-methylpiperazin-4-yl | O | 3-CH3, 5-CN | 3-chloro-2-pyridinyl | Cl |
| 1-methylpiperazin-4-yl | O | 3-CH3, 5-Cl | 3-chloro-2-pyridinyl | Br |
| 1-methylpiperazin-4-yl | O | 3-Br, 5-Cl | 3-chloro-2-pyridinyl | Br |
| 1-methylpiperazin-4-yl | O | 3-Br, 5-Br | 3-chloro-2-pyridinyl | Br |
| 1-methylpiperazin-4-yl | O | 3-CH3, 5-CN | 3-chloro-2-pyridinyl | Br |
| 1-methylpiperazin-4-yl | O | 3-CH3, 5-Cl | 3-chloro-2-pyridinyl | CF3 |
| 1-methylpiperazin-4-yl | O | 3-Br, 5-Cl | 3-chloro-2-pyridinyl | CF3 |
| 1-methylpiperazin-4-yl | O | 3-Br, 5-Br | 3-chloro-2-pyridinyl | CF3 |
| 1-methylpiperazin-4-yl | O | 3-CH3, 5-CN | 3-chloro-2-pyridinyl | CF3 |

TABLE 51

| NR8R9 | A34 | (R4)n | R13a-1 | R14a-1 |
|---|---|---|---|---|
| NH2 | S | 3-CH3, 5-Cl | 3-chloro-2-pyridinyl | H |
| NH2 | S | 3-Br, 5-Cl | 3-chloro-2-pyridinyl | H |
| NH2 | S | 3-Br, 5-Br | 3-chloro-2-pyridinyl | H |
| NH2 | S | 3-CH3, 5-CN | 3-chloro-2-pyridinyl | H |
| NH2 | S | 3-CH3, 5-Cl | 3-chloro-2-pyridinyl | Cl |
| NH2 | S | 3-Br, 5-Cl | 3-chloro-2-pyridinyl | Cl |

TABLE 51-continued

| NR$^8$R$^9$ | A$^{34}$ | (R$^4$)$_n$ | R$^{13a-1}$ | R$^{14a-1}$ |
|---|---|---|---|---|
| NH$_2$ | S | 3-Br, 5-Br | 3-chloro-2-pyridinyl | Cl |
| NH$_2$ | S | 3-CH$_3$, 5-CN | 3-chloro-2-pyridinyl | Cl |
| NH$_2$ | S | 3-CH$_3$, 5-Cl | 3-chloro-2-pyridinyl | Br |
| NH$_2$ | S | 3-Br, 5-Cl | 3-chloro-2-pyridinyl | Br |
| NH$_2$ | S | 3-Br, 5-Br | 3-chloro-2-pyridinyl | Br |
| NH$_2$ | S | 3-CH$_3$, 5-CN | 3-chloro-2-pyridinyl | Br |
| NH$_2$ | S | 3-CH$_3$, 5-Cl | 3-chloro-2-pyridinyl | CF$_3$ |
| NH$_2$ | S | 3-Br, 5-Cl | 3-chloro-2-pyridinyl | CF$_3$ |
| NH$_2$ | S | 3-Br, 5-Br | 3-chloro-2-pyridinyl | CF$_3$ |
| NH$_2$ | S | 3-CH$_3$, 5-CN | 3-chloro-2-pyridinyl | CF$_3$ |
| NHCH$_3$ | S | 3-CH$_3$, 5-Cl | 3-chloro-2-pyridinyl | H |
| NHCH$_3$ | S | 3-Br, 5-Cl | 3-chloro-2-pyridinyl | H |
| NHCH$_3$ | S | 3-Br, 5-Br | 3-chloro-2-pyridinyl | H |
| NHCH$_3$ | S | 3-CH$_3$, 5-CN | 3-chloro-2-pyridinyl | H |
| NHCH$_3$ | S | 3-CH$_3$, 5-Cl | 3-chloro-2-pyridinyl | Cl |
| NHCH$_3$ | S | 3-Br, 5-Cl | 3-chloro-2-pyridinyl | Cl |
| NHCH$_3$ | S | 3-Br, 5-Br | 3-chloro-2-pyridinyl | Cl |
| NHCH$_3$ | S | 3-CH$_3$, 5-CN | 3-chloro-2-pyridinyl | Cl |
| NHCH$_3$ | S | 3-CH$_3$, 5-Cl | 3-chloro-2-pyridinyl | Br |
| NHCH$_3$ | S | 3-Br, 5-Cl | 3-chloro-2-pyridinyl | Br |
| NHCH$_3$ | S | 3-Br, 5-Br | 3-chloro-2-pyridinyl | Br |
| NHCH$_3$ | S | 3-CH$_3$, 5-CN | 3-chloro-2-pyridinyl | Br |
| NHCH$_3$ | S | 3-CH$_3$, 5-Cl | 3-chloro-2-pyridinyl | CF$_3$ |
| NHCH$_3$ | S | 3-Br, 5-Cl | 3-chloro-2-pyridinyl | CF$_3$ |
| NHCH$_3$ | S | 3-Br, 5-Br | 3-chloro-2-pyridinyl | CF$_3$ |
| NHCH$_3$ | S | 3-CH$_3$, 5-CN | 3-chloro-2-pyridinyl | CF$_3$ |

TABLE 52

| NR$^8$R$^9$ | A$^{34}$ | (R$^4$)$_n$ | R$^{13a-1}$ | R$^{14a-1}$ |
|---|---|---|---|---|
| NHCH$_2$CH$_3$ | S | 3-CH$_3$, 5-Cl | 3-chloro-2-pyridinyl | H |
| NHCH$_2$CH$_3$ | S | 3-Br, 5-Cl | 3-chloro-2-pyridinyl | H |
| NHCH$_2$CH$_3$ | S | 3-Br, 5-Br | 3-chloro-2-pyridinyl | H |
| NHCH$_2$CH$_3$ | S | 3-CH$_3$, 5-CN | 3-chloro-2-pyridinyl | H |
| NHCH$_2$CH$_3$ | S | 3-CH$_3$, 5-Cl | 3-chloro-2-pyridinyl | Cl |
| NHCH$_2$CH$_3$ | S | 3-Br, 5-Cl | 3-chloro-2-pyridinyl | Cl |
| NHCH$_2$CH$_3$ | S | 3-Br, 5-Br | 3-chloro-2-pyridinyl | Cl |
| NHCH$_2$CH$_3$ | S | 3-CH$_3$, 5-CN | 3-chloro-2-pyridinyl | Cl |
| NHCH$_2$CH$_3$ | S | 3-CH$_3$, 5-Cl | 3-chloro-2-pyridinyl | Br |
| NHCH$_2$CH$_3$ | S | 3-Br, 5-Cl | 3-chloro-2-pyridinyl | Br |
| NHCH$_2$CH$_3$ | S | 3-Br, 5-Br | 3-chloro-2-pyridinyl | Br |
| NHCH$_2$CH$_3$ | S | 3-CH$_3$, 5-CN | 3-chloro-2-pyridinyl | Br |
| NHCH$_2$CH$_3$ | S | 3-CH$_3$, 5-Cl | 3-chloro-2-pyridinyl | CF$_3$ |
| NHCH$_2$CH$_3$ | S | 3-Br, 5-Cl | 3-chloro-2-pyridinyl | CF$_3$ |
| NHCH$_2$CH$_3$ | S | 3-Br, 5-Br | 3-chloro-2-pyridinyl | CF$_3$ |
| NHCH$_2$CH$_3$ | S | 3-CH$_3$, 5-CN | 3-chloro-2-pyridinyl | CF$_3$ |
| NHCH(CH$_3$)$_2$ | S | 3-CH$_3$, 5-Cl | 3-chloro-2-pyridinyl | H |
| NHCH(CH$_3$)$_2$ | S | 3-Br, 5-Cl | 3-chloro-2-pyridinyl | H |
| NHCH(CH$_3$)$_2$ | S | 3-Br, 5-Br | 3-chloro-2-pyridinyl | H |
| NHCH(CH$_3$)$_2$ | S | 3-CH$_3$, 5-CN | 3-chloro-2-pyridinyl | H |
| NHCH(CH$_3$)$_2$ | S | 3-CH$_3$, 5-Cl | 3-chloro-2-pyridinyl | Cl |
| NHCH(CH$_3$)$_2$ | S | 3-Br, 5-Cl | 3-chloro-2-pyridinyl | Cl |
| NHCH(CH$_3$)$_2$ | S | 3-Br, 5-Br | 3-chloro-2-pyridinyl | Cl |
| NHCH(CH$_3$)$_2$ | S | 3-CH$_3$, 5-CN | 3-chloro-2-pyridinyl | Cl |
| NHCH(CH$_3$)$_2$ | S | 3-CH$_3$, 5-Cl | 3-chloro-2-pyridinyl | Br |
| NHCH(CH$_3$)$_2$ | S | 3-Br, 5-Cl | 3-chloro-2-pyridinyl | Br |
| NHCH(CH$_3$)$_2$ | S | 3-Br, 5-Br | 3-chloro-2-pyridinyl | Br |
| NHCH(CH$_3$)$_2$ | S | 3-CH$_3$, 5-CN | 3-chloro-2-pyridinyl | Br |
| NHCH(CH$_3$)$_2$ | S | 3-CH$_3$, 5-Cl | 3-chloro-2-pyridinyl | CF$_3$ |
| NHCH(CH$_3$)$_2$ | S | 3-Br, 5-Cl | 3-chloro-2-pyridinyl | CF$_3$ |
| NHCH(CH$_3$)$_2$ | S | 3-Br, 5-Br | 3-chloro-2-pyridinyl | CF$_3$ |
| NHCH(CH$_3$)$_2$ | S | 3-CH$_3$, 5-CN | 3-chloro-2-pyridinyl | CF$_3$ |

TABLE 53

| NR$^8$R$^9$ | A$^{34}$ | (R$^4$)$_n$ | R$^{13a-1}$ | R$^{14a-1}$ |
|---|---|---|---|---|
| NHC(CH$_3$)$_3$ | S | 3-CH$_3$, 5-Cl | 3-chloro-2-pyridinyl | H |
| NHC(CH$_3$)$_3$ | S | 3-Br, 5-Cl | 3-chloro-2-pyridinyl | H |
| NHC(CH$_3$)$_3$ | S | 3-Br, 5-Br | 3-chloro-2-pyridinyl | H |
| NHC(CH$_3$)$_3$ | S | 3-CH$_3$, 5-CN | 3-chloro-2-pyridinyl | H |

TABLE 53-continued

| NR$^8$R$^9$ | A$^{34}$ | (R$^4$)$_n$ | R$^{13a-1}$ | R$^{14a-1}$ |
|---|---|---|---|---|
| NHC(CH$_3$)$_3$ | S | 3-CH$_3$, 5-Cl | 3-chloro-2-pyridinyl | Cl |
| NHC(CH$_3$)$_3$ | S | 3-Br, 5-Cl | 3-chloro-2-pyridinyl | Cl |
| NHC(CH$_3$)$_3$ | S | 3-Br, 5-Br | 3-chloro-2-pyridinyl | Cl |
| NHC(CH$_3$)$_3$ | S | 3-CH$_3$, 5-CN | 3-chloro-2-pyridinyl | Cl |
| NHC(CH$_3$)$_3$ | S | 3-CH$_3$, 5-Cl | 3-chloro-2-pyridinyl | Br |
| NHC(CH$_3$)$_3$ | S | 3-Br, 5-Cl | 3-chloro-2-pyridinyl | Br |
| NHC(CH$_3$)$_3$ | S | 3-Br, 5-Br | 3-chloro-2-pyridinyl | Br |
| NHC(CH$_3$)$_3$ | S | 3-CH$_3$, 5-CN | 3-chloro-2-pyridinyl | Br |
| NHC(CH$_3$)$_3$ | S | 3-CH$_3$, 5-Cl | 3-chloro-2-pyridinyl | CF$_3$ |
| NHC(CH$_3$)$_3$ | S | 3-Br, 5-Cl | 3-chloro-2-pyridinyl | CF$_3$ |
| NHC(CH$_3$)$_3$ | S | 3-Br, 5-Br | 3-chloro-2-pyridinyl | CF$_3$ |
| NHC(CH$_3$)$_3$ | S | 3-CH$_3$, 5-CN | 3-chloro-2-pyridinyl | CF$_3$ |
| N(CH$_3$)$_2$ | S | 3-CH$_3$, 5-Cl | 3-chloro-2-pyridinyl | H |
| N(CH$_3$)$_2$ | S | 3-Br, 5-Cl | 3-chloro-2-pyridinyl | H |
| N(CH$_3$)$_2$ | S | 3-Br, 5-Br | 3-chloro-2-pyridinyl | H |
| N(CH$_3$)$_2$ | S | 3-CH$_3$, 5-CN | 3-chloro-2-pyridinyl | H |
| N(CH$_3$)$_2$ | S | 3-CH$_3$, 5-Cl | 3-chloro-2-pyridinyl | Cl |
| N(CH$_3$)$_2$ | S | 3-Br, 5-Cl | 3-chloro-2-pyridinyl | Cl |
| N(CH$_3$)$_2$ | S | 3-Br, 5-Br | 3-chloro-2-pyridinyl | Cl |
| N(CH$_3$)$_2$ | S | 3-CH$_3$, 5-CN | 3-chloro-2-pyridinyl | Cl |
| N(CH$_3$)$_2$ | S | 3-CH$_3$, 5-Cl | 3-chloro-2-pyridinyl | Br |
| N(CH$_3$)$_2$ | S | 3-Br, 5-Cl | 3-chloro-2-pyridinyl | Br |
| N(CH$_3$)$_2$ | S | 3-Br, 5-Br | 3-chloro-2-pyridinyl | Br |
| N(CH$_3$)$_2$ | S | 3-CH$_3$, 5-CN | 3-chloro-2-pyridinyl | Br |
| N(CH$_3$)$_2$ | S | 3-CH$_3$, 5-Cl | 3-chloro-2-pyridinyl | CF$_3$ |
| N(CH$_3$)$_2$ | S | 3-Br, 5-Cl | 3-chloro-2-pyridinyl | CF$_3$ |
| N(CH$_3$)$_2$ | S | 3-Br, 5-Br | 3-chloro-2-pyridinyl | CF$_3$ |
| N(CH$_3$)$_2$ | S | 3-CH$_3$, 5-CN | 3-chloro-2-pyridinyl | CF$_3$ |

TABLE 54

| NR$^8$R$^9$ | A$^{34}$ | (R$^4$)$_n$ | R$^{13a-1}$ | R$^{14a-1}$ |
|---|---|---|---|---|
| N(CH$_2$CH$_3$)$_2$ | S | 3-CH$_3$, 5-Cl | 3-chloro-2-pyridinyl | H |
| N(CH$_2$CH$_3$)$_2$ | S | 3-Br, 5-Cl | 3-chloro-2-pyridinyl | H |
| N(CH$_2$CH$_3$)$_2$ | S | 3-Br, 5-Br | 3-chloro-2-pyridinyl | H |
| N(CH$_2$CH$_3$)$_2$ | S | 3-CH$_3$, 5-CN | 3-chloro-2-pyridinyl | H |
| N(CH$_2$CH$_3$)$_2$ | S | 3-CH$_3$, 5-Cl | 3-chloro-2-pyridinyl | Cl |
| N(CH$_2$CH$_3$)$_2$ | S | 3-Br, 5-Cl | 3-chloro-2-pyridinyl | Cl |
| N(CH$_2$CH$_3$)$_2$ | S | 3-Br, 5-Br | 3-chloro-2-pyridinyl | Cl |
| N(CH$_2$CH$_3$)$_2$ | S | 3-CH$_3$, 5-CN | 3-chloro-2-pyridinyl | CL |
| N(CH$_2$CH$_3$)$_2$ | S | 3-CH$_3$, 5-Cl | 3-chloro-2-pyridinyl | Br |
| N(CH$_2$CH$_3$)$_2$ | S | 3-Br, 5-Cl | 3-chloro-2-pyridinyl | Br |
| N(CH$_2$CH$_3$)$_2$ | S | 3-Br, 5-Br | 3-chloro-2-pyridinyl | Br |
| N(CH$_2$CH$_3$)$_2$ | S | 3-CH$_3$, 5-CN | 3-chloro-2-pyridinyl | Br |
| N(CH$_2$CH$_3$)$_2$ | S | 3-CH$_3$, 5-Cl | 3-chloro-2-pyridinyl | CF$_3$ |
| N(CH$_2$CH$_3$)$_2$ | S | 3-Br, 5-Cl | 3-chloro-2-pyridinyl | CF$_3$ |
| N(CH$_2$CH$_3$)$_2$ | S | 3-Br, 5-Br | 3-chloro-2-pyridinyl | CF$_3$ |
| N(CH$_2$CH$_3$)$_2$ | S | 3-CH$_3$, 5-CN | 3-chloro-2-pyridinyl | CF$_3$ |
| cyclopropylamino | S | 3-CH$_3$, 5-Cl | 3-chloro-2-pyridinyl | H |
| cyclopropylamino | S | 3-Br, 5-Cl | 3-chloro-2-pyridinyl | H |
| cyclopropylamino | S | 3-Br, 5-Br | 3-chloro-2-pyridinyl | H |
| cyclopropylamino | S | 3-CH$_3$, 5-CN | 3-chloro-2-pyridinyl | H |
| cyclopropylamino | S | 3-CH$_3$, 5-Cl | 3-chloro-2-pyridinyl | Cl |
| cyclopropylamino | S | 3-Br, 5-Cl | 3-chloro-2-pyridinyl | Cl |
| cyclopropylamino | S | 3-Br, 5-Br | 3-chloro-2-pyridinyl | Cl |
| cyclopropylamino | S | 3-CH$_3$, 5-CN | 3-chloro-2-pyridinyl | Cl |
| cyclopropylamino | S | 3-CH$_3$, 5-Cl | 3-chloro-2-pyridinyl | Br |
| cyclopropylamino | S | 3-Br, 5-Cl | 3-chloro-2-pyridinyl | Br |
| cyclopropylamino | S | 3-Br, 5-Br | 3-chloro-2-pyridinyl | Br |
| cyclopropylamino | S | 3-CH$_3$, 5-CN | 3-chloro-2-pyridinyl | Br |
| cyclopropylamino | S | 3-CH$_3$, 5-Cl | 3-chloro-2-pyridinyl | CF$_3$ |
| cyclopropylamino | S | 3-Br, 5-Cl | 3-chloro-2-pyridinyl | CF$_3$ |
| cyclopropylamino | S | 3-Br, 5-Br | 3-chloro-2-pyridinyl | CF$_3$ |
| cyclopropylamino | S | 3-CH$_3$, 5-CN | 3-chloro-2-pyridinyl | CF$_3$ |

TABLE 55

| NR$^8$R$^9$ | A$^{34}$ | (R$^4$)$_n$ | R$^{13a-1}$ | R$^{14a-1}$ |
|---|---|---|---|---|
| cyclobutylamino | S | 3-CH$_3$, 5-Cl | 3-chloro-2-pyridinyl | H |
| cyclobutylamino | S | 3-Br, 5-Cl | 3-chloro-2-pyridinyl | H |

TABLE 55-continued

| NR$^8$R$^9$ | A$^{34}$ | (R$^4$)$_n$ | R$^{13a-1}$ | R$^{14a-1}$ |
|---|---|---|---|---|
| cyclobutylamino | S | 3-Br, 5-Br | 3-chloro-2-pyridinyl | H |
| cyclobutylamino | S | 3-CH$_3$, 5-CN | 3-chloro-2-pyridinyl | H |
| cyclobutylamino | S | 3-CH$_3$, 5-Cl | 3-chloro-2-pyridinyl | Cl |
| cyclobutylamino | S | 3-Br, 5-Cl | 3-chloro-2-pyridinyl | Cl |
| cyclobutylamino | S | 3-Br, 5-Br | 3-chloro-2-pyridinyl | Cl |
| cyclobutylamino | S | 3-CH$_3$, 5-CN | 3-chloro-2-pyridinyl | Cl |
| cyclobutylamino | S | 3-CH$_3$, 5-Cl | 3-chloro-2-pyridinyl | Br |
| cyclobutylamino | S | 3-Br, 5-Cl | 3-chloro-2-pyridinyl | Br |
| cyclobutylamino | S | 3-Br, 5-Br | 3-chloro-2-pyridinyl | Br |
| cyclobutylamino | S | 3-CH$_3$, 5-CN | 3-chloro-2-pyridinyl | Br |
| cyclobutylamino | S | 3-CH$_3$, 5-Cl | 3-chloro-2-pyridinyl | CF$_3$ |
| cyclobutylamino | S | 3-Br, 5-Cl | 3-chloro-2-pyridinyl | CF$_3$ |
| cyclobutylamino | S | 3-Br, 5-Br | 3-chloro-2-pyridinyl | CF$_3$ |
| cyclobutylamino | S | 3-CH$_3$, 5-CN | 3-chloro-2-pyridinyl | CF$_3$ |
| cyclopentylamino | S | 3-CH$_3$, 5-Cl | 3-chloro-2-pyridinyl | H |
| cyclopentylamino | S | 3-Br, 5-Cl | 3-chloro-2-pyridinyl | H |
| cyclopentylamino | S | 3-Br, 5-Br | 3-chloro-2-pyridinyl | H |
| cyclopentylamino | S | 3-CH$_3$, 5-CN | 3-chloro-2-pyridinyl | H |
| cyclopentylamino | S | 3-CH$_3$, 5-Cl | 3-chloro-2-pyridinyl | Cl |
| cyclopentylamino | S | 3-Br, 5-Cl | 3-chloro-2-pyridinyl | Cl |
| cyclopentylamino | S | 3-Br, 5-Br | 3-chloro-2-pyridinyl | Cl |
| cyclopentylamino | S | 3-CH$_3$, 5-CN | 3-chloro-2-pyridinyl | Cl |
| cyclopentylamino | S | 3-CH$_3$, 5-Cl | 3-chloro-2-pyridinyl | Br |
| cyclopentylamino | S | 3-Br, 5-Cl | 3-chloro-2-pyridinyl | Br |
| cyclopentylamino | S | 3-Br, 5-Br | 3-chloro-2-pyridinyl | Br |
| cyclopentylamino | S | 3-CH$_3$, 5-CN | 3-chloro-2-pyridinyl | Br |
| cyclopentylamino | S | 3-CH$_3$, 5-Cl | 3-chloro-2-pyridinyl | CF$_3$ |
| cyclopentylamino | S | 3-Br, 5-Cl | 3-chloro-2-pyridinyl | CF$_3$ |
| cyclopentylamino | S | 3-Br, 5-Br | 3-chloro-2-pyridinyl | CF$_3$ |
| cyclopentylamino | S | 3-CH$_3$, 5-CN | 3-chloro-2-pyridinyl | CF$_3$ |

TABLE 56

| NR$^8$R$^9$ | A$^{34}$ | (R$^4$)$_n$ | R$^{13a-1}$ | R$^{14a-1}$ |
|---|---|---|---|---|
| cyclohexylamino | S | 3-CH$_3$, 5-Cl | 3-chloro-2-pyridinyl | H |
| cyclohexylamino | S | 3-Br, 5-Cl | 3-chloro-2-pyridinyl | H |
| cyclohexylamino | S | 3-Br, 5-Br | 3-chloro-2-pyridinyl | H |
| cyclohexylamino | S | 3-CH$_3$, 5-CN | 3-chloro-2-pyridinyl | H |
| cyclohexylamino | S | 3-CH$_3$, 5-Cl | 3-chloro-2-pyridinyl | Cl |
| cyclohexylamino | S | 3-Br, 5-Cl | 3-chloro-2-pyridinyl | Cl |
| cyclohexylamino | S | 3-Br, 5-Br | 3-chloro-2-pyridinyl | Cl |
| cyclohexylamino | S | 3-CH$_3$, 5-CN | 3-chloro-2-pyridinyl | Cl |
| cyclohexylamino | S | 3-CH$_3$, 5-Cl | 3-chloro-2-pyridinyl | Br |
| cyclohexylamino | S | 3-Br, 5-Cl | 3-chloro-2-pyridinyl | Br |
| cyclohexylamino | S | 3-Br, 5-Br | 3-chloro-2-pyridinyl | Br |
| cyclohexylamino | S | 3-CH$_3$, 5-CN | 3-chloro-2-pyridinyl | Br |
| cyclohexylamino | S | 3-CH$_3$, 5-Cl | 3-chloro-2-pyridinyl | CF$_3$ |
| cyclohexylamino | S | 3-Br, 5-Cl | 3-chloro-2-pyridinyl | CF$_3$ |
| cyclohexylamino | S | 3-Br, 5-Br | 3-chloro-2-pyridinyl | CF$_3$ |
| cyclohexylamino | S | 3-CH$_3$, 5-CN | 3-chloro-2-pyridinyl | CF$_3$ |
| anilino | S | 3-CH$_3$, 5-Cl | 3-chloro-2-pyridinyl | H |
| anilino | S | 3-Br, 5-Cl | 3-chloro-2-pyridinyl | H |
| anilino | S | 3-Br, 5-Br | 3-chloro-2-pyridinyl | H |
| anilino | S | 3-CH$_3$, 5-CN | 3-chloro-2-pyridinyl | H |
| anilino | S | 3-CH$_3$, 5-Cl | 3-chloro-2-pyridinyl | Cl |
| anilino | S | 3-Br, 5-Cl | 3-chloro-2-pyridinyl | Cl |
| anilino | S | 3-Br, 5-Br | 3-chloro-2-pyridinyl | Cl |
| anilino | S | 3-CH$_3$, 5-CN | 3-chloro-2-pyridinyl | Cl |
| anilino | S | 3-CH$_3$, 5-Cl | 3-chloro-2-pyridinyl | Br |
| anilino | S | 3-Br, 5-Cl | 3-chloro-2-pyridinyl | Br |
| anilino | S | 3-Br, 5-Br | 3-chloro-2-pyridinyl | Br |
| anilino | S | 3-CH$_3$, 5-CN | 3-chloro-2-pyridinyl | Br |
| anilino | S | 3-CH$_3$, 5-Cl | 3-chloro-2-pyridinyl | CF$_3$ |
| anilino | S | 3-Br, 5-Cl | 3-chloro-2-pyridinyl | CF$_3$ |
| anilino | S | 3-Br, 5-Br | 3-chloro-2-pyridinyl | CF$_3$ |
| anilino | S | 3-CH$_3$, 5-CN | 3-chloro-2-pyridinyl | CF$_3$ |

TABLE 57

| NR$^8$R$^9$ | A$^{34}$ | (R$^4$)$_n$ | R$^{13a-1}$ | R$^{14a-1}$ |
|---|---|---|---|---|
| morpholin-4-yl | S | 3-CH$_3$, 5-Cl | 3-chloro-2-pyridinyl | H |
| morpholin-4-yl | S | 3-Br, 5-Cl | 3-chloro-2-pyridinyl | H |
| morpholin-4-yl | S | 3-Br, 5-Br | 3-chloro-2-pyridinyl | H |
| morpholin-4-yl | S | 3-CH$_3$, 5-CN | 3-chloro-2-pyridinyl | H |
| morpholin-4-yl | S | 3-CH$_3$, 5-Cl | 3-chloro-2-pyridinyl | Cl |
| morpholin-4-yl | S | 3-Br, 5-Cl | 3-chloro-2-pyridinyl | Cl |
| morpholin-4-yl | S | 3-Br, 5-Br | 3-chloro-2-pyridinyl | Cl |
| morpholin-4-yl | S | 3-CH$_3$, 5-CN | 3-chloro-2-pyridinyl | Cl |
| morpholin-4-yl | S | 3-CH$_3$, 5-Cl | 3-chloro-2-pyridinyl | Br |
| morpholin-4-yl | S | 3-Br, 5-Cl | 3-chloro-2-pyridinyl | Br |
| morpholin-4-yl | S | 3-Br, 5-Br | 3-chloro-2-pyridinyl | Br |
| morpholin-4-yl | S | 3-CH$_3$, 5-CN | 3-chloro-2-pyridinyl | Br |
| morpholin-4-yl | S | 3-CH$_3$, 5-Cl | 3-chloro-2-pyridinyl | CF$_3$ |
| morpholin-4-yl | S | 3-Br, 5-Cl | 3-chloro-2-pyridinyl | CF$_3$ |
| morpholin-4-yl | S | 3-Br, 5-Br | 3-chloro-2-pyridinyl | CF$_3$ |
| morpholin-4-yl | S | 3-CH$_3$, 5-CN | 3-chloro-2-pyridinyl | CF$_3$ |

A compound represented by the formula (1-E):

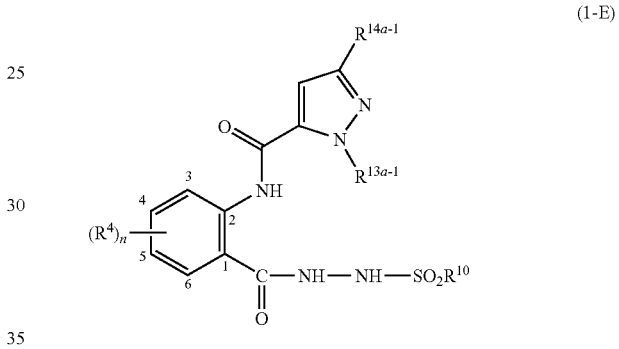

(1-E)

wherein R$^{10}$, (R$^4$)$_n$, R$^{13a-1}$ and R$^{14a-1}$ represent combinations shown in Table 58 to Table 60.

TABLE 58

| R$^{10}$ | (R$^4$)$_n$ | R$^{13a-1}$ | R$^{14a-1}$ |
|---|---|---|---|
| CH$_3$ | 3-CH$_3$, 5-Cl | 3-chloro-2-pyridinyl | H |
| CH$_3$ | 3-Br, 5-Cl | 3-chloro-2-pyridinyl | H |
| CH$_3$ | 3-Br, 5-Br | 3-chloro-2-pyridinyl | H |
| CH$_3$ | 3-CH$_3$, 5-CN | 3-chloro-2-pyridinyl | H |
| CH$_3$ | 3-CH$_3$, 5-Cl | 3-chloro-2-pyridinyl | Cl |
| CH$_3$ | 3-Br, 5-Cl | 3-chloro-2-pyridinyl | Cl |
| CH$_3$ | 3-Br, 5-Br | 3-chloro-2-pyridinyl | Cl |
| CH$_3$ | 3-CH$_3$, 5-CN | 3-chloro-2-pyridinyl | Cl |
| CH$_3$ | 3-CH$_3$, 5-Cl | 3-chloro-2-pyridinyl | Br |
| CH$_3$ | 3-Br, 5-Cl | 3-chloro-2-pyridinyl | Br |
| CH$_3$ | 3-Br, 5-Br | 3-chloro-2-pyridinyl | Br |
| CH$_3$ | 3-CH$_3$, 5-CN | 3-chloro-2-pyridinyl | Br |
| CH$_3$ | 3-CH$_3$, 5-Cl | 3-chloro-2-pyridinyl | CF$_3$ |
| CH$_3$ | 3-Br, 5-Cl | 3-chloro-2-pyridinyl | CF$_3$ |
| CH$_3$ | 3-Br, 5-Br | 3-chloro-2-pyridinyl | CF$_3$ |
| CH$_3$ | 3-CH$_3$, 5-CN | 3-chloro-2-pyridinyl | CF$_3$ |
| CH$_2$CH$_3$ | 3-CH$_3$, 5-Cl | 3-chloro-2-pyridinyl | H |
| CH$_2$CH$_3$ | 3-Br, 5-Cl | 3-chloro-2-pyridinyl | H |
| CH$_2$CH$_3$ | 3-Br, 5-Br | 3-chloro-2-pyridinyl | H |
| CH$_2$CH$_3$ | 3-CH$_3$, 5-CN | 3-chloro-2-pyridinyl | H |
| CH$_2$CH$_3$ | 3-CH$_3$, 5-Cl | 3-chloro-2-pyridinyl | Cl |
| CH$_2$CH$_3$ | 3-Br, 5-Cl | 3-chloro-2-pyridinyl | Cl |
| CH$_2$CH$_3$ | 3-Br, 5-Br | 3-chloro-2-pyridinyl | Cl |
| CH$_2$CH$_3$ | 3-CH$_3$, 5-CN | 3-chloro-2-pyridinyl | Cl |
| CH$_2$CH$_3$ | 3-CH$_3$, 5-Cl | 3-chloro-2-pyridinyl | Br |
| CH$_2$CH$_3$ | 3-Br, 5-Cl | 3-chloro-2-pyridinyl | Br |
| CH$_2$CH$_3$ | 3-Br, 5-Br | 3-chloro-2-pyridinyl | Br |
| CH$_2$CH$_3$ | 3-CH$_3$, 5-CN | 3-chloro-2-pyridinyl | Br |
| CH$_2$CH$_3$ | 3-CH$_3$, 5-Cl | 3-chloro-2-pyridinyl | CF$_3$ |

TABLE 58-continued

| $R^{10}$ | $(R^4)_n$ | $R^{13a-1}$ | $R^{14a-1}$ |
|---|---|---|---|
| $CH_2CH_3$ | 3-Br, 5-Cl | 3-chloro-2-pyridinyl | $CF_3$ |
| $CH_2CH_3$ | 3-Br, 5-Br | 3-chloro-2-pyridinyl | $CF_3$ |
| $CH_2CH_3$ | 3-$CH_3$, 5-CN | 3-chloro-2-pyridinyl | $CF_3$ |

TABLE 59

| $R^{10}$ | $(R^4)_n$ | $R^{13a-1}$ | $R^{14a-1}$ |
|---|---|---|---|
| $CF_3$ | 3-$CH_3$, 5-Cl | 3-chloro-2-pyridinyl | H |
| $CF_3$ | 3-Br, 5-Cl | 3-chloro-2-pyridinyl | H |
| $CF_3$ | 3-Br, 5-Br | 3-chloro-2-pyridinyl | H |
| $CF_3$ | 3-$CH_3$, 5-CN | 3-chloro-2-pyridinyl | H |
| $CF_3$ | 3-$CH_3$, 5-Cl | 3-chloro-2-pyridinyl | Cl |
| $CF_3$ | 3-Br, 5-Cl | 3-chloro-2-pyridinyl | Cl |
| $CF_3$ | 3-Br, 5-Br | 3-chloro-2-pyridinyl | Cl |
| $CF_3$ | 3-$CH_3$, 5-CN | 3-chloro-2-pyridinyl | Cl |
| $CF_3$ | 3-$CH_3$, 5-Cl | 3-chloro-2-pyridinyl | Br |
| $CF_3$ | 3-Br, 5-Cl | 3-chloro-2-pyridinyl | Br |
| $CF_3$ | 3-Br, 5-Br | 3-chloro-2-pyridinyl | Br |
| $CF_3$ | 3-$CH_3$, 5-CN | 3-chloro-2-pyridinyl | Br |
| $CF_3$ | 3-$CH_3$, 5-Cl | 3-chloro-2-pyridinyl | $CF_3$ |
| $CF_3$ | 3-Br, 5-Cl | 3-chloro-2-pyridinyl | $CF_3$ |
| $CF_3$ | 3-Br, 5-Br | 3-chloro-2-pyridinyl | $CF_3$ |
| $CF_3$ | 3-$CH_3$, 5-CN | 3-chloro-2-pyridinyl | $CF_3$ |
| phenyl | 3-$CH_3$, 5-Cl | 3-chloro-2-pyridinyl | H |
| phenyl | 3-Br, 5-Cl | 3-chloro-2-pyridinyl | H |
| phenyl | 3-Br, 5-Br | 3-chloro-2-pyridinyl | H |
| phenyl | 3-$CH_3$, 5-CN | 3-chloro-2-pyridinyl | H |
| phenyl | 3-$CH_3$, 5-Cl | 3-chloro-2-pyridinyl | Cl |
| phenyl | 3-Br, 5-Cl | 3-chloro-2-pyridinyl | Cl |
| phenyl | 3-Br, 5-Br | 3-chloro-2-pyridinyl | Cl |
| phenyl | 3-$CH_3$, 5-CN | 3-chloro-2-pyridinyl | Cl |
| phenyl | 3-$CH_3$, 5-Cl | 3-chloro-2-pyridinyl | Br |
| phenyl | 3-Br, 5-Cl | 3-chloro-2-pyridinyl | Br |
| phenyl | 3-Br, 5-Br | 3-chloro-2-pyridinyl | Br |
| phenyl | 3-$CH_3$, 5-CN | 3-chloro-2-pyridinyl | Br |
| phenyl | 3-$CH_3$, 5-Cl | 3-chloro-2-pyridinyl | $CF_3$ |
| phenyl | 3-Br, 5-Cl | 3-chloro-2-pyridinyl | $CF_3$ |
| phenyl | 3-Br, 5-Br | 3-chloro-2-pyridinyl | $CF_3$ |
| phenyl | 3-$CH_3$, 5-CN | 3-chloro-2-pyridinyl | $CF_3$ |

TABLE 60

| $R^{10}$ | $(R^4)_n$ | $R^{13a-1}$ | $R^{14a-1}$ |
|---|---|---|---|
| 4-methylphenyl | 3-$CH_3$, 5-Cl | 3-chloro-2-pyridinyl | H |
| 4-methylphenyl | 3-Br, 5-Cl | 3-chloro-2-pyridinyl | H |
| 4-methylphenyl | 3-Br, 5-Br | 3-chloro-2-pyridinyl | H |
| 4-methylphenyl | 3-$CH_3$, 5-CN | 3-chloro-2-pyridinyl | H |
| 4-methylphenyl | 3-$CH_3$, 5-Cl | 3-chloro-2-pyridinyl | Cl |
| 4-methylphenyl | 3-Br, 5-Cl | 3-chloro-2-pyridinyl | Cl |
| 4-methylphenyl | 3-Br, 5-Br | 3-chloro-2-pyridinyl | Cl |
| 4-methylphenyl | 3-$CH_3$, 5-CN | 3-chloro-2-pyridinyl | Cl |
| 4-methylphenyl | 3-$CH_3$, 5-Cl | 3-chloro-2-pyridinyl | Br |
| 4-methylphenyl | 3-Br, 5-Cl | 3-chloro-2-pyridinyl | Br |
| 4-methylphenyl | 3-Br, 5-Br | 3-chloro-2-pyridinyl | Br |
| 4-methylphenyl | 3-$CH_3$, 5-CN | 3-chloro-2-pyridinyl | Br |
| 4-methylphenyl | 3-$CH_3$, 5-Cl | 3-chloro-2-pyridinyl | $CF_3$ |
| 4-methylphenyl | 3-Br, 5-Cl | 3-chloro-2-pyridinyl | $CF_3$ |
| 4-methylphenyl | 3-Br, 5-Br | 3-chloro-2-pyridinyl | $CF_3$ |
| 4-methylphenyl | 3-$CH_3$, 5-CN | 3-chloro-2-pyridinyl | $CF_3$ |

A compound represented by the formula (1-F):

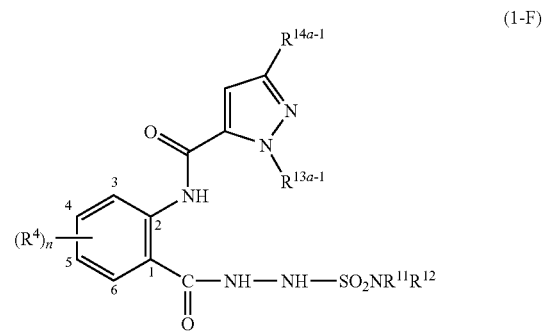

(1-F)

wherein $NR^{11}R^{12}$, $(R^4)_n$, $R^{13a-1}$ and $R^{14a-1}$ represent combinations shown in Table 61.

TABLE 61

| $NR^{11}R^{12}$ | $(R^4)_n$ | $R^{13a-1}$ | $R^{14a-1}$ |
|---|---|---|---|
| $N(CH_3)_2$ | 3-$CH_3$, 5-Cl | 3-chloro-2-pyridinyl | H |
| $N(CH_3)_2$ | 3-Br, 5-Cl | 3-chloro-2-pyridinyl | H |
| $N(CH_3)_2$ | 3-Br, 5-Br | 3-chloro-2-pyridinyl | H |
| $N(CH_3)_2$ | 3-$CH_3$, 5-CN | 3-chloro-2-pyridinyl | H |
| $N(CH_3)_2$ | 3-$CH_3$, 5-Cl | 3-chloro-2-pyridinyl | Cl |
| $N(CH_3)_2$ | 3-Br, 5-Cl | 3-chloro-2-pyridinyl | Cl |
| $N(CH_3)_2$ | 3-Br, 5-Br | 3-chloro-2-pyridinyl | Cl |
| $N(CH_3)_2$ | 3-$CH_3$, 5-CN | 3-chloro-2-pyridinyl | Cl |
| $N(CH_3)_2$ | 3-$CH_3$, 5-Cl | 3-chloro-2-pyridinyl | Br |
| $N(CH_3)_2$ | 3-Br, 5-Cl | 3-chloro-2-pyridinyl | Br |
| $N(CH_3)_2$ | 3-Br, 5-Br | 3-chloro-2-pyridinyl | Br |
| $N(CH_3)_2$ | 3-$CH_3$, 5-CN | 3-chloro-2-pyridinyl | Br |
| $N(CH_3)_2$ | 3-$CH_3$, 5-Cl | 3-chloro-2-pyridinyl | $CF_3$ |
| $N(CH_3)_2$ | 3-Br, 5-Cl | 3-chloro-2-pyridinyl | $CF_3$ |
| $N(CH_3)_2$ | 3-Br, 5-Br | 3-chloro-2-pyridinyl | $CF_3$ |
| $N(CH_3)_2$ | 3-$CH_3$, 5-CN | 3-chloro-2-pyridinyl | $CF_3$ |
| anilino | 3-$CH_3$, 5-Cl | 3-chloro-2-pyridinyl | H |
| anilino | 3-Br, 5-Cl | 3-chloro-2-pyridinyl | H |
| anilino | 3-Br, 5-Br | 3-chloro-2-pyridinyl | H |
| anilino | 3-$CH_3$, 5-CN | 3-chloro-2-pyridinyl | H |
| anilino | 3-$CH_3$, 5-Cl | 3-chloro-2-pyridinyl | Cl |
| anilino | 3-Br, 5-Cl | 3-chloro-2-pyridinyl | Cl |
| anilino | 3-Br, 5-Br | 3-chloro-2-pyridinyl | Cl |
| anilino | 3-$CH_3$, 5-CN | 3-chloro-2-pyridinyl | Cl |
| anilino | 3-$CH_3$, 5-Cl | 3-chloro-2-pyridinyl | Br |
| anilino | 3-Br, 5-Cl | 3-chloro-2-pyridinyl | Br |
| anilino | 3-Br, 5-Br | 3-chloro-2-pyridinyl | Br |
| anilino | 3-$CH_3$, 5-CN | 3-chloro-2-pyridinyl | Br |
| anilino | 3-$CH_3$, 5-Cl | 3-chloro-2-pyridinyl | $CF_3$ |
| anilino | 3-Br, 5-Cl | 3-chloro-2-pyridinyl | $CF_3$ |
| anilino | 3-Br, 5-Br | 3-chloro-2-pyridinyl | $CF_3$ |
| anilino | 3-$CH_3$, 5-CN | 3-chloro-2-pyridinyl | $CF_3$ |

A compound represented by the formula (1-G):

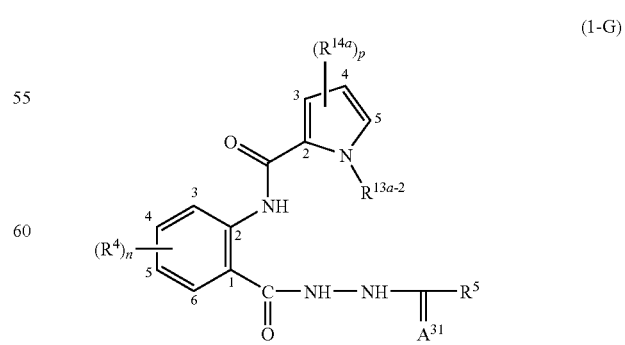

(1-G)

wherein $R^5$, $A^{31}$, $(R^4)_n$, $R^{13a-2}$ and $(R^{14a})_p$ represent combinations shown in Table 62.

TABLE 62

| R⁵ | A³¹ | (R⁴)ₙ | R¹³ᵃ⁻² | (R¹⁴ᵃ)ₚ |
|---|---|---|---|---|
| H | O | 3-CH₃, 5-Cl | 3-chloro-2-pyridinyl | H |
| H | O | 3-Br, 5-Cl | 3-chloro-2-pyridinyl | H |
| H | O | 3-Br, 5-Br | 3-chloro-2-pyridinyl | H |
| H | O | 3-CH₃, 5-CN | 3-chloro-2-pyridinyl | H |
| H | O | 3-CH₃, 5-Cl | 3-chloro-2-pyridinyl | 4-Cl |
| H | O | 3-Br, 5-Cl | 3-chloro-2-pyridinyl | 4-Cl |
| H | O | 3-Br, 5-Br | 3-chloro-2-pyridinyl | 4-Cl |
| H | O | 3-CH₃, 5-CN | 3-chloro-2-pyridinyl | 4-Cl |
| H | O | 3-CH₃, 5-Cl | 3-chloro-2-pyridinyl | 4-Br |
| H | O | 3-Br, 5-Cl | 3-chloro-2-pyridinyl | 4-Br |
| H | O | 3-Br, 5-Br | 3-chloro-2-pyridinyl | 4-Br |
| H | O | 3-CH₃, 5-CN | 3-chloro-2-pyridinyl | 4-Br |
| H | O | 3-CH₃, 5-Cl | 3-chloro-2-pyridinyl | 4-CF₃ |
| H | O | 3-Br, 5-Cl | 3-chloro-2-pyridinyl | 4-CF₃ |
| H | O | 3-Br, 5-Br | 3-chloro-2-pyridinyl | 4-CF₃ |
| H | O | 3-CH₃, 5-CN | 3-chloro-2-pyridinyl | 4-CF₃ |
| CH₃ | O | 3-CH₃, 5-Cl | 3-chloro-2-pyridinyl | H |
| CH₃ | O | 3-Br, 5-Cl | 3-chloro-2-pyridinyl | H |
| CH₃ | O | 3-Br, 5-Br | 3-chloro-2-pyridinyl | H |
| CH₃ | O | 3-CH₃, 5-CN | 3-chloro-2-pyridinyl | H |
| CH₃ | O | 3-CH₃, 5-Cl | 3-chloro-2-pyridinyl | 4-Cl |
| CH₃ | O | 3-Br, 5-Cl | 3-chloro-2-pyridinyl | 4-Cl |
| CH₃ | O | 3-Br, 5-Br | 3-chloro-2-pyridinyl | 4-Cl |
| CH₃ | O | 3-CH₃, 5-CN | 3-chloro-2-pyridinyl | 4-Cl |
| CH₃ | O | 3-CH₃, 5-Cl | 3-chloro-2-pyridinyl | 4-Br |
| CH₃ | O | 3-Br, 5-Cl | 3-chloro-2-pyridinyl | 4-Br |
| CH₃ | O | 3-Br, 5-Br | 3-chloro-2-pyridinyl | 4-Br |
| CH₃ | O | 3-CH₃, 5-CN | 3-chloro-2-pyridinyl | 4-Br |
| CH₃ | O | 3-CH₃, 5-Cl | 3-chloro-2-pyridinyl | 4-CF₃ |
| CH₃ | O | 3-Br, 5-Cl | 3-chloro-2-pyridinyl | 4-CF₃ |
| CH₃ | O | 3-Br, 5-Br | 3-chloro-2-pyridinyl | 4-CF₃ |
| CH₃ | O | 3-CH₃, 5-CN | 3-chloro-2-pyridinyl | 4-CF₃ |

A compound represented by the formula (1-H):

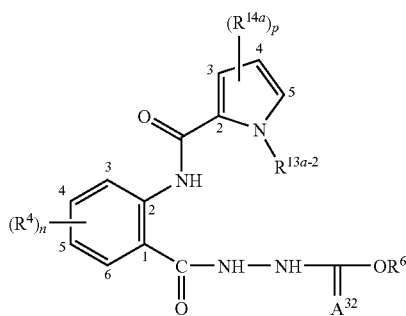

(1-H)

wherein $R^6$, $A^{32}$, $(R^4)_n$, $R^{13a-2}$ and $(R^{14a})_p$ represent combinations shown in Table 63 to Table 74.

TABLE 63

| R⁶ | A³² | (R⁴)ₙ | R¹³ᵃ⁻² | (R¹⁴ᵃ)ₚ |
|---|---|---|---|---|
| CH₃ | O | 3-CH₃ | 3-chloro-2-pyridinyl | H |
| CH₃ | O | 3-CH₃, 5-Cl | 3-chloro-2-pyridinyl | H |
| CH₃ | O | 3-CH₃, 5-Br | 3-chloro-2-pyridinyl | H |
| CH₃ | O | 3-CH₃, 5-I | 3-chloro-2-pyridinyl | H |
| CH₃ | O | 3-CH₃, 5-CH₃ | 3-chloro-2-pyridinyl | H |
| CH₃ | O | 3-CH₃, 5-CN | 3-chloro-2-pyridinyl | H |
| CH₃ | O | 3-Cl | 3-chloro-2-pyridinyl | H |
| CH₃ | O | 3-Cl, 5-Cl | 3-chloro-2-pyridinyl | H |
| CH₃ | O | 3-Cl, 5-Br | 3-chloro-2-pyridinyl | H |
| CH₃ | O | 3-Cl, 5-I | 3-chloro-2-pyridinyl | H |
| CH₃ | O | 3-Cl, 5-CH₃ | 3-chloro-2-pyridinyl | H |

TABLE 63-continued

| R⁶ | A³² | (R⁴)ₙ | R¹³ᵃ⁻² | (R¹⁴ᵃ)ₚ |
|---|---|---|---|---|
| CH₃ | O | 3-Cl, 5-CN | 3-chloro-2-pyridinyl | H |
| CH₃ | O | 3-Br | 3-chloro-2-pyridinyl | H |
| CH₃ | O | 3-Br, 5-Cl | 3-chloro-2-pyridinyl | H |
| CH₃ | O | 3-Br, 5-Br | 3-chloro-2-pyridinyl | H |
| CH₃ | O | 3-Br, 5-I | 3-chloro-2-pyridinyl | H |
| CH₃ | O | 3-Br, 5-CH₃ | 3-chloro-2-pyridinyl | H |
| CH₃ | O | 3-Br, 5-CN | 3-chloro-2-pyridinyl | H |
| CH₃ | O | 3-I | 3-chloro-2-pyridinyl | H |
| CH₃ | O | 3-I, 5-Cl | 3-chloro-2-pyridinyl | H |
| CH₃ | O | 3-I, 5-Br | 3-chloro-2-pyridinyl | H |
| CH₃ | O | 3-I, 5-I | 3-chloro-2-pyridinyl | H |
| CH₃ | O | 3-I, 5-CH₃ | 3-chloro-2-pyridinyl | H |
| CH₃ | O | 3-I, 5-CN | 3-chloro-2-pyridinyl | H |

TABLE 64

| R⁶ | A³² | (R⁴)ₙ | R¹³ᵃ⁻² | (R¹⁴ᵃ)ₚ |
|---|---|---|---|---|
| CH₃ | O | 3-CH₃ | 3-chloro-2-pyridinyl | 4-Cl |
| CH₃ | O | 3-CH₃, 5-Cl | 3-chloro-2-pyridinyl | 4-Cl |
| CH₃ | O | 3-CH₃, 5-Br | 3-chloro-2-pyridinyl | 4-Cl |
| CH₃ | O | 3-CH₃, 5-I | 3-chloro-2-pyridinyl | 4-Cl |
| CH₃ | O | 3-CH₃, 5-CH₃ | 3-chloro-2-pyridinyl | 4-Cl |
| CH₃ | O | 3-CH₃, 5-CN | 3-chloro-2-pyridinyl | 4-Cl |
| CH₃ | O | 3-Cl | 3-chloro-2-pyridinyl | 4-Cl |
| CH₃ | O | 3-Cl, 5-Cl | 3-chloro-2-pyridinyl | 4-Cl |
| CH₃ | O | 3-Cl, 5-Br | 3-chloro-2-pyridinyl | 4-Cl |
| CH₃ | O | 3-Cl, 5-I | 3-chloro-2-pyridinyl | 4-Cl |
| CH₃ | O | 3-Cl, 5-CH₃ | 3-chloro-2-pyridinyl | 4-Cl |
| CH₃ | O | 3-Cl, 5-CN | 3-chloro-2-pyridinyl | 4-Cl |
| CH₃ | O | 3-Br | 3-chloro-2-pyridinyl | 4-Cl |
| CH₃ | O | 3-Br, 5-Cl | 3-chloro-2-pyridinyl | 4-Cl |
| CH₃ | O | 3-Br, 5-Br | 3-chloro-2-pyridinyl | 4-Cl |
| CH₃ | O | 3-Br, 5-I | 3-chloro-2-pyridinyl | 4-Cl |
| CH₃ | O | 3-Br, 5-CH₃ | 3-chloro-2-pyridinyl | 4-Cl |
| CH₃ | O | 3-Br, 5-CN | 3-chloro-2-pyridinyl | 4-Cl |
| CH₃ | O | 3-I | 3-chloro-2-pyridinyl | 4-Cl |
| CH₃ | O | 3-I, 5-Cl | 3-chloro-2-pyridinyl | 4-Cl |
| CH₃ | O | 3-I, 5-Br | 3-chloro-2-pyridinyl | 4-Cl |
| CH₃ | O | 3-I, 5-I | 3-chloro-2-pyridinyl | 4-Cl |
| CH₃ | O | 3-I, 5-CH₃ | 3-chloro-2-pyridinyl | 4-Cl |
| CH₃ | O | 3-I, 5-CN | 3-chloro-2-pyridinyl | 4-Cl |

TABLE 65

| R⁶ | A³² | (R⁴)ₙ | R¹³ᵃ⁻² | (R¹⁴ᵃ)ₚ |
|---|---|---|---|---|
| CH₃ | O | 3-CH₂CH₃ | 3-chloro-2-pyridinyl | 4-Cl |
| CH₃ | O | 3-CH(CH₃)₂ | 3-chloro-2-pyridinyl | 4-Cl |
| CH₃ | O | 3-C(CH₃)₃ | 3-chloro-2-pyridinyl | 4-Cl |
| CH₃ | O | 3-CF₃ | 3-chloro-2-pyridinyl | 4-Cl |
| CH₃ | O | 3-OCH₃ | 3-chloro-2-pyridinyl | 4-Cl |
| CH₃ | O | 3-phenyl | 3-chloro-2-pyridinyl | 4-Cl |
| CH₃ | O | 3-CH₂CH₃, 5-Cl | 3-chloro-2-pyridinyl | 4-Cl |
| CH₃ | O | 3-CH(CH₃)₂, 5-Cl | 3-chloro-2-pyridinyl | 4-Cl |
| CH₃ | O | 3-C(CH₃)₃, 5-Cl | 3-chloro-2-pyridinyl | 4-Cl |
| CH₃ | O | 3-CF₃, 5-Cl | 3-chloro-2-pyridinyl | 4-Cl |
| CH₃ | O | 3-OCH₃, 5-Cl | 3-chloro-2-pyridinyl | 4-Cl |
| CH₃ | O | 3-phenyl, 5-Cl | 3-chloro-2-pyridinyl | 4-Cl |
| CH₃ | O | 3-CH₃, 4-Cl | 3-chloro-2-pyridinyl | 4-Cl |
| CH₃ | O | 3-Cl, 4-Cl | 3-chloro-2-pyridinyl | 4-Cl |
| CH₃ | O | 3-CH₃, 6-Cl | 3-chloro-2-pyridinyl | 4-Cl |
| CH₃ | O | 3-Cl, 6-Cl | 3-chloro-2-pyridinyl | 4-Cl |
| CH₃ | O | 3-CH₃, 4-Cl, 5-Cl | 3-chloro-2-pyridinyl | 4-Cl |
| CH₃ | O | 3-Cl, 4-Cl, 5-Cl | 3-chloro-2-pyridinyl | 4-Cl |
| CH₃ | O | 3-CH₃, 5-Cl, 6-Cl | 3-chloro-2-pyridinyl | 4-Cl |
| CH₃ | O | 3-Cl, 5-Cl, 6-Cl | 3-chloro-2-pyridinyl | 4-Cl |
| CH₃ | O | 3-CH₃, 5-F | 3-chloro-2-pyridinyl | 4-Cl |
| CH₃ | O | 3-Cl, 5-F | 3-chloro-2-pyridinyl | 4-Cl |
| CH₃ | O | 3-Br, 5-F | 3-chloro-2-pyridinyl | 4-Cl |
| CH₃ | O | 3-I, 5-F | 3-chloro-2-pyridinyl | 4-Cl |

TABLE 65-continued

| R⁶ | A³² | (R⁴)ₙ | R¹³ᵃ⁻² | (R¹⁴ᵃ)ₚ |
|---|---|---|---|---|
| CH₃ | O | 3-Me,4,5-CH=CH—CH=CH— | 3-chloro-2-pyridinyl | 4-Cl |
| CH₃ | O | 3-Cl,4,5-CH=CH—CH=CH— | 3-chloro-2-pyridinyl | 4-Cl |
| CH₃ | O | 3-Br,4,5-CH=CH—CH=CH— | 3-chloro-2-pyridinyl | 4-Cl |
| CH₃ | O | 3-I,4,5-CH=CH—CH=CH— | 3-chloro-2-pyridinyl | 4-Cl |

TABLE 66

| R⁶ | A³² | (R⁴)ₙ | R¹³ᵃ⁻² | (R¹⁴ᵃ)ₚ |
|---|---|---|---|---|
| CH₃ | O | 3-CH₃ | 3-chloro-2-pyridinyl | 4-Br |
| CH₃ | O | 3-CH₃, 5-Cl | 3-chloro-2-pyridinyl | 4-Br |
| CH₃ | O | 3-CH₃, 5-Br | 3-chloro-2-pyridinyl | 4-Br |
| CH₃ | O | 3-CH₃, 5-I | 3-chloro-2-pyridinyl | 4-Br |
| CH₃ | O | 3-CH₃, 5-CH₃ | 3-chloro-2-pyridinyl | 4-Br |
| CH₃ | O | 3-CH₃, 5-CN | 3-chloro-2-pyridinyl | 4-Br |
| CH₃ | O | 3-Cl | 3-chloro-2-pyridinyl | 4-Br |
| CH₃ | O | 3-Cl, 5-Cl | 3-chloro-2-pyridinyl | 4-Br |
| CH₃ | O | 3-Cl, 5-Br | 3-chloro-2-pyridinyl | 4-Br |
| CH₃ | O | 3-Cl, 5-I | 3-chloro-2-pyridinyl | 4-Br |
| CH₃ | O | 3-Cl, 5-CH₃ | 3-chloro-2-pyridinyl | 4-Br |
| CH₃ | O | 3-Cl, 5-CN | 3-chloro-2-pyridinyl | 4-Br |
| CH₃ | O | 3-Br | 3-chloro-2-pyridinyl | 4-Br |
| CH₃ | O | 3-Br, 5-Cl | 3-chloro-2-pyridinyl | 4-Br |
| CH₃ | O | 3-Br, 5-Br | 3-chloro-2-pyridinyl | 4-Br |
| CH₃ | O | 3-Br, 5-I | 3-chloro-2-pyridinyl | 4-Br |
| CH₃ | O | 3-Br, 5-CH₃ | 3-chloro-2-pyridinyl | 4-Br |
| CH₃ | O | 3-Br, 5-CN | 3-chloro-2-pyridinyl | 4-Br |
| CH₃ | O | 3-I | 3-chloro-2-pyridinyl | 4-Br |
| CH₃ | O | 3-I, 5-Cl | 3-chloro-2-pyridinyl | 4-Br |
| CH₃ | O | 3-I, 5-Br | 3-chloro-2-pyridinyl | 4-Br |
| CH₃ | O | 3-I, 5-I | 3-chloro-2-pyridinyl | 4-Br |
| CH₃ | O | 3-I, 5-CH₃ | 3-chloro-2-pyridinyl | 4-Br |
| CH₃ | O | 3-I, 5-CN | 3-chloro-2-pyridinyl | 4-Br |

TABLE 67

| R⁶ | A³² | (R⁴)ₙ | R¹³ᵃ⁻² | (R¹⁴ᵃ)ₚ |
|---|---|---|---|---|
| CH₃ | O | 3-CH₂CH₃ | 3-chloro-2-pyridinyl | 4-Br |
| CH₃ | O | 3-CH(CH₃)₂ | 3-chloro-2-pyridinyl | 4-Br |
| CH₃ | O | 3-C(CH₃)₃ | 3-chloro-2-pyridinyl | 4-Br |
| CH₃ | O | 3-CF₃ | 3-chloro-2-pyridinyl | 4-Br |
| CH₃ | O | 3-OCH₃ | 3-chloro-2-pyridinyl | 4-Br |
| CH₃ | O | 3-phenyl | 3-chloro-2-pyridinyl | 4-Br |
| CH₃ | O | 3-CH₂CH₃, 5-Cl | 3-chloro-2-pyridinyl | 4-Br |
| CH₃ | O | 3-CH(CH₃)₂, 5-Cl | 3-chloro-2-pyridinyl | 4-Br |
| CH₃ | O | 3-C(CH₃)₃, 5-Cl | 3-chloro-2-pyridinyl | 4-Br |
| CH₃ | O | 3-CF₃, 5-Cl | 3-chloro-2-pyridinyl | 4-Br |
| CH₃ | O | 3-OCH₃, 5-Cl | 3-chloro-2-pyridinyl | 4-Br |
| CH₃ | O | 3-phenyl, 5-Cl | 3-chloro-2-pyridinyl | 4-Br |
| CH₃ | O | 3-CH₃, 4-Cl | 3-chloro-2-pyridinyl | 4-Br |
| CH₃ | O | 3-Cl, 4-Cl | 3-chloro-2-pyridinyl | 4-Br |
| CH₃ | O | 3-CH₃, 6-Cl | 3-chloro-2-pyridinyl | 4-Br |
| CH₃ | O | 3-Cl, 6-Cl | 3-chloro-2-pyridinyl | 4-Br |
| CH₃ | O | 3-CH₃, 4-Cl, 5-Cl | 3-chloro-2-pyridinyl | 4-Br |
| CH₃ | O | 3-Cl, 4-Cl, 5-Cl | 3-chloro-2-pyridinyl | 4-Br |
| CH₃ | O | 3-CH₃, 5-Cl, 6-Cl | 3-chloro-2-pyridinyl | 4-Br |
| CH₃ | O | 3-Cl, 5-Cl, 6-Cl | 3-chloro-2-pyridinyl | 4-Br |
| CH₃ | O | 3-CH₃, 5-F | 3-chloro-2-pyridinyl | 4-Br |
| CH₃ | O | 3-Cl, 5-F | 3-chloro-2-pyridinyl | 4-Br |
| CH₃ | O | 3-Br, 5-F | 3-chloro-2-pyridinyl | 4-Br |
| CH₃ | O | 3-I, 5-F | 3-chloro-2-pyridinyl | 4-Br |
| CH₃ | O | 3-Me,4,5-CH=CH—CH=CH— | 3-chloro-2-pyridinyl | 4-Br |
| CH₃ | O | 3-Cl,4,5-CH=CH—CH=CH— | 3-chloro-2-pyridinyl | 4-Br |

TABLE 67-continued

| R⁶ | A³² | (R⁴)ₙ | R¹³ᵃ⁻² | (R¹⁴ᵃ)ₚ |
|---|---|---|---|---|
| CH₃ | O | 3-Br,4,5-CH=CH—CH=CH— | 3-chloro-2-pyridinyl | 4-Br |
| CH₃ | O | 3-I,4,5-CH=CH—CH=CH— | 3-chloro-2-pyridinyl | 4-Br |

TABLE 68

| R⁶ | A³² | (R⁴)ₙ | R¹³ᵃ⁻² | (R¹⁴ᵃ)ₚ |
|---|---|---|---|---|
| CH₃ | O | 3-CH₃ | 3-chloro-2-pyridinyl | 4-CF₃ |
| CH₃ | O | 3-CH₃, 5-Cl | 3-chloro-2-pyridinyl | 4-CF₃ |
| CH₃ | O | 3-CH₃, 5-Br | 3-chloro-2-pyridinyl | 4-CF₃ |
| CH₃ | O | 3-CH₃, 5-I | 3-chloro-2-pyridinyl | 4-CF₃ |
| CH₃ | O | 3-CH₃, 5-CH₃ | 3-chloro-2-pyridinyl | 4-CF₃ |
| CH₃ | O | 3-CH₃, 5-CN | 3-chloro-2-pyridinyl | 4-CF₃ |
| CH₃ | O | 3-Cl | 3-chloro-2-pyridinyl | 4-CF₃ |
| CH₃ | O | 3-Cl, 5-Cl | 3-chloro-2-pyridinyl | 4-CF₃ |
| CH₃ | O | 3-Cl, 5-Br | 3-chloro-2-pyridinyl | 4-CF₃ |
| CH₃ | O | 3-Cl, 5-I | 3-chloro-2-pyridinyl | 4-CF₃ |
| CH₃ | O | 3-Cl, 5-CH₃ | 3-chloro-2-pyridinyl | 4-CF₃ |
| CH₃ | O | 3-Cl, 5-CN | 3-chloro-2-pyridinyl | 4-CF₃ |
| CH₃ | O | 3-Br | 3-chloro-2-pyridinyl | 4-CF₃ |
| CH₃ | O | 3-Br, 5-Cl | 3-chloro-2-pyridinyl | 4-CF₃ |
| CH₃ | O | 3-Br, 5-Br | 3-chloro-2-pyridinyl | 4-CF₃ |
| CH₃ | O | 3-Br, 5-I | 3-chloro-2-pyridinyl | 4-CF₃ |
| CH₃ | O | 3-Br, 5-CH₃ | 3-chloro-2-pyridinyl | 4-CF₃ |
| CH₃ | O | 3-Br, 5-CN | 3-chloro-2-pyridinyl | 4-CF₃ |
| CH₃ | O | 3-I | 3-chloro-2-pyridinyl | 4-CF₃ |
| CH₃ | O | 3-I, 5-Cl | 3-chloro-2-pyridinyl | 4-CF₃ |
| CH₃ | O | 3-I, 5-Br | 3-chloro-2-pyridinyl | 4-CF₃ |
| CH₃ | O | 3-I, 5-I | 3-chloro-2-pyridinyl | 4-CF₃ |
| CH₃ | O | 3-I, 5-CH₃ | 3-chloro-2-pyridinyl | 4-CF₃ |
| CH₃ | O | 3-I, 5-CN | 3-chloro-2-pyridinyl | 4-CF₃ |

TABLE 69

| R⁶ | A³² | (R⁴)ₙ | R¹³ᵃ⁻² | (R¹⁴ᵃ)ₚ |
|---|---|---|---|---|
| CH₃ | O | 3-CH₃, 5-Cl | 3-chloro-2-pyridinyl | 4-F |
| CH₃ | O | 3-Br, 5-Cl | 3-chloro-2-pyridinyl | 4-F |
| CH₃ | O | 3-Br, 5-Br | 3-chloro-2-pyridinyl | 4-F |
| CH₃ | O | 3-CH₃, 5-CN | 3-chloro-2-pyridinyl | 4-F |
| CH₃ | O | 3-CH₃, 5-Cl | 3-chloro-2-pyridinyl | 4-I |
| CH₃ | O | 3-Br, 5-Cl | 3-chloro-2-pyridinyl | 4-I |
| CH₃ | O | 3-Br, 5-Br | 3-chloro-2-pyridinyl | 4-I |
| CH₃ | O | 3-CH₃, 5-CN | 3-chloro-2-pyridinyl | 4-I |
| CH₃ | O | 3-CH₃, 5-Cl | 3-chloro-2-pyridinyl | 4-CH₃ |
| CH₃ | O | 3-Br, 5-Cl | 3-chloro-2-pyridinyl | 4-CH₃ |
| CH₃ | O | 3-Br, 5-Br | 3-chloro-2-pyridinyl | 4-CH₃ |
| CH₃ | O | 3-CH₃, 5-CN | 3-chloro-2-pyridinyl | 4-CH₃ |
| CH₃ | O | 3-CH₃, 5-Cl | 3-chloro-2-pyridinyl | 5-Cl |
| CH₃ | O | 3-Br, 5-Cl | 3-chloro-2-pyridinyl | 5-Cl |
| CH₃ | O | 3-Br, 5-Br | 3-chloro-2-pyridinyl | 5-Cl |
| CH₃ | O | 3-CH₃, 5-CN | 3-chloro-2-pyridinyl | 5-Cl |
| CH₃ | O | 3-CH₃, 5-Cl | 3-chloro-2-pyridinyl | 5-Br |
| CH₃ | O | 3-Br, 5-Cl | 3-chloro-2-pyridinyl | 5-Br |
| CH₃ | O | 3-Br, 5-Br | 3-chloro-2-pyridinyl | 5-Br |
| CH₃ | O | 3-CH₃, 5-CN | 3-chloro-2-pyridinyl | 5-Br |
| CH₃ | O | 3-CH₃, 5-Cl | 3-chloro-2-pyridinyl | 5-CF₃ |
| CH₃ | O | 3-Br, 5-Cl | 3-chloro-2-pyridinyl | 5-CF₃ |
| CH₃ | O | 3-Br, 5-Br | 3-chloro-2-pyridinyl | 5-CF₃ |
| CH₃ | O | 3-CH₃, 5-CN | 3-chloro-2-pyridinyl | 5-CF₃ |
| CH₃ | O | 3-CH₃, 5-Cl | 3-chloro-2-pyridinyl | 4,5-Cl₂ |
| CH₃ | O | 3-Br, 5-Cl | 3-chloro-2-pyridinyl | 4,5-Cl₂ |
| CH₃ | O | 3-Br, 5-Br | 3-chloro-2-pyridinyl | 4,5-Cl₂ |
| CH₃ | O | 3-CH₃, 5-CN | 3-chloro-2-pyridinyl | 4,5-Cl₂ |
| CH₃ | O | 3-CH₃, 5-Cl | 3-chloro-2-pyridinyl | 4,5-Br₂ |
| CH₃ | O | 3-Br, 5-Cl | 3-chloro-2-pyridinyl | 4,5-Br₂ |
| CH₃ | O | 3-Br, 5-Br | 3-chloro-2-pyridinyl | 4,5-Br₂ |
| CH₃ | O | 3-CH₃, 5-CN | 3-chloro-2-pyridinyl | 4,5-Br₂ |

TABLE 70

| $R^6$ | $A^{32}$ | $(R^4)_n$ | $R^{13a-2}$ | $(R^{14a})_p$ |
|---|---|---|---|---|
| $CH_3$ | O | 3-$CH_3$, 5-Cl | 3-fluoro-2-pyridinyl | H |
| $CH_3$ | O | 3-Br, 5-Cl | 3-fluoro-2-pyridinyl | H |
| $CH_3$ | O | 3-Br, 5-Br | 3-fluoro-2-pyridinyl | H |
| $CH_3$ | O | 3-$CH_3$, 5-CN | 3-fluoro-2-pyridinyl | H |
| $CH_3$ | O | 3-$CH_3$, 5-Cl | 3-fluoro-2-pyridinyl | 4-Cl |
| $CH_3$ | O | 3-Br, 5-Cl | 3-fluoro-2-pyridinyl | 4-Cl |
| $CH_3$ | O | 3-Br, 5-Br | 3-fluoro-2-pyridinyl | 4-Cl |
| $CH_3$ | O | 3-$CH_3$, 5-CN | 3-fluoro-2-pyridinyl | 4-Cl |
| $CH_3$ | O | 3-$CH_3$, 5-Cl | 3-fluoro-2-pyridinyl | 4-Br |
| $CH_3$ | O | 3-Br, 5-Cl | 3-fluoro-2-pyridinyl | 4-Br |
| $CH_3$ | O | 3-Br, 5-Br | 3-fluoro-2-pyridinyl | 4-Br |
| $CH_3$ | O | 3-$CH_3$, 5-CN | 3-fluoro-2-pyridinyl | 4-Br |
| $CH_3$ | O | 3-$CH_3$, 5-Cl | 3-fluoro-2-pyridinyl | 4-$CF_3$ |
| $CH_3$ | O | 3-Br, 5-Cl | 3-fluoro-2-pyridinyl | 4-$CF_3$ |
| $CH_3$ | O | 3-Br, 5-Br | 3-fluoro-2-pyridinyl | 4-$CF_3$ |
| $CH_3$ | O | 3-$CH_3$, 5-CN | 3-fluoro-2-pyridinyl | 4-$CF_3$ |
| $CH_3$ | O | 3-$CH_3$, 5-Cl | 3-bromo-2-pyridinyl | H |
| $CH_3$ | O | 3-Br, 5-Cl | 3-bromo-2-pyridinyl | H |
| $CH_3$ | O | 3-Br, 5-Br | 3-bromo-2-pyridinyl | H |
| $CH_3$ | O | 3-$CH_3$, 5-CN | 3-bromo-2-pyridinyl | H |
| $CH_3$ | O | 3-$CH_3$, 5-Cl | 3-bromo-2-pyridinyl | 4-Cl |
| $CH_3$ | O | 3-Br, 5-Cl | 3-bromo-2-pyridinyl | 4-Cl |
| $CH_3$ | O | 3-Br, 5-Br | 3-bromo-2-pyridinyl | 4-Cl |
| $CH_3$ | O | 3-$CH_3$, 5-CN | 3-bromo-2-pyridinyl | 4-Cl |
| $CH_3$ | O | 3-$CH_3$, 5-Cl | 3-bromo-2-pyridinyl | 4-Br |
| $CH_3$ | O | 3-Br, 5-Cl | 3-bromo-2-pyridinyl | 4-Br |
| $CH_3$ | O | 3-Br, 5-Br | 3-bromo-2-pyridinyl | 4-Br |
| $CH_3$ | O | 3-$CH_3$, 5-CN | 3-bromo-2-pyridinyl | 4-Br |
| $CH_3$ | O | 3-$CH_3$, 5-Cl | 3-bromo-2-pyridinyl | 4-$CF_3$ |
| $CH_3$ | O | 3-Br, 5-Cl | 3-bromo-2-pyridinyl | 4-$CF_3$ |
| $CH_3$ | O | 3-Br, 5-Br | 3-bromo-2-pyridinyl | 4-$CF_3$ |
| $CH_3$ | O | 3-$CH_3$, 5-CN | 3-bromo-2-pyridinyl | 4-$CF_3$ |

TABLE 71

| $R^6$ | $A^{32}$ | $(R^4)_n$ | $R^{13a-2}$ | $(R^{14a})_p$ |
|---|---|---|---|---|
| $CH_3$ | O | 3-$CH_3$, 5-Cl | 3-methyl-2-pyridinyl | H |
| $CH_3$ | O | 3-Br, 5-Cl | 3-methyl-2-pyridinyl | H |
| $CH_3$ | O | 3-Br, 5-Br | 3-methyl-2-pyridinyl | H |
| $CH_3$ | O | 3-$CH_3$, 5-CN | 3-methyl-2-pyridinyl | H |
| $CH_3$ | O | 3-$CH_3$, 5-Cl | 3-methyl-2-pyridinyl | 4-Cl |
| $CH_3$ | O | 3-Br, 5-Cl | 3-methyl-2-pyridinyl | 4-Cl |
| $CH_3$ | O | 3-Br, 5-Br | 3-methyl-2-pyridinyl | 4-Cl |
| $CH_3$ | O | 3-$CH_3$, 5-CN | 3-methyl-2-pyridinyl | 4-Cl |
| $CH_3$ | O | 3-$CH_3$, 5-Cl | 3-methyl-2-pyridinyl | 4-Br |
| $CH_3$ | O | 3-Br, 5-Cl | 3-methyl-2-pyridinyl | 4-Br |
| $CH_3$ | O | 3-Br, 5-Br | 3-methyl-2-pyridinyl | 4-Br |
| $CH_3$ | O | 3-$CH_3$, 5-CN | 3-methyl-2-pyridinyl | 4-Br |
| $CH_3$ | O | 3-$CH_3$, 5-Cl | 3-methyl-2-pyridinyl | 4-$CF_3$ |
| $CH_3$ | O | 3-Br, 5-Cl | 3-methyl-2-pyridinyl | 4-$CF_3$ |
| $CH_3$ | O | 3-Br, 5-Br | 3-methyl-2-pyridinyl | 4-$CF_3$ |
| $CH_3$ | O | 3-$CH_3$, 5-CN | 3-methyl-2-pyridinyl | 4-$CF_3$ |
| $CH_3$ | O | 3-$CH_3$, 5-Cl | 3-trifluoromethyl-2-pyridinyl | H |
| $CH_3$ | O | 3-Br, 5-Cl | 3-trifluoromethyl-2-pyridinyl | H |
| $CH_3$ | O | 3-Br, 5-Br | 3-trifluoromethyl-2-pyridinyl | H |
| $CH_3$ | O | 3-$CH_3$, 5-CN | 3-trifluoromethyl-2-pyridinyl | H |
| $CH_3$ | O | 3-$CH_3$, 5-Cl | 3-trifluoromethyl-2-pyridinyl | 4-Cl |
| $CH_3$ | O | 3-Br, 5-Cl | 3-trifluoromethyl-2-pyridinyl | 4-Cl |
| $CH_3$ | O | 3-Br, 5-Br | 3-trifluoromethyl-2-pyridinyl | 4-Cl |
| $CH_3$ | O | 3-$CH_3$, 5-CN | 3-trifluoromethyl-2-pyridinyl | 4-Cl |
| $CH_3$ | O | 3-$CH_3$, 5-Cl | 3-trifluoromethyl-2-pyridinyl | 4-Br |
| $CH_3$ | O | 3-Br, 5-Cl | 3-trifluoromethyl-2-pyridinyl | 4-Br |
| $CH_3$ | O | 3-Br, 5-Br | 3-trifluoromethyl-2-pyridinyl | 4-Br |
| $CH_3$ | O | 3-$CH_3$, 5-CN | 3-trifluoromethyl-2-pyridinyl | 4-Br |
| $CH_3$ | O | 3-$CH_3$, 5-Cl | 3-trifluoromethyl-2-pyridinyl | 4-$CF_3$ |
| $CH_3$ | O | 3-Br, 5-Cl | 3-trifluoromethyl-2-pyridinyl | 4-$CF_3$ |
| $CH_3$ | O | 3-Br, 5-Br | 3-trifluoromethyl-2-pyridinyl | 4-$CF_3$ |
| $CH_3$ | O | 3-$CH_3$, 5-CN | 3-trifluoromethyl-2-pyridinyl | 4-$CF_3$ |

TABLE 72

| $R^6$ | $A^{32}$ | $(R^4)_n$ | $R^{13a-2}$ | $(R^{14a})_p$ |
|---|---|---|---|---|
| $CH_3$ | O | 3-$CH_3$, 5-Cl | 3-cyano-2-pyridinyl | H |
| $CH_3$ | O | 3-Br, 5-Cl | 3-cyano-2-pyridinyl | H |
| $CH_3$ | O | 3-Br, 5-Br | 3-cyano-2-pyridinyl | H |
| $CH_3$ | O | 3-$CH_3$, 5-CN | 3-cyano-2-pyridinyl | H |
| $CH_3$ | O | 3-$CH_3$, 5-Cl | 3-cyano-2-pyridinyl | 4-Cl |
| $CH_3$ | O | 3-Br, 5-Cl | 3-cyano-2-pyridinyl | 4-Cl |
| $CH_3$ | O | 3-Br, 5-Br | 3-cyano-2-pyridinyl | 4-Cl |
| $CH_3$ | O | 3-$CH_3$, 5-CN | 3-cyano-2-pyridinyl | 4-Cl |
| $CH_3$ | O | 3-$CH_3$, 5-Cl | 3-cyano-2-pyridinyl | 4-Br |
| $CH_3$ | O | 3-Br, 5-Cl | 3-cyano-2-pyridinyl | 4-Br |
| $CH_3$ | O | 3-Br, 5-Br | 3-cyano-2-pyridinyl | 4-Br |
| $CH_3$ | O | 3-$CH_3$, 5-CN | 3-cyano-2-pyridinyl | 4-Br |
| $CH_3$ | O | 3-$CH_3$, 5-Cl | 3-cyano-2-pyridinyl | 4-$CF_3$ |
| $CH_3$ | O | 3-Br, 5-Cl | 3-cyano-2-pyridinyl | 4-$CF_3$ |
| $CH_3$ | O | 3-Br, 5-Br | 3-cyano-2-pyridinyl | 4-$CF_3$ |
| $CH_3$ | O | 3-$CH_3$, 5-CN | 3-cyano-2-pyridinyl | 4-$CF_3$ |
| $CH_3$ | O | 3-$CH_3$, 5-Cl | 3-nitro-2-pyridinyl | H |
| $CH_3$ | O | 3-Br, 5-Cl | 3-nitro-2-pyridinyl | H |
| $CH_3$ | O | 3-Br, 5-Br | 3-nitro-2-pyridinyl | H |
| $CH_3$ | O | 3-$CH_3$, 5-CN | 3-nitro-2-pyridinyl | H |
| $CH_3$ | O | 3-$CH_3$, 5-Cl | 3-nitro-2-pyridinyl | 4-Cl |
| $CH_3$ | O | 3-Br, 5-Cl | 3-nitro-2-pyridinyl | 4-Cl |
| $CH_3$ | O | 3-Br, 5-Br | 3-nitro-2-pyridinyl | 4-Cl |
| $CH_3$ | O | 3-$CH_3$, 5-CN | 3-nitro-2-pyridinyl | 4-Cl |
| $CH_3$ | O | 3-$CH_3$, 5-Cl | 3-nitro-2-pyridinyl | 4-Br |
| $CH_3$ | O | 3-Br, 5-Cl | 3-nitro-2-pyridinyl | 4-Br |
| $CH_3$ | O | 3-Br, 5-Br | 3-nitro-2-pyridinyl | 4-Br |
| $CH_3$ | O | 3-$CH_3$, 5-CN | 3-nitro-2-pyridinyl | 4-Br |
| $CH_3$ | O | 3-$CH_3$, 5-Cl | 3-nitro-2-pyridinyl | 4-$CF_3$ |
| $CH_3$ | O | 3-Br, 5-Cl | 3-nitro-2-pyridinyl | 4-$CF_3$ |
| $CH_3$ | O | 3-Br, 5-Br | 3-nitro-2-pyridinyl | 4-$CF_3$ |
| $CH_3$ | O | 3-$CH_3$, 5-CN | 3-nitro-2-pyridinyl | 4-$CF_3$ |

TABLE 73

| $R^6$ | $A^{32}$ | $(R^4)_n$ | $R^{13a-2}$ | $(R^{14a})_p$ |
|---|---|---|---|---|
| $CH_3$ | O | 3-$CH_3$, 5-Cl | 2-chlorophenyl | H |
| $CH_3$ | O | 3-Br, 5-Cl | 2-chlorophenyl | H |
| $CH_3$ | O | 3-Br, 5-Br | 2-chlorophenyl | H |
| $CH_3$ | O | 3-$CH_3$, 5-CN | 2-chlorophenyl | H |
| $CH_3$ | O | 3-$CH_3$, 5-Cl | 2-chlorophenyl | 4-Cl |
| $CH_3$ | O | 3-Br, 5-Cl | 2-chlorophenyl | 4-Cl |
| $CH_3$ | O | 3-Br, 5-Br | 2-chlorophenyl | 4-Cl |
| $CH_3$ | O | 3-$CH_3$, 5-CN | 2-chlorophenyl | 4-Cl |
| $CH_3$ | O | 3-$CH_3$, 5-Cl | 2-chlorophenyl | 4-Br |
| $CH_3$ | O | 3-Br, 5-Cl | 2-chlorophenyl | 4-Br |
| $CH_3$ | O | 3-Br, 5-Br | 2-chlorophenyl | 4-Br |
| $CH_3$ | O | 3-$CH_3$, 5-CN | 2-chlorophenyl | 4-Br |
| $CH_3$ | O | 3-$CH_3$, 5-Cl | 2-chlorophenyl | 4-$CF_3$ |
| $CH_3$ | O | 3-Br, 5-Cl | 2-chlorophenyl | 4-$CF_3$ |
| $CH_3$ | O | 3-Br, 5-Br | 2-chlorophenyl | 4-$CF_3$ |
| $CH_3$ | O | 3-$CH_3$, 5-CN | 2-chlorophenyl | 4-$CF_3$ |
| $CH_3$ | O | 3-$CH_3$, 5-Cl | 2,6-dichlorophenyl | H |
| $CH_3$ | O | 3-Br, 5-Cl | 2,6-dichlorophenyl | H |
| $CH_3$ | O | 3-Br, 5-Br | 2,6-dichlorophenyl | H |
| $CH_3$ | O | 3-$CH_3$, 5-CN | 2,6-dichlorophenyl | H |
| $CH_3$ | O | 3-$CH_3$, 5-Cl | 2,6-dichlorophenyl | 4-Cl |
| $CH_3$ | O | 3-Br, 5-Cl | 2,6-dichlorophenyl | 4-Cl |
| $CH_3$ | O | 3-Br, 5-Br | 2,6-dichlorophenyl | 4-Cl |
| $CH_3$ | O | 3-$CH_3$, 5-CN | 2,6-dichlorophenyl | 4-Cl |
| $CH_3$ | O | 3-$CH_3$, 5-Cl | 2,6-dichlorophenyl | 4-Br |
| $CH_3$ | O | 3-Br, 5-Cl | 2,6-dichlorophenyl | 4-Br |
| $CH_3$ | O | 3-Br, 5-Br | 2,6-dichlorophenyl | 4-Br |
| $CH_3$ | O | 3-$CH_3$, 5-CN | 2,6-dichlorophenyl | 4-Br |
| $CH_3$ | O | 3-$CH_3$, 5-Cl | 2,6-dichlorophenyl | 4-$CF_3$ |
| $CH_3$ | O | 3-Br, 5-Cl | 2,6-dichlorophenyl | 4-$CF_3$ |
| $CH_3$ | O | 3-Br, 5-Br | 2,6-dichlorophenyl | 4-$CF_3$ |
| $CH_3$ | O | 3-$CH_3$, 5-CN | 2,6-dichlorophenyl | 4-$CF_3$ |

TABLE 74

| R⁶ | A³² | (R⁴)ₙ | R¹³ᵃ⁻² | (R¹⁴ᵃ)ₚ |
|---|---|---|---|---|
| CH₂CH₃ | O | 3-CH₃, 5-Cl | 3-chloro-2-pyridinyl | H |
| CH₂CH₃ | O | 3-Br, 5-Cl | 3-chloro-2-pyridinyl | H |
| CH₂CH₃ | O | 3-Br, 5-Br | 3-chloro-2-pyridinyl | H |
| CH₂CH₃ | O | 3-CH₃, 5-CN | 3-chloro-2-pyridinyl | H |
| CH₂CH₃ | O | 3-CH₃, 5-Cl | 3-chloro-2-pyridinyl | 4-Cl |
| CH₂CH₃ | O | 3-Br, 5-Cl | 3-chloro-2-pyridinyl | 4-Cl |
| CH₂CH₃ | O | 3-Br, 5-Br | 3-chloro-2-pyridinyl | 4-Cl |
| CH₂CH₃ | O | 3-CH₃, 5-CN | 3-chloro-2-pyridinyl | 4-Cl |
| CH₂CH₃ | O | 3-CH₃, 5-Cl | 3-chloro-2-pyridinyl | 4-Br |
| CH₂CH₃ | O | 3-Br, 5-Cl | 3-chloro-2-pyridinyl | 4-Br |
| CH₂CH₃ | O | 3-Br, 5-Br | 3-chloro-2-pyridinyl | 4-Br |
| CH₂CH₃ | O | 3-CH₃, 5-CN | 3-chloro-2-pyridinyl | 4-Br |
| CH₂CH₃ | O | 3-CH₃, 5-Cl | 3-chloro-2-pyridinyl | 4-CF₃ |
| CH₂CH₃ | O | 3-Br, 5-Cl | 3-chloro-2-pyridinyl | 4-CF₃ |
| CH₂CH₃ | O | 3-Br, 5-Br | 3-chloro-2-pyridinyl | 4-CF₃ |
| CH₂CH₃ | O | 3-CH₃, 5-CN | 3-chloro-2-pyridinyl | 4-CF₃ |
| CH₃ | O | 3-Cl, 5-Cl | 3-chloro-2-pyridinyl | 4-F |
| CH₃ | O | 3-Cl, 5-Cl | 3-chloro-2-pyridinyl | 4-I |
| CH₃ | O | 3-Cl, 5-Cl | 3-chloro-2-pyridinyl | 4-CH₃ |
| CH₃ | O | 3-Cl, 5-Cl | 3-chloro-2-pyridinyl | 5-Cl |
| CH₃ | O | 3-Cl, 5-Cl | 3-chloro-2-pyridinyl | 5-Br |
| CH₃ | O | 3-Cl, 5-Cl | 3-chloro-2-pyridinyl | 5-CF₃ |
| CH₃ | O | 3-Cl, 5-Cl | 3-chloro-2-pyridinyl | 4,5-Cl₂ |
| CH₃ | O | 3-Cl, 5-Cl | 3-chloro-2-pyridinyl | 4,5-Br₂ |
| CH₃ | O | 3-CH₃, 5-Cl | 3-chloro-2-pyridinyl | 4-Cl, 5-Br |
| CH₃ | O | 3-Br, 5-Cl | 3-chloro-2-pyridinyl | 4-Cl, 5-Br |
| CH₃ | O | 3-Br, 5-Br | 3-chloro-2-pyridinyl | 4-Cl, 5-Br |
| CH₃ | O | 3-CH₃, 5-CN | 3-chloro-2-pyridinyl | 4-Cl, 5-Br |
| CH₃ | O | 3-Cl, 5-Cl | 3-chloro-2-pyridinyl | 4-Cl, 5-Br |
| CH₃ | O | 3-CH₃, 5-Cl | 3-chloro-2-pyridinyl | 4-Br, 5-Cl |
| CH₃ | O | 3-Br, 5-Cl | 3-chloro-2-pyridinyl | 4-Br, 5-Cl |
| CH₃ | O | 3-Br, 5-Br | 3-chloro-2-pyridinyl | 4-Br, 5-Cl |
| CH₃ | O | 3-CH₃, 5-CN | 3-chloro-2-pyridinyl | 4-Br, 5-Cl |
| CH₃ | O | 3-Cl, 5-Cl | 3-chloro-2-pyridinyl | 4-Br, 5-Cl |

A compound represented by the formula (1-S):

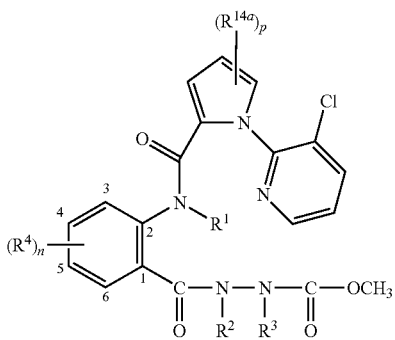

(1-S)

wherein R¹, R², R³, (R⁴)ₙ and (R¹⁴ᵃ)ₚ represent combinations shown in Table 75 to Table 82.

TABLE 75

| R¹ | R² | R³ | (R⁴)ₙ | (R¹⁴ᵃ)ₚ |
|---|---|---|---|---|
| H | CH₃ | H | 3-CH₃, 5-Cl | H |
| H | CH₃ | H | 3-Br, 5-Cl | H |
| H | CH₃ | H | 3-Br, 5-Br | H |
| H | CH₃ | H | 3-CH₃, 5-CN | H |
| H | CH₃ | H | 3-CH₃, 5-Cl | 4-Cl |
| H | CH₃ | H | 3-Br, 5-Cl | 4-Cl |
| H | CH₃ | H | 3-Br, 5-Br | 4-Cl |
| H | CH₃ | H | 3-CH₃, 5-CN | 4-Cl |
| H | CH₃ | H | 3-CH₃, 5-Cl | 4-Br |
| H | CH₃ | H | 3-Br, 5-Cl | 4-Br |

TABLE 75-continued

| R¹ | R² | R³ | (R⁴)ₙ | (R¹⁴ᵃ)ₚ |
|---|---|---|---|---|
| H | CH₃ | H | 3-Br, 5-Br | 4-Br |
| H | CH₃ | H | 3-CH₃, 5-CN | 4-Br |
| H | CH₃ | H | 3-CH₃, 5-Cl | 4-CF₃ |
| H | CH₃ | H | 3-Br, 5-Cl | 4-CF₃ |
| H | CH₃ | H | 3-Br, 5-Br | 4-CF₃ |
| H | CH₃ | H | 3-CH₃, 5-CN | 4-CF₃ |
| H | H | CH₃ | 3-CH₃, 5-Cl | H |
| H | H | CH₃ | 3-Br, 5-Cl | H |
| H | H | CH₃ | 3-Br, 5-Br | H |
| H | H | CH₃ | 3-CH₃, 5-CN | H |
| H | H | CH₃ | 3-CH₃, 5-Cl | 4-Cl |
| H | H | CH₃ | 3-Br, 5-Cl | 4-Cl |
| H | H | CH₃ | 3-Br, 5-Br | 4-Cl |
| H | H | CH₃ | 3-CH₃, 5-CN | 4-Cl |
| H | H | CH₃ | 3-CH₃, 5-Cl | 4-Br |
| H | H | CH₃ | 3-Br, 5-Cl | 4-Br |
| H | H | CH₃ | 3-Br, 5-Br | 4-Br |
| H | H | CH₃ | 3-CH₃, 5-CN | 4-Br |
| H | H | CH₃ | 3-CH₃, 5-Cl | 4-CF₃ |
| H | H | CH₃ | 3-Br, 5-Cl | 4-CF₃ |
| H | H | CH₃ | 3-Br, 5-Br | 4-CF₃ |
| H | H | CH₃ | 3-CH₃, 5-CN | 4-CF₃ |

TABLE 76

| R¹ | R² | R³ | (R⁴)ₙ | (R¹⁴ᵃ)ₚ |
|---|---|---|---|---|
| H | CH₃ | CH₃ | 3-CH₃, 5-Cl | H |
| H | CH₃ | CH₃ | 3-Br, 5-Cl | H |
| H | CH₃ | CH₃ | 3-Br, 5-Br | H |
| H | CH₃ | CH₃ | 3-CH₃, 5-CN | H |
| H | CH₃ | CH₃ | 3-CH₃, 5-Cl | 4-Cl |
| H | CH₃ | CH₃ | 3-Br, 5-Cl | 4-Cl |
| H | CH₃ | CH₃ | 3-Br, 5-Br | 4-Cl |
| H | CH₃ | CH₃ | 3-CH₃, 5-CN | 4-Cl |
| H | CH₃ | CH₃ | 3-CH₃, 5-Cl | 4-Br |
| H | CH₃ | CH₃ | 3-Br, 5-Cl | 4-Br |
| H | CH₃ | CH₃ | 3-Br, 5-Br | 4-Br |
| H | CH₃ | CH₃ | 3-CH₃, 5-CN | 4-Br |
| H | CH₃ | CH₃ | 3-CH₃, 5-Cl | 4-CF₃ |
| H | CH₃ | CH₃ | 3-Br, 5-Cl | 4-CF₃ |
| H | CH₃ | CH₃ | 3-Br, 5-Br | 4-CF₃ |
| H | CH₃ | CH₃ | 3-CH₃, 5-CN | 4-CF₃ |
| H | H | CH₂CH₃ | 3-CH₃, 5-Cl | H |
| H | H | CH₂CH₃ | 3-Br, 5-Cl | H |
| H | H | CH₂CH₃ | 3-Br, 5-Br | H |
| H | H | CH₂CH₃ | 3-CH₃, 5-CN | H |
| H | H | CH₂CH₃ | 3-CH₃, 5-Cl | 4-Cl |
| H | H | CH₂CH₃ | 3-Br, 5-Cl | 4-Cl |
| H | H | CH₂CH₃ | 3-Br, 5-Br | 4-Cl |
| H | H | CH₂CH₃ | 3-CH₃, 5-CN | 4-Cl |
| H | H | CH₂CH₃ | 3-CH₃, 5-Cl | 4-Br |
| H | H | CH₂CH₃ | 3-Br, 5-Cl | 4-Br |
| H | H | CH₂CH₃ | 3-Br, 5-Br | 4-Br |
| H | H | CH₂CH₃ | 3-CH₃, 5-CN | 4-Br |
| H | H | CH₂CH₃ | 3-CH₃, 5-Cl | 4-CF₃ |
| H | H | CH₂CH₃ | 3-Br, 5-Cl | 4-CF₃ |
| H | H | CH₂CH₃ | 3-Br, 5-Br | 4-CF₃ |
| H | H | CH₂CH₃ | 3-CH₃, 5-CN | 4-CF₃ |

TABLE 77

| R¹ | R² | R³ | (R⁴)ₙ | (R¹⁴ᵃ)ₚ |
|---|---|---|---|---|
| H | H | CH(CH₃)₂ | 3-CH₃, 5-Cl | H |
| H | H | CH(CH₃)₂ | 3-Br, 5-Cl | H |
| H | H | CH(CH₃)₂ | 3-Br, 5-Br | H |
| H | H | CH(CH₃)₂ | 3-CH₃, 5-CN | H |
| H | H | CH(CH₃)₂ | 3-CH₃, 5-Cl | 4-Cl |
| H | H | CH(CH₃)₂ | 3-Br, 5-Cl | 4-Cl |
| H | H | CH(CH₃)₂ | 3-Br, 5-Br | 4-Cl |
| H | H | CH(CH₃)₂ | 3-CH₃, 5-CN | 4-Cl |

TABLE 77-continued

| R¹ | R² | R³ | (R⁴)ₙ | (R¹⁴ᵃ)ₚ |
|---|---|---|---|---|
| H | H | CH(CH₃)₂ | 3-CH₃, 5-Cl | 4-Br |
| H | H | CH(CH₃)₂ | 3-Br, 5-Cl | 4-Br |
| H | H | CH(CH₃)₂ | 3-Br, 5-Br | 4-Br |
| H | H | CH(CH₃)₂ | 3-CH₃, 5-CN | 4-Br |
| H | H | CH(CH₃)₂ | 3-CH₃, 5-Cl | 4-CF₃ |
| H | H | CH(CH₃)₂ | 3-Br, 5-Cl | 4-CF₃ |
| H | H | CH(CH₃)₂ | 3-Br, 5-Br | 4-CF₃ |
| H | H | CH(CH₃)₂ | 3-CH₃, 5-CN | 4-CF₃ |
| H | H | C(CH₃)₃ | 3-CH₃, 5-Cl | H |
| H | H | C(CH₃)₃ | 3-Br, 5-Cl | H |
| H | H | C(CH₃)₃ | 3-Br, 5-Br | H |
| H | H | C(CH₃)₃ | 3-CH₃, 5-CN | H |
| H | H | C(CH₃)₃ | 3-CH₃, 5-Cl | 4-Cl |
| H | H | C(CH₃)₃ | 3-Br, 5-Cl | 4-Cl |
| H | H | C(CH₃)₃ | 3-Br, 5-Br | 4-Cl |
| H | H | C(CH₃)₃ | 3-CH₃, 5-CN | 4-Cl |
| H | H | C(CH₃)₃ | 3-CH₃, 5-Cl | 4-Br |
| H | H | C(CH₃)₃ | 3-Br, 5-Cl | 4-Br |
| H | H | C(CH₃)₃ | 3-Br, 5-Br | 4-Br |
| H | H | C(CH₃)₃ | 3-CH₃, 5-CN | 4-Br |
| H | H | C(CH₃)₃ | 3-CH₃, 5-Cl | 4-CF₃ |
| H | H | C(CH₃)₃ | 3-Br, 5-Cl | 4-CF₃ |
| H | H | C(CH₃)₃ | 3-Br, 5-Br | 4-CF₃ |
| H | H | C(CH₃)₃ | 3-CH₃, 5-CN | 4-CF₃ |

TABLE 78

| R¹ | R² | R³ | (R⁴)ₙ | (R¹⁴ᵃ)ₚ |
|---|---|---|---|---|
| H | H | C(=O)OCH₃ | 3-CH₃, 5-Cl | H |
| H | H | C(=O)OCH₃ | 3-Br, 5-Cl | H |
| H | H | C(=O)OCH₃ | 3-Br, 5-Br | H |
| H | H | C(=O)OCH₃ | 3-CH₃, 5-CN | H |
| H | H | C(=O)OCH₃ | 3-CH₃, 5-Cl | 4-Cl |
| H | H | C(=O)OCH₃ | 3-Br, 5-Cl | 4-Cl |
| H | H | C(=O)OCH₃ | 3-Br, 5-Br | 4-Cl |
| H | H | C(=O)OCH₃ | 3-CH₃, 5-CN | 4-Cl |
| H | H | C(=O)OCH₃ | 3-CH₃, 5-Cl | 4-Br |
| H | H | C(=O)OCH₃ | 3-Br, 5-Cl | 4-Br |
| H | H | C(=O)OCH₃ | 3-Br, 5-Br | 4-Br |
| H | H | C(=O)OCH₃ | 3-CH₃, 5-CN | 4-Br |
| H | H | C(=O)OCH₃ | 3-CH₃, 5-Cl | 4-CF₃ |
| H | H | C(=O)OCH₃ | 3-Br, 5-Cl | 4-CF₃ |
| H | H | C(=O)OCH₃ | 3-Br, 5-Br | 4-CF₃ |
| H | H | C(=O)OCH₃ | 3-CH₃, 5-CN | 4-CF₃ |
| H | H | C(=O)N(CH₃)₂ | 3-CH₃, 5-Cl | H |
| H | H | C(=O)N(CH₃)₂ | 3-Br, 5-Cl | H |
| H | H | C(=O)N(CH₃)₂ | 3-Br, 5-Br | H |
| H | H | C(=O)N(CH₃)₂ | 3-CH₃, 5-CN | H |
| H | H | C(=O)N(CH₃)₂ | 3-CH₃, 5-Cl | 4-Cl |
| H | H | C(=O)N(CH₃)₂ | 3-Br, 5-Cl | 4-Cl |
| H | H | C(=O)N(CH₃)₂ | 3-Br, 5-Br | 4-Cl |
| H | H | C(=O)N(CH₃)₂ | 3-CH₃, 5-CN | 4-Cl |
| H | H | C(=O)N(CH₃)₂ | 3-CH₃, 5-Cl | 4-Br |
| H | H | C(=O)N(CH₃)₂ | 3-Br, 5-Cl | 4-Br |
| H | H | C(=O)N(CH₃)₂ | 3-Br, 5-Br | 4-Br |
| H | H | C(=O)N(CH₃)₂ | 3-CH₃, 5-CN | 4-Br |
| H | H | C(=O)N(CH₃)₂ | 3-CH₃, 5-Cl | 4-CF₃ |
| H | H | C(=O)N(CH₃)₂ | 3-Br, 5-Cl | 4-CF₃ |
| H | H | C(=O)N(CH₃)₂ | 3-Br, 5-Br | 4-CF₃ |
| H | H | C(=O)N(CH₃)₂ | 3-CH₃, 5-CN | 4-CF₃ |

TABLE 79

| R¹ | R² | R³ | (R⁴)ₙ | (R¹⁴ᵃ)ₚ |
|---|---|---|---|---|
| CH₃ | CH₃ | H | 3-CH₃, 5-Cl | H |
| CH₃ | CH₃ | H | 3-Br, 5-Cl | H |
| CH₃ | CH₃ | H | 3-Br, 5-Br | H |
| CH₃ | CH₃ | H | 3-CH₃, 5-CN | H |
| CH₃ | CH₃ | H | 3-CH₃, 5-Cl | 4-Cl |
| CH₃ | CH₃ | H | 3-Br, 5-Cl | 4-Cl |

TABLE 79-continued

| R¹ | R² | R³ | (R⁴)ₙ | (R¹⁴ᵃ)ₚ |
|---|---|---|---|---|
| CH₃ | CH₃ | H | 3-Br, 5-Br | 4-Cl |
| CH₃ | CH₃ | H | 3-CH₃, 5-CN | 4-Cl |
| CH₃ | CH₃ | H | 3-CH₃, 5-Cl | 4-Br |
| CH₃ | CH₃ | H | 3-Br, 5-Cl | 4-Br |
| CH₃ | CH₃ | H | 3-Br, 5-Br | 4-Br |
| CH₃ | CH₃ | H | 3-CH₃, 5-CN | 4-Br |
| CH₃ | CH₃ | H | 3-CH₃, 5-Cl | 4-CF₃ |
| CH₃ | CH₃ | H | 3-Br, 5-Cl | 4-CF₃ |
| CH₃ | CH₃ | H | 3-Br, 5-Br | 4-CF₃ |
| CH₃ | CH₃ | H | 3-CH₃, 5-CN | 4-CF₃ |
| CH₃ | H | CH₃ | 3-CH₃, 5-Cl | H |
| CH₃ | H | CH₃ | 3-Br, 5-Cl | H |
| CH₃ | H | CH₃ | 3-Br, 5-Br | H |
| CH₃ | H | CH₃ | 3-CH₃, 5-CN | H |
| CH₃ | H | CH₃ | 3-CH₃, 5-Cl | 4-Cl |
| CH₃ | H | CH₃ | 3-Br, 5-Cl | 4-Cl |
| CH₃ | H | CH₃ | 3-Br, 5-Br | 4-Cl |
| CH₃ | H | CH₃ | 3-CH₃, 5-CN | 4-Cl |
| CH₃ | H | CH₃ | 3-CH₃, 5-Cl | 4-Br |
| CH₃ | H | CH₃ | 3-Br, 5-Cl | 4-Br |
| CH₃ | H | CH₃ | 3-Br, 5-Br | 4-Br |
| CH₃ | H | CH₃ | 3-CH₃, 5-CN | 4-Br |
| CH₃ | H | CH₃ | 3-CH₃, 5-Cl | 4-CF₃ |
| CH₃ | H | CH₃ | 3-Br, 5-Cl | 4-CF₃ |
| CH₃ | H | CH₃ | 3-Br, 5-Br | 4-CF₃ |
| CH₃ | H | CH₃ | 3-CH₃, 5-CN | 4-CF₃ |

TABLE 80

| R¹ | R² | R³ | (R⁴)ₙ | (R¹⁴ᵃ)ₚ |
|---|---|---|---|---|
| CH₃ | CH₃ | CH₃ | 3-CH₃, 5-Cl | H |
| CH₃ | CH₃ | CH₃ | 3-Br, 5-Cl | H |
| CH₃ | CH₃ | CH₃ | 3-Br, 5-Br | H |
| CH₃ | CH₃ | CH₃ | 3-CH₃, 5-CN | H |
| CH₃ | CH₃ | CH₃ | 3-CH₃, 5-Cl | 4-Cl |
| CH₃ | CH₃ | CH₃ | 3-Br, 5-Cl | 4-Cl |
| CH₃ | CH₃ | CH₃ | 3-Br, 5-Br | 4-Cl |
| CH₃ | CH₃ | CH₃ | 3-CH₃, 5-CN | 4-Cl |
| CH₃ | CH₃ | CH₃ | 3-CH₃, 5-Cl | 4-Br |
| CH₃ | CH₃ | CH₃ | 3-Br, 5-Cl | 4-Br |
| CH₃ | CH₃ | CH₃ | 3-Br, 5-Br | 4-Br |
| CH₃ | CH₃ | CH₃ | 3-CH₃, 5-CN | 4-Br |
| CH₃ | CH₃ | CH₃ | 3-CH₃, 5-Cl | 4-CF₃ |
| CH₃ | CH₃ | CH₃ | 3-Br, 5-Cl | 4-CF₃ |
| CH₃ | CH₃ | CH₃ | 3-Br, 5-Br | 4-CF₃ |
| CH₃ | CH₃ | CH₃ | 3-CH₃, 5-CN | 4-CF₃ |
| CH₃ | H | CH₂CH₃ | 3-CH₃, 5-Cl | H |
| CH₃ | H | CH₂CH₃ | 3-Br, 5-Cl | H |
| CH₃ | H | CH₂CH₃ | 3-Br, 5-Br | H |
| CH₃ | H | CH₂CH₃ | 3-CH₃, 5-CN | H |
| CH₃ | H | CH₂CH₃ | 3-CH₃, 5-Cl | 4-Cl |
| CH₃ | H | CH₂CH₃ | 3-Br, 5-Cl | 4-Cl |
| CH₃ | H | CH₂CH₃ | 3-Br, 5-Br | 4-Cl |
| CH₃ | H | CH₂CH₃ | 3-CH₃, 5-CN | 4-Cl |
| CH₃ | H | CH₂CH₃ | 3-CH₃, 5-Cl | 4-Br |
| CH₃ | H | CH₂CH₃ | 3-Br, 5-Cl | 4-Br |
| CH₃ | H | CH₂CH₃ | 3-Br, 5-Br | 4-Br |
| CH₃ | H | CH₂CH₃ | 3-CH₃, 5-CN | 4-Br |
| CH₃ | H | CH₂CH₃ | 3-CH₃, 5-Cl | 4-CF₃ |
| CH₃ | H | CH₂CH₃ | 3-Br, 5-Cl | 4-CF₃ |
| CH₃ | H | CH₂CH₃ | 3-Br, 5-Br | 4-CF₃ |
| CH₃ | H | CH₂CH₃ | 3-CH₃, 5-CN | 4-CF₃ |

TABLE 81

| R¹ | R² | R³ | (R⁴)ₙ | (R¹⁴ᵃ)ₚ |
|---|---|---|---|---|
| CH₃ | H | CH(CH₃)₂ | 3-CH₃, 5-Cl | H |
| CH₃ | H | CH(CH₃)₂ | 3-Br, 5-Cl | H |
| CH₃ | H | CH(CH₃)₂ | 3-Br, 5-Br | H |
| CH₃ | H | CH(CH₃)₂ | 3-CH₃, 5-CN | H |

TABLE 81-continued

| R¹ | R² | R³ | (R⁴)ₙ | (R¹⁴ᵃ)ₚ |
|---|---|---|---|---|
| CH₃ | H | CH(CH₃)₂ | 3-CH₃, 5-Cl | 4-Cl |
| CH₃ | H | CH(CH₃)₂ | 3-Br, 5-Cl | 4-Cl |
| CH₃ | H | CH(CH₃)₂ | 3-Br, 5-Br | 4-Cl |
| CH₃ | H | CH(CH₃)₂ | 3-CH₃, 5-CN | 4-Cl |
| CH₃ | H | CH(CH₃)₂ | 3-CH₃, 5-Cl | 4-Br |
| CH₃ | H | CH(CH₃)₂ | 3-Br, 5-Cl | 4-Br |
| CH₃ | H | CH(CH₃)₂ | 3-Br, 5-Br | 4-Br |
| CH₃ | H | CH(CH₃)₂ | 3-CH₃, 5-CN | 4-Br |
| CH₃ | H | CH(CH₃)₂ | 3-CH₃, 5-Cl | 4-CF₃ |
| CH₃ | H | CH(CH₃)₂ | 3-Br, 5-Cl | 4-CF₃ |
| CH₃ | H | CH(CH₃)₂ | 3-Br, 5-Br | 4-CF₃ |
| CH₃ | H | CH(CH₃)₂ | 3-CH₃, 5-CN | 4-CF₃ |
| CH₃ | H | C(CH₃)₃ | 3-CH₃, 5-Cl | H |
| CH₃ | H | C(CH₃)₃ | 3-Br, 5-Cl | H |
| CH₃ | H | C(CH₃)₃ | 3-Br, 5-Br | H |
| CH₃ | H | C(CH₃)₃ | 3-CH₃, 5-CN | H |
| CH₃ | H | C(CH₃)₃ | 3-CH₃, 5-Cl | 4-Cl |
| CH₃ | H | C(CH₃)₃ | 3-Br, 5-Cl | 4-Cl |
| CH₃ | H | C(CH₃)₃ | 3-Br, 5-Br | 4-Cl |
| CH₃ | H | C(CH₃)₃ | 3-CH₃, 5-CN | 4-Cl |
| CH₃ | H | C(CH₃)₃ | 3-CH₃, 5-Cl | 4-Br |
| CH₃ | H | C(CH₃)₃ | 3-Br, 5-Cl | 4-Br |
| CH₃ | H | C(CH₃)₃ | 3-Br, 5-Br | 4-Br |
| CH₃ | H | C(CH₃)₃ | 3-CH₃, 5-CN | 4-Br |
| CH₃ | H | C(CH₃)₃ | 3-CH₃, 5-Cl | 4-CF₃ |
| CH₃ | H | C(CH₃)₃ | 3-Br, 5-Cl | 4-CF₃ |
| CH₃ | H | C(CH₃)₃ | 3-Br, 5-Br | 4-CF₃ |
| CH₃ | H | C(CH₃)₃ | 3-CH₃, 5-CN | 4-CF₃ |

TABLE 82

| R¹ | R² | R³ | (R⁴)ₙ | (R¹⁴ᵃ)ₚ |
|---|---|---|---|---|
| CH₃ | H | C(=O)OCH₃ | 3-CH₃, 5-Cl | H |
| CH₃ | H | C(=O)OCH₃ | 3-Br, 5-Cl | H |
| CH₃ | H | C(=O)OCH₃ | 3-Br, 5-Br | H |
| CH₃ | H | C(=O)OCH₃ | 3-CH₃, 5-CN | H |
| CH₃ | H | C(=O)OCH₃ | 3-CH₃, 5-Cl | 4-Cl |
| CH₃ | H | C(=O)OCH₃ | 3-Br, 5-Cl | 4-Cl |
| CH₃ | H | C(=O)OCH₃ | 3-Br, 5-Br | 4-Cl |
| CH₃ | H | C(=O)OCH₃ | 3-CH₃, 5-CN | 4-Cl |
| CH₃ | H | C(=O)OCH₃ | 3-CH₃, 5-Cl | 4-Br |
| CH₃ | H | C(=O)OCH₃ | 3-Br, 5-Cl | 4-Br |
| CH₃ | H | C(=O)OCH₃ | 3-Br, 5-Br | 4-Br |
| CH₃ | H | C(=O)OCH₃ | 3-CH₃, 5-CN | 4-Br |
| CH₃ | H | C(=O)OCH₃ | 3-CH₃, 5-Cl | 4-CF₃ |
| CH₃ | H | C(=O)OCH₃ | 3-Br, 5-Cl | 4-CF₃ |
| CH₃ | H | C(=O)OCH₃ | 3-Br, 5-Br | 4-CF₃ |
| CH₃ | H | C(=O)OCH₃ | 3-CH₃, 5-CN | 4-CF₃ |
| CH₃ | H | C(=O)N(CH₃)₂ | 3-CH₃, 5-Cl | H |
| CH₃ | H | C(=O)N(CH₃)₂ | 3-Br, 5-Cl | H |
| CH₃ | H | C(=O)N(CH₃)₂ | 3-Br, 5-Br | H |
| CH₃ | H | C(=O)N(CH₃)₂ | 3-CH₃, 5-CN | H |
| CH₃ | H | C(=O)N(CH₃)₂ | 3-CH₃, 5-Cl | 4-Cl |
| CH₃ | H | C(=O)N(CH₃)₂ | 3-Br, 5-Cl | 4-Cl |
| CH₃ | H | C(=O)N(CH₃)₂ | 3-Br, 5-Br | 4-Cl |
| CH₃ | H | C(=O)N(CH₃)₂ | 3-CH₃, 5-CN | 4-Cl |
| CH₃ | H | C(=O)N(CH₃)₂ | 3-CH₃, 5-Cl | 4-Br |
| CH₃ | H | C(=O)N(CH₃)₂ | 3-Br, 5-Cl | 4-Br |
| CH₃ | H | C(=O)N(CH₃)₂ | 3-Br, 5-Br | 4-Br |
| CH₃ | H | C(=O)N(CH₃)₂ | 3-CH₃, 5-CN | 4-Br |
| CH₃ | H | C(=O)N(CH₃)₂ | 3-CH₃, 5-Cl | 4-CF₃ |
| CH₃ | H | C(=O)N(CH₃)₂ | 3-Br, 5-Cl | 4-CF₃ |
| CH₃ | H | C(=O)N(CH₃)₂ | 3-Br, 5-Br | 4-CF₃ |
| CH₃ | H | C(=O)N(CH₃)₂ | 3-CH₃, 5-CN | 4-CF₃ |
| H | CH₃ | H | 3-Cl, 5-Cl | H |
| H | CH₃ | H | 3-Cl, 5-Cl | 4-Cl |
| H | CH₃ | H | 3-Cl, 5-Cl | 4-Br |
| H | CH₃ | H | 3-Cl, 5-Cl | 4-CF₃ |
| H | CH₃ | H | 3-Cl, 5-Cl | 4,5-Cl₂ |
| H | CH₃ | H | 3-Cl, 5-Cl | 4,5-Br₂ |
| H | CH₃ | H | 3-CH₃, 5-Cl | 4-Cl, 5-Br |
| H | CH₃ | H | 3-Br, 5-Cl | 4-Cl, 5-Br |
| H | CH₃ | H | 3-Br, 5-Br | 4-Cl, 5-Br |

TABLE 82-continued

| R¹ | R² | R³ | (R⁴)ₙ | (R¹⁴ᵃ)ₚ |
|---|---|---|---|---|
| H | CH₃ | H | 3-CH₃, 5-CN | 4-Cl, 5-Br |
| H | CH₃ | H | 3-Cl, 5-Cl | 4-Cl, 5-Br |
| H | CH₃ | H | 3-CH₃, 5-Cl | 4-Br, 5-Cl |
| H | CH₃ | H | 3-Br, 5-Cl | 4-Br, 5-Cl |
| H | CH₃ | H | 3-Br, 5-Br | 4-Br, 5-Cl |
| H | CH₃ | H | 3-CH₃, 5-CN | 4-Br, 5-Cl |
| H | CH₃ | H | 3-Cl, 5-Cl | 4-Br, 5-Cl |
| H | H | CH₃ | 3-Cl, 5-Cl | H |
| H | H | CH₃ | 3-Cl, 5-Cl | 4-Cl |
| H | H | CH₃ | 3-Cl, 5-Cl | 4-Br |
| H | H | CH₃ | 3-Cl, 5-Cl | 4-CF₃ |
| H | H | CH₃ | 3-Cl, 5-Cl | 4,5-Cl₂ |
| H | H | CH₃ | 3-Cl, 5-Cl | 4,5-Br₂ |
| H | H | CH₃ | 3-CH₃, 5-Cl | 4-Cl, 5-Br |
| H | H | CH₃ | 3-Br, 5-Cl | 4-Cl, 5-Br |
| H | H | CH₃ | 3-Br, 5-Br | 4-Cl, 5-Br |
| H | H | CH₃ | 3-CH₃, 5-CN | 4-Cl, 5-Br |
| H | H | CH₃ | 3-Cl, 5-Cl | 4-Cl, 5-Br |
| H | H | CH₃ | 3-CH₃, 5-Cl | 4-Br, 5-Cl |
| H | H | CH₃ | 3-Br, 5-Cl | 4-Br, 5-Cl |
| H | H | CH₃ | 3-Br, 5-Br | 4-Br, 5-Cl |
| H | H | CH₃ | 3-CH₃, 5-CN | 4-Br, 5-Cl |
| H | H | CH₃ | 3-Cl, 5-Cl | 4-Br, 5-Cl |
| H | CH₃ | CH₃ | 3-Cl, 5-Cl | H |
| H | CH₃ | CH₃ | 3-Cl, 5-Cl | 4-Cl |
| H | CH₃ | CH₃ | 3-Cl, 5-Cl | 4-Br |
| H | CH₃ | CH₃ | 3-Cl, 5-Cl | 4-CF₃ |
| H | CH₃ | CH₃ | 3-Cl, 5-Cl | 4,5-Cl₂ |
| H | CH₃ | CH₃ | 3-Cl, 5-Cl | 4,5-Br₂ |
| H | CH₃ | CH₃ | 3-CH₃, 5-Cl | 4-Cl, 5-Br |
| H | CH₃ | CH₃ | 3-Br, 5-Cl | 4-Cl, 5-Br |
| H | CH₃ | CH₃ | 3-Br, 5-Br | 4-Cl, 5-Br |
| H | CH₃ | CH₃ | 3-CH₃, 5-CN | 4-Cl, 5-Br |
| H | CH₃ | CH₃ | 3-Cl, 5-Cl | 4-Cl, 5-Br |
| H | CH₃ | CH₃ | 3-CH₃, 5-Cl | 4-Br, 5-Cl |
| H | CH₃ | CH₃ | 3-Br, 5-Cl | 4-Br, 5-Cl |
| H | CH₃ | CH₃ | 3-Br, 5-Br | 4-Br, 5-Cl |
| H | CH₃ | CH₃ | 3-CH₃, 5-CN | 4-Br, 5-Cl |
| H | CH₃ | CH₃ | 3-Cl, 5-Cl | 4-Br, 5-Cl |
| H | H | CH₂CH₃ | 3-Cl, 5-Cl | H |
| H | H | CH₂CH₃ | 3-Cl, 5-Cl | 4-Cl |
| H | H | CH₂CH₃ | 3-Cl, 5-Cl | 4-Br |
| H | H | CH₂CH₃ | 3-Cl, 5-Cl | 4-CF₃ |
| H | H | CH(CH₃)₂ | 3-Cl, 5-Cl | H |
| H | H | CH(CH₃)₂ | 3-Cl, 5-Cl | 4-Cl |
| H | H | CH(CH₃)₂ | 3-Cl, 5-Cl | 4-Br |
| H | H | CH(CH₃)₂ | 3-Cl, 5-Cl | 4-CF₃ |
| H | H | C(CH₃)₃ | 3-Cl, 5-Cl | H |
| H | H | C(CH₃)₃ | 3-Cl, 5-Cl | 4-Cl |
| H | H | C(CH₃)₃ | 3-Cl, 5-Cl | 4-Br |
| H | H | C(CH₃)₃ | 3-Cl, 5-Cl | 4-CF₃ |
| H | H | C(=O)OCH₃ | 3-Cl, 5-Cl | H |
| H | H | C(=O)OCH₃ | 3-Cl, 5-Cl | 4-Cl |
| H | H | C(=O)OCH₃ | 3-Cl, 5-Cl | 4-Br |
| H | H | C(=O)OCH₃ | 3-Cl, 5-Cl | 4-CF₃ |
| H | H | C(=O)N(CH₃)₂ | 3-Cl, 5-Cl | H |
| H | H | C(=O)N(CH₃)₂ | 3-Cl, 5-Cl | 4-Cl |
| H | H | C(=O)N(CH₃)₂ | 3-Cl, 5-Cl | 4-Br |
| H | H | C(=O)N(CH₃)₂ | 3-Cl, 5-Cl | 4-CF₃ |
| CH₃ | CH₃ | H | 3-Cl, 5-Cl | H |
| CH₃ | CH₃ | H | 3-Cl, 5-Cl | 4-Cl |
| CH₃ | CH₃ | H | 3-Cl, 5-Cl | 4-Br |
| CH₃ | CH₃ | H | 3-Cl, 5-Cl | 4-CF₃ |
| CH₃ | H | CH₃ | 3-Cl, 5-Cl | H |
| CH₃ | H | CH₃ | 3-Cl, 5-Cl | 4-Cl |
| CH₃ | H | CH₃ | 3-Cl, 5-Cl | 4-Br |
| CH₃ | H | CH₃ | 3-Cl, 5-Cl | 4-CF₃ |
| CH₃ | CH₃ | CH₃ | 3-Cl, 5-Cl | H |
| CH₃ | CH₃ | CH₃ | 3-Cl, 5-Cl | 4-Cl |
| CH₃ | CH₃ | CH₃ | 3-Cl, 5-Cl | 4-Br |
| CH₃ | CH₃ | CH₃ | 3-Cl, 5-Cl | 4-CF₃ |
| CH₃ | H | CH₂CH₃ | 3-Cl, 5-Cl | H |
| CH₃ | H | CH₂CH₃ | 3-Cl, 5-Cl | 4-Cl |
| CH₃ | H | CH₂CH₃ | 3-Cl, 5-Cl | 4-Br |
| CH₃ | H | CH₂CH₃ | 3-Cl, 5-Cl | 4-CF₃ |
| CH₃ | H | CH(CH₃)₂ | 3-Cl, 5-Cl | H |
| CH₃ | H | CH(CH₃)₂ | 3-Cl, 5-Cl | 4-Cl |

TABLE 82-continued

| R$^1$ | R$^2$ | R$^3$ | (R$^4$)$_n$ | (R$^{14a}$)$_p$ |
|---|---|---|---|---|
| CH$_3$ | H | CH(CH$_3$)$_2$ | 3-Cl, 5-Cl | 4-Br |
| CH$_3$ | H | CH(CH$_3$)$_2$ | 3-Cl, 5-Cl | 4-CF$_3$ |
| CH$_3$ | H | C(CH$_3$)$_3$ | 3-Cl, 5-Cl | H |
| CH$_3$ | H | C(CH$_3$)$_3$ | 3-Cl, 5-Cl | 4-Cl |
| CH$_3$ | H | C(CH$_3$)$_3$ | 3-Cl, 5-Cl | 4-Br |
| CH$_3$ | H | C(CH$_3$)$_3$ | 3-Cl, 5-Cl | 4-CF$_3$ |
| CH$_3$ | H | C(=O)OCH$_3$ | 3-Cl, 5-Cl | H |
| CH$_3$ | H | C(=O)OCH$_3$ | 3-Cl, 5-Cl | 4-Cl |
| CH$_3$ | H | C(=O)OCH$_3$ | 3-Cl, 5-Cl | 4-Br |
| CH$_3$ | H | C(=O)OCH$_3$ | 3-Cl, 5-Cl | 4-CF$_3$ |
| CH$_3$ | H | C(=O)N(CH$_3$)$_2$ | 3-Cl, 5-Cl | H |
| CH$_3$ | H | C(=O)N(CH$_3$)$_2$ | 3-Cl, 5-Cl | 4-Cl |
| CH$_3$ | H | C(=O)N(CH$_3$)$_2$ | 3-Cl, 5-Cl | 4-Br |
| CH$_3$ | H | C(=O)N(CH$_3$)$_2$ | 3-Cl, 5-Cl | 4-CF$_3$ |

A compound represented by the formula (1-I):

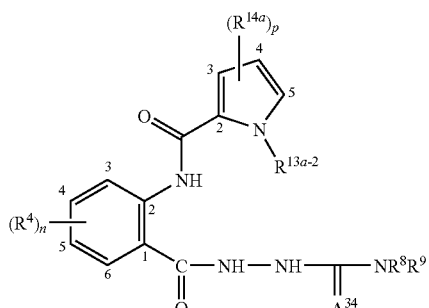

(1-I)

wherein NR$^8$R$^9$, A$^{34}$, (R$^4$)$_n$, R$^{13-2}$ and (R$^{14a}$)$_p$ represent combinations shown in Table 83.

TABLE 83

| NR$^8$R$^9$ | A$^{34}$ | (R$^4$)$_n$ | R$^{13a-2}$ | (R$^{14a}$)$_p$ |
|---|---|---|---|---|
| N(CH$_3$)$_2$ | O | 3-CH$_3$, 5-Cl | 3-chloro-2-pyridinyl | H |
| N(CH$_3$)$_2$ | O | 3-Br, 5-Cl | 3-chloro-2-pyridinyl | H |
| N(CH$_3$)$_2$ | O | 3-Br, 5-Br | 3-chloro-2-pyridinyl | H |
| N(CH$_3$)$_2$ | O | 3-CH$_3$, 5-CN | 3-chloro-2-pyridinyl | H |
| N(CH$_3$)$_2$ | O | 3-CH$_3$, 5-Cl | 3-chloro-2-pyridinyl | 4-Cl |
| N(CH$_3$)$_2$ | O | 3-Br, 5-Cl | 3-chloro-2-pyridinyl | 4-Cl |
| N(CH$_3$)$_2$ | O | 3-Br, 5-Br | 3-chloro-2-pyridinyl | 4-Cl |
| N(CH$_3$)$_2$ | O | 3-CH$_3$, 5-CN | 3-chloro-2-pyridinyl | 4-Cl |
| N(CH$_3$)$_2$ | O | 3-CH$_3$, 5-Cl | 3-chloro-2-pyridinyl | 4-Br |
| N(CH$_3$)$_2$ | O | 3-Br, 5-Cl | 3-chloro-2-pyridinyl | 4-Br |
| N(CH$_3$)$_2$ | O | 3-Br, 5-Br | 3-chloro-2-pyridinyl | 4-Br |
| N(CH$_3$)$_2$ | O | 3-CH$_3$, 5-CN | 3-chloro-2-pyridinyl | 4-Br |
| N(CH$_3$)$_2$ | O | 3-CH$_3$, 5-Cl | 3-chloro-2-pyridinyl | 4-CF$_3$ |
| N(CH$_3$)$_2$ | O | 3-Br, 5-Cl | 3-chloro-2-pyridinyl | 4-CF$_3$ |
| N(CH$_3$)$_2$ | O | 3-Br, 5-Br | 3-chloro-2-pyridinyl | 4-CF$_3$ |
| N(CH$_3$)$_2$ | O | 3-CH$_3$, 5-CN | 3-chloro-2-pyridinyl | 4-CF$_3$ |

A compound represented by the formula (1-K):

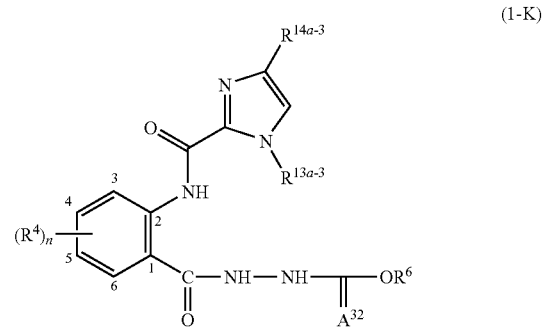

(1-K)

wherein R$^6$, A$^{32}$, (R$^4$)$_n$, R$^{13a-3}$ and R$^{14a-3}$ represent combinations shown in Table 84.

TABLE 84

| R$^6$ | A$^{32}$ | (R$^4$)$_n$ | R$^{13a-3}$ | R$^{14a-3}$ |
|---|---|---|---|---|
| CH$_3$ | O | 3-CH$_3$, 5-Cl | 3-chloro-2-pyridinyl | H |
| CH$_3$ | O | 3-Br, 5-Cl | 3-chloro-2-pyridinyl | H |
| CH$_3$ | O | 3-Br, 5-Br | 3-chloro-2-pyridinyl | H |
| CH$_3$ | O | 3-CH$_3$, 5-CN | 3-chloro-2-pyridinyl | H |
| CH$_3$ | O | 3-CH$_3$, 5-Cl | 3-chloro-2-pyridinyl | Cl |
| CH$_3$ | O | 3-Br, 5-Cl | 3-chloro-2-pyridinyl | Cl |
| CH$_3$ | O | 3-Br, 5-Br | 3-chloro-2-pyridinyl | Cl |
| CH$_3$ | O | 3-CH$_3$, 5-CN | 3-chloro-2-pyridinyl | Cl |
| CH$_3$ | O | 3-CH$_3$, 5-Cl | 3-chloro-2-pyridinyl | Br |
| CH$_3$ | O | 3-Br, 5-Cl | 3-chloro-2-pyridinyl | Br |
| CH$_3$ | O | 3-Br, 5-Br | 3-chloro-2-pyridinyl | Br |
| CH$_3$ | O | 3-CH$_3$, 5-CN | 3-chloro-2-pyridinyl | Br |
| CH$_3$ | O | 3-CH$_3$, 5-Cl | 3-chloro-2-pyridinyl | CF$_3$ |
| CH$_3$ | O | 3-Br, 5-Cl | 3-chloro-2-pyridinyl | CF$_3$ |
| CH$_3$ | O | 3-Br, 5-Br | 3-chloro-2-pyridinyl | CF$_3$ |
| CH$_3$ | O | 3-CH$_3$, 5-CN | 3-chloro-2-pyridinyl | CF$_3$ |
| CH$_2$CH$_3$ | O | 3-CH$_3$, 5-Cl | 3-chloro-2-pyridinyl | H |
| CH$_2$CH$_3$ | O | 3-Br, 5-Cl | 3-chloro-2-pyridinyl | H |
| CH$_2$CH$_3$ | O | 3-Br, 5-Br | 3-chloro-2-pyridinyl | H |
| CH$_2$CH$_3$ | O | 3-CH$_3$, 5-CN | 3-chloro-2-pyridinyl | H |
| CH$_2$CH$_3$ | O | 3-CH$_3$, 5-Cl | 3-chloro-2-pyridinyl | Cl |
| CH$_2$CH$_3$ | O | 3-Br, 5-Cl | 3-chloro-2-pyridinyl | Cl |
| CH$_2$CH$_3$ | O | 3-Br, 5-Br | 3-chloro-2-pyridinyl | Cl |
| CH$_2$CH$_3$ | O | 3-CH$_3$, 5-CN | 3-chloro-2-pyridinyl | Cl |
| CH$_2$CH$_3$ | O | 3-CH$_3$, 5-Cl | 3-chloro-2-pyridinyl | Br |
| CH$_2$CH$_3$ | O | 3-Br, 5-Cl | 3-chloro-2-pyridinyl | Br |
| CH$_2$CH$_3$ | O | 3-Br, 5-Br | 3-chloro-2-pyridinyl | Br |
| CH$_2$CH$_3$ | O | 3-CH$_3$, 5-CN | 3-chloro-2-pyridinyl | Br |
| CH$_2$CH$_3$ | O | 3-CH$_3$, 5-Cl | 3-chloro-2-pyridinyl | CF$_3$ |
| CH$_2$CH$_3$ | O | 3-Br, 5-Cl | 3-chloro-2-pyridinyl | CF$_3$ |
| CH$_2$CH$_3$ | O | 3-Br, 5-Br | 3-chloro-2-pyridinyl | CF$_3$ |
| CH$_2$CH$_3$ | O | 3-CH$_3$, 5-CN | 3-chloro-2-pyridinyl | CF$_3$ |

A compound represented by the formula (1-N):

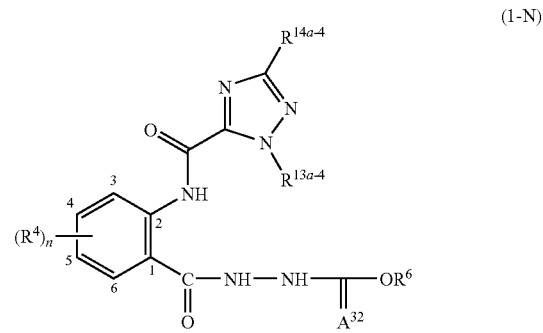

(1-N)

wherein R$^6$, A$^{32}$, (R$^4$)$_n$, R$^{13a-4}$ and R$^{14a-4}$ represent combinations shown in Table 85.

TABLE 85

| $R^6$ | $A^{32}$ | $(R^4)_n$ | $R^{13a-4}$ | $R^{14a-4}$ |
|---|---|---|---|---|
| $CH_3$ | O | 3-$CH_3$, 5-Cl | 3-chloro-2-pyridinyl | H |
| $CH_3$ | O | 3-Br, 5-Cl | 3-chloro-2-pyridinyl | H |
| $CH_3$ | O | 3-Br, 5-Br | 3-chloro-2-pyridinyl | H |
| $CH_3$ | O | 3-$CH_3$, 5-CN | 3-chloro-2-pyridinyl | H |
| $CH_3$ | O | 3-$CH_3$, 5-Cl | 3-chloro-2-pyridinyl | Cl |
| $CH_3$ | O | 3-Br, 5-Cl | 3-chloro-2-pyridinyl | Cl |
| $CH_3$ | O | 3-Br, 5-Br | 3-chloro-2-pyridinyl | Cl |
| $CH_3$ | O | 3-$CH_3$, 5-CN | 3-chloro-2-pyridinyl | Cl |
| $CH_3$ | O | 3-$CH_3$, 5-Cl | 3-chloro-2-pyridinyl | Br |
| $CH_3$ | O | 3-Br, 5-Cl | 3-chloro-2-pyridinyl | Br |
| $CH_3$ | O | 3-Br, 5-Br | 3-chloro-2-pyridinyl | Br |
| $CH_3$ | O | 3-$CH_3$, 5-CN | 3-chloro-2-pyridinyl | Br |
| $CH_3$ | O | 3-$CH_3$, 5-Cl | 3-chloro-2-pyridinyl | $CF_3$ |
| $CH_3$ | O | 3-Br, 5-Cl | 3-chloro-2-pyridinyl | $CF_3$ |
| $CH_3$ | O | 3-Br, 5-Br | 3-chloro-2-pyridinyl | $CF_3$ |
| $CH_3$ | O | 3-$CH_3$, 5-CN | 3-chloro-2-pyridinyl | $CF_3$ |
| $CH_2CH_3$ | O | 3-$CH_3$, 5-Cl | 3-chloro-2-pyridinyl | H |
| $CH_2CH_3$ | O | 3-Br, 5-Cl | 3-chloro-2-pyridinyl | H |
| $CH_2CH_3$ | O | 3-Br, 5-Br | 3-chloro-2-pyridinyl | H |
| $CH_2CH_3$ | O | 3-$CH_3$, 5-CN | 3-chloro-2-pyridinyl | H |
| $CH_2CH_3$ | O | 3-$CH_3$, 5-Cl | 3-chloro-2-pyridinyl | Cl |
| $CH_2CH_3$ | O | 3-Br, 5-Cl | 3-chloro-2-pyridinyl | Cl |
| $CH_2CH_3$ | O | 3-Br, 5-Br | 3-chloro-2-pyridinyl | Cl |
| $CH_2CH_3$ | O | 3-$CH_3$, 5-CN | 3-chloro-2-pyridinyl | Cl |
| $CH_2CH_3$ | O | 3-$CH_3$, 5-Cl | 3-chloro-2-pyridinyl | Br |
| $CH_2CH_3$ | O | 3-Br, 5-Cl | 3-chloro-2-pyridinyl | Br |
| $CH_2CH_3$ | O | 3-Br, 5-Br | 3-chloro-2-pyridinyl | Br |
| $CH_2CH_3$ | O | 3-$CH_3$, 5-CN | 3-chloro-2-pyridinyl | Br |
| $CH_2CH_3$ | O | 3-$CH_3$, 5-Cl | 3-chloro-2-pyridinyl | $CF_3$ |
| $CH_2CH_3$ | O | 3-Br, 5-Cl | 3-chloro-2-pyridinyl | $CF_3$ |
| $CH_2CH_3$ | O | 3-Br, 5-Br | 3-chloro-2-pyridinyl | $CF_3$ |
| $CH_2CH_3$ | O | 3-$CH_3$, 5-CN | 3-chloro-2-pyridinyl | $CF_3$ |

A compound represented by the formula (1-Q):

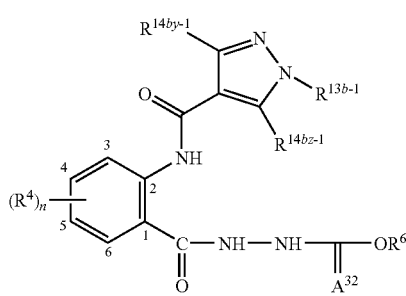

(1-Q)

wherein $R^6$, $A^{32}$, $(R^4)_n$, $R^{13b-1}$, $R^{14bz-1}$ and $R^{14by-1}$ represent combinations shown in Table 86 to Table 89.

TABLE 86

| $R^6$ | $A^{32}$ | $(R^4)_n$ | $R^{14bz-1}$ | $R^{14by-1}$ | $R^{13b-1}$ |
|---|---|---|---|---|---|
| $CH_3$ | O | 3-$CH_3$, 5-Cl | 2-chlorophenyl | H | $CH_3$ |
| $CH_3$ | O | 3-Br, 5-Cl | 2-chlorophenyl | H | $CH_3$ |
| $CH_3$ | O | 3-Br, 5-Br | 2-chlorophenyl | H | $CH_3$ |
| $CH_3$ | O | 3-$CH_3$, 5-CN | 2-chlorophenyl | H | $CH_3$ |
| $CH_3$ | O | 3-$CH_3$, 5-Cl | 3-chloro-2-pyridinyl | H | $CH_3$ |
| $CH_3$ | O | 3-Br, 5-Cl | 3-chloro-2-pyridinyl | H | $CH_3$ |
| $CH_3$ | O | 3-Br, 5-Br | 3-chloro-2-pyridinyl | H | $CH_3$ |
| $CH_3$ | O | 3-$CH_3$, 5-CN | 3-chloro-2-pyridinyl | H | $CH_3$ |
| $CH_3$ | O | 3-$CH_3$, 5-Cl | H | 2-chlorophenyl | $CH_3$ |
| $CH_3$ | O | 3-Br, 5-Cl | H | 2-chlorophenyl | $CH_3$ |
| $CH_3$ | O | 3-Br, 5-Br | H | 2-chlorophenyl | $CH_3$ |
| $CH_3$ | O | 3-$CH_3$, 5-CN | H | 2-chlorophenyl | $CH_3$ |
| $CH_3$ | O | 3-$CH_3$, 5-Cl | H | 3-chloro-2-pyridinyl | $CH_3$ |
| $CH_3$ | O | 3-Br, 5-Cl | H | 3-chloro-2-l pyridiny | $CH_3$ |
| $CH_3$ | O | 3-Br, 5-Br | H | 3-chloro-2-pyridinyl | $CH_3$ |
| $CH_3$ | O | 3-$CH_3$, 5-CN | H | 3-chloro-2-pyridinyl | $CH_3$ |
| $CH_3$ | O | 3-$CH_3$, 5-Cl | 2-chlorophenyl | H | $C(CH_3)_3$ |
| $CH_3$ | O | 3-Br, 5-Cl | 2-chlorophenyl | H | $C(CH_3)_3$ |
| $CH_3$ | O | 3-Br, 5-Br | 2-chlorophenyl | H | $C(CH_3)_3$ |
| $CH_3$ | O | 3-$CH_3$, 5-CN | 2-chlorophenyl | H | $C(CH_3)_3$ |
| $CH_3$ | O | 3-$CH_3$, 5-Cl | 3-chloro-2-pyridinyl | H | $C(CH_3)_3$ |
| $CH_3$ | O | 3-Br, 5-Cl | 3-chloro-2-pyridinyl | H | $C(CH_3)_3$ |
| $CH_3$ | O | 3-Br, 5-Br | 3-chloro-2-pyridinyl | H | $C(CH_3)_3$ |
| $CH_3$ | O | 3-$CH_3$, 5-CN | 3-chloro-2-pyridinyl | H | $C(CH_3)_3$ |
| $CH_3$ | O | 3-$CH_3$, 5-Cl | H | 2-chlorophenyl | $C(CH_3)_3$ |
| $CH_3$ | O | 3-Br, 5-Cl | H | 2-chlorophenyl | $C(CH_3)_3$ |
| $CH_3$ | O | 3-Br, 5-Br | H | 2-chlorophenyl | $C(CH_3)_3$ |
| $CH_3$ | O | 3-$CH_3$, 5-CN | H | 2-chlorophenyl | $C(CH_3)_3$ |
| $CH_3$ | O | 3-$CH_3$, 5-Cl | H | 3-chloro-2-pyridinyl | $C(CH_3)_3$ |
| $CH_3$ | O | 3-Br, 5-Cl | H | 3-chloro-2-pyridinyl | $C(CH_3)_3$ |
| $CH_3$ | O | 3-Br, 5-Br | H | 3-chloro-2-pyridinyl | $C(CH_3)_3$ |
| $CH_3$ | O | 3-$CH_3$, 5-CN | H | 3-chloro-2-pyridinyl | $C(CH_3)_3$ |

TABLE 87

| $R^6$ | $A^{32}$ | $(R^4)_n$ | $R^{14bz-1}$ | $R^{14by-1}$ | $R^{13b-1}$ |
|---|---|---|---|---|---|
| $CH_3$ | O | 3-$CH_3$, 5-Cl | 2-chlorophenyl | H | $CH_2CF_3$ |
| $CH_3$ | O | 3-Br, 5-Cl | 2-chlorophenyl | H | $CH_2CF_3$ |
| $CH_3$ | O | 3-Br, 5-Br | 2-chlorophenyl | H | $CH_2CF_3$ |
| $CH_3$ | O | 3-$CH_3$, 5-CN | 2-chlorophenyl | H | $CH_2CF_3$ |
| $CH_3$ | O | 3-$CH_3$, 5-Cl | 3-chloro-2-pyridinyl | H | $CH_2CF_3$ |
| $CH_3$ | O | 3-Br, 5-Cl | 3-chloro-2-pyridinyl | H | $CH_2CF_3$ |
| $CH_3$ | O | 3-Br, 5-Br | 3-chloro-2-pyridinyl | H | $CH_2CF_3$ |
| $CH_3$ | O | 3-$CH_3$, 5-CN | 3-chloro-2-pyridinyl | H | $CH_2CF_3$ |
| $CH_3$ | O | 3-$CH_3$, 5-Cl | H | 2-chlorophenyl | $CH_2CF_3$ |
| $CH_3$ | O | 3-Br, 5-Cl | H | 2-chlorophenyl | $CH_2CF_3$ |
| $CH_3$ | O | 3-Br, 5-Br | H | 2-chlorophenyl | $CH_2CF_3$ |
| $CH_3$ | O | 3-$CH_3$, 5-CN | H | 2-chlorophenyl | $CH_2CF_3$ |
| $CH_3$ | O | 3-$CH_3$, 5-Cl | H | 3-chloro-2-pyridinyl | $CH_2CF_3$ |
| $CH_3$ | O | 3-Br, 5-Cl | H | 3-chloro-2-pyridinyl | $CH_2CF_3$ |
| $CH_3$ | O | 3-Br, 5-Br | H | 3-chloro-2-pyridinyl | $CH_2CF_3$ |
| $CH_3$ | O | 3-$CH_3$, 5-CN | H | 3-chloro-2-pyridinyl | $CH_2CF_3$ |
| $CH_2CH_3$ | O | 3-$CH_3$, 5-Cl | 2-chlorophenyl | H | $CH_3$ |
| $CH_2CH_3$ | O | 3-Br, 5-Cl | 2-chlorophenyl | H | $CH_3$ |
| $CH_2CH_3$ | O | 3-Br, 5-Br | 2-chlorophenyl | H | $CH_3$ |

TABLE 87-continued

| $R^6$ | $A^{32}$ | $(R^4)_n$ | $R^{14bz-1}$ | $R^{14by-1}$ | $R^{13b-1}$ |
|---|---|---|---|---|---|
| $CH_2CH_3$ | O | 3-$CH_3$, 5-CN | 2-chlorophenyl | H | $CH_3$ |
| $CH_2CH_3$ | O | 3-$CH_3$, 5-Cl | 3-chloro-2-pyridinyl | H | $CH_3$ |
| $CH_2CH_3$ | O | 3-Br, 5-Cl | 3-chloro-2-pyridinyl | H | $CH_3$ |
| $CH_2CH_3$ | O | 3-Br, 5-Br | 3-chloro-2-pyridinyl | H | $CH_3$ |
| $CH_2CH_3$ | O | 3-$CH_3$, 5-CN | 3-chloro-2-pyridinyl | H | $CH_3$ |
| $CH_2CH_3$ | O | 3-$CH_3$, 5-Cl | H | 2-chlorophenyl | $CH_3$ |
| $CH_2CH_3$ | O | 3-Br, 5-Cl | H | 2-chlorophenyl | $CH_3$ |
| $CH_2CH_3$ | O | 3-Br, 5-Br | H | 2-chlorophenyl | $CH_3$ |
| $CH_2CH_3$ | O | 3-$CH_3$, 5-CN | H | 2-chlorophenyl | $CH_3$ |
| $CH_2CH_3$ | O | 3-$CH_3$, 5-Cl | H | 3-chloro-2-pyridinyl | $CH_3$ |
| $CH_2CH_3$ | O | 3-Br, 5-Cl | H | 3-chloro-2-pyridinyl | $CH_3$ |
| $CH_2CH_3$ | O | 3-Br, 5-Br | H | 3-chloro-2-pyridinyl | $CH_3$ |
| $CH_2CH_3$ | O | 3-$CH_3$, 5-CN | H | 3-chloro-2-pyridinyl | $CH_3$ |

TABLE 88

| $R^6$ | $A^{32}$ | $(R^4)_n$ | $R^{14bz-1}$ | $R^{14by-1}$ | $R^{13b-1}$ |
|---|---|---|---|---|---|
| $CH_2CH_3$ | O | 3-$CH_3$, 5-Cl | 2-chlorophenyl | H | $C(CH_3)_3$ |
| $CH_2CH_3$ | O | 3-Br, 5-Cl | 2-chlorophenyl | H | $C(CH_3)_3$ |
| $CH_2CH_3$ | O | 3-Br, 5-Br | 2-chlorophenyl | H | $C(CH_3)_3$ |
| $CH_2CH_3$ | O | 3-$CH_3$, 5-CN | 2-chlorophenyl | H | $C(CH_3)_3$ |
| $CH_2CH_3$ | O | 3-$CH_3$, 5-Cl | 3-chloro-2-pyridinyl | H | $C(CH_3)_3$ |
| $CH_2CH_3$ | O | 3-Br, 5-Cl | 3-chloro-2-pyridinyl | H | $C(CH_3)_3$ |
| $CH_2CH_3$ | O | 3-Br, 5-Br | 3-chloro-2-pyridinyl | H | $C(CH_3)_3$ |
| $CH_2CH_3$ | O | 3-$CH_3$, 5-CN | 3-chloro-2-pyridinyl | H | $C(CH_3)_3$ |
| $CH_2CH_3$ | O | 3-$CH_3$, 5-Cl | H | 2-chlorophenyl | $C(CH_3)_3$ |
| $CH_2CH_3$ | O | 3-Br, 5-Cl | H | 2-chlorophenyl | $C(CH_3)_3$ |
| $CH_2CH_3$ | O | 3-Br, 5-Br | H | 2-chlorophenyl | $C(CH_3)_3$ |
| $CH_2CH_3$ | O | 3-$CH_3$, 5-CN | H | 2-chlorophenyl | $C(CH_3)_3$ |
| $CH_2CH_3$ | O | 3-$CH_3$, 5-Cl | H | 3-chloro-2-pyridinyl | $C(CH_3)_3$ |
| $CH_2CH_3$ | O | 3-Br, 5-Cl | H | 3-chloro-2-pyridinyl | $C(CH_3)_3$ |
| $CH_2CH_3$ | O | 3-Br, 5-Br | H | 3-chloro-2-pyridinyl | $C(CH_3)_3$ |
| $CH_2CH_3$ | O | 3-$CH_3$, 5-CN | H | 3-chloro-2-pyridinyl | $C(CH_3)_3$ |
| $CH_2CH_3$ | O | 3-$CH_3$, 5-Cl | 2-chlorophenyl | H | $CH_2CF_3$ |
| $CH_2CH_3$ | O | 3-Br, 5-Cl | 2-chlorophenyl | H | $CH_2CF_3$ |
| $CH_2CH_3$ | O | 3-Br, 5-Br | 2-chlorophenyl | H | $CH_2CF_3$ |
| $CH_2CH_3$ | O | 3-$CH_3$, 5-CN | 2-chlorophenyl | H | $CH_2CF_3$ |
| $CH_2CH_3$ | O | 3-$CH_3$, 5-Cl | 3-chloro-2-pyridinyl | H | $CH_2CF_3$ |
| $CH_2CH_3$ | O | 3-Br, 5-Cl | 3-chloro-2-pyridinyl | H | $CH_2CF_3$ |
| $CH_2CH_3$ | O | 3-Br, 5-Br | 3-chloro-2-pyridinyl | H | $CH_2CF_3$ |
| $CH_2CH_3$ | O | 3-$CH_3$, 5-CN | 3-chloro-2-pyridinyl | H | $CH_2CF_3$ |
| $CH_2CH_3$ | O | 3-$CH_3$, 5-Cl | H | 2-chlorophenyl | $CH_2CF_3$ |
| $CH_2CH_3$ | O | 3-Br, 5-Cl | H | 2-chlorophenyl | $CH_2CF_3$ |
| $CH_2CH_3$ | O | 3-Br, 5-Br | H | 2-chlorophenyl | $CH_2CF_3$ |
| $CH_2CH_3$ | O | 3-$CH_3$, 5-CN | H | 2-chlorophenyl | $CH_2CF_3$ |
| $CH_2CH_3$ | O | 3-$CH_3$, 5-Cl | H | 3-chloro-2-pyridinyl | $CH_2CF_3$ |
| $CH_2CH_3$ | O | 3-Br, 5-Cl | H | 3-chloro-2-pyridinyl | $CH_2CF_3$ |
| $CH_2CH_3$ | O | 3-Br, 5-Br | H | 3-chloro-2-pyridinyl | $CH_2CF_3$ |
| $CH_2CH_3$ | O | 3-$CH_3$, 5-CN | H | 3-chloro-2-pyridinyl | $CH_2CF_3$ |

TABLE 89

| $R^6$ | $A^{32}$ | $(R^4)_n$ | $R^{14bz-1}$ | $R^{14by-1}$ | $R^{13b-1}$ |
|---|---|---|---|---|---|
| $CH_3$ | O | 3-$CH_3$, 5-Cl | 2-chlorophenyl | H | $CHF_2$ |
| $CH_3$ | O | 3-Br, 5-Cl | 2-chlorophenyl | H | $CHF_2$ |
| $CH_3$ | O | 3-Br, 5-Br | 2-chlorophenyl | H | $CHF_2$ |
| $CH_3$ | O | 3-$CH_3$, 5-CN | 2-chlorophenyl | H | $CHF_2$ |
| $CH_3$ | O | 3-$CH_3$, 5-Cl | 3-chloro-2-pyridinyl | H | $CHF_2$ |
| $CH_3$ | O | 3-Br, 5-Cl | 3-chloro-2-pyridinyl | H | $CHF_2$ |
| $CH_3$ | O | 3-Br, 5-Br | 3-chloro-2-pyridinyl | H | $CHF_2$ |
| $CH_3$ | O | 3-$CH_3$, 5-CN | 3-chloro-2-pyridinyl | H | $CHF_2$ |
| $CH_3$ | O | 3-$CH_3$, 5-Cl | H | 2-chlorophenyl | $CHF_2$ |
| $CH_3$ | O | 3-Br, 5-Cl | H | 2-chlorophenyl | $CHF_2$ |
| $CH_3$ | O | 3-Br, 5-Br | H | 2-chlorophenyl | $CHF_2$ |
| $CH_3$ | O | 3-$CH_3$, 5-CN | H | 2-chlorophenyl | $CHF_2$ |
| $CH_3$ | O | 3-$CH_3$, 5-Cl | H | 3-chloro-2-pyridinyl | $CHF_2$ |
| $CH_3$ | O | 3-Br, 5-Cl | H | 3-chloro-2-pyridinyl | $CHF_2$ |
| $CH_3$ | O | 3-Br, 5-Br | H | 3-chloro-2-pyridinyl | $CHF_2$ |

TABLE 89-continued

| $R^6$ | $A^{32}$ | $(R^4)_n$ | $R^{14bz-1}$ | $R^{14by-1}$ | $R^{13b-1}$ |
|---|---|---|---|---|---|
| $CH_3$ | O | 3-$CH_3$, 5-CN | H | 3-chloro-2-pyridinyl | $CHF_2$ |
| $CH_3$ | O | 3-$CH_3$, 5-Cl | 2-chlorophenyl | H | $CBrF_2$ |
| $CH_3$ | O | 3-Br, 5-Cl | 2-chlorophenyl | H | $CBrF_2$ |
| $CH_3$ | O | 3-Br, 5-Br | 2-chlorophenyl | H | $CBrF_2$ |
| $CH_3$ | O | 3-$CH_3$, 5-CN | 2-chlorophenyl | H | $CBrF_2$ |
| $CH_3$ | O | 3-$CH_3$, 5-Cl | 3-chloro-2-pyridinyl | H | $CBrF_2$ |
| $CH_3$ | O | 3-Br, 5-Cl | 3-chloro-2-pyridinyl | H | $CBrF_2$ |
| $CH_3$ | O | 3-Br, 5-Br | 3-chloro-2-pyridinyl | H | $CBrF_2$ |
| $CH_3$ | O | 3-$CH_3$, 5-CN | 3-chloro-2-pyridinyl | H | $CBrF_2$ |
| $CH_3$ | O | 3-$CH_3$, 5-Cl | H | 2-chlorophenyl | $CBrF_2$ |
| $CH_3$ | O | 3-Br, 5-Cl | H | 2-chlorophenyl | $CBrF_2$ |
| $CH_3$ | O | 3-Br, 5-Br | H | 2-chlorophenyl | $CBrF_2$ |
| $CH_3$ | O | 3-$CH_3$, 5-CN | H | 2-chlorophenyl | $CBrF_2$ |
| $CH_3$ | O | 3-$CH_3$, 5-Cl | H | 3-chloro-2-pyridinyl | $CBrF_2$ |
| $CH_3$ | O | 3-Br, 5-Cl | H | 3-chloro-2-pyridinyl | $CBrF_2$ |
| $CH_3$ | O | 3-Br, 5-Br | H | 3-chloro-2-pyridinyl | $CBrF_2$ |
| $CH_3$ | O | 3-$CH_3$, 5-CN | H | 3-chloro-2-pyridinyl | $CBrF_2$ |

Examples of the pests against which the present compound has controlling efficacy include harmful arthropods such as harmful insects and harmful mites, and nemathelminths such as nematodes, and specific examples are as shown below.

Hemiptera:—

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Myzus persicae*), cabbage aphid (*Brevicoryne brassicae*), spiraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*) bean bug (*Riptortus clavetus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), silver leaf whitefly (*Bemisia argentifolii*), citrus whitefly (*Dialeurodes citri*), and citrus spiny white fly (*Aleurocanthus spiniferus*); scales (Coccidae) such as Calfomia red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinis*), and white peach scale (*Pseudaulacaspis pentagona*); lace bags (Tingidae); psyllids (Psyllidae); etc.

Lepidoptera:—

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; whites and sulfer butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), *Adoxophyes* sp., oriental tea tortrix (*Homona magnanima*), apple tortrix (*Archips fuscocupreanus*), and *Cydia pomonella*; leafblotch miners (Gracillariidae) such as tea leafroller (*Caloptilia theivora*), and apple leafminer (*Phyllonorycter ringoneella*); Carposinidae such as peach fruit moth (*Carposina niponensis*); lyonetiid moths (Lyonetiidae) such as *Lyonetia* spp.; tussock moths (Lymantriidae) such as *Lyymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*); etc.

Thysanoptera:—

Thrips (Thripidae) such as yellow citrus thrips (*Frankliniella occidentalis*), *Thrips parmi*, yellow tea thrips (*Scirtothrips dorsalis*), onion thrip (*Thrips tabaci*), flower thrips (*Frankliniella intonsa*), etc.

Diptera:—

Housefly (*Musca domestica*), common mosquito (*Culex popiens pallens*), horsefly (*Tabanus trigonus*), onion maggot (*Hylemya antiqua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), *Ceratitis capitata*, legume leafminer (*Liriomyza trifolii*), tomato leafminer (*Liriomyza sativae*), garden pea leafminer (*Chromatomyia horticola*), etc.

Coleoptera:—

Twenty-eight-spotted ladybird (*Epilachna vigintioctopunctata*), cucurbit leaf beetle (*Aulacophora femoralis*), striped flea beetle (*Phyllotreta striolata*), rice leaf beetle (*Oulema oryzae*), rice curculio (*Echinocnemus squameus*), rice water weevil (*Lissorhoptrus oryzophilus*), *Anthonomus grandis*, azuki bean weevil (*Callosobruchus chinensis*), *Sphenophorus venatus*, Japanese beetle (*Popillia japonica*), cupreous chafer (*Anomala cuprea*), corn root worm (*Diabrotica* spp.), Colorado beetle (*Leptinotarsa decemlineata*), click beetle (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), pine shoot beetle (*Tomicus piniperda*), etc.

Orthoptera:—

Asiatic locust (*Locusta migratoria*), African mole cricket (*Gryllotalpa africana*), rice grasshopper (*Oxya yezoensis*), rice grasshopper (*Oxya japonica*), etc.

Hymenoptera:—

Cabbage sawfly (*Athalia rosae*), *Acromyrmex* spp., fire ant (*Solenopsis* spp.), etc.

Nematodes:—

Rice white-tip nematode (*Aphelenchoides besseyi*), strawberry bud nematode (*Nothotylenchus acris*), southern root-knot nematode (*Meloidogyne incognita*), northern root-knot nematode (*Meloidogyne hapla*), Javanese root-knot nematode (*Meloidogyne javanica*), soybean cyst nematode (*Heterodera glycines*), potato cyst nematode (*Globodera rostochiensis*), coffee root-lesion nematode (*Pratylenchus coffeae*), California root-lesion nematode (*Pratylenchus neglectus*), etc.

Dictyoptera:—

German cockroach (*Blattella germanica*), smokybrown cockroach (*Periplaneta fuliginosa*), American cockroach (*Periplaneta americana*), *Periplaneta brunnea*, oriental cockroach (*Blatta orientalis*), etc.

Acarina:—

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), pink citrus rust mite (*Phyllocoptruta citri*), tomato rust mite (*Aculops lycopersici*), purple tea mite (*Calacarus carinatus*), pink tea rust mite (*Acaphylla theavagran*), and *Eriophyes chibaensis*; tarosonemid mites (Tarsonemidae) such as broad mite (*Polyphagotarsonemus latus*); false spider mites (Tenuipalpidae) such as *Brevipalpus phoenicis*; Tuckerellidae; ticks (Ixodidae) such as *Haemaphysalis longicornis*, *Haemaphysalis flava*, *Dermacentor taiwanicus*, *Ixodes ovatus*, *Ixodes persulcatus*, *Boophilus microplus*, and *Rhipicephalus sanguineus*; acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides ptrenyssnus*; cheyletide mites (Cheyletidae) such as *Cheyletus eruditus*, *Cheyletus malaccensis*, and *Cheyletus moorei*; parasitoid mites (Dermanyssidae); etc.

The pesticide of the present invention may be the present compound itself but, usually, the present compound is mixed with an inert carrier such as a solid carrier, a liquid carrier, a gaseous carrier and the like and, if necessary, a surfactant, and other preparation additives are added to formulate into a composition or a preparation such as an emulsion, oil, powder, granules, a wettable preparation, a flowable preparation, microcapsules, an aerosol, a fumigant, poison bait, a resin preparation or the like. These compositions or preparations usually contain 0.01 to 95% by weight of the present compound.

Examples of the solid carrier to be used include fine powders and granules such as clays (kaolin clay, diatomaceous earth, bentonite, fubasami clay, acid clay, etc.), synthetic hydrous silicon oxide, talc, ceramic, other inorganic minerals (sericite, quartz, sulfur, active carbon, calcium carbonate, hydrated silica, etc.), chemical fertilizers (ammonium sulfate, ammonium phosphate, ammonium nitrate, urea, ammonium chloride, etc.) and the like.

Examples of the liquid carrier include water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, gas oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxyl-3-methyl-1-butanol, etc.), acid amides (N,N-dimethylformamide, N,N-dimethylacetamide, etc.), halogenated hydrocarbons (dichloromethane, trichloroethane, carbon tetrachloride, etc.), sulfoxides (dimethyl sulfoxide, etc.), carbonic propylene and vegetable oils (soybean oil, cottonseed oil, etc.).

Examples of the gaseous carrier include fluorocarbon, butane gas, LPG (liquefied petroleum gas), dimethyl ether, and carbonic acid gas.

Examples of the surfactant include nonionic surfactants such as polyoxyethylene alkyl ether, polyoxyethylene alkyl aryl ether, polyethylene glycol fatty acid ester, and the like, and anionic surfactants such as alkyl sulfonate salts, alkylbenzene sulfonate salts and alkyl sulfate salts.

Examples of other preparation additives include binders, dispersing agents, coloring agents and stabilizers, specifically, casein, gelatin, sugars (starch, gum arabic, cellulose derivatives, alginic acid, etc.), lignin derivatives, bentonite, synthetic water-soluble polymers (polyvinyl alcohol, polyvinylpyrrolidone, polyacrylic acids, etc.), PAP (acidic isopropyl phosphate), BHT (2,6-di-tert-butyl-4-methylphenol), and BHA (a mixture of 2-tert-butyl-4-methoxyphenol and 3-tert-butyl-4-methoxyphenol).

The method of controlling a pest of the present invention is usually performed by applying the pesticide of the present invention directly to a pest or to a place where a pest inhabits (plant, soil, in house, animal, etc.).

When the pesticide of the present invention is used for controlling a pest in the agricultural field, an amount to be applied is usually 1 to 10,000 g per 10,000 $m^2$ in terms of the amount of the present compound. When the pesticide of the present invention is formulated into an emulsion, a wettable preparation, a flowable preparation or the like, usually, the agent is applied by diluting with water so that the active ingredient concentration becomes 0.01 to 10,000 ppm, and granules, powder or the like are usually applied as they are.

These preparations, or preparations diluted with water may be directly applied to a pest or to a plant such as a crop to be protected against a pest, or may be applied to soil of a cultivated land in order to control a pest inhabiting in the soil.

Alternatively, treatment may be performed for example, by winding a sheet-like or string-like-processed resin preparation on a crop, surrounding a crop with the resin preparation, or laying the resin preparation on soil about roots of a crop.

When the pesticide of the present invention is used for controlling a pest which inhabits in a house (e.g. fly, mosquito, cockroach, etc.), the amount to be applied is usually 0.01 to 1000 mg per 1 $m^2$ of treating area in terms of the amount of the present compound in case of surface treatment, and is usually 0.01 to 500 mg per 1 $m^3$ of treating space in terms of the amount of the present of compound in case of spatial treatment. When the pesticide of the present invention is formulated into an emulsion, a wettable preparation, a flowable preparation or the like, usually, the agent is applied by diluting with water so that the active ingredient concentration becomes 0.1 to 1000 ppm, and oil, an aerosol, a fumigant, poison bait or the like is applied as it is.

The pesticide of the present invention may contain other harmful arthropod controlling agents, acaricides, nematicides, fungicides, herbicides, plant growth regulators, synergists, fertilizers, soil conditioners, animal feeds, and the like.

As the active ingredients of the aforementioned other harmful arthropod controlling agents, acaricides and/or nematicides, for example, the following compounds can be mentioned.

(1) Organic Phosphorus Compounds

Acephate, aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropyl ether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, hydrogen phosphide, isofenphos, isoxathion, malathion, mesulfenfos, methidathion: DMTP, monocrotophos, naled: BRP, oxydeprofos:ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon:DEP, vamidothion, and the like.

(2) Carbamate Compounds

Alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and the like.

(3) Synthetic Pyrethroid Compounds

Acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, 2,3,5,6-tetrafluoro-4-(methoxymethyl)benzyl (EZ)-(1RS, 3RS; 1RS,3SR)-2,2-dimethyl-3-prop-1-enylcyclopropanecarboxylate, 2,3,5,6-tetrafluoro-4-methylbenzyl (EZ)-(1RS,3RS; 1RS,3SR)-2,2-dimethyl-3-prop-1-enylcyclopropanecarboxylate, 2,3,5,6-tetrafluoro-4-(methoxymethyl)benzyl (1RS,3RS;1RS,3SR)-2,2-dimethyl-3-(2-methyl-1-propenyl)cyclopropanecarboxylate, and the like.

(4) Nereistoxin Compounds

Cartap, bensultap, thiocyclam, monosultap, bisultap, and the like.

(5) Neonicotinoid Compounds

Imidacloprid, nitenpyram, acetamiprid, thiamethoxam, thiacloprid, dinotefuran, clothianidin, and the like.

(6) Benzoylurea Compounds

Chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, and the like.

(7) Phenylpyrazole Compounds

Acetoprole, ethiprole, fipronil, vaniliprole, pyriprole, pyrafluprole, and the like.

(8) Bt Toxin Insecticides

Viable endospores derived from *Bacillus thuringiensis* and crystalline toxins produced by it, as well as a mixture of thereof.

(9) Hydrazine Compounds

Chromafenozide, halofenozide, methoxyfenozide, tebufenozide, and the like.

(10) Organic Chlorine Compounds

Aldrin, dieldrin, dienochlor, endosulfan, methoxychlor, and the like.

(11) Natural Insecticides

Machine oil, nicotine-sulfate, and the like.

(12) Other Insecticides

Avermectin-B, bromopropylate, buprofezin, chlorphenapyr, cyromazine, 1,3-Dichloropropene, emamectin-benzoate, fenazaquin, flupyrazofos, hydroprene, indoxacarb, metoxadiazone, milbemycin-A, pymetrozine, pyridalyl, pyriproxyfen, spinosad, sulfluramid, tolfenpyrad, triazamate, flubendiamide, SI-0009, cyflumetofen, arsenic acid, benclothiaz, calcium cyanamide, calcium polysulfide, chlordane, DDT, DSP, flufenerim, flonicamid, flurimfen, formetanate, metam-ammonium, metam-sodium, Methyl bromide, nidinotefuran, Potassium oleate, protrifenbute, spiromesifen, sulfur, metaflumizone, spirotetramat, and the like.

Acaricides

Acequinocyl, amitraz, benzoximate, bromopropylate, chinomethionat, chlorobenzilate, CPCBS(chlorfenson), clofentezine, Kelthane(dicofol), etoxazole, fenbutatinoxide, fenothiocarb, fenpyroximate, fluacrypyrim, fluproxyfen, hexythiazox, propargite:BPPS, polynactins, pyridaben, Pyrimidifen, tebufenpyrad, tetradifon, spirodiclofen, amidoflumet, Bifenazate, Cyflumetofen, and the like. Nematicides (nematicidal active ingredients)

DCIP, fosthiazate, levamisol, methylsothiocyanate, morantel tartarate, and the like.

The present invention will be explained in more detail below by way of Preparation Examples, Formulation Examples, Test Examples, but the present invention is not limited to these Examples.

First, Preparation Examples of the present compound will be explained.

PREPARATION EXAMPLE 1

A mixture of 0.22 g of N-(2-aminobenzoyl)-N'-ethoxycarbonylhydrazine, 0.31 g of 1-(3-chloro-2-pyridinyl)-3-trifluoromethyl-1H-pyrazole-5-carbonyl chloride and 10 ml of pyridine was stirred at room temperature for 2 hours. Water was poured into the reaction mixture, and a deposited precipitate was collected by filtration to obtain 0.13 g of the present compound (1) of the formula:

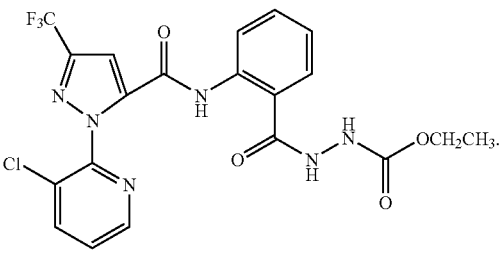

The present compound (1)

$^1$H-NMR (CDCl$_3$, TMS) δ (ppm): 1.35 (3H, t, J=8 Hz), 4.29 (2H, q, J=8 Hz), 6.85 (1H, brs), 7.10 (1H, t, J=8 Hz), 7.24 (1H, s), 7.44 (1H, t, J=8 Hz), 7.47 (1H, dd, J=8 Hz, 4 Hz), 7.62 (1H, d, J=8 Hz), 7.93 (1H, d, J=4 Hz), 8.42 (1H, brs), 8.46 (1H, d, J=8 Hz), 8.52 (1H, d, J=8 Hz), 11.86 (1H, brs)

PREPARATION EXAMPLE 2

A mixture of 0.13 g of 1-methyl-1H-pyrrole-2-carboxylic acid, 0.15 g of thionyl chloride and 5 ml of hexane was heated under reflux for 2 hours. The reaction mixture was concentrated under reduced pressure to obtain 0.14 g of 1-methyl- 1H-pyrrole-2-carbonyl chloride. To a mixture of 0.22 g of N-(2-aminobenzoyl)-N'-ethoxycarbonylhydrazine and 10 ml of pyridine was added 0.14 g of the resulting 1-methyl-1H-pyrrole-2-carbonyl chloride, and the mixture was stirred at room temperature for 2 hours. Water was poured into the reaction mixture, and a deposited precipitate was collected by filtration to obtain 0.11 g of the present compound (2) of the formula:

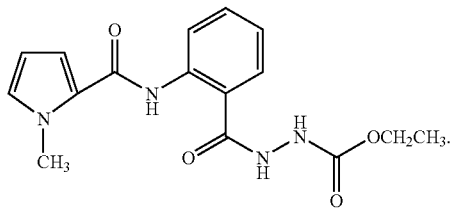

(2)

The present compound (2)
$^1$H-NMR (DMSO-d$_6$, TMS) δ (ppm): 1.02-1.28 (3H, m), 3.91 (3H, s), 4.00-4.16 (2H, m), 6.13 (1H, d, J=4 Hz), 6.78 (1H, d, J=4 Hz), 7.06 (1H, m), 7.15 (1H, t, J=8 Hz), 7.56 (1H, t, J=8 Hz), 7.79 (1H, d, J=8 Hz), 8.57 (1H, d, J=8 Hz), 9.30 (1H, brs), 10.57 (1H, brs), 11.63 (1H, brs)

PREPARATION EXAMPLE 3

A mixture of 0.19 g of 1-methyl-3-trifluoromethyl-1H-pyrazole-5-carboxylic acid, 0.15 g of thionyl chloride and 5 ml of hexane was heated under reflux for 2 hours. The reaction mixture was concentrated under reduced pressure to obtain 0.14 g of 1-methyl-3-trifluoromethyl-1H-pyrazole-5-carbonyl chloride. To a mixture of 0.22 g of N-(2-aminobenzoyl)-N'-ethoxycarbonylhydrazine and 10 ml of pyridine was added 0.14 g of the resulting 1-methyl-3-trifluoromethyl-1H-pyrazole-5-carbonyl chloride and the mixture was stirred at room temperature for 2 hours. Water was poured into the reaction mixture, and a deposited precipitates were collected by filtration to obtain 0.23 g of the present compound (3) of the formula:

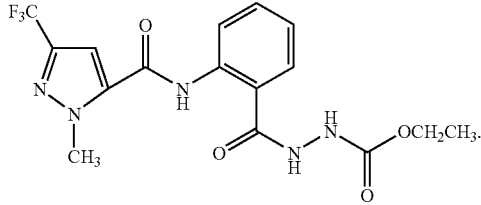

(3)

The present compound (3)
$^1$H-NMR (DMSO-d$_6$, TMS) δ (ppm): 1.20 (3H, t, J=8 Hz), 4.10 (2H, q, J=8 Hz), 4.19 (3H, s), 7.17 (1H, s), 7.28 (1H, t, J=8 Hz), 7.60 (1H, t, J=8 Hz), 7.79 (1H, d, J=8 Hz), 8.37 (1H, d, J=8 Hz), 9.02 (1H, brs), 10.41 (1H, brs), 11.50 (1H, brs)

PREPARATION EXAMPLE 4

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.06 g of ethyl chloroformate and 10 ml of pyridine was stirred at room temperature for 2 hours. Water was poured into the reaction mixture, and a deposited precipitate was collected by filtration to obtain 0.08 g of the present compound (4) of the formula:

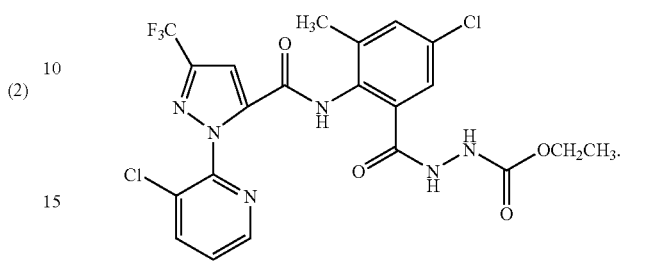

(4)

The present compound (4)
$^1$H-NMR (DMSO-d$_6$, TMS) δ (ppm): 0.96-1.26 (3H, m), 2.16 (3H, s), 3.90-4.12 (2H, m), 7.38 (1H, s), 7.55 (1H, s), 7.66 (1H, dd, J=8 Hz, 4 Hz), 7.71 (1H, s), 8.22 (1H, d, J=8 Hz), 8.53 (1H, d, J=4 Hz), 9.25 (1H, brs), 10.14 (1H, brs), 10.37 (1H, brs)

PREPARATION EXAMPLE 5

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.05 g of methyl chloroformate and 10 ml of pyridine was stirred at room temperature for 2 hours. Water was poured into the reaction mixture, and a deposited precipitate was collected by filtration to obtain 0.16 g of the present compound (5) of the formula:

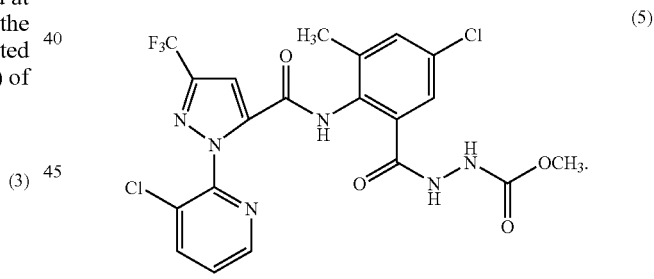

(5)

The present compound (5)
$^1$H-NMR (DMSO-d$_6$, TMS) δ (ppm): 2.16 (3H, s), 3.62 (3H, s), 7.39 (1H, s), 7.56 (1H, s), 7.67 (1H, dd, J=8 Hz, 4 Hz), 7.70 (1H, s), 8.22 (1H, d, J=8 Hz), 8.54 (1H, d, J=4 Hz), 9.31 (1H, brs), 10.17 (1H, brs), 10.38 (1H, brs)

PREPARATION EXAMPLE 6

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.05 g of isopropyl chloroformate and 10 ml of pyridine was stirred at room temperature for 2 hours. Water was poured into the reaction mixture, and a deposited precipitate was collected by filtration to obtain 0.21 g of the present compound (6) of the formula:

(6)

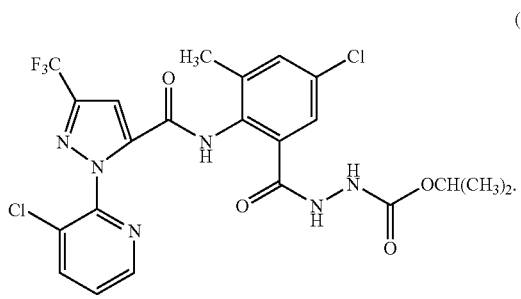

The present compound (6)

$^1$H-NMR (DMSO-d$_6$, TMS) δ (ppm): 0.97-1.31 (6H, m), 2.16 (3H, s), 4.68-4.89 (1H, m), 7.38 (1H, s), 7.55 (1H, s), 7.66 (1H, dd, J=8 Hz, 4 Hz), 7.71 (1H, s), 8.22 (1H, d, J=8 Hz), 8.53 (1H, d, J=4 Hz), 9.18 (1H, brs), 10.12 (1H, brs), 10.37 (1H, brs)

PREPARATION EXAMPLE 7

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.05 g of cyclopropanecarbonyl chloride and 10 ml of pyridine was stirred at room temperature for 2 hours. Water was poured into the reaction mixture, and a deposited precipitate was collected by filtration to obtain 0.20 g of the present compound (7) of the formula:

(7)

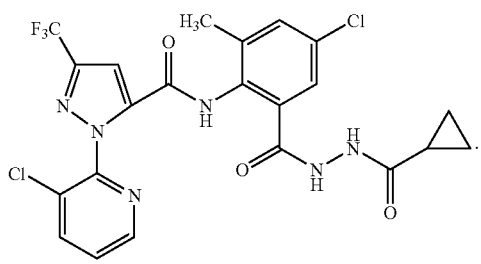

The present compound (7)

$^1$H-NMR (DMSO-d$_6$, TMS) δ (ppm): 0.57-0.82 (4H, m), 1.63-1.73 (1H, m), 2.16 (3H, s), 7.43 (1H, s), 7.54 (1H, s), 7.66 (1H, dd, J=8 Hz, 4 Hz), 7.74 (1H, s), 8.22 (1H, d, J=8 Hz), 8.53 (1H, d, J=4 Hz), 10.19 (2H, brs), 10.40 (1H, brs)

PREPARATION EXAMPLE 8

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.07 g of benzoyl chloride and 10 ml of pyridine was stirred at room temperature for 2 hours. Water was poured into the reaction mixture, and a deposited precipitate was collected by filtration to obtain 0.15 g of the present compound (8) of the formula:

(8)

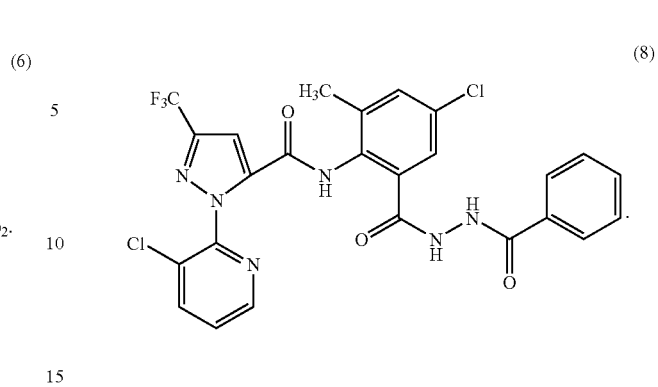

The present compound (8)

$^1$H-NMR (DMSO-d$_6$, TMS) δ (ppm): 2.18 (3H, s), 7.48-7.69 (5H, m), 7.77 (1H, s), 7.90-7.96 (3H, m), 8.22 (1H, d, J=8 Hz), 8.55 (1H, d, J=4 Hz), 10.36 (1H, brs), 10.42 (1H, brs), 10.60 (1H, brs)

PREPARATION EXAMPLE 9

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.07 g of 4-morpholinecarbonyl chloride and 10 ml of pyridine was stirred at room temperature for 2 hours. Water was poured into the reaction mixture, and a deposited precipitate was collected by filtration to obtain 0.12 g of the present compound (9) of the formula:

(9)

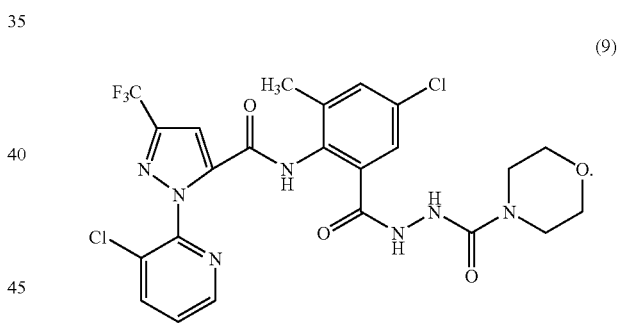

The present compound (9)

$^1$H-NMR (DMSO-d$_6$, TMS) δ (ppm): 2.15 (3H, s), 3.22-3.42 (4H, m), 3.53-3.63 (4H, m), 7.44 (1H, s), 7.53 (1H, s), 7.66 (1H, dd, J=8 Hz, 4 Hz), 7.77 (1H, s), 8.22 (1H, d, J=8 Hz), 8.54 (1H, d, J=4 Hz), 8.78 (1H, brs), 9.88 (1H, brs), 10.33 (1H, brs)

PREPARATION EXAMPLE 10

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.06 g of N,N-dimethylcarbamoyl chloride and 10 ml of pyridine was stirred at room temperature for 2 hours. Water was poured into the reaction mixture, and a deposited precipitate was collected by filtration to obtain 0.13 g of the present compound (10) of the formula:

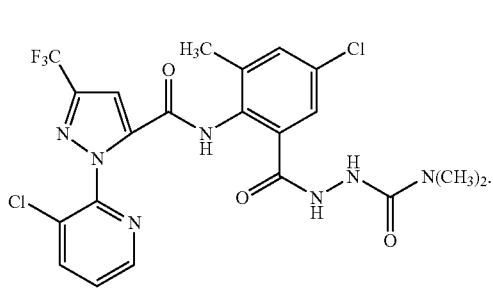

(10)

The present compound (10)

$^1$H-NMR (DMSO-d$_6$, TMS) δ (ppm): 2.14 (3H, s), 2.86 (6H, s), 7.42 (1H, s), 7.52 (1H, s), 7.67 (1H, dd, J=8 Hz, 4 Hz), 7.82 (1H, s), 8.22 (1H, d, J=8 Hz), 8.48-8.58 (2H, m), 9.83 (1H, brs), 10.31 (1H, brs)

PREPARATION EXAMPLE 11

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.06 g of N-propyl chloroformate and 10 ml of pyridine was stirred at room temperature for 2 hours. Water was poured into the reaction mixture, and a deposited precipitate was collected by filtration to obtain 0.24 g of the present compound (11) of the formula:

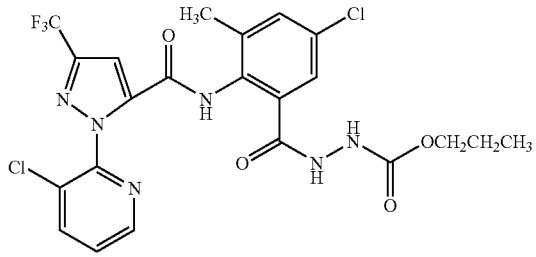

(11)

The present compound (11)

$^1$H-NMR (DMSO-d$_6$, TMS) δ (ppm): 0.66-0.98 (3H, m), 1.37-1.66 (2H, m), 2.16 (3H, s), 3.83-4.08 (2H, m), 7.38 (1H, s), 7.55 (1H, s), 7.66 (1H, dd, J=8 Hz, 4 Hz), 7.71 (1H, s), 8.22 (1H, d, J=8 Hz), 8.53 (1H, d, J=4 Hz), 9.26 (1H, brs), 10.14 (1H, brs), 10.37 (1H, brs)

PREPARATION EXAMPLE 12

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.05 g of ethyl isocyanate and 10 ml of tetrahydrofuran was stirred at room temperature for 2 hours. Water was poured into the reaction mixture, and a deposited precipitate was collected by filtration to obtain 0.16 g of the present compound (12) of the formula:

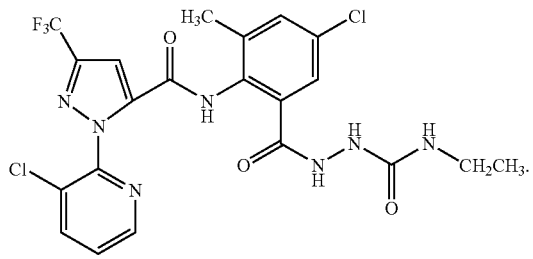

(12)

The present compound (12)

$^1$H-NMR (DMSO-d$_6$, TMS) δ (ppm): 1.12 (3H, t, J=6 Hz), 2.18 (3H, s), 3.78 (2H, q, J=6 Hz), 6.34 (1H, m), 7.48 (1H, s), 7.54 (1H, s), 7.65-7.69 (2H, m), 7.74 (1H, brs), 8.23 (1H, d, J=8 Hz), 8.54 (1H, d, J=4 Hz), 9.99 (1H, brs), 10.34 (1H, brs)

PREPARATION EXAMPLE 13

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.07 g of phenyl isocyanate and 10 ml of tetrahydrofuran was stirred at room temperature for 2 hours. Water was poured into the reaction mixture, and a deposited precipitates were collected by filtration to obtain 0.12 g of the present compound (13) of the formula:

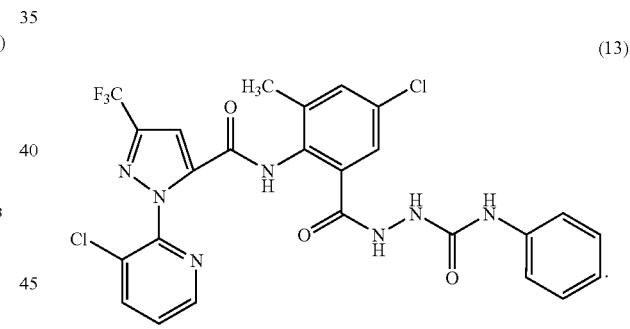

(13)

The present compound (13)

$^1$H-NMR (DMSO-d$_6$, TMS) δ (ppm): 2.18 (3H, s), 6.93-7.00 (2H, m), 7.21-7.31 (2H, m), 7.40-7.47 (2H, m), 7.51 (1H, s), 7.54-7.58 (1H, m), 7.66 (1H, dd, J=8 Hz, 4 Hz), 7.71 (1H, s), 8.22 (1H, d, J=8 Hz), 8.53 (1H, d, J=4 Hz), 8.73 (1H, brs), 10.18 (1H, brs), 10.40 (1H, brs)

PREPARATION EXAMPLE 14

A mixture of 0.24 g of N-(2-methylaminobenzoyl)-N'-ethoxycarbonylhydrazine, 0.31 g of 1-(3-chloro-2-pyridinyl)-3-trifluoromethyl-1H-pyrazole-5-carbonyl chloride and 10 ml of pyridine was stirred at room temperature for 2 hours. Water was poured into the reaction mixture, and a deposited precipitate was collected by filtration to obtain 0.20 g of the present compound (14) of the formula:

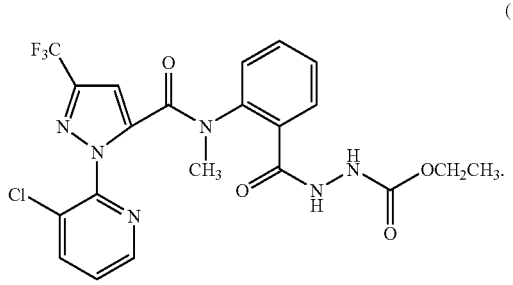

(14)

The present compound (14)

$^1$H-NMR (DMSO-d$_6$, TMS) δ (ppm): 1.06-1.27 (3H, m), 3.18 (3H, s), 4.01-4.16 (2H, m), 6.34 (1H, s), 7.31-7.37 (1H, m), 7.53-7.61 (3H, m), 7.71 (1H, dd, J=8 Hz, 4 Hz), 8.31 (1H, d, J=8 Hz), 8.62 (1H, d, J=4 Hz), 9.33 (1H, brs), 10.44 (1H, brs)

PREPARATION EXAMPLE 15

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.05 g of ethanesulfonyl chloride and 10 ml of pyridine was stirred at room temperature for 2 hours. Water was poured into the reaction mixture, and a deposited precipitate was collected by filtration to obtain 0.14 g of the present compound (15) of the formula:

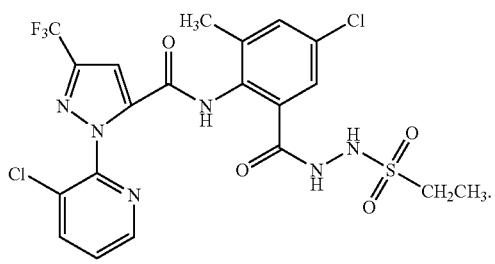

(15)

The present compound (15)

$^1$H-NMR (DMSO-d$_6$, TMS) δ (ppm): 1.20 (3H, t, J=8 Hz), 2.18 (3H, s), 3.02 (2H, q, J=8 Hz), 7.39 (1H, s), 7.57 (1H, s), 7.66 (1H, dd, J=8 Hz, 4 Hz), 7.68 (1H, s), 8.22 (1H, d, J=8 Hz), 8.53 (1H, d, J=4 Hz), 9.95 (1H, brs), 10.41 (1H, brs), 10.57 (1H, brs)

PREPARATION EXAMPLE 16

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.05 g of N,N-dimethylsulfamoyl chloride and 10 ml of pyridine was stirred at room temperature for 2 hours. Water was poured into the reaction mixture, and a deposited precipitate was collected by filtration to obtain 0.14 g of the present compound (16) of the formula:

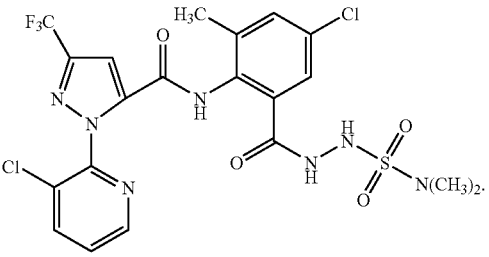

(16)

The present compound (16)

$^1$H-NMR (DMSO-d$_6$, TMS) δ (ppm): 2.16 (3H, s), 2.71 (6H, s), 7.28 (1H, s), 7.57 (1H, s), 7.66 (1H, dd, J=8 Hz, 4 Hz), 7.75 (1H, s), 8.22 (1H, d, J=8 Hz), 8.53 (1H, d, J=4 Hz), 9.31 (1H, brs), 10.42 (1H, brs), 10.51 (1H, brs)

PREPARATION EXAMPLE 17

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 10 mL of formic acid and 5 ml of acetic anhydride prepared under ice-cooling was stirred at room temperature for 2 hours. Water was poured into the reaction mixture, and a deposited precipitate was collected by filtration to obtain 0.02 g of the present compound (17) of the formula:

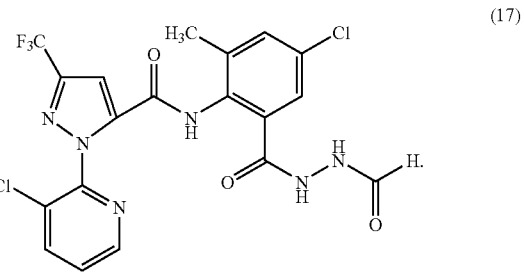

(17)

The present compound (17)

$^1$H-NMR (DMSO-d$_6$, TMS) δ (ppm): 2.16 (3H, s), 7.43 (1H, s), 7.56 (1H, s), 7.66 (1H, dd, J=8 Hz, 4 Hz), 7.73 (1H, s), 8.05 (1H, s), 8.22 (1H, d, J=8 Hz), 8.53 (1H, d, J=4 Hz), 10.13 (1H, brs), 10.39 (1H, brs), 10.46 (1H, brs)

PREPARATION EXAMPLE 18

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.05 g of propionyl chloride and 10 ml of pyridine was stirred at room temperature for 2 hours. Water was poured into the reaction mixture, and a deposited precipitate was collected by filtration to obtain 0.15 g of the present compound (18) of the formula:

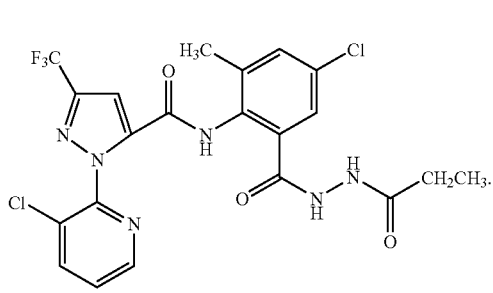

(18)

The present compound (18)

$^1$H-NMR (DMSO-$d_6$, TMS) δ(ppm): 1.04 (3H, t, J=8 Hz), 2.13 (5H, m), 7.44 (1H, s), 7.55 (1H, s), 7.66 (1H, dd, J=8 Hz, 4 Hz), 7.74 (1H, s), 8.22 (1H, d, J=8 Hz), 8.54 (1H, d, J=4 Hz), 9.91 (1H, brs), 10.16 (1H, brs), 10.36 (1H, brs)

PREPARATION EXAMPLE 19

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.05 g of n-butyl chloroformate and 10 ml of pyridine was stirred at room temperature for 2 hours. Water was poured into the reaction mixture, and a deposited precipitate was collected by filtration to obtain 0.19 g of the present compound (19) of the formula:

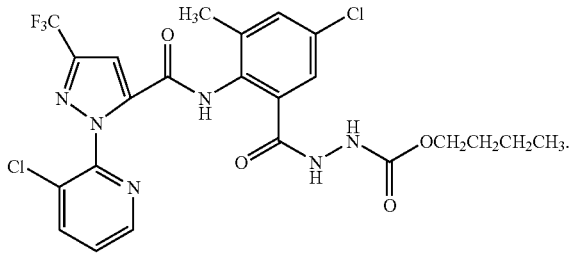

(19)

The present compound (19)

$^1$H-NMR (DMSO-$d_6$, TMS) δ (ppm): 0.79-0.94 (3H, m), 1.22-1.40 (2H, m), 1.46-1.62 (2H, m), 2.17 (3H, s), 3.92-4.13 (2H, m), 7.37 (1H, s), 7.56 (1H, s), 7.66 (1H, dd, J=8 Hz, 4 Hz), 7.70 (1H, s), 8.22 (1H, d, J=8 Hz), 8.53 (1H, d, J=4 Hz), 9.25 (1H, brs), 10.14 (1H, brs), 10.37 (1H, brs)

PREPARATION EXAMPLE 20

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.05 g of allyl chloroformate and 10 ml of pyridine was stirred at room temperature for 2 hours. Water was poured into the reaction mixture, and a deposited precipitate was collected by filtration to obtain 0.23 g of the present compound (20) of the formula:

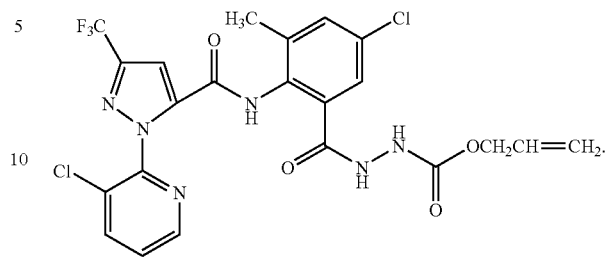

(20)

The present compound (20)

$^1$H-NMR (DMSO-$d_6$, TMS) δ (ppm): 2.16 (3H, s), 4.43-4.60 (2H, m), 5.21 (1H, d, J=6 Hz), 5.33 (1H, d, J=8 Hz), 5.86-6.00 (1H, m), 7.39 (1H, s), 7.56 (1H, s), 7.66 (1H, dd, J=8 Hz, 4 Hz), 7.70 (1H, s), 8.22 (1H, d, J=8 Hz), 8.54 (1H, d, J=4 Hz), 9.39 (1H, brs), 10.18 (1H, brs), 10.38 (1H, brs)

PREPARATION EXAMPLE 21

A mixture of 0.22 g of N-[4-chloro-2-(N-methylhydrazinocarbonyl)-6-methylphenyl]-1-(3-chloro-2-pyridinyl)-3-trifluoromethyl-1H-pyrazole-5-carboxamide, 0.05 g of methyl chloroformate and 10 ml of pyridine was stirred at room temperature for 2 hours. Water was poured into the reaction solution, and a deposited precipitate was collected by filtration to obtain 0.09 g of the present compound (21) of the formula:

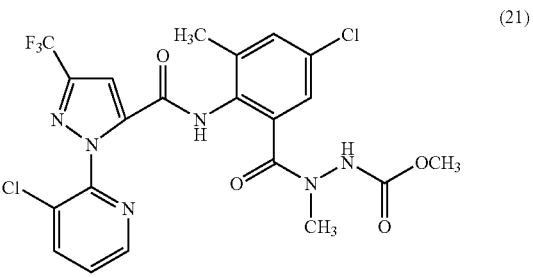

(21)

The present compound (21)

$^1$H-NMR (DMSO-$d_6$, TMS) δ (ppm): 2.11 (3H, s), 3.06 (3H, s), 3.33 (3H, s), 7.07 (1H, s), 7.45 (1H, s), 7.68 (1H, s), 7.69 (1H, dd, J=8 Hz, 4 Hz), 8.24 (1H, d, J=8 Hz), 8.55 (1H, d, J=4 Hz), 9.11 (0.6H, brs), 10.20 (1H, brs), 10.54 (0.4H, brs)

PREPARATION EXAMPLE 22

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.05 g of N,N-diethylcarbamoyl chloride and 10 ml of pyridine was stirred at room temperature for 2 hours. Water was poured into the reaction mixture, and a deposited precipitate was collected by filtration to obtain 0.19 g of the present compound (22) of the formula:

(22)

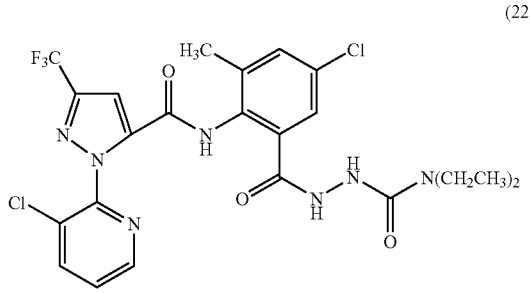

The present compound (22)

¹H-NMR (DMSO-d₆, TMS) δ (ppm): 1.06 (6H, t, J=6 Hz), 2.14 (3H, s), 3.26 (4H, q, J=6 Hz), 7.42 (1H, s), 7.52 (1H, s), 7.68 (1H, dd, J=8 Hz, 4 Hz), 7.82 (1H, s), 8.23 (1H, d, J=8 Hz), 8.48 (1H, brs), 8.53 (1H, d, J=4 Hz), 9.84 (1H, brs), 10.35 (1H, brs)

PREPARATION EXAMPLE 23

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.10 g of N-methyl-N-phenylcarbamoyl chloride and 10 ml of pyridine was stirred at room temperature for 2 hours. Water was poured into the reaction mixture, and a deposited precipitate was collected by filtration to obtain 0.19 g of the present compound (23) of a formula:

(23)

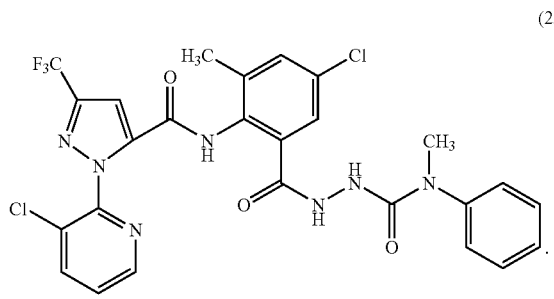

The present compound (23)

¹H-NMR (DMSO-d₆, TMS) δ (ppm): 2.15 (3H, s), 3.08 (3H, s), 7.10-7.45 (6H, m), 7.53 (1H, s), 7.66 (1H, dd, J=8 Hz, 4 Hz), 7.76 (1H, s), 8.14 (1H, brs), 8.20 (1H, d, J=8 Hz), 8.50 (1H, d, J=4 Hz), 9.97 (1H, brs), 10.32 (1H, brs)

PREPARATION EXAMPLE 24

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.15 g of N,N-diphenylcarbamoyl chloride and 10 ml of pyridine was stirred at room temperature for 2 hours. Water was poured into the reaction mixture, and a deposited precipitate was collected by filtration to obtain 0.24 g of the present compound (24) of the formula:

(24)

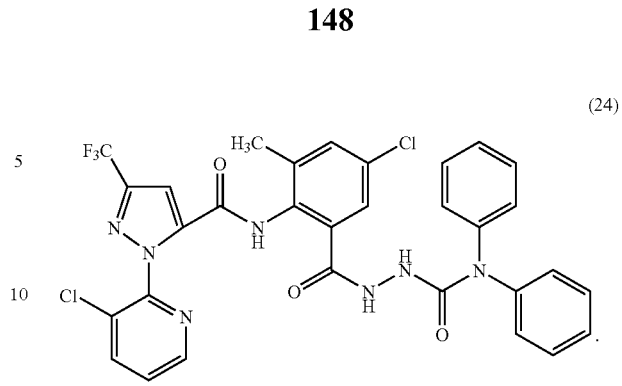

The present compound (24)

¹H-NMR (DMSO-d₆, TMS) δ (ppm): 2.15 (3H, s), 6.77 (1H, t, J=8 Hz), 6.81 (1H, t, J=8 Hz), 7.05-7.39 (9H, m), 7.52 (1H, s), 7.64 (1H, dd, J=8 Hz, 4 Hz), 7.72 (1H, s), 8.13 (1H, brs), 8.19 (1H, d, J=8 Hz) 8.47 (1H, d, J=4 Hz), 10.08 (1H, brs), 10.34 (1H, brs)

PREPARATION EXAMPLE 25

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.07 g of picolinoyl chloride hydrochloride and 10 ml of pyridine was stirred at room temperature for 2 hours. Water was poured into a reaction mixture, and a deposited precipitate was collected by filtration to obtain 0.16 g of the present compound (25) of the formula:

(25)

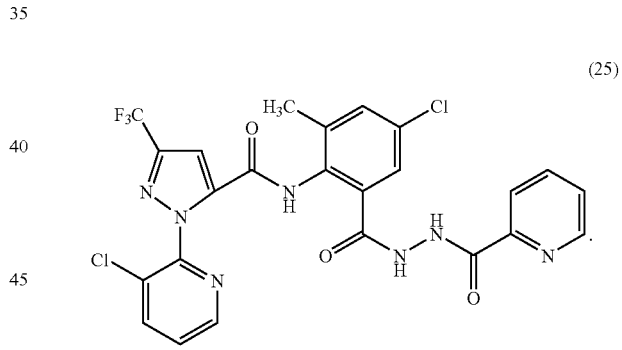

The present compound (25)

¹H-NMR (DMSO-d₆, TMS) δ (ppm): 2.18 (3H, s), 7.50-7.59 (2H, m), 7.63-7.71 (3H, m), 7.77-7.88 (1H, m), 8.05 (1H, s), 8.06 (1H, s), 8.23 (1H, d, J=8 Hz), 8.54 (1H, d, J=4 Hz), 8.70 (1H, d, J=4 Hz), 10.35-10.70 (2H, m)

PREPARATION EXAMPLE 26

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.07 g of phenyl chloroformate and 10 ml of pyridine was stirred at room temperature for 2 hours. Water was poured into the reaction mixture, and a deposited precipitate was collected by filtration to obtain 0.16 g of the present compound (26) of a formula:

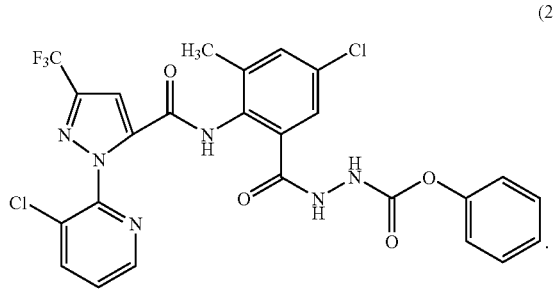

(26)

The present compound (26)

$^1$H-NMR (DMSO-d$_6$, TMS) δ (ppm): 2.17 (3H, s), 7.13-7.69 (9H, m), 8.22 (1H, d, J=8 Hz) 8.53 (1H, d, J=4 Hz), 9.95 (1H, brs), 10.43 (1H, brs), 10.45 (1H, brs)

PREPARATION EXAMPLE 27

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.04 g of acetyl chloride and 10 ml of pyridine was stirred at room temperature for 2 hours. Water was poured into the reaction mixture, and a deposited precipitate was collected by filtration to obtain 0.22 g of the present compound (27) of the formula:

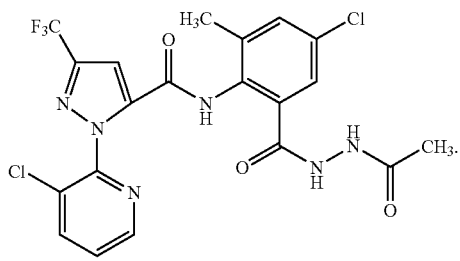

(27)

The present compound (27)

$^1$H-NMR (DMSO-d$_6$, TMS) δ (ppm): 1.89 (3H, s), 2.16 (3H, s), 7.44 (1H, s), 7.55 (1H, s), 7.66 (1H, dd, J=8 Hz, 4 Hz), 7.73 (1H, s), 8.21 (1H, d, J=8 Hz), 8.54 (1H, d, J=4 Hz), 9.94 (1H, brs), 10.17 (1H, brs), 10.38 (1H, brs)

PREPARATION EXAMPLE 28

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.06 g of trimethylacetyl chloride and 10 ml of pyridine was stirred at room temperature for 2 hours. Water was poured into the reaction mixture, and a deposited precipitate was collected by filtration to obtain 0.25 g of the present compound (28) of the formula:

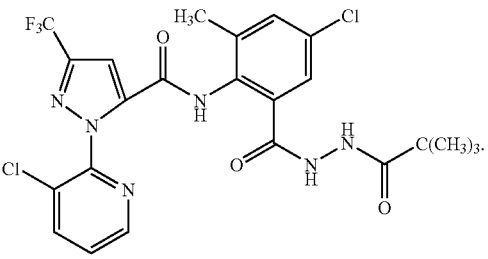

(28)

The present compound (28)

$^1$H-NMR (DMSO-d$_6$, TMS) δ (ppm): 1.17 (9H, s), 2.15 (3H, s), 7.46 (1H, s), 7.54 (1H, s), 7.66 (1H, dd, J=8 Hz, 4 Hz), 7.76 (1H, s), 8.23 (1H, d, J=8 Hz), 8.54 (1H, d, J=4 Hz), 9.66 (1H, brs), 10.01 (1H, brs), 10.32 (1H, brs)

PREPARATION EXAMPLE 29

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.05 g of methyl chlorothiol formate of the formula:

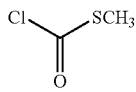

and 10 ml of pyridine was stirred at room temperature for 2 hours. Water was poured into the reaction mixture, and a deposited precipitate was collected by filtration to obtain 0.10 g of the present compound (29) of the formula:

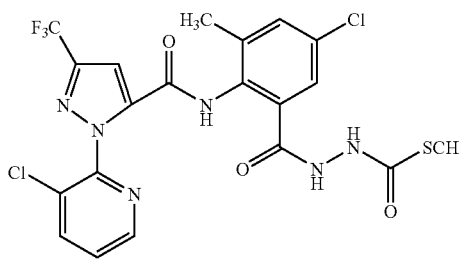

(29)

The present compound (29)

$^1$H-NMR (DMSO-d$_6$, TMS) δ (ppm): 2.03-2.34 (6H, m), 7.40 (1H, s), 7.58 (1H, s), 7.66 (1H, dd, J=8 Hz, 4 Hz), 7.71 (1H, s), 8.22 (1H, d, J=8 Hz), 8.53 (1H, d, J=4 Hz), 9.84 (1H, brs), 10.41 (1H, brs), 10.56 (1H, brs)

PREPARATION EXAMPLE 30

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.09 g of 3-methylbenzoyl chloride and 10 ml of pyridine was stirred at room temperature for 2 hours. Water was poured into the reaction mixture, and a deposited precipitate was collected by filteration to obtain 0.19 g of the present compound (30) of the formula:

(30)

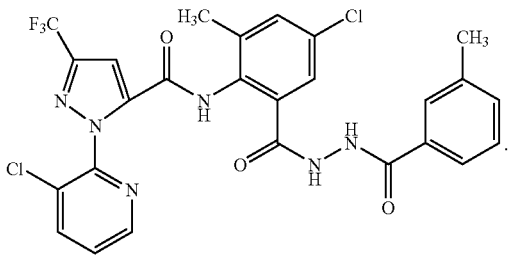

The present compound (30)

¹H-NMR (DMSO-d₆, TMS)$_\delta$(ppm): 2.18 (3H, s), 2.30 (3H, s), 7.40 (1H, s), 7.55 (1H, s), 7.58 (1H, s), 7.65-7.73 (4H, m), 7.77 (1H, s), 8.23 (1H, d, J=8 Hz), 8.54 (1H, d, J=4 Hz), 10.35 (1H, brs), 10.41 (1H, brs), 10.54 (1H, brs)

PREPARATION EXAMPLE 31

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.09 g of 4-methoxybenzoyl chloride and 10 ml of pyridine was stirred at room temperature for 2 hours. Water was poured into the reaction mixture, and a deposited precipitate was collected by filtration to obtain 0.09 g of the present compound (31) of the formula:

(31)

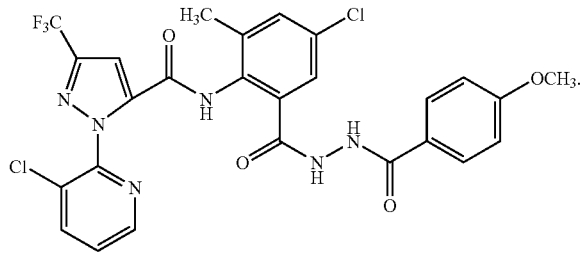

The present compound (31)

¹H-NMR (DMSO-d₆, TMS) δ (ppm): 2.18 (3H, s), 3.83 (3H, s), 7.04 (2H, d, J=8 Hz), 7.55 (1H, s), 7.58 (1H, s), 7.69 (1H, dd, J=8 Hz, 4 Hz), 7.77 (1H, s), 7.90 (2H, d, 8 Hz), 8.23 (1H, d, J=8 Hz), 8.54 (1H, d, J=4 Hz), 10.28 (1H, brs), 10.41 (1H, brs), 10.45 (1H, brs)

PREPARATION EXAMPLES 32

A mixture of 0.18 g of 1-(3-chloro-2-pyridinyl)-N-[2-(hydrazinocarbonyl)-6-methylphenyl]-3-trifluoromethyl-1H-pyrazole-5-carboxamide, 0.06 ml of ethyl chloroformate and 1 ml of pyridine was stirred at room temperature for 2 hours. Water and toluene were added successively to the reaction mixture, and the mixture was concentrated under reduced pressure. The resulting residue was mixed with methyl tert-butyl ether and water, the mixture was separated into layers, the resulting organic layer was washed with an aqueous saturated sodium chloride solution, dried over anhydrous magnesium sulfate, and concentrated under reduced pressure. The resulting residue was subjected to silica gel column chromatography to obtain 0.14 g of the present compound (32) of the formula:

(32)

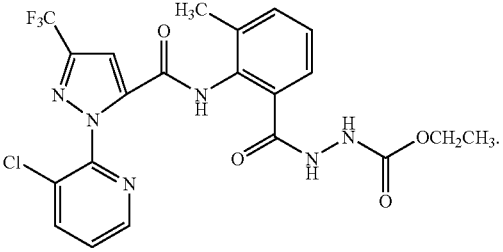

The present compound (32)

¹H-NMR (CDCl₃, TMS)$_\delta$(ppm): 1.26 (3H, brm), 2.21 (3H, s), 4.18 (2H, brq, J=7 Hz), 6.88 (1H, brs), 7.17 (1H, t, J=8 Hz), 7.28-7.39 (4H, m), 7.86 (1H, d, J=8 Hz), 8.05 (1H, brs), 8.43 (1H, d, J=4 Hz), 9.73 (1H, brs)

PREPARATION EXAMPLE 33

A mixture of 0.21 g of N-[2-chloro-6-(hydrazinocarbonyl)phenyl]-1-(3-chloro-2-pyridinyl)-3-trifluoromethyl-1H-pyrazole-5-carboxamide, 0.06 ml of ethyl chloroformate and 5 ml of pyridine was stirred at room temperature for 2 hours. Water was poured into the reaction mixture, and the mixture was extracted with methyl tert-butyl ether three times. The organic layers were combined, washed successively with 2 mol/L-hydrochloric acid, an aqueous saturated sodium bicarbonate solution and an aqueous saturated sodium chloride solution, dried over anhydrous magnesium sulfate, and concentrated under reduced pressure. The resulting residue was subjected to silica gel column chromatography to obtain 0.16 g of the present compound (33) of the formula:

(33)

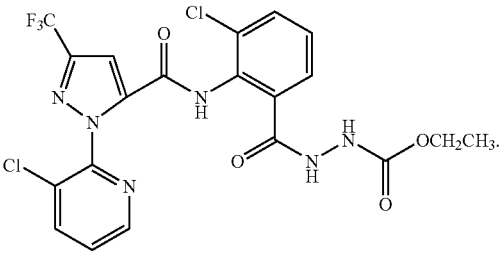

The present compound (33)

¹H-NMR (CDCl₃, TMS) δ (ppm): 1.28 (3H, t, J=7 Hz), 4.21 (2H, q, J=7 Hz), 6.76 (1H, brs), 7.23-7.30 (2H, m), 7.42 (1H, dd, J=8 Hz, 4 Hz), 7.50 (1H, d, J=8 Hz), 7.55 (1H, d, J=8 Hz), 7.85 (1H, brs), 7.90 (1H, dd, J=8 Hz, 1Hz), 8.47 (1H, dd, J=4 Hz, 1Hz), 9.16 (1H, brs)

PREPARATION EXAMPLE 34

A mixture of 0.30 g of 3-bromo-N-[4-chloro-2-(hydrazinocarbonyl)-6-methylphenyl]-1-(3-chloro-2-pyridinyl)-1H-pyrazole-5-carboxamide, 0.20 ml of methyl chloroformate, 0.09 ml of triethylamine, 20 ml of acetonitrile and 10 ml of N,N-dimethylformamide was stirred at room temperature for 3 hours. Water was poured into the reaction mixture, and the mixture was extracted with methyl tert-butyl ether three times. The organic layers were combined, washed with an aqueous saturated sodium chloride solution, dried with anhydrous magnesium sulfate, and concentrated under reduced pressure. The resulting residue was subjected to silica gel column chromatography to obtain 0.13 g of the present compound (34) of the formula:

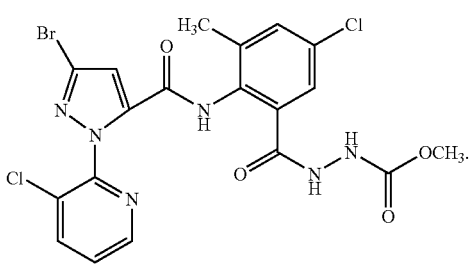

(34)

The present compound (34)

¹H-NMR (DMSO-d₆) δ (ppm): 2.14 (3H, s), 3.61 (3H, brs), 7.33 (1H, s), 7.37 (1H, brs), 7.53 (1H, brs), 7.60 (1H, dd, J=8 Hz, 4 Hz), 8.16 (1H, dd, J=8 Hz, 1Hz), 8.49 (1H, dd, J=4 Hz, 1Hz), 9.29 (1H, brs), 10.15 (1H, brs), 10.22 (1H, brs)

PREPARATION EXAMPLE 35

A mixture of 0.30 g of 3-bromo-N-[4-chloro-2-(hydrazinocarbonyl)-6-methylphenyl]-1-(3-chloro-2-pyridinyl)-1H-pyrazole-5-carboxamide, 0.09 ml of ethyl chloroformate and 3 ml of pyridine was stirred at room temperature for 3 hours, and concentrated under reduced pressure. Water and toluene were added to the resulting residue, the mixture was filtered, the resulting filter cake was mixed with methyl tert-butyl ether and water, and the mixture was separated into layers. The organic layer was washed with an aqueous saturated sodium chloride solution, dried over anhydrous magnesium sulfate, and concentrated under reduced pressure. The resulting residue was subjected to silica gel column chromatography to obtain 0.23 g of the present compound (35) of the formula:

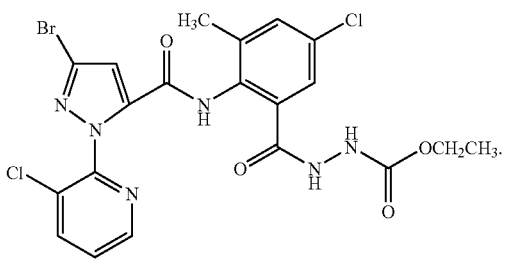

(35)

The present compound (35)

¹H-NMR (DMSO-d₆) δ (ppm): 1.18 (3H, brm), 2.14 (3H, s), 4.06 (2H, brm), 7.34 (1H, s), 7.37 (1H, brs), 7.53 (1H, s), 7.60 (1H, dd, J=8 Hz, 4 Hz), 8.16 (1H, dd, J=8 Hz, 1Hz), 8.49 (1H, dd, J=4 Hz, 1Hz), 9.24 (1H, brs), 10.12 (1H, brs), 10.21 (1H, brs)

PREPARATION EXAMPLES 36 AND 37

To a solution of 0.30 g of N-[4-chloro-2-(hydrazinocarbonyl)-6-methylphenyl]-1-(2-chlorophenyl)-3-trifluoromethyl-1H-pyrazole-5-carboxamide in 10 ml of acetonitrile were added 0.10 ml of methyl chloroformate and 0.09 ml of triethylamine, the mixture was stirred at room temperature for 1 hour, and 0.10 ml of methyl chloroformate was added to the mixture, followed by further stirring for 3 hours. Water was poured into the reaction mixture, and the mixture was extracted with methyl tert-butyl ether three times. The organic layers were combined, washed with an aqueous saturated sodium chloride solution, dried over anhydrous magnesium sulfate, and concentrated under reduced pressure. The resulting residue was subjected to silica gel column chromatography to obtain 0.16 g of the present compound (36) and 0.16 g of the present compound (37) of the fromulas:

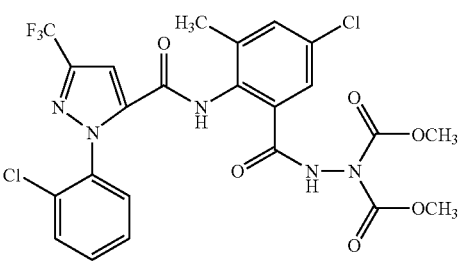

(36)

The present compound (36)

¹H-NMR (CDCl₃, TMS) δ (ppm): 2.15 (3H, s), 3.76 (6H, s), 7.23-7.27 (3H, m), 7.30-7.40 (2H, m), 7.43-7.47 (2H, m), 8.84 (1H, brs), 9.29 (1H, brs)

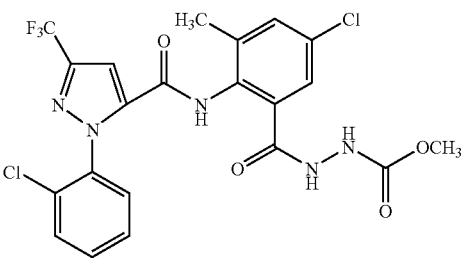

(37)

The present compound (37)

¹H-NMR (DMSO-d₆) δ (ppm): 2.22 (3H, s), 3.68 (3H, brs), 7.44 (1H, brs), 7.53-7.72 (6H, m), 9.35 (1H, brs), 10.23 (1H, brs), 10.32 (1H, brs)

PREPARATION EXAMPLE 38

A mixture of 0.30 g of N-[4-chloro-2-(hydrazinocarbonyl)-6-methylphenyl]-1-(2-chlorophenyl)-3-trifluoromethyl-1H-pyrazole-5-carboxamide, 2 ml of pyridine and 0.09 ml of ethyl chloroformate was stirred at room temperature for 1 hour, and concentrated under reduced pressure. Water and toluene were added to the resulting residue, and the mixture was filtered. The filter cake was subjected to silica gel column chromatography to obtain 0.22 g of the present compound (38) or the formula:

(38)

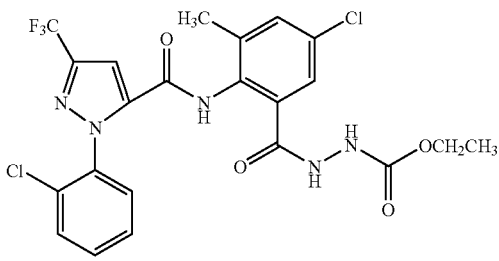

The present compound (38)

$^1$H-NMR (DMSO-d$_6$) δ (ppm): 1.19 (3H, brm), 2.15 (3H, s), 4.05 (2H, brm), 7.37 (1H, s), 7.49-7.66 (6H, m), 9.22 (1H, brs), 10.14 (1H, brs), 10.25 (1H, brs)

PREPARATION EXAMPLE 39

A mixture of 0.18 g of 1-(3-chloro-2-pyridinyl)-N-[2-(hydrazinocarbonyl)-6-methylphenyl]-3-trifluoromethyl-1H-pyrazole-5-carboxamide, 0.05 ml of methyl chloroformate and 1 ml of pyridine was stirred at room temperature for 2 hours. Water was poured into the reaction mixture, and toluene was added, followed by concentration under reduced pressure. The resulting residue was mixed with methyl tert-butyl ether and water, the mixture was separated into layers, and the organic layer was washed with an aqueous saturated sodium chloride solution, dried with anhydrous magnesium sulfate, and concentrated under reduced pressure. The resulting residue was subjected to silica gel column chromatography to obtain 0.13 g of the present compound (39) of the formula:

(39)

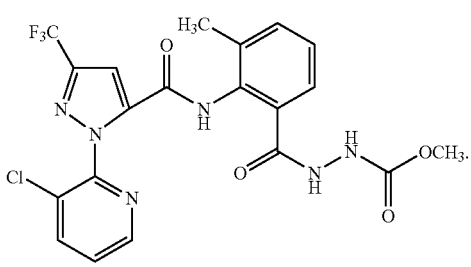

The present compound (39)

$^1$H-NMR (CDCl$_3$, TMS) δ (ppm): 2.22 (3H, s), 3.75 (3H, brs), 6.86 (1H, brs), 7.19 (1H, t, J=8 Hz), 7.27 (1H, s), 7.34-7.40 (3H, m), 7.87 (1H, dd, J=8 Hz, 1.5 Hz), 7.97 (1H, brs), 8.44 (1H, J=4 Hz, 1Hz), 9.68 (1H, brs)

PREPARATION EXAMPLE 40

A mixture of 0.30 g of N-[4-chloro-2-(hydrazinocarbonyl)-6-methylphenyl]-1-(3-chloro-2-pyridinyl)-1H-pyrazole-5-carboxamide, 0.09 ml of methyl chloroformate and 3 ml of pyridine was stirred at room temperature for 1.5 hours. Water and toluene were successively added to the reaction mixture, followed by concentration under reduced pressure. The resulting residue was mixed with ethyl acetate and water, the mixture was separated into layers, and the organic layer was washed with an aqueous saturated sodium chloride solution, dried over anhydrous magnesium sulfate, and concentrated under reduced pressure. The resulting residue was subjected to silica gel column chromatography to obtain 0.20 g of the present compound (40) of the formula:

(40)

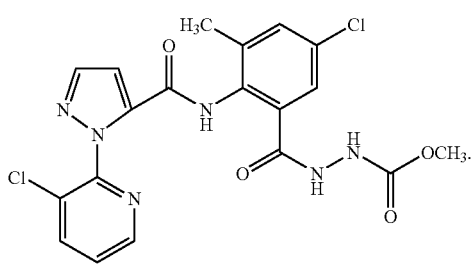

The present compound (40)

$^1$H-NMR (DMSO-d$_6$) δ (ppm): 2.17 (3H, s), 3.62 (3H, brs), 7.25 (1H, d, J=2 Hz), 7.40 (1H, brs), 7.52 (1H, d, J=2 Hz), 7.56 (1H, dd, J=8 Hz, 4 Hz), 7.86 (1H, d, J=2 Hz), 8.11 (1H, dd, J=8 Hz, 1Hz), 8.48 (1H, dd, J=4 Hz, 1Hz), 9.31 (1H, brs), 10.11 (1H, brs), 10.13 (1H, brs)

PREPARATION EXAMPLE 41

According to the same manner as that of Preparation Example 5, N-[4,6-dimethyl-2-(hydrazinocarbonyl)phenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (41) of the formula:

(41)

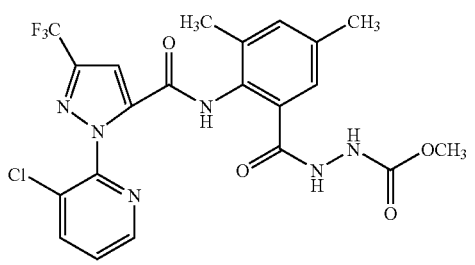

The present compound (41)

$^1$H-NMR (DMSO-d$_6$, TMS) δ (ppm): 2.11 (3H, s), 2.29 (3H, s), 3.55-3.68 (3H, m), 7.19-7.25 (2H, m), 7.66 (1H, dd, J=8 Hz, 4 Hz), 7.71 (1H, s), 8.22 (1H, d, J=8 Hz), 8.53 (1H, d, J=4 Hz), 9.23 (1H, brs), 9.98 (1H, brs), 10.22 (1H, brs)

PREPARATION EXAMPLE 42

According to the same manner as that of Preparation Example 10, N-[4,6-dimethyl-2-(hydrazinocarbonyl)phenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluormethyl-1H-pyrazole-5-carboxamide to obtain the present compound (42) of the formula:

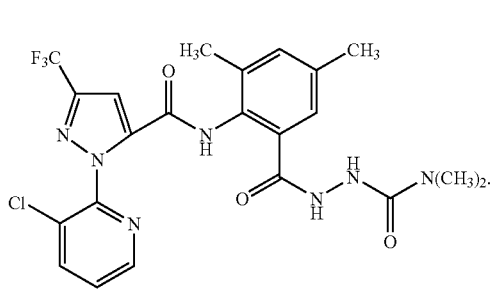

(42)

The present compound (42)

$^1$H-NMR (DMSO-$d_6$, TMS) δ (ppm): 2.13 (3H, s), 2.31 (3H, s), 2.86 (6H, s), 7.14-7.27 (2H, m), 7.65-7.70 (1H, m), 7.82 (1H, s), 8.23 (1H, d, J=8 Hz), 8.48 (1H, brs), 8.53 (1H, d, J=4 Hz), 9.65 (1H, brs), 10.16 (1H, brs)

PREPARATION EXAMPLE 43

According to the same manner as that of Preparation Example 5, N-[6-bromo-2-(hydrazinocarbonyl)-4-methylphenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (43) of the formula:

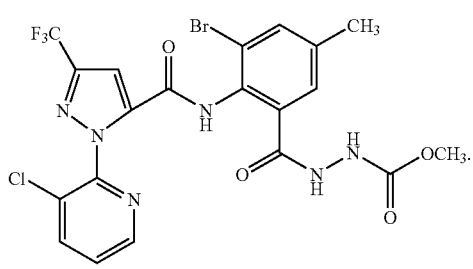

(43)

The present compound (43)

$^1$H-NMR (DMSO-$d_6$, TMS) δ (ppm): 2.35 (3H, s), 3.53-3.65 (3H, m), 7.35 (1H, s), 7.65 (1H, dd, J=8 Hz, 4 Hz), 7.68-7.70 (1H, m), 7.76 (1H, s), 8.20 (1H, d, J=8 Hz), 8.53 (1H, d, J=4 Hz), 9.27 (1H, brs), 10.04 (1H, brs), 10.47 (1H, brs)

PREPARATION EXAMPLE 44

According to the same manner as that of Preparation Example 10, N-[6-bromo-2-(hydrazinocarbonyl)-4-methylphenyl]-1-(3-chloro-2-pyridinyl)-3-trifluormethyl-1H-pyrazole-5-carboxamide was used in place of N-[4-chloro-2-(hydrazinocarbonyl)-6-methylphenyl]-1-(3-chloro-2-pyridinyl)-3-trifluormethyl-1H-pyrazole-5-carboxamide to obtain the present compound (44) of the formula:

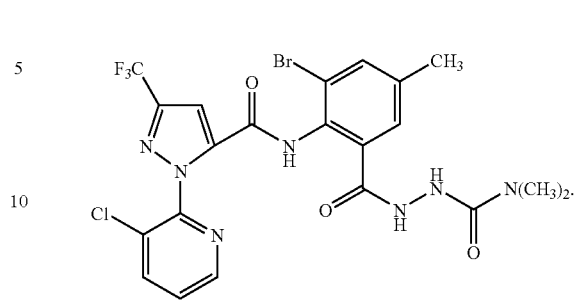

(44)

The present compound (44)

$^1$H-NMR (DMSO-$d_6$, TMS) δ (ppm): 2.34 (3H, s), 2.84 (6H, s), 7.40 (1H, s), 7.62-7.70 (2H, m), 7.83 (1H, s), 8.20 (1H, d, J=8 Hz), 8.48 (1H, brs), 8.51-8.56 (1H, m), 9.69 (1H, brs), 10.42 (1H, brs)

PREPARATION EXAMPLE 45

According to the same manner as that of Preparation Example 5, N-[3-chloro-2-(hydrazinocarbonyl)phenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (45) of the formula:

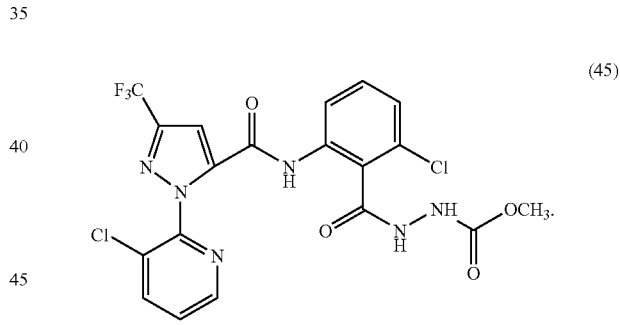

(45)

The present compound (45)

$^1$H-NMR (DMSO-$d_6$, TMS) δ (ppm): 3.67-3.74 (3H, m), 7.37-7.47 (2H, m), 7.69-7.74 (1H, m), 7.82-7.88 (2H, m), 8.25-8.33 (1H, m), 8.57 (1H, d, J=4 Hz), 9.71 (1H, brs), 9.83 (1H, brs), 10.56 (1H, brs)

PREPARATION EXAMPLE 46

According to the same manner as that of Preparation Example 10, N-[4-chloro-2-(hydrazinocarbonyl)phenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluormethyl-1H-pyrazole-5-carboxamide to obtain the present compound (46) of the formula:

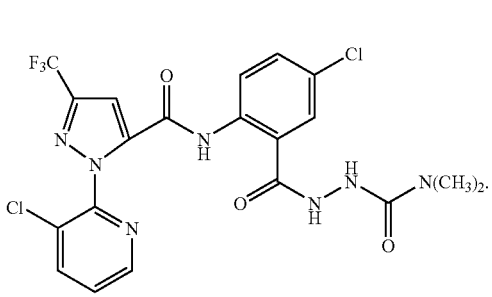

(46)

The present compound (46)

$^1$H-NMR (DMSO-d$_6$, TMS) δ (ppm): 2.90 (6H, s), 7.57 (1H, d, J=8 Hz), 7.68-7.70 (1H, m), 7.73 (1H, dd, 8 Hz, 4 Hz), 7.81 (1H, s), 8.18 (1H, d, J=8 Hz), 8.29 (1H, d, J=8 Hz), 8.57 (1H, d, J=4 Hz), 8.83 (1H, brs), 10.36 (1H, brs), 11.27 (1H, brs)

PREPARATION EXAMPLE 47

According to the same manner as that of Preparation Example 5, N-[4-chloro-2-(hydrazinocarbonyl)phenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (47) of the formula:

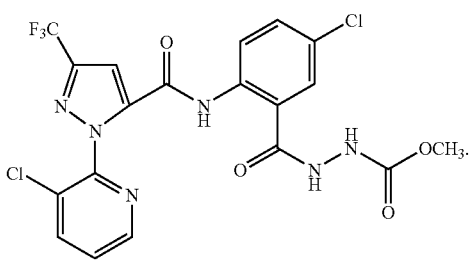

(47)

The present compound (47)

$^1$H-NMR (DMSO-d$_6$, TMS) δ (ppm): 3.64-3.71 (3H, m), 7.59 (1H, s), 7.63 (1H, d, J=8 Hz), 7.72 (1H, dd, J=8 Hz, 4 Hz), 7.86 (1H, s), 8.12 (1H, d, J=8 Hz), 8.29 (1H, d, J=8 Hz), 8.58 (1H, d, J=4 Hz), 9.51 (1H, brs), 10.75 (1H, brs), 11.68 (1H, brs)

PREPARATION EXAMPLE 48

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.04 g of sodium cyanate, 0.5 ml of acetic acid and 5 ml of chloroform was stirred under ice-cooling for 4 hours. The reaction mixture was concentrated under reduced pressure, and the resulting residue was washed successively with water and chloroform to obtain 0.080 g of the present compound (48) of the formula:

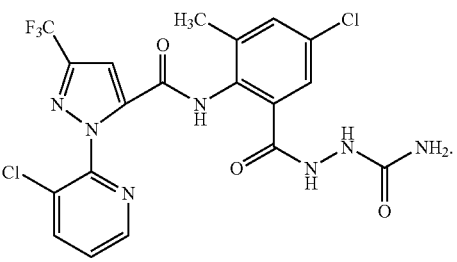

(48)

The present compound (48)

$^1$H-NMR (DMSO-d$_6$, TMS) δ (ppm): 2.16 (3H, s), 5.97 (2H, brs), 7.52-7.54 (2H, m), 7.67 (1H, dd, J=8 Hz, 4 Hz), 7.70 (1H, s), 7.76 (1H, brs), 8.22 (1H, d, J=8 Hz), 8.54 (1H, d, J=4 Hz), 10.01 (1H, brs), 10.39 (1H, brs)

PREPARATION EXAMPLE 49

According to the same manner as that of Preparation Example 5 except that N-[4,6-dibromo-2-(hydrazinocarbonyl)phenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (49) of the formula:

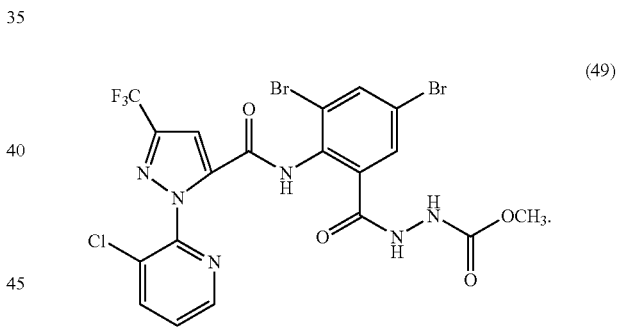

(49)

The present compound (49)

$^1$H-NMR (DMSO-d$_6$, TMS) δ (ppm): 3.40-3.70 (3H, m), 7.63-7.69 (2H, m), 7.76 (1H, s), 8.16 (1H, s), 8.21 (1H, d, J=8 Hz), 8.54 (1H, d, J=4 Hz), 9.35 (1H, brs), 10.23 (1H, brs), 10.63 (1H, brs)

PREPARATION EXAMPLE 50

According to the same manner as that of Preparation Example 5 except that N-[4,6-diiodo-2-(hydrazinocarbonyl)phenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (50) of the formula:

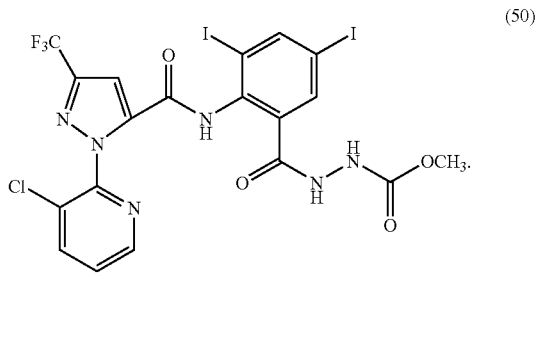

(50)

The present compound (50)

¹H-NMR (DMSO-d₆, TMS) δ (ppm): 3.55-3.65 (3H, m), 7.65 (1H, dd, J=8 Hz, 4 Hz), 7.75-7.82 (2H, m), 8.20 (1H, d, J=8 Hz), 8.39 (1H, s), 8.53 (1H, d, J=4 Hz), 9.31 (1H, brs), 10.14 (1H, brs), 10.59 (1H, brs)

PREPARATION EXAMPLE 51

A mixture of 0.22 g of N-[4-chloro-2-(hydrazinocarbonyl)-6-methylphenyl]-1-(3-chloro-2-pyridinyl)-3-trifluoromethyl-1H-pyrazole-5-carboxamide, 0.05 g of methyl isothiocyanate and 10 ml of tetrahydrofuran was stirred at room temperature for 2 hours. Water was poured into the reaction mixture, and a deposited precipitate was collected by filtration to obtain 0.20 g of the present compound (51) of the formula:

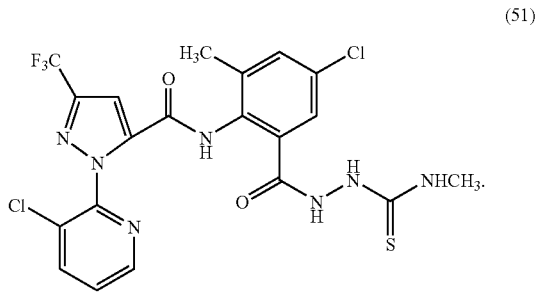

(51)

The present compound (51)

¹H-NMR (DMSO-d₆, TMS) δ (ppm): 2.20 (3H, s), 2.85 (3H, d, J=4 Hz), 7.57 (1H, s), 7.60-7.63 (2H, m), 7.68 (1H, dd, J=8 Hz, 4 Hz), 7.72 (1H, brs), 8.24 (1H, d, J=8 Hz), 8.57 (1H, d, J=4 Hz), 9.13 (1H, brs), 10.31 (1H, brs), 10.42 (1H, brs)

PREPARATION EXAMPLE 52

According to the same manner as that of Preparation Example 5 except that N-[5-chloro-2-(hydrazinocarbonyl)phenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (52) of the formula:

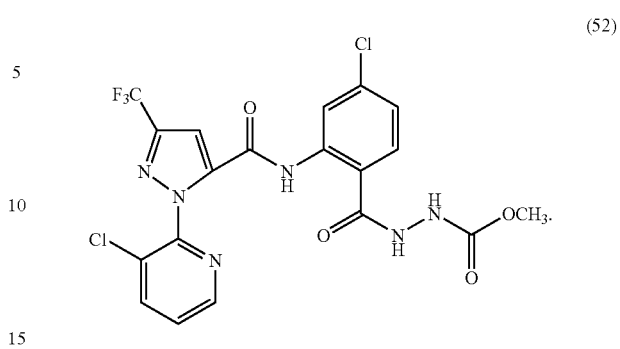

(52)

The present compound (52)

¹H-NMR (DMSO-d₆, TMS) δ (ppm): 3.60-3.77 (3H, m), 7.40 (1H, d, J=8 Hz), 7.57 (1H, s), 7.74 (1H, dd, J=8 Hz, 4 Hz), 7.85 (1H, d, J=8 Hz), 8.22 (1H, s), 8.31 (1H, d, J=8 Hz), 8.59 (1H, d, J=4 Hz), 9.49 (1H, brs), 10.77 (1H, brs), 12.04 (1H, brs)

PREPARATION EXAMPLE 53

According to the same manner as that of Preparation Example 5 except that N-[2-(hydrazinocarbonyl)-4-methylphenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (53) of the formula:

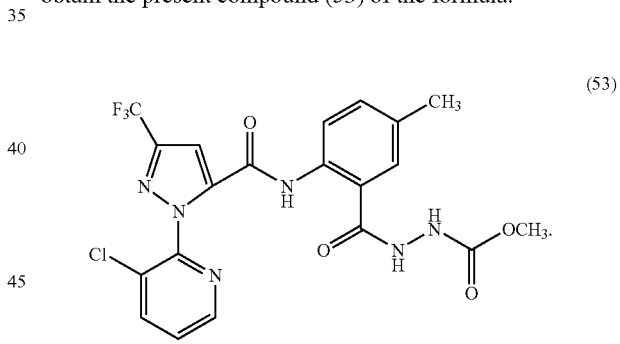

(53)

The present compound (53)

¹H-NMR (DMSO-d₆, TMS) δ (ppm): 2.32 (3H, s), 3.60-3.72 (3H, m), 7.37 (1H, d, J=8 Hz), 7.55 (1H, s), 7.65 (1H, s), 7.73 (1H, dd, J=8 Hz, 4 Hz), 8.02 (1H, d, J=8 Hz), 8.29 (1H, d, J=8 Hz), 8.57 (1H, d, J=4 Hz), 9.43 (1H, brs), 10.64 (1H, brs), 11.72 (1H, brs)

PREPARATION EXAMPLE 54

According to the same manner as that of Preparation Example 10 except that N-[2-(hydrazinocarbonyl)-4-methylphenyl]-1-(3-chloro-2-pyridinyl)-3-trifluormethyl-1H-pyrazole-5-carboxamide was used in place of N-[4-chloro-2-(hydrazinocarbonyl)-6-methylphenyl]-1-(3-chloro-2-pyridinyl)-3-trifluormethyl-1H-pyrazole-5-carboxamide to obtain the present compound (54) of the formula:

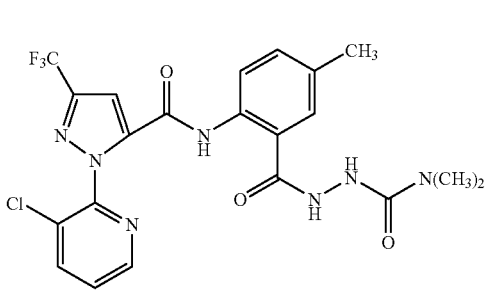

(54)

The present compound (54)

¹H-NMR (DMSO-d₆, TMS) δ (ppm): 2.31 (3H, s), 2.91 (6H, s), 7.29-7.34 (1H, m), 7.48-7.51 (1H, m), 7.70-7.79 (2H, m), 8.04-8.09 (1H, m), 8.26-8.33 (1H, m), 8.55-8.60 (1H, m), 8.75 (1H, brs), 10.24 (1H, brs), 11.30 (1H, brs)

PREPARATION EXAMPLE 55

According to the same manner as that of Preparation Example 5 except that N-[2-(hydrazinocarbonyl)-3-methylphenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (55) of the formula:

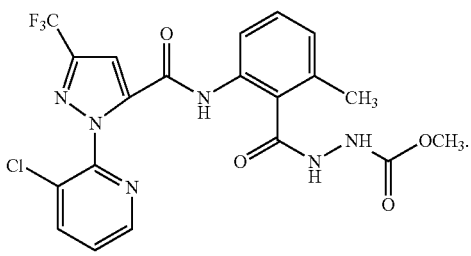

(55)

The present compound (55)

¹H-NMR (DMSO-d₆, TMS) δ (ppm): 2.32 (3H, s), 3.62-3.75 (3H, m), 7.12 (1H, d, J=8 Hz), 7.31 (1H, t, J=8 Hz), 7.61 (1H, d, J=8 Hz), 7.68-7.73 (1H, m), 7.80 (1H, s), 8.27 (1H, d, J=8 Hz), 8.56 (1H, d, J=4 Hz), 9.59 (1H, brs), 9.66 (1H, brs), 10.30 (1H, brs)

PREPARATION EXAMPLE 56

According to the same manner as that of Preparation Example 5 except that N-[4,6-dichloro-2-(hydrazinocarbonyl)phenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (56) of the formula:

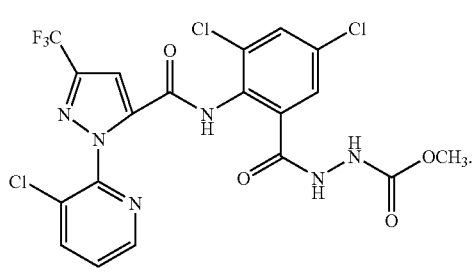

(56)

The present compound (56)

¹H-NMR (DMSO-d₆, TMS)ᵦ(ppm): 3.45-3.66 (3H, m), 7.51 (1H, s), 7.66 (1H, dd, J=8 Hz, 4 Hz), 7.76 (1H, s), 7.94 (1H, s), 8.21 (1H, d, J=8 Hz), 8.53 (1H, d, J=4 Hz), 9.37 (1H, brs), 10.27 (1H, brs), 10.64 (1H, brs)

PREPARATION EXAMPLE 57

According to the same manner as that of Preparation Example 10 except that N-[4,6-dichloro-2-(hydrazinocarbonyl)phenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluormethyl-1H-pyrazole-5-carboxamide to obtain the present compound (57) of the formula:

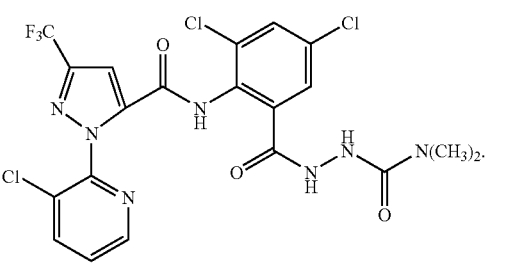

(57)

The present compound (57)

¹H-NMR (DMSO-d₆, TMS) δ (ppm): 2.85 (6H, s), 7.58 (1H, s), 7.64-7.70 (1H, m), 7.85 (1H, s), 7.90 (1H, s), 8.22 (1H, d, J=8 Hz), 8.54 (1H, d, J=4 Hz), 8.58 (1H, brs), 9.91 (1H, brs), 10.59 (1H, brs)

PREPARATION EXAMPLE 58

According to the same manner as that of Preparation Example 10 except that N-[4,6-dibromo-2-(hydrazinocarbonyl)phenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluormethyl-1H-pyrazole-5-carboxamide to obtain the present compound (58) of the formula:

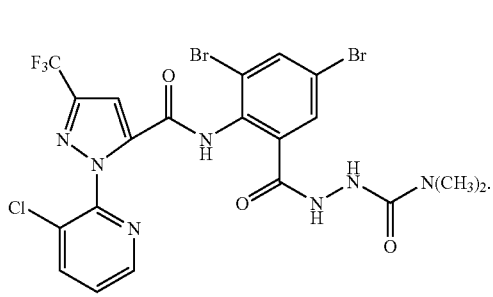

(58)

The present compound (58)

$^1$H-NMR (DMSO-d$_6$, TMS) δ (ppm): 2.84 (6H, s), 7.67 (1H, dd, J=8 Hz, 4 Hz), 7.74 (1H, s), 7.83 (1H, s), 8.13 (1H, s), 8.21 (1H, d, J=8 Hz), 8.52-8.57 (2H, m), 9.88 (1H, brs), 10.60 (1H, brs)

PREPARATION EXAMPLE 59

According to the same manner as that of Preparation Example 5 except that N-[6-bromo-4-chloro-2-(hydrazinocarbonyl)phenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (59) of the formula:

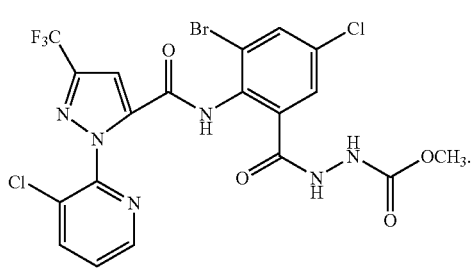

(59)

The present compound (59)

$^1$H-NMR (DMSO-d$_6$, TMS) δ (ppm): 3.55-3.65 (3H, m), 7.54 (1H, s), 7.66 (1H, dd, J=8 Hz, 4 Hz), 7.76 (1H, s), 8.06 (1H, s), 8.21 (1H, d, J=8 Hz), 8.53 (1H, d, J=4 Hz), 9.36 (1H, brs), 10.23 (1H, brs), 10.64 (1H, brs)

PREPARATION EXAMPLE 60

According to the same manner as that of Preparation Example 10 except that N-[6-bromo-4-chloro-2-(hydrazinocarbonyl)phenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluormethyl-1H-pyrazole-5-carboxamide to obtain the present compound (60) of the formula:

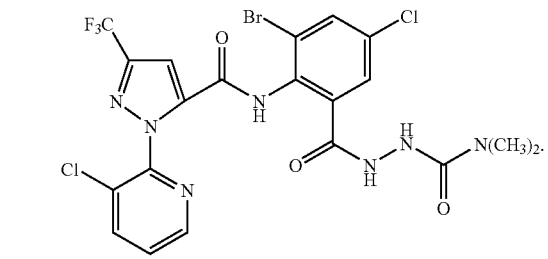

(60)

The present compound (60)

$^1$H-NMR (DMSO-d$_6$, TMS) δ (ppm): 2.84 (6H, s), 7.62 (1H, s), 7.67 (1H, dd, J=8 Hz, 4 Hz), 7.83 (1H, s), 8.02 (1H, s), 8.21 (1H, d, J=8 Hz), 8.52-8.57 (2H, m), 9.87 (1H, brs), 10.60 (1H, brs)

PREPARATION EXAMPLE 61

According to the same manner as that of Preparation Example 10 except that N-[4,6-diiodo-2-(hydrazinocarbonyl)phenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluormethyl-1H-pyrazole-5-carboxamide to obtain the present compound (61) of the formula:

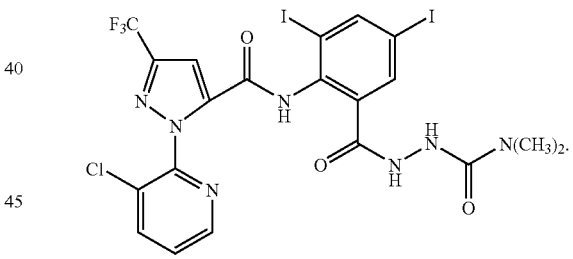

(61)

The present compound (61)

$^1$H-NMR (DMSO-d$_6$, TMS) δ (ppm): 2.83 (6H, s), 7.66 (1H, dd, J=8 Hz, 4 Hz), 7.82 (1H, s), 7.88 (1H, s), 8.21 (1H, d, J=8 Hz), 8.37 (1H, s), 8.48 (1H, brs), 8.53 (1H, d, J=4 Hz), 9.78 (1H, brs), 10.55 (1H, brs)

PREPARATION EXAMPLE 62

According to the same manner as that of Preparation Example 10 except that N-[5-chloro-2-(hydrazinocarbonyl)phenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (62) of the formula:

(62)

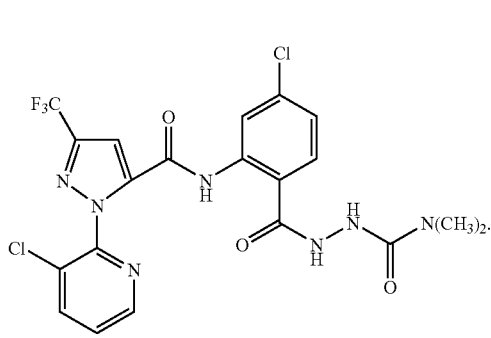

The present compound (62)

¹H-NMR (DMSO-d₆, TMS) δ (ppm): 2.91 (6H, s), 7.33-7.48 (1H, m), 7.67-7.81 (3H, m), 8.24-8.35 (2H, m), 8.56-8.63 (1H, m), 8.80 (1H, brs), 10.38 (1H, brs), 11.57 (1H, brs)

PREPARATION EXAMPLE 63

According to the same manner as that of Preparation Example 5 except that N-[2-(hydrazinocarbonyl)-5-methyphenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (63) of the formula:

(63)

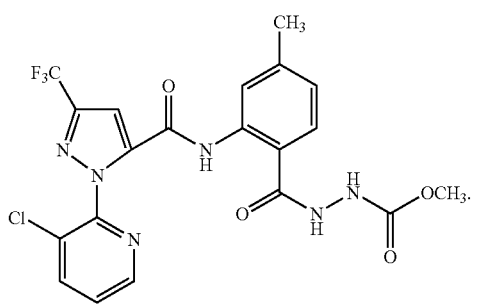

The present compound (63)

¹H-NMR (DMSO-d₆, TMS) δ (ppm): 2.32 (3H, s), 3.60-3.69 (3H, m), 7.09 (1H, d, J=8 Hz), 7.54 (1H, s), 7.71-7.79 (2H, m), 8.06 (1H, s), 8.30 (1H, d, J=8 Hz), 8.58 (1H, d, J=4 Hz), 9.41 (1H, brs), 10.64 (1H, brs), 12.19 (1H, brs)

PREPARATION EXAMPLE 64

According to the same manner as that of Preparation Example 10 except that N-[2-(hydrazinocarbonyl)-5-methylphenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluormethyl-1H-pyrazole-5-carboxamide to obtain the present compound (64) of the formula:

(64)

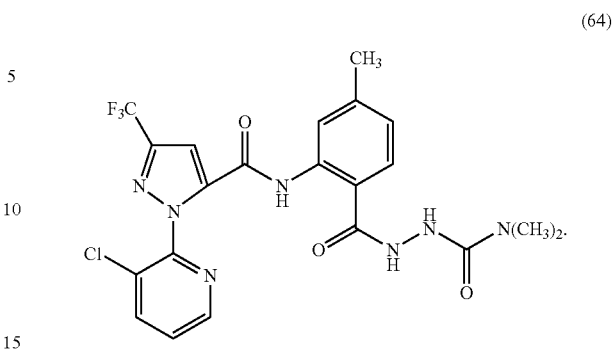

¹H-NMR (DMSO-d₆, TMS) δ (ppm): 2.31 (3H, s), 2.90 (6H, s), 7.07 (1H, d, J=8 Hz), 7.64-7.68 (2H, m), 7.74 (1H, dd, J=8 Hz, 4 Hz), 8.07 (1H, s), 8.31 (1H, d, J=8 Hz), 8.58 (1H, d, J=4 Hz), 8.67 (1H, brs), 10.28 (1H, brs), 11.82 (1H, brs)

PREPARATION EXAMPLE 65

According to the same manner as that of Preparation Example 3 except that N-(2-amino-5-chloro-3-methylbenzoyl)-N'-methoxycarbonylhydrazine was used in place of N-(2-aminobenzoyl)-N'-ethoxycarbonylhydrazine to obtain the present compound (65) of the formula:

(65)

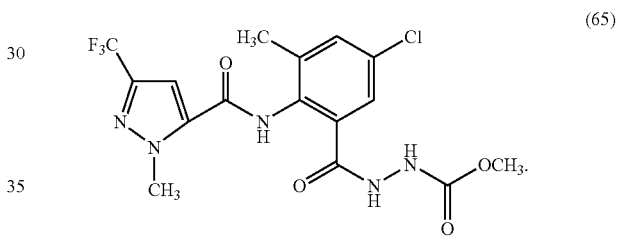

The present compound (65)

¹H-NMR (DMSO-d₆, TMS) δ (ppm): 2.25 (3H, s), 3.59 (3H, s), 4.13 (3H, s), 7.40 (1H, s), 7.44 (1H, s), 7.59 (1H, s), 9.26 (1H, brs), 10.11 (1H, brs), 10.17 (1H, brs)

PREPARATION EXAMPLE 66

A mixture of 0.28 g of N-[1-chloro-3-(hydrazinocarbonyl)-2-naphthyl]-1-(3-chloro-2-pyridinyl)-3-trifluoromethyl-1H-pyrazole-5-carboxamide, 0.06 g of methyl chloroformate and 10 ml of pyridine was stirred at room temperature for 2 hours. Water was poured into the reaction mixture, and a deposited precipitate was collected by filtration to obtain 0.08 g of the present compound (66) of the formula:

(66)

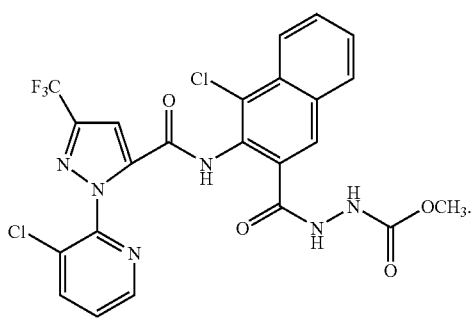

The present compound (66)

¹H-NMR (DMSO-d₆, TMS) δ (ppm): 3.60-3.68 (3H, m), 7.35-7.43 (1H, m), 7.60-7.85 (3H, m), 8.12-8.28 (3H, m), 8.52-8.60 (2H, m), 9.35 (1H, brs), 10.32 (1H, brs), 10.76 (1H, brs)

PREPARATION EXAMPLE 67

According to the same manner as that of Preparation Example 66 except that N-[1-bromo-3-(hydrazinocarbonyl)-2-naphthyl]-1-(3-chloro-2-pyridinyl)-3-trifluoromethyl-1H-pyrazole-5-carboxamide was used in place of N-[1-chloro-3-(hydrazinocarbonyl)-2-naphthyl]-1-(3-chloro-2-pyridinyl)-3-trifluoromethyl-1H-pyrazole-5-carboxamide to obtain the present compound (67) of the formula:

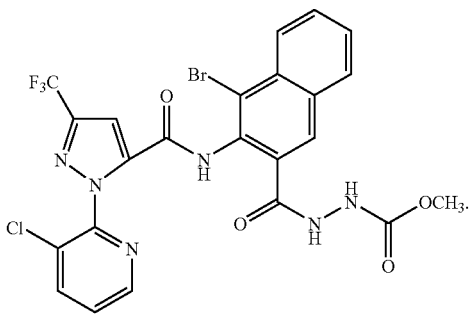

(67)

The present compound (67)

¹H-NMR (DMSO-d₆, TMS) δ (ppm): 3.58-3.69 (3H, m), 7.34-7.44 (1H, m), 7.60-7.85 (3H, m), 8.10-8.28 (3H, m), 8.50-8.62 (2H, m), 9.33 (1H, brs), 10.28 (1H, brs), 10.78 (1H, brs)

PREPARATION EXAMPLE 68

A mixture of 0.30 g of 2-[3-bromo-1-(3-chloro-2-pyridinyl)-1H-pyrazole-5-yl]-6,8-dibromo-4H-3,1-benzoxazine-4-one, 0.45 g of methyl carbazate and 10 ml of N,N-dimethylformamide was stirred at room temperature for 10 hours. Into the reaction mixture, 30 ml of water was poured, and the mixture was extracted with ethyl acetate three times. The organic layers were combined, washed with an aqueous saturated sodium chloride solution, dried over anhydrous magnesium sulfate, and concentrated under reduced pressure. The resulting residue was subjected to silica gel column chromatography to obtain 0.14 g of the present compound (68) of the formula:

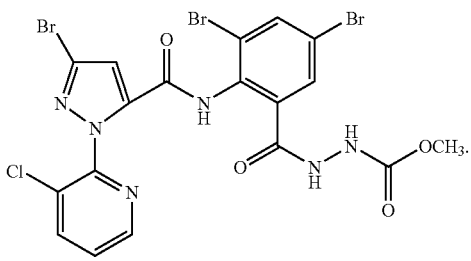

(68)

The present compound (68)

¹H-NMR (DMSO-d₆, TMS) δ (ppm): 3.44-3.66 (3H, m), 7.45 (1H, s), 7.60 (1H, dd, J=8 Hz, 4 Hz), 7.65 (1H, s), 8.14-8.18 (2H, m), 8.50 (1H, d, J=4 Hz), 9.36 (1H, brs), 10.26 (1H, brs), 10.55 (1H, brs)

PREPARATION EXAMPLE 69

According to the same manner as that of Preparation Example 5 except that N-[4-chloro-2-(hydrazinocarbonyl)-6-methyphenyl]-1-(2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (69) of the formula:

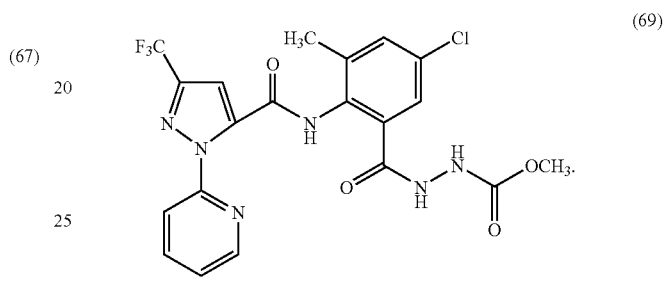

(69)

The present compound (69)

¹H-NMR (DMSO-d₆) δ (ppm): 2.33 (3H, s), 3.63 (3H, s), 7.36 (2H, s), 7.52 (1H, dd, J=8 Hz, 4 Hz), 7.58 (1H, s), 7.81 (1H, d, J=8 Hz), 8.06 (1H, t, J=8 Hz), 8.46 (1H, d, J=4 Hz), 9.33 (1H, brs), 10.19 (1H, brs), 10.34 (1H, brs)

PREPARATION EXAMPLE 70

A mixture of 0.30 g of 2-[3-bromo-1-(3-chloro-2-pyridinyl)-1H-pyrazole-5-yl]-8-bromo-6-chloro-4H-3,1-benzoxazine-4-one, 0.45 g of methyl carbazate and 10 ml of N,N-dimethylformamide was stirred at room temperature for 10 hours. Into the reaction mixture, 30 ml of water was poured and the mixture was extracted with ethyl acetate three times. The organic layers were combined, washed with an aqueous saturated sodium chloride solution, dried over anhydrous magnesium sulfate, and concentrated under reduced pressure. The resulting residue was subjected to silica gel column chromatography to obtain 0.13 g of the present compound (70) of the formula:

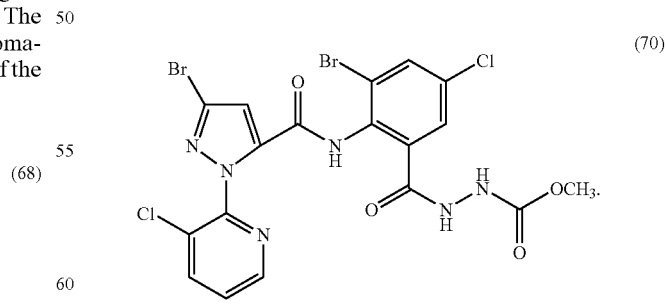

(70)

The present compound (70)

¹H-NMR (DMSO-d₆, TMS) δ (ppm): 3.48-3.62 (3H, m), 7.41 (1H, s), 7.53-7.62 (2H, m), 8.05 (1H, s), 8.16 (1H, d, J=8 Hz), 8.50 (1H, d, J=4 Hz), 9.36 (1H, brs), 10.21 (1H, brs), 10.48 (1H, brs)

PREPARATION EXAMPLE 71

A mixture of 0.30 g of 2-[3-bromo-1-(3-chloro-2-pyridinyl)-1H-pyrazole-5-yl]-8-bromo-6-methyl-4H-3,1-benzoxazine-4-one, 0.45 g of methyl carbazate and 10 ml of N,N-dimethylformamide was stirred at room temperature for 10 hours. Into the reaction mixture, 30 ml of water was poured, and the mixture was extracted with ethyl acetate three times. The organic layers were combined, washed with an aqueous saturated sodium chloride solution, dried over anhydrous magnesium sulfate, and concentrated under reduced pressure. The resulting residue was subjected to silica gel column chromatography to obtain 0.17 g of the present compound (71) of the formula:

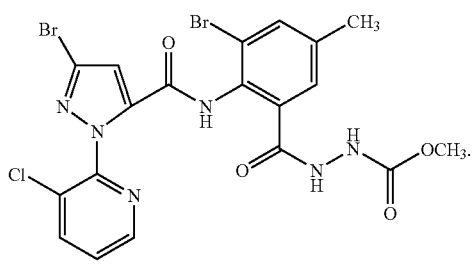
(71)

The present compound (71)
$^1$H-NMR (DMSO-$d_6$, TMS) δ (ppm): 2.34 (3H, s), 3.56-3.64 (3H, m), 7.32-7.44 (2H, m), 7.59 (1H, dd, J=8 Hz, 4 Hz), 7.66-7.71 (1H, m), 8.15 (1H, d, J=8 Hz), 8.49 (1H, d, J=4 Hz), 9.27 (1H, brs), 10.01 (1H, brs), 10.31 (1H, brs)

PREPARATION EXAMPLE 72

A mixture of 0.21 g of 2-[3-bromo-1-(3-chloro-2-pyridinyl)-1H-pyrazole-5-yl]-8-chloro-4H-3,1-benzoxazine-4-one, 0.9 g of methyl carbazate and 10 ml of N,N-dimethylformamide was stirred at room temperature for 10 hours. Water was poured into the reaction mixture, and this was extracted with ethyl acetate. The organic layer was washed with water, dried over sodium sulfate, and concentrated under reduced pressure. The resulting residue was subjected to silica gel column chromatography to obtain 0.10 g of the present compound (72) of the formula:

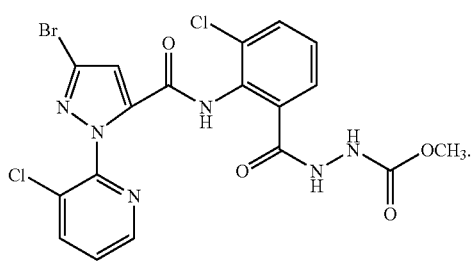
(72)

The present compound (72)
$^1$H-NMR (DMSO-$d_6$, TMS) δ (ppm): 3.44-3.65 (3H, m), 7.40-7.54 (3H, m), 7.59 (1H, dd, J=8 Hz, 4 Hz), 7.68 (1H, d, J=8 Hz), 8.15 (1H, d, J=8 Hz), 8.49 (1H, d, J=4 Hz), 9.29 (1H, brs), 10.11 (1H, brs), 10.39 (1H, brs)

PREPARATION EXAMPLE 73

According to the same manner as that of Preparation Example 5 except that N-[4-chloro-2-(hydrazinocarbonyl)-6-methyphenyl]-1-phenyl-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (73) of the formula:

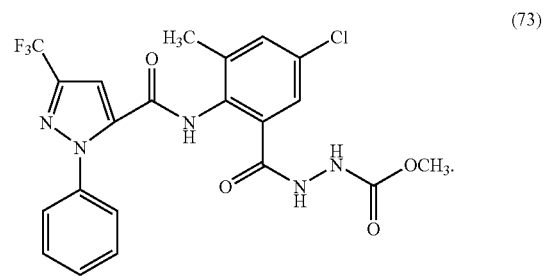
(73)

The present compound (73)
$^1$H-NMR (DMSO-$d_6$) δ (ppm): 2.18 (3H, s), 3.61 (3H, s), 7.37 (1H, s), 7.49-7.55 (7H, m), 9.31 (1H, brs), 10.22 (1H, brs), 10.30 (1H, brs)

PREPARATION EXAMPLE 74

According to the same manner as that of Preparation Example 72 except that 6-bromo-2-[1-(3-chloro-2-pyridinyl)-3-trifluoromethyl-1H-pyrazole-5-yl]-8-methyl-4H-3,1-benzoxazine-4-one was used in place of 2-[3-bromo-1-(3-chloro-2-pyridinyl)-1H-pyrazole-5-yl]-8-chloro-4H-3,1-benzoxazine-4-one to obtain the present compound (74) of the formula:

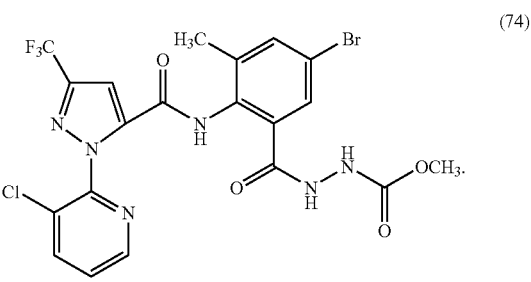
(74)

The present compound (74)
$^1$H-NMR (DMSO-$d_6$, TMS) δ (ppm): 2.15 (3H, s), 3.56-3.65 (3H, m), 7.47-7.55 (1H, m), 7.62-7.75 (3H, m), 8.22 (1H, d, J=8 Hz), 8.53 (1H, d, J=4 Hz), 9.31 (1H, brs), 10.17 (1H, brs), 10.38 (1H, brs)

PREPARATION EXAMPLE 75

According to the same manner as that of Preparation Example 72 except that 2-[1-(3-chloro-2-pyridinyl)-3-trifluoromethyl-1H-pyrazole-5-yl]-6-iodo-8-methyl-4H-3,1-benzoxazine-4-one was used in place of 2-[3-bromo-1-(3- chloro-2-pyridinyl)-1H-pyrazole-5-yl]-8-chloro-4H-3,1-benzoxazine-4-one to obtain the present compound (75) of the formula:.

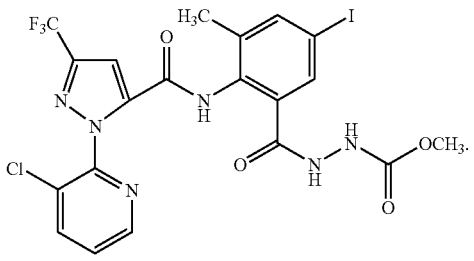

(75)

The present compound (75)

¹H-NMR (DMSO-d₆, TMS) δ (ppm): 2.12 (3H, s), 3.55-3.66 (3H, m), 7.63-7.72 (3H, m), 7.83 (1H, s), 8.22 (1H, d, J=8 Hz), 8.53 (1H, d, J=4 Hz), 9.28 (1H, brs), 10.14 (1H, brs), 10.35 (1H, brs)

PREPARATION EXAMPLE 76

A mixture of 0.18 g of N-[4-chloro-2-(hydrazinocarbonyl)-6-methylphenyl]-3-(2-chlorophenyl)-1-methyl-1H-pyrazole-4-carboxamide, 45 mg of methyl chloroformate, 68 mg of pyridine and 5 ml of acetonitrile was prepared under ice-cooling, and the mixture was stirred at room temperature for 0.5 hour. Water was poured into the reaction mixture, and the mixture was extracted with ethyl acetate. The organic layer was washed with water, dried over anhydrous sodium sulfate, and concentrated under reduce pressure. The resulting residue was subjected to silica gel column chromatography to obtain 0.12 g of the present compound (76) of the formula:

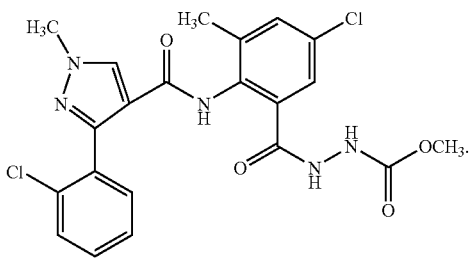

(76)

The present compound (76)

¹H-NMR (DMSO-d₆) δ (ppm): 2.13 (3H, s), 3.37-3.67 (6H, m), 7.37 (1H, brs), 7.42-7.52 (4H, m), 7.60 (1H, d, J=8 Hz), 8.13 (1H, s), 9.28-9.37 (2H, m), 10.13 (1H, brs)

PREPARATION EXAMPLE 77

According to the same manner as that of Preparation Example (76) except that N-[4-chloro-2-(hydrazinocarbonyl)-6-methylphenyl]-5-(2-chlorophenyl)-1-methyl-1H-pyrazole-4-carboxamide was used in place of N-[4-chloro-2-(hydrazinocarbonyl)-6-methylphenyl]-3-(2-chlorophenyl)-1-methyl-1H-pyrazole-4-carboxamide to obtain the present compound (77) of the formula:

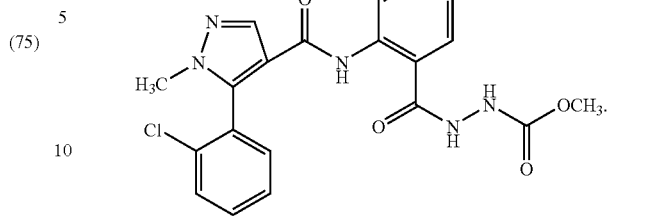

(77)

The present compound (77)

¹H-NMR (DMSO-d₆) δ (ppm): 2.17 (3H, s), 3.46-3.62 (3H, m), 3.94 (3H, s), 7.32-7.41 (4H, m), 7.44-7.46 (1H, m), 7.50 (1H, s), 8.36 (1H, s), 9.30-9.34 (2H, m), 10.17 (1H, brs)

PREPARATION EXAMPLE 78

According to the same manner as that of Preparation Example 72 except that 2-[3-bromo-1-(3-chloro-2-pyridinyl)-1H-pyrazole-5-yl]-6-chloro-8-methoxy-4H-3,1-benzoxazine-4-one was used in place of 2-[3-bromo-1-(3-chloro-2-pyridinyl)-1H-pyrazole-5-yl]-8-chloro-4H-3,1-benzoxazine-4-one to obtain the present compound (78) of the formula:

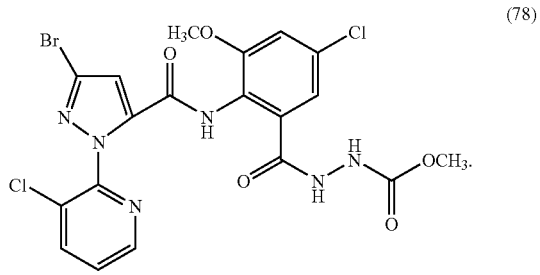

(78)

The present compound (78)

¹H-NMR (DMSO-d₆, TMS) δ (ppm): 3.56-3.64 (3H, m), 3.77-3.80 (3H, m), 7.12 (1H, brs), 7.32 (1H, brs), 7.38 (1H, brs), 7.59 (1H, dd, J=8 Hz, 4 Hz), 8.15 (1H, d, J=8 Hz), 8.49 (1H, d, J=4 Hz), 9.28 (1H, brs), 9.95 (1H, brs), 10.07 (1H, brs)

PREPARATION EXAMPLE 79

According to the same manner as that of Preparation Example 72 except that 2-[3-bromo-1-(3-chloro-2-pyridinyl)-1H-pyrazole-5-yl]-6-chloro-8-iodo-4H-3,1-benzoxazine-4-one was used in place of 2-[3-bromo-1-(3-chloro-2-pyridinyl)-1H-pyrazole-5-yl]-8-chloro-4H-3,1-benzoxazine-4-one to obtain the present compound (79) of the formula:

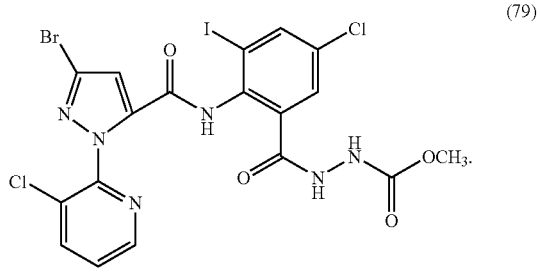

(79)

The present compound (79)

¹H-NMR (DMSO-d₆, TMS) δ (ppm): 3.56-3.64 (3H, m), 7.43 (1H, s), 7.53 (1H, s), 7.60 (1H, dd, J=8 Hz, 4 Hz), 8.12-8.19 (2H, m), 8.50 (1H, d, J=4 Hz), 9.34 (1H, brs), 10.16 (1H, brs), 10.47 (1H, brs)

PREPARATION EXAMPLE 80

According to the same manner as that of Preparation Example 72 except that 2-[3-bromo-1-(3-chloro-2-pyridinyl)-1H-pyrazole-5-yl]-8-methoxy-4H-3,1-benzoxazine-4-one was used in place of 2-[3-bromo-1-(3-chloro-2-pyridinyl)-1H-pyrazole-5-yl]-8-chloro-4H-3,1-benzoxazine-4-one to obtain the present compound (80) of the formula:

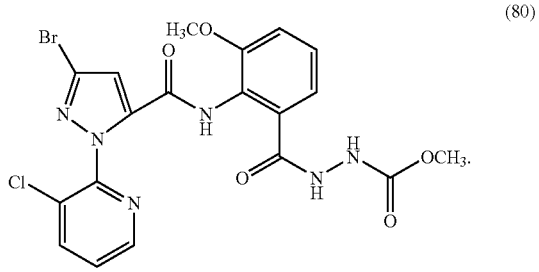

(80)

The present compound (80)

¹H-NMR (DMSO-d₆, TMS) δ (ppm): 3.52-3.64 (3H, m), 3.74 (3H, s), 7.07-7.14 (1H, m), 7.21 (1H, d, J=8 Hz), 7.31-7.42 (2H, m), 7.59 (1H, dd, J=8 Hz, 4 Hz), 8.15 (1H, d, J=8 Hz), 8.49 (1H, d, J=4 Hz), 9.21 (1H, brs), 9.87 (1H, brs), 9.92 (1H, brs)

PREPARATION EXAMPLE 81

According to the same manner as that of Preparation Example 72 except that 2-[3-bromo-1-(3-chloro-2-pyridinyl)-1H-pyrazole-5-yl]-8-trifluoromethyl-4H-3,1-benzoxazine-4-one was used in place of 2-[3-bromo-1-(3-chloro-2-pyridinyl)-1H-pyrazole-5-yl]-8-chloro-4H-3,1-benzoxazine-4-one to obtain the present compound (81) of the formula:

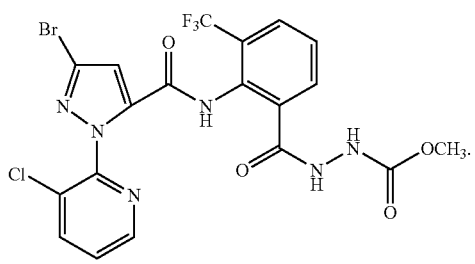

(81)

The present compound (81)

¹H-NMR (DMSO-d₆, TMS) δ (ppm): 3.46-3.69 (3H, m), 7.41 (1H, s), 7.59 (1H, dd, J=8 Hz, 4 Hz), 7.68 (1H, t, J=8 Hz), 7.77-7.87 (1H, m), 7.90-7.97 (1H, m), 8.14 (1H, d, J=8 Hz), 8.48 (1H, d, J=4 Hz), 9.32 (1H, brs), 10.14 (1H, brs), 10.48 (1H, brs)

PREPARATION EXAMPLE 82

To a mixture of 0.25 g of 3-chloro-2-(3-trifluoromethyl-1H-1,2,4-triazol-1-yl)pyridine and 5 ml of tetrahydrofuran was added dropwise 0.50 ml of a 2.0M lithium diisopropylamide solution in heptane/tetrahydrofuran/ethylbenzene at −78° C. and the mixture was stirred at −78° C. for 15 minutes. Carbon dioxide was introduced into the mixture at such a rate that an inner temperature was maintained at −60° C. or lower and, after the mixture turned yellow, the mixture was further stirred at −78° C. for 10 minutes. The temperature of the reaction mixture was raised to room temperature, followed by concentration. A 2N aqueous sodium hydroxide solution was added to adjust the pH of the aqueous layer to 10 to 12, the layers were separated, and the organic layer was extracted with a 0.5N aqueous sodium hydroxide solution. The aqueous layers were combined, and washed with chloroform, and 2N hydrochloric acid was added so that the pH of the aqueous layer became about 3, followed by extraction with ethyl acetate three times. The organic layers were combined, washed with an aqueous saturated sodium chloride solution, dried over magnesium sulfate, and concentrated under reduced pressure to obtain 0.13 g of crude 1-(3-chloro-2-pyridinyl)-3-trifluoromethyl-1H-1,2,4-triazole 5-carboxylic acid of the formula:

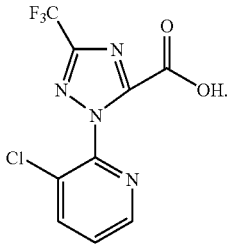

A mixture of 0.13 g of the resulting crude 1-(3-chloro-2-pyridinyl)-3-trifluoromethyl-1H-1,2,4-triazole 5-carboxylic acid and 0.10 ml of thionyl chloride was heated under reflux in 10 ml of acetonitrile for 2 hours. The reaction mixture was allowed to cool to room temperature, and concentrated under reduced pressure, the resulting residue was dissolved in 10 ml of acetonitrile, 0.11 g of N-(2-amino-5-chloro-3-methylbenzoyl)-N'-methoxycarbonylhydrazine and 0.10 ml of diisopropylethylamine were added, and the mixture was stirred at room temperature for 16 hours. Water was poured into the reaction mixture, and the mixture was extracted with ethyl acetate two times. The organic layers were combined, washed with an aqueous saturated sodium chloride solution, dried over anhydrous magnesium sulfate, and concentrated under reduced pressure. The resulting residue was subjected to silica gel column chromatography to obtain 12 mg of the present compound (82) of the formula:

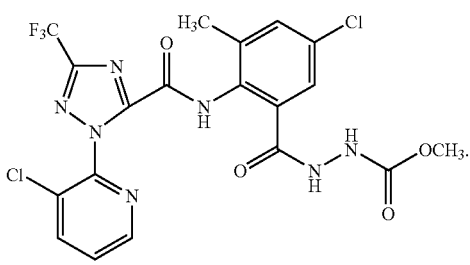

(82)

The present compound (82)

¹H-NMR (DMSO-d₆, TMS) δ (ppm): 2.31 (3H, s), 3.64 (3H, s), 7.40 (1H, s), 7.60 (1H, s), 7.90 (1H, brs), 8.77 (1H, d, J=7 Hz), 9.33 (1H, brs), 9.50 (1H, brs), 10.27 (1H, brs), 10.44 (1H, brs)

PREPARATION EXAMPLE 83

According to the same manner as that of Preparation Example 5 except that N-[4-chloro-2-(hydrazinocarbonyl)-6-methyphenyl]-1-ethyl-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (83) of the formula:

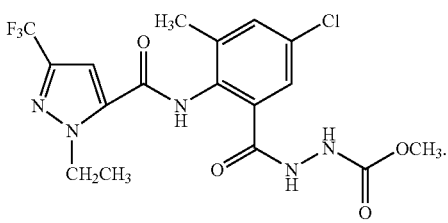

(83)

The present compound (83)

¹H-NMR (DMSO-d₆) δ (ppm): 1.37 (3H, t, J=7 Hz), 2.26 (3H, s), 3.60 (3H, s), 4.55 (2H, q, J=7 Hz), 7.41 (2H, s), 7.58 (1H, s), 9.26 (1H, brs), 10.12 (1H, brs), 10.18 (1H, brs)

PREPARATION EXAMPLE 84

According to the same manner as that of Preparation Example 76 except that 1-tert-butyl-N-[4-chloro-2-(hydrazinocarbonyl)-6-methylphenyl]-5-(2-chlorophenyl)-1H-pyrazole-4-carboxamide was used in place of N-[4-chloro-2-(hydrazinocarbonyl)-6-methylphenyl]-3-(2-chlorophenyl)-1-methyl-1H-pyrazole-4-carboxamide to obtain the present compound (84) of the formula:

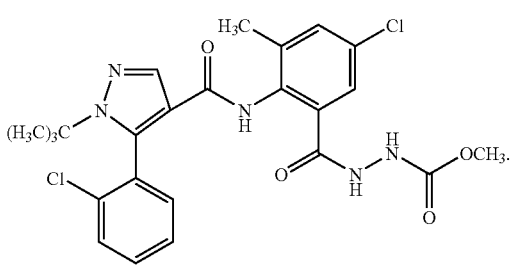

(84)

The present compound (84)

¹H-NMR (DMSO-d₆) δ (ppm): 1.39 (9H, s), 2.05 (3H, s), 3.47-3.62 (3H, m), 7.36-7.53 (6H, m), 8.10 (1H, s), 9.19-9.26 (2H, m), 10.12 (1H, brs)

PREPARATION EXAMPLE 85

According to the same manner as that of Preparation Example 72 except that 2-[3-bromo-1-(3-chloro-2-pyridinyl)-1H-pyrazole-5-yl]-7-chloro-8-methyl-4H-3,1-benzoxazine-4-one was used in place of 2-[3-bromo-1-(3-chloro-2-pyridinyl)-1H-pyrazole-5-yl]-8-chloro-4H-3,1-benzoxazine-4-one to obtain the present compound (85) of the formula:

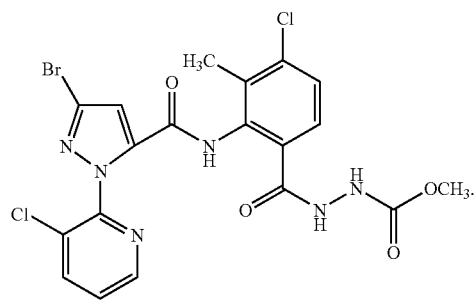

(85)

The present compound (85)

¹H-NMR (DMSO-d₆, TMS) δ (ppm): 2.17 (3H, s), 3.60-3.65 (3H, m), 7.35-7.43 (2H, m), 7.54 (1H, d, J=8 Hz), 7.61 (1H, dd, J=8 Hz, 4 Hz), 8.17 (1H, d, J=8 Hz), 8.50 (1H, d, J=4 Hz), 9.28 (1H, brs), 10.14 (1H, brs), 10.41 (1H, brs)

PREPARATION EXAMPLE 86

According to the same manner as that of Preparation Example 5 except that N-[4-chloro-2-(hydrazinocarbonyl)-6-methyphenyl]-1-isopropyl-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (86) of the formula:

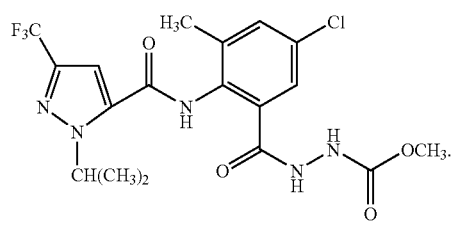

(86)

The present compound (86)

¹H-NMR (DMSO-d₆) δ (ppm): 1.43 (6H, d, J=6 Hz), 2.26 (3H, s), 3.60 (3H, s), 5.41-5.45 (1H, m), 7.35 (1H, s), 7.40 (1H, s), 7.59 (1H, s), 9.26 (1H, brs), 10.10 (1H, brs), 10.17 (1H, brs)

PREPARATION EXAMPLE 87

According to the same manner as that of Preparation Example 72 except that 2-[3-bromo-1-(3-chloro-2-pyridinyl)-1H-pyrazole-5-yl]-5,8-dichloro-4H-3,1-benzoxazine-4-one was used in place of 2-[3-bromo-1-(3-chloro-2-pyridinyl)-1H-pyrazole-5-yl]-8-chloro-4H-3,1-benzoxazine-4-one to obtain the present compound (87) of the formula:

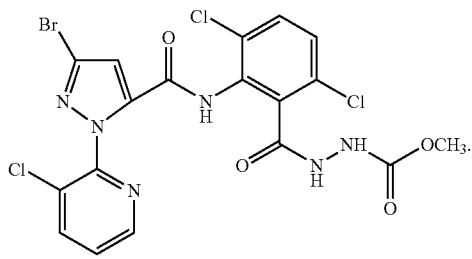

(87)

The present compound (87)
$^1$H-NMR (DMSO-d$_6$, TMS) δ (ppm): 3.50-3.68 (3H, m), 7.47 (1H, s), 7.52-7.65 (3H, m), 8.17 (1H, d, J=8 Hz), 8.49 (1H, d, J=4 Hz), 9.43 (1H, brs), 10.17 (1H, brs), 10.47 (1H, brs)

PREPARATION EXAMPLE 88

According to the same manner as that of Preparation Example 72 except that 2-[3-bromo-1-(3-chloro-2-pyridinyl)-11H-pyrazole-5-yl]-5-chloro-8-methyl-4H-3,1-benzoxazine-4-one was used in place of 2-[3-bromo-1-(3-chloro-2-pyridinyl)-1H-pyrazole-5-yl]-8-chloro-4H-3,1-benzoxazine-4-one to obtain the present compound (88) of the formula:

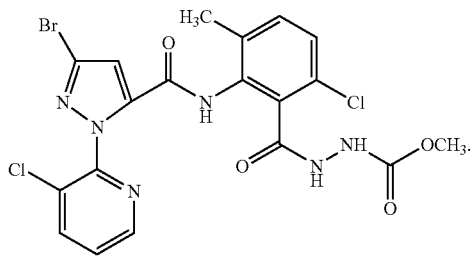

(88)

The present compound (88)
$^1$H-NMR (DMSO-d$_6$, TMS) δ (ppm): 2.09 (3H, s), 3.51-3.68 (3H, m), 7.31-7.45 (3H, m), 7.61 (1H, dd, J=8 Hz, 4 Hz), 8.19 (1H, d, J=8 Hz), 8.49 (1H, d, J=4 Hz), 9.43 (1H, brs), 10.04 (1H, brs), 10.13 (1H, brs)

PREPARATION EXAMPLE 89

According to the same manner as that of Preparation Example 5 except that N-[4-chloro-2-(hydrazinocarbonyl)-6-methyphenyl]-1-tert-butyl-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (89) of the formula:

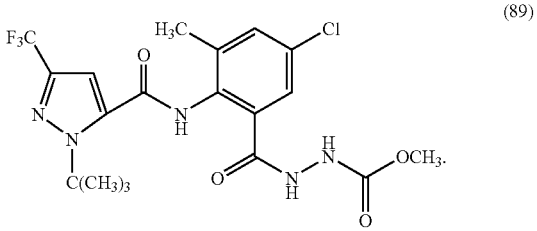

(89)

The present compound (89)
$^1$H-NMR (DMSO-d$_6$) δ (ppm): 1.67 (9H, s), 2.28 (3H, s), 3.64 (3H, s), 7.11 (1H, s), 7.42 (1H, s), 7.55 (1H, s), 9.29 (1H, brs), 10.18 (1H, brs), 10.23 (1H, brs)

PREPARATION EXAMPLE 90

According to the same manner as that of Preparation Example 5 except that N-[4-chloro-2-(hydrazinocarbonyl)-6-methylphenyl]-1-tert-butyl-5-trifluoromethyl-1H-pyrazole-3-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (90) of the formula:

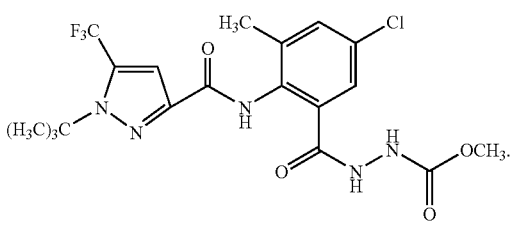

(90)

The present compound (90)
$^1$H-NMR (DMSO-d$_6$) δ (ppm): 1.69 (9H, s), 2.26 (3H, s), 3.57 (3H, s), 7.43 (1H, s), 7.62 (1H, d, J=2 Hz), 7.82 (1H, d, J=2 Hz), 9.30 (1H, brs), 10.23 (1H, brs), 10.56 (1H, brs)

PREPARATION EXAMPLE 91

According to the same manner as that of Preparation Example 72 except that 2-[3-bromo-1-(3-chloro-2-pyridinyl)-1H-pyrazole-5-yl]-8-methyl-4H-3,1-benzoxazine-4-one was used in place of 2-[3-bromo-1-(3-chloro-2-pyridinyl)-1H-pyrazole-5-yl]-8-chloro-4H-3,1-benzoxazine-4-one to obtain the present compound (91) of the formula:

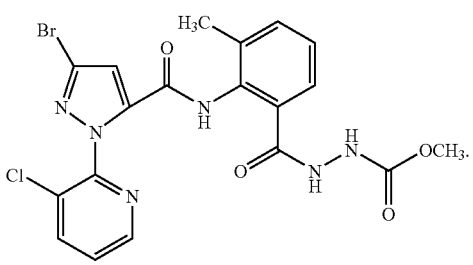

(91)

The present compound (91)

¹H-NMR (DMSO-d₆, TMS) δ (ppm): 2.15 (3H, s), 3.55-3.67 (3H, m), 7.25-7.45 (3H, m), 7.61 (1H, dd, J=8 Hz, 4 Hz), 7.94-7.97 (1H, m), 8.17 (1H, d, J=8 Hz), 8.48-8.53 (1H, m), 9.25 (1H, brs), 10.04 (1H, brs), 10.20 (1H, brs)

PREPARATION EXAMPLE 92

According to the same manner as that of Preparation Example 72 except that 8-bromo-2-[3-bromo-1-(3-chloro-2-pyridinyl)-1H-pyrazole-5-yl]-4H-3,1-benzoxazine-4-one was used in place of 2-[3-bromo-1-(3-chloro-2-pyridinyl)-1H-pyrazole-5-yl]-8-chloro-4H-3,1-benzoxazine-4-one to obtain the present compound (92) of the formula:

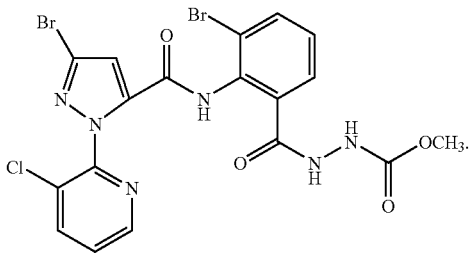

(92)

The present compound (92)

¹H-NMR (DMSO-d₆, TMS) δ (ppm): 3.45-3.67 (3H, m), 7.34-7.44 (2H, m), 7.53 (1H, s), 7.60 (1H, dd, J=8 Hz, 4 Hz), 7.84 (1H, d, J=8 Hz), 8.15 (1H, d, J=8 Hz), 8.50 (1H, d, J=4 Hz), 9.29 (1H, brs), 10.08 (1H, brs), 10.42 (1H, brs)

PREPARATION EXAMPLE 93

A mixture of 0.20 g of 4-bromo-N-[4-chloro-2-(hydrazinocarbonyl)-6-methylphenyl]-1-(3-chloro-2-pyridinyl)-1H-pyrrole-2-carboxamide, 0.05 g of methyl chloroformate and 0.07 ml of pyridine in N,N-dimethylformamide was stirred at room temperature for 8 hours. Water was poured into the reaction mixture, and a deposited precipitate was collected by filtration to obtain 0.16 g of the present compound (93) of the formula:

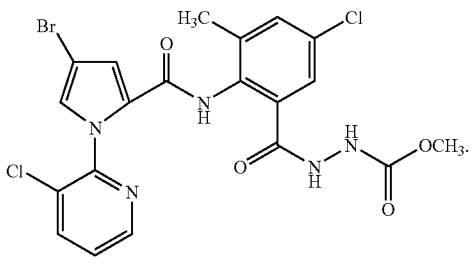

(93)

The present compound (93)

¹H-NMR (DMSO-d₆) δ (ppm): 2.16 (3H, s), 3.63 (3H, s), 7.23 (1H, s), 7.41 (1H, d, J=2 Hz), 7.48-7.51 (3H, m), 8.05 (1H, dd, J=8 Hz, 2 Hz), 8.43 (1H, dd, J=5 Hz, 2 Hz) 9.31 (1H, brs), 9.75 (1H, brs), 10.12 (1H, brs)

PREPARATION EXAMPLE 94

A mixture of 0.26 g of 3-bromo-N-[4-chloro-2-(N'-isopropylhydrazinocarbonyl)-6-methylphenyl]-1-(3-chloro-2-pyridinyl)-1H-pyrazole-5-carboxamide, 0.06 ml of methyl chloroformate and 2 ml of pyridine was stirred at room temperature for 1.5 hours. Water was poured into the reaction mixture, and the mixture was extracted with methyl t-butyl ether three times. The organic layers were combined, washed successively with 1N hydrochloric acid, an aqueous saturated sodium bicarbonate solution and an aqueous saturated sodium chloride solution, dried over anhydrous magnesium sulfate, and concentrated under reduced pressure. The resulting residue was subjected to silica gel column chromatography to obtain 0.18 g of the present compound (94) of the formula:

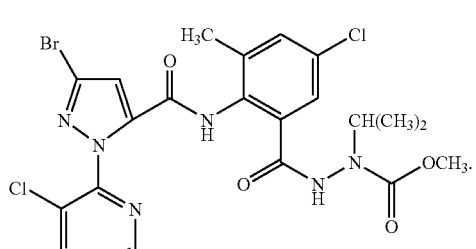

(94)

The present compound (94)

¹H-NMR (DMSO-d₆, 80° C.) δ (ppm): 1.03 (6H, d, J=7 Hz), 2.18 (3H, s), 3.53 (3H, s), 4.24 (1H, hept., J=7 Hz), 7.29 (1H, s), 7.37 (1H, d, J=2 Hz), 7.49 (1H, d, J=2 Hz), 7.57 (1H, dd, J=8 Hz, 4 Hz), 8.10 (1H, dd, J=8 Hz, 1Hz), 8.45 (1H, dd, J=4 Hz, 1Hz), 9.92 (1H, s), 9.98 (1H, s)

PREPARATION EXAMPLE 95

To a mixture of 4.11 g of the present compound (34), 1.45 ml of triethylamine and 80 ml of tetrahydrofuran was added dropwise 0.69 ml of methyl chloroformate under ice-cooling. After the resulting mixture was stirred at room temperature for 1 hour, water was poured into the reaction mixture, and the mixture was extracted with ethyl acetate three times. The organic layers were combined, washed with an aqueous saturated sodium chloride solution, dried over anhydrous magnesium sulfate, and concentrated under reduced pressure. The resulting residue was subjected to silica gel column chromatography to obtain 2.66 g of the present compound (95) of the formula:

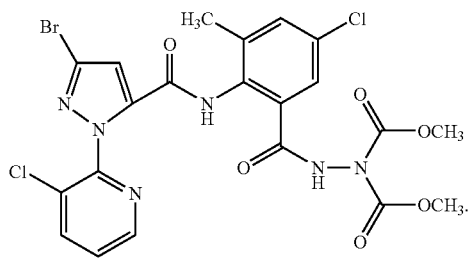

(95)

The present compound (95)

¹H-NMR (CDCl₃, TMS)δ(ppm): 2.22 (3H, s), 3.82 (6H, s), 6.99 (1H, s), 7.34-7.37 (2H, m), 7.41 (1H, d, J=2 Hz), 7.88 (1H, dd, J=8 Hz, 1Hz), 8.37 (1H, dd, J=4 Hz, 1Hz), 8.43 (1H, s), 9.21 (1H, s)

PREPARATION EXAMPLE 96

A mixture of 0.11 g of N-[4-chloro-2-(hydrazinocarbonyl)-6-methylphenyl]-1-(3-chloro-2-pyridinyl)-3-iodo-1H-pyrazole-5-carboxamide, 0.095 ml of methyl chloroformate and 2 ml of pyridine were mixed, and the mixture was stirred at room temperature for 2.75 hours. Water and toluene were poured into the reaction mixture, followed by concentration under reduced pressure. The residue was distributed between water and ethyl acetate, and the organic layer was washed with an aqueous saturated sodium chloride solution, dried over anhydrous magnesium sulfate, and concentrated under reduced pressure. The resulting residue was subjected to silica gel column chromatography to obtain 0.11 g of the present compound (96) of the formula:

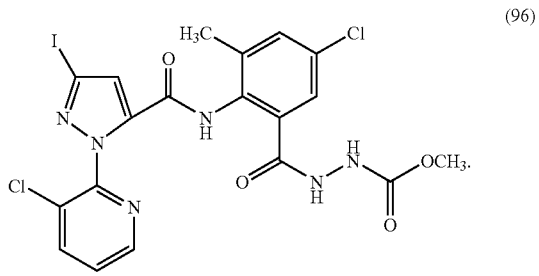

(96)

The present compound (96)
$^1$H-NMR (DMSO-$d_6$) δ (ppm): 2.15 (3H, s), 3.63 (3H, brs), 7.40 (2H, brs), 7.54 (1H, s), 7.59 (1H, dd, J=8 Hz, 4 Hz), 8.15 (1H, d, J=8 Hz), 8.49 (1H, d, J=4 Hz), 9.31 (1H, brs), 10.16 (2H, brs)

PREPARATION EXAMPLE 97

A mixture of 0.27 g of 4-bromo-N-[4-chloro-2-(hydrazinocarbonyl)-6-methylphenyl]-1-(3-chloro-2-pyridinyl)-1H-pyrazole-5-carboxamide, 0.13 ml of methyl chloroformate and 3 ml of pyridine was stirred at room temperature for 1.75 hours. Water and toluene were poured into the reaction mixture, followed by concentration under reduced pressure. The residue was distributed between water and ethyl acetate, and the organic layer was washed with an aqueous saturated sodium chloride solution, dried over anhydrous magnesium sulfate, and concentrated under reduced pressure. The resulting residue was subjected to silica gel column chromatography to obtain 0.24 g of the present compound (97) of the formula:

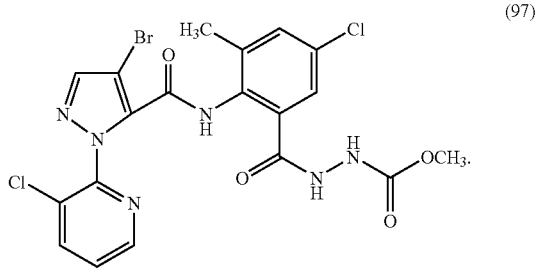

(97)

The present compound (97)
$^1$H-NMR (DMSO-$d_6$, 80° C.) δ (ppm): 2.14 (3H, s), 3.59 (3H, brs), 7.43 (1H, s), 7.48 (1H, s), 7.57 (1H, dd, J=8 Hz, 4 Hz), 8.03 (1H, s), 8.12 (1H, d, J=8 Hz), 8.47 (1H, d, J=4 Hz), 8.94 (1H, brs), 9.81 (1H, brs), 10.11 (1H, brs)

PREPARATION EXAMPLE 98

A mixture of 0.30 g of N-[4-chloro-2-(hydrazinocarbonyl)-6-methylphenyl]-1-(3-chloro-2-pyridinyl)-3-phenyl-1H-pyrazole-5-carboxamide, 0.15 ml of methyl chloroformate and 3 ml of pyridine was stirred at room temperature for 1.75 hours. Water and toluene were poured into the reaction mixture, followed by the concentration under reduced pressure. The residue was distributed between water and ethyl acetate, and the organic layer was washed with an aqueous saturated sodium chloride solution, dried over anhydrous magnesium sulfate, and concentrated under reduced pressure. The resulting residue was subjected to silica gel column chromatography to obtain 0.30 g of the present compound (98) of the formula:

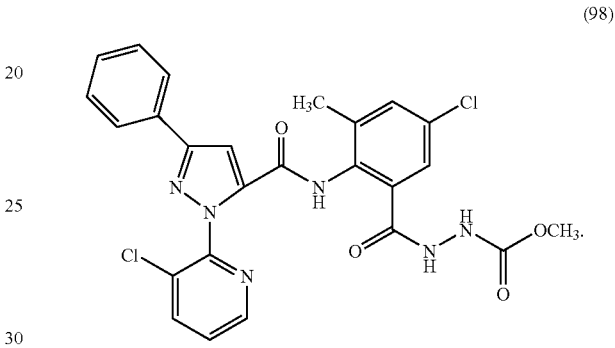

(98)

The present compound (98)
$^1$H-NMR (DMSO-$d_6$) δ (ppm): 2.19 (3H, s), 3.62 (3H, brs), 7.42-7.52 (4H, m), 7.55 (1H, brs), 7.60 (1H, dd, J=8 Hz, 4 Hz), 7.70 (1H, brs), 7.88 (2H, d, J=7 Hz), 8.17 (1H, dd, J=8 Hz, 1Hz), 8.32 (1H, dd, J=4 Hz, 1Hz), 9.34 (1H, brs), 10.19 (2H, brs)

PREPARATION EXAMPLE 99

A mixture of 0.27 g of N-[4-chloro-2-(hydrazinocarbonyl)-6-methylphenyl]-1-(3-chloro-2-pyridinyl)-3-methylthio-1H-pyrazole-5-carboxamide, 0.14 ml of methyl chloroformate and 3 ml of pyridine was stirred at room temperature for 2 hours. Water and toluene were poured into the reaction mixture, followed by concentration under reduced pressure. The residue was distributed between water and ethyl acetate, and the organic layer was washed with an aqueous saturated sodium chloride solution, dried over anhydrous magnesium sulfate, and concentrated under reduced pressure. The resulting residue was subjected to silica gel column chromatography to obtain 0.14 g of the present compound (99) of the formula:

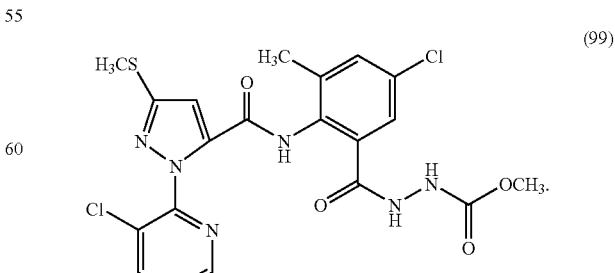

(99)

The present compound (99)
¹H-NMR (DMSO-d₆) δ (ppm): 2.16 (3H, s), 2.54 (3H, s) 3.62 (3H, brs), 7.20 (1H, s), 7.38 (1H, brs), 7.54-7.58 (2H, m), 8.13 (1H, dd, J=8 Hz, 1Hz), 8.48 (1H, dd, J=4 Hz, 1.5 Hz), 9.32 (1H, brs), 10.11 (1H, s), 10.14 (1H, s)

PREPARATION EXAMPLE 100

A mixture of 0.20 g of 6-chloro-2-[1-(3-chloro-2-pyrizinyl)-3-methylsulfonyl-1H-pyrazol-5-yl]-8-methyl-4H-3,1-benzoxazine-4-one, 0.40 g of methyl carbazate and 8 ml of N,N-dimethylformamide was stirred at room temperature for 22 hours. Water was poured into the reaction mixture, the mixture was extracted with methyl t-butyl ether three times. The organic layers were combined, washed successively with water and an aqueous saturated sodium chloride solution, dried over anhydrous magnesium sulfate, and concentrated under reduced pressure. The resulting residue was subjected to silica gel column chromatography to obtain 0.13 g of the present compound (100) of the formula:

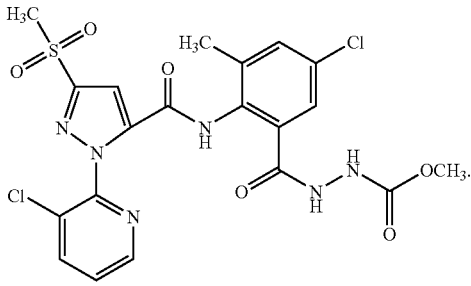
(100)

The present compound (100)
¹H-NMR (DMSO-d₆) δ (ppm): 2.16 (3H, s), 3.39 (3H, s) 3.62 (3H, brs), 7.39 (1H, brs), 7.56 (1H, s), 7.67 (1H, dd, J=8 Hz, 4Hz), 7.78 (1H, s), 8.23 (1H, dd, J=8 Hz, 1Hz), 8.54 (1H, dd, J=4 Hz, 1 Hz), 9.31 (1H, brs), 10.16 (1H, brs), 10.41 (1H, brs)

PREPARATION EXAMPLE 101

A mixture of 0.10 g of 6-chloro-2-[1-(3-chloro-2-pyridinyl)-3-methylsulfinyl-1H-pyrazol-5-yl]-8-methyl-4H-3,1-benzoxazine-4-one, 0.21 g of methyl carbazate and 4 ml of N,N-dimethylformamide was stirred at room temperature for 20 hours. Water was poured into the reaction mixture, and the mixture was extracted with methyl t-butyl ether three times. The organic layers were combined, washed successively with water and an aqueous saturated sodium chloride solution, dried over anhydrous magnesium sulfate, and concentrated under reduced pressure. The resulting residue was subjected to silica gel column chromatography to obtain 0.092 g of the present compound (101) of the formula:

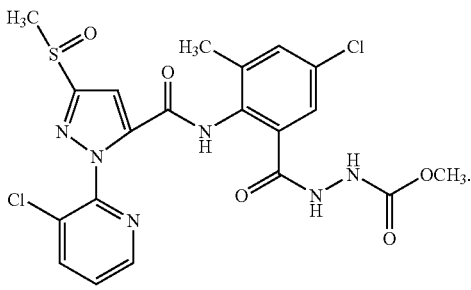
(101)

The present compound (101)
¹H-NMR (DMSO-d₆) δ (ppm): 2.16 (3H, s), 2.99 (3H, s) 3.62 (3H, brs), 7.39 (1H, brs), 7.55 (1H, s), 7.64 (1H, dd, J=8 Hz, 4 Hz), 7.74 (1H, s), 8.20 (1H, dd, J=8 Hz, 1.5 Hz), 8.52 (1H, dd, J=4 Hz, 1Hz), 9.32 (1H, brs), 10.15 (1H, brs), 10.35 (1H, brs)

PREPARATION EXAMPLE 102

A mixture 0.12 g of 6-chloro-2-[1-(3-chloro-2-pyridinyl)-3-methyl-1H-pyrazole-5-yl]-8-methyl-4H-3,1-benzoxazine-4-one, 0.27 g of methyl carbazate and 4 ml of N,N-dimethylformamide was stirred at room temperature for 24 hours. Water was poured into the reaction mixture, and the mixture was extracted with methyl t-butyl ether three times. The organic layers were combined, washed successively with water and an aqueous saturated sodium chloride solution, dried over anhydrous magnesium sulfate, and concentrated under reduced pressure. The resulting residue was subjected to silica gel column chromatography to obtain 0.10 g of the present compound (102) or the formula:

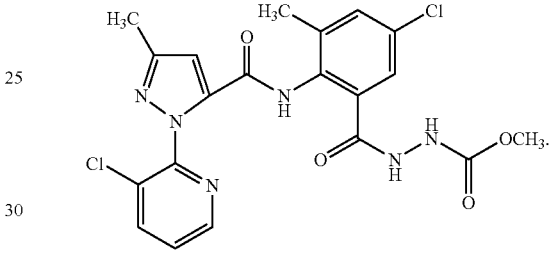
(102)

The present compound (102)
¹H-NMR (DMSO-d₆) δ (ppm): 2.15 (3H, s), 2.31 (3H, s) 3.62 (3H, brs), 7.02 (1H, s), 7.40 (1H, brs), 7.52-7.55 (2H, m), 8.11 (1H, dd, J=8 Hz, 1Hz), 8.46 (1H, dd, J=4 Hz, 1Hz), 9.31 (1H, brs), 10.03 (1H, brs), 10.14 (1H, brs)

PREPARATION EXAMPLE 103

According to the same manner as that of Preparation Example 10 except that N-[2-(hydrazinocarbonyl)-3-methylphenyl]-1-(3-chloro-2-pyridinyl)-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (103) of the formula:

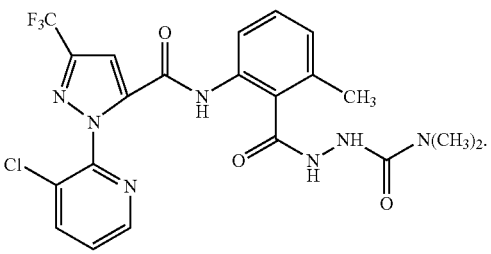
(103)

The present compound (103)
¹H-NMR (DMSO-d₆) δ (ppm): 2.29 (3H, s), 2.93 (6H, s), 7.07 (1H, d, J=8 Hz), 7.27 (1H, t, J=8 Hz), 7.71 (1H, dd, J=8 Hz, 4 Hz), 7.86 (1H, d, J=8 Hz), 8.11 (1H, s), 8.28 (1H, d, J=8 Hz), 8.56 (1H, d, J=4 Hz), 8.99 (1H, brs), 10.10 (1H, brs), 10.19 (1H, brs)

PREPARATION EXAMPLE 104

A mixture of 0.20 g of 6-chloro-2-[1-(3-chloro-2-pyridinyl)-3-isopropyl-1H-pyrazol-5-yl]-8-methyl-4H-3,1-benzoxazine-4-one, 0.43 g of methyl carbazate and 5 ml of N,N-dimethylformamide was stirred at room temperature for 20 hours. Water was poured into the reaction mixture, and the mixture was extracted with methyl t-butyl ether three times. The organic layers were combined, washed successively with water and an aqueous saturated sodium chloride solution, dried over anhydrous magnesium sulfate, and concentrated under reduced pressure. The resulting residue was subjected to silica gel column chromatography to obtain 0.22 g of the present compound (104) of the formula:

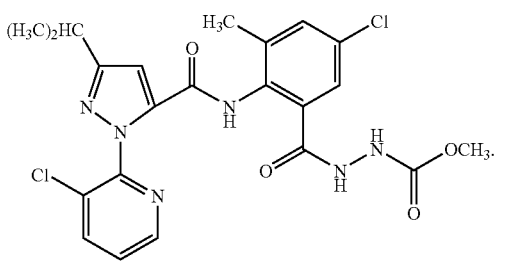

(104)

The present compound (104)

$^1$H-NMR (DMSO-$d_6$) δ (ppm): 1.35 (6H, d, J=7 Hz), 2.22 (3H, s), 3.08 (1H, hept., J=7 Hz), 3.68 (3H, brs), 7.17 (1H, s), 7.45 (1H, brs), 7.58-7.62 (2H, m), 8.17 (1H, dd, J=8 Hz, 1Hz), 8.52 (1H, dd, J=4 Hz, 1Hz), 9.39 (1H, brs), 10.09 (1H, brs), 10.20 (1H, brs)

PREPARATION EXAMPLE 105

A mixture of 0.20 g of 2-[1-(3-chloro-2-pyridinyl)-3-isopropyl-1H-pyrazol-5-yl]-6,8-dibromo-4H-3,1-benzoxazine-4-one, 0.34 g of methyl carbazate and 4 ml of N,N-dimethylformamide was stirred at room temperature for 17 hours. Water was poured into the reaction mixture, and the mixture was extracted with methyl t-butyl ether three times. The organic layers were combined, washed successively with water and an aqueous saturated sodium chloride solution, dried over anhydrous magnesium sulfate, and concentrated under reduced pressure. The resulting residue was subjected to silica gel column chromatography to obtain 0.16 g of the present compound (105) of the formula:

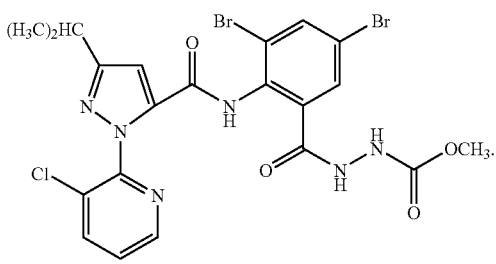

(105)

The present compound (105)

$^1$H-NMR (DMSO-$d_6$) δ (ppm): 1.27 (6H, d, J=7 Hz), 3.01 (1H, hept., J=7 Hz), 3.60 (3H, brs), 7.16 (1H, s), 7.53 (1H, dd, J=8 Hz, 4 Hz), 7.64 (1H, brs), 8.07 (1H, dd, J=8 Hz, 1Hz), 8.11 (1H, brs), 8.45 (1H, dd, J=4 Hz, 1Hz). 9.35 (1H, brs), 10.16 (1H, brs), 10.22 (1H, brs)

PREPARATION EXAMPLE 106

According to the same manner as that of Preparation Example 95 except that the present compound (59) was used in place of the present compound (34) to obtain the present compound (106) of the formula:

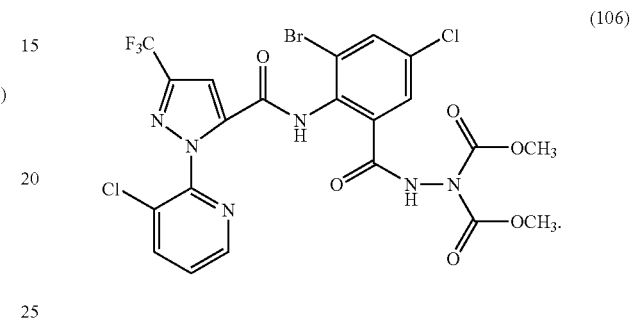

(106)

The present compound (106)

$^1$H-NMR (CDCl$_3$, TMS) δ (ppm): 3.73 (6H, s), 7.38-7.45 (3H, m), 7.64 (1H, d, J=2 Hz), 7.89 (1H, d, J=8 Hz), 8.37 (1H, d, J=4 Hz), 8.67 (1H, brs), 9.21 (1H, brs)

PREPARATION EXAMPLE 107

According to the same manner as that of Preparation Example 95 except that the present compound (70) was used in place of the present compound (34) to obtain the present compound (107) of the formula:

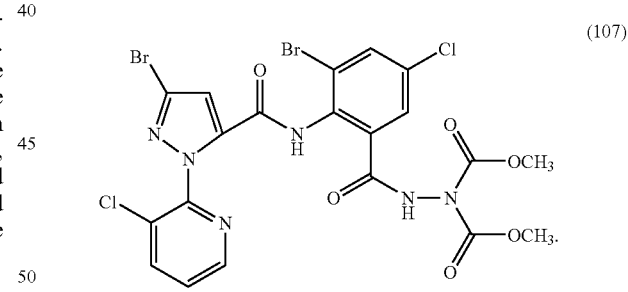

(107)

The present compound (107)

$^1$H-NMR (CDCl$_3$, TMS) δ (ppm): 3.77 (6H, s), 7.09 (1H, s), 7.36 (1H, dd, J=8 Hz, 4 Hz), 7.51 (1H, d, J=2 Hz), 7.69 (1H, d, J=2 Hz), 7.88 (1H, dd, J=8 Hz, 1Hz), 8.35 (1H, dd, J=4 Hz, 1Hz), 8.63 (1H, brs), 8.95 (1H, brs)

PREPARATION EXAMPLE 108

According to the same manner as that of Preparation Example 95 except that the present compound (5) was used in place of the present compound (34) to obtain the present compound (108) of the formula:

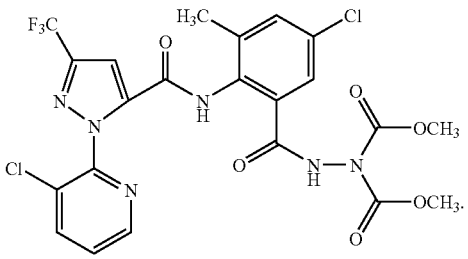

(108)

The present compound (108)

¹H-NMR (CDCl₃, TMS) δ (ppm): 2.23 (3H, s), 3.81 (6H, s), 7.24 (1H, s), 7.36 (1H, d, J=2 Hz), 7.39-7.42 (2H, m), 7.91 (1H, dd, J=8 Hz, 1Hz), 8.28 (1H, s), 8.40 (1H, dd, J=4 Hz, 1Hz), 9.27 (1H, s).

PREPARATION EXAMPLE 109

According to the same manner as that of Preparation Example 95 except that the present compound (49) was used in place of the present compound (34) to obtain the present compound (109) of the formula:

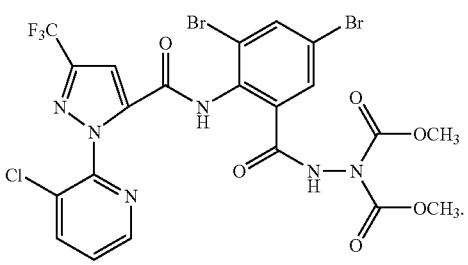

(109)

The present compound (109)

¹H-NMR (CDCl₃, TMS) δ (ppm): 3.75 (6H, s), 7.37-7.43 (2H, m), 7.63 (1H, d, J=2 Hz), 7.84 (1H, d, J=2 Hz), 7.90 (1H, dd, J=8 Hz, 1Hz), 8.38 (1H, dd, J=4 Hz, J=1 Hz), 8.57 (1H, brs), 9.17 (1H, brs).

PREPARATION EXAMPLE 110

According to the same manner as that of Preparation Example 95 except that the present compound (68) was used in place of the present compound (34) to obtain the present compound (110) of the formula:

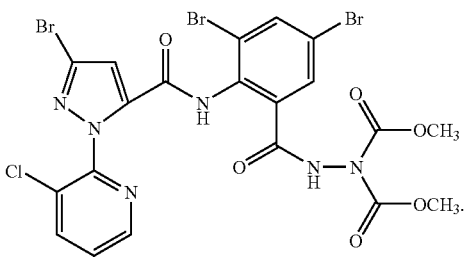

(110)

The present compound (110)

¹H-NMR (CDCl₃, TMS) δ (ppm): 3.78 (6H, s), 7.08 (1H, s), 7.37 (1H, dd, J=8 Hz, 4 Hz), 7.67 (1H, d, J=2 Hz), 7.87-7.90 (2H, m), 8.35 (1H, dd, J=4 Hz, 1Hz), 8.54 (1H, brs), 8.88 (1H, brs).

PREPARATION EXAMPLE 111

According to the same manner as that of Preparation Example 95 except that ethyl chloroformate was used in place of methyl chloroformate to obtain the present compound (111) of the formula:

(111)

The present compound (111)

¹H-NMR (CDCl₃, TMS) δ (ppm): 1.30 (3H, t, J=7 Hz), 2.24 (3H, s), 3.82 (3H, s), 4.30 (2H, q, J=7 Hz), 6.97 (1H, s), 7.34-7.38 (2H, m), 7.45 (1H, s), 7.88 (1H, dd, J=8 Hz, 2 Hz), 8.27 (1H, s), 8.38 (1H, dd, J=5 Hz, 2 Hz), 9.21 (1H, s).

PREPARATION EXAMPLE 112

According to the same manner as that of Preparation Example 95 except that isobutyl chloroformate was used in place of methyl chloroformate to obtain the present compound (112) of the formula:

(112)

The present compound (112)

¹H-NMR (CDCl₃, TMS) δ (ppm): 0.94 (6H, d, J=7 Hz), 1.98 (1H, hept, J=7 Hz), 2.24 (3H, s), 3.82 (3H, s), 4.04 (2H, d, J=7 Hz), 6.96 (1H, s), 7.34-7.37 (2H, m), 7.45 (1H, d, J=2 Hz), 7.88 (1H, dd, J=8 Hz, 2 Hz), 8.29 (1H, s), 8.38 (1H, dd, J=5 Hz, 2 Hz), 9.23 (1H, s).

PREPARATION EXAMPLE 113

A mixture of 0.10 g of 6-chloro-2-[1-(3-chloro-2-pyridinyl)-3-cyano-1H-pyrazole-5-yl]-8-methyl-4H-3,1-benzoxazine-4-one, 0.23 g of methyl carbazate and 4 ml of N,N-dimethylformamide was stirred at room temperature for 18 hours. Water was poured into the reaction mixture, and the mixture was extracted with methyl t-butyl ether three times. The organic layers were combined, washed successively with water and an aqueous saturated sodium chloride solution, dried over anhydrous magnesium sulfate, and concentrated under reduced pressure. The resulting residue was subjected to silica gel column chromatography to obtain 0.090 g of the present compound (113) of the formula:

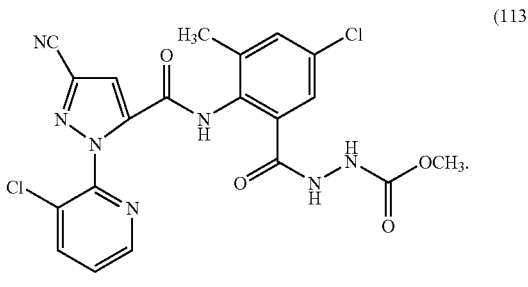

The present compound (113)
$^1$H-NMR (DMSO-$d_6$) δ (ppm): 2.14 (3H, s), 3.61 (3H, brs), 7.38 (1H, brs), 7.54 (1H, s), 7.67 (1H, dd, J=8 Hz, 5 Hz), 7.81 (1H, s), 8.22 (1H, d, J=8 Hz), 8.53 (1H, d, J=5 Hz), 9.29 (1H, brs), 10.16 (1H, brs), 10.44 (1H, brs).

PREPARATION EXAMPLE 114

A mixture of 0.30 g of 2-[3-bromo-1-(3-chloro-2-pyridinyl)-1H-pyrazole-5-yl]-6-chloro-8-methyl-4H-3,1-benzoxazine-4-one, 0.69 g of N-methyl-N-methoxycarbonylhydrazine and 15 ml of N,N-dimethylformamide was stirred at 60° C. for 9 hours and at 80° C. for 22 hours. Water was poured into the reaction mixture, and the mixture was extracted with methyl tert-butyl ether three times. The organic layers were combined, washed with water and an aqueous saturated sodium chloride solution, dried over anhydrous magnesium sulfate, and concentrated under reduced pressure. The residue was subjected to silica gel column chromatography to obtain 0.036 g of the present compound (114) of the formula:

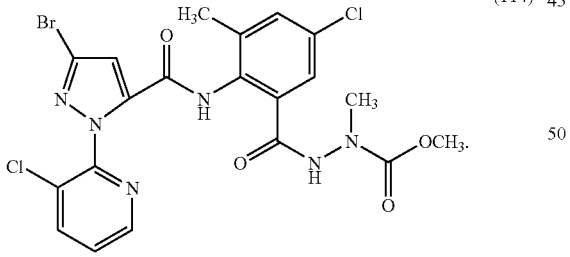

The present compound (114)
$^1$H-NMR (CDCl$_3$, TMS) δ (ppm): 2.20 (3H, s), 3.21 (3H, s), 3.74 (3H, brs), 7.05 (1H, s), 7.26-7.38 (3H, m), 7.86 (1H, dd, J=8 Hz, 2 Hz), 8.03 (1H, s), 8.42 (1H, dd, J=5 Hz, 2 Hz), 9.47 (1H, s).

PREPARATION EXAMPLE 115

A mixture of 0.60 g of 3-bromo-N-[4-chloro-2-(N-methylhydrazinocarbonyl)-6-methylphenyl]-1-(3-chloro-2-pyridinyl)-1H-pyrazole-5-carboxamide, 0.41 ml of methyl chloroformate and 6 ml of pyridine was stirred at room temperature for 3 hours. Water was poured into the reaction mixture, followed by concentration under reduced pressure. The residue was distributed between water and ethyl acetate, and the organic layer was washed with an aqueous saturated sodium chloride solution, dried over anhydrous magnesium sulfate, and concentrated under reduced pressure. The residue was subjected to silica gel column chromatography to obtain 0.46 g of the present compound (115) of the formula:

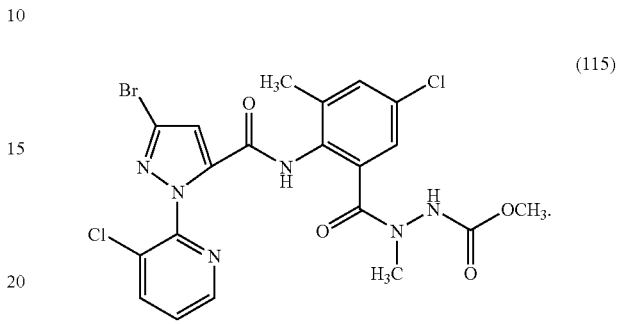

The present compound (115)
$^1$H-NMR (CDCl$_3$, TMS) δ (ppm): 2.04 (3H, s), 3.22 (3H, s), 3.57 (2.6H, s), 3.80 (0.4H, s), 7.01 (1H, s), 7.04 (1H, s), 7.28 (1H, s), 7.40 (1H, dd, J=8 Hz, 5 Hz), 7.61 (1H, brs), 7.87 (1H, dd, J=8 Hz, 2 Hz), 8.46 (1H, dd, J=5 Hz, 2 Hz), 9.80 (1H, brs).

PREPARATION EXAMPLE 116

According to the same manner as that of Preparation Example 72 except that 2-[3-bromo-1-(3-chloro-2-pyridinyl)-1H-pyrazole-5-yl]-6,7-dichloro-8-methyl-4H-3,1-benzoxazine-4-one was used in place of 2-[3-bromo-1-(3-chloro-2-pyridinyl)-1H-pyrazole-5-yl]-8-chloro-4H-3,1-benzoxazine-4-one to obtain the present compound (116) of the formula:

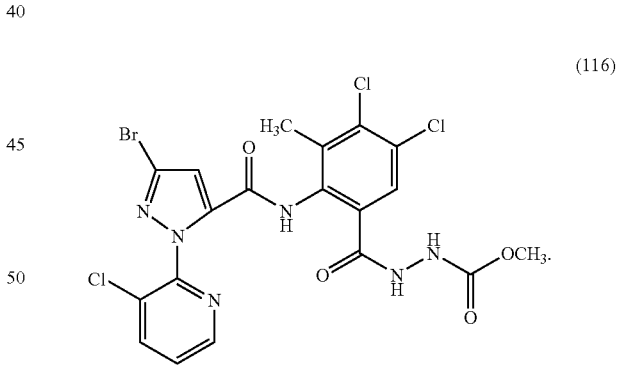

The present compound (116)
$^1$H-NMR (DMSO-$d_6$, TMS) δ (ppm): 2.25 (3H, s), 3.45-3.68 (3H, m), 7.36 (1H, s), 7.57-7.65 (2H, m), 8.18 (1H, d, J=8 Hz), 8.50 (1H, d, J=4 Hz), 9.36 (1H, brs), 10.24 (1H, brs), 10.49 (1H, brs).

PREPARATION EXAMPLE 117

According to the same manner as that of Preparation Example 72 except that 2-[3-bromo-1-(3-chloro-2-pyridinyl)-1H-pyrazole-5-yl]-8-methyl-6-cyano-4H-3,1-benzoxazine-4-one was used in place of 2-[3-bromo-1-(3-chloro-2- pyridinyl)-1H-pyrazole-5-yl]-8-chloro-4H-3,1-benzoxazine-4-one to obtain the present compound (117) of the formula:

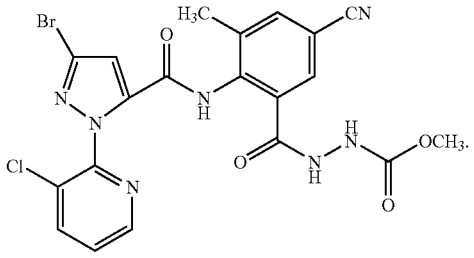

(117)

The present compound (117)
$^1$H-NMR (DMSO-d$_6$, TMS) δ (ppm): 2.20 (3H, s), 3.45-3.68 (3H, m), 7.38 (1H, s), 7.61 (1H, dd, J=8 Hz, 5 Hz), 7.77 (1H, s), 7.96 (1H, s), 8.17 (1H, d, J=8 Hz), 8.50 (1H, d, J=5 Hz), 9.36 (1H, brs), 10.27 (1H, brs), 10.49 (1H, brs).

PREPARATION EXAMPLE 118

A mixture of 0.59 g of 3,5-dibromo-2-{N-[3-bromo-1-(3-chloro-2-pyridinyl)-1H-pyrazole-5-carbonyl]-N-methylamino}benzoic acid, 2 ml of thionyl chloride and one droplet of N,N-dimethylformamide was stirred at 80° C. for 1 hour. The reaction mixture was concentrated under reduced pressure, 10 ml of hexane was added thereto, and the mixture was further concentrated under reduced pressure. The resulting residue, 10 ml of tetrahydrofuran, 0.10 g of methyl carbazate and 1 ml of pyridine were mixed, and the mixture was stirred at room temperature for 3 hours. The reaction mixture was poured into 30 ml of water, and the mixture was extracted with ethyl acetate three times. The organic layers were combined, washed successively with water and an aqueous saturated sodium chloride solution, dried over anhydrous sodium sulfate, and concentrated under reduced pressure. The resulting residue was subjected to silica gel column chromatography to obtain 0.23 g of the present compound (118) of the formula:

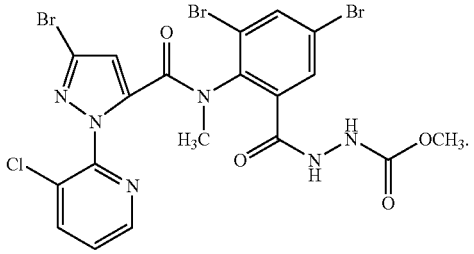

(118)

The present compound (118)
$^1$H-NMR (DMSO-d$_6$, TMS) δ (ppm): 3.05 (1.9H, s), 3.38 (1.1H, s), 3.52-3.73 (3H, m), 5.68 (0.7H, brs), 7.11 (0.3H, brs), 7.57-7.81 (2H, m), 8.16-8.32 (2H, m), 8.49-8.55 (1H, m), 9.42 (1H, brs), 10.54 (1H, brs).

PREPARATION EXAMPLE 119

A mixture of 0.30 g of 3-bromo-N-[4-chloro-2-(N,N'-dimethylhydrazinocarbonyl)-6-methylphenyl]-1-(3-chloro-2-pyridinyl)-1H-pyrazole-5-carboxamide, 0.07 ml of methyl chloroformate and 5 ml of pyridine was stirred at room temperature for 1 hour. Water was poured into the reaction mixture, and the mixture was extracted with ethyl acetate three times. The organic layers were combined, dried over anhydrous sodium sulfate, and concentrated under reduced pressure. The resulting residue was washed with a mixed solvent of ethyl acetate and hexane to obtain 0.09 g of the present compound (119) of the formula:

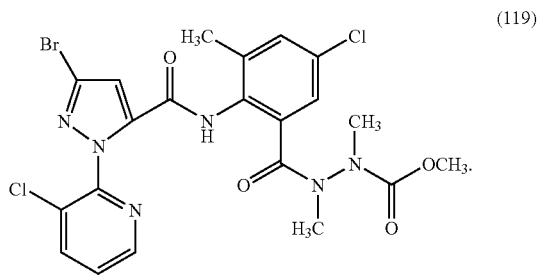

(119)

The present compound (119)
$^1$H-NMR (DMSO-d$_6$, TMS) δ (ppm): 2.10-2.24 (3H, m), 2.61-2.87 (3H, m), 2.90-3.18 (3H, m), 3.45-3.74 (3H, m), 7.12-7.30 (1H, m), 7.33-7.44 (1H, m), 7.44-7.58 (1H, m), 7.58-7.66 (1H, m), 8.20 (1H, d, J=8 Hz), 8.47-8.54 (1H, m), 10.10-10.50 (1H, m).

PREPARATION EXAMPLE 120

According to the same manner as that of Preparation Example 72 except that 2-[3-bromo-1-(3-chloro-2-pyridinyl)-1H-pyrazole-5-yl]-8-bromo-6-fluoro-4H-3,1-benzoxazine-4-one was used in place of 2-[3-bromo-1-(3-chloro-2-pyridinyl)-1H-pyrazole-5-yl]-8-chloro-4H-3,1-benzoxazine-4-one to obtain the present compound (120) of the formula:

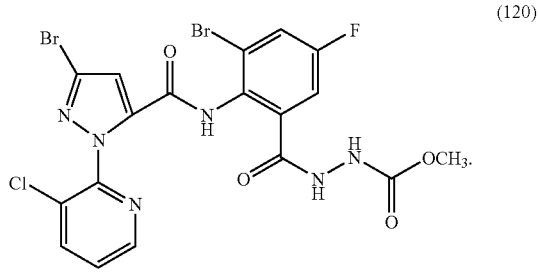

(120)

The present compound (120)
$^1$H-NMR (DMSO-d$_6$, TMS) δ (ppm): 3.42-3.69 (3H, m), 7.34 (1H, d, J=8 Hz), 7.41 (1H, s), 7.60 (1H, dd, J=8 Hz, 5 Hz), 7.89 (1H, d, J=8 Hz), 8.16 (1H, d, J=8 Hz), 8.50 (1H, d, J=5 Hz), 9.36 (1H, brs), 10.18 (1H, brs), 10.42 (1H, brs).

PREPARATION EXAMPLE 121

According to the same manner as that of Preparation Example 72 except that 2-[3-bromo-1-(3-chloro-2-pyridinyl)-1H-pyrazole-5-yl]-8-phenyl-4H-3,1-benzoxazine-4-one was used in place of 2-[3-bromo-1-(3-chloro-2-pyridinyl)-1H-pyrazole-5-yl]-8-chloro-4H-3,1-benzoxazine-4-one to obtain the present compound (121) of the formula:

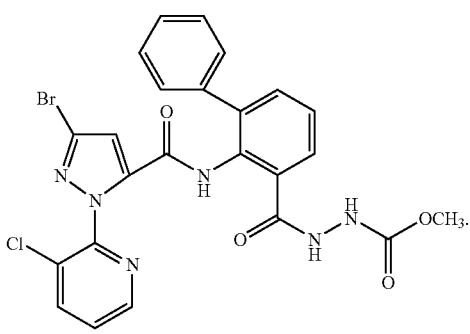

(121)

The present compound (121)

¹H-NMR (DMSO-d₆, TMS) δ (ppm): 3.49-3.68 (3H, m), 7.24-7.67 (10H, m), 8.08 (1H, d, J=8 Hz), 8.43 (1H, d, J=4 Hz), 9.29 (1H, brs), 10.08 (1H, brs), 10.19 (1H, brs).

PREPARATION EXAMPLE 122

A mixture of 0.17 g of 6,8-dibromo-2-[4-bromo-1-(3-chloro-2-pyridinyl)-1H-pyrrol-2-yl]-4H-3,1-benzoxazine-4-one, 0.27 g of methyl carbazate and 20 ml of N,N-dimethylformamide was stirred at room temperature for 2 days. Water was poured into the reaction mixture, and the mixture was extracted with ethyl acetate. The organic layer was washed with water, dried over sodium sulfate, and concentrated under reduced pressure to obtain 0.15 g of the present compound (122) of the formula:

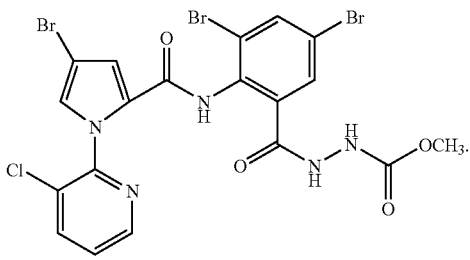

(122)

The present compound (122)

¹H-NMR (DMSO-d₆) δ (ppm): 3.67 (3H, s), 7.36 (1H, s), 7.46 (1H, d, J=2 Hz), 7.54 (1H, dd, J=8 Hz, 5 Hz), 7.70 (1H, s), 8.09 (1H, d, J=8 Hz), 8.13 (1H, d, J=2 Hz), 8.48 (1H, d, J=5 Hz), 9.40 (1H, brs), 9.97 (1H, brs), 10.18 (1H, brs)

PREPARATION EXAMPLE 123

According to the same manner as that of Preparation Example 122 except that 8-bromo-2-[4-bromo-1-(3-chloro-2-pyridinyl)-1H-pyrrol-2-yl]-6-chloro-4H-3,1-benzoxazine-4-one was used in place of 6,8-dibromo-2-[4-bromo-1-(3-chloro-2-pyridinyl)-1H-pyrrol-2-yl]-4H-3,1-benzoxazine-4-one to obtain the present compound (123) of the formula:

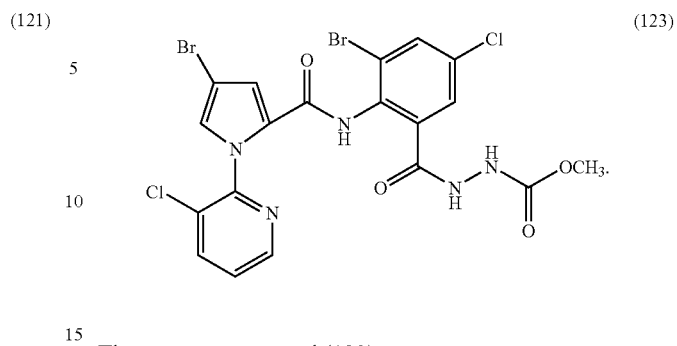

(123)

The present compound (123)

¹H-NMR (DMSO-d₆) δ (ppm): 3.62 (3H, s), 7.30 (1H, s), 7.39 (1H, d, J=2 Hz), 7.48 (1H, dd, J=8 Hz, 5 Hz), 7.52 (1H, s), 7.96 (1H, d, J=2 Hz), 8.03 (1H, dd, J=8 Hz, 2 Hz), 8.42 (1H, dd, J=5 Hz, 2 Hz), 9.35 (1H, brs), 9.92 (1H, brs), 10.11 (1H, brs)

PREPARATION EXAMPLE 124

According to the same manner as that of Preparation Example 122 except that 2-[4-bromo-1-(3-chloro-2-pyridinyl)-1H-pyrrol-2-yl]-6-cyano-8-methyl-4H-3,1-benzoxazine-4-one was used in place of 6,8-dibromo-2-[4-bromo-1-(3-chloro-2-pyridinyl)-1H-pyrrole-2-yl]-4H-3,1-benzoxazine-4-one to obtain the present compound (124) of the formula:

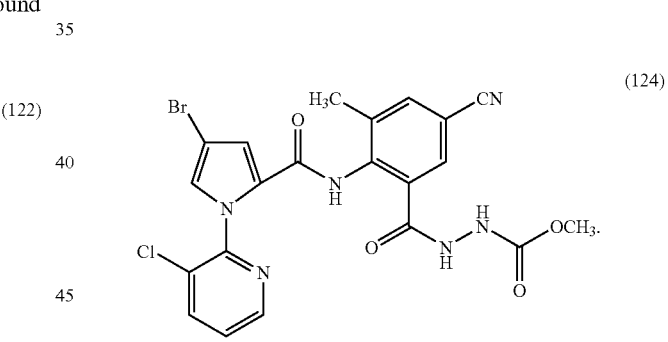

(124)

The present compound (124)

¹H-NMR (DMSO-d₆) δ (ppm): 2.21 (3H, s), 3.64 (3H, s), 7.25 (1H, d, J=2 Hz), 7.41 (1H, d, J=2 Hz), 7.49 (1H, dd, J=8 Hz, 5 Hz), 7.77 (1H, s), 7.88 (1H, s), 8.04 (1H, dd, J=8 Hz, 2 Hz), 8.43 (1H, dd, J=5 Hz, 2 Hz), 9.36 (1H, brs), 10.05 (1H, brs), 10.27 (1H, brs)

PREPARATION EXAMPLE 125

According to the same manner as that of Preparation Example 72, 2-[3-bromo-1-(3-chloro-2-pyridinyl)-1H-pyrazol-5-yl]-8-ethyl-4H-3,1-benzoxazine-4-one was used in place of 2-[3-bromo-1-(3-chloro-2-pyridinyl)-1H-pyrazol-5-yl]-8-chloro-4H-3,1-benzoxazine-4-one to obtain the present compound (125) of the formula:

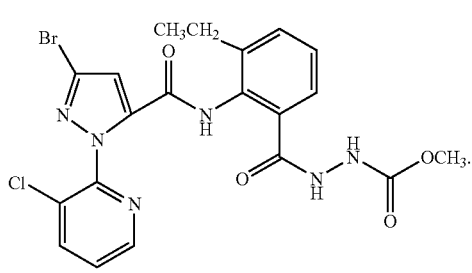

The present compound (125)

¹H-NMR (DMSO-d₆, TMS) δ (ppm): 1.06-1.13 (3H, m), 2.45-2.60 (2H, m), 3.55-3.70 (3H, m), 7.25-7.47 (4H, m), 7.57-7.63 (1H, m), 8.14-8.19 (1H, m), 8.46-8.53 (1H, m), 9.24 (1H, brs), 9.98 (1H, brs), 10.16 (1H, brs).

PREPARATION EXAMPLE 126

According to the same manner as that of Preparation Example 5, N-[4-chloro-2-(hydrazinocarbonyl)-6-methylphenyl]-1-cyclohexyl-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (126) of the formula:

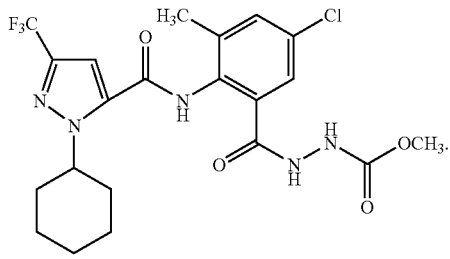

The present compound (126)

¹H-NMR (DMSO-d₆) δ (ppm): 1.20-1.41 (3H, m), 1.67-1.80 (5H, m), 1.98-2.00 (2H, m), 2.25 (3H, s), 3.56 (3H, s), 5.00-5.08 (1H, m), 7.33 (1H, s), 7.40 (1H, d, J=2 Hz), 7.55 (1H, d, J=2 Hz), 9.02 (1H, brs), 9.94 (1H, brs), 10.04 (1H, brs).

PREPARATION EXAMPLE 127

According to the same manner as that of Preparation Example 93, 4,5-dibromo-N-[4-chloro-2-(hydrazinocarbonyl)-6-methylphenyl]-1-(3-chloro-2-pyridinyl)-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (127) of the formula:

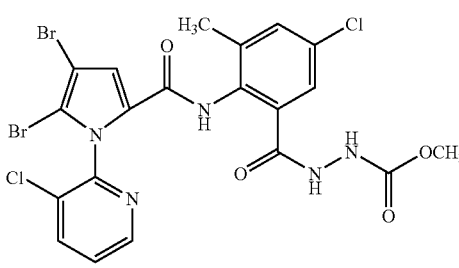

The present compound (127)

¹H-NMR (DMSO-d₆) δ (ppm): 2.09 (3H, s), 3.63 (3H, s), 7.36 (1H, s), 7.42 (1H, s), 7.49 (1H, s), 7.57 (1H, dd, J=8 Hz, 5 Hz), 8.14 (1H, d, J=8 Hz), 8.50 (1H, d, J=5 Hz), 9.29 (1H, brs), 9.79 (1H, brs), 10.12 (1H, brs).

PREPARATION EXAMPLE 128

A mixture of 0.20 g of 4,5-dibromo-N-[4-chloro-2-(hydrazinocarbonyl)-6-methylphenyl]-1-(3-chloro-2-pyridinyl)-1H-pyrrole-2-carboxamide, 0.04 g of N,N-dimethylcarbamoyl chloride and 0.08 ml of pyridine in N,N-dimethylformamide was stirred at room temperature for 14 hours. Water was poured into the reaction mixture and the mixture was extracted with ethyl acetate. The organic layer was washed with water, dried over sodium sulfate, and concentrated under reduced pressure. The resulting residue was subjected to silica gel column chromatography to obtain 0.16 g of the present compound (128) of the formula:

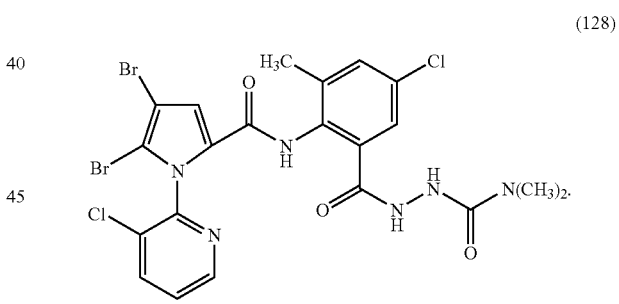

The present compound (128)

¹H-NMR (DMSO-d₆) δ (ppm): 2.08 (3H, s), 2.88 (6H, s), 7.40 (1H, d, J=2 Hz), 7.44 (1H, d, J=2 Hz), 7.52 (1H, s), 7.58 (1H, dd, J=8 Hz, 5 Hz), 8.14 (1H, dd, J=8 Hz, 1Hz), 8.50 (1H, dd, J=5 Hz, 1Hz), 8.56 (1H, brs), 9.75 (1H, brs), 9.81 (1H, brs).

PREPARATION EXAMPLE 129

According to the same manner as that of Preparation Example 122, 2-[5-chloro-1-(3-chloro-2-pyridinyl)-1H-pyrrol-2-yl]-6-chloro-8-methyl-4H-3,1-benzoxazine-4-one was used in place of 6,8-dibromo-2-[4-bromo-1-(3-chloro-2-pyridinyl)-1H-pyrrol-2-yl]-4H-3,1-benzoxazine-4-one to obtain the present compound (129) of the formula:

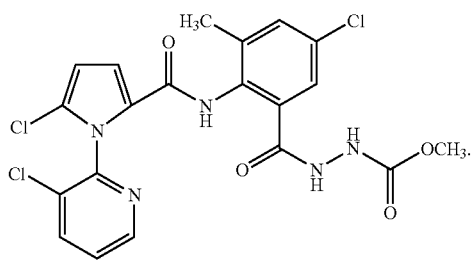

(129)

The present compound (129)

$^1$H-NMR (DMSO-$d_6$, TMS) δ (ppm): 2.11 (3H, s), 3.63 (3H, s), 6.48 (1H, d, J=4 Hz), 7.24 (1H, d, J=4 Hz), 7.48 (1H, s), 7.55 (1H, dd, J=8 Hz, 5 Hz), 7.95 (1H, s), 8.12 (1H, dd, J=8 Hz, 2 Hz), 8.49 (1H, dd, J=5 Hz, 2 Hz), 9.31 (1H, brs), 9.74 (1H, brs), 10.13 (1H, brs)

PREPARATION EXAMPLE 130

According to the same manner as that of Preparation Example 93, N-[4-chloro-2-(hydrazinocarbonyl)-6-methylphenyl]-1-(3-chloro-2-pyridinyl)-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (130) of the formula:

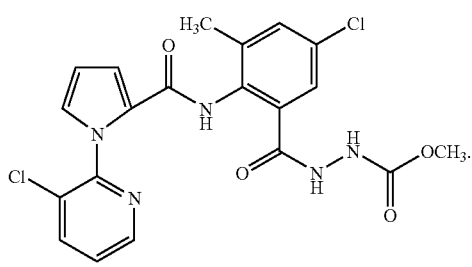

(130)

The present compound (130)

$^1$H-NMR (DMSO-$d_6$, TMS) δ (ppm): 2.16 (3H, s), 3.61 (3H, s), 6.37 (1H, d, J=3 Hz), 7.12-7.18 (2H, m), 7.40 (1H, s), 7.45-7.50 (2H, m), 8.03 (1H, d, J=8 Hz), 8.42 (1H, d, J=5 Hz), 9.33 (1H, brs), 9.71 (1H, brs), 10.14 (1H, brs)

PREPARATION EXAMPLE 131

According to the same manner as that of Preparation Example 10, 3-bromo-1-(3-chloro-2-pyridinyl)-N-[4-cyano-2-(hydrazinocarbonyl)-6-methylphenyl]-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (131) of the formula:

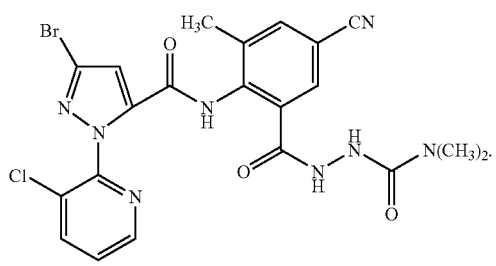

(131)

The present compound (131)

$^1$H-NMR (DMSO-$d_6$, TMS) δ (ppm): 2.18 (3H, s), 2.88 (6H, s), 7.49 (1H, s), 7.62 (1H, dd, J=8 Hz, 5 Hz), 7.82 (1H, s), 7.93 (1H, s), 8.19 (1H, dd, J=8 Hz, 1Hz), 8.50 (1H, dd, J=5 Hz, 1Hz), 8.63 (1H, brs), 9.93 (1H, brs), 10.42 (1H, brs)

PREPARATION EXAMPLE 132

According to the same manner as that of Preparation Example 93, 4,5-dichloro-N-[4-chloro-2-(hydrazinocarbonyl)-6-methylphenyl]-1-(3-chloro-2-pyridinyl)-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (132) of the formula:

(132)

The present compound (132)

$^1$H-NMR (DMSO-$d_6$, TMS) δ (ppm): 2.10 (3H, s), 3.63 (3H, s), 7.39 (2H, s), 7.49 (1H, s), 7.59 (1H, dd, J=8 Hz, 5 Hz), 8.15 (1H, dd, J=8 Hz, 1Hz), 8.51 (1H, dd, J=5 Hz, 1Hz), 9.30 (1H, brs), 9.82 (1H, brs), 10.12 (1H, brs)

PREPARATION EXAMPLE 133

According to the same manner as that of Preparation Example 128, 4,5-dichloro-N-[4-chloro-2-(hydrazinocarbonyl)-6-methylphenyl]-1-(3-chloro-2-pyridinyl)-1H-pyrrole-2-carboxamide was used in place of 4,5-dibromo-N-[4-chloro-2-(hydrazinocarbonyl)-6-methylphenyl]-1-(3-chloro-2-pyridinyl)-1H-pyrrole-2-carboxamide to obtain the present compound (133) of the formula:

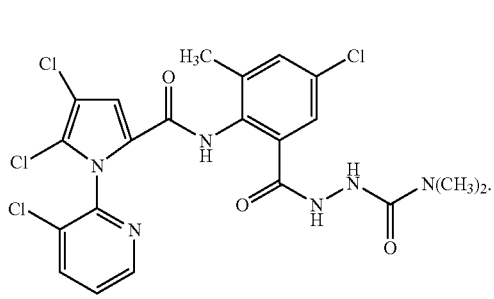

(133)

The present compound (133)

¹H-NMR (DMSO-d₆, TMS) δ (ppm): 2.10 (3H, s), 2.53 (6H, s), 7.37-7.39 (2H, m), 7.51 (1H, d, J=2 Hz), 7.59 (1H, dd, J=8 Hz, 5 Hz), 8.17 (1H, dd, J=8 Hz, 2 Hz), 8.52 (1H, dd, J=5 Hz, 2 Hz), 9.31 (1H, brs), 9.82 (1H, brs), 10.13 (1H, brs)

PREPARATION EXAMPLE 134

A mixture of 0.50 g of 4-bromo-N-[4-chloro-2-(N-methylhydrazinocarbonyl)-6-methylphenyl]-1-(3-chloro-2-pyridinyl)-1H-pyrrole-2-carboxamide, 0.11 g of methyl chloroformate, 0.18 ml of pyridine and 5 ml of N,N-dimethylformamide was stirred at room temperature for 3 hours. The reaction mixture was poured into water, and extracted with ethyl acetate three times. The organic layers were combined, washed successively with water and an aqueous saturated sodium chloride solution, dried over anhydrous sodium sulfate, and concentrated under reduced pressure. The resulting residue was subjected to silica gel column chromatography to obtain 0.09 g of the present compound (134) of the formula:

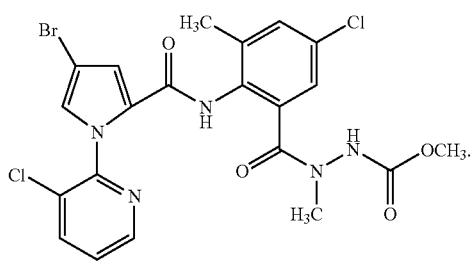

(134)

The present compound (134)

¹H-NMR (CDCl₃, TMS) δ (ppm): 2.05-2.12 (3H, m), 3.21 (3H, s), 3.54-3.76 (3H, m), 7.02 (1H, d, J=2 Hz), 7.06 (2H, s), 7.29 (1H, brs), 7.33 (1H, dd, J=8 Hz, 5 Hz), 7.80-7.86 (2H, m), 8.40 (1H, dd, J=5 Hz, 2 Hz), 8.99 (1H, brs)

PREPARATION EXAMPLE 135

According to the same manner as that of Preparation Example 72, 2-[3-bromo-1-(3-chloro-2-pyridinyl)-1H-pyrazol-5-yl]-6,8-dichloro-4H-3,1-benzoxazine-4-one was used in place of 2-[3-bromo-1-(3-chloro-2-pyridinyl)-1H-pyrazol-5-yl]-8-chloro-4H-3,1-benzoxazine-4-one to obtain the present compound (135) of the formula:

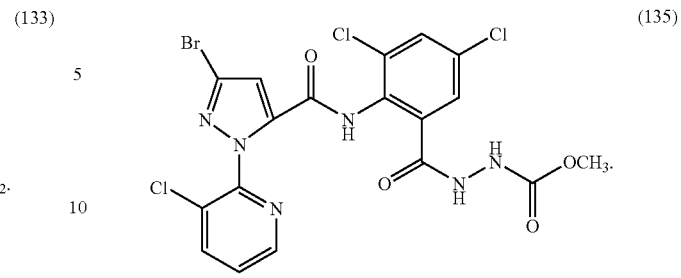

(135)

The present compound (135)

¹H-NMR (DMSO-d₆, TMS) δ (ppm): 3.47-3.62 (3H, m), 7.40 (1H, s), 7.51 (1H, s), 7.60 (1H, dd, J=8 Hz, 5 Hz), 7.93 (1H, s), 8.16 (1H, dd, J=8 Hz, 1Hz), 8.50 (1H, dd, J=5 Hz, 1Hz), 9.37 (1H, brs), 10.24 (1H, brs), 10.48 (1H, brs)

PREPARATION EXAMPLE 136

A mixture of 0.25 g of 4-bromo-N-[4-chloro-2-(N-methylhydrazinocarbonyl)-6-methylphenyl]-1-(3-chloro-2-pyridinyl)-1H-pyrrole-2-carboxamide, 0.06 g of N,N-dimethylcarbamoyl chloride, 0.09 ml of pyridine and 5 ml of N,N-dimethylformamide was stirred at 70° C. for 8 hours. The reaction mixture was poured into water, and a deposited precipitate was collected by filtration. The resulting solid was washed with acetonitrile to obtain 0.10 g of the present compound (136) of the formula:

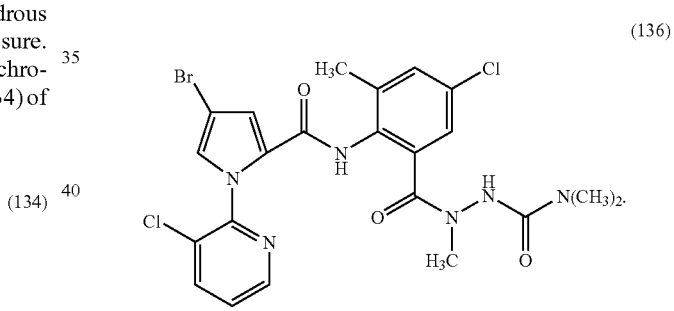

(136)

The present compound (136)

¹H-NMR (DMSO-d₆, TMS) δ (ppm): 2.11 (3H, s), 2.65-2.85 (6H, m), 3.19-3.29 (3H, m), 7.07 (1H, s), 7.14 (1H, s), 7.28 (1H, s), 7.40 (1H, s), 7.50 (1H, dd, J=8 Hz, 5 Hz), 7.60 (1H, brs), 8.06 (1H, d, J=8 Hz), 8.43 (1H, d, J=5 Hz), 9.86 (1H, brs)

PREPARATION EXAMPLE 137

Under ice-cooling, 0.50 g of 4-bromo-N-[4-chloro-2-(hydrazinocarbonyl)-6-methylphenyl]-1-(3-chloro-2-pyridinyl)-1H-pyrrole-2-carboxamide, 4 ml of formic acid and 2 ml of acetic anhydride were mixed. The mixture was stirred at room temperature for 2 hours. The reaction mixture was poured into water, and extracted with ethyl acetate three times. The organic layers were combined, washed successively with water and an aqueous saturated sodium chloride solution, dried over anhydrous sodium sulfate, and concentrated under reduced pressure. The residue was washed with acetonitrile to obtain 0.20 g of the present compound (137) of the formula:

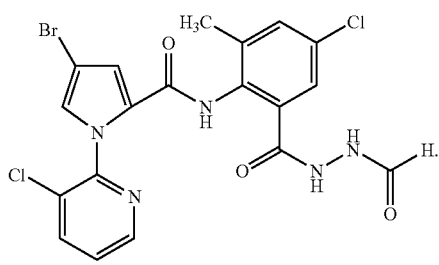

(137)

The present compound (137)

¹H-NMR (DMSO-d₆, TMS) δ (ppm): 2.15 (3H, s), 7.23 (1H, s), 7.42-7.44 (2H, m), 7.48-7.52 (2H, m), 8.05 (1H, d, J=7 Hz), 8.43 (1H, d, J=3 Hz), 8.98 (1H, s), 9.76 (1H, s), 9.96 (1H, brs), 10.12 (1H, brs)

PREPARATION EXAMPLE 138

According to the same manner as that of Preparation Example 115, 3-bromo-1-(3-chloro-2-pyridinyl)-N-[4-cyano-2-(N-methylhydrazinocarbonyl)-6-methylphenyl]-1H-pyrazole-5-carboxamide was used in place of 3-bromo-N-[4-chloro-2-(N-methylhydrazinocarbonyl)-6-methylphenyl]-1-(3-chloro-2-pyridinyl)-1H-pyrazole-5-carboxamide to obtain the present compound (138) of the formula:

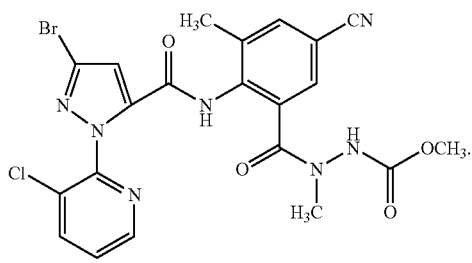

(138)

The present compound (138)

¹H-NMR (DMSO-d₆, TMS) δ (ppm): 2.21 (3H, s), 3.08 (3H, s), 3.45-3.70 (3H, m), 7.30-7.43 (1H, m), 7.44-7.61 (1H, m), 7.63 (1H, dd, J=8 Hz, 5 Hz), 7.82-7.94 (1H, m), 8.21 (1H, d, J=8 Hz, 1Hz), 8.51 (1H, dd, J=5 Hz, 1Hz), 9.21 (1H, brs), 10.24 (1H, brs)

PREPARATION EXAMPLE 139

According to the same manner as that of Preparation Example 134, 4-bromo-1-(3-chloro-2-pyridinyl)-N-[4-cyano-2-(N-methylhydrazinocarbonyl)-6-methylphenyl]-1H-pyrrole-2-carboxamide was used in place of 4-bromo-N-[4-chloro-2-(N-methylhydrazinocarbonyl)-6-methylphenyl]-1-(3-chloro-2-pyridinyl)-1H-pyrrole-2-carboxamide to obtain the present compound (139) of the formula:

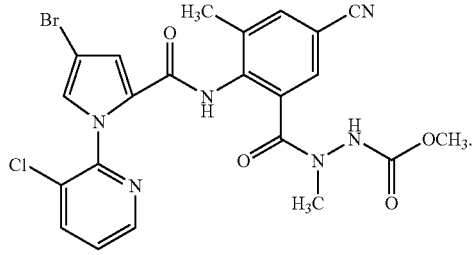

(139)

The present compound (139)

¹H-NMR (DMSO-d₆, TMS) δ (ppm): 2.21 (3H, s), 3.08 (3H, s), 3.47-3.70 (3H, m), 7.18-7.30 (1H, m), 7.41-7.50 (1H, m), 7.51-7.56 (2H, m), 7.80-7.90 (1H, m), 8.12 (1H, dd, J=8 Hz, 1Hz), 8.45 (1H, dd, J=5 Hz, 1Hz), 9.10 (1H, brs), 9.73 (1H, brs)

PREPARATION EXAMPLE 140

According to the same manner as that of Preparation Example 66, 3-bromo-N-[1-bromo-3-(hydrazinocarbonyl)-2-naphthyl]-1-(3-chloro-2-pyridinyl)-1H-pyrazole-5-carboxamide was used in place of N-[1-chloro-3-(hydrazinocarbonyl)-2-naphthyl]-1-(3-chloro-2-pyridinyl)-3-trifluoromethyl-1H-pyrazole-5-carboxamide to obtain the present compound (140) of the formula:

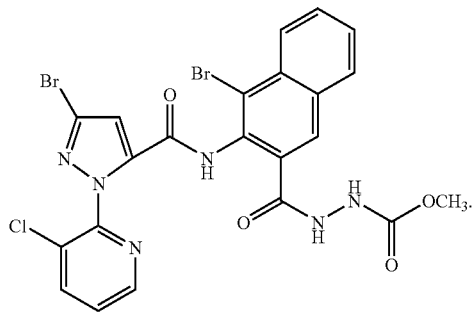

(140)

The present compound (140)

¹H-NMR (DMSO-d₆, TMS) δ (ppm): 3.42-3.71 (3H, m), 7.48 (1H, s), 7.58 (1H, dd, J=8 Hz, 5 Hz), 7.72 (1H, t, J=7 Hz), 7.81 (1H, t, J=7 Hz), 8.10-8.21 (3H, m), 8.24 (1H, d, J=8 Hz), 8.50 (1H, d, J=5 Hz), 9.34 (1H, brs), 10.26 (1H, brs), 10.64 (1H, brs)

PREPARATION EXAMPLE 141

According to the same manner as that of Preparation Example 66, 4-bromo-N-[1-bromo-3-(hydrazinocarbonyl)-2-naphthyl]-1-(3-chloro-2-pyridinyl)-1H-pyrrole-2-carboxamide was used in place of N-[1-chloro-3-(hydrazinocarbonyl)-2-naphthyl]-1-(3-chloro-2-pyridinyl)-3-trifluoromethyl-1H-pyrazole-5-carboxamide to obtain the present compound (141) of the formula:

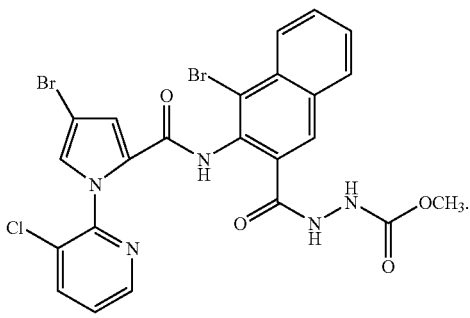

(141)

The present compound (141)

¹H-NMR (DMSO-d₆, TMS) δ (ppm): 3.43-3.70 (3H, m), 7.37 (1H, s), 7.42-7.52 (2H, m), 7.70 (1H, t, J=7 Hz), 7.79 (1H, t, J=7 Hz), 8.03 (1H, d, J=7 Hz), 8.06-8.20 (2H, m), 8.23 (1H, d, J=8 Hz), 8.43 (1H, d, J=4 Hz), 9.34 (1H, brs), 10.09 (1H, brs), 10.19 (1H, brs)

PREPARATION EXAMPLE 142

According to the same manner as that of Preparation Example 17, 3-bromo-1-(3-chloro-2-pyridinyl)-N-[4-cyano-2-(hydrazinocarbonyl)-6-methylphenyl]-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (142) of the formula:

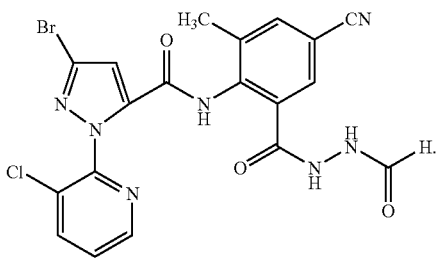

(142)

The present compound (142)

¹H-NMR (DMSO-d₆, TMS) δ (ppm): 2.16-2.34 (3H, m), 7.35-7.45 (1H, m), 7.57-7.66 (1H, m), 7.76-7.88 (1H, m), 7.93-8.02 (1H, m), 8.03-8.12 (1H, m), 8.17 (1H, d, J=7 Hz), 8.50 (1H, brs), 9.55-10.03 (1H, m), 10.17-10.58 (2H, m)

PREPARATION EXAMPLE 143

According to the same manner as that of Preparation Example 17, 4-bromo-1-(3-chloro-2-pyridinyl)-N-[4-cyano-2-(hydrazinocarbonyl)-6-methylphenyl]-1H-pyrrole-2-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (143) of the formula:

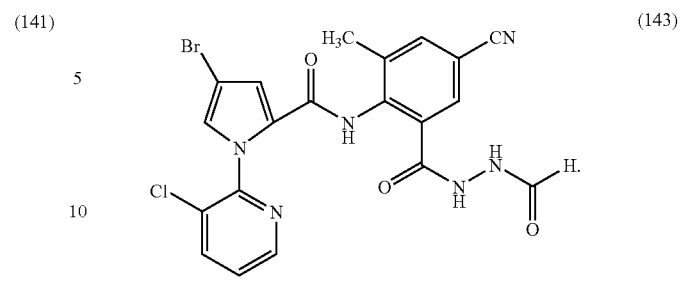

(143)

The present compound (143)

¹H-NMR (DMSO-d₆, TMS) δ (ppm): 2.17-2.30 (3H, m), 7.24-7.36 (1H, m), 7.45-7.55 (2H, m), 7.74-7.82 (1H, m), 7.88-7.95 (1H, m), 8.03-8.09 (2H, m), 8.44 (1H, d, J=5 Hz), 10.02 (1H, brs), 10.21 (1H, brs), 10.46 (1H, brs)

PREPARATION EXAMPLE 144

According to the same manner as that of Preparation Example 119, 3-bromo-1-(3-chloro-2-pyridinyl)-N-[4-cyano-2-(N,N'-dimethylhydrazinocarbonyl)-6-methylphenyl]-1H-pyrazole-5-carboxamide was used in place of 3-bromo-N-[4-chloro-2-(N,N'-dimethylhydrazinocarbonyl)-6-methylphenyl]-1-(3-chloro-2-pyridinyl)-1H-pyrazole-5-carboxamide to obtain the present compound (144) of the formula:

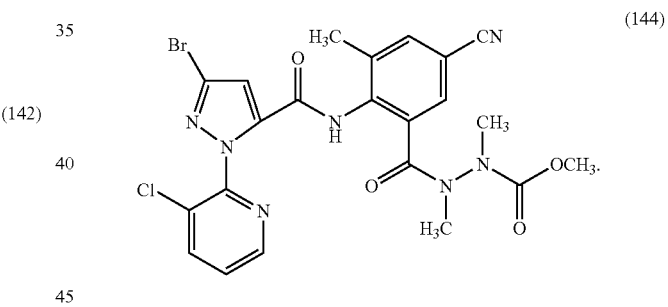

(144)

The present compound (144)

¹H-NMR (DMSO-d₆, TMS) δ (ppm): 2.14-2.29 (3H, m), 2.64-2.87 (3H, m), 2.87-3.15 (3H, m), 3.42-3.73 (3H, m), 7.30-7.45 (1H, m), 7.54-7.81 (2H, m), 7.83-8.01 (1H, m), 8.15-8.24 (1H, m), 8.50 (1H, brs), 10.20-10.68 (1H, m)

PREPARATION EXAMPLE 145

A mixture of 0.25 g of 3-bromo-N-[1-bromo-3-(hydrazinocarbonyl)-2-naphthyl]-1-(3-chloro-2-pyridinyl)-1H-pyrazole-5-carboxamide, 0.22 g of N,N-dimethylcarbamoyl chloride, 4 ml of acetonitrile and 1 ml of pyridine was stirred at room temperature for 2 hours, and allowed to stand at room temperature overnight. Water was poured into the reaction mixture, and the mixture was extracted with ethyl acetate three times. The organic layers were combined, washed successively with water and an aqueous saturated sodium chloride solution, dried over anhydrous magnesium sulfate, and concentrated under reduced pressure to obtain 0.20 g of the present compound (145) of the formula:

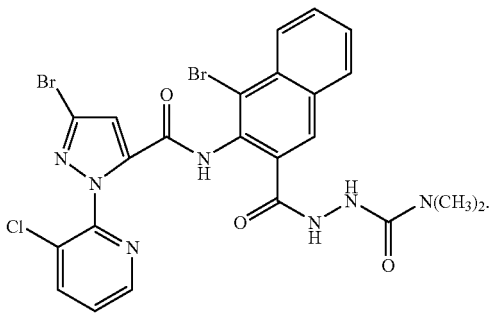

(145)

The present compound (145)
$^1$H-NMR (DMSO-d$_6$, TMS) δ (ppm): 2.88 (6H, s), 7.54 (1H, s), 7.59 (1H, dd, J=8 Hz, 5 Hz), 7.72 (1H, t, J=7 Hz), 7.79 (1H, t, J=7 Hz), 8.09 (1H, d, J=7 Hz), 8.15 (1H, dd, J=8 Hz, 1Hz), 8.19-8.26 (2H, m), 8.50 (1H, dd, J=5.1 Hz), 8.54 (1H, brs), 9.90 (1H, brs), 10.57 (1H, brs)

PREPARATION EXAMPLE 146

According to the same manner as that of Preparation Example 145, 4-bromo-N-[1-bromo-3-(hydrazinocarbonyl)-2-naphthyl]-1-(3-chloro-2-pyridinyl)-1H-pyrrole-2-carboxamide was used in place of 3-bromo-N-[1-bromo-3-(hydrazinocarbonyl)-2-naphthyl]-1-(3-chloro-2-pyridinyl)-1H-pyrazole-5-carboxamide to obtain the present compound (146) of the formula:

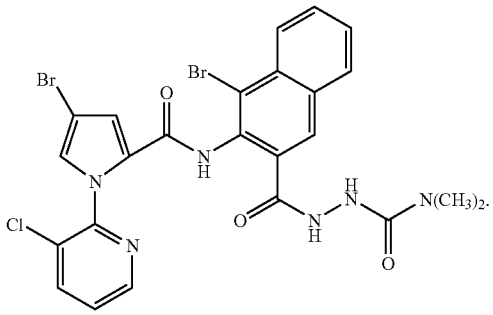

(146)

The present compound (146)
$^1$H-NMR (DMSO-d$_6$, TMS) δ (ppm): 2.88 (6H, s), 7.37-7.44 (1H, m), 7.44-7.51 (2H, m), 7.69 (1H, t, J=7 Hz), 7.77 (1H, t, J=7 Hz), 8.01-8.10 (2H, m), 8.19-8.25 (2H, m), 8.43 (1H, dd, J=5 Hz, 1Hz), 8.55 (1H, brs), 9.84 (1H, brs), 10.05 (1H, brs)

PREPARATION EXAMPLE 147

A mixture of 0.26 g of 4-bromo-N-[4-chloro-2-(N,N'-dimethylhydrazinocarbonyl)-6-methylphenyl]-1-(3-chloro-2-pyridinyl)-1H-pyrrole-2-carboxamide, 0.05 g of methyl chloroformate, 0.09 ml of pyridine and 5 ml of N,N-dimethylformamide was stirred at room temperature for 3 hours. The reaction mixture was poured into water, and extracted with ethyl acetate three times. The organic layers were combined, washed successively with water and an aqueous saturated sodium chloride solution, dried over anhydrous sodium sulfate, and concentrated under reduced pressure. The resulting residue was subjected to silica gel column chromatography to obtain 0.20 g of the present compound (147) of the formula:

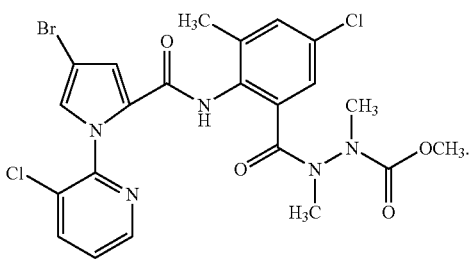

(147)

The present compound (147)
$^1$H-NMR (CDCl$_3$, TMS) δ (ppm): 2.18 (3H, s), 2.88-2.98 (3H, m), 3.13-3.22 (3H, m), 3.63-3.82 (3H, m), 7.01-7.12 (3H, m), 7.20 (1H, s), 7.30 (1H, d, J=5 Hz), 7.79-7.80 (1H, m), 8.37-8.38 (1H, m), 8.45-8.58 (1H, brm)

PREPARATION EXAMPLE 148

According to the same manner as that of Preparation Example 93, N-[4,6-dibromo-2-(hydrazinocarbonyl)phenyl]-4,5-dichloro-1-(3-chloro-2-pyridinyl)-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (148) of the formula:

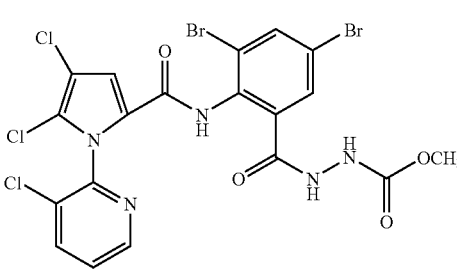

(148)

The present compound (148)
$^1$H-NMR (DMSO-d$_6$, TMS) δ (ppm): 3.62 (3H, s), 7.45 (1H, s), 7.58 (1H, dd, J=8 Hz, 5 Hz), 7.63 (1H, s), 8.10 (1H, s), 8.15 (1H, dd, J=8 Hz, 2 Hz), 8.51 (1H, dd, J=5 Hz, 2 Hz), 9.34 (1H, brs), 10.00 (1H, brs), 10.15 (1H, brs)

PREPARATION EXAMPLE 149

A mixture of 0.50 g of 3-bromo-N-[4-chloro-2-(N-methylhydrazinocarbonyl)-6-methylphenyl]-1-(3-chloro-2-pyridinyl)-1H-pyrazole-5-carboxamide, 0.09 g of acetyl chloride, 0.09 g of pyridine and 10 ml of tetrahydrofuran was stirred at room temperature for 2 hours. Water was poured into the reaction mixture, and the mixture was extracted with ethyl acetate. The organic layer was washed with water, dried over anhydrous magnesium sulfate, and concentrated under reduced pressure. The resulting residue was washed with methyl t-butyl ether and hexane to obtain 0.48 g of the present compound (149) of the formula:

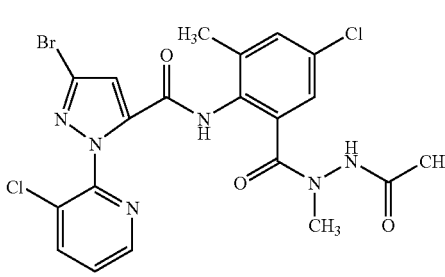

(149)

The present compound (149)

$^1$H-NMR (CDCl$_3$, TMS) δ (ppm): 1.56 (3H, s), 2.01 (3H, s), 3.24 (3H, s), 6.97 (2H, d, J=2 Hz), 7.39-7.42 (2H, m), 7.88 (1H, dd, J=8 Hz, 1Hz), 8.39 (1H, s), 8.47 (1H, dd, J=5 Hz, 1Hz), 10.12 (1H, brs)

PREPARATION EXAMPLE 150

A mixture of 0.50 g of 3-bromo-N-[4-chloro-2-(N-methylhydrazinocarbonyl)-6-methylphenyl]-1-(3-chloro-2-pyridinyl)-1H-pyrazole-5-carboxamide, 0.12 g of methyl chlorothiol formate, 0.09 g of pyridine and 10 ml of tetrahydrofuran was stirred at room temperature for 2 hours. Water was poured into the reaction mixture, and the mixture was extracted with ethyl acetate. The organic layer was washed with water, dried over anhydrous magnesium sulfate, and concentrated under reduced pressure. The resulting residue was washed with methyl t-butyl ether and hexane to obtain 0.50 g of the present compound (150) of the formula:

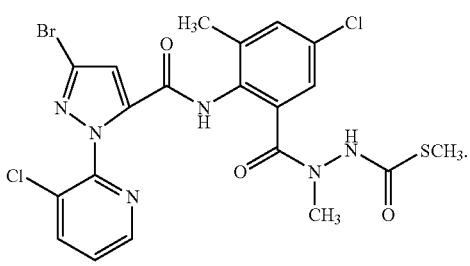

(150)

The present compound (150)

$^1$H-NMR (CDCl$_3$, TMS) δ (ppm): 2.06 (3H, brs), 2.25 (3H, brs), 3.20 (3H, brs), 6.99-7.29 (3H, m), 7.41 (1H, dd, J=8 Hz, 5 Hz), 7.88 (1H, dd, J=8 Hz, 1Hz), 8.01-8.23 (1H, brm), 8.46 (1H, d, J=5 Hz), 9.49-9.79 (1H, brm)

PREPARATION EXAMPLE 151

A mixture of 0.49 g of 2-[3-bromo-1-(3-chloro-2-pyridinyl)-1H-pyrazol-5-yl]-10-chloro-4H-naphtho[2,3-d][1,3]oxazine-4-one, 0.90 g of methyl carbazate and 5 ml of N,N-dimethylformamide was stirred at room temperature for 2 hours. Water was poured into the reaction mixture, and the mixture was extracted with ethyl acetate three times. The organic layers were combined, washed successively with water and an aqueous saturated sodium chloride solution, dried over anhydrous magnesium sulfate, and concentrated under reduced pressure to obtain 0.31 g of the present compound (151) of the formula:

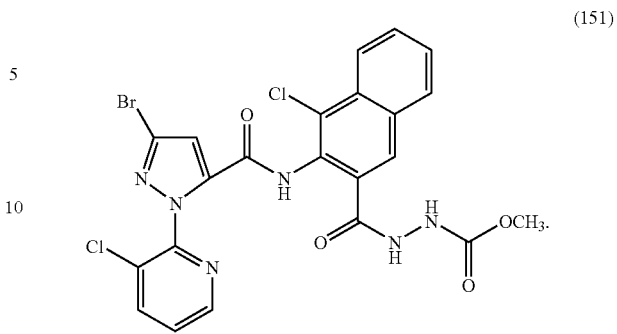

(151)

The present compound (151)

$^1$H-NMR (DMSO-d$_6$, TMS) δ (ppm): 3.59-3.68 (3H, m), 7.47 (1H, s), 7.56-7.62 (1H, m), 7.74 (1H, d, J=7 Hz), 7.80 (1H, d, J=7 Hz), 8.12-8.18 (3H, m), 8.25 (1H, d, J=7 Hz), 8.50 (1H, d, J=5 Hz), 9.35 (1H, brs), 10.30 (1H, brs), 10.60 (1H, brs)

PREPARATION EXAMPLE 152

According to the same manner as that of Preparation Example 151, 2-[4-bromo-1-(3-chloro-2-pyridinyl)-1H-pyrrol-2-yl]-10-chloro-4H-naphtho[2,3-d][1,3]oxazine-4-one was used in place of 2-[3-bromo-1-(3-chloro-2-pyridinyl)-1H-pyrazol-5-yl]-10-chloro-4H-naphtho[2,3-d][1,3]oxazine-4-one to obtain the present compound (152) of the formula:

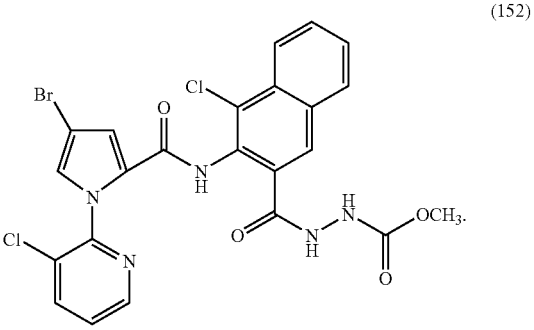

(152)

The present compound (152)

$^1$H-NMR (DMSO-d$_6$, TMS) δ (ppm): 3.55-3.70 (3H, m), 7.35 (1H, s), 7.43-7.51 (2H, m), 7.71 (1H, t, J=8 Hz), 7.79 (1H, t, J=8 Hz), 8.04 (1H, d, J=8 Hz), 8.12 (2H, d, J=8 Hz), 8.23 (1H, d, J=8 Hz), 8.43 (1H, d, J=5 Hz), 9.35 (1H, brs), 10.06 (1H, brs), 10.24 (1H, brs)

PREPARATION EXAMPLE 153

According to the same manner as that of Preparation Example 93, 4-chloro-N-[4-chloro-2-(hydrazinocarbonyl)-6-methylphenyl]-1-(3-chloro-2-pyridinyl))-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (153) of the formula:

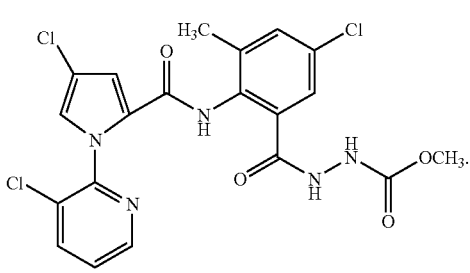
(153)

The present compound (153)

¹H-NMR (DMSO-d₆, TMS) δ (ppm): 2.17 (3H, s), 3.63 (3H, s), 7.18 (1H, d, J=2 Hz), 7.35 (1H, d, J=2 Hz), 7.39 (1H, s), 7.47 (1H, s), 7.49 (1H, dd, J=8 Hz, 5 Hz), 8.03 (1H, dd, J=8 Hz, 2 Hz), 8.42 (1H, dd, J=5 Hz, 2 Hz), 9.31 (1H, brs), 9.76 (1H, brs), 10.12 (1H, brs)

PREPARATION EXAMPLE 154

A mixture of 0.52 g of 3-bromo-N-[4,6-dichloro-2-(N-methylhydrazinocarbonyl)phenyl]-1-(3-chloro-2-pyridinyl)-1H-pyrazole-5-carboxamide, 0.10 g of methyl chloroformate, 0.09 g of pyridine and 7 ml of tetrahydrofuran was stirred at room temperature for 1 hour. Water was poured into the reaction mixture, and the mixture was extracted with ethyl acetate. The organic layer was washed with water, dried over anhydrous magnesium sulfate, and concentrated under reduced pressure. The resulting residue was washed with methyl t-butyl ether and hexane to obtain 0.49 g of the present compound (154) of the formula:

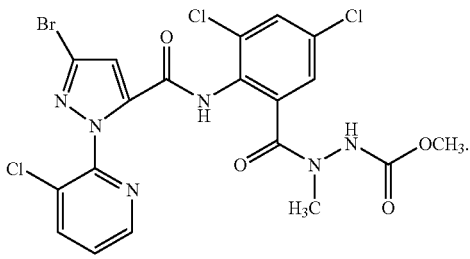
(154)

The present compound (154)

¹H-NMR (CDCl₃, TMS) δ (ppm): 3.12-3.18 (3H, brm), 3.60-3.84 (3H, brm), 7.21-7.22 (2H, m), 7.34 (1H, brs), 7.41 (1H, dd, J=8 Hz, 5 Hz), 7.51 (1H, brs), 7.88 (1H, dd, J=8 Hz, 1Hz), 8.48 (1H, dd, J=5 Hz, 1Hz), 9.85 (1H, brs)

PREPARATION EXAMPLE 155

According to the same manner as that of Preparation Example 154, ethyl chloroformate was used in place of methyl chloroformate to obtain the present compound (155) of the formula:

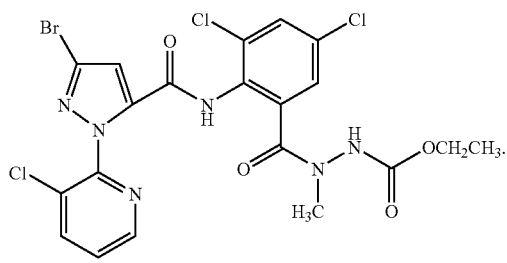
(155)

The present compound (155)

¹H-NMR (CDCl₃, TMS) δ (ppm): 1.11-1.39 (3H, m), 3.12-3.18 (3H, brm), 4.06-4.25 (2H, brm), 7.08-7.22 (2H, m), 7.34 (1H, brs), 7.41 (1H, dd, J=8 Hz, 5 Hz), 7.43 (1H, brs), 7.88 (1H, dd, J=8 Hz, 1Hz), 8.49 (1H, dd, J=5 Hz, 1Hz), 9.87 (1H, brs)

PREPARATION EXAMPLE 156

A mixture of 0.50 g of 3-bromo-N-[4-chloro-2-(N-methylhydrazinocarbonyl)-6-methylphenyl]-1-(3-chloro-2-pyridinyl)-1H-pyrazole-5-carboxamide and 5 ml of formic acid was stirred at 50° C. for 1 hour. Water was poured into the reaction mixture, and the mixture was extracted with ethyl acetate. The organic layer was washed with water, dried over anhydrous magnesium sulfate, and concentrated under reduced pressure. The resulting residue was washed with t-butyl ether and hexane to obtain 0.40 g of the present compound (156) of the formula:

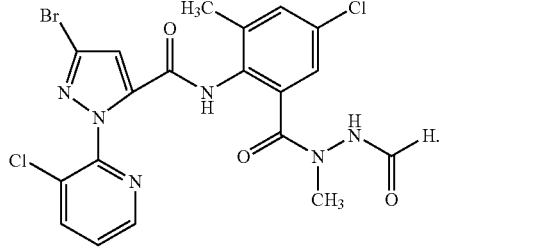
(156)

The present compound (156)

¹H-NMR (CDCl₃, TMS) δ (ppm): 2.02 (3H, s), 3.25 (3H, s), 6.99 (2H, d, J=4 Hz), 7.35 (1H, s), 7.41 (1H, dd, J=8 Hz, 5 Hz), 7.64 (1H, s), 7.88 (1H, dd, J=8 Hz, 2 Hz), 8.47 (1H, dd, J=5 Hz, 2 Hz), 8.58 (1H, s), 10.08 (1H, s)

PREPARATION EXAMPLE 157

According to the same manner as that of Preparation Example 93, 5-bromo-N-[4-chloro-2-(hydrazinocarbonyl)-6-methylphenyl]-1-(3-chloro-2-pyridinyl)-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (157) of the formula:

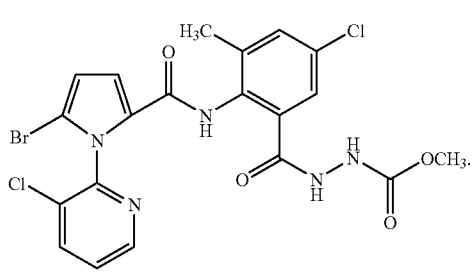
(157)

The present compound 157

$^1$H-NMR (DMSO-d$_6$, TMS) δ (ppm): 2.11 (3H, s), 3.63 (3H, s), 6.54 (1H, d, J=3 Hz), 7.24 (1H, d, J=3 Hz), 7.39 (1H, s), 7.46 (1H, s), 7.54 (1H, dd, J=8 Hz, 4 Hz), 8.09 (1H, d, J=8 Hz), 8.28 (1H, d, J=4 Hz), 9.30 (1H, brs), 9.74 (1H, brs), 10.13 (1H, brs)

PREPARATION EXAMPLE 158

Under ice-cooling, 0.14 ml of methyl chloroformate was added to a mixture of 0.50 g of the present compound (93), 0.26 ml of triethylamine and 15 ml of tetrahydrofuran. The mixture was stirred at room temperature for 5 hours. Water was poured into the reaction mixture, and the mixture was extracted with ethyl acetate three times. The organic layers were combined, washed successively with water and an aqueous saturated sodium chloride solution, dried over anhydrous magnesium sulfate, and concentrated under reduced pressure. The resulting residue was subjected to silica gel column chromatography to obtain 0.21 g of the present compound (158) of the formula:

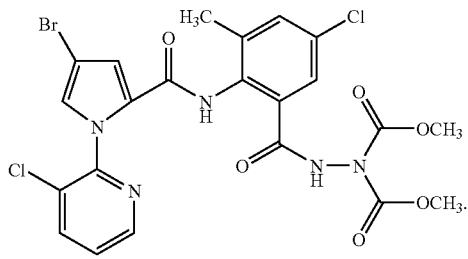
(158)

The present compound (158)

$^1$H-NMR (CDCl$_3$, TMS) δ (ppm): 2.22 (3H, s), 3.79 (6H, s), 7.01 (1H, d, J=2 Hz), 7.07 (1H, d, J=2 Hz), 7.30 (1H, dd, J=8 Hz, 5 Hz), 7.32 (1H, s), 7.39 (1H, s), 7.82 (1H, d, J=8 Hz), 8.33 (1H, d, J=5 Hz), 8.45 (1H, brs), 8.88 (1H, brs)

PREPARATION EXAMPLE 159

According to the same manner as that of Preparation Example (158), the present compound (153) was used in place of the present compound (93) to obtain the present compound (159) of the formula:

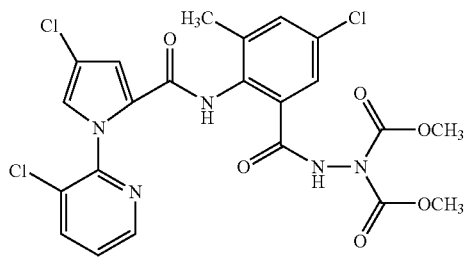
(159)

The present compound (159)

$^1$H-NMR (CDCl$_3$, TMS) δ (ppm): 2.18 (3H, s), 3.73 (6H, s), 7.00-7.01 (2H, m), 7.24-7.28 (3H, m), 7.79 (1H, d, J=8 Hz), 8.29 (1H, d, J=4 Hz), 8.82 (1H, brs), 9.06 (1H, brs)

PREPARATION EXAMPLE 160

Under ice-cooling, 0.50 g of 3-bromo-N-[4-chloro-2-(N-methylhydrazinocarbonyl)-6-methylphenyl]-1-(3-chloro-2-pyridinyl)-1H-pyrazole-5-carboxamide, 0.12 g of N,N-dimethylcarbamoyl chloride, 0.09 g of pyridine and 20 ml of tetrahydrofuran were mixed, and the mixture was stirred at 50° C. for 14 hours. To the mixture were further added 0.12 g of N,N-dimethylcarbamoyl chloride and 0.09 g of pyridine. The mixture was stirred at 50° C. for 9 hours. Water was poured into the reaction mixture, and the mixture was extracted with ethyl acetate. The organic layer was washed with water, dried over anhydrous magnesium sulfate, and concentrated under reduced pressure. The resulting residue was washed with methyl t-butyl ether and hexane to obtain 0.15 g of the present compound (160) of the formula:

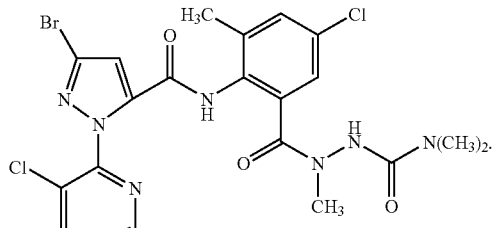
(160)

The present compound (160)

$^1$H-NMR (CDCl$_3$, TMS) δ (ppm): 1.98 (3H, s), 2.46 (6H, s), 3.30 (3H, s), 6.95 (1H, d, J=2 Hz), 7.05 (1H, d, J=2 Hz), 7.37 (1H, dd, J=8 Hz, 5 Hz), 7.51 (1H, s), 7.81 (1H, s), 7.85 (1H, dd, J=8 Hz, 2 Hz), 8.45 (1H, dd, J=5 Hz, 2 Hz), 10.34 (1H, brs).

PREPARATION EXAMPLE 161

According to the same manner as that of Preparation Example 93, 5-bromo-N-[4-chloro-2-(hydrazinocarbonyl)-6-methylphenyl]-1-(2-pyrimidinyl)-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (161) of the formula:

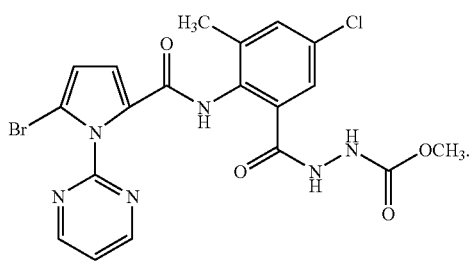

(161)

The present compound (161)

¹H-NMR (DMSO-d₆, TMS) δ (ppm): 2.14 (3H, s), 3.46-3.67 (3H, m), 6.08-6.50 (1H, m), 7.08-7.29 (1H, m), 7.38 (1H, s), 7.51 (1H, s), 7.58-7.65 (1H, m), 8.89-8.95 (2H, m), 9.09-9.39 (1H, m), 9.74-9.90 (1H, m), 10.11 (1H, brs)

PREPARATION EXAMPLE 162

According to the same manner as that of Preparation Example 93, 4-bromo-N-[4-chloro-2-(hydrazinocarbonyl)-6-methylphenyl]-1-(2,6-dichlorophenyl)-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (162) of the formula:

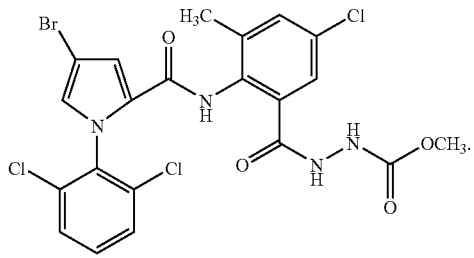

(162)

The present compound (162)

¹H-NMR (DMSO-d₆, TMS) δ (ppm): 2.11 (3H, s), 3.46-3.68 (3H, m), 7.27 (1H, s), 7.30-7.47 (3H, m), 7.50 (1H, s), 7.53-7.65 (2H, m), 9.02-9.38 (1H, m), 9.71 (1H, brs), 10.13 (1H, brs)

PREPARATION EXAMPLE 163

According to the same manner as that of Preparation Example 93, 4-bromo-N-[4-chloro-2-(hydrazinocarbonyl)-6-methylphenyl]-1-(3,5-dichloro-4-pyridinyl)-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (163) of the formula:

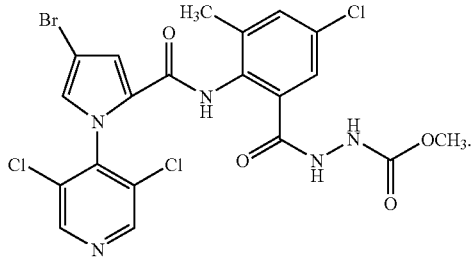

(163)

The present compound (163)

¹H-NMR (DMSO-d₆, TMS) δ (ppm): 2.12 (3H, s), 3.48-3.67 (3H, m), 7.33-7.40 (2H, m), 7.46 (1H, d, J=2 Hz), 7.51 (1H, d, J=2 Hz), 8.76 (2H, s), 9.31 (1H, brs), 9.82 (1H, brs), 10.14 (1H, brs)

PREPARATION EXAMPLE 164

According to the same manner as that of Preparation Example 137, 4,5-dichloro-N-[4-chloro-2-(hydrazinocarbonyl)-6-methylphenyl]-1-(3-chloro-2-pyridinyl)-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (164) of the formula:

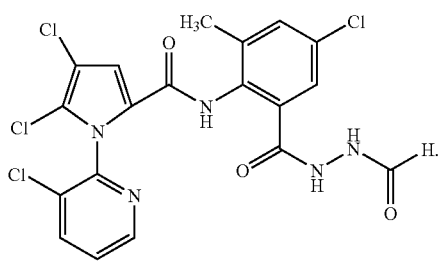

(164)

The present compound (164)

¹H-NMR (DMSO-d₆, TMS) δ (ppm): 2.09-2.19 (3H, s), 7.34-7.53 (3H, m), 7.59 (1H, dd, J=8 Hz, 5 Hz), 8.06 (1H, s), 8.16 (1H, d, J=8 Hz), 8.52 (1H, d, J=5 Hz), 9.87 (1H, brs), 10.13 (1H, brs) 10.38 (1H, brs)

PREPARATION EXAMPLE 165

Under ice-cooling, 0.43 g of N-[4-chloro-2-(hydrazinocarbonyl)-6-methylphenyl]-1-(2,6-dichlorophenyl)-1H-pyrrole-3-carboxamide, 0.15 g of methyl chloroformate, 2 ml of pyridine and 10 ml of acetonitrile were mixed, and the mixture was stirred for 1 hour under ice-cooling. Water was poured into a reaction mixture, and the mixture was extracted with ethyl acetate three times. The organic layers were combined, washed successively with water and an aqueous saturated sodium chloride solution, dried over anhydrous magnesium sulfate, and concentrated under reduced pressure to obtain 0.16 g of the present compound (165) of the formula:

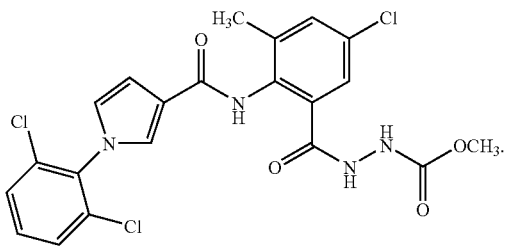

The present compound (165)
¹H-NMR (DMSO-d₆, TMS) δ (ppm): 2.24 (3H, s), 3.38-3.65 (3H, m), 6.81 (1H, brs), 6.96 (1H, brs), 7.33-7.61 (4H, m), 7.68-7.74 (2H, m), 9.37 (1H, brs), 9.52 (1H, brs), 10.21 (1H, brs)

PREPARATION EXAMPLE 166

A mixture of 0.56 g of 2-[3-bromo-1-(3-chloro-2-pyridinyl)-1H-pyrazol-5-yl]-6,8-dibromo-4H-3,1-benzoxazine-4-one, 0.47 g of 2,4,4-trimethylsemicarbazide and 15 ml of 1-methyl-2-pyrrolidone was stirred at room temperature for 22 hours. Water was poured into the reaction mixture, and the mixture was extracted with ethyl acetate. The organic layer was washed with water, dried over anhydrous magnesium sulfate, and concentrated under reduced pressure. The resulting residue was washed with ethyl acetate to obtain 0.11 g of the present compound (166) of the formula:

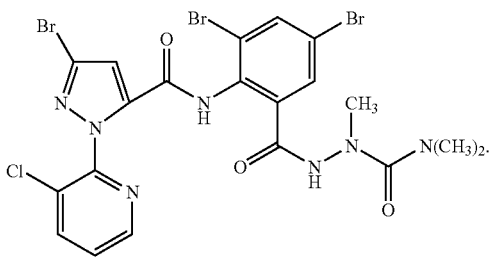

The present compound (166)
¹H-NMR (DMSO-d₆, TMS) δ (ppm): 2.66 (6H, s), 2.68 (3H, s), 7.45 (1H, brs), 7.59-7.63 (2H, m), 8.15-8.17 (2H, m), 8.49 (1H, d, J=4 Hz), 10.50 (1H, brs), 10.55 (1H, brs).

PREPARATION EXAMPLE 167

According to the same manner as that of Preparation Example 158, the present compound (132) was used in place of the present compound (93) to obtain the present compound (167) of the formula:

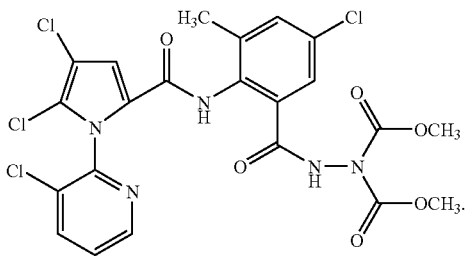

The present compound (167)
¹H-NMR (CDCl₃, TMS) δ (ppm): 2.18 (3H, s), 3.82 (6H, s), 7.00 (1H, s), 7.32 (1H, d, J=2 Hz), 7.36-7.39 (2H, m), 7.86 (1H, dd, J=8 Hz, 2 Hz), 8.12 (1H, s), 8.43 (1H, dd, J=5 Hz, 2 Hz), 8.85 (1H, brs)

PREPARATION EXAMPLE 168

According to the same manner as that of Preparation Example 134, 4,5-dichloro-N-[4-chloro-2-(N-methylhydrazinocarbonyl)-6-methylphenyl]-1-(3-chloro-2-pyridinyl)-1H-pyrrole-2-carboxamide was used in place of 4-bromo-N-[4-chloro-2-(N-methylhydrazinocarbonyl)-6-methylphenyl]-1-(3-chloro-2-pyridinyl)-1H-pyrrole-2-carboxamide to obtain the present compound (168) of the formula:

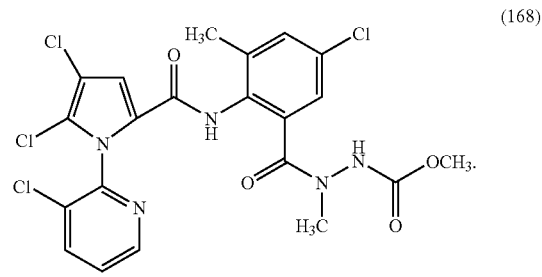

The present compound (168)
¹H-NMR (CDCl₃, TMS) δ (ppm): 2.02-2.11 (3H, m), 3.02-3.28 (3H, m), 3.54-3.89 (3H, m), 6.95-7.15 (1H, m), 7.22-7.31 (2H, m), 7.39 (1H, dd, J=8 Hz, 5 Hz), 7.70 (1H, brs), 7.87 (1H, dd, J=8 Hz, 2 Hz), 8.47 (1H, dd, J=5 Hz, 2 Hz), 9.23 (1H, brs)

PREPARATION EXAMPLE 169

According to the same manner as that of Preparation Example 5, N-[4-chloro-2-(hydrazinocarbonyl)-6-methylphenyl]-1-[(2-fluoro-3-pyridinyl)methyl]-3-trifluoromethyl-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (169) of the formula:

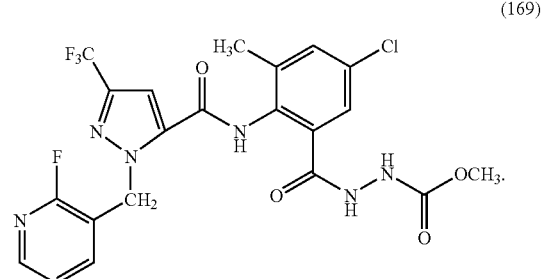

The present compound (169)
¹H-NMR (DMSO-d₆, TMS) δ (ppm): 2.14 (3H, s), 3.52-3.62 (3H, m), 5.85 (2H, s), 7.30-7.36 (1H, m), 7.39 (1H, s), 7.51 (1H, s), 7.59 (1H, d, J=2 Hz), 7.61-7.71 (1H, m), 8.19 (1H, d, J=5 Hz), 9.26 (1H, brs), 10.20 (1H, brs), 10.25 (1H, brs)

PREPARATION EXAMPLE 170

Under ice-cooling, 0.08 g of N-[4-chloro-2-(hydrazinocarbonyl)-6-methylphenyl]-1-[(3-chloro-2-pyridinyl)methyl]-5-trifluoromethyl-1H-pyrazole-3-carboxamide, 0.05 g of methyl chloroformate, 1 ml of pyridine and 10 ml of acetonitrile were mixed, and the mixture was stirred for 1 hour under ice-cooling. Water was poured into the reaction mixture, and the mixture was extracted with ethyl acetate three times. The organic layers were combined, washed successively with water and an aqueous saturated sodium chloride solution, dried over anhydrous magnesium sulfate, and concentrated under reduced pressure to obtain 0.06 g of the present compound (170) of the formula:

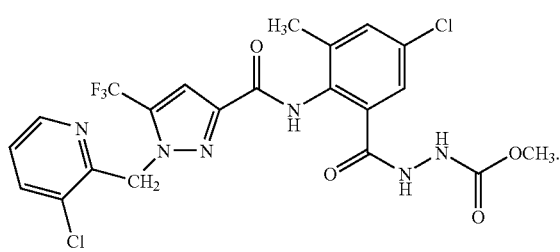

(170)

The present compound (170)
$^1$H-NMR (DMSO-d$_6$, TMS) δ (ppm): 2.20 (3H, s), 3.53-3.64 (3H, m), 5.86 (2H, s), 7.41-7.49 (3H, m), 7.59 (1H, s), 8.03 (1H, d, J=7 Hz), 8.44 (1H, d, J=4 Hz), 9.32 (1H, brs), 9.96 (1H, brs), 10.25 (1H, brs)

PREPARATION EXAMPLE 171

According to the same manner as that of Preparation Example 93, N-[4-chloro-2-(hydrazinocarbonyl)-6-methylphenyl]-1-(3-chloro-2-pyridinyl)-4-iodo-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (171) of the formula:

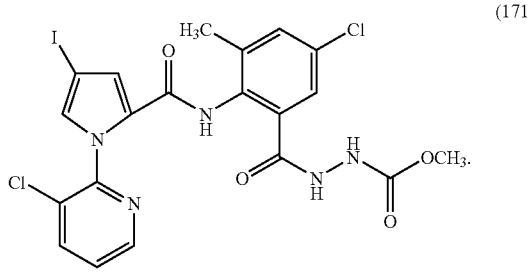

(171)

The present compound (171)
$^1$H-NMR (DMSO-d$_6$, TMS) δ (ppm): 2.15 (3H, s), 3.63 (3H, s), 7.25 (1H, s), 7.38 (1H, s), 7.40 (1H, s), 7.49 (1H, dd, J=8 Hz, 5 Hz), 7.51 (1H, s), 8.05 (1H, dd, J=8 Hz, 2 Hz), 8.43 (1H, dd, J=5 Hz, 2 Hz), 9.33 (1H, brs), 9.72 (1H, brs), 10.12 (1H, brs)

PREPARATION EXAMPLE 172

According to the same manner as that of Preparation Example 158, the present compound (171) was used in place of the present compound (93) to obtain the present compound (172) of the formula:

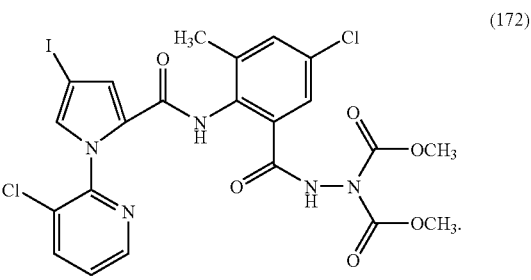

(172)

The present compound (172)
$^1$H-NMR (CDCl$_3$, TMS) δ (ppm): 2.19 (3H, s), 3.73 (6H, s), 7.10 (1H, d, J=1 Hz), 7.14 (1H, d, J=1 Hz), 7.25-7.31 (3H, m), 7.79 (1H, dd, J=8 Hz, 2 Hz), 8.31 (1H, dd, J=5 Hz, 2 Hz), 9.20 (1H, s), 9.23 (1H, brs)

PREPARATION EXAMPLE 173

According to the same manner as that of Preparation Example 151, 10-chloro-2-[4,5-dichloro-1-(3-chloro-2-pyridinyl)-1H-pyrrol-2-yl]-4H-naphtho[2,3-d][1,3]oxazine-4-one was used in place of 2-[3-bromo-1-(3-chloro-2-pyridinyl)-1H-pyrazol-5-yl]-10-chloro-4H-naphtho[2,3-d][1,3]oxazine-4-one to obtain the present compound (173) of the formula:

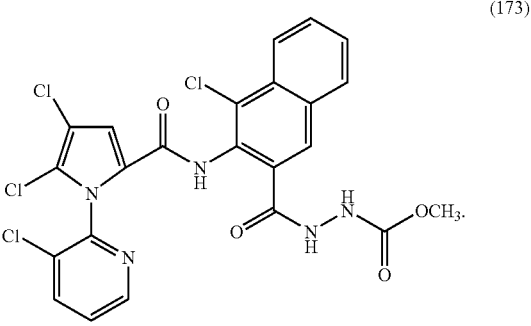

(173)

The present compound (173)
$^1$H-NMR (CDCl$_3$, TMS) δ (ppm): 3.60 (3H, s), 7.46-7.59 (2H, m), 7.69-7.81 (2H, m), 8.11-8.23 (4H, m), 8.48-8.52 (1H, m), 9.32 (1H, brs), 10.09 (1H, brs), 10.22 (1H, brs)

PREPARATION EXAMPLE 174

According to the same manner as that of Preparation Example 93, 4-bromo-N-[4-chloro-2-(hydrazinocarbonyl)-6-methylphenyl]-1-(2-chloro-3-pyridinyl)-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (174) of the formula:

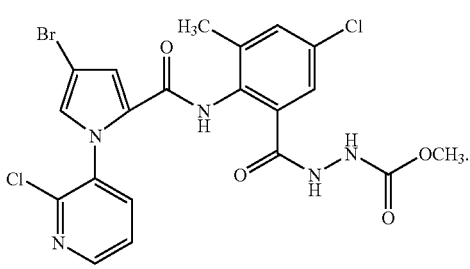

(174)

The present compound (174)

¹H-NMR (DMSO-d₆, TMS) δ (ppm): 2.15 (3H, s), 3.45-3.67 (3H, m), 7.27 (1H, s), 7.36 (1H, s), 7.42 (1H, d, J=1 Hz), 7.48-7.54 (2H, m), 7.94 (1H, dd, J=8 Hz, 1Hz), 8.42 (1H, dd, J=5 Hz, 1Hz), 9.29 (1H, brs), 9.73 (1H, brs), 10.12 (1H, brs)

PREPARATION EXAMPLE 175

According to the same manner as that of Preparation Example 151, 7-bromo-2-[3-bromo-1-(3-chloro-2-pyridinyl)-1H-pyrazol-5-yl]-10-chloro-4H-naphtho[2,3-d][1,3]oxazine-4-one was used in place of 2-[3-bromo-1-(3-chloro-2-pyridinyl)-1H-pyrazol-5-yl]-10-chloro-4H-naphtho[2,3-d][1,3]oxazine-4-one to obtain the present compound (175) of the formula:

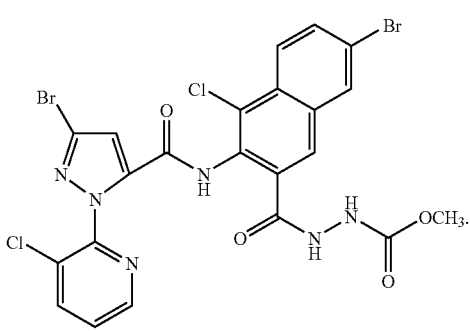

(175)

The present compound (175)

¹H-NMR (DMSO-d₆, TMS) δ (ppm): 3.58-3.70 (3H, m), 7.46 (1H, s), 7.59 (1H, dd, J=8 Hz, 5 Hz), 7.93 (1H, d, J=9 Hz), 8.08-8.21 (3H, m), 8.46-8.53 (2H, m), 9.36 (1H, brs), 10.33 (1H, brs), 10.62 (1H, brs)

PREPARATION EXAMPLE 176

According to the same manner as that of Preparation Example 151, 7,10-dibromo-2-[3-bromo-1-(3-chloro-2-pyridinyl)-1H-pyrazol-5-yl]-4H-naphtho[2,3-d][1,3]oxazine-4-one was used in place of 2-[3-bromo-1-(3-chloro-2-pyridinyl)-1H-pyrazol-5-yl]-10-chloro-4H-naphtho[2,3-d][1,3]oxazine-4-one to obtain the present compound (176) of the formula:

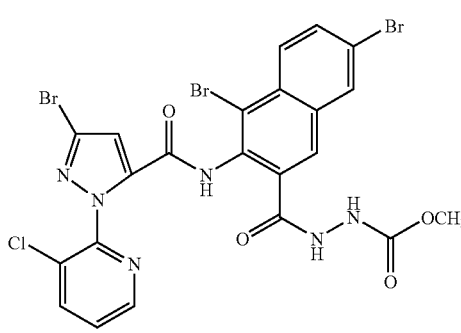

(176)

The present compound (176)

¹H-NMR (DMSO-d₆, TMS) δ (ppm): 3.59-3.69 (3H, m), 7.47 (1H, s), 7.56-7.62 (1H, m), 7.92 (1H, d, J=9 Hz), 8.10-8.20 (3H, m), 8.45-8.54 (2H, m), 9.35 (1H, brs), 10.29 (1H, brs), 10.66 (1H, brs)

PREPARATION EXAMPLE 177

According to the same manner as that of Preparation Example 93, 5-chloro-N-[4-chloro-2-(hydrazinocarbonyl)-6-methylphenyl]-1-(2-pyridinyl)-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (177) of the formula:

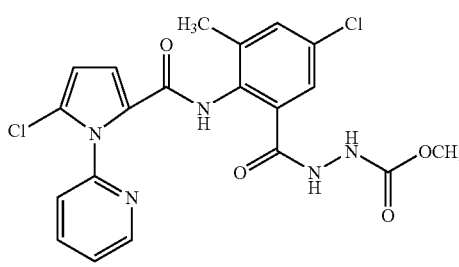

(177)

The present compound (177)

¹H-NMR (DMSO-d₆, TMS) δ (ppm): 2.13 (3H, s), 3.63 (3H, s), 6.42 (1H, d, J=4 Hz), 7.13 (1H, d, J=4 Hz), 7.37 (1H, s), 7.42-7.47 (2H, m), 7.50 (1H, d, J=2 Hz), 7.94 (1H, td, J=8 Hz, 2 Hz), 8.50 (1H, dd, J=5 Hz, 2 Hz), 9.33 (1H, brs), 9.69 (1H, brs), 10.12 (1H, brs)

PREPARATION EXAMPLE 178

According to the same manner as that of Preparation Example 134, 4-bromo-N-[6-bromo-4-chloro-2-(N-methylhydrazinocarbonyl)phenyl]-1-(3-chloro-2-pyridinyl)-1H-pyrrole-2-carboxamide was used in place of 4-bromo-N-[4-chloro-2-(N-methylhydrazinocarbonyl)-6-methylphenyl]-1-(3-chloro-2-pyridinyl)-1H-pyrrole-2-carboxamide to obtain the present compound (178) of the formula:

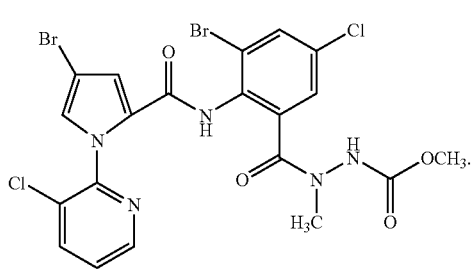

(178)

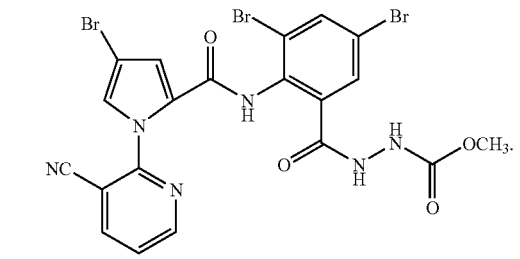

(180)

The present compound (178)

¹H-NMR (CDCl₃, TMS) δ (ppm): 3.15 (3H, s), 3.58 (3H, s), 7.04 (1H, d, J=2 Hz), 7.26 (1H, s), 7.35 (1H, dd, J=8 Hz, 5 Hz), 7.46 (1H, d, J=2 Hz), 7.70 (1H, s), 7.82 (1H, dd, J=8 Hz, 2 Hz), 8.43 (1H, dd, J=5 Hz, 2 Hz), 8.55 (1H, brs), 8.80 (1H, brs)

PREPARATION EXAMPLE 179

According to the same manner as that of Preparation Example 158, the present compound (173) was used in place of the present compound (93) to obtain the present compound (179) of the formula:

The present compound (180)

¹H-NMR (DMSO-d₆, TMS) δ (ppm): 3.62 (3H, s), 7.36 (1H, d, J=2 Hz), 7.64 (1H, d, J=2 Hz), 7.64 (1H, s), 7.67 (1H, dd, J=8 Hz, 5 Hz), 8.11 (1H, s), 8.47 (1H, dd, J=8 Hz, 2 Hz), 8.74 (1H, dd, J=5 Hz, 2 Hz), 9.24 (1H, brs), 10.03 (1H, brs), 10.14 (1H, brs)

PREPARATION EXAMPLE 181

According to the same manner as that of Preparation Example 122, 6,8-dibromo-2-[4-bromo-1-(3-trifluoromethyl-2-pyridinyl)-1H-pyrrol-2-yl]-4H-3,1-benzoxazine-4-one was used in place of 6,8-dibromo-2-[4-bromo-1-(3-chloro-2-pyridinyl)-1H-pyrrol-2-yl]-4H-3,1-benzoxazine-4-one to obtain the present compound (181) of the formula:

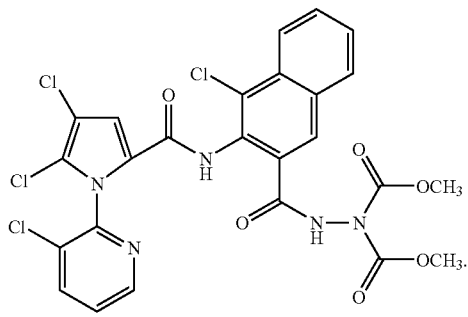

(179)

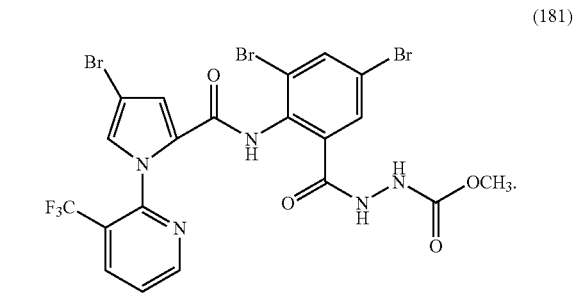

(181)

The present compound (179)

¹H-NMR (CDCl₃, TMS) δ (ppm): 3.81 (6H, s), 7.15 (1H, s), 7.35 (1H, dd, J=8 Hz, 5 Hz), 7.52-7.63 (2H, m), 7.84 (1H, d, J=8 Hz), 7.85 (1H, d, J=8 Hz), 8.04 (1H, s), 8.15 (1H, dd, J=8 Hz, 2 Hz), 8.41 (1H, dd, J=5 Hz, 2 Hz), 8.46 (1H, brs), 8.68 (1H, brs)

PREPARATION EXAMPLE 180

According to the same manner as that of Preparation Example 122, 6,8-dibromo-2-[4-bromo-1-(3-cyano-2-pyridinyl)-1H-pyrrol-2-yl]-4H-3,1-benzoxazine-4-one was used in place of 6,8-dibromo-2-[4-bromo-1-(3-chloro-2-pyridinyl)-1H-pyrrol-2-yl]-4H-3,1-benzoxazine-4-one to obtain the present compound (180) of the formula:

The present compound (181)

¹H-NMR (DMSO-d₆, TMS) δ (ppm): 3.62 (3H, s), 7.33 (1H, s), 7.50 (1H, s), 7.63 (1H, s), 7.72 (1H, dd, J=8 Hz, 5 Hz), 8.08 (1H, s), 8.33 (1H, d, J=8 Hz), 8.74 (1H, d, J=5 Hz), 9.35 (1H, brs), 9.88 (1H, brs), 10.11 (1H, brs)

PREPARATION EXAMPLE 182

According to the same manner as that of Preparation Example 93, N-[4-chloro-2-(hydrazinocarbonyl)-6-methylphenyl]-1-(3-chloro-2-pyridinyl)-5-iodo-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (182) of the formula:

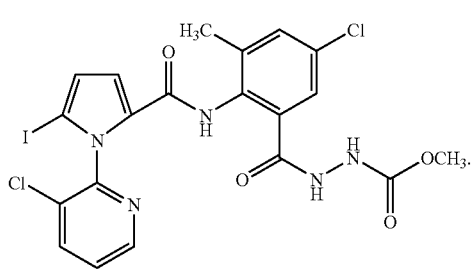

(182)

The present compound (182)

¹H-NMR (DMSO-d₆, TMS) δ (ppm): 2.11 (3H, s), 3.63 (3H, s), 6.63 (1H, d, J=4 Hz), 7.19 (1H, d, J=4 Hz), 7.40 (1H, s), 7.43 (1H, s), 7.52 (1H, dd, J=8 Hz, 5 Hz), 8.06 (1H, dd, J=8 Hz, 2 Hz), 8.48 (1H, dd, J=5 Hz, 2 Hz), 9.28 (1H, brs), 9.71 (1H, brs), 10.13 (1H, brs)

PREPARATION EXAMPLE 183

According to the same manner as that of Preparation Example 72, 2-[3-bromo-1-(3-chloro-2-pyridinyl)-1H-pyrazol-5-yl]-8-methyl-6-nitro-4H-3,1-benzoxazine-4-one was used in place of 2-[3-bromo-1-(3-chloro-2-pyridinyl)-1H-pyrazol-5-yl]-8-chloro-4H-3,1-benzoxazine-4-one to obtain the present compound (183) of the formula:

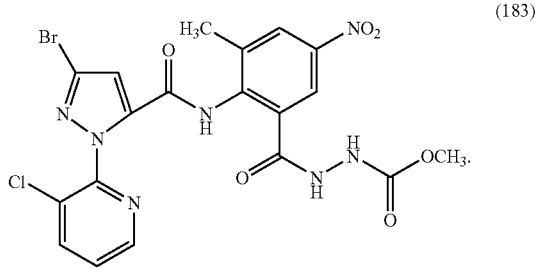

(183)

The present compound (183)

¹H-NMR (DMSO-d₆, TMS) δ (ppm): 2.29 (3H, s), 3.51-3.68 (3H, m), 7.37-7.42 (1H, m), 7.58-7.65 (1H, m), 8.14-8.22 (2H, m), 8.32-8.39 (1H, m), 8.48-8.54 (1H, m), 9.39 (1H, brs), 10.41 (1H, brs), 10.58 (1H, brs)

PREPARATION EXAMPLE 184

To a mixture of 0.26 g of N,N'-dimethylhydrazine dihydrochloride, 2 ml of water, 0.5 g of potassium carbonate and 10 ml of N,N-dimethylformamide was added 0.20 g of 2-[3-bromo-1-(3-chloro-2-pyridinyl)-1H-pyrazol-5-yl]-8-methyl-6-nitro-4H-3,1-benzoxazine-4-one. The resulting mixture was stirred at room temperature for 2 hours. The reaction mixture was poured into water, and extracted with ethyl acetate three times. The organic layers were combined, washed successively with water and an aqueous saturated sodium chloride solution, dried over anhydrous sodium sulfate, and concentrated under reduced pressure to obtain 3-bromo-1-(3-chloro-2-pyridinyl)-N-[2-(N,N'-dimethylhydrazinocarbonyl)-6-methyl-4-nitrophenyl]-1H-pyrazole-5-carboxamide of the formula:

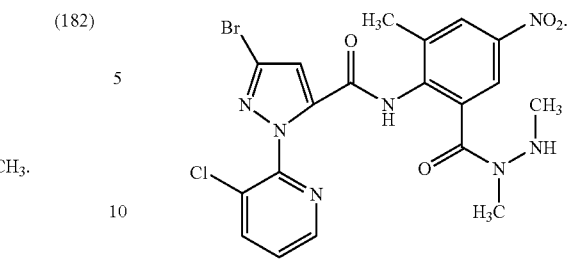

Under ice-cooling, 0.1 g of methyl chloroformate was added to a mixture of 3-bromo-1-(3-chloro-2-pyridinyl)-N-[2-(N,N'-dimethylhydrazinocarbonyl)-6-methyl-4-nitrophenyl]-1H-pyrazole-5-carboxamide, 1 ml of pyridine and 10 ml of acetonitrile, and the mixture was stirred at room temperature for 2 hours. Water was poured into the reaction mixture, and the mixture was extracted with ethyl acetate two times. The organic layers were combined, washed successively with water and an aqueous saturated sodium chloride solution, dried over anhydrous sodium sulfate, and concentrated under reduced pressure. The resulting residue was subjected to silica gel column chromatography to obtain 0.07 g of the present compound (184) of the formula:

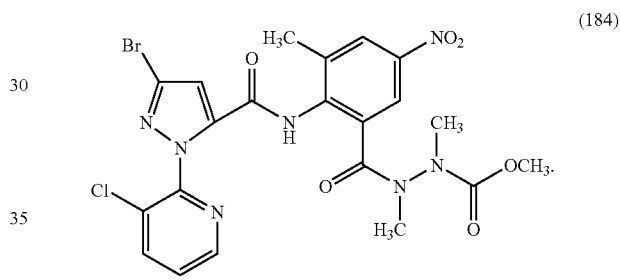

(184)

The present compound (184)

¹H-NMR (DMSO-d₆, TMS) δ (ppm): 2.27-2.37 (3H, m), 2.70-2.88 (3H, m), 2.88-3.11 (3H, m), 3.45-3.74 (3H, m), 7.38-7.46 (1H, m), 7.63 (1H, dd, J=8 Hz, 5 Hz), 7.92-8.04 (1H, m), 8.21 (1H, dd, J=8 Hz, 1Hz), 8.24-8.34 (1H, m), 8.51 (1H, dd, J=5 Hz, 1Hz), 10.40-10.75 (1H, m)

PREPARATION EXAMPLE 185

According to the same manner as that of Preparation Example 122, 6,8-dibromo-2-[4-bromo-1-(3-nitro-2-pyridinyl)-1H-pyrrol-2-yl]-4H-3,1-benzoxazine-4-one was used in place of 6,8-dibromo-2-[4-bromo-1-(3-chloro-2-pyridinyl)-1H-pyrrol-2-yl]-4H-3,1-benzoxazine-4-one to obtain the present compound (185) of the formula:

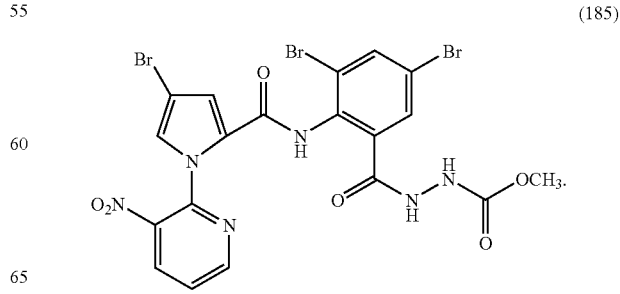

(185)

The present compound (185)

¹H-NMR (DMSO-d₆, TMS) δ (ppm): 3.61 (3H, s), 7.36 (1H, s), 7.57 (1H, d, J=2 Hz), 7.62 (1H, s), 7.78 (1H, dd, J=8 Hz, 5 Hz), 8.10 (1H, d, J=2 Hz), 8.61 (1H, dd, J=8 Hz, 2 Hz), 8.79 (1H, dd, J=5 Hz, 2 Hz), 9.24 (1H, brs), 9.95 (1H, brs), 10.12 (1H, brs)

PREPARATION EXAMPLE 186

According to the same manner as that of Preparation Example 122, 6,8-dibromo-2-[4-bromo-1-(3-bromo-2-pyridinyl)-1H-pyrrol-2-yl]-4H-3,1-benzoxazine-4-one was used in place of 6,8-dibromo-2-[4-bromo-1-(3-chloro-2-pyridinyl)-1H-pyrrol-2-yl]-4H-3,1-benzoxazine-4-one to obtain the present compound (186) of the formula:

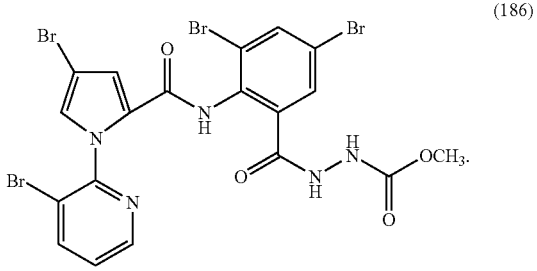

The present compound (186)

¹H-NMR (DMSO-d₆, TMS) δ (ppm): 3.61 (3H, s), 7.32 (1H, s), 7.40 (1H, dd, J=8 Hz, 5 Hz), 7.42 (1H, s), 7.63 (1H, s), 8.10 (1H, s), 8.17 (1H, d, J=8 Hz), 8.46 (1H, d, J=5 Hz), 9.36 (1H, brs), 9.90 (1H, brs), 10.16 (1H, brs)

PREPARATION EXAMPLE 187

According to the same manner as that of Preparation Example 93, 4-bromo-N-[4-chloro-2-(hydrazinocarbonyl)-6-methylphenyl]-1-(3-chloro-4-pyridinyl)-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (187) of the formula:

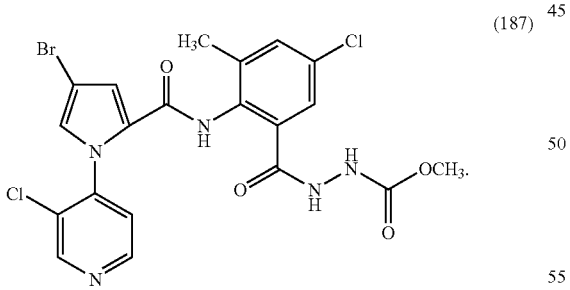

The present compound (187)

¹H-NMR (DMSO-d₆, TMS) δ (ppm): 2.16 (3H, s), 3.41-3.68 (3H, m), 7.29 (1H, brs), 7.33-7.40 (1H, m), 7.43 (1H, d, J=2 Hz), 7.52 (1H, d, J=2 Hz), 7.55 (1H, d, J=5 Hz), 8.59 (1H, d, J=5 Hz), 8.72 (1H, brs), 9.30 (1H, brs), 9.78 (1H, brs), 10.15 (1H, brs)

PREPARATION EXAMPLE 188

According to the same manner as that of Preparation Example 72, 2-[3-bromo-1-(3-chloro-2-pyridinyl)-1H-pyrazol-5-yl]-6-chloro-4H-3,1-benzoxazine-4-one was used in place of 2-[3-bromo-1-(3-chloro-2-pyridinyl)-1H-pyrazol-5-yl]-8-chloro-4H-3,1-benzoxazine-4-one to obtain the present compound (188) of the formula:

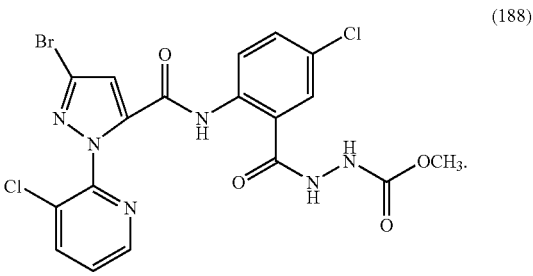

The present compound (188)

¹H-NMR (DMSO-d₆, TMS) δ (ppm): 3.68 (3H, brs), 7.23 (1H, brs), 7.62 (1H, dd, J=9 Hz, 2 Hz), 7.67 (1H, dd, J=8 Hz, 5 Hz), 7.88 (1H, s), 8.18 (1H, d, J=9 Hz), 8.25 (1H, dd, J=8 Hz, 1Hz), 8.54 (1H, dd, J=5 Hz, 1Hz), 9.49 (1H, brs), 10.78 (1H, brs), 11.77 (1H, brs)

PREPARATION EXAMPLE 189

According to the same manner as that of Preparation Example 115, 3-bromo-N-[4-chloro-2-(N-methylhydrazinocarbonyl)phenyl]-1-(3-chloro-2-pyridinyl)-1H-pyrazole-5-carboxamide was used in place of 3-bromo-N-[4-chloro-2-(N-methylhydrazinocarbonyl)-6-methylphenyl]-1-(3-chloro-2-pyridinyl)-1H-pyrazole-5-carboxamide to obtain the present compound (189) of the formula:

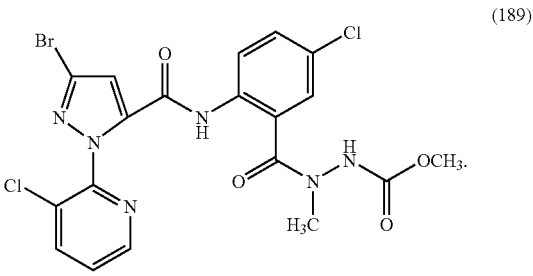

The present compound (189)

¹H-NMR (DMSO-d₆, TMS) δ (ppm): 3.07 (3H, s), 3.51 (3H, brs), 7.29 (2H, brs), 7.47-7.54 (2H, m), 7.65 (1H, dd, J=8 Hz, 5 Hz), 8.22 (1H, dd, J=8 Hz, 1Hz), 8.52 (1H, dd, J=5 Hz, 1Hz), 9.55 (1H, brs), 10.14 (1H, brs)

PREPARATION EXAMPLE 190

According to the same manner as that of Preparation Example 119, 3-bromo-N-[4-chloro-2-(N,N'-dimethylhydrazinocarbonyl)phenyl]-1-(3-chloro-2-pyridinyl)-1H-pyrazole-5-carboxamide was used in place of 3-bromo-N-[4-chloro-2-(N,N'-dimethylhydrazinocarbonyl)-6-methylphenyl]-1-(3-chloro-2-pyridinyl)-1H-pyrazole-5-carboxamide to obtain the present compound (190) of the formula:

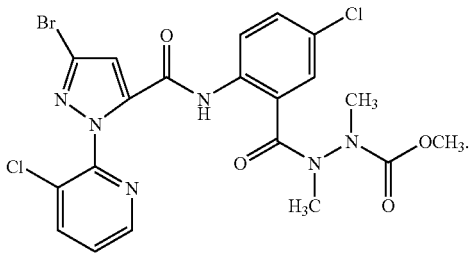

The present compound (190)

¹H-NMR (DMSO-d$_6$, TMS) δ (ppm): 2.83-3.07 (6H, m), 3.52-3.70 (3H, m), 7.29-7.60 (4H, m), 7.64 (1H, dd, J=8 Hz, 5 Hz), 8.22 (1H, dd, J=8 Hz, 2 Hz), 8.51 (1H, dd, J=5 Hz, 2 Hz), 10.53-10.68 (1H, brm).

PREPARATION EXAMPLE 191

According to the same manner as that of Preparation Example 93, 4,5-dichloro-N-[4-chloro-2-(hydrazinocarbonyl)-6-methylphenyl]-1-(2-pyridinyl)-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (191) of the formula:

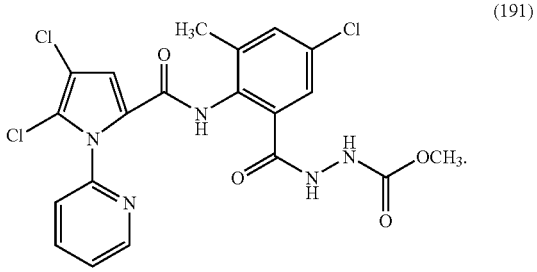

The present compound (191)

¹H-NMR (DMSO-d$_6$, TMS) δ (ppm): 2.13 (3H, s), 3.63 (3H, s), 7.24 (1H, s), 7.35 (1H, s), 7.49-7.51 (3H, m), 7.97 (1H, td, J=8 Hz, 2 Hz), 8.52 (1H, dd, J=6 Hz, 2 Hz), 9.31 (1H, brs), 9.78 (1H, brs), 10.12 (1H, brs)

PREPARATION EXAMPLE 192

According to the same manner as that of Preparation Example 93, 3,5-dichloro-N-[4-chloro-2-(hydrazinocarbonyl)-6-methylphenyl]-1-(2-pyridinyl)-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (192) of the formula:

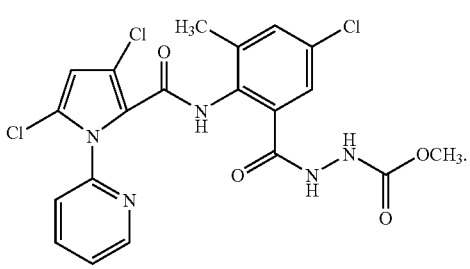

The present compound (192)

¹H-NMR (DMSO-d$_6$, TMS) δ (ppm): 2.09 (3H, s), 3.68 (3H, s), 6.69 (1H, s), 7.42 (1H, s), 7.48-7.60 (3H, m), 7.94-8.01 (1H, m), 8.51 (1H, d, J=5 Hz), 9.37 (1H, brs), 9.71 (1H, brs), 10.33 (1H, brs)

PREPARATION EXAMPLE 193

According to the same manner as that of Preparation Example 93, 4-bromo-N-[4,6-dibromo-2-(hydrazinocarbonyl)phenyl]-5-chloro-1-(3-chloro-2-pyridinyl)-1H-pyrrole-2-carboxamide was used in place of 4-bromo-N-[4-chloro-2-(hydrazinocarbonyl)-6-methylphenyl]-1-(3-chloro-2-pyridinyl)-1H-pyrrole-2-carboxamide to obtain the present compound (193) of the formula:

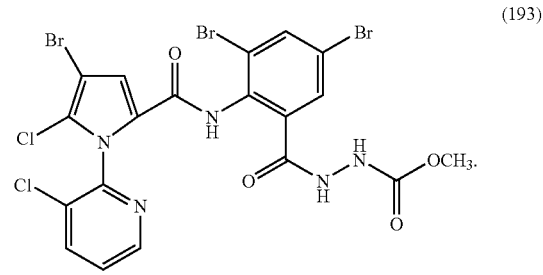

The present compound (193)

¹H-NMR (DMSO-d$_6$, TMS) δ (ppm): 3.62 (3H, s), 7.47 (1H, s), 7.58 (1H, dd, J=8 Hz, 5 Hz), 7.63 (1H, s), 8.10 (1H, s), 8.15 (1H, d, J=8 Hz), 8.51 (1H, d, J=5 Hz), 9.34 (1H, brs), 10.00 (1H, brs), 10.15 (1H, brs)

PREPARATION EXAMPLE 194

According to the same manner as that of Preparation Example 128, 4-bromo-N-[4,6-dibromo-2-(hydrazinocarbonyl)phenyl]-5-chloro-1-(3-chloro-2-pyridinyl)-1H-pyrrole-2-carboxamide was used in place of 4,5-dibromo-N-[4-chloro-2-(hydrazinocarbonyl)-6-methylphenyl]-1-(3-chloro-2-pyridinyl)-1H-pyrrole-2-carboxamide to obtain the present compound (194) of the formula:

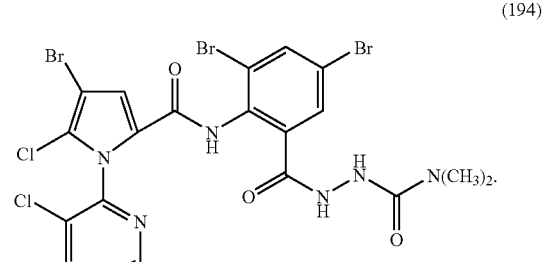

The present compound (194)

¹H-NMR (DMSO-d$_6$, TMS) δ (ppm): 2.85 (6H, s), 7.53 (1H, s), 7.59 (1H, dd, J=8 Hz, 5 Hz), 7.70 (1H, s), 8.06 (1H, s), 8.16 (1H, d, J=8 Hz), 8.51 (1H, d, J=5 Hz), 8.56 (1H, brs), 9.82 (1H, brs), 9.97 (1H, brs)

PREPARATION EXAMPLE 195

A mixture of 0.59 g of 3-bromo-N-[4,6-dibromo-2-(hydrazinocarbonyl)phenyl]-1-(3-chloro-2-pyridinyl)-1H-pyrazole-5-carboxamide, 0.23 g of propargyl chloroformate, 0.16 g of pyridine and 2 ml of acetonitrile was stirred at room temperature for 1 hour. Water was poured into the reaction mixture, and the mixture was extracted with ethyl acetate. The organic layer was washed with water, dried over sodium sulfate, and concentrated under reduced pressure. The resulting residue was washed with ethyl acetate to obtain 0.22 g of the present compound (195) of the formula:

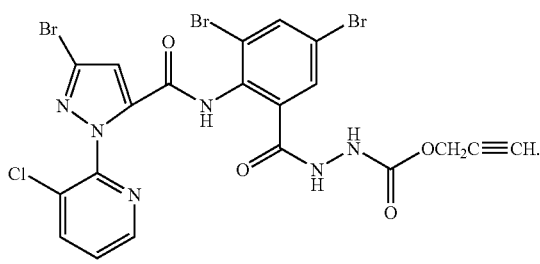

(195)

The present compound (195)
$^1$H-NMR (DMSO-$d_6$, TMS) δ (ppm): 3.56 (1H, s), 4.71 (2H, s), 7.41 (1H, s), 7.60 (1H, dd, J=8 Hz, 5 Hz), 7.66 (1H, s), 8.14-8.16 (2H, m), 8.50 (1H, dd, J=5 Hz, 1Hz), 9.60 (1H, brs), 10.29 (1H, brs), 10.50 (1H, brs).

PREPARATION EXAMPLE 196

According to the same manner as that of Preparation Example 34, propargyl chloroformate was used in place of methyl chloroformate to obtain the present compound (196) of the formula:

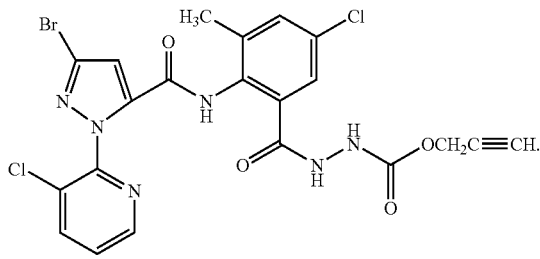

(196)

The present compound (196)
$^1$H-NMR (DMSO-$d_6$, TMS) δ (ppm): 2.15 (3H, s), 3.56 (1H, brs), 4.72 (2H, s), 7.35 (1H, s), 7.39 (1H, brs), 7.55 (1H, s), 7.61 (1H, dd, J=8 Hz, 5 Hz), 8.17 (1H, dd, J=8 Hz, 1Hz), 8.50 (1H, dd, J=5 Hz, 1Hz), 9.55 (1H, s), 10.23-10.26 (2H, brm).

PREPARATION EXAMPLE 197

According to the same manner as that of Preparation Example 10, 3-bromo-N-[4-chloro-2-(hydrazinocarbonyl)-6-methylphenyl]-1-(3-chloro-2-pyridinyl)-1H-pyrazole-5-carboxamide was used in place of N-[4-chloro-2-(hydrazinocarbonyl)-6-methylphenyl]-1-(3-chloro-2-pyridinyl)-3-trifluoromethyl-1H-pyrazole-5-carboxamide to obtain the present compound (197) of the formula:

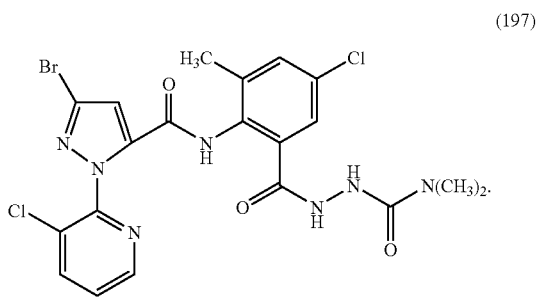

(197)

The present compound (197)
$^1$H-NMR (DMSO-$d_6$, TMS) δ (ppm): 2.20 (3H, s), 2.93 (6H, s), 7.50-7.52 (2H, m), 7.58 (1H, brs), 7.67 (1H, dd, J=8 Hz, 5 Hz), 8.24 (1H, d, J=8 Hz), 8.56 (1H, d, J=5 Hz), 8.60 (1H, s), 9.89 (1H, brs), 10.23 (1H, brs)

PREPARATION EXAMPLE 198

To a mixture of 0.20 g of the present compound (197), 0.10 ml of triethylamine and 5 ml of tetrahydrofuran was added dropwise 0.040 ml of methyl chloroformate under ice-cooling. The mixture was stirred at room temperature for 2.5 hours. Water was poured into the reaction mixture, and the mixture was extracted with ethyl acetate three times. The organic layers were combined, washed with water and an aqueous saturated sodium chloride solution, dried over anhydrous magnesium sulfate, and concentrated under reduced pressure. The resulting residue was subjected to silica gel column chromatography to 0.13 g of the present compound (198) of the formula:

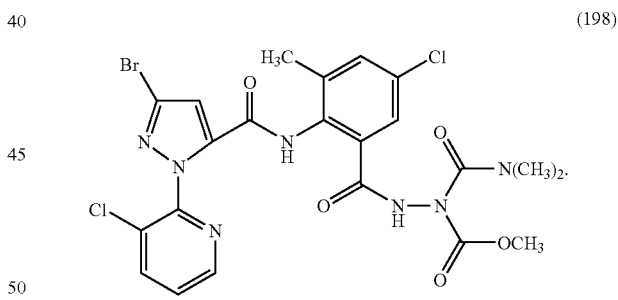

(198)

The present compound (198)
$^1$H-NMR (CDCl$_3$, TMS) δ (ppm): 2.22 (3H, s), 3.05 (3H, brs), 3.15 (3H, brs), 3.76 (3H, s), 6.99 (1H, s), 7.35-7.38 (2H, m), 7.44 (1H, s), 7.86 (1H, d, J=8 Hz), 8.39 (1H, s), 8.46 (1H, d, J=5 Hz), 9.40 (1H, s)

PREPARATION EXAMPLE 199

A mixture of 1.0 g of 2-[3-bromo-1-(3-chloro-2-pyridinyl)-1H-pyrazol-5-yl]-6-chloro-8-methyl-4H-3,1-benzoxazine-4-one, 1.33 g of formic hydrazide and 40 ml of N,N-dimethylformamide was stirred at 50° C. for 3.5 hours, and at 70° C. for 7 hours. The reaction mixture was allowed to cool to room temperature, and thereto water was poured. The mixture was extracted with methyl tert-butyl ether. The organic layer was washed with water and an aqueous saturated sodium chloride solution, dried over anhydrous magnesium sulfate, and concentrated under reduced pressure. The resulting residue was subjected to silica gel column chromatography to obtain 0.36 g of the present compound (199) of the formula:

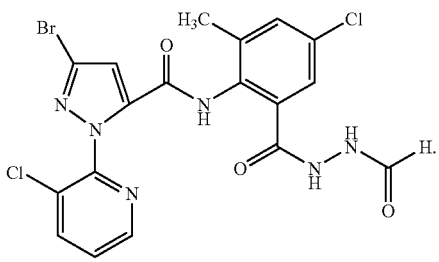

(199)

The present compound (199)

$^1$H-NMR (DMSO-d$_6$, TMS) δ (ppm): 2.10-2.21 (3.0H, m), 7.25-7.62 (4.7H, m), 7.79-7.81 (0.2H, m), 8.05 (0.3H, s), 8.16 (1.0H, d, J=8 Hz), 8.49 (1.0H, d, J=5 Hz), 9.48-9.55 (0.7H, m), 10.05-10.45 (2.1H, m)

PREPARATION EXAMPLE 200

To a mixture of 0.20 g of the present compound (115), 0.14 ml of triethylamine and 10 ml of acetonitrile was added 0.12 ml of methyl chloroformate at room temperature. The resulting mixture was stirred at room temperature for 18 hours. Water was poured into the reaction mixture, and the mixture was extracted with ethyl acetate three times. The organic layers were combined, washed successively with water and an aqueous saturated sodium chloride solution, dried over anhydrous magnesium sulfate, and concentrated under reduced pressure. The resulting residue was subjected to silica gel column chromatography to obtain 0.010 g of the present compound (200) of the formula:

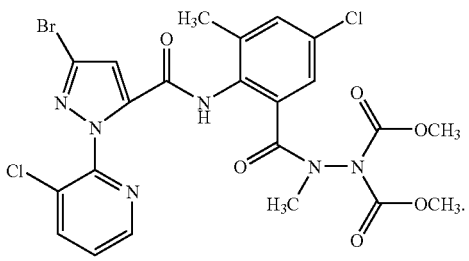

(200)

The present compound (200)

$^1$H-NMR (CDCl$_3$, TMS) δ (ppm): 2.21 (3H, s), 3.23 (3H, s), 3.89 (6H, brs), 6.46 (1H, s), 7.08 (1H, s), 7.30 (1H, s), 7.43 (1H, dd, J=8 Hz, 5 Hz), 8.92 (1H, d, J=8 Hz), 8.51 (1H, d, J=5 Hz), 9.21 (1H, s)

PREPARATION EXAMPLE 201

According to the same manner as that of Preparation Example 158, that the present compound (122) was used in place of the present compound (93) to obtain the present compound (201) of the formula:

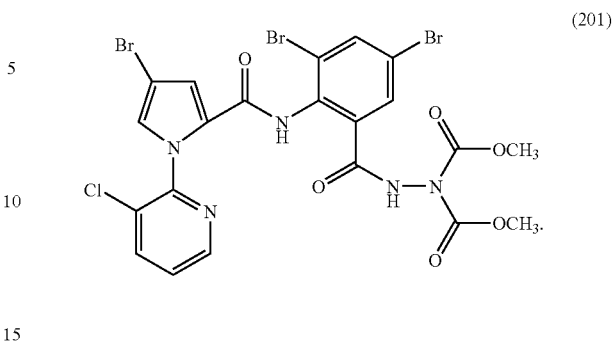

(201)

The present compound (201)

$^1$H-NMR (CDCl$_3$, TMS) δ (ppm): 3.74 (6H, s), 7.08 (2H, s), 7.30 (1H, dd, J=8 Hz, 5 Hz), 7.66 (1H, s), 7.82 (1H, d, J=8 Hz), 7.86 (1H, s), 8.28 (1H, brs), 8.32 (1H, d, J=5 Hz), 8.60 (1H, brs)

PREPARATION EXAMPLE 202

According to the same manner as that of Preparation Example 134, 4-bromo-N-[4,6-dibromo-2-(N-methylhydrazinocarbonyl)phenyl]-1-(3-chloro-3-pyridinyl)-1H-pyrrole-2-carboxamide was used in place of 4-bromo-N-[4-chloro-2-(N-methylhydrazinocarbonyl)-6-methylphenyl]-1-(3-chloro-2-pyridinyl)-1H-pyrrole-2-carboxamide to obtain the present compound (202) of the formula:

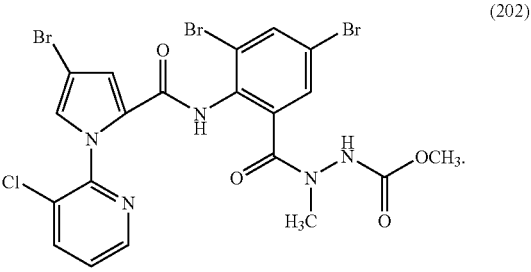

(202)

The present compound (202)

$^1$H-NMR (CDCl$_3$, TMS) δ (ppm): 3.05 (0.5H, brs), 3.13 (2.5H, s), 3.59 (2.5H, s), 3.82 (0.5H, brs), 7.05 (1.0H, d, J=2 Hz), 7.21 (1.0H, s), 7.35 (1.3H, dd, J=8 Hz, 5 Hz), 7.42 (1.0H, s), 7.65 (2.0H, s), 7.82 (1.0H, d, J=8 Hz), 8.43 (1.0H, dd, J=5H, 2 Hz), 8.57 (0.7H, s)

PREPARATION EXAMPLE 203

According to the same manner as that of Preparation Example 115, 3-bromo-N-[4,6-dibromo-2-(N-methylhydrazinocarbonyl)phenyl]-1-(3-chloro-2-pyridinyl)-1H-pyrazole-5-carboxamide was used in place of 3-bromo-N-[4-chloro-2-(N-methylhydrazinocarbonyl)-6-methylphenyl]-1-(3-chloro-2-pyridinyl)-1H-pyrazole-5-carboxamide to obtain the present compound (203) of the formula:

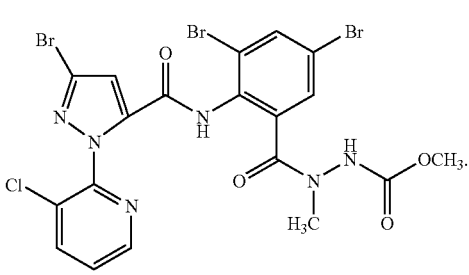

(203)

The present compound (203)

$^1$H-NMR (100° C., DMSO-d$_6$, TMS) δ (ppm): 2.96 (3H, s), 3.04 (3H, brs), 7.30 (1H, s), 7.38 (1H, s), 7.58 (1H, dd, J=8 Hz, 5 Hz), 7.96 (1H, s), 8.11 (1H, d, J=8 Hz), 8.47 (1H, d, J=5 Hz), 8.68 (1H, brs), 10.08 (1H, brs)

PREPARATION EXAMPLE 204

A mixture of 0.30 g of 3-bromo-N-[4,6-dibromo-2-(N,N'-dimethylhydrazinocarbonyl)phenyl]-1-(3-chloro-2-pyridinyl)-1H-pyrazole-5-carboxamide, 0.15 ml of methyl chloroformate and 3 ml of pyridine was stirred at room temperature for 2.5 hours. Then, 0.08 ml of methyl chloroformate was added thereto, and the mixture was stirred for 1 hour. Then, 0.08 ml of methyl chloroformate was added thereto, and the mixture was further stirred for 0.5 hour. Water was poured into the reaction mixture, and the mixture was extracted with ethyl acetate. The organic layer was dried over anhydrous magnesium sulfate, and concentrated under reduced pressure. The resulting residue was subjected to silica gel column chromatography to obtain 0.24 g of the present compound (204) of the formula:

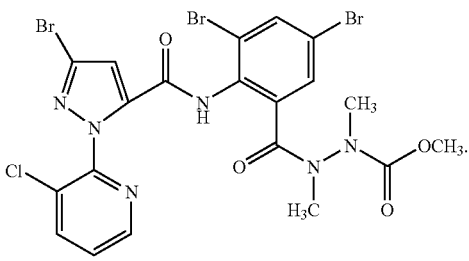

(204)

The present compound (204)

$^1$H-NMR (DMSO-d$_6$, TMS) δ (ppm): 2.71 (1.4H, s), 2.83 (1.6H, s), 2.94 (1.5H, s), 3.06 (1.5H, s), 3.35-3.70 (3.0H, m), 7.41 (0.5H, s), 7.45 (0.6H, s), 7.47 (0.6H, s), 7.60-7.64 (1.3H, m), 8.07 (0.5H, d, J=2 Hz), 8.13 (0.5H, s), 8.18 (1.0H, d, J=8 Hz), 8.50 (1.0H, m), 10.52 (0.5H, s), 10.67 (0.5H, s)

PREPARATION EXAMPLE 205

According to the same manner as that of Preparation Example 147, 4-bromo-N-[4,6-dibromo-2-(N,N'-dimethylhydrazinocarbonyl)phenyl]-1-(3-chloro-2-pyridinyl)-1H-pyrrole-2-carboxamide was used in place of 4-bromo-N-[4-chloro-2-(N,N'-dimethylhydrazinocarbonyl)-6-methylphenyl]-1-(3-chloro-2-pyridinyl)-1H-pyrrole-2-carboxamide to obtain the present compound (205) of the formula:

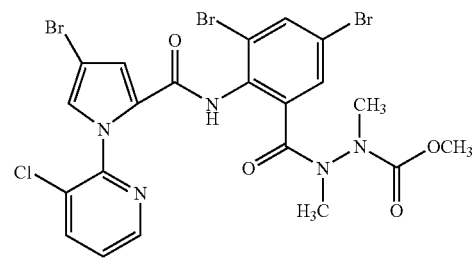

(205)

The present compound (205)

$^1$H-NMR (DMSO-d$_6$, TMS) δ (ppm): 2.73 (1.4H, s), 2.82 (1.8H, s), 2.89 (1.3H, s), 3.06 (1.5H, s), 3.35-3.70 (3.0H, m), 7.32 (0.5H, s), 7.34-7.38 (0.6H, m), 7.43 (0.5H, s), 7.48-7.53 (2.4H, m), 8.03 (0.4H, d, J=2 Hz), 8.07-8.10 (1.6H, m), 8.43-8.45 (1.0H, m), 9.93 (0.5H, s), 10.07 (0.5H, s)

PREPARATION EXAMPLE 206

According to the same manner as that of Preparation Example 136, 4-bromo-N-[4,6-dibromo-2-(N-methylhydrazinocarbonyl)phenyl]-1-(3-chloro-2-pyridinyl)-1H-pyrrole-2-carboxamide was used in place of 4-bromo-N-[4-chloro-2-(N-methylhydrazinocarbonyl)-6-methylphenyl]-1-(3-chloro-2-pyridinyl)-1H-pyrrole-2-carboxamide to obtain the present compound (206) of the formula:

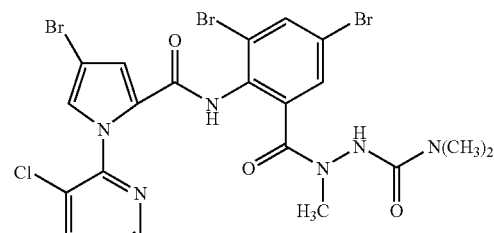

(206)

The present compound (206)

$^1$H-NMR (CDCl$_3$, TMS) δ (ppm): 2.47 (6H, s), 3.29 (3H, s), 7.04 (1H, d, J=2 Hz), 7.31 (1H, dd, J=8 Hz, 5 Hz), 7.43 (1H, d, J=2 Hz), 7.51 (1H, d, J=2 Hz), 7.53 (1H, d, J=2 Hz), 7.80 (1H, dd, J=8 Hz, 2 Hz), 8.09 (1H, s), 8.41 (1H, dd, J=5 Hz, 2 Hz), 9.67 (1H, s)

PREPARATION EXAMPLE 207

According to the same manner as that of Preparation Example 199, 6,8-dibromo-2-[4-bromo-1-(3-chloro-2-pyridinyl)-1H-pyrrol-2-yl]-4H-3,1-benzoxazine-4-one was used in place of 2-[3-bromo-1-(3-chloro-2-pyridinyl)-1H-pyrazol-5-yl]-6-chloro-8-methyl-4H-3,1-benzoxazine-4-one to obtain the present compound (207) of the formula:

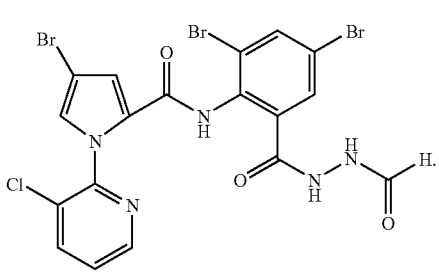

(207)

The present compound (207)
$^1$H-NMR (DMSO-d$_6$, TMS) δ (ppm): 7.31 (0.6H, s), 7.38 (0.3H, s), 7.44 (0.6H, d, J=2 Hz), 7.47-7.52 (1.5H, m), 7.65-7.75 (1.3H, m), 8.03-8.12 (2.7H, m), 8.43 (1.0H, dd, J=5 Hz, 2 Hz), 9.49-9.52 (0.3H, m), 9.94-9.99 (0.4H, m), 10.17 (1.0H, s), 10.39-10.44 (1.0H, m)

PREPARATION EXAMPLE 208

According to the same manner as that of Preparation Example 199, 2-[3-bromo-1-(3-chloro-2-pyridinyl)-1H-pyrazol-5-yl]-6,8-dibromo-4H-3,1-benzoxazine-4-one was used in place of 2-[3-bromo-1-(3-chloro-2-pyridinyl)-1H-pyrazol-5-yl]-6-chloro-8-methyl-4H-3,1-benzoxazine-4-one to obtain the present compound (208) of the formula:

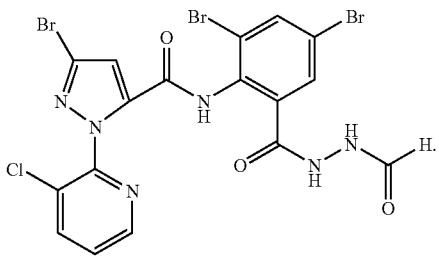

(208)

The present compound (208)
$^1$H-NMR (DMSO-d$_6$, TMS) δ (ppm): 7.41 (0.7H, s), 7.45 (0.3H, s), 7.58-7.63 (1.0H, m), 7.69-7.73 (1.0H, m), 7.77-7.79 (0.4H, m), 8.04 (0.6H, s), 8.13-8.18 (2.0H, m), 8.49-8.51 (1.0H, m), 9.55-9.58 (0.4H, m), 10.18 (0.6H, s), 10.45-10.60 (2.0H, m)

PREPARATION EXAMPLE 209

A mixture of 0.30 g of 6,8-dibromo-2-[4-bromo-1-(3-chloro-2-pyridinyl)-1H-pyrrol-2-yl]-4H-3,1-benzoxazine-4-one, 0.28 g of N-methyl-N-methoxycarbonylhydrazine and 15 ml of N,N-dimethylformamide was stirred at 80° C. for 35 hours, and then allowed to cool to room temperature. Water was poured into the reaction mixture, and the mixture was extracted with methyl tert-butyl ether. The organic layer was washed successively with water and an aqueous saturated sodium chloride solution, dried over anhydrous magnesium sulfate, and concentrated under reduced pressure. The resulting residue was subjected to silica gel column chromatography to obtain 0.18 g of the present compound (209) of the formula:

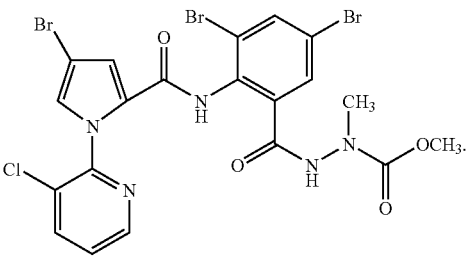

(209)

The present compound (209)
$^1$H-NMR (DMSO-d$_6$, TMS) δ (ppm): 2.84 (3H, s), 3.45-3.70 (3H, brm), 7.38 (1H, brs), 7.47 (1H, d, J=2 Hz), 7.50 (1H, dd, J=8 Hz, 5 Hz), 7.54 (1H, d, J=2 Hz), 8.05 (1H, dd, J=8 Hz, 2 Hz), 8.12 (1H, d, J=2 Hz), 8.41 (1H, dd, J=5 Hz, 2 Hz), 9.95 (1H, s), 10.50 (1H, s)

PREPARATION EXAMPLE 210

A mixture of 0.16 g of 4-bromo-N-[4,6-dibromo-2-(N,N'-dimethylhydrazinocarbonyl)phenyl]-1-(3-chloro-2-pyridinyl)-1H-pyrrole-2-carboxamide, 0.12 ml of N,N-dimethylcarbamoyl chloride and 0.2 ml of pyridine was stirred at 80° C. for 5 hours and then allowed to cool to room temperature. Water was poured into the reaction mixture, and the mixture was extracted with ethyl acetate. The organic layer was washed successively with water and an aqueous saturated sodium chloride solution, dried over anhydrous magnesium sulfate, and concentrated under reduced pressure. The resulting residue was subjected to silica gel column chromatography to obtain 0.15 g of the present compound (210) of the formula:

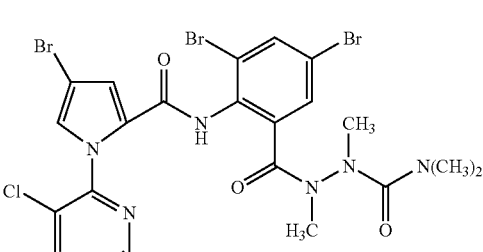

(210)

The present compound (210)
$^1$H-NMR (DMSO-d$_6$, TMS) δ (ppm): 2.44 (4.5H, s), 2.58 (3.0H, s), 2.74 (1.5H, brs), 2.78 (1.0H, s), 3.12 (2.0H, s), 7.14 (0.7H, d, J=2 Hz), 7.32 (0.7H, d, J=2 Hz), 7.38 (0.3H, s), 7.47-7.54 (2.3H, m), 8.00 (0.7H, d, J=2 Hz), 8.07-8.10 (1.3H, m), 8.42-8.45 (1.0H, m), 9.95 (0.7H, brs), 10.08 (0.3H, brs)

PREPARATION EXAMPLE 211

A mixture of 0.16 g of 3-bromo-N-[4,6-dibromo-2-(N,N'-dimethylhydrazinocarbonyl)phenyl]-1-(3-chloro-2-pyridinyl)-1H-pyrazole-5-carboxamide, 0.12 ml of N,N-dimethylcarbamoyl chloride and 2 ml of pyridine was stirred at 80° C. for 5 hours, and then allowed to cool to room temperature. Water was poured into the reaction mixture, and the mixture was extracted with ethyl acetate. The organic layer was washed successively with water and an aqueous saturated sodium chloride solution, dried over anhydrous magnesium sulfate, and concentrated under reduced pressure. The resulting residue was subjected to silica gel column chromatography to obtain 0.12 g of the present compound (211) of the formula:

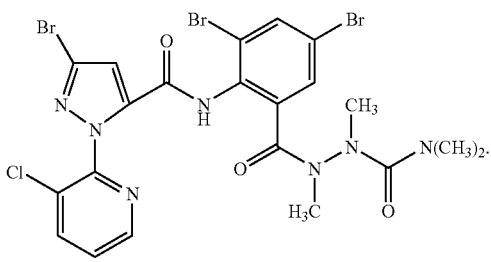

(211)

The present compound (211)

$^1$H-NMR (DMSO-d$_6$, TMS) δ (ppm): 2.35 (4.5H, s), 2.49 (2.0H, s), 2.57 (1.0H, brs), 2.67 (1.5H, brs), 2.73 (1.0H, s), 3.05 (2.0H, s), 7.10 (0.7H, s), 7.34 (0.7H, s), 7.39 (0.3H, s), 7.52-7.57 (1.3H, m), 7.97 (0.7H, d, J=2 Hz), 8.06 (0.3H, s), 8.11 (1.0H, dd, J=8 Hz, 2 Hz), 8.41-8.45 (1.0H, m), 10.49 (0.7H, s), 10.62 (0.3H, s)

PREPARATION EXAMPLE 212

According to the same manner as that of Preparation Example 160, 3-bromo-N-[4,6-dibromo-2-(N-methylhydrazinocarbonyl)phenyl]-1-(3-chloro-2-pyridinyl)-1H-pyrazole-5-carboxamide was used in place of 3-bromo-N-[4-chloro-2-(N-methylhydrazinocarbonyl)-6-methylphenyl]-1-(3-chloro-2-pyridinyl)-1H-pyrazole-5-carboxamide to obtain the present compound (212) of the formula:

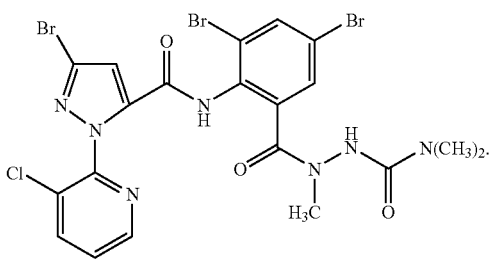

(212)

The present compound (212)

$^1$H-NMR (CDCl$_3$, TMS) δ (ppm): 2.50 (6H, s), 3.28 (3H, s), 7.38 (1H, dd, J=8 Hz, 5 Hz), 7.46 (1H, d, J=2 Hz), 7.50 (1H, s), 7.55 (1H, d, J=2 Hz), 7.78 (1H, s), 7.86 (1H, d, J=8 Hz), 8.46 (1H, d, J=5 Hz), 10.20 (1H, s).

PREPARATION EXAMPLE 213

According to the same manner as that of Preparation Example 114, 2-[3-bromo-1-(3-chloro-2-pyridinyl)-1H-pyrazol-5-yl]-6,8-dibromo-4H-3,1-benzoxazine-4-one was used in place of 2-[3-bromo-1-(3-chloro-2-pyridinyl)-1H-pyrazol-5-yl]-6-chloro-8-methyl-4H-3,1-benzoxazine-4-one to obtain the present compound (213) of the formula:

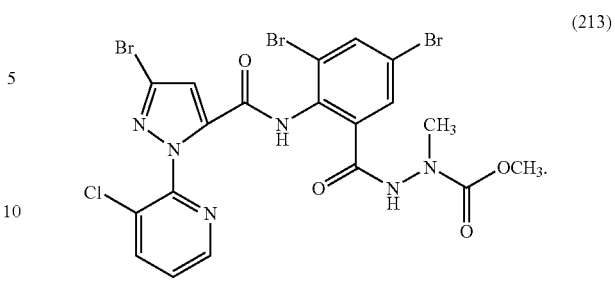

(213)

The present compound (213)

$^1$H-NMR (DMSO-d$_6$) δ (ppm): 2.87 (3H, s), 3.46-3.66 (3H, brm), 7.46 (1H, s), 7.58-7.61 (2H, m), 8.13-8.18 (2H, m), 8.47 (1H, dd, J=5 Hz, 2 Hz), 10.54 (1H, s), 10.61 (1H, s)

PREPARATION EXAMPLE 214

According to the same manner as that of Preparation Example 34, 2-methoxyethyl chloroformate was used in place of methyl chloroformate to obtain the present compound (214) of the formula:

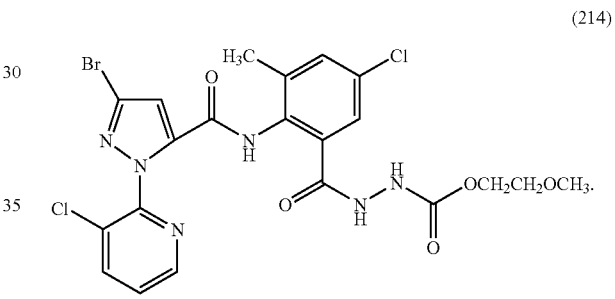

(214)

The present compound (214)

$^1$H-NMR (CDCl$_3$, TMS) δ (ppm): 2.21 (3H, s), 3.39 (3H, brs), 3.61 (2H, brs), 4.31 (2H, brs), 6.96 (1H, brs), 7.01 (1H, s), 7.32-7.39 (3H, m), 7.85 (1H, dd, J=8 Hz, 2 Hz), 8.03 (1H, brs), 8.41 (1H, d, J=5 Hz), 9.47 (1H, s)

PREPARATION EXAMPLE 215

According to the same manner as that of Preparation Example 95, the present compound (214) was used in place of the present compound (34) to obtain the present compound (215) of the formula:

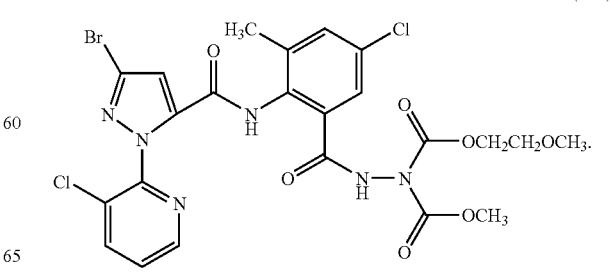

(215)

The present compound (215)

¹H-NMR (CDCl₃, TMS) δ (ppm): 2.24 (3H, s), 3.31 (3H, s), 3.58 (2H, t, J=5 Hz), 3.83 (3H, s), 4.32 (2H, brs), 6.98 (1H, s), 7.32-7.37 (2H, m), 7.46 (1H, d, J=2 Hz), 7.88 (1H, d, J=8 Hz), 8.34 (1H, d, J=5 Hz), 8.70 (1H, s), 9.33 (1H, s)

PREPARATION EXAMPLE 216

According to the same manner as that of Preparation Example 34, 2,2,2-trichloroethyl chloroformate was used in place of methyl chloroformate to obtain the present compound (216) of the formula:

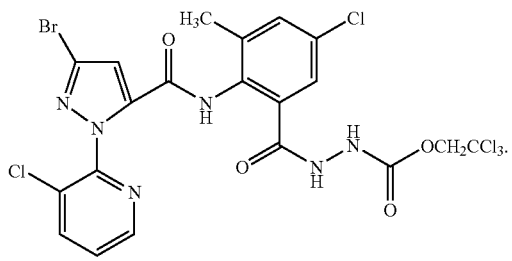

(216)

The present compound (216)

¹H-NMR (DMSO-d₆, TMS) δ (ppm): 2.22 (3.0H, s), 4.89 (0.4H, s), 4.97 (1.6H, s), 7.41 (1.0H, s), 7.46 (0.8H, s), 7.53 (0.2H, s), 7.62 (1.0H, s), 7.67 (1.0H, dd, J=8 Hz, 5 Hz), 8.24 (1.0H, dd, J=8 Hz, 2 Hz), 8.56 (1.0H, dd, J=5 Hz, 2 Hz), 9.52 (0.2H, s), 10.00 (0.8H, s), 10.31-10.36 (1.0H, brm), 10.41 (0.8H, s), 10.50 (0.2H, s)

PREPARATION EXAMPLE 217

According to the same manner as that of Preparation Example 195, 2,2,2-trichloroethyl chloroformate was used in place of propargyl chloroformate to obtain the present compound (217) of the formula:

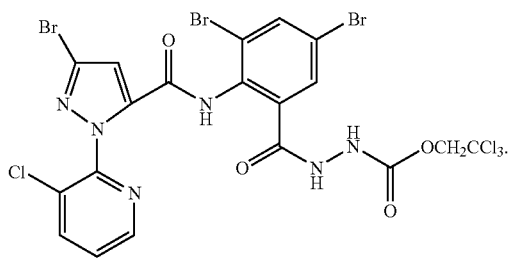

(217)

The present compound (217)

¹H-NMR (DMSO-d₆, TMS) δ (ppm): 4.83-4.90 (2.0H, brm), 7.40 (1.0H, s), 7.60 (1.0H, dd, J=8 Hz, 5 Hz), 7.67 (0.7H, s), 7.74 (0.3H, s), 8.14-8.18 (2.0H, m), 8.50 (1.0H, d, J=5 Hz), 9.51 (0.3H, s), 9.99 (0.7H, s), 10.41 (0.7H, s), 10.48-10.54 (1.3H, m)

PREPARATION EXAMPLE 218

According to the same manner as that of Preparation Example 34, butyl chloroformate was used in place of methyl chloroformate to obtain the present compound (218) of the formula:

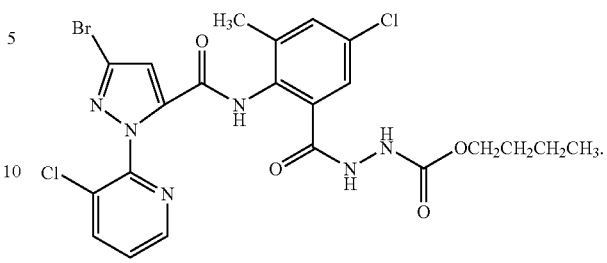

(218)

The present compound (218)

¹H-NMR (DMSO-d₆, TMS) δ (ppm): 0.90 (3H, brs), 1.36 (2H, brs), 1.56 (2H, brs), 2.15 (3H, s), 3.92-4.06 (2H, brm), 7.34-7.39 (2H, brm), 7.55 (1H, d, J=2 Hz), 7.61 (1H, dd, J=8 Hz, 5 Hz), 8.17 (1H, dd, J=8 Hz, 2 Hz), 8.49 (1H, dd, J=5 Hz, 2 Hz), 9.26 (1H, s), 10.13 (1H, s), 10.23 (1H, s)

PREPARATION EXAMPLE 219

According to the same manner as that of Preparation Example 95, the present compound (218) was used in place of the present compound (34) to obtain the present compound (219) of the formula:

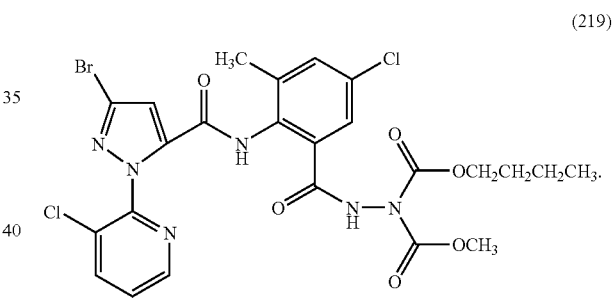

(219)

The present compound (219)

¹H-NMR (CDCl₃, TMS) δ (ppm): 0.93 (3H, t, J=7 Hz), 1.38 (2H, qt, J=7 Hz, 7 Hz), 1.65 (2H, tt, J=7 Hz, 7 Hz), 2.23 (3H, s), 3.81 (3H, s), 4.24 (2H, t, J=7 Hz), 6.97 (1H, s), 7.34-7.38 (2H, m), 7.44 (1H, d, J=2 Hz), 7.88 (1H, dd, J=8 Hz, 2 Hz), 8.35 (1H, s), 8.38 (1H, dd, J=5 Hz, 2 Hz), 9.24 (1H, s)

PREPARATION EXAMPLE 220

A mixture of 0.30 g of 3-bromo-N-[4-chloro-2-(hydrazinocarbonyl)-6-methylphenyl]-1-(3-chloro-2-pyridinyl)-1H-pyrazole-5-carboxamide, 0.10 g of methoxyacetyl chloride and 3 ml of pyridine was stirred at room temperature for 2.5 hours. Water was poured into the reaction mixture, and the mixture was extracted with ethyl acetate three times. The organic layers were combined, and was washed with an aqueous saturated sodium chloride solution, dried over anhydrous magnesium sulfate, and concentrated under reduced pressure. The resulting residue was subjected to silica gel column chromatography to obtain 0.21 g of the present compound (220) of the formula:

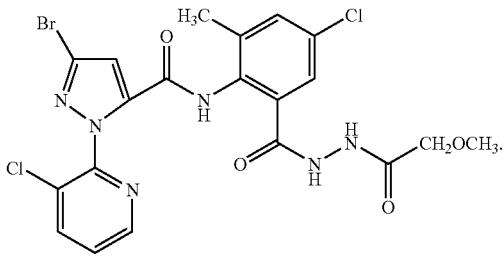

The present compound (220)
¹H-NMR (CDCl₃, TMS) δ (ppm): 2.21 (3H, s), 3.50 (3H, s), 4.08 (2H, s), 7.02 (1H, s), 7.34-7.40 (3H, m), 7.86 (1H, dd, J=8 Hz, 2 Hz), 8.44 (1H, dd, J=5 Hz, 2 Hz), 8.57 (1H, d, J=5 Hz), 8.85 (1H, d, J=5 Hz), 9.58 (1H, s).

PREPARATION EXAMPLE 221

According to the same manner as that of Preparation Example 34, 2-fluoroethyl chloroformate was used in place of methyl chloroformate to obtain the present compound (221) of the formula:

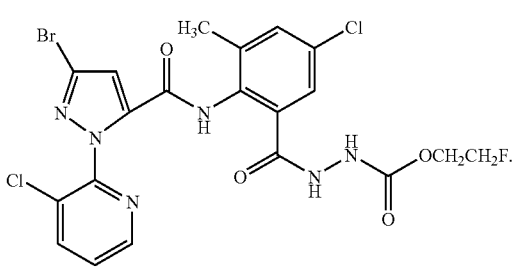

The present compound (221)
¹H-NMR (DMSO-d₆, TMS) δ (ppm): 2.13 (3H, s), 4.20-4.34 (2H, m), 4.53-4.70 (2H, m), 7.35 (1H, s), 7.39 (1H, s), 7.55 (1H, s), 7.61 (1H, dd, J=8 Hz, 5 Hz), 8.17 (1H, dd, J=8 Hz, 2 Hz), 8.50 (1H, dd, J=5 Hz, 2 Hz), 9.49 (1H, s), 10.19 (1H, brs), 10.24 (1H, brs)

PREPARATION EXAMPLE 222

According to the same manner as that of Preparation Example 122, 6,8-dibromo-2-[1-(3-chloro-2-pyridinyl)-5-thiocyanato-1H-pyrrol-2-yl]-4H-3,1-benzoxazine-4-one was used in place of 6,8-dibromo-2-[4-bromo-1-(3-chloro-2-pyridinyl)-1H-pyrrol-2-yl]-4H-3,1-benzoxazine-4-one to obtain the present compound (222) of the formula:

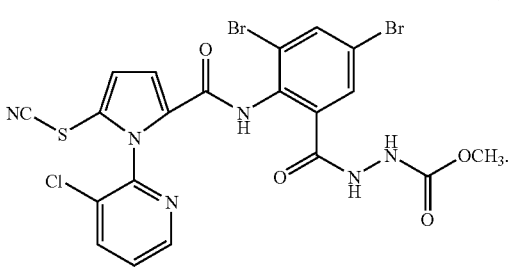

The present compound (222)
¹H-NMR (DMSO-d₆, TMS) δ (ppm): 3.61 (3H, s), 7.10 (1H, d, J=4 Hz), 7.38 (1H, d, J=4 Hz), 7.59 (1H, dd, J=8 Hz, 5 Hz), 7.64 (1H, brs), 8.11 (1H, d, J=2 Hz), 8.15 (1H, dd, J=8 Hz, 1Hz), 8.54 (1H, dd, J=5 Hz, 1Hz), 9.35 (1H, brs), 10.14 (2H, brs)

PREPARATION EXAMPLE 223

According to the same manner as that of Preparation Example 93, 4-bromo-N-[4,6-dibromo-2-(hydrazinocarbonyl)phenyl]-1-(3-chloro-2-pyridinyl)-1H-pyrrole-2-carboxamide and propargyl chloroformate were used in place of 4-bromo-N-[4-chloro-2-(hydrazinocarbonyl)-6-methylphenyl]-1-(3-chloro-2-pyridinyl)-1H-pyrrole-2-carboxamide and methyl chloroformate respectively to obtain the present compound (223) of the formula:

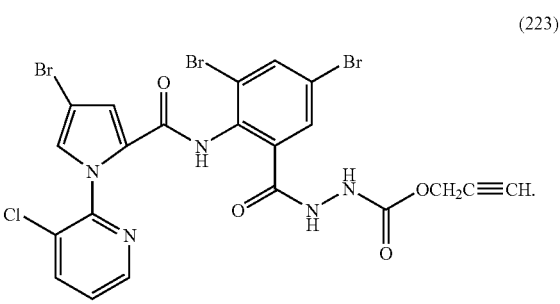

The present compound (223)
¹H-NMR (DMSO-d₆, TMS) δ (ppm): 3.55 (1H, s), 4.70 (2H, s), 7.30 (1H, s), 7.44 (1H, d, J=1 Hz), 7.49 (1H, dd, J=8 Hz, 5 Hz), 7.64 (1H, s), 8.05 (1H, d, J=8 Hz), 8.11 (1H, s), 8.43 (1H, dd, J=5 Hz, 1Hz), 9.60 (1H, brs), 9.94 (1H, brs), 10.22 (1H, brs)

PREPARATION EXAMPLE 224

According to the same manner as that of Preparation Example 93, N-[4,6-dibromo-2-(hydrazinocarbonyl)phenyl]-4,5-dichloro-1-(3-chloro-2-pyridinyl)-1H-pyrrole-2-carboxamide and propargyl chloroformate were used in place of 4-bromo-N-[4-chloro-2-(hydrazinocarbonyl)-6-methylphenyl]-1-(3-chloro-2-pyridinyl)-1H-pyrrole-2-carboxamide and methyl chloroformate respectively to obtain the present compound (224) of the formula:

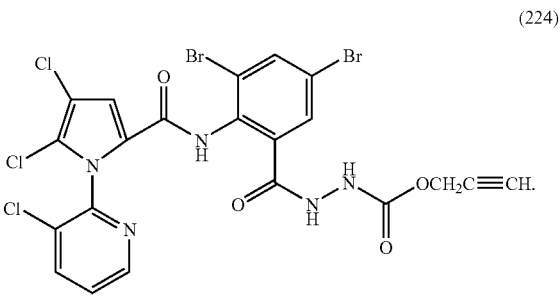

The present compound (224)

¹H-NMR (DMSO-d₆, TMS) δ (ppm): 3.55 (1H, s), 4.71 (2H, s), 7.44 (1H, s), 7.56-7.64 (2H, m), 8.10 (1H, s), 8.15 (1H, dd, J=8 Hz, 1Hz), 8.51 (1H, dd, J=5 Hz, 1Hz), 9.58 (1H, brs), 10.02 (1H, brs), 10.23 (1H, brs)

PREPARATION EXAMPLE 225

A mixture of 0.10 g of 6,8-dibromo-2-[4-bromo-1-(3-chloro-2-pyridinyl)-1H-imidazol-2-yl]-4H-3,1-benzoxazine-4-one, 0.16 g of methyl carbazate and 10 ml of N,N-dimethylformamide was stirred at room temperature for 1 day. The reaction mixture was poured into water, and extracted with ethyl acetate three times. The organic layers were combined, washed successively with water and an aqueous saturated sodium chloride solution, dried over anhydrous sodium sulfate, and concentrated under reduced pressure. The resulting residue was subjected to silica gel column chromatography to obtain 0.080 g of the present compound (125) of the formula:

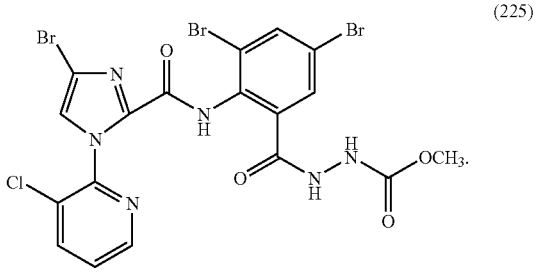

(225)

The present compound (225)

¹H-NMR (DMSO-d₆, TMS) δ (ppm): 3.63 (3H, s), 7.59 (1H, dd, J=8 Hz, 5 Hz), 7.90 (1H, s), 8.04 (1H, d, J=2 Hz), 8.11 (1H, d, J=8 Hz), 8.24 (1H, s), 8.49 (1H, d, J=5 Hz), 9.36 (1H, brs), 10.17 (1H, brs), 10.27 (1H, brs)

PREPARATION EXAMPLE 226

According to the same manner as that of Preparation Example 122, 6,8-dibromo-2-[1-(3-chloro-2-pyridinyl)-5-methylsulfonyl-1H-pyrrol-2-yl]-4H-3,1-benzoxazine-4-one was used in place of 6,8-dibromo-2-[4-bromo-1-(3-chloro-2-pyridinyl)-1H-pyrrol-2-yl]-4H-3,1-benzoxazine-4-one to obtain the present compound (226) of the formula:

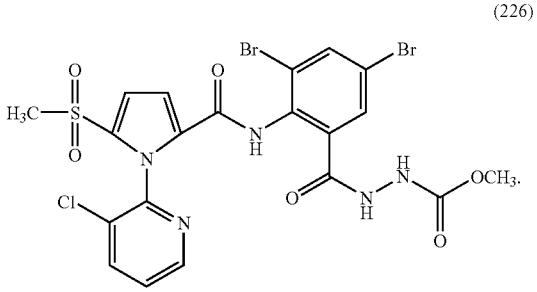

(226)

The present compound (226)

¹H-NMR (DMSO-d₆, TMS) δ (ppm): 3.27 (3H, s), 3.61 (3H, s), 7.11 (1H, d, J=4 Hz), 7.36 (1H, d, J=4 Hz), 7.53 (1H, dd, J=8 Hz, 5 Hz), 7.65 (1H, brs), 8.04 (1H, dd, J=8 Hz, 2 Hz), 8.12 (1H, d, J=2 Hz), 8.46 (1H, dd, J=5 Hz, 2 Hz), 9.36 (1H, brs), 10.16 (1H, brs), 10.22 (1H, brs)

PREPARATION EXAMPLE 227

According to the same manner as that of Preparation Example 122, 6,8-dibromo-2-[1-(3-chloro-2-pyridinyl)-5-methylthio-1H-pyrrol-2-yl]-4H-3,1-benzoxazine-4-one was used in place of 6,8-dibromo-2-[4-bromo-1-(3-chloro-2-pyridinyl)-1H-pyrrol-2-yl]-4H-3,1-benzoxazine-4-one to obtain the present compound (227) of the formula:

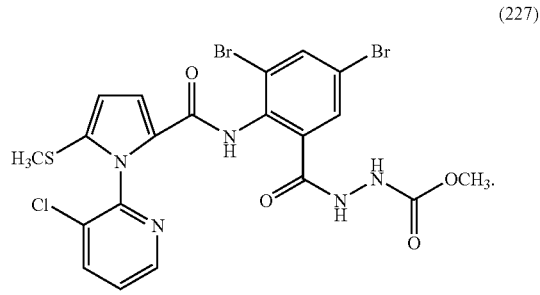

(227)

The present compound (227)

¹H-NMR (DMSO-d₆, TMS) δ (ppm): 2.25 (3H, s), 3.60 (3H, s), 6.52 (1H, d, J=4 Hz), 7.27 (1H, d, J=4 Hz), 7.49 (1H, dd, J=8 Hz, 5 Hz), 7.62 (1H, brs), 8.04 (1H, dd, J=8 Hz, 1Hz), 8.07 (1H, d, J=2 Hz), 8.45 (1H, dd, J=5 Hz, 1Hz), 9.34 (1H, brs), 9.77 (1H, brs), 10.10 (1H, brs)

PREPARATION EXAMPLE 228

According to the same manner as that of Preparation Example 72, 6-chloro-2-{1-(3-chloro-2-pyridinyl)-3-[1,1,2-trifluoro-2-(trifluoromethoxy)ethoxy]-1H-pyrazol-5-yl}-8-methyl-4H-3,1-benzoxazine-4-one was used in place of 2-[3-bromo-1-(3-chloro-2-pyridinyl)-1H-pyrazol-5-yl]-8-chloro-4H-3,1-benzoxazine-4-one to obtain the present compound (228) of the formula:

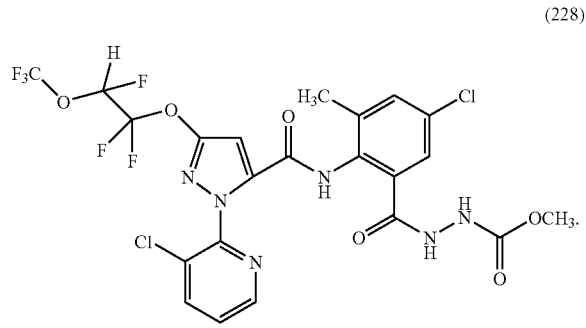

(228)

The present compound (228)

¹H-NMR (DMSO-d₆, TMS) δ (ppm): 2.16 (3H, s), 3.62 (3H, brs), 7.20 (1H, s), 7.37 (1H, dt, J=51 Hz, 4 Hz), 7.38 (1H, s), 7.55 (1H, s), 7.61 (1H, dd, J=8 Hz, 5 Hz), 8.17 (1H, d, J=8 Hz), 8.50 (1H, d, J=5 Hz), 9.32 (1H, s), 10.16 (1H, s), 10.30 (1H, s)

PREPARATION EXAMPLE 229

According to the same manner as that of Preparation Example 114, 6-chloro-2-{1-(3-chloro-2-pyridinyl)-3-[1,1, 2-trifluoro-2-(trifluoromethoxy)ethoxy]-1H-pyrazol-5-yl}-8-methyl-4H-3,1-benzoxazine-4-one was used in place of 2-[3-bromo-1-(3-chloro-2-pyridinyl)-1H-pyrazole-5-yl]-6-chloro-8-methyl-4H-3,1-benzoxazine-4-one to obtain the present compound (229) of the formula:

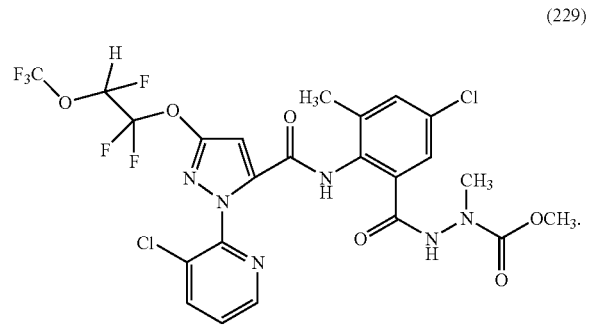

The present compound (229)
¹H-NMR (DMSO-d₆, TMS) δ (ppm): 2.22 (3H, s), 2.91 (3H, s), 3.47-3.68 (3H, brm), 7.24 (1H, s), 7.31 (1H, s), 7.37 (1H, dt, J=51 Hz, 4 Hz), 7.57 (1H, d, J=2 Hz), 7.61 (1H, dd, J=8 Hz, 5 Hz), 8.17 (1H, dd, J=8 Hz, 1Hz), 8.48 (1H, dd, J=5 Hz, 1Hz), 10.32 (1H, s), 10.53 (1H, s)

PREPARATION EXAMPLE 230

According to the same manner as that of Preparation Example 72, 6-chloro-2-[1-(3-chloro-2-pyridinyl)-3-(trifluoromethylthio)-1H-pyrazol-5-yl]-8-methyl-4H-3,1-benzoxazine-4-one was used in place of 2-[3-bromo-1-(3-chloro-2-pyridinyl)-1H-pyrazol-5-yl]-8-chloro-4H-3,1-benzoxazine-4-one to obtain the present compound (230) of the formula:

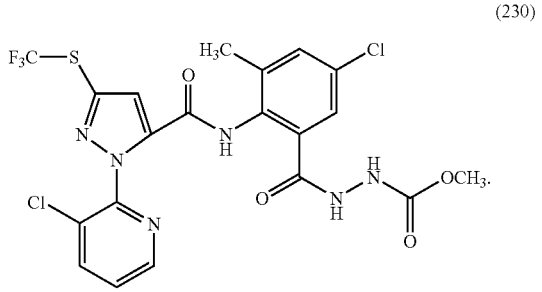

The present compound (230)
¹H-NMR (DMSO-d₆, TMS) δ (ppm): 2.15 (3H, s), 3.62 (3H, brs), 7.39 (1H, brs), 7.55 (1H, s), 7.62-7.68 (2H, m), 8.20 (1H, dd, J=8 Hz, 2 Hz), 8.52 (1H, dd, J=5 Hz, 2 Hz), 9.32 (1H, brs), 10.16 (1H, brs), 10.36 (1H, brs)

PREPARATION EXAMPLE 231

A mixture of 0.50 g of 3-bromo-N-[4,6-dichloro-2-(N,N'-dimethylhydrazinocarbonyl)phenyl]-1-(3-chloro-2-pyridinyl)-1H-pyrazole-5-carboxamide, 0.18 g of methyl chloroformate, 0.16 g of pyridine and 10 ml of acetonitrile were mixed under ice-cooling, and the mixture was stirred for 3.5 hours under ice-cooling. Water was poured into the reaction mixture, and the mixture was extracted with ethyl acetate. The organic layer was washed successively with water and an aqueous saturated sodium chloride solution, dried over anhydrous magnesium sulfate, and concentrated under reduced pressure. The resulting residue was washed with a mixture of methyl tert-butyl ether and hexane to obtain 0.47 g of the present compound (231) of the formula:

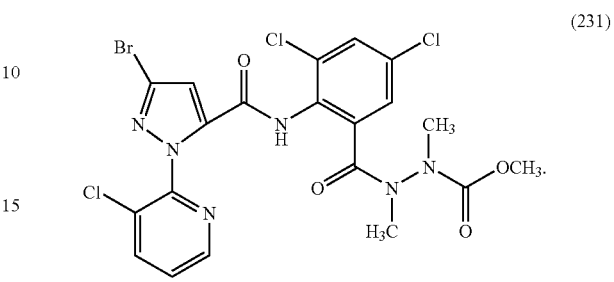

The present compound (231)
¹H-NMR (DMSO-d₆, TMS) δ (ppm): 2.73 (1.4H, s), 2.83 (1.6H, s), 2.95 (1.6H, s), 3.07 (1.4H, s), 3.49-3.68 (3.0H, m), 7.32-7.44 (2.0H, m), 7.62 (1.0H, dd, J=8 Hz, 5 Hz), 7.85 (0.5H, d, J=2 Hz), 7.92 (0.5H, s), 8.19 (1.0H, dd, J=8 Hz, 1Hz), 8.49-8.52 (1.0H, m), 10.53 (0.5H, s), 10.71 (0.5H, s)

Then, examples of preparation methods for intermediate compounds used in Preparation Examples will be shown in Reference Preparation Examples.

REFERENCE PREPARATION EXAMPLE 1

A mixture of 0.44 g of 6-chloro-2-[1-(3-chloro-2-pyridinyl)-3-trifluoromethyl-1H-pyrazol-5-yl]-8-methyl-4H-3,1-benzoxazine-4-one, 0.05 g of hydrazine monohydrate and 10 ml of tetrahydrofuran was stirred at room temperature for 2 hours. After the reaction mixture was mixed with water and ethyl acetate, layers were separated. The organic layer was washed with water, dried over sodium sulfate, and concentrated under reduced pressure. The resulting residue was subjected to silica gel column chromatography to obtain 0.10 g of N-[4-chloro-2-(hydrazinocarbonyl)-6-methylphenyl]-1-(3-chloro-2-pyridinyl)-3-trifluoromethyl-1H-pyrazole-5-carboxamide of the formula:

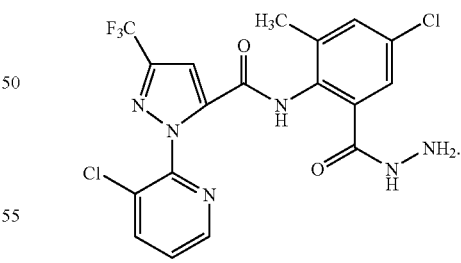

N-[4-chloro-2-(hydrazinocarbonyl)-6-methylphenyl]-1-(3-chloro-2-pyridinyl)-3-trifluoromethyl-1H-pyrazole-5-carboxamide ¹H-NMR (DMSO-d₆, TMS) δ (ppm): 2.16 (3H, s), 4.36 (2H, s), 7.32 (1H, s), 7.48 (1H, s), 7.66 (1H, dd, J=4 Hz, 8 Hz), 7.74 (1H, s), 8.22 (1H, d, J=8 Hz), 8.54 (1H, d, J=4 Hz), 9.56 (1H, brs), 10.39 (1H, brs).

REFERENCE PREPARATION EXAMPLE 2

A mixture of 0.44 g of 6-chloro-2-[1-(3-chloro-2-pyridinyl)-3-trifluoromethyl-1H-pyrazol-5-yl]-8-methyl-4H-3,1-benzoxazine-4-one, 0.05 g of methylhydrazine and 10 ml of tetrahydrofuran was stirred at room temperature for 2 hours. After the reaction mixture was mixed with water and ethyl acetate, layers were separated. The organic layer was washed with water, dried over sodium sulfate, and concentrated under reduced pressure. The resulting residue was subjected to silica gel column chromatography to obtain 0.40 g of N-[4-chloro-2-(N-methylhydrazinocarbonyl)-6-methylphenyl]-1-(3-chloro-2-pyridinyl)-3-trifluoromethyl-1H-pyrazole-5-carboxamide of the formula:

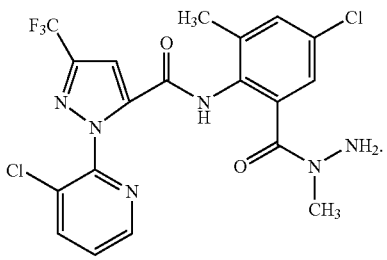

N-[4-chloro-2-(N-methylhydrazinocarbonyl)-6-methylphenyl]-1-(3-chloro-2-pyridinyl)-3-trifluoromethyl-1H-pyrazole-5-carboxamide $^1$H-NMR (DMSO-d$_6$, TMS) δ (ppm): 2.17 (1.8H, s), 2.30 (1.2H, s), 2.76 (1.2H, s), 3.05 (1.8H, s), 4.54 (1.2H, brs), 4.99 (0.8H, brs), 7.16-7.23 (1H, m), 7.36 (0.6H, s), 7.46 (0.4H, s), 7.66-7.70 (2H, m), 8.24 (1H, d, J=8 Hz), 8.54 (1H, d, J=4 Hz), 10.25 (0.6H, brs), 10.51 (0.4H, brs).

REFERENCE PREPARATION EXAMPLE 3

A mixture of 0.40 g of 2-[1-(3-chloro-2-pyridinyl)-3-trifluoromethyl-1H-pyrazol-5-yl]-8-methyl-4H-3,1-benzoxazine-4-one, 0.09 ml of hydrazine monohydrate and 20 ml of tetrahydrofuran was stirred at room temperature for 3 hours. Water was poured into the reaction mixture, and the mixture was extracted with ethyl acetate three times. The organic layers were combined, washed with an aqueous saturated sodium chloride solution, dried over anhydrous magnesium sulfate, and concentrated under reduced pressure to obtain 0.26 g of 1-(3-chloro-2-pyridinyl)-N-[2-(hydrazinocarbonyl)-6-methylphenyl]-3-trifluoromethyl-1H-pyrazole-5-carboxamide of the formula:

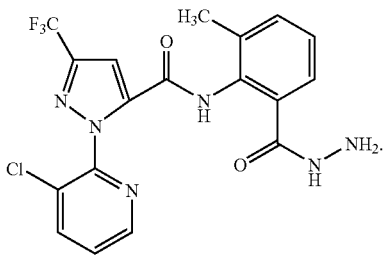

1-(3-Chloro-2-pyridinyl)-N-[2-(hydrazinocarbonyl)-6-methylphenyl]-3-trifluoromethyl-1H-pyrazole-5-carboxamide $^1$H-NMR (CDCl$_3$, TMS) δ (ppm): 2.22 (3H, s), 4.05 (2H, s), 7.18-7.40 (5H, m), 7.42 (1H, dd, J=8 Hz, 4 Hz), 7.89 (1H, dd, J=8 Hz, 1Hz), 8.48 (1H, dd, J=4 Hz, 1Hz), 10.04 (1H, s).

REFERENCE PREPARATION EXAMPLE 4

A mixture of 0.27 g of 8-chloro-2-[1-(3-chloro-2-pyridinyl)-3-trifluoromethyl-1H-pyrazol-5-yl]-4H-3,1-benzoxazine-4-one, 0.025 ml of hydrazine monohydrate and 10 ml of tetrahydrofuran was stirred at room temperature for 3 hours. Water was poured into the reaction mixture, and the mixture was extracted with ethyl acetate three times. The organic layers were combined, washed with an aqueous saturated sodium chloride solution, dried over anhydrous magnesium sulfate, and concentrated under reduced pressure. The resulting residue was washed with a mixed solvent of chloroform and methyl t-butyl ether to obtain 0.21 g of N-[2-chloro-6-(hydrazinocarbonyl)phenyl]-1-(3-chloro-2-pyridinyl)-3-trifluoromethyl-1H-pyrazole-5-carboxamide of the formula:

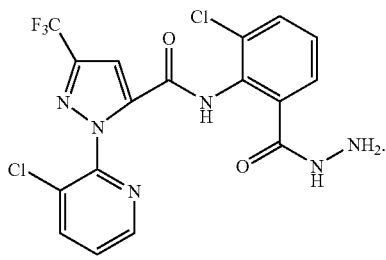

N-[2-chloro-6-(hydrazinocarbonyl)phenyl]-1-(3-chloro-2-pyridinyl)-3-trifluoromethyl-1H-pyrazole-5-carboxamide $^1$H-NMR (DMSO-d$_6$) δ (ppm): 4.35 (2H, brs), 7.38-7.39 (2H, m), 7.61-7.66 (2H, m), 7.79 (1H, s), 8.20 (1H, d, J=8 Hz), 8.53 (1H, d, J=4 Hz), 9.52 (1H, s), 10.04 (1H, s).

REFERENCE PREPARATION EXAMPLE 5

A mixture of 0.40 g of 2-[3-bromo-1-(3-chloro-2-pyridinyl)-1H-pyrazol-5-yl]-6-chloro-8-methyl-4H-3,1-benzoxazine-4-one, 0.08 ml of hydrazine monohydrate and 10 ml of tetrahydrofuran was stirred at room temperature for 3 hours. The reaction mixture was poured into water and then filtered. The resulting filter cake was washed with water and methyl tert-butyl ether. The filter cake was dissolved in ethyl acetate, dried over anhydrous magnesium sulfate, and concentrated under reduced pressure to obtain 0.35 g of 3-bromo-N-[4-chloro-2-(hydrazinocarbonyl)-6-methylphenyl]-1-(3-chloro-2-pyridinyl)-1H-pyrazole-5-carboxamide of the formula:

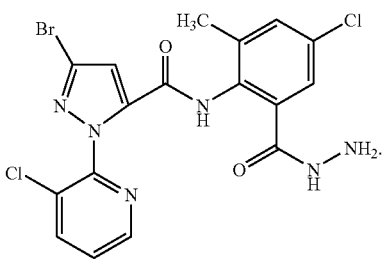

3-Bromo-N-[4-chloro-2-(hydrazinocarbonyl)-6-methylphenyl]-1-(3-chloro-2-pyridinyl)-1H-pyrazole-5-carboxamide $^1$H-NMR (DMSO-$d_6$) δ (ppm): 2.14 (3H, s), 4.37 (2H, brs), 7.31 (1H, s), 7.38 (1H, s), 7.47 (1H, s), 7.61 (1H, dd, J=8 Hz, 4 Hz), 8.17 (1H, dd, J=8 Hz, 1Hz), 8.50 (1H, dd, J=4 Hz, 1Hz), 9.55 (1H, brs), 10.26 (1H, brs).

REFERENCE PREPARATION EXAMPLE 6

A mixture of 0.88 g of 6-chloro-2-[1-(2-chlorophenyl)-3-trifluoromethyl-1H-pyrazol-5-yl]-8-methyl-4H-3,1-benzoxazine-4-one, 0.19 ml of hydrazine monohydrate and 3 ml of tetrahydrofuran was stirred at room temperature for 2 hours. Water was poured into the reaction mixture, and the mixture was extracted with ethyl acetate three times. The organic layers were combined, washed with an aqueous saturated sodium chloride solution, dried over anhydrous magnesium sulfate, and concentrated under reduced pressure to obtain 0.94 g of N-[4-chloro-2-(hydrazinocarbonyl)-6-methylphenyl]-1-(2-chlorophenyl)-3-trifluoromethyl-1H-pyrazole-5-carboxamide of the formula:

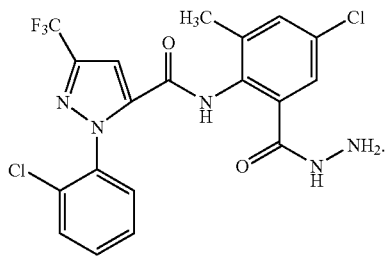

N-[4-chloro-2-(hydrazinocarbonyl)-6-methylphenyl]-1-(2-chlorophenyl)-3-trifluoromethyl-1H-pyrazole-5-carboxamide $^1$H-NMR (CDCl$_3$, TMS) δ (ppm): 2.18 (3H, s), 4.03 (2H, brs), 7.19-7.54 (8H, m), 9.74 (1H, s).

REFERENCE PREPARATION EXAMPLE 7

A mixture of 0.50 g of 6-chloro-2-[1-(3-chloro-2-pyridinyl)-1H-pyrazol-5-yl]-8-methyl-4H-3,1-benzoxazine-4-one, 0.13 ml of hydrazine monohydrate and 20 ml of tetrahydrofuran was stirred at room temperature for 4 hours. Water was poured into the reaction mixture, and the mixture was extracted with ethyl acetate two times. The organic layers were combined, washed with an aqueous saturated sodium chloride solution, dried over anhydrous magnesium sulfate, and concentrated under reduced pressure. The resulting residue was washed with a mixed solvent of ethyl acetate and hexane to obtain 0.44 g of N-[4-chloro-2-(hydrazinocarbonyl)-6-methylphenyl]-1-(3-chloro-2-pyridinyl)-1H-pyrazole-5-carboxamide of the formula:

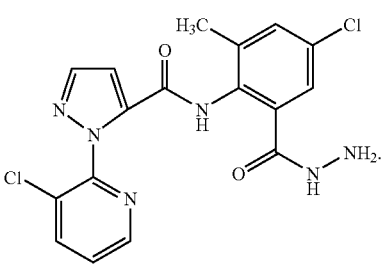

N-[4-chloro-2-(hydrazinocarbonyl)-6-methylphenyl]-1-(3-chloro-2-pyridinyl)-1H-pyrazole-5-carboxamide $^1$H-NMR (CDCl$_3$, TMS) δ (ppm): 2.19 (3H, s), 4.03 (2H, brs), 7.05 (1H, d, J=2 Hz), 7.19 (1H, d, J=2 Hz), 7.36 (1H, dd, J=8 Hz, 4 Hz), 7.50 (1H, s), 7.83-7.86 (2H, m), 8.46 (1H, dd, J=4 Hz, 1Hz), 9.64 (1H, s).

REFERENCE PREPARATION EXAMPLE 8

To a solution of 3.1 g of 1-(3-chloro-2-pyridinyl)-3-trifluoromethyl-1H-pyrazole-5-carbonyl chloride in 100 ml of acetonitrile, 1.9 g of 2-amino-5-chloro-3-methylbenzoic acid was added. The mixture was stirred at room temperature for 10 minutes and then, 1.0 g of triethylamine was added thereto. The mixture was stirred at room temperature for 20 minutes and then, 2.0 g of triethylamine was further added thereto. After the mixture was stirred at room temperature for 20 minutes, 1.2 g of methanesulfonyl chloride was added and the mixture was stirred at room temperature for 3 hours. After the reaction mixture was concentrated under reduced pressure, ethyl acetate and water were poured into the residue to separate layers. The organic layer was washed with water, dried over sodium sulfate, and concentrated under reduced pressured. The resulting residue was subjected to silica gel column chromatography to obtain 4.2 g of 6-chloro-2-[1-(3-chloro-2-pyridinyl)-3-trifluoromethyl-1H-pyrazol-5-yl]-8-methyl-4H-3,1-benzoxazine-4-one of the formula:

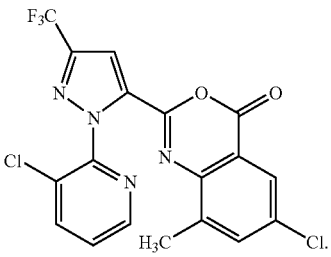

6-Chloro-2-[1-(3-chloro-2-pyridinyl)-3-trifluoromethyl-1H-pyrazol-5-yl]-8-methyl-4H-3,1-benzoxazine-4-one $^1$H-NMR (CDCl$_3$, TMS) δ (ppm): 1.73 (3H, s), 7.80 (1H, s), 7.82 (1H, dd, J=4 Hz, 8 Hz), 7.90 (1H, s), 7.91 (1H, s), 8.39 (1H, d, J=8 Hz), 8.66 (1H, d, J=4 Hz).

REFERENCE PREPARATION EXAMPLE 9

To a solution of 2.0 g of 1-(3-chloro-2-pyridinyl)-3-trifluoromethyl-1H-pyrazole-5-carbonyl chloride in 50 ml of acetonitrile, 0.98 g of 2-amino-3-methylbenzoic acid was added. The mixture was stirred at room temperature for 10 minutes and then, 0.9 ml of triethylamine was added thereto. The mixture was stirred at room temperature for 20 minutes and then, 1.8 ml of triethylamine was further added thereto. After the mixture was stirred at room temperature for 20 minutes, 0.56 ml of methanesulfonyl chloride was added and the mixture was stirred at room temperature for 3 hours. Water was poured into the reaction mixture, and the mixture was extracted with ethyl acetate two times. The organic layers were combined, washed with an aqueous saturated sodium chloride solution, dried over anhydrous magnesium sulfate, and concentrated under reduced pressure. The resulting residue was subjected to silica gel column chromatography to obtain 1.17 g of 2-[1-(3-chloro-2-pyridinyl)-3-trifluoromethyl-1H-pyrazol-5-yl]-8-methyl-4H-3,1-benzoxazine-4-one of the formula:

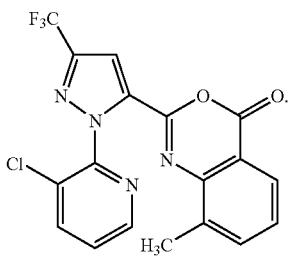

2-[1-(3-Chloro-2-pyridinyl)-3-trifluoromethyl-1H-pyrazol-5-yl]-8-methyl-4H-3,1-benzoxazine-4-one $^1$H-NMR (CDCl$_3$, TMS) δ (ppm): 1.84 (3H, s), 7.39 (1H, t, J=8 Hz), 7.50-7.55 (3H, m), 7.99 (1H, dd, J=8 Hz, 1Hz), 8.01 (1H, d, J=8 Hz), 8.59 (1H, dd, J=4.5 Hz, 1Hz).

REFERENCE PREPARATION EXAMPLE 10

To a solution of 0.80 g of 1-(3-chloro-2-pyridinyl)-3-trifluoromethyl-1H-pyrazole-5-carbonyl chloride in 20 ml of acetonitrile, 0.44 g of 2-amino-3-chlorobenzoic acid was added. The mixture was stirred at room temperature for 10 minutes and then, 0.36 ml of triethylamine was added thereto. The mixture was stirred at room temperature for 20 minutes and then, 0.72 ml of triethylamine was further added thereto. After the mixture was stirred at room temperature for 20 minutes, 0.22 ml of methanesulfonyl chloride was added and the mixture was stirred at room temperature for 20 hours. Water was poured into the reaction mixture, and the mixture was extracted with ethyl acetate two times. The organic layers were combined, washed with an aqueous saturated sodium chloride solution, dried over anhydrous magnesium sulfate, and concentrated under reduced pressure. The resulting residue was subjected to silica gel column chromatography to obtain 1.17 g of 8-chloro-2-[1-(3-chloro-2-pyridinyl)-3-trifluoromethyl-1H-pyrazol-5-yl]-4H-3,1-benzoxazine-4-one of the formula:

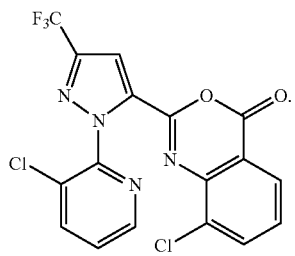

8-Chloro-2-[1-(3-chloro-2-pyridinyl)-3-trifluoromethyl-1H-pyrazol-5-yl]-4H-3,1-benzoxazine-4-one $^1$H-NMR (CDCl$_3$, TMS) δ (ppm): 7.43 (1H, t, J=8 Hz), 7.52 (1H, dd, J=8 Hz, 4 Hz), 7.53 (1H, s), 7.75 (1H, dd, J=8 Hz, 1Hz), 8.00 (1H, dd, J=8 Hz, 1Hz), 8.11 (1H, dd, J=8 Hz, 1Hz), 8.57 (1H, dd, J=4 Hz, 1Hz)

REFERENCE PREPARATION EXAMPLE 11

To a mixture of 0.44 g of 3-bromo-1-(3-chloro-2-pyridinyl)-1H-pyrazole-5-carboxylic acid, 6 ml of acetonitrile and 0.20 g of triethylamine was added 0.125 ml of methanesulfonyl chloride. After the resulting mixture was stirred at room temperature for 15 minutes, 0.27 g of 2-amino-5-chloro-3-methylbenzoic acid was added and the mixture was stirred at room temperature for 20 minutes. To the mixture, 0.40 ml of triethylamine was added. After the mixture was stirred at room temperature for 20 minutes, 0.13 ml of methanesulfonyl chloride was added and the mixture was stirred at room temperature for 16 hours. The reaction mixture was filtered and the filter cake was washed with methyl tert-butyl ether. The resulting filter cake was dissolved in ethyl acetate, washed successively with water and an aqueous saturated sodium chloride solution, dried over anhydrous magnesium sulfate, and concentrated under reduced pressure to obtain 0.098 g of 2-[3-bromo-1-(3-chloro-2-pyridinyl)-1H-pyrazol-5-yl]-6-chloro-8-methyl-4H-3,1-benzoxazine-4-one. In addition, the filtrate was concentrated under reduced pressure, and the resulting residue was subjected to silica gel column chromatography to obtain 0.093 g of 2-[3-bromo-1-(3-chloro-2-pyridinyl)-1H-pyrazol-5-yl]-6-chloro-8-methyl-4H-3,1-benzoxazine-4-one of the formula:

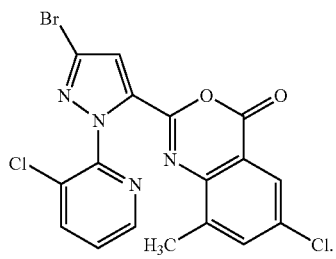

2-[3-Bromo-1-(3-chloro-2-pyridinyl)-1H-pyrazol-5-yl]-6-chloro-8-methyl-4H-3,1-benzoxazine-4-one $^1$H-NMR (CDCl$_3$, TMS) δ (ppm): 1.81 (3H, s), 7.25 (1H, s), 7.48-7.51 (2H, m), 7.95-7.98 (2H, m), 8.56 (1H, dd, J=4 Hz, 1Hz)

REFERENCE PREPARATION EXAMPLE 12

To a mixture of 1.0 g of 1-(2-chlorophenyl)-3-trifluoromethyl-1H-pyrazole-5-carbonyl chloride and 10 ml of acetonitrile was added 0.60 g of 2-amino-5-chloro-3-methylbenzoic acid, and the resulting mixture was stirred at room temperature for 10 minutes. To the mixture, 0.46 ml of triethylamine was added. After the mixture was stirred at room temperature for 20 minutes, 0.92 ml of triethylamine was further added thereto. After the mixture was stirred at room temperature for 20 minutes, 0.28 ml of methanesulfonyl chloride was added thereto and the mixture was stirred at room temperature for 3 hours. The reaction mixture was filtered, and the resulting filtrate was concentrated under reduced pressure. The resulting residue was subjected to silica gel column chromatography to obtain 0.98 g of 6-chloro-2-[1-(2-chlorophenyl)-3-trifluoromethyl-1H-pyrazol-5-yl]-8-methyl-4H-3,1-benzoxazine-4-one of the formula:

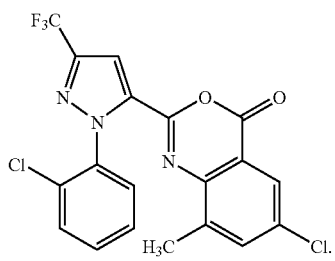

6-chloro-2-[1-(2-chlorophenyl)-3-trifluoromethyl-1H-pyrazol-5-yl]-8-methyl-4H-3,1-benzoxazine-4-one $^1$H-NMR (CDCl$_3$, TMS) δ (ppm): 1.82 (3H, s), 7.45-7.60 (6H, m), 7.99 (1H, s).

REFERENCE PREPARATION EXAMPLE 13

A mixture of 1.22 g of 1-(3-chloro-2-pyridinyl)-1H-pyrazole-5-carboxylic acid and 1.15 ml of thionyl chloride was heated to reflux for 2 hours. The reaction mixture was allowed to cool to room temperature and then concentrated under reduced pressure. The resulting residue was dissolved in 15 ml of acetonitrile, and 0.27 g of 2-amino-5-chloro-3-methylbenzoic acid was added thereto. The mixture was stirred at room temperature for 10 minutes. To the mixture was added 0.73 ml of triethylamine, and the mixture was stirred at room temperature for 20 minutes. Thereto 1.45 ml of triethylamine was further added, and the mixture was stirred at room temperature for 20 minutes. Then 0.44 ml of methanesulfonyl chloride was added, and the mixture was stirred at room temperature for 3 hours. Water was poured into the reaction mixture, and the mixture was extracted with ethyl acetate two times. The organic layers were combined, washed with an aqueous saturated sodium chloride solution, dried over anhydrous magnesium sulfate, and concentrated under reduced pressure. The resulting residue was washed with methyl tert-butyl ether to obtain 0.68 g of 6-chloro-2-[1-(3-chloro-2-pyridinyl)-1H-pyrazol-5-yl]-8-methyl-4H-3,1-benzoxazine-4-one of the formula:

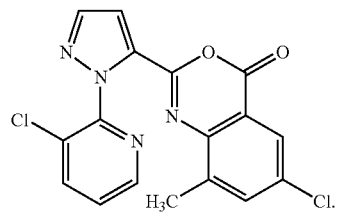

6-Chloro-2-[1-(3-chloro-2-pyridinyl)-1H-pyrazol-5-yl]-8-methyl-4H-3,1-benzoxazine-4-one $^1$H-NMR (CDCl$_3$, TMS) δ (ppm): 1.82 (3H, s), 7.28 (1H, d, J=2 Hz), 7.46-7.49 (2H, m), 7.91 (1H, d, J=2 Hz), 7.95-7.99 (2H, m), 8.57 (1H, dd, J=4 Hz, 1 Hz).

REFERENCE PREPARATION EXAMPLE 14

A mixture of 15.30 g of 3-trifluoromethyl-1H-pyrazole, 16.64 g of 2,3-dichloropyridine, 26.42 g of potassium carbonate and 100 ml of N,N-dimethylformamide was stirred at 130° C. for 14 hours. The reaction mixture was allowed to cool to room temperature and then water was poured thereto. The mixture was extracted with ethyl acetate two times. The organic layers were combined, washed successively with water and an aqueous saturated sodium chloride solution, dried over magnesium sulfate, and concentrated under reduced pressure. The resulting residue was subjected to silica gel column chromatography to obtain 22.88 g of 3-chloro-2-(3-trifluoromethyl-1H-pyrazol-1-yl)pyridine of the formula:

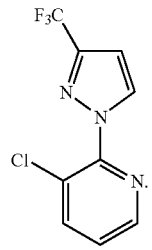

3-Chloro-2-(3-trifluoromethyl-1H-pyrazol-1-yl)pyridine $^1$H-NMR (CDCl$_3$, TMS) δ (ppm): 6.75 (1H, d, J=2 Hz), 7.37 (1H, dd, J=8 Hz, 4 Hz), 7.95 (1H, dd, J=8 Hz, 1Hz), 8.14 (1H, d, J=1Hz), 8.49 (1H, dd, J=4 Hz, 1Hz).

REFERENCE PREPARATION EXAMPLE 15

To a mixture of 15 g of 3-chloro-2-(3-trifluoromethyl-1H-pyrazol-1-yl)pyridine and 150 ml of tetrahydrofuran was added dropwise 39 ml of a 2.0 mol/L lithium diisopropylamide solution in heptane/tetrahydrofuran/ethylbenzene at −78° C., and then stirred at −78° C. for 15 minutes. Carbon dioxide was introduced into the mixture at such a rate that the inner temperature was retained at −60° C. or lower. After the mixture turned yellow, it was further stirred at −78° C. for 10 minutes. After the temperature of the reaction mixture was allowed to rise to room temperature, 200 ml of water and 200 ml of hexane were poured. The aqueous layer was adjusted to pH 10-12 by an addition of a 2N aqueous sodium hydroxide solution and then layers were separated. The organic layer was extracted with a 0.5N aqueous sodium hydroxide solution. The aqueous layers were combined, washed with diethyl ether, adjusted to around pH 3 by an addition of 2N hydrochloric acid, and then extracted with methyl tert-butyl ether three times. The organic layers were combined, washed with an aqueous saturated sodium chloride solution, dried over magnesium sulfate, and concentrated under reduced pressure to obtain 16.08 g of 1-(3-chloro-2-pyridinyl)-3-trifluoromethyl-1H-pyrazole-5-carboxylic acid of the formula:

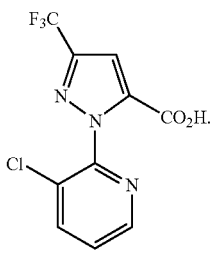

1-(3-Chloro-2-pyridinyl)-3-trifluoromethyl-1H-pyrazole-5-carboxylic acid $^1$H-NMR (DMSO-$d_6$) δ (ppm): 7.60 (1H, s), 7.74 (1H, dd, J=8 Hz, 4 Hz), 8.30 (1H, dd, J=8 Hz, 1Hz), 8.60 (1H, dd, J=4 Hz, 1Hz).

REFERENCE PREPARATION EXAMPLE 16

A mixture of 16.08 g of 1-(3-chloro-2-pyridinyl)-3-trifluoromethyl-1H-pyrazole-5-carboxylic acid and 12 ml of thionyl chloride was heated to reflux for 2 hours. The reaction mixture was allowed to cool to room temperature and subjected to distillation under reduced pressure (125° C./3 mmHg) to obtain 14.2 g of 1-(3-chloro-2-pyridinyl)-3-trifluoromethyl-1H-pyrazole-5-carbonyl chloride of the formula:

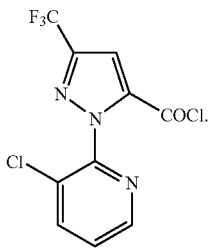

1-(3-Chloro-2-pyridinyl)-3-trifluoromethyl-1H-pyrazole-5-carbonyl Chloride $^1$H-NMR (CDCl$_3$, TMS) δ (ppm): 7.52 (1H, s), 7.52 (1H, dd, J=8 Hz, 4 Hz), 7.97 (1H, dd, J=8 Hz, 1Hz), 8.53 (1H, dd, J=4 Hz, 1Hz).

REFERENCE PREPARATION EXAMPLE 17

To a mixture of 18 g of 4-ethoxy-1,1,1-trifluoro-3-butene-2-one and 50 ml of methanol was added 5.7 ml of methylhydrazine, and the mixture was heated to reflux for 4 hours. The reaction mixture was allowed to cool to room temperature, concentrated under reduced pressure, and subjected to distillation under reduced pressure (60° C./15 mmHg) to obtain 8.71 g of 1-methyl-3-trifluoromethyl-1H-pyrazole of the formula:

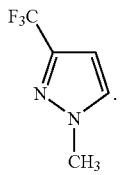

1-Methyl-3-trifluoromethyl-1H-pyrazole $^1$H-NMR (CDCl$_3$, TMS) δ (ppm): 3.97 (3H, s), 6.51 (1H, d, J=2 Hz) 7.40 (1H, d, J=2 Hz).

REFERENCE PREPARATION EXAMPLE 18

To a mixture of 8.71 g of 1-methyl-3-trifluoromethyl-1H-pyrazole and 130 ml of tetrahydrofuran was added dropwise 32 ml of a 2.0 mol/L lithium diisopropylamide solution in heptane/tetrahydrofuran/ethylbenzene at −78° C. The mixture of stirred at −78° C. for 2 hours and then poured into a mixture was dry ice and 50 ml of tetrahydrofuran. The mixture was stirred for 2 hours while allowing it to rise to around room temperature. Water and diethyl ether were poured into the reaction mixture. The aqueous layer was adjusted to pH 10-12 by an addition of a 2N aqueous sodium hydroxide solution, and then layers were separated. The resulting aqueous layer was washed with diethyl ether two times, adjusted to around pH 3 by an addition of 2N hydrochloric acid, and then extracted with methyl tert-butyl ether three times. The organic layers were combined, washed with an aqueous saturated sodium chloride solution, dried over magnesium sulfate, and concentrated under reduced pressure to obtain 8.19 g of 1-methyl-3-trifluoromethyl-1H-pyrazole-5-carboxylic acid of the formula:

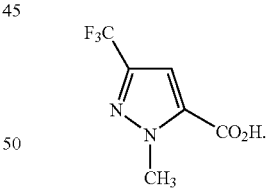

1-Methyl-3-trifluoromethyl-1H-pyrazole-5-carboxylic acid $^1$H-NMR (CDCl$_3$, TMS) δ (ppm): 4.13 (3H, s), 7.22 (1H, s).

REFERENCE PREPARATION EXAMPLE 19

To a mixture of 15 g of pyrazole and 200 ml of toluene was added dropwise 23.7 ml of dimethylsulfamoyl chloride at room temperature. Then, 40 ml of triethylamine was added to the mixture, and the mixture was stirred at room temperature for 18 hours. The reaction mixture was filtered, and the filtrate was concentrated under reduced pressure. The resulting residue was subjected to silica gel column chromatography to obtain 17.6 g of N,N-dimethyl-1H-pyrazole-1-sulfonamide of the formula:

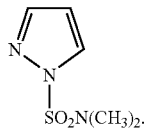

N,N-dimethyl-1H-pyrazole-1-sulfonamide $^1$H-NMR (CDCl$_3$, TMS) δ (ppm): 2.95 (6H, s), 6.40 (1H, dd, J=2 Hz, J=1 Hz), 7.75 (1H, d, J=1 Hz), 7.95 (1H, d, J=2 Hz,).

REFERENCE PREPARATION EXAMPLE 20

To a mixture of 17.6 g of N,N-dimethyl-1H-pyrazole-1-sulfonamide and 200 ml of tetrahydrofuran was added dropwise 80 ml of a 1.3M solution of n-butyl lithium in hexane at −78° C., and the resulting mixture was stirred at −78° C. for 15 minutes. To the mixture, a solution of 35.8 g of 1,2-dibromo-1,1,2,2-tetrachloroethane in 60 ml of tetrahydrofuran was added dropwise, and the resulting mixture was stirred at −78° C. for 15 minutes. The reaction mixture was returned to room temperature, and stirred for 1 hour. Water was poured into the reaction mixture, and the mixture was extracted with ethyl acetate three times. The organic layers were combined, washed with an aqueous saturated sodium chloride solution, dried over magnesium sulfate, and concentrated under reduced pressure. The resulting residue was subjected to silica gel column chromatography to obtain 21.3 g of 5-bromo-N,N-dimethyl-1H-pyrazole-1-sulfonamide of the formula:

5-Bromo-N,N-dimethyl-1H-pyrazole-1-sulfonamide $^1$H-NMR (CDCl$_3$, TMS) δ (ppm): 3.08 (6H, s), 6.43 (1H, m), 7.61 (1H, m).

REFERENCE PREPARATION EXAMPLE 21

A mixture of 21.3 g of 5-bromo-N,N-dimethyl-1H-pyrazole-1-sulfonamide and 30 ml of trifluoroacetic acid was stirred at room temperature for 2 hours. After hexane was poured into the reaction mixture, the mixture was filtered. After methyl tert-butyl ether was added to the resulting filtrate, the mixture was washed successively with an aqueous saturated sodium hydrogen carbonate solution, water and an aqueous saturated sodium chloride solution, dried over magnesium sulfate, and concentrated under reduced pressure to obtain 10.7 g of 3-bromo-1H-pyrazole of the formula:

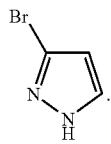

3-Bromo-1H-pyrazole $^1$H-NMR (CDCl$_3$, TMS) δ (ppm): 6.37 (1H, d, J=2 Hz), 7.55 (1H, d, J=2 Hz), 12.6 (1H, brs).

REFERENCE PREPARATION EXAMPLE 22

A mixture of 10.7 g of 3-bromo-1H-pyrazole, 11.8 g of 2,3-dichloropyridine, 57.3 g of cesium carbonate and 80 ml of N,N-dimethylformamide was stirred at 100° C. for 8 hours. The reaction mixture was allowed to cool to room temperature, and water was poured thereto. The mixture was extracted with methyl tert-butyl ether two times. The organic layers were combined, washed successively with water and an aqueous saturated sodium chloride solution, dried over magnesium sulfate, and concentrated under reduced pressure. The resulting residue was subjected to silica gel column chromatography to obtain 12.9 g of 2-(3-bromo-1H-pyrazol-1-yl)-3-chloropyridine of the formula:

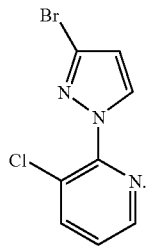

2-(3-Bromo-1H-pyrazole-1-yl)-3-chloropyridine $^1$H-NMR (CDCl$_3$, TMS) δ (ppm): 6.51 (1H, d, J=2 Hz), 7.31 (1H, dd, J=8 Hz, 4 Hz), 7.91 (1H, dd, J=8 Hz, 1Hz), 8.04 (1H, d, J=2 Hz), 8.45 (1H, dd, J=4 Hz, 1Hz).

REFERENCE PREPARATION EXAMPLE 23

To a mixture of 9.2 g of 2-(3-bromo-1H-pyrazol-1-yl)-3-chloropyridine and 80 ml of tetrahydrofuran was added dropwise 21.3 ml of a 2.0M lithium diisopropylamide solution in heptane/tetrahydrofuran/ethylbenzene at −78° C. The resulting mixture was stirred at −78° C. for 15 minutes, poured to a mixture of dry ice and 50 ml of tetrahydrofuran, and stirred for 1 hour with allowing it to rise to around room temperature. After water and diethyl ether were poured into the reaction mixture, the aqueous layer was adjusted to pH 10-12 by an addition of a 2N aqueous sodium hydroxide solution and layers were separated. The resulting aqueous layer was washed with diethyl ether two times, adjusted to around pH 3 by an addition of 2N hydrochloric acid, and extracted with methyl tert-butyl ether three times. The organic layers were combined, washed with an aqueous saturated sodium chloride solution, dried over magnesium sulfate, and concentrated under reduced pressure to obtain 7.96 g of 3-bromo-1-(3-chloro-2-pyridinyl)-1H-pyrazole-5-carboxylic acid of the formula:

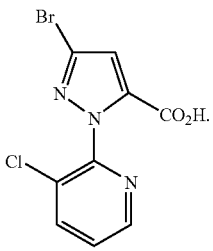

3-Bromo-1-(3-chloro-2-pyridinyl)-1H-pyrazole-5-carboxylic acid

¹H-NMR (DMSO-d₆) δ (ppm): 7.25 (1H, s), 7.68 (1H, dd, J=8 Hz, 4 Hz), 8.24 (1H, dd, J=8 Hz, J=1 Hz), 8.56 (1H, dd, J=4 Hz, 1Hz).

REFERENCE PREPARATION EXAMPLE 24

To a mixture of 12.96 g of 4,4,4-trifluoro-1-(2-furyl)-1,3-butanedione, 8.56 g of sodium acetate and 40 ml of acetic acid was added 11.26 g of 2-chlorophenylhydrazine hydrochloride at room temperature. The mixture was stirred at 60° C. for 1 hour, and concentrated under reduced pressure. After the reaction mixture was concentrated under reduced pressure and water was poured into the residue, the mixture was extracted with chloroform three times. The organic layers were combined, washed with an aqueous saturated sodium chloride solution, dried over magnesium sulfate, and concentrated under reduced pressure. The resulting residue was subjected to silica gel column chromatography to obtain 18.43 g of 1-(2-chlorophenyl)-5-(2-furyl)-3-trifluoromethyl-1H-pyrazole of the formula:

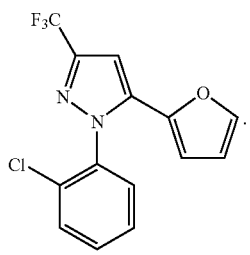

1-(2-Chlorophenyl)-5-(2-furyl)-3-trifluoromethyl-1H-pyrazole

¹H-NMR (CDCl₃, TMS) δ (ppm): 5.76 (1H, d, J=3 Hz), 6.31 (1H, dd, J=3 Hz, 2 Hz), 6.95 (1H, s), 7.40 (1H, d, J=2 Hz), 7.43-7.59 (4H, m).

REFERENCE PREPARATION EXAMPLE 25

An aqueous solution of 27.94 g of potassium permanganate in 100 ml of water was added dropwise to a mixture of 18.43 g of 1-(2-chlorophenyl)-5-(2-furyl)-3-trifluoromethyl-1H-pyrazole and 250 ml of acetone with being kept at 40° C. or lower. Then, the mixture was stirred at room temperature for 20 hours. The reaction mixture was filtered through Celite (registered trademark) to obtain a filtrate. The filtrate was adjusted to pH 10-12 by an addition of a 2N aqueous sodium hydroxide solution, and then extracted with ethyl acetate two times. The aqueous layer was adjusted to around pH 3 by an addition of 2 N hydrochloric acid, and then extracted with methyl tert-butyl ether three times. The organic layers were combined, washed with an aqueous saturated sodium chloride solution, dried over magnesium sulfate, and concentrated under reduced pressure to obtain 10.65 g of 1-(2-chlorophenyl)-3-trifluoromethyl-1H-pyrazole-5-carboxylic acid of the formula:

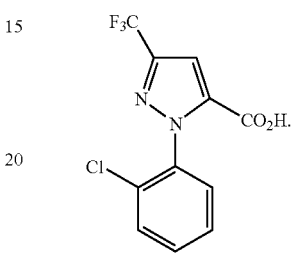

1-(2-Chlorophenyl)-3-trifluoromethyl-1H-pyrazole-5-carboxylic acid

¹H-NMR (CDCl₃, TMS) δ (ppm): 7.33 (1H, s), 7.42-7.54 (4H, m)

REFERENCE PREPARATION EXAMPLE 26

A mixture of 10.65 g of 1-(2-chlorophenyl)-3-trifluoromethyl-1H-pyrazole-5-carboxylic acid and 8 ml of thionyl chloride heated to reflux for 2 hours. The reaction mixture was allowed to cool to room temperature, concentrated under reduced pressure, and subjected to distillation under reduced pressure (110° C./5 mmHg) to obtain 8.39 g of 1-(2-chlorophenyl)-3-trifluoromethyl-1H-pyrazole-5-carbonyl chloride of the formula:

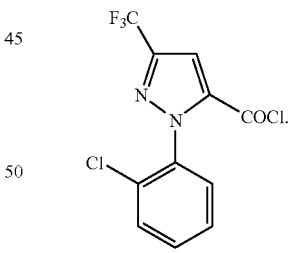

1-(2-Chlorophenyl)-3-trifluoromethyl-1H-pyrazole-5-carbonyl Chloride

¹H-NMR (CDCl₃, TMS) δ (ppm): 7.42-7.57 (5H, m).

REFERENCE PREPARATION EXAMPLE 27

A mixture of 2 g of pyrazole, 4.34 g of 2,3-dichloropyridine, 9.58 g of cesium carbonate and 40 ml N,N-dimethylformamide was stirred at 100° C. for 8 hours. The reaction mixture was allowed to cool to room temperature, and water was added thereto. The mixture was extracted with methyl tert-butyl ether three times. The organic layers were combined, washed successively with water and an aqueous saturated sodium chloride solution, dried over magnesium sulfate, and concentrated under reduced pressure. The resulting residue was subjected to silica gel column chromatography to obtain 3.57 g of 3-chloro-2-(1H-pyrazol-1-yl)pyridine of the formula:

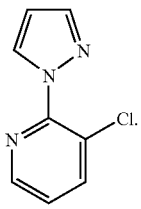

3-Chloro-2-(1H-pyrazole-1-yl)pyridine $^1$H-NMR (CDCl$_3$, TMS) δ (ppm): 6.50 (1H, dd, J=2 Hz, 1Hz), 7.28 (1H, dd, J=8 Hz, 4 Hz), 7.83 (1H, d, J=1 Hz), 7.92 (1H, dd, J=8 Hz, 1Hz), 8.17 (1H, d, J=2 Hz), 8.46 (1H, dd, J=4 Hz, 1Hz).

REFERENCE PREPARATION EXAMPLE 28

To a mixture of 2.0 g of 3-chloro-2-(1H-pyrazol-1-yl)pyridine and 100 ml of tetrahydrofuran was added dropwise 6.7 ml of a 2.0 mol/L lithium diisopropylamide solution in heptane/tetrahydrofuran/ethylbenzene at −78° C. The mixture was stirred at −78° C. for 10 minutes, poured into a mixture of dry ice and 50 ml of tetrahydrofuran, and stirred for 0.5 hour with allowing it to rise to around room temperature. After water and diethyl ether were added to the reaction mixture, the aqueous layer was adjusted to pH 10-12 by an addition of a 2N aqueous sodium hydroxide solution and layers were separated. After the aqueous layer was washed with diethyl ether two times, the aqueous layer was adjusted to around pH 3 by an addition of 2N hydrochloric acid, and the mixture was extracted with methyl tert-butyl ether three times. The organic layers were combined, washed with an aqueous saturated sodium chloride solution, dried over magnesium sulfate, and concentrated under reduced pressure to obtain 1.22 g of 1-(3-chloro-2-pyridinyl)-1H-pyrazole-5-carboxylic acid of the formula:

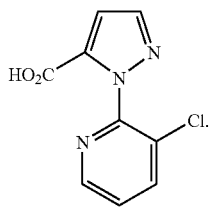

1-(3-Chloro-2-pyridinyl)-1H-pyrazole-5-carboxylic acid $^1$H-NMR (CDCl$_3$, TMS) δ (ppm): 7.10 (1H, d, J=2 Hz), 7.42 (1H, dd, J=8 Hz, 4 Hz), 7.82 (1H, d, J=2 Hz), 7.91 (1H, dd, J=8 Hz, 1Hz), 8.51 (1H, dd, J=4 Hz, 1Hz).

REFERENCE PREPARATION EXAMPLE 29

A mixture of 16.3 g of isatoic anhydride, 10.4 g of ethyl carbazate and 50 ml of ethanol was heated to reflux for 3 hours. After the reaction mixture was allowed to cool to around room temperature, ethyl acetate was added thereto and the mixture was washed with water two times. The organic layer was dried over anhydrous sodium sulfate and concentrated under reduced pressure. The resulting residue was washed with methyl tert-butyl ether to obtain 14.9 g of N-(2-aminobenzoyl)-N'-ethoxycarbonylhydrazine of the formula:

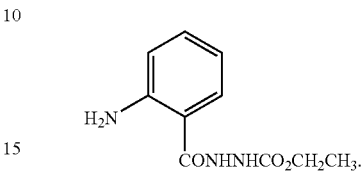

N-(2-aminobenzoyl)-N'-ethoxycarbonylhydrazine $^1$H-NMR (CDCl$_3$, TMS) δ (ppm): 1.28 (3H, t, J=8 Hz), 4.22 (2H, q, J=8 Hz), 5.45 (2H, brs), 6.63-6.68 (2H, m), 6.85 (1H, brs), 7.22 (1H, brs), 7.43 (1H, d, J=8 Hz), 7.95 (1H, brs).

REFERENCE PREPARATION EXAMPLE 30

A mixture of 8.86 g of N-methylisatoic anhydride, 5.73 g of ethyl carbazate and 25 ml of ethanol was heated to reflux for 2 hours. After the reaction mixture was allowed to around room temperature, ethyl acetate was added thereto and the mixture was washed with water two times. The organic layer was dried over anhydrous sodium sulfate, and concentrated under reduced pressure. The resulting residue was washed with methyl tert-butyl ether to obtain 5.99 g of N-(2-methylaminobenzoyl)-N'-ethoxycarbonylhydrazine of the formula:

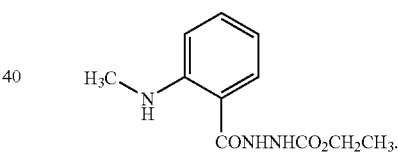

N-(2-methylaminobenzoyl)-N'-ethoxycarbonylhydrazine $^1$H-NMR (CDCl$_3$, TMS) δ (ppm): 1.28 (3H, t, J=7 Hz), 2.85 (3H, d, J=5 Hz), 4.21 (2H, q, J=7 Hz), 6.55-6.59 (1H, m), 6.66 (1H, d, J=8 Hz), 6.78 (1H, brs), 7.29-7.37 (2H, m), 7.43 (1H, dd, J=8 Hz, 1Hz), 7.91 (1H, brs).

REFERENCE PREPARATION EXAMPLE 31-(1)

A mixture of 1.0 g of 1-(3-chloro-2-pyridinyl)-3-trifluoromethyl-1H-pyrazole-5-carboxylic acid and 2 ml of thionyl chloride was heated to reflux for 2 hours. The reaction mixture was allowed to cool to room temperature, and concentrated under reduced pressure. The resulting residue was dissolved in 15 ml of acetonitrile, and 0.49 g of 2-amino-3,5-dimethylbenzoic acid was added thereto. The mixture was stirred at room temperature for 30 minutes. To the mixture, 0.7 ml of triethylamine was added, and the mixture was stirred at room temperature for 30 minutes. Further 1.4 ml of triethylamine was added, and the mixture was stirred at room temperature for 30 minutes. Then 0.5 ml of methanesulfonyl chloride was added, and the mixture was stirred at room temperature for 5 hours. Water was poured into the reaction mixture, and the mixture was concentrated under reduced pressure. The resulting residue was washed with water and methyl tert-butyl ether to obtain 0.71 g of 2-[1-(3-chloro-2-pyridinyl)-3-trifluoromethyl-1H-pyrazol-5-yl]-6,8-dimethyl-4H-3,1-benzoxazine-4-one of the formula:

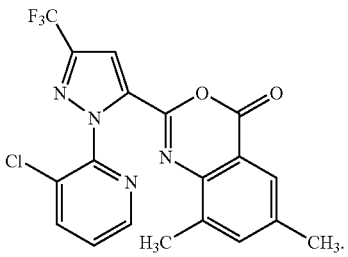

2-[1-(3-Chloro-2-pyridinyl)-3-trifluoromethyl-1H-pyrazole-5-yl]-6,8-dimethyl-4H-3,1-benzoxazine-4-one $^1$H-NMR (DMSO-d$_6$, TMS) δ (ppm): 1.72 (3H, s), 2.37 (3H, s), 7.54 (1H, s), 7.77 (1H, s), 7.78-7.85 (2H, m), 8.39 (1H, d, J=8 Hz), 8.66 (1H, d, J=4 Hz).

REFERENCE PREPARATION EXAMPLE 31-(2)

According to the same manner as that of Reference Preparation Example 1, 2-[1-(3-chloro-2-pyridinyl)-3-trifluoromethyl-1H-pyrazol-5-yl]-6,8-dimethyl-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[4,6-dimethyl-2-(hydrazinocarbonyl)phenyl]-1-(3-chloro-2-pyridinyl)-3-trifluoromethyl-1H-pyrazole-5-carboxamide of the formula:

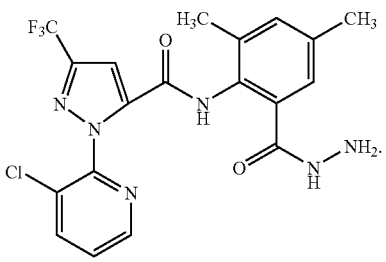

N-[4,6-dimethyl-2-(hydrazinocarbonyl)phenyl]-1-(3-chloro-2-pyridinyl)-3-trifluoromethyl-1H-pyrazole-5-carboxamide $^1$H-NMR (DMSO-d$_6$, TMS) δ (ppm): 2.11 (3H, s), 2.27 (3H, s), 4.34 (2H, brs), 7.11 (1H, s), 7.17 (1H, s), 7.66 (1H, dd, J=8 Hz, 4 Hz), 7.74 (1H, s), 8.21 (1H, d, J=8 Hz), 8.53 (1H, d, J=4 Hz), 9.37 (1H, brs), 10.26 (1H, brs).

REFERENCE PREPARATION EXAMPLE 32-(1)

According to the same manner as that of Reference Preparation Example 31-(1), 2amino-3-bromo-5-methylbenzoic acid was used in place of 2-amino-3,5-dimethylbenzoic acid to obtain 8-bromo-2-[1-(3-chloro-2-pyridinyl)-3-trifluoromethyl-1H-pyrazol-5-yl]-6-methyl-4H-3,1-benzoxazine-4-one of the formula:

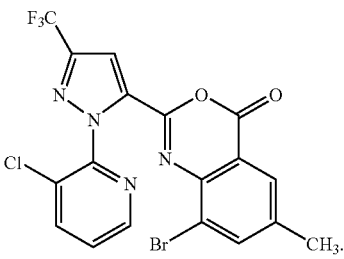

8-Bromo-2-[1-(3-chloro-2-pyridinyl)-3-trifluoromethyl-1H-pyrazol-5-yl]-6-methyl-4H-3,1-benzoxazine-4-one $^1$H-NMR (DMSO-d$_6$,TMS) δ (ppm): 2.41 (3H, s), 7.77 (1H, dd, J=8 Hz, 4 Hz), 7.87 (1H, s), 7.93 (1H, s), 7.98 (1H, s), 8.36 (1H, d, J=8 Hz), 8.63 (1H, d, J=4 Hz).

REFERENCE PREPARATION EXAMPLE 32-(2)

According to the same manner as that of Reference Preparation Example 1, 8-bromo-2-[1-(3-chloro-2-pyridinyl)-3-trifluoromethyl-1H-pyrazol-5-yl]-6-methyl-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[6-bromo-2-(hydrazinocarbonyl)-4-methylphenyl]-1-(3-chloro-2-pyridinyl)-3-trifluoromethyl-1H-pyrazole-5-carboxamide of the formula:

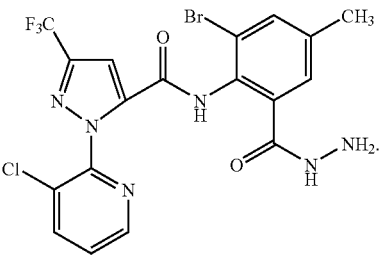

N-[6-bromo-2-(hydrazinocarbonyl)-4-methylphenyl]-1-(3-chloro-2-pyridinyl)-3-trifluoromethyl-1H-pyrazole-5-carboxamide $^1$H-NMR (DMSO-d$_6$, TMS) δ (ppm): 2.31 (3H, s), 4.33 (2H, brs), 7.24 (1H, s), 7.43 (1H, s), 7.57-7.65 (2H, m), 8.15 (1H, d, J=8 Hz), 8.49 (1H, d, J=4 Hz), 9.38 (1H, brs), 10.31 (1H, brs).

REFERENCE PREPARATION EXAMPLE 33-(1)

According to the same manner as that of Reference Preparation Example 31-(1), 2-amino-6-chlorobenzoic acid was used in place of 2-amino-3,5-dimethylbenzoic acid to obtain 5-chloro-2-[1-(3-chloro-2-pyridinyl)-3-trifluoromethyl-1H-pyrazol-5-yl]-4H-3,1-benzoxazine-4-one of the formula:

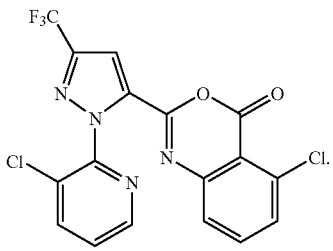

5-Chloro-2-[1-(3-chloro-2-pyridinyl)-3-trifluoromethyl-1H-pyrazole-5-yl]-4H-3,1-benzoxazine-4-one $^1$H-NMR (DMSO-d$_6$, TMS) δ (ppm): 6.91 (1H, d, J=8 Hz), 7.68 (1H, d, J=8 Hz), 7.77 (1H, t, J=8 Hz), 7.83 (1H, dd, J=8 Hz, 4 Hz), 7.91 (1H, s), 8.37 (1H, d, J=8 Hz), 8.64 (1H, d, J=4 Hz).

REFERENCE PREPARATION EXAMPLE 33-(2)

According to the same manner as that of Reference Preparation Example 1, 5-chloro-2-[1-(3-chloro-2-pyridinyl)-3-trifluoromethyl-1H-pyrazol-5-yl]-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[3-chloro-2-(hydrazinocarbonyl)phenyl]-1-(3-chloro-2-pyridinyl)-3-trifluoromethyl-1H-pyrazole-5-carboxamide of the formula:

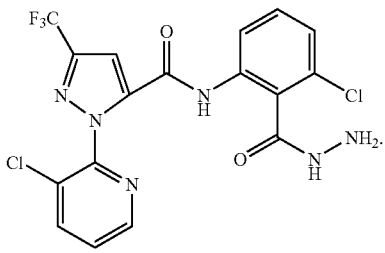

N-[3-chloro-2-(hydrazinocarbonyl)phenyl]-1-(3-chloro-2-pyridinyl)-3-trifluoromethyl-1H-pyrazole-5-carboxamide $^1$H-NMR (DMSO-d$_6$, TMS) δ (ppm): 4.47 (2H, brs), 7.32-7.50 (3H, m), 7.65-7.75 (2H, m), 8.25 (1H, d, J=8 Hz), 8.56 (1H, d, J=4 Hz), 9.58 (1H, brs), 10.29 (1H, brs).

REFERENCE PREPARATION EXAMPLE 34-(1)

According to the same manner as that of Reference Preparation Example 31-(1), 2-amino-5-chlorobenzoic acid was used in place of 2-amino-3,5-dimethylbenzoic acid to obtain 6-chloro-2-[1-(3-chloro-2-pyridinyl)-3-trifluoromethyl-1H-pyrazol-5-yl]-4H-3,1-benzoxazine-4-one of the formula:

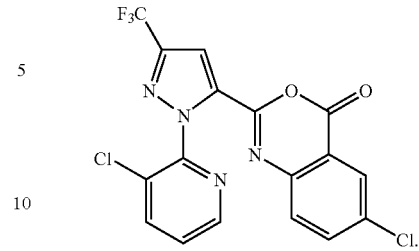

6-Chloro-2-[1-(3-chloro-2-pyridinyl)-3-trifluoromethyl-1H-pyrazol-5-yl]-4H-3,1-benzoxazine-4-one $^1$H-NMR (DMSO-d$_6$, TMS) δ (ppm): 7.02 (1H, d, J=8 Hz), 7.83 (1H, dd, J=8 Hz, 4 Hz), 7.87-7.92 (2H, m), 8.08 (1H, s), 8.37 (1H, d, J=8 Hz), 8.64 (1H, d, J=4 Hz).

REFERENCE PREPARATION EXAMPLE 34-(2)

According to the same manner as that of Reference Preparation Example 1, 6-chloro-2-[1-(3-chloro-2-pyridinyl)-3-trifluoromethyl-1H-pyrazol-5-yl]-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[4-chloro-2-(hydrazinocarbonyl)phenyl]-1-(3-chloro-2-pyridinyl)-3-trifluoromethyl-1H-pyrazole-5-carboxamide of the formula:

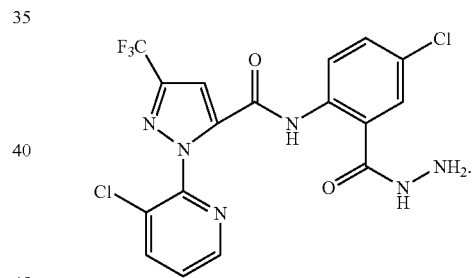

N-[4-chloro-2-(hydrazinocarbonyl)phenyl]-1-(3-chloro-2-pyridinyl)-3-trifluoromethyl-1H-pyrazole-5-carboxamide $^1$H-NMR (DMSO-d$_6$, TMS) δ (ppm): 7.52-7.56 (2H, m), 7.73 (1H, dd, J=8 Hz, 4 Hz), 7.85 (1H, s), 8.19 (1H, d, J=8 Hz), 8.29 (1H, d, J=8 Hz), 8.58 (1H, d, J=4 Hz), 10.30 (1H, brs), 12.52 (1H, brs)

REFERENCE PREPARATION EXAMPLE 35-(1)

According to the same manner as that of Reference Preparation Example 31-(1), 2-amino-3,5-dibromobenzoic acid was used in place of 2-amino-3,5-dimethylbenzoic acid to obtain 2-[1-(3-chloro-2-pyridinyl)-3-trifluoromethyl-1H-pyrazol-5-yl]-6,8-dibromo-4H-3,1-benzoxazine-4-one of the formula:

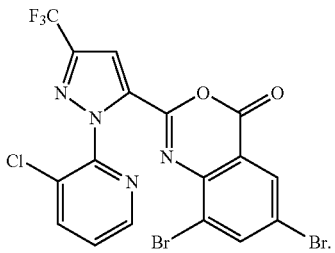

2-[1-(3-Chloro-2-pyridinyl)-3-trifluoromethyl-1H-pyrazol-5-yl]-6,8-dibromo-4H-3,1-benzoxazine-4-one $^1$H-NMR (DMSO-$d_6$, TMS) δ (ppm): 7.77 (1H, dd, J=8 Hz, 4 Hz), 7.94 (1H, s), 8.19-8.21 (1H, m), 8.35-8.39 (2H, m), 8.63 (1H, d, J=4 Hz).

REFERENCE PREPARATION EXAMPLE 35-(2)

According to the same manner as that of Reference Preparation Example 1, 2-[1-(3-chloro-2-pyridinyl)-3-trifluoromethyl-1H-pyrazol-5-yl]-6,8-dibromo-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[4,6-dibromo-2-(hydrazinocarbonyl)phenyl]-1-(3-chloro-2-pyridinyl)-3-trifluoromethyl-1H-pyrazole-5-carboxamide of the formula:

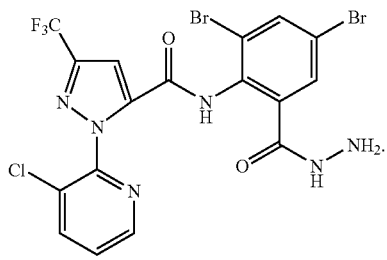

N-[4,6-dibromo-2-(hydrazinocarbonyl)phenyl]-1-(3-chloro-2-pyridinyl)-3-trifluoromethyl-1H-pyrazole-5-carboxamide $^1$H-NMR (DMSO-$d_6$, TMS) δ (ppm): 4.40 (2H, brs), 7.61 (1H, s), 7.66 (1H, dd, J=8 Hz, 4 Hz), 7.79 (1H, s), 8.08 (1H, s), 8.21 (1H, d, J=8 Hz), 8.54 (1H, d, J=4 Hz), 9.60 (1H, brs), 10.62 (1H, brs).

REFERENCE PREPARATION EXAMPLE 36-(1)

According to the same manner as that of Reference Preparation Example 31-(1), 2-amino-3,5-diiodobenzoic acid was used in place of 2-amino-3,5-dimethylbenzoic acid to obtain 2-[1-(3-chloro-2-pyridinyl)-3-trifluoromethyl-1H-pyrazol-5-yl]-6,8-diiodo-4H-3,1-benzoxazine-4-one of the formula:

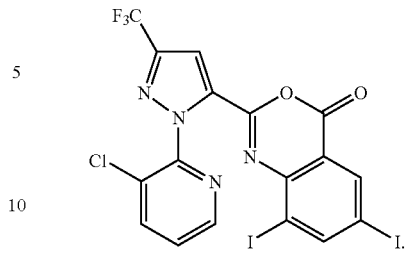

2-[1-(3-Chloro-2-pyridinyl)-3-trifluoromethyl-1H-pyrazol-5-yl]-6,8-diiodo-4H-3,1-benzoxazine-4-one $^1$H-NMR (DMSO-$d_6$, TMS) δ (ppm): 7.74 (1H, dd, J=8 Hz, 4 Hz), 7.89 (1H, s), 8.31-8.35 (2H, m), 8.59-8.63 (2H, m).

REFERENCE PREPARATION EXAMPLE 36-(2)

According to the same manner as that of Reference Preparation Example 1, 2-[1-(3-chloro-2-pyridinyl)-3-trifluoromethyl-1H-pyrazol-5-yl]-6,8-diiodo-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[4,6-diiodo-2-(hydrazinocarbonyl)phenyl]-1-(3-chloro-2-pyridinyl)-3-trifluoromethyl-1H-pyrazole-5-carboxamide of the formula:

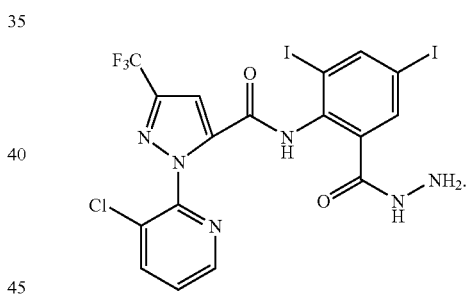

N-[4,6-diiodo-2-(hydrazinocarbonyl)phenyl]-1-(3-chloro-2-pyridinyl)-3-trifluoromethyl-1H-pyrazole-5-carboxamide $^1$H-NMR (DMSO-$d_6$, TMS) δ (ppm): 4.39 (2H, brs), 7.66 (1H, dd, J=8 Hz, 4 Hz), 7.71 (1H, s), 7.79 (1H, s), 8.20 (1H, d, J=8 Hz), 8.33 (1H, s), 8.53 (1H, d, J=4 Hz), 9.51 (1H, brs), 10.58 (1H, brs).

REFERENCE PREPARATION EXAMPLE 37-(1)

According to the same manner as that of Reference Preparation Example 31-(1), 2-amino-4-chlorobenzoic acid was used in place of 2-amino-3,5-dimethylbenzoic acid to obtain 7-chloro-2-[1-(3-chloro-2-pyridinyl)-3-trifluoromethyl-1H-pyrazol-5-yl]-4H-3,1-benzoxazine-4-one of the formula:

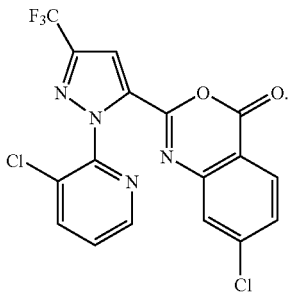

7-Chloro-2-[1-(3-chloro-2-pyridinyl)-3-trifluoromethyl-1H-pyrazol-5-yl]-4H-3,1-benzoxazine-4-one $^1$H-NMR (DMSO-d$_6$, TMS) δ (ppm): 7.02 (1H, s), 7.68 (1H, d, J=8 Hz), 7.84 (1H, dd, J=8 Hz, 4 Hz), 7.91 (1H, s), 8.10 (1H, d, J=8 Hz), 8.38 (1H, d, J=8 Hz), 8.64 (1H, d, J=4 Hz)

REFERENCE PREPARATION EXAMPLE 37-(2)

According to the same manner as that of Reference Preparation Example 1, 7-chloro-2-[1-(3-chloro-2-pyridinyl)-3-trifluoromethyl-1H-pyrazol-5-yl]-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[5-chloro-2-(hydrazinocarbonyl)phenyl]-1-(3-chloro-2-pyridinyl)-3-trifluoromethyl-1H-pyrazole-5-carboxamide of the formula:

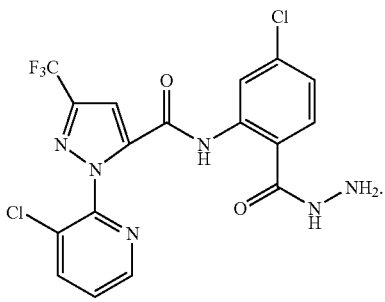

N-[5-chloro-2-(hydrazinocarbonyl)phenyl]-1-(3-chloro-2-pyridinyl)-3-trifluoromethyl-1H-pyrazole-5-carboxamide $^1$H-NMR (DMSO-d$_6$, TMS) δ (ppm): 7.31 (1H, d, J=8 Hz), 7.55 (1H, s), 7.75 (1H, dd, J=8 Hz, 4 Hz), 7.82 (1H, d, J=8 Hz), 8.27 (1H, s), 8.31 (1H, d, J=8 Hz), 8.59 (1H, d, J=4 Hz), 10.32 (1H, brs), 12.86 (1H, brs).

REFERENCE PREPARATION EXAMPLE 38-(1)

According to the same manner as that of Reference Preparation Example 31-(1), 2-amino-5-methylbenzoic acid was used in place of 2-amino-3,5-dimethylbenzoic acid to obtain 2-[1-(3-chloro-2-pyridinyl)-3-trifluoromethyl-1H-pyrazol-5-yl]-6-methyl-4H-3,1-benzoxazine-4-one of the formula:

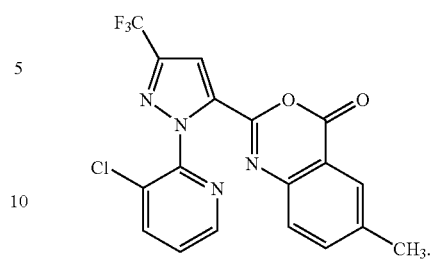

2-[1-(3-Chloro-2-pyridinyl)-3-trifluoromethyl-1H-pyrazole-5-yl]-6-methyl-4H-3,1-benzoxazine-4-one $^1$H-NMR (DMSO-d$_6$, TMS) δ (ppm): 2.43 (3H, s), 6.94 (1H, d, J=8 Hz), 7.69 (1H, d, J=8 Hz), 7.80-7.85 (2H, m), 7.92 (1H, s), 8.36 (1H, d, J=8 Hz), 8.63 (1H, d, J=4 Hz)

REFERENCE PREPARATION EXAMPLE 38-(2)

According to the same manner as that of Reference Preparation Example 1, 2-[1-(3-chloro-2-pyridinyl)-3-trifluoromethyl-1H-pyrazol-5-yl]-6-methyl-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[2-(hydrazinocarbonyl)-4-methylphenyl]-1-(3-chloro-2-pyridinyl)-3-trifluoromethyl-1H-pyrazole-5-carboxamide of the formula:

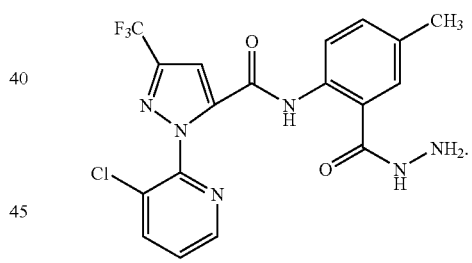

N-[2-(hydrazinocarbonyl)-4-methylphenyl]-1-(3-chloro-2-pyridinyl)-3-trifluoromethyl-1H-pyrazole-5-carboxamide $^1$H-NMR (DMSO-d$_6$, TMS) δ (ppm): 2.29 (3H, s), 4.71 (2H, brs), 7.29 (1H, d, J=8 Hz), 7.51-7.54 (1H, m), 7.61-7.63 (1H, m), 7.72-7.74 (1H, m), 8.07 (1H, d, J=8 Hz), 8.29 (1H, d, J=8 Hz), 8.56-8.59 (1H, m), 10.13 (1H, brs), 12.52 (1H, brs)

REFERENCE PREPARATION EXAMPLE 39-(1)

According to the same manner as that of Reference Preparation Example 31-(1), 2-amino-6-methylbenzoic acid was used in place of 2-amino-3,5-dimethylbenzoic acid to obtain 2-[1-(3-chloro-2-pyridinyl)-3-trifluoromethyl-1H-pyrazol-5-yl]-5-methyl-4H-3,1-benzoxazine-4-one of the formula:

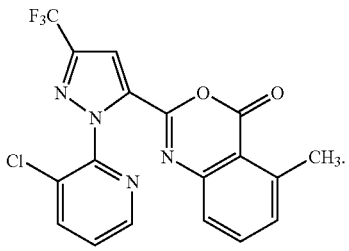

2-[1-(3-Chloro-2-pyridinyl)-3-trifluoromethyl-1H-pyrazole-5-yl]-5-methyl-4H-3,1-benzoxazine-4-one $^1$H-NMR (DMSO-$d_6$, TMS) δ (ppm): 2.68 (3H, s), 6.82 (1H, d, J=8 Hz) 7.44 (1H, d, J=8 Hz), 7.70 (1H, t, J=8 Hz), 7.82 (1H, dd, J=8 Hz, 4 Hz), 7.85 (1H, s), 8.36 (1H, d, J=8 Hz), 8.64 (1H, d, J=4 Hz).

REFERENCE PREPARATION EXAMPLE 39-(2)

According to the same manner as that of Reference Preparation Example 1, 2-[1-(3-chloro-2-pyridinyl)-3-trifluoromethyl-1H-pyrazol-5-yl]-5-methyl-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[2-(hydrazinocarbonyl)-3-methylphenyl]-1-(3-chloro-2-pyridinyl)-3-trifluoromethyl-1H-pyrazole-5-carboxamide of the formula:

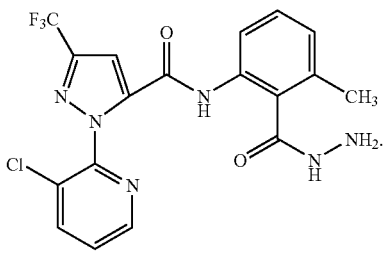

N-[2-(hydrazinocarbonyl)-3-methylphenyl]-1-(3-chloro-2-pyridinyl)-3-trifluoromethyl-1H-pyrazole-5-carboxamide $^1$H-NMR (DMSO-$d_6$, TMS) δ (ppm): 2.27 (3H, s), 4.48 (2H, brs), 7.11 (1H, d, J=8 Hz), 7.24-7.35 (2H, m), 7.65-7.72 (2H, m), 8.25 (1H, d, J=8 Hz), 8.55 (1H, d, J=4 Hz), 9.35 (1H, brs), 10.15 (1H, brs)

REFERENCE PREPARATION EXAMPLE 40-(1)

According to the same manner as that of Reference Preparation Example 31-(1), 2-amino-3,5-dichlorobenzoic acid was used in place of 2-amino-3,5-dimethylbenozoic acid to obtain 2-[1-(3-chloro-2-pyridinyl)-3-trifluoromethyl-1H-pyrazol-5-yl]-6,8-dichloro-4H-3,1-benzooxazine-4-one of the formula:

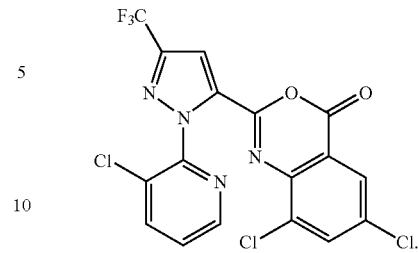

2-[1-(3-Chloro-2-pyridinyl)-3-trifluoromethyl-1H-pyrazole-5-yl]-6,8-dichloro-4H-3,1-benzooxazine-4-one $^1$H-NMR (DMSO-$d_6$, TMS) δ (ppm): 7.78 (1H, dd, J=8 Hz, 4 Hz), 7.95 (1H, s), 8.06 (1H, s), 8.14 (1H, s), 8.37 (1H, d, J=8 Hz), 8.63 (1H, d, J=4 Hz).

REFERENCE PREPARATION EXAMPLE 40-(2)

According to the same manner as that of Reference Preparation Example 1, 2-[1-(3-chloro-2-pyridinyl)-3-trifluoromethyl-1H-pyrazol-5-yl]-6,8-dichloro-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[4,6-dichloro-2-(hydrazinocarbonyl)phenyl]-1-(3-chloro-2-pyridinyl)-3-trifluoromethyl-1H-pyrazole-5-carboxamide of the formula:

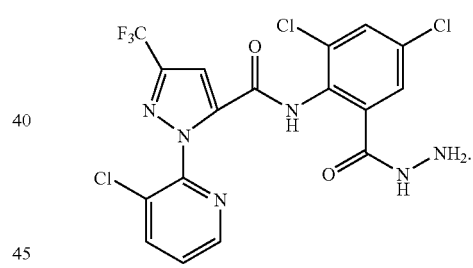

N-[4,6-dichloro-2-(hydrazinocarbonyl)phenyl]-1-(3-chloro-2-pyridinyl)-3-trifluoromethyl-1H-pyrazole-5-carboxamide $^1$H-NMR (DMSO-$d_6$, TMS) δ (ppm): 4.38 (2H, brs), 7.47 (1H, s), 7.66 (1H, dd, J=8 Hz, 4 Hz), 7.79 (1H, s), 7.86 (1H, s), 8.21 (1H, d, J=8 Hz), 8.53 (1H, d, J=4 Hz), 9.64 (1H, brs), 10.63 (1H, brs).

REFERENCE PREPARATION EXAMPLE 41-(1)

To a mixture of 1.7 g of 2-amino-5-chlorobenzoic acid and 100 ml of N,N-dimethylformamide was added 1.8 g of N-bromosuccinimide at room temperature, and the mixture was stirred at room temperature for 10 hours. Water was poured into the reaction mixture, and a deposited precipitate was collected by filtration to obtain 1.1 g of 2-amino-3-bromo-5-chlorobenzoic acid of the formula:

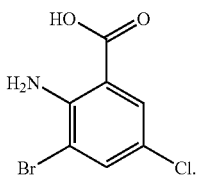

2-Amino-3-bromo-5-chlorobenzoic acid

¹H-NMR (DMSO-d₆, TMS) δ (ppm): 6.87 (2H, brs), 7.74 (1H, d, J=2 Hz), 7.76 (1H, d, J=2 Hz).

REFERENCE PREPARATION EXAMPLE 41-(2)

According to the same manner as that of Reference Preparation Example 31-(1), 2-amino-3-bromo-5-chlorobenzoic acid was used in place of 2-amino-3,5-dimethylbenzoic acid to obtain 8-bromo-6-chloro-2-[1-(3-chloro-2-pyridinyl)-3-trifluoromethyl-1H-pyrazol-5-yl]-4H-3,1-benzoxazine-4-one of the formula:

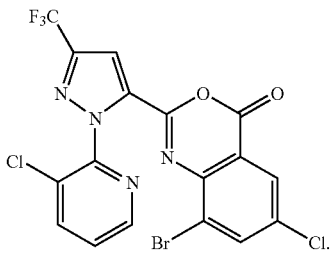

8-Bromo-6-chloro-2-[1-(3-chloro-2-pyridinyl)-3-trifluoromethyl-1H-pyrazol-5-yl]-4H-3,1-benzoxazine-4-one ¹H-NMR (DMSO-d₆, TMS) δ (ppm): 7.77 (1H, dd, J=8, 5 Hz), 7.94 (1H, s), 8.10 (1H, d, J=2 Hz), 8.27 (1H, d, J=2 Hz), 8.37 (1H, d, J=8 Hz), 8.63 (1H, d, J=4 Hz).

REFERENCE PREPARATION EXAMPLE 41-(3)

According to the same manner as that of Reference Preparation Example 1, 8-bromo-6-chloro-2-[1-(3-chloro-2-pyridinyl)-3-trifluoromethyl-1H-pyrazol-5-yl]-4H-3,1-benzoxazine-4-one was used in place of 6-chloro-2-[1-(3-chloro-2-pyridinyl)-3-trifluoromethyl-1H-pyrazol-5-yl]-8-methyl-4-H-3,1-benzoxazine-4-one to obtain N-[6-bromo-4-chloro-2-(hydrazinocarbonyl)phenyl]-1-(3-chloro-2-pyridinyl)-3-trifluoromethyl-1H-pyrazole-5-carboxamide of the formula:

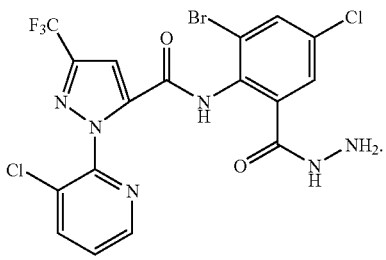

N-[6-bromo-4-chloro-2-(hydrazinocarbonyl)phenyl]-1-(3-chloro-2-pyridinyl)-3-trifluoromethyl-1H-pyrazole-5-carboxamide ¹H-NMR (DMSO-d₆, TMS) δ (ppm): 4.35 (2H, brs), 7.50 (1H, s), 7.66 (1H, dd, J=8 Hz, 4 Hz), 7.79 (1H, s), 7.98 (1H, s), 8.21 (1H, d, J=8 Hz), 8.53 (1H, d, J=4 Hz), 9.60 (1H, brs), 10.63 (1H, brs)

REFERENCE PREPARATION EXAMPLE 42-(1)

According to the same manner as that of Reference Preparation Example 31-(1), 2-amino-4-methylbenzoic acid was used in place of 2-amino-3,5-dimethylbenzoic acid to obtain 2-[1-(3-chloro-2-pyridinyl)-3-trifluoromethyl-1H-pyrazol-5-yl]-7-methyl-4H-3,1-benzoxazine-4-one of the formula:

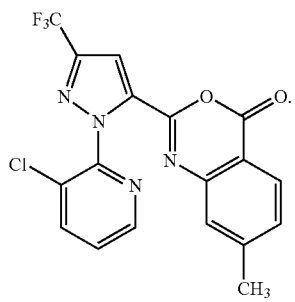

2-[1-(3-Chloro-2-pyridinyl)-3-trifluoromethyl-1H-pyrazole-5-yl]-7-methyl-4H-3,1-benzoxazine-4-one ¹H-NMR (DMSO-d₆, TMS) δ (ppm): 2.41 (3H, s), 6.84 (1H, s), 7.46 (1H, d, J=8 Hz), 7.82-7.85 (2H, m), 8.00 (1H, d, J=8 Hz), 8.37 (1H, d, J=8 Hz), 8.64 (1H, d, J=4 Hz).

REFERENCE PREPARATION EXAMPLE 42-(2)

According to the same manner as that of Reference Preparation Example 1, 2-[1(3-chloro -2-pyridinyl)-3 -trifluoromethyl-1 H-pyrazol-5-yl]-7-methyl-4H-3 , 1-benzoxazine-4-one was used in place of 6-chloro-2-[1-(3-chloro-2-pyridinyl)-3-trifluoromethyl-1H-pyrazol-5-yl]-8-methyl-4H-3 , 1-benzoxazine-4-one to obtain N[2-(hydrazinocarbonyl)-5 -methylphenyl]-1 -(3chloro -2-pyridinyl)-3-trifluoromethyl-1H-pyrazole-5carboxamide of the formula:

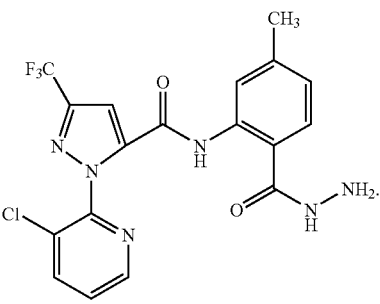

REFERENCE PREPARATION EXAMPLE 43-(1)

A mixture of 1.85 g of 2-amino-5-chloro-3-methylbenzoic acid, 0.90 g of triphosgene and 10 ml of tetrahydrofuran was stirred at room temperature for 5 hours. The reaction mixture was concentrated under reduced pressure, and a precipitated crystal was washed with water to obtain 1.20 g of 6-chloro-8-methyl-1H-benzo[d]-1,3-oxazine-2,4-dione of the formula:

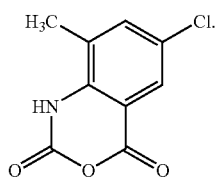

6-Chloro-8-methyl-1H-benzo[d]-1,3-oxazine-2,4-dione $^1$H-NMR (DMSO-d, TMS) δ (ppm): 2.33 (3H, s), 7.69 (1H, d, J=2 Hz), 7.73 (1H, d, J=2 Hz), 11.18 (1H, s).

REFERENCE PREPARATION EXAMPLE 43-(2)

A mixture of 1.05 g of 6-chloro-8-methyl-1H-benzo[d]-1,3-oxazine-2,4-dione, 0.46 g of methyl carbazate and 20 ml of methanol was heated to reflux for 3 hours. After the reaction mixture was allowed to cool to around room temperature, water was poured thereto and the mixture was extracted with ethyl acetate three times. The resulting organic layer was concentrated under reduced pressure, and the residue was washed with toluene to obtain 0.77 g of N-(2-amino-5-chloro-3-methylbenzoyl)-N'-methoxycarbonylhydrazine of the formula:

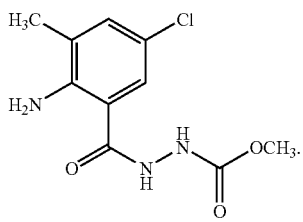

N-(2-amino-5-chloro-3-methylbenzoyl)-N'-ethoxycarbonylhydrazine $^1$H-NMR (DMSO-d$_6$, TMS) δ (ppm): 2.10 (3H, s), 3.63 (3H, s), 6.32 (2H, brs), 7.19 (1H, d, J=2 Hz), 7.45 (1H, d, J=2 Hz), 9.14 (1H, brs), 10.12 (1H, brs).

REFERENCE PREPARATION EXAMPLE 44-(1)

To a mixture of 1.9 g of 3-amino-2-naphthoic acid and 100 ml of N,N-dimethylformamide was added 1.3 g of N-chlorosuccinimde at room temperature, and the mixture was stirred at room temperature for 10 hours. After water was added to the reaction mixture, a deposited precipitate was collected by filtration to obtain 1.3 g of 3-amino-4-chloro-2-naphthoic acid of the formula:

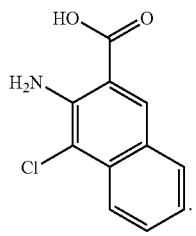

3-Amino-4-chloro-2-naphthoic acid $^1$H-NMR (DMSO-d$_6$, TMS) δ (ppm): 7.27-7.31 (1H, m), 7.60-7.64 (1H, m), 7.88 (1H, d, J=8 Hz), 7.93 (1H, d, J=8 Hz), 8.53 (1H, s).

REFERENCE PREPARATION EXAMPLE 44-(2)

According to the same manner as that of Reference Preparation Example 31-(1), 3-amino-4-chloro-2-naphthoic acid was used in place of 2-amino-3,5-dimethylbenzoic acid to obtain 10-chloro-2-[1-(3-chloro-2-pyridinyl)-3-trifluoromethyl-1H-pyrazol-5-yl]-4H-naphtho[2,3-d][1,3]oxazine-4-one of the formula:

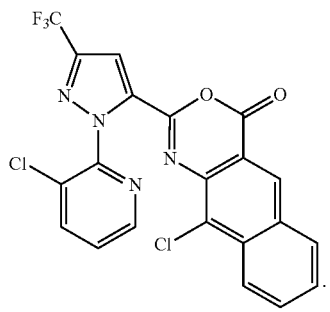

10-Chloro-2-[1-(3-chloro-2-pyridinyl)-3-trifluoromethyl-1H-pyrazole-5-yl]-4H-naphtho[2,3-d][1,3]oxazine-4-one $^1$H-NMR (DMSO-d$_6$, TMS) δ (ppm): 7.77 (1H, t, J=7 Hz), 7.84 (1H, dd, J=8 Hz, 4 Hz), 7.87-7.94 (2H, m), 8.24 (1H, d, J=8 Hz), 8.35 (1H, d, J=8 Hz), 8.42 (1H, d, J=8 Hz), 8.67 (1H, d, J=4 Hz), 8.91 (1H, s).

REFERENCE PREPARATION EXAMPLE 44-(3)

According to the same manner as that of Reference Preparation Example 1, 10-chloro-2-[1-(3-chloro-2-pyridinyl)-3-trifluoromethyl-1H-pyrazol-5-yl]-4H-naphtho[2,3-d][1,3]oxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[1-chloro-3-(hydrazinocarbonyl)-2naphthyl]-1-(3-chloro-2-pyridinyl)-3-trifluoromethyl-1H-pyrazole-5-carboxamide of the formula:

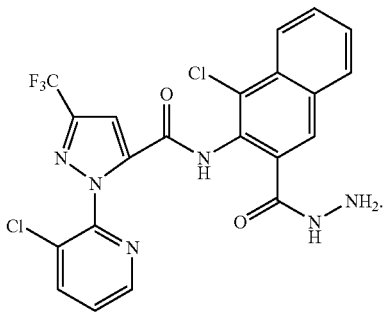

N-[1-chloro-3-(hydrazinocarbonyl)-2-naphthyl]-1-(3-chloro-2-pyridinyl)-3-trifluoromethyl-1H-pyrazole-5-carboxamide $^1$H-NMR (DMSO-d$_6$,TMS) δ (ppm): 4.39(2H, brs), 7.65 (1H, dd, J=8 Hz, 4 Hz), 7.70 (1H, t, J=8 Hz), 7.78 (1H, t, J=8 Hz), 7.86 (1H, s), 8.05-8.11 (2H, m), 8.18-8.24 (2H, m), 8.53 (1H, d, J=4 Hz), 9.70 (1H, brs), 10.77 (1H, brs).

REFERENCE PREPARATION EXAMPLE 45-(1)

According to the same manner as that of Reference Preparation Example 44-(1), N-bromosuccinimide was used in place of N-chlorosuccinimide to obtain 3-amino-4-bromo-2-naphthoic acid of the formula:

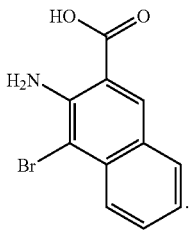

3-Amino-4-bromo-2-naphthoic acid $^1$H-NMR (DMSO-d$_6$, TMS) δ (ppm): 7.28 (1H, t, J=8 Hz), 7.61 (1H, t, J=8 Hz), 7.86 (1H, d, J=8 Hz), 7.92 (1H, d, J=8 Hz), 8.57 (1H, s)

REFERENCE PREPARATION EXAMPLE 45-(2)

According to the same manner as that of Reference Preparation Example 31-(1), 3-amino-4-bromo-2-naphthoic acid was used in place of 2-amino-3,5-dimethylbenzoic acid to obtain 10-bromo-2-[1-(3-chloro-2-pyridinyl)-3-trifluoromethyl-1H-pyrazol-5-yl]-4H-naphtho[2,3-d][1,3]oxazine-4-one of the formula:

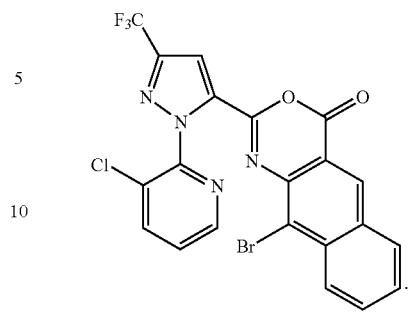

10-Bromo-2-[1-(3-chloro-2-pyridinyl)-3-trifluoromethyl-1H-pyrazol-5-yl]-4H-naphtho[2,3-d][1,3]oxazine-4-one $^1$H-NMR (DMSO-d$_6$, TMS) δ (ppm): 7.76 (1H, t, J=8 Hz), 7.82 (1H, dd, J=8 Hz, 4 Hz), 7.87-7.94 (2H, m), 8.24 (1H, d, J=8 Hz), 8.34 (1H, d, J=8 Hz), 8.42 (1H, d, J=8 Hz), 8.67 (1H, d, J=4 Hz), 8.95 (1H, s).

REFERENCE PREPARATION EXAMPLE 45-(3)

According to the same manner as that of Reference Preparation Example 1, 10-bromo-2-[1-(3-chloro-2-pyridinyl)-3-trifluoromethyl-1H-pyrazol-5-yl]-4H-naphtho[2, 3-d][1, 3]oxazine-4-one was used in place of 6-chloro-2-[1-(3-chloro-2-pyridinyl)-3-trifluoromethyl-1H-pyrazol-5-yl]-8-methyl-4H-3, 1-benzoxazine-4-one to obtain N-[1-bromo-3-(hydrazinocarbonyl)-2-naphthyl]-1-(3-chloro-2-pyridinyl)-3-trifluoromethyl-1H-pyrazole-5-carboxamide of the formula:

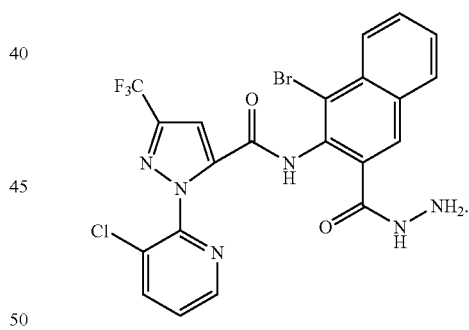

N-[1-bromo-3-(hydrazinolcarbonyl)-2-naphthyl]-1-(3-chloro-2-pyridinyl)-3-trifluoromethyl-1H-pyrazole-5-carboxamide $^1$H-NMR (DMSO-d$_6$,TMS) δ (ppm): 4.37 (2H, brs), 7.64 (1H, dd, J=8 Hz, 4 Hz), 7.70 (1H, d, J=8 Hz), 7.77 (1H, t, J=8 Hz), 7.87 (1H, s), 8.05-8.10 (2H, m), 8.17-8.24 (2H, m), 8.53 (1H, d, J=4 Hz), 9.66 (1H, brs), 10.80 (1H, brs).

REFERENCE PREPARATION EXAMPLE 46-(1)

A mixture of 11.0 g of 3-bromo-1-(3-chloro-2-pyridinyl)-1H-pyrazole-5-carboxylic acid and 2 ml of thionyl chloride was heated to reflux for 2 hours. The reaction mixture was allowed to cool to room temperature, and concentrated under reduced pressure. The resulting residue was dissolved in 15 ml of acetonitrile, and 0.88 g of 2-amino-3,5-dibromobenzoic acid was added. The mixture was stirred at room temperature for 30 minutes. To the mixture, 0.7 ml of triethylamine was added. After the mixture was stirred at room temperature for 30 minutes, 1.4 ml of triethylamine was further added. After the mixture was stirred at room temperature for 30 minutes, 0.5 ml of methanesulfonyl chloride was added, and the mixture was stirred at room temperature for 5 hours. Water was poured into the reaction mixture, and the mixture was concentrated under reduced pressure. The resulting residue was washed with water and methyl tert-butyl ether to obtain 0.80 g of 2-[3-bromo-1-(3-chloro-2-pyridinyl)-1H-pyrazol-5-yl]-6,8-dibromo-4H-3,1-benzoxazine-4-one of the formula:

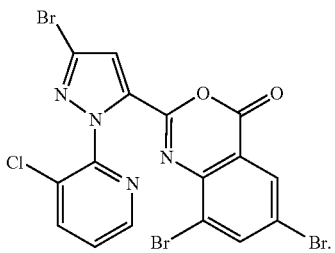

2-[3-Bromo-1-(3-chloro-2-pyridinyl)-1H-pyrazol-5-yl]-6,8-dibromo-4H-3,1-benzoxazine-4-one $^1$H-NMR (DMSO-$d_6$, TMS) δ (ppm): 7.56 (1H, s), 7.71 (1H, dd, J=8 Hz, 4 Hz), 8.18 (1H, d, J=2 Hz), 8.32 (1H, d, J=8 Hz), 8.35 (1H, d, J=2 Hz), 8.59 (1H, d, J=4 Hz).

REFERENCE PREPARATION EXAMPLE 47-(1)

According to the same manner as that of Reference Preparation Example 14, 2-chloropyridine was used in place of 2,3-dichloropyridine to obtain 2-(3-trifluoromethyl-1H-pyrazol-1-yl)pyridine of the formula:

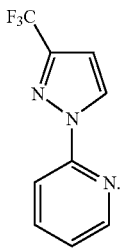

2-(3-Trifluoromethyl-1H-pyrazol-1-yl)pyridine $^1$H-NMR (CDCl$_3$, TMS) δ (ppm): 6.71 (1H, d, J=2 Hz), 7.27-7.28 (1H, m), 7.86 (1H, t, J=8 Hz), 8.04 (1H, d, J=8 Hz), 8.44 (1H, d, J=4 Hz), 8.63 (1H, d, J=2 Hz).

REFERENCE PREPARATION EXAMPLE 47-(2)

According to the same manner as that of Reference Preparation Example 15, 2-(3-trifluoromethyl-1H-pyrazol-1-yl)pyridine was used in place of 3-chloro-2-(3-trifluoromethyl-1H-pyrazol-1-yl)pyridine to obtain 1-(2-pyridinyl)-3-trifluoromethyl-1H-pyrazole-5-carboxylic acid of the formula:

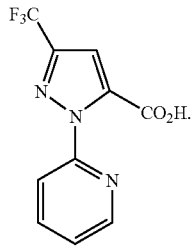

1-(2-Pyridinyl)-3-trifluoromethyl-1H-pyrazole-5-carboxylic acid $^1$H-NMR (DMSO-$d_6$) δ (ppm): 7.47 (1H, s), 7.59 (1H, dd, J=8 Hz, 5 Hz), 7.78 (1H, d, J=8 Hz), 8.09 (1H, t, J=8 Hz), 8.55 (1H, d, J=5 Hz).

REFERENCE PREPARATION EXAMPLE 47-(3)

According to the same manner as that of Reference Preparation Example 13, 1-(2-pyridinyl)-3-trifluoromethyl-1H-pyrazole-5-carboxylic acid was used in place of 1-(3-chloro-2-pyridinyl)-1H-pyrazole-5-carboxylic acid to obtain 6-chloro-2-[1-(2-pyridinyl)-3-trifluoromethyl-1H-pyrazol-5-yl]-8-methyl-4H-3,1-benzoxazine-4-one of the formula:

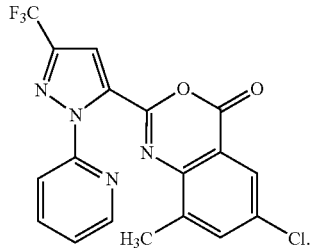

6-Chloro-2-[1-(2-pyridinyl)-3-trifluoromethyl-1H-pyrazol-5-yl]-8-methyl-4H-3,1-benzoxazine-4-one $^1$H-NMR (CDCl$_3$, TMS) δ (ppm): 2.15 (3H, s), 7.26 (1H, s), 7.42 (1H, dd, J=8 Hz, 4 Hz), 7.58 (1H, s), 7.79 (1H, d, J=8 Hz), 7.96-8.00 (2H, m), 8.43 (1H, d, J=4 Hz).

REFERENCE PREPARATION EXAMPLE 47-(4)

According to the same manner as that of Reference Preparation Example 1, 6-chloro-2-[1-(2-pyridinyl)-3-trifluoromethyl-1H-pyrazol-5-yl]-8-methyl-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[4-chloro-2-(hydrazinocarbonyl)-6-methylphenyl]-1-(2-pyridinyl)-3-trifluoromethyl-1H-pyrazole-5-carboxamide of the formula:

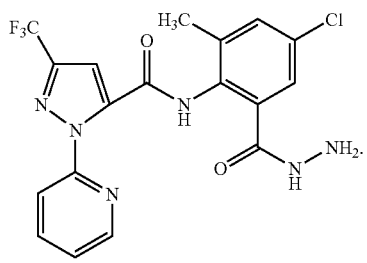

N-[4-chloro-2-(hydrazinocarbonyl)-6-methylphenyl]-1-(2-pyridinyl)-3-trifluoromethyl-1H-pyrazole-5-carboxamide $^1$H-NMR (DMSO-$d_6$, TMS) δ (ppm): 2.31 (3H, s), 4.44 (2H, s), 7.34-7.35 (2H, m), 7.50-7.55 (2H, m), 7.81 (1H, d, J=8 Hz), 8.07 (1H, t, J=8 Hz), 8.48 (1H, d, J=4 Hz), 9.55 (1H, brs), 10.39 (1H, brs).

REFERENCE PREPARATION EXAMPLE 48-(1)

According to the same manner as that of Reference Preparation Example 46-(1), 2-amino-3-bromo-5-chlorobenzoic acid was used in place of 2-amino-3,5-dibromobenzoic acid to obtain 8-bromo-2-[3-bromo-1-(3-chloro-2-pyridinyl)-1H-pyrazol-5-yl]-6-chloro-4H-3,1-benzoxazine-4-one of the formula:

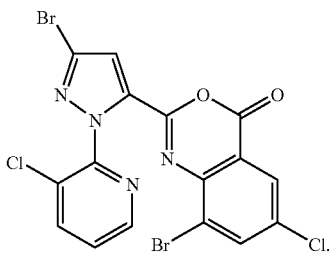

8-Bromo-2-[3-bromo-1-(3-chloro-2-pyridinyl)-1H-pyrazol-5-yl]-6-chloro-4H-3,1-benzoxazine-4-one $^1$H-NMR (DMSO-$d_6$, TMS) δ (ppm): 7.56 (1H, s), 7.72 (1H, dd, J=8 Hz, 4 Hz), 8.08 (1H, d, J=2 Hz), 8.25 (1H, d, J=2 Hz), 8.32 (1H, dd, J=8 Hz, 2 Hz), 8.59 (1H, dd, J=4 Hz, 2 Hz).

REFERENCE PREPARATION EXAMPLE 49-(1)

According to the same manner as that of Reference Preparation Example 46-(1), 2-amino-3-bromo-5-methylbenzoic acid was used in place of 2-amino-3,5-dibromobenzoic acid to obtain 8-bromo-2-[3-bromo-1-(3-chloro-2-pyridinyl)-1H-pyrazol-5-yl]-6-methyl-4H-3,1-benzoxazine-4-one of the formula:

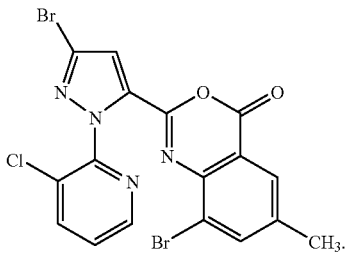

8-Bromo-2-[3-bromo-1-(3-chloro-2-pyridinyl)-1H-pyrazole-5-yl]-6-methyl-4H-3,1-benzoxazine-4-one $^1$H-NMR (DMSO-$d_6$, TMS) δ (ppm): 2.40 (3H, s), 7.50 (1H, s), 7.71 (1H, dd, J=8 Hz, 4 Hz), 7.91 (1H, s), 7.96 (1H, s), 8.31 (1H, d, J=8 Hz), 8.59 (1H, d, J=4 Hz).

REFERENCE PREPARATION EXAMPLE 50

According to the same manner as that of Reference Preparation Example 46-(1), 2-amino-3-chlorobenzoic acid was used in place of 2-amino-3,5-dibromobenzoic acid to obtain 2-[3-bromo-1-(3-chloro-2-pyridinyl)-1H-pyrazol-5-yl]-8-chloro-4H-3,1-benzoxazine-4-one of the formula:

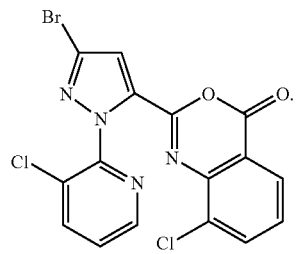

2-[3-Bromo-1-(3-chloro-2-pyridinyl)-1H-pyrazole-5-yl]-8-chloro-4H-3,1-benzoxazine-4-one $^1$H-NMR (DMSO-$d_6$, TMS) δ (ppm): 7.52-7.61 (2H, m), 7.73 (1H, dd, J=8 Hz, 4 Hz), 7.93 (1H, dd, J=8 Hz, 2 Hz), 8.04 (1H, dd, J=8 Hz, 2 Hz), 8.32 (1H, dd, J=8 Hz, 2 Hz), 8.60 (1H, dd, J=4 Hz, 2 Hz).

REFERENCE PREPARATION EXAMPLE 51-(1)

According to the same manner as that of Reference Preparation Example 24, phenylhydrazine was used in place of 2-chlorophenylhydrazine to obtain 5-(2-furyl)-1-phenyl-3-trifluoromethyl-1H-pyrazole of the formula:

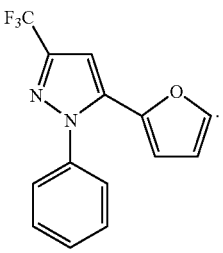

5-(2-Furyl)-1-phenyl-3-trifluoromethyl-1H-pyrazole $^1$H-NMR (CDCl$_3$, TMS) δ (ppm): 5.96 (1H, d, J=4 Hz), 6.33 (1H, dd, J=4 Hz, 2 Hz), 6.90 (1H, s), 7.43-7.48 (6H, m).

REFERENCE PREPARATION EXAMPLE 51-(2)

According to the same manner as that of Reference Preparation Example 25, 5-(2-furyl)-1-phenyl-3-trifluoromethyl-1H-pyrazole was used in place of 5-(2-furyl)-1-(2-chlorophenyl)-3-trifluoromethyl-1H-pyrazole to obtain 1-phenyl-3-trifluoromethyl-1H-pyrazole-5-carboxylic acid of the formula:

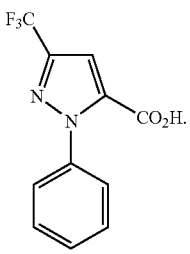

1-Phenyl-3-trifluoromethyl-1H-pyrazole-5-carboxylic acid $^1$H-NMR (CDCl$_3$, TMS) δ (ppm): 7.29 (1H, s), 7.46-7.51 (5H, m)

REFERENCE PREPARATION EXAMPLE 51-(3)

According to the same manner as that of Reference Preparation Example 13, 1-phenyl-3-trifluoromethyl-1H-pyrazole-5-carboxylic acid was used in place of 1-(3-chloro-2-pyridinyl)-1H-pyrazole-5-carboxylic acid to obtain 6-chloro-2-(1-phenyl-3-trifluoromethyl-1H-pyrazol-5-yl)-8-methyl-4H-3,1-benzoxazine-4-one of the formula:

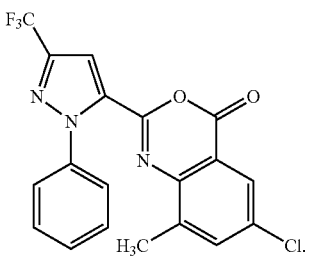

6-Chloro-2-(1-phenyl-3-trifluoromethyl-1H-pyrazol-5-yl)-8-methyl-4H-3,1-benzoxazine-4-one $^1$H-NMR (CDCl$_3$, TMS) δ (ppm): 1.88 (3H, s), 7.47-7.54 (7H, m), 7.99 (1H, d, J=2 Hz).

REFERENCE PREPARATION EXAMPLE 51-(4)

According to the same manner as that of Reference Preparation Example 1, 6-chloro-2-(1-phenyl-3-trifluoromethyl-1H-pyrazol-5-yl)-8-methyl-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[4-chloro-2-(hydrazinocarbonyl)-6-methylphenyl]-1-phenyl-3-trifluoromethyl-1H-pyrazole-5-carboxamide of the formula:

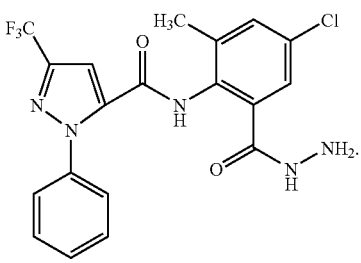

N-[4-chloro-2-(hydrazinocarbonyl)-6-methylphenyl]-1-phenyl-3-trifluoromethyl-1H-pyrazole-5-carboxamide $^1$H-NMR (DMSO-d$_6$, TMS) δ (ppm): 2.19 (3H, s), 4.41 (2H, brs), 7.32 (1H, d, J=2 Hz), 7.46-7.52 (5H, m), 7.56 (2H, d, J=7 Hz), 9.61 (1H, brs), 10.29 (1H, brs).

REFERENCE PREPARATION EXAMPLE 52-(1)

To a mixture of 1.5 g of 2-amino-5-chlorobenzoic acid and 100 ml of N,N-dimethylformamide was added 1.8 g of N-bromosuccinimide at room temperature, and the mixture was stirred at room temperature for 10 hours. After 30 ml of water was poured into the reaction mixture, the mixture was extracted with ethyl acetate three times. The organic layers were combined, washed with an aqueous saturated sodium chloride solution, dried over anhydrous magnesium sulfate, and concentrated under reduced pressure to obtain 1.2 g of 2-amino-5-bromo-3-methylbenzoic acid of the formula:

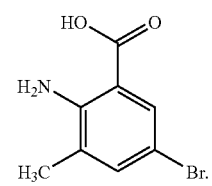

2-Amino-5-bromo-3-methylbenzoic acid $^1$H-NMR (DMSO-d$_6$, TMS) δ (ppm): 2.11 (3H, s), 7.33 (1H, d, J=2 Hz), 7.68 (1H, d, J=2 Hz).

REFERENCE PREPARATION EXAMPLE 52-(2)

According to the same manner as that of Reference Preparation Example 31-(1), 2-amino-5-bromo-3-methylbenzoic acid was used in place of 2-amino-3,5-dimethylbenzoic acid to obtain 6-bromo-2-[1-(3-chloro-2-pyridinyl)-3-trifluoromethyl-1H-pyrazol-5-yl]-8-methyl-4H-3,1-benzoxazine-4-one of the formula:

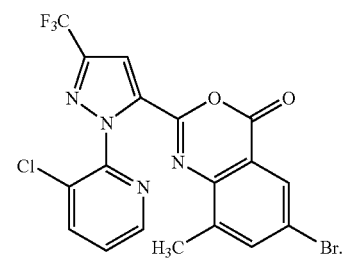

6-Bromo-2-[1-(3-chloro-2-pyridinyl)-3-trifluoromethyl-1H-pyrazol-5-yl]-8-methyl-4H-3,1-benzoxazine-4-one $^1$H-NMR (DMSO-d$_6$, TMS) δ (ppm): 1.73 3H, s), 7.81 (1H, dd, J=8 Hz, 4 Hz), 7.90 (1H, s), 7.93 (1H, s), 8.04 (1H, t, J=1 Hz), 8.39 (1H, d, J=8 Hz), 8.66 (1H, d, J=4 Hz).

REFERENCE PREPARATION EXAMPLE 53-(1)

To a mixture of 2.6 g of 2-amino-3-methylbenzoic acid and 100 ml of N,N-dimethylformamide was added 2.3 g of N-iodosuccinimide at room temperature, and the mixture was stirred at room temperature for 10 hours. After water was poured to the reaction mixture, a deposited precipitate was collected by filtration to obtain 1.7 g of 2-amino-5-iodo-3-methylbenzoic acid of the formula:

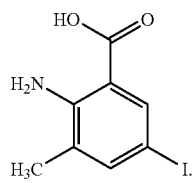

2-Amino-5-iodo-3-methylbenzoic acid $^1$H-NMR (DMSO-$d_6$, TMS) δ (ppm): 2.08 (3H, s), 7.44 (1H, d, J=1 Hz), 7.86 (1H, d, J=1 Hz)

REFERENCE PREPARATION EXAMPLE 53-(2)

According to the same manner as that of Reference Preparation Example 31-(1), 2-amino-5-iodo-3-methylbenzoic acid was used in place of 2-amino-3,5-dimethylbenzoic acid to obtain 2-[1-(3-chloro-2-pyridinyl)-3-trifluoromethyl-1H-pyrazol-5-yl]-6-iodo-8-methyl-4H-3,1-benzoxazine-4-one of the formula:

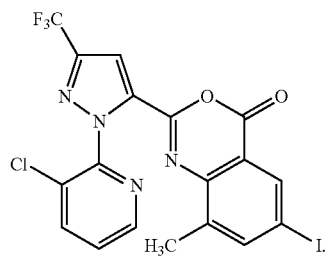

2-[1-(3-Chloro-2-pyridinyl)-3-trifluoromethyl-1H-pyrazol-5-yl]-6-iodo-8-methyl-4H-3,1-benzoxazine-4-one $^1$H-NMR (DMSO-$d_6$, TMS) δ (ppm): 1.70 (3H, s), 7.81 (1H, dd, J=8 Hz, 4 Hz), 7.89 (1H, s), 8.07 (1H, s), 8.19 (1H, s), 8.39 (1H, d, J=8 Hz), 8.66 (1H, d, J=4 Hz).

REFERENCE PREPARATION EXAMPLE 54-(1)

A mixture of 1.41 g of ethyl 2-(2-chlorobenzoyl)-3-(N,N-dimethylamino)acrylate (a compound described in JP-A 7-101940), 0.30 g of hydrazine monohydrate and 5 ml of acetic acid was stirred at room temperature for 10 hours. The reaction mixture was concentrated under reduced pressure. Water was poured into the residue, and the mixture was extracted with ethyl acetate. The organic layer was washed with water, dried over anhydrous sodium sulfate, and concentrated under reduced pressure to obtain ethyl 3-(2-chlorophenyl)-1H-pyrazole-4-carboxylate of the formula:

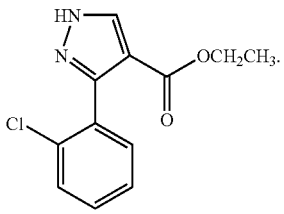

The resulting ethyl 3-(2-chlorophenyl)-1H-pyrazole-4-carboxylate, 1.07 g of methyl iodide, 1.04 g of potassium carbonate and 5 ml of N,N-dimethylformaide were mixed under ice-cooling, and the mixture was stirred at room temperature for 10 hours. Water was poured into the reaction mixture, and the mixture was extracted with ethyl acetate. The organic layer was washed with water, dried over anhydrous sodium sulfate, and concentrated under reduced pressure. The resulting residue was subjected to silica gel column chromatography to obtain 0.72 g of ethyl 3-(2-chlorophenyl)-1-methyl-1H-pyrazole-4-carboxylate of the formula:

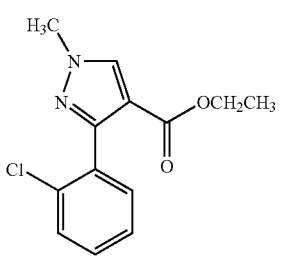

and 0.48 g of ethyl 5-(2-chlorophenyl)-1-methyl-1H-pyrazole-4-carboxylate.

Ethyl 3-(2-chlorophenyl)-1-methyl-1H-pyrazole-4-carboxylate $^1$H-NMR (CDCl$_3$) δ (ppm): 1.12 (3H, t, J=7 Hz), 3.68 (3H, s), 4.09-4.15 (2H, m), 7.31 (1H, dd, J=7 Hz, 2 Hz), 7.38 (1H, td, J=7 Hz, 1Hz), 7.44 (1H, td, J=8 Hz, 2 Hz), 7.52 (1H, dd, J=8 Hz, 1Hz), 8.01 (1H, s).

Ethyl 5-(2-chlorophenyl)-1-methyl-1H-pyrazole-4-carboxylate $^1$H-NMR (CDCl$_3$) δ (ppm): 1.13 (3H, t, J=7 Hz), 3.98 (3H, s), 4.14 (2H, q, J=7 Hz), 7.27-7.35 (2H, m), 7.38-7.41 (1H, m), 7.43-7.45 (1H, m), 7.96 (1H, s).

REFERENCE PREPARATION EXAMPLE 54-(2)

A mixture of 0.72 g of ethyl 3-(2-chlorophenyl)-1-methyl-1H-pyrazole-4-carboxylate, 0.23 g of potassium hydroxide, 1 ml of water and 5 ml of ethanol was stirred at room temperature for 3 days. After the reaction mixture was concentrated under reduced pressure, water was poured into the resulting residue and the mixture was washed with methyl tert-butyl ether. The aqueous layer was adjusted to around pH 3 by an addition of a 10% aqueous citric acid, and then extracted with ethyl acetate. The organic layer was washed with water, dried over anhydrous sodium sulfate, and concentrated under reduced pressure to obtain 0.61 g of 3-(2-chlorophenyl)-1-methyl-1H-pyrazole-4-carboxylic acid of the formula:

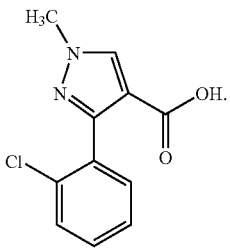

3-(2-Chlorophenyl)-1-methyl-1H-pyrazole-4-carboxylic acid $^1$H-NMR (CDCl$_3$) δ (ppm): 3.66 (3H, s), 7.30 (1H, dd, J=8 Hz, 2 Hz), 7.37 (1H, td, J=8 Hz, 1Hz), 7.43 (1H, td, J=8 Hz, 2 Hz), 7.51 (1H, dd, J=8 Hz, 1Hz), 8.02 (1H, s).

REFERENCE PREPARATION EXAMPLE 54-(3)

A mixture of 0.61 g of 3-(2-chlorophenyl)-1-methyl-1H-pyrazole-4-carboxylic acid, 0.28 ml of thionyl chloride and 10 ml of toluene was heated to reflux for 1 hour. After the reaction mixture was allowed to cool to room temperature, it was concentrated under reduced pressure and the resulting residue was dissolved in 10 ml of acetonitrile. Thereto 0.48 g of 2-amino-5-chloro-3-methylbenzoic acid was added, and the resulting mixture was stirred at room temperature for 30 minutes. To the mixture, 0.26 g of triethylamine was added, the mixture was stirred at room temperature for 30 minutes. Thereto 0.52 g of triethylamine was further added, and the resulting mixture was stirred at room temperature for 30 minutes. Then, 0.30 g of methanesulfonyl chloride was added to the reaction mixture under ice-cooling, and the mixture was stirred at room temperature for 10 hours. Water and ethyl acetate were poured into the reaction mixture, and 0.26 g of a solid was collected by filtration. In addition, the filtrate was separated into two layers. The organic layer was washed with water, dried over anhydrous sodium sulfate, and concentrated under reduced pressure. The resulting residue was washed with ethyl acetate to obtain 0.25 g of a solid. Both of these solids were 6-chloro-2-[3-(2-chlorophenyl)-1-methyl-1H-pyrazol-4-yl]-8-methyl-4H-3,1-benzoxazine-4-one of the formula:

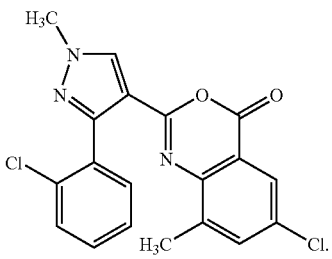

6-Chloro-2-[3-(2-chlorophenyl)-1-methyl-1H-pyrazol-4-yl]-8-methyl-4H-3,1-benzoxazine-4-one $^1$H-NMR (DMSO-d$_6$) δ (ppm): 1.86 (3H, s), 3.68 (3H, s), 7.52-7.63 (3H, m), 7.69-7.72 (2H, m), 7.81 (1H, d, J=2 Hz), 8.18 (1H, s)

REFERENCE PREPARATION EXAMPLE 54-(4)

After 0.19 g of 6-chloro -2-[3 -(2-chlorophenyl)-1-methyl-1H-pyrazol-4-yl]-8-methyl-4H-3,1-benzoxazine-4-one, 0.10 g of hydrazine monohydrate and 10 ml of N-methylpyrrolidinone were mixed under ice-cooling, the mixture was stirred at room temperature for 8 hours. Water was poured into the reaction mixture, and the mixture was extracted with ethyl acetate. The organic layer was washed with water, dried over anhydrous sodium sulfate, and concentrated under reduced pressure to obtain 0.18 g of N-[4-chloro-2-(hydrazinocarbonyl)-6-methylphenyl]-3-(2-chlorophenyl)-1-methyl-1H-pyrazole-4-carboxamide of the formula:

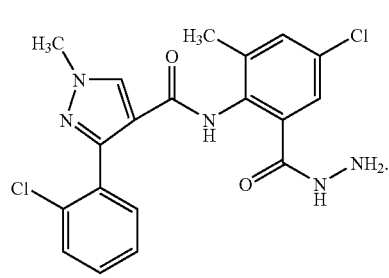

N-[4-chloro-2-(hydrazinocarbonyl)-6-methylphenyl]-3-(2-chlorophenyl)-1methyl -1H-pyrazole-4-carboxamide $^1$H-NMR (DMSO-d$_6$) δ (ppm): 2.13 (3H, s), 3.60 (3H, s), 4.39 (2H, brs), 7.29 (1H, d, J=2 Hz), 7.42-7.53 (4H, m), 7.60 (1H, d, J=8 Hz), 8.11 (1H, s), 9.53 (2H, brs).

REFERENCE PREPARATION EXAMPLE 55-(1)

According to the same manner as that of Reference Preparation Example 54-(2), ethyl 5-(2-chlorophenyl)-1-methyl-1H-pyrazole-4-carboxylate was used in place of ethyl 3-(2-chlorophenyl)-1-methyl-1H-pyrazole-4-carboxylate to obtain 5-(2-chlorophenyl)-1-methyl-1H-pyrazole-4-carboxylic acid of the formula:

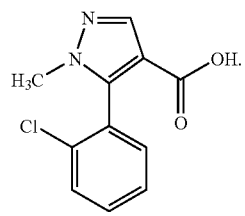

5-(2-Chlorophenyl)-1-methyl-1H-pyrazole-4-carboxylic acid $^1$H-NMR (CDCl$_3$) δ (ppm): 3.97 (3H, s), 7.26-7.35 (2H, m), 7.37-7.39 (1H, m), 7.42-7.44 (1H, m), 7.98 (1H, s).

REFERENCE PREPARATION EXAMPLE 55-(2)

According to the same manner as that of Reference Preparation Example 54-(3), 5-(2-chlorophenyl)-1-methyl-1H-pyrazole-4-carboxylic acid was used in place of 3-(2-chlorophenyl)-1-methyl-1H-pyrazole-4-carboxylic acid to obtain 6-chloro-2-[5-(2-chlorophenyl)-1-methyl-1H-pyrazol-4-yl]-8-methyl-4H-3,1-benzoxazine-4-one of the formula:

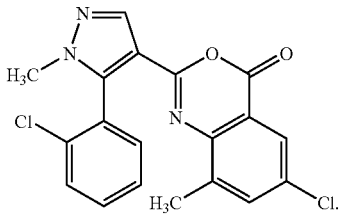

6-Chloro-2-[5-(2-chlorophenyl)-1-methyl-1H-pyrazol-4-yl]-8-methyl-4H-3,1-benzoxazine-4-one $^1$H-NMR (DMSO-d$_6$) δ (ppm): 1.90 (3H, s), 3.99 (3H, s), 7.40-7.50 (3H, m), 7.56 (1H, d, J=8 Hz), 7.71 (1H, d, J=2 Hz), 7.82 (1H, d, J=2 Hz), 8.63 (1H, s).

REFERENCE PREPARATION EXAMPLE 55-(3)

According to the same manner as that of Reference Preparation Example 54-(4), 6-chloro-2-[5-(2-chlorophenyl)-1-methyl-1H-pyrazol-4-yl]-8-methyl-4H-3,1-benzoxazine-4-one was used in place of 6-chloro-2-[3-(2-chlorophenyl)-1-methyl-1H-pyrazol-4-yl]-8-methyl-4H-3,1-benzoxazine-4-one to obtain N-[4-chloro-2-(hydrazinocarbonyl)-6-methylphenyl]-5-(2-chlorophenyl)-1-methyl-1H-pyrazole-4-carboxamide of the formula:

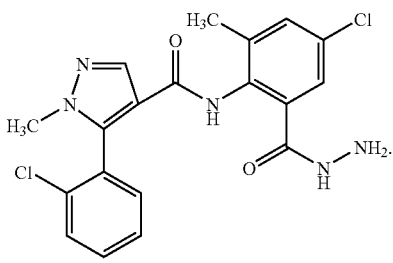

N-[4-chloro-2-(hydrazinocarbonyl)-6-methylphenyl]-5-(2-chlorophenyl)-1-methyl-1H-pyrazole-4-carboxamide $^1$H-NMR (DMSO-d$_6$) δ (ppm): 2.16 (3H, s), 3.94 (3H, s), 4.39 (2H, brs), 7.30 (1H, d, J=2 Hz), 7.33-7.46 (5H, m), 8.36 (1H, s), 9.49-9.59 (2H, brm).

REFERENCE PREPARATION EXAMPLE 56-(1)

To a mixture of 1.67 g of 2-amino-3-methoxybenzoic acid and 100 ml of N,N-dimethylformamide was added 1.3 g of N-chlorosuccinimide at room temperature, and the resulting mixture was stirred at room temperature for 10 hours. Water was poured into the reaction mixture, and a deposited precipitate was collected by filtration to obtain 1.2 g of 2-amino-5-chloro-3-methoxybenzoic acid.

2-Amino-5-chloro-3-methoxybenzoic acid $^1$H-NMR (DMSO-d$_6$, TMS) δ (ppm): 3.84 (3H, s), 6.99 (1H, s), 7.28 (1H, s).

REFERENCE PREPARATION EXAMPLE 56-(2)

According to the same manner as that of Reference Preparation Example 46-(1), 2-amino-5-chloro-3-methoxybenzoic acid was used in place of 2-amino-3,5-dibromobenzoic acid to obtain 2-[3-bromo-1-(3-chloro-2-pyridinyl)-1H-pyrazol-5-yl]-6-chloro-8-methoxy-4H-3,1-benzoxazine-4-one of the formula:

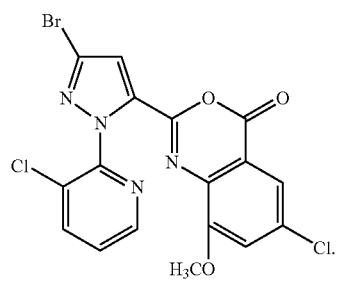

2-[3-Bromo-1-(3-chloro-2-pyridinyl)-1H-pyrazol-5-yl]-6-chloro-8-methoxy-4H-3,1-benzoxazine-4-one $^1$H-NMR (DMSO-d$_6$, TMS) δ (ppm): 3.71 (3H, s), 7.45 (1H, d, J=2 Hz), 7.48 (1H, s), 7.57 (1H, d, J=2 Hz), 7.78 (1H, dd, J=8 Hz, 4 Hz), 8.28 (1H, dd, J=8 Hz, 2 Hz), 8.57 (1H, dd, J=4 Hz, 2 Hz).

REFERENCE PREPARATION EXAMPLE 57-(1)

To a mixture of 1.5 g of 2-amino-5-chlorobenzoic acid and 100 ml of N,N-dimethylformamide was added 2.7 g of N-iodosuccinimide at room temperature, and the mixture was stirred at room temperature for 24 hours. After 30 ml of water was poured into the reaction mixture, the mixture was extracted with ethyl acetate three times. The organic layers were combined, washed with an aqueous saturated sodium chloride solution, dried over anhydrous magnesium sulfate, and concentrated under reduced pressure to obtain 1.2 g of 2-amino-5-chloro-3-iodobenzoic acid of the formula:

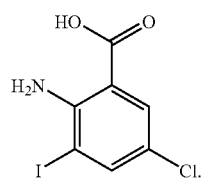

2-Amino-5-chloro-3-iodobenzoic acid

¹H-NMR (DMSO-d₆, TMS) δ (ppm): 6.76 (2H, brs), 7.75 (1H, d, J=1 Hz), 7.87 (1H, d, J=1 Hz).

REFERENCE PREPARATION EXAMPLE 57-(2)

According to the same manner as that of Reference Preparation Example 46-(1), 2amino-5-chloro-3-iodobenzoic acid was used in place of 2-amino-3,5-dibromobenzoic acid to obtain 2-[3-bromo-1-(3-chloro-2-pyridinyl)-1H-pyrazol-5-yl]-6-chloro-8-iodo-4H-3,1-benzoxazine-4-one of the formula:

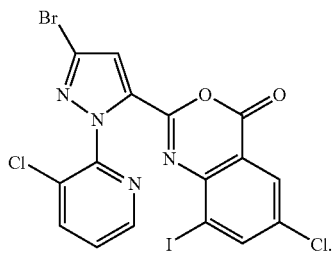

2-[3-Bromo-1-(3-chloro-2-pyridinyl)-1H-pyrazol-5-yl]6-chloro-8-iodo-4H-3,1-benzoxazine-4-one ¹H-NMR (DMSO-d₆,TMS) δ (ppm): 7.53 (1H, s), 7.69 (1H, dd, J=8 Hz, 4 Hz), 8.08 (1H, d, J=2 Hz), 8.29 (1H, d, J=8 Hz), 8.38 (1H, d, J=2 Hz), 8.57 (1H, d, J=4 Hz).

REFERENCE PREPARATION EXAMPLE 58

According to the same manner as that of Reference Preparation Example 46-(1), 2-amino-3-methoxybenzoic acid was used in place of 2-amino-3,5-dibromobenzoic acid to obtain 2-[3-bromo-1-(3-chloro-2-pyridinyl)-1H-pyrazol-5-yl]-8-methoxy-4H-3,1-benzoxazine-4-one of the formula:

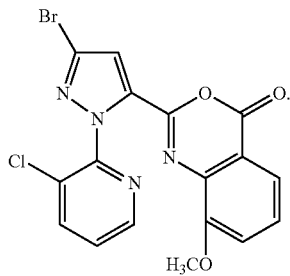

2-[3-Bromo-1-(3-chloro-2-pyridinyl)-1H-pyrazol-5-yl]-8-methoxy-4H-3,1-benzoxazine-4-one ¹H-NMR (DMSO-d₆, TMS) δ (ppm): 3.67 (3H, s), 7.40 (1H, dd, J=8 Hz, 1Hz), 7.46 (1H, s), 7.52 (1H, t, J=8 Hz), 7.61 (1H, dd, J=8 Hz, 1Hz), 7.78 (1H, dd, J=8 Hz, 4 Hz), 8.28 (1H, dd, J=8 Hz, 1Hz), 8.57 (1H, dd, J=4 Hz, 1Hz).

REFERENCE PREPARATION EXAMPLE 59

According to the same manner as that of Reference Preparation Example 46-(1), 2-amino-3-trifluoromethylbenzoic acid was used in place of 2-amino-3,5-dibromobenzoic acid to obtain 2-[3-bromo-1-(3-chloro-2-pyridinyl)-1H-pyrazol-5-yl]-8-trifluoromethyl-4H-3,1-benzoxazine-4-one of the formula:

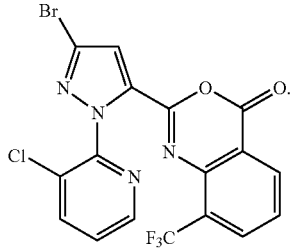

2-[3-Bromo-1-(3-chloro-2-pyridinyl)-1H-pyrazol-5-yl]-8-trifluoromethyl-4H-3,1-benzoxazine-4-one ¹H-NMR (DMSO-d₆, TMS) δ (ppm): 7.56 (1H, s), 7.69-7.77 (2H, m) 8.15 (1H, d, J=8 Hz), 8.29 (1H, dd, J=8 Hz, 1Hz), 8.37 (1H, d, J=8 Hz), 8.55 (1H, dd, J=4 Hz, 1Hz).

REFERENCE PREPARATION EXAMPLE 60-(1)

To a solution of 4.8 g of hydrazine monohydrate in 160 ml of ethanol, 14.2 g of ethyl trifluoroacetate was added dropwise. The resulting mixture was stirred at room temperature for 1 hour. The reaction mixture was concentrated under reduced pressure. The resulting residue was dissolved in 100 ml of ethanol, and 9.9 g of formamidine acetate was added thereto. The mixture was stirred for 3 hours under heat refluxing. The reaction mixture was allowed to cool to room temperature, and then concentrated under reduced pressure. An aqueous sodium bicarbonate solution was poured into the resulting residue, and the mixture was extracted with ethyl acetate two times. The organic layers were combined, washed successively with water and an aqueous saturated sodium chloride solution, dried over magnesium sulfate, and concentrated under reduced pressure. The resulting residue was subjected to silica gel column chromatography to obtain 7.0 g of 3-trifluoromethyl-1H-1,2,4-triazole of the formula:

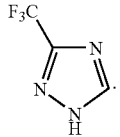

3-Trifluoromethyl-1H-1,2,4-triazole

¹H-NMR (CDCl₃, TMS) δ (ppm): 8.48 (1H, s).

REFERENCE PREPARATION EXAMPLE 60-(2)

A mixture of 3.5 g of 3-trifluoromethyl-1H-1,2,4-triazole, 3.8 g of 2,3-dichloropyridine, 6.0 g of potassium carbonate and 30 ml of N,N-dimethylformamide was stirred at 120° C. for 27 hours. After the reaction mixture was allowed to cool to room temperature, water was poured and the mixture was extracted with ethyl acetate two times. The organic layers were combined, washed successively with water and an aqueous saturated sodium chloride solution, dried over magnesium sulfate, and concentrated under reduced pressure. The resulting residue was subjected to silica gel column chromatography to obtain 0.72 g of 3-chloro-2-(3-trifluoromethyl-1H-1,2,4-triazol-1-yl)pyridine of the formula:

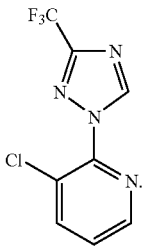

3-Chloro-2-(3-trifluoromethyl-1H-1,2,4-triazol-1-yl)pyridine $^1$H-NMR (DMSO-$d_6$) δ (ppm): 7.47 (1H, dd, J=8 Hz, 5 Hz), 8.01 (1H, dd, J=8 Hz, 2 Hz), 8.53 (1H, dd, J=5 Hz, 2 Hz), 8.82 (1H, s).

REFERENCE PREPARATION EXAMPLE 61-(1)

According to the same manner as that of Reference Preparation Example 17, ethylhydrazine was used in place of methylhydrazine to obtain 1-ethyl-3-trifluoromethyl-1H-pyrazole of the formula:

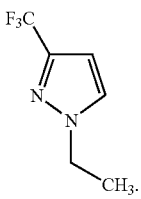

1-Ethyl-3-trifluoromethyl-1H-pyrazole $^1$H-NMR (CDCl$_3$, TMS) δ (ppm): 1.52 (3H, t, J=7 Hz), 4.23 (2H, q, J=7 Hz), 6.51 (1H, d, J=2 Hz), 7.44 (1H, d, J=2 Hz).

REFERENCE PREPARATION EXAMPLE 61-(2)

According to the same manner as that of Reference Preparation Example 18, 1-ethyl-3-trifluoromethyl-1H-pyrazole was used in place of 1-methyl-3-trifluormethyl-1H-pyrazole to obtain 1-ethyl-3-trifluoromethyl-1H-pyrazole-5-carboxylic acid of the formula:

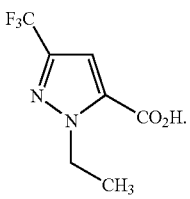

1-Ethyl-3-trifluoromethyl-1H-pyrazole-5-carboxylic acid $^1$H-NMR (CDCl$_3$, TMS) δ (ppm): 1.51 (3H, t, J=7 Hz), 4.68 (2H, q, J=7 Hz), 7.21 (1H, s).

REFERENCE PREPARATION EXAMPLE 61-(3)

According to the same manner as that of Reference Preparation Example 13, 1-ethyl-3-trifluoromethyl-1H-pyrazole-5-carboxylic acid was used in place of 1-(3-chloro-2-pyridinyl)-1H-pyrazole-5-carboxylic acid to obtain 6-chloro-2-(1-ethyl-3-trifluoromethyl-1H-pyrazol-5-yl)-8-methyl-4H-3,1-benzoxazine-4-one of the formula:

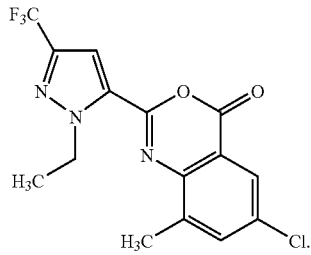

6-Chloro-2-(1-ethyl-3-trifluoromethyl-1H-pyrazol-5-yl)-8-methyl-4H-3,1-benzoxazine-4-one $^1$H-NMR (CDCl$_3$, TMS) δ (ppm): 1.58 (3H, t, J=7 Hz), 2.59 (3H, s), 4.89 (2H, q, J=7 Hz), 7.33 (1H, s), 7.69 (1H, d, J=2 Hz), 8.07 (1H, d, J=2 Hz).

REFERENCE PREPARATION EXAMPLE 61-(4)

According to the same manner as that of Reference Preparation Example 1, 6-chloro-2-(1-ethyl-3 -trifluoromethyl-1H-pyrazol-5-yl)-8-methyl-4H-3, 1 -benzoxazine-4-one was used in place of 6-chloro-2-[1-(3-chloro-2-pyridinyl)-3 - trifluoromethyl-1 H-pyrazol-5 -yl]-8-methyl-4H-3,1-benzoxazine-4-one to obtain N-[4-chloro-2-(hydrazinocarbonyl)-6-methylphenyl]-1-ethyl-3-trifluoromethyl-1H-pyrazole-5-carboxamide of the formula:

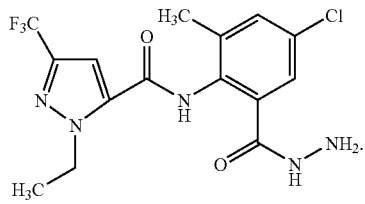

N-[4-chloro-2-(hydrazinocarbonyl)-6-methylphenyl]-1-ethyl-3-trifluoromethyl-1H-pyrazole-5-carboxamide $^1$H-NMR (CDCl$_3$, TMS) δ (ppm): 1.48 (3H, t, J=7 Hz), 2.30 (3H, s), 4.04 (2H, s), 4.66 (2H, q, J=7 Hz), 7.08 (1H, s), 7.29 (1H, s), 7.40 (1H, s), 7.45 (1H, brs), 9.81 (1H, brs).

REFERENCE PREPARATION EXAMPLE 62-(1)

A mixture of 2.82 g of ethyl 2-(2-chlorobenzoyl)-3-(N,N-dimethylamino)acrylate (a compound described in JP-A 7-101940), 1.25 g of tert-butylhydrazine hydrochloride and 10 ml of ethanol was heated to reflux for 8 hours. After the reaction mixture was allowed to cool to room temperature, water was poured and the mixture was extracted with ethyl acetate. The organic layer was washed with water, dried over anhydrous sodium sulfate, and concentrated under reduced pressure. The resulting residue was subjected to silica gel column chromatography to obtain 0.48 g of ethyl 1-tert-butyl-5-(2-chlorophenyl)-1H-pyrazole-4-carboxylate of the formula:

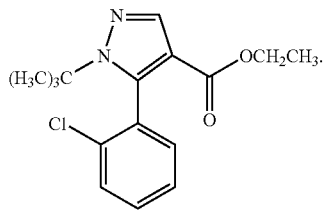

Ethyl 1-tert-butyl-5-(2-chlorophenyl)-1H-pyrazole-4-carboxylate $^1$H-NMR (CDCl$_3$) δ (ppm): 1.04 (3H, t, J=7 Hz), 1.47 (9H, s), 3.98-4.12 (2H, m), 7.28-7.35 (2H, m), 7.38-7.42 (1H, m), 7.45-7.48 (1H, m), 7.99 (1H, s).

REFERENCE PREPARATION EXAMPLE 62-(2)

According to the same manner as that of Reference Preparation Example 54-(2), ethyl 1-tert-butyl-5-(2-chlorophenyl)-1H-pyrazole-4-carboxylate was used in place of ethyl 3-(2-chlorophenyl)-1-methyl-1H-pyrazole-4-carboxylate to obtain 1-tert-butyl-5-(2-chlorophenyl)-1H-pyrazole-4-carboxylic acid of the formula:

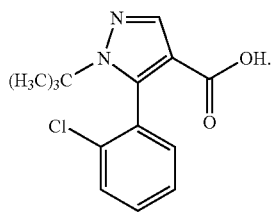

1-tert-Butyl-5-(2-chlorophenyl)-1H-pyrazole-4-carboxylic acid $^1$H-NMR (CDCl$_3$) δ (ppm): 1.45 (9H, s), 7.25-7.33 (2H, m), 7.39 (1H, td, J=7 Hz, 2 Hz), 7.44 (1H, dd, J=8 Hz, 1Hz), 8.00 (1H, s)

REFERENCE PREPARATION EXAMPLE 62-(3)

According to the same manner as that of Reference Preparation Example 54-(3), 1-tert-butyl-5-(2-chlorophenyl)-1H-pyrazole-4-carboxylic acid was used in place of 3-(2-chlorophenyl)-1-methyl-1H-pyrazole-4-carboxylic acid to obtain 2-[1-tert-butyl-5-(2-chlorophenyl)-1H-pyrazol-4-yl]-6-chloro-8-methyl-4H-3,1-benzoxazine-4-one of the formula:

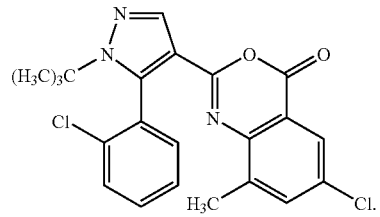

2-[1-tert-Butyl-5-(2-chlorophenyl)-1H-pyrazole-4-yl]-6-chloro-8-methyl-4H-3,1-benzoxazine-4-one $^1$H-NMR (DMSO-d$_6$) δ (ppm): 1.44 (9H, s), 1.77 (3H, s), 7.47-7.59 (3H, m), 7.65-7.68 (2H, m), 7.80 (1H, d, J=2 Hz), 8.18 (1H, s)

REFERENCE PREPARATION EXAMPLE 62-(4)

According to the same manner as that of Reference Preparation Example 54-(4), 2-[1-tert-butyl-5-(2-chlorophenyl)-1H-pyrazol-4-yl]-6-chloro-8-methyl-4H-3,1-benzoxazine-4-one was used in place of 6-chloro-2-[3-(2-chlorophenyl)-1-methyl-1H-pyrazol-4-yl]-8-methyl-4H-3,1-benzoxazine-4-one to obtain 1-tert-butyl-N-[4-chloro-2-(hydrazinocarbonyl)-6-methylphenyl]-5-(2-chlorophenyl)-1H-pyrazole-4-carboxamide of the formula:

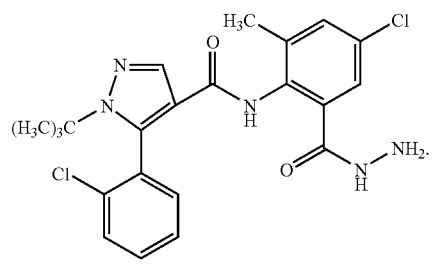

1-tert-Butyl-N-[4-chloro-2-(hydrazinocarbonyl)-6-methylphenyl]-5-(2-chlorophenyl)-1H-pyrazole-4-carboxamide $^1$H-NMR (DMSO-d$_6$) δ (ppm): 1.40 (9H, s), 2.06 (3H, s), 4.37 (2H, brs), 7.28 (1H, d, J=2 Hz), 7.38-7.53 (5H, m), 8.10 (1H, s), 9.36 (1H, brs), 9.53 (1H, brs).

REFERENCE PREPARATION EXAMPLE 63-(1)

A mixture of 4.62 g of chloral hydrate, 3.5 g of 3-chloro-2-methylaniline, 30 g of anhydrous sodium sulfate, 120 ml of water and 2 ml of 2N hydrochloric acid was stirred at room temperature for 2 hours. Then, to the resulting mixture, 1.8 g of hydroxylamine hydrochloride was added, and the mixture was heated to reflux for 30 minutes. The reaction mixture was ice-cooled, and a deposited precipitate was collected by filtration to obtain 2.5 g of N-(3-chloro-2-methylphenyl)-2-(hydroxyimino)acetamide of the formula:

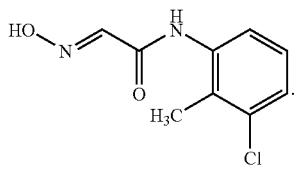

N-(3-chloro-2-methylphenyl)-2-(hydroxyimino)acetamide $^1$H-NMR (DMSO-d$_6$, TMS) δ (ppm): 2.22 (3H, s), 7.22 (1H, t, J=8 Hz), 7.33 (1H, d, J=8 Hz), 7.38 (1H, d, J=8 Hz), 7.67 (1H, s), 9.78 (1H, brs), 12.21 (1H, s).

REFERENCE PREPARATION EXAMPLE 63-(2)

To 2.5 g of concentrated sulfuric acid was added 2.5 g of N-(3-chloro-2-methylphenyl)-2-(hydroxyimino)acetamide at 50° C., and the mixture was stirred at 80° C. for 30 minutes. The reaction mixture was poured into 200 g of ice, and a deposited precipitate was collected by filtration to obtain 1.3 g of 6-chloro-7-methyl-1H-indole-2,3-dione of the formula:

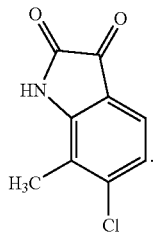

6-Chloro-7-methyl-1H-indole-2,3-dione $^1$H-NMR (DMSO-d$_6$, TMS) δ (ppm): 2.22 (3H, s), 7.15 (1H, d, J=8 Hz), 7.37 (1H, d, J=8 Hz), 11.28 (1H, s).

REFERENCE PREPARATION EXAMPLE 63-(3)

A mixed solution of 1.3 g of 6-chloro-7-methyl-1H-indole-2,3-dione and 50 ml of a 2N aqueous sodium hydroxide solution was added dropwise to 2 g of aqueous hydrogen peroxide (30%), and the mixture was stirred at room temperature for 1 hour. The reaction mixture was adjusted to pH 4 by an addition of 2N hydrochloric acid, and a deposited precipitate was collected by filtration to obtain 0.6 g of 2-amino-4-chloro-3-methylbenzoic acid of the formula:

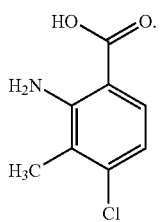

2-Amino-4-chloro-3-methylbenzoic acid $^1$H-NMR (DMSO-d$_6$, TMS) δ (ppm): 2.18 (3H, s), 6.62 (1H, d, J=9 Hz) 7.61 (1H, d, J=9 Hz).

REFERENCE PREPARATION EXAMPLE 63-(4)

According to the same manner as that of Reference Preparation Example 46-(1), 2-amino-4-chloro-3-methylbenzoic acid was used in place of 2-amino-3,5-dibromobenzoic acid to obtain 2-[3-bromo-1-(3-chloro-2-pyridinyl)-1H-pyrazol-5-yl]-7-chloro-8-methyl-4H-3,1-benzoxazine-4-one of the formula:

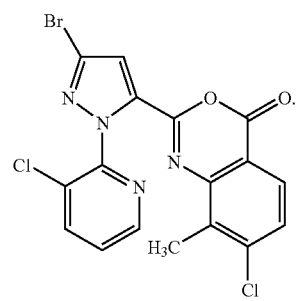

2-[2-Bromo-1-(3-chloro-2-pyridinyl)-1H-pyrazol-5-yl]-7-chloro-8-methyl-4H-3,1-benzoxazine-4-one $^1$H-NMR (DMSO-d$_6$, TMS) δ (ppm): 1.76 (3H, s), 7.55 (1H, s), 7.65 (1H, d, J=9 Hz), 7.77 (1H, dd, J=8 Hz, 4 Hz), 7.94 (1H, d, J=9 Hz), 8.35 (1H, dd, J=8 Hz, 1Hz), 8.64 (1H, dd, J=4 Hz, 1Hz).

REFERENCE PREPARATION EXAMPLE 64-(1)

According to the same manner as that of Reference Preparation Example 14, isopropyl iodide was used in place of 2,3-dichloropyridine to obtain 1-isopropyl-3-trifluoromethyl-1H-pyrazole of the formula:

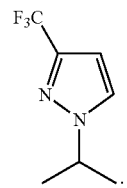

1-Isopropyl-3-trifluoromethyl-1H-pyrazole $^1$H-NMR (CDCl$_3$, TMS) δ (ppm): 1.53 (6H, d, J=7 Hz), 4.53-4.60 (1H, m), 6.50 (1H, d, J=2 Hz), 7.45 (1H, d, J=2 Hz).

REFERENCE PREPARATION EXAMPLE 64-(2)

According to the same manner as that of Reference Preparation Example 18, 1-isopropyl-3-trifluoromethyl-1H-pyrazole was used in place of 1-methyl-3-trifluoromethyl-1H-pyrazole to obtain 1-isopropyl-3-trifluoromethyl-1H-pyrazole-5-carboxylic acid of the formula:

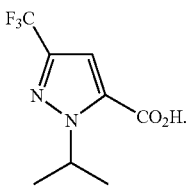

1-Isopropyl-3-trifluoromethyl-1H-pyrazole-5-carboxylic acid $^1$H-NMR (CDCl$_3$, TMS) δ (ppm): 1.53 (6H, d, J=7 Hz), 5.49-5.56 (1H, m), 7.17 (1H, s).

REFERENCE PREPARATION EXAMPLE 64-(3)

According to the same manner as that of Reference Preparation Example 13, 1-isopropyl-3-trifluoromethyl-1H-pyrazole-5-carboxylic acid was used in place of 1-(3-chloro-2-pyridinyl)-1H-pyrazole-5-carboxylic acid to obtain 6-chloro-2-(1-isopropyl-3-trifluoromethyl-1H-pyrazol-5-yl)-8-methyl-4H-3,1-benzoxazine-4-one of the formula:

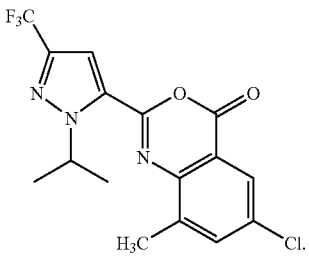

6-Chloro-2-(1-isopropyl-3-trifluoromethyl-1H-pyrazol-5-yl)-8-methyl-4H-3,1-benzoxazine-4-one $^1$H-NMR (CDCl$_3$, TMS) δ (ppm): 1.62 (6H, d, J=7 Hz), 2.59 (3H, s), 5.83-5.90 (1H, m), 7.31 (1H, s), 7.68 (1H, s), 8.07 (1H, s).

REFERENCE PREPARATION EXAMPLE 64-(4)

According to the same manner as that of Reference Preparation Example 1, 6-chloro-2(1-isopropyl-3-trifluoromethyl-1H-pyrazol-5-yl)-8-methyl-4H-3, 1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[4-chloro-2-(hydrazinocarbonyl)-6-methylphenyl]-1-isopropyl-3-trifluoromethyl-1H-pyrazole-5-carboxamide of the formula:

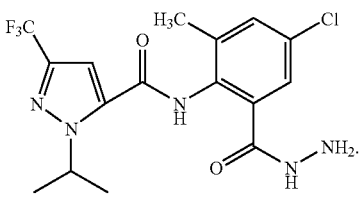

N-[4-chloro-2-(hydrazinocarbonyl)-6-methylphenyl]-1-isopropyl-3-trifluoromethyl-1H-pyrazole -5 carboxiamide carboxamide $^1$H-NMR (DMSO-d$_6$,TMS) δ (ppm): 1.44 (6H, d, J=7Hz), 2.25 (3H, s), 4.36 (2H, s), 5.42-5.47 (1H, m), 7.34 (1H, s), 7.36 (1H, s), 7.50 (1H, s), 9.61 (1H, brs), 10.16 (1H, brs).

REFERENCE PREPARATION EXAMPLE 65

According to the same manner as that of Reference Preparation Example 46-(1), 2-amino-3,6-dichlorobenzoic acid was used in place of 2-amino-3,5-dibromobenzoic acid to obtain 2-[3-bromo-1-(3-chloro-2-pyridinyl)-1H-pyrazol-5-yl]-5,8-dichloro-4H-3,1-benzoxazine-4-one of the formula:

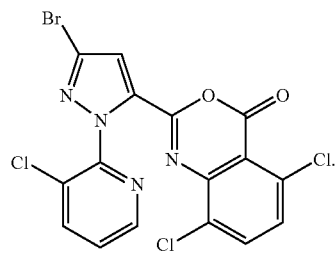

2-[3-Bromo-1-(3-chloro-2-pyridinyl)-1H-pyrazol-5-yl]-5,8-dichloro-4H-3,1-benzoxazine-4-one $^1$H-NMR (DMSO-d$_6$, TMS) δ (ppm): 7.57 (1H, s), 7.62 (1H, d, J=8 Hz) 7.72 (1H, dd, J=8 Hz, 4 Hz), 7.87 (1H, d, J=8 Hz), 8.31 (1H, d, J=8 Hz), 8.59 (1H, d, J=4 Hz).

REFERENCE PREPARATION EXAMPLE 66-(1)

According to the same manner as that of Reference Preparation Example 63-(1), 5-chloro-2-methylaniline was used in place of 3-chloro-2-methylaniline to obtain N-(5-chloro-2-methylphenyl)-2-(hydroxyimino)acetamide of the formula:

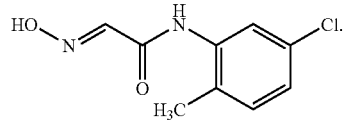

N-(5-Chloro-2-methylphenyl)-2-(hydroxyimino) acetamide $^1$H-NMR (DMSO-d$_6$, TMS) δ (ppm): 2.20 (3H, s), 7.17 (1H, dd, J=8 Hz, 2 Hz), 7.27 (1H, d, J=8 Hz), 7.64 (1H, d, J=2 Hz), 7.70 (1H, d, J=2 Hz), 9.56 (1H, s), 12.27 (1H, s).

REFERENCE PREPARATION EXAMPLE 66-(2)

According to the same manner as that of Reference Preparation Example 63-(2), N-(5-chloro-2-methylphenyl)-2-(hydroxyimino)acetamide was used in place of N-(3-chloro-2-methylphenyl)-2-(hydroxyimino)acetamide to obtain 4-chloro-7-methyl-1H-indole-2,3-dione of the formula:

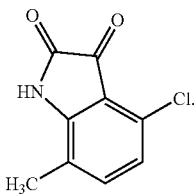

4-Chloro-7-methyl-1H-indole-2,3-dione $^1$H-NMR (DMSO-d$_6$, TMS) δ (ppm): 2.16 (3H, s), 6.99 (1H, d, J=8 Hz) 7.40 (1H, d, J=8 Hz), 11.24 (1H, s).

REFERENCE PREPARATION EXAMPLE 66-(3)

According to the same manner as that of Reference Preparation Example 63-(3), 4-chloro-7-methyl-1H-indole-2,3-dione was used in place of 6-chloro-7-methyl-1H-indole-2,3-dione to obtain 2-amino-6-chloro-3-methylbenzoic acid of the formula:

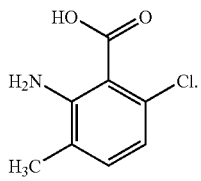

2-Amino-6-chloro-3-methylbenzoic acid $^1$H-NMR (DMSO-d$_6$, TMS) δ (ppm): 2.07 (3H, s), 6.57 (1H, d, J=8 Hz), 7.01 (1H, d, J=8 Hz).

REFERENCE PREPARATION EXAMPLE 66-(4)

According to the same manner as that of Reference Preparation Example 46-(1), 2-amino-6-chloro-3-methylbenzoic acid was used in place of 2-amino-3,5-dibromobenzoic acid to obtain 2-[3-bromo-1-(3-chloro-2-pyridinyl)-1H-pyrazol-5-yl]-5-chloro-8-methyl-4H-3,1-benzoxazine-4-one of the formula:

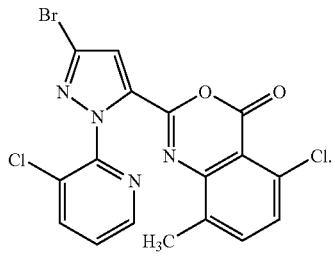

2-[3-Bromo-1-(3-chloro-2-pyridinyl)-1H-pyrazol-5-yl]-5-chloro-8-methyl-4H-3,1-benzoxazine-4-one $^1$H-NMR (DMSO-d$_6$, TMS) δ (ppm): 1.66 (3H, s), 7.52-7.56 (2H, m), 7.62 (1H, d, J=8 Hz), 7.76 (1H, dd, J=8 Hz, 4 Hz), 8.34 (1H, d, J=8 Hz), 8.63 (1H, d, J=4 Hz).

REFERENCE PREPARATION EXAMPLE 67-(1)

To a mixture of 5 g of 4-ethoxy-1,1,1-trifluoro-3-butene-2-one, 3 g of sodium acetate and 15 ml of ethanol was added 4.6 g of tert-butylhydrazine hydrochloride, and the mixture was heated to reflux for 2 days. Water was added to the reaction mixture, and the mixture was extracted with diethyl ether three times. The organic layers were combined, washed with an aqueous saturated sodium chloride solution, dried over anhydrous magnesium sulfate, and concentrated under reduced pressure to obtain 3.0 g of 1-tert-butyl-3-trifluoromethyl-1H-pyrazole of the formula:

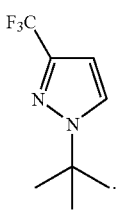

1-tert-Butyl-3-trifluoromethyl-1H-pyrazole $^1$H-NMR (CDCl$_3$, TMS) δ (ppm): 1.61 (9H, s), 6.48 (1H, d, J=2 Hz), 7.54 (1H, d, J=2 Hz).

REFERENCE PREPARATION EXAMPLE 67-(2)

According to the same manner as that of Reference Preparation Example 18, 1-tert-butyl-3-trifluoromethyl-1H-pyrazole was used in place of 1-methyl-3-trifluoromethyl-1H-pyrazole to obtain 1-tert-butyl-3-trifluoromethyl-1H-pyrazole-5-carboxylic acid of the formula:

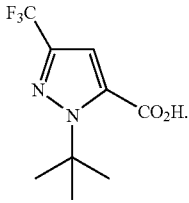

1-tert-Butyl-3-trifluoromethyl-1H-pyrazole-5-carboxylic acid $^1$H-NMR (CDCl$_3$, TMS) δ (ppm): 1.75 (9H, s), 7.28 (1H, s).

REFERENCE PREPARATION EXAMPLE 67-(3)

According to the same manner as that of Reference Preparation Example 13, 1-tert-butyl-3-trifluoromethyl-1H-pyrazole-5-carboxylic acid was used in place of 1-(3-chloro-2-pyridinyl)-1H-pyrazole-5-carboxylic acid to obtain 6-chloro-2-(1-tert-butyl-3-trifluoromethyl-1H-pyrazol-5-yl)-8-methyl-4H-3,1-benzoxazine-4-one of the formula:

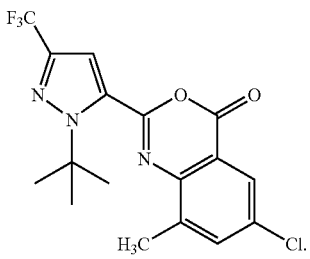

6-Chloro-2-(1-tert-butyl-3-trifluoromethyl-1H-pyrazol-5-yl)-8-methyl-4H-3,1-benzoxazine-4-one $^1$H-NMR (CDCl$_3$, TMS) δ (ppm): 1.86 (9H, s), 2.61 (3H, s), 7.32 (1H, s), 7.68 (1H, d, J=2 Hz), 8.08 (1H, d, J=2 Hz).

REFERENCE PREPARATION EXAMPLE 67-(4)

According to the same manner as that of Reference Preparation Example 1, 6-chloro-2-(1-tert-butyl-3-trifluoromethyl-1H-pyrazol-5-yl)-8-methyl-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[4-chloro-2-(hydrazinocarbonyl)-6-methylphenyl]-1-tert-butyl-3-trifluoromethyl-1H-pyrazole-5-carboxamide of the formula:

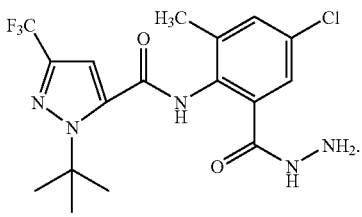

N-[4-chloro-2-(hydrazinocarbonyl)-6-methylphenyl]-1-tert-butyl-3-trifluoromethyl-1H-pyrazole-5-carboxamide 1 H-NMR (DMSO-d$_6$,TMS) δ (ppm): 1.67 (9H, s), 2.27 (3H, s), 4.36 (2H, s), 7.11 (1H, s), 7.34 (1H, s), 7.48 (1H, s), 9.63 (1H, brs), 10.22 (1H, brs).

REFERENCE PREPARATION EXAMPLE 68-(1)

According to the same manner as that of Reference Preparation Example 24, tert-butylhydrazine hydrochloride was used in place of 2-chlorophenylhydrazine hydrochloride to obtain 1-tert-butyl-3-(2-furyl)-5-trifluoromethyl-1H-pyrazole of the formula:

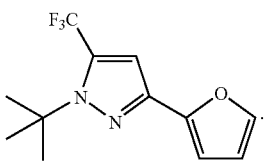

1-tert-Butyl-3-(2-furyl)-5-trifluoromethyl-1H-pyrazole $^1$H-NMR (CDCl$_3$, TMS) δ (ppm): 1.53 (9H, s), 6.48-6.51 (2H, m) 6.59 (1H, s), 7.55 (1H, dd, J=2 Hz, 1Hz).

REFERENCE PREPARATION EXAMPLE 68-(2)

According to the same manner as that of Reference Preparation Example 25, 1-tert-butyl-3-(2-furyl)-5-trifluoromethyl-1H-pyrazole was used in place of 1-(2-chlorophenyl)-5-(2-furyl)-3-trifluoromethyl-1H-pyrazole to obtain 1-tert-butyl-5-trifluoromethyl-1H-pyrazole-3-carboxylic acid of the formula:

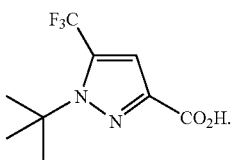

1-tert-Butyl-5-trifluoromethyl-1H-pyrazole-3-carboxylic acid $^1$H-NMR (CDCl$_3$, TMS) δ (ppm): 1.73 (9H, s), 7.90 (1H, brs).

REFERENCE PREPARATION EXAMPLE 68-(3)

According to the same manner as that of Reference Preparation Example 13, 1-tert-butyl-5-trifluoromethyl-1H-pyrazole-3-carboxylic acid was used in place of 1-(3-chloro-2-pyridinyl)-1H-pyrazole-5-carboxylic acid to obtain 6-chloro-2-[1-tert-butyl-5-trifluoromethyl-1H-pyrazol-3-yl]-8-methyl-4H-3,1-benzoxazine-4-one of the formula:

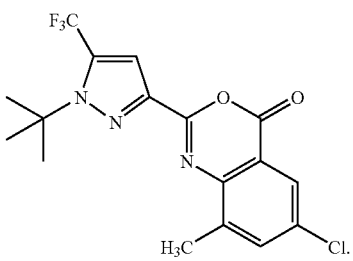

6-Chloro-2-[1-tert-butyl-5-trifluoromethyl-1H-pyrazol-3-yl]-8-methyl-4H-3,1-benzoxazine-4-one $^1$H-NMR (CDCl$_3$, TMS) δ (ppm): 1.76 (9H, s), 2.58 (3H, s), 7.57 (1H, s), 7.74 (1H, d, J=2 Hz), 8.12 (1H, d, J=2 Hz).

REFERENCE PREPARATION EXAMPLE 68-(4)

According to the same manner as that of Reference Preparation Example 1, 6-chloro-2-(1-tert-butyl-5-trifluoromethyl-1H-pyrazol-3-yl)-8-methyl-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[4-chloro-2-(hydrazinocarbonyl)-6-methylphenyl]-1-tert-butyl-5-trifluoromethyl-1H-pyrazole-3-carboxamide of the formula:

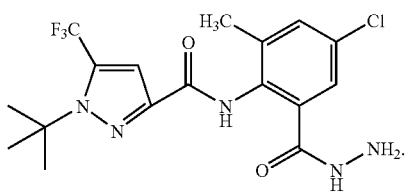

N-[4-chloro-2-(hydrazinocarbonyl)-6-methylphenyl]-1-tert-butyl-5-trifluoromethyl-1H-pyrazole-3-carboxamide $^1$H-NMR (DMSO-d$_6$, TMS) δ (ppm): 1.70 (9H, s), 2.26 (3H, s), 4.39 (2H, s), 7.37 (1H, s), 7.50 (1H, s), 7.85 (1H, s), 9.75 (1H, brs), 10.67 (1H, brs).

REFERENCE PREPARATION EXAMPLE 69

According to the same manner as that of Reference Preparation Example 46-(1), 2-amino-3-methylbenzoic acid was used in place of 2-amino-3,5-dibromobenzoic acid to obtain 2-[3-bromo-1-(3-chloro-2-pyridinyl)-1H-pyrazol-5-yl]-8-methyl-4H-3,1-benzoxazine-4-one of the formula:

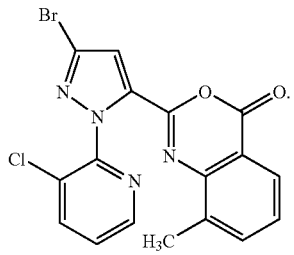

2-[3-Bromo-1-(3-chloro-2-pyridinyl)-1H-pyrazol-5-yl]-8-methyl-4H-3,1-benzoxazine-4-one $^1$H-NMR (DMSO-d$_6$, TMS) δ (ppm): 1.74 (3H, s), 7.46-7.51 (2H, m), 7.68 (1H, d, J=8 Hz), 7.76 (1H, dd, J=8 Hz, 4 Hz), 7.94 (1H, d, J=8 Hz), 8.35 (1H, dd, J=8 Hz, 1Hz), 8.63 (1H, dd, J=4 Hz, 1Hz).

REFERENCE PREPARATION EXAMPLE 70

According to the same manner as that of Reference Preparation Example 46-(1), 2-amino-3-bromobenzoic acid was used in place of 2-amino-3,5-dibromobenzoic acid to obtain 8-bromo-2-[3-bromo-1-(3-chloro-2-pyridinyl)-1H-pyrazol-5-yl ]-4H-3,1-benzoxazine-4-one of the formula:

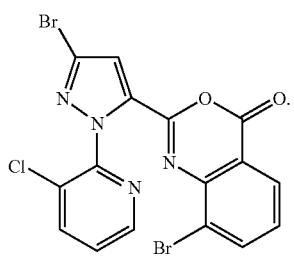

8-Bromo-2-[3-bromo-1-(3-chloro-2-pyridinyl)-1H-pyrazol-5-yl ]-4H-3,1-benzoxazine-4-one $^1$H-NMR (DMSO-d$_6$, TMS) δ (ppm): 7.49 (1H, t, J=8 Hz), 7.54 (1H, s), 7.72 (1H, dd, J=8 Hz, 4 Hz), 8.08 (1H, s), 8.10 (1H, s), 8.32 (1H, t, J=4 Hz), 8.60 (1H, d, J=4 Hz).

REFERENCE PREPARATION EXAMPLE 71-(1)

A mixture of 1.0 g of pyrrole, 3.0 g of 3-chloro-2-methanesulfonylpyridine, 6.6 g of cesium carbonate and 10 ml of N,N-dimethylformamide was stirred at 60° C. for 27 hours. After the reaction mixture was allowed to cool to room temperature, water was poured and the mixture was extracted with ethyl acetate two times. The organic layers were combined, washed successively with water and an aqueous saturated sodium chloride solution, dried over magnesium sulfate, and concentrated under reduced pressure. The resulting residue was subjected to silica gel column chromatography to obtain 1.7 g of 3-chloro-2-(1H-pyrrol-1-yl)pyridine of the formula:

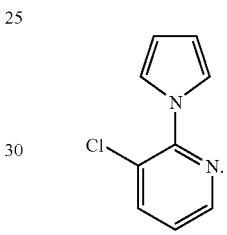

3-Chloro-2-(1H-pyrrol-1-yl)pyridine $^1$H-NMR (CDCl$_3$, TMS) δ (ppm): 6.35 (2H, t, J=2 Hz), 7.15 (1H, dd, J=8 Hz, 5 Hz), 7.42 (2H, t, J=2 Hz), 7.83 (1H, dd, J=8 Hz, 2 Hz), 8.39 (1H, dd, J=5 Hz, 2 Hz).

REFERENCE PREPARATION EXAMPLE 71-(2)

To 3.8 ml of N,N-dimethylformamide was added dropwise 4.2 ml of phosphorus oxychloride at room temperature, and the mixture was stirred at room temperature for 30 minutes. Thereto 1.6 g of 3-chloro-2-(1H-pyrrol-1-yl)pyridine was added, and the resulting mixture was stirred at 60° C. for 2 hours. The reaction mixture was allowed to cool to room temperature, and then slowly added to ice-water. The mixture was adjusted to pH 4 by an addition of a 2N aqueous sodium hydroxide solution. A deposited precipitate was collected by filtration to obtain 1.7 g of 3-chloro-2-(2-formyl-1H-pyrrol-1-yl)pyridine of the formula:

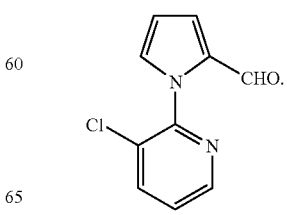

3-Chloro-2-(2-formyl-1H-pyrrol-1-yl)pyridine $^1$H-NMR (CDCl$_3$, TMS) δ (ppm): 6.48 (1H, dd, J=4 Hz, 3 Hz), 7.14-7.15 (2H, m), 7.39 (1H, dd, J=8 Hz, 5 Hz), 7.89 (1H, dd, J=8 Hz, 2 Hz), 8.47 (1H, dd, J=5 Hz, 2 Hz), 9.57 (1H, d, J=1 Hz).

REFERENCE PREPARATION EXAMPLE 71-(3)

To a solution of 1.5 g of 3-chloro-2-(2-formyl-1H-pyrrol-1-yl)pyridine in 20 ml of N,N-dimethylformamide, 1.3 g of N-bromosuccinimide was added. The mixture was stirred at room temperature for 3 hours. Water was poured into the reaction mixture, and a deposited precipitate was collected by filtration to obtain 1.9 g of 4-bromo-1-(3-chloro-2-pyridinyl)-1H-pyrrole-2-carbaldehyde of the formula:

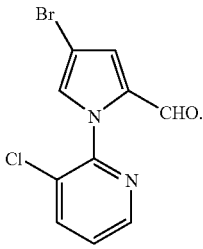

4-Bromo-1-(3-chloro-2-pyridinyl)-1H-pyrrole-2-carbaldehyde $^1$H-NMR (CDCl$_3$, TMS) δ (ppm): 7.11 (1H, d, J=2 Hz), 7.14 (1H, dd, J=2 Hz, 1Hz), 7.41 (1H, dd, J=8 Hz, 5 Hz), 7.89 (1H, dd, J=8 Hz, 2 Hz), 8.46 (1H, dd, J=5 Hz, 2 Hz), 9.51 (1H, d, J=1 Hz).

REFERENCE PREPARATION EXAMPLE 71-(4)

An aqueous solution of 1.2 g of potassium permanganate in 10 ml of water was added dropwise to a mixture of 0.72 g of 4-bromo-1-(3-chloro-2-pyridinyl)-1H-pyrrole-2-carbaldehyde and 15 ml of acetone while the mixture was retained at 40° C. The mixture was then stirred at 60° C. for 8 hours. Precipitates were filtered off to obtain a filtrate. The filtrate was adjusted to pH 10-12 by an addition of a 2N aqueous sodium hydroxide solution, and then washed with chloroform two times. The aqueous layer was adjusted to around pH 3 by an addition of 2N hydrochloric acid. A deposited precipitate was collected by filtration to obtain 0.56 g of 4-bromo-1-(3-chloro-2-pyridinyl)-1H-pyrrole-2-carboxylic acid of the formula:

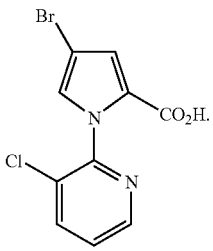

4-Bromo-1-(3-chloro-2-pyridinyl)-1H-pyrrole-2-carboxylic acid $^1$H-NMR (DMSO-d$_6$, TMS) δ (ppm): 6.99 (1H, d, J=2 Hz), 7.38 (1H, d, J=2 Hz), 7.56 (1H, dd, J=8 Hz, 5 Hz), 8.10 (1H, dd, J=8 Hz, 2 Hz), 8.48 (1H, dd, J=5 Hz, 2 Hz).

REFERENCE PREPARATION EXAMPLE 71-(5)

A mixture of 0.56 g of 4-bromo-1-(3-chloro-2-pyridinyl)-1H-pyrrole-2-carboxylic acid and 0.40 ml of thionyl chloride was heated to reflux in acetonitrile for 2 hours. The reaction mixture was allowed to cool to room temperature, and then concentrated under reduced pressure. The resulting residue was dissolved in 10 ml of acetonitrile. Thereto 0.35 g of 2-amino-5-chloro-3-methylbenzoic acid was added, and the resulting mixture was stirred at room temperature for 10 minutes. To the mixture, 0.53 ml of pyridine was added, and the mixture was stirred at room temperature for 6 hours. Then 0.19 ml of methanesulfonyl chloride was added, and the mixture was stirred at room temperature for 1 hour. Water was poured into the reaction mixture, and a deposited precipitate was collected by filtration to obtain 0.29 g of 2-[4-bromo-1-(3-chloro-2-pyridinyl)-1H-pyrrol-2-yl]-6-chloro-8-methyl-4H-3,1-benzoxazine-4-one of the formula:

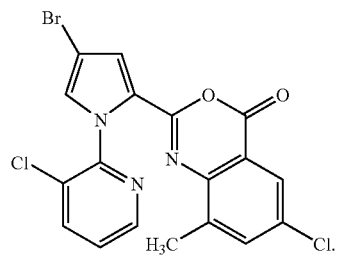

2-[4-Bromo-1-(3-chloro-2-pyridinyl)-1H-pyrrol-2-yl]-6-chloro-8-methyl-4H-3,1-benzoxazine-4-one $^1$H-NMR (CDCl$_3$, TMS) δ (ppm): 1.73 (3H, s), 7.07 (1H, d, J=2 Hz), 7.32 (1H, d, J=2 Hz), 7.42-7.44 (2H, m), 7.91 (1H, dd, J=8 Hz, 2 Hz), 7.93 (1H, d, J=2 Hz), 8.51 (1H, dd, J=5 Hz, 2 Hz).

REFERENCE PREPARATION EXAMPLE 71-(6)

A mixture of 0.29 g of 2-[4-bromo-1-(3-chloro-2-pyridinyl)-1H-pyrrol-2-yl]-6-chloro-8-methyl-4H-3,1-benzoxazine-4-one, 0.10 g of hydrazine monohydrate and 10 ml of tetrahydrofuran was stirred at room temperature for 2 hours. Water was added to the reaction mixture, and the mixture was extracted with ethyl acetate three times. The organic layers were combined, washed with an aqueous saturated sodium chloride solution, dried over anhydrous magnesium sulfate, and concentrated under reduced pressure to obtain 0.30 g of 4-bromo-N-[4-chloro-2-(hydrazinocarbonyl)-6-methylphenyl]-1-(3-chloro-2-pyridinyl)-1H-pyrrole-2-carboxamide of the formula:

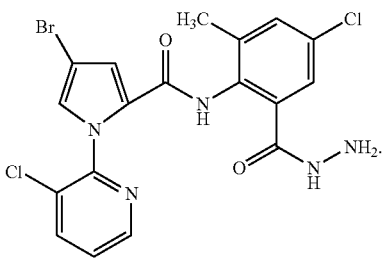

4-Bromo-N-[4-chloro-2-(hydrazinocarbonyl)-6-methylphenyl]-1-(3-chloro-2-pyridinyl)-1H-pyrrole-2-carboxamide ¹H-NMR (CDCl₃, TMS) δ (ppm): 2.20 (3H, s), 4.04 (2H, brs), 7.02 (1H, d, J=2 Hz), 7.04 (1H, d, J=2 Hz), 7.21 (1H, d, J=2 Hz), 7.28 (1H, d, J=2 Hz), 7.31 (1H, dd, J=8 Hz, 5 Hz), 7.34 (1H, brs), 7.80 (1H, dd, J=8 Hz, 2 Hz), 8.41 (1H, dd, J=5 Hz, 2 Hz), 9.27 (1H, brs)

REFERENCE PREPARATION EXAMPLE 72

A mixture of 0.60 g of 2-[3-bromo-1-(3-chloro-2-pyridinyl)-1H-pyrazol-5-yl]-6-chloro-8-methyl-4H-3,1-benzoxazine-4-one, 0.29 g of isopropylhydrazine hydrochloride, 0.27 g of triethylamine and 6 ml of tetrahydrofuran was stirred at room temperature for 3 hours. Water was poured into the reaction mixture, and the mixture was extracted with ethyl acetate two times. The combined organic layer was washed with an aqueous saturated sodium chloride solution, dried over anhydrous magnesium sulfate, and concentrated under reduced pressure. The residue was subjected to silica gel column chromatography to obtain 0.35 g of 3-bromo-N-[4-chloro-2-(N'-isopropylhydrazinocarbonyl)-6-methylphenyl]-1-(3-chloro-2-pyridinyl)-1H-pyrazole-5-carboxamide of the formula:

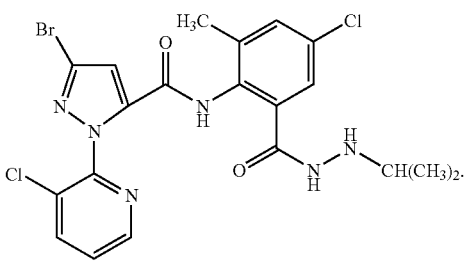

3-Bromo-N-[4-chloro-2-(N'-isopropylhydrazinocarbonyl)-6-methylphenyl]-1-(3-chloro-2-pyridinyl)-1H-pyrazole-5-carboxamide ¹H-NMR (CDCl₃, TMS) δ (ppm): 1.08 (6H, d, J=6 Hz), 2.11 (3H, s), 3.12 (1H, hept., J=6 Hz), 4.60 (1H, brs), 7.11 (1H, s), 7.14 (1H, d, J=2 Hz), 7.20 (1H, d, J=2 Hz), 7.37 (1H, dd, J₁=8 Hz, J₂=4 Hz), 7.79 (1H, brs), 7.84 (1H, dd, J₁=8 Hz, J₂=1 Hz), 8.44 (1H, dd, J=4 Hz, 1Hz), 9.93 (1H, brs).

REFERENCE PREPARATION EXAMPLE 73-(1)

According to the same manner as that of Reference Preparation Example 20, N-iodosuccinimide was used in place of 1,2-dibromo-1,1,2,2-tetrachloroethane to obtain N,N-dimethyl-5-iodo-1H-pyrazole-1-sulfonamide of the formula:

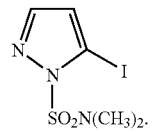

N,N-dimethyl-5-iodo-1H-pyrazole-1-sulfonamide

¹H-NMR (CDCl₃, TMS) δ (ppm): 3.07 (6H, s), 6.60 (1H, d, J=1 Hz), 7.62 (1H, d, J=1 Hz)

REFERENCE PREPARATION EXAMPLE 73-(2)

According to the same manner as that of Reference Preparation Example 21, N,N-dimethyl-5-iodo-1H-pyrazole-1-sulfonamide was used in place of 5-bromo-N,N-dimethyl-1H-pyrazole-1-sulfonamide to obtain 3-iodo-1H-pyrazole of the formula:

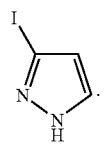

3-Iodo-1H-pyrazole

¹H-NMR (CDCl₃, TMS) δ (ppm): 6.74 (1H, d, J=3 Hz), 8.10 (1H, d, J=3 Hz).

REFERENCE PREPARATION EXAMPLE 73-(3)

According to the same manner as that of Reference Preparation Example 22, 3-iodo-1H-pyrazole was used in place of 3-bromo-1H-pyrazole to obtain 3-chloro-2-(3-iodo-1H-pyrazol-1-yl)pyridine of the formula:

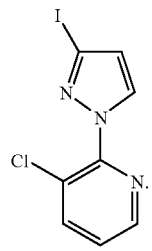

3-Chloro-2-(3-iodo-1H-pyrazol-1-yl)pyridine

¹H-NMR (CDCl₃, TMS) δ (ppm): 6.65 (1H, d, J=2 Hz), 7.31 (1H, dd, J=8 Hz, 4 Hz), 7.91 (1H, dd, J=8 Hz, 1Hz), 7.95 (1H, d, J=2 Hz), 8.46 (1H, dd, J=4 Hz, 1Hz).

REFERENCE PREPARATION EXAMPLE 73-(4)

According to the same manner as that of Reference Preparation Example 23, 3-chloro-2-(3-iodo-1H-pyrazol-1-yl)pyridine was used in place of 2-(3-bromo-1H-pyrazol-1-yl)-3-chloropyridine to obtain 1-(3-chloro-2-pyridinyl)-3-iodo-1H-pyrazole-5-carboxylic acid of the formula:

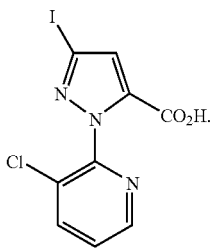

1-(3-Chloro-2-pyridinyl)-3-iodo-1H-pyrazole-5-carboxylic acid

¹H-NMR (CDCl₃, TMS) δ (ppm): 7.20 (1H, s), 7.44 (1H, dd, J=8 Hz, 4 Hz), 7.91 (1H, dd, J=8 Hz, 1Hz), 8.50 (1H, dd, J=4 Hz, 1Hz).

REFERENCE PREPARATION EXAMPLE 73-(5)

According to the same manner as that of Reference Preparation Example 13, 1-(3-chloro-2-pyridinyl)-3-iodo-1H-pyrazole-5-carboxylic acid was used in place of 1-(3-chloro-2-pyridinyl)-1H-pyrazole-5-carboxylic acid to obtain 6-chloro-2-[1-(3-chloro-2-pyridinyl)-3-iodo-1H-pyrazol-5-yl]-8-methyl-4H-3,1-benzoxazine-4-one of the formula:

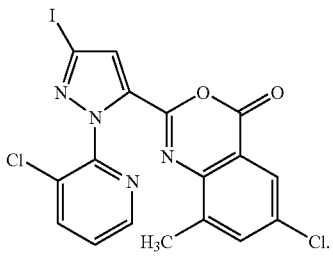

6-Chloro-2-[1-(3-chloro-2-pyridinyl)-3-iodo-1H-pyrazol-5-yl]-8-methyl-4H-3,1-benzoxazine-4-one ¹H-NMR (CDCl₃, TMS) δ (ppm): 1.82 (3H, s), 7.39 (1H, s), 7.47-7.50 (2H, m), 7.95-7.98 (2H, m), 8.56 (1H, dd, J=4 Hz, 1Hz).

REFERENCE PREPARATION EXAMPLE 73-(6)

According to the same manner as that of Reference Preparation Example 7, 6-chloro-2-[1-(3-chloro-2-pyridinyl)-3-iodo-1H-pyrazol-5-yl]-8-methyl-4H-3,1-benzoxazine-4-one was used in place of 6-chloro-2-[1-(3-chloro-2-pyridinyl)-1H-pyrazol-5-yl]-8-methyl-4H-3,1-benzoxazine-4-one to obtain N-[4-chloro-2-(hydrazinocarbonyl)-6-methylphenyl]-1-(3-chloro-2-pyridinyl)-3-iodo-1H-pyrazole-5-carboxamide of the formula:

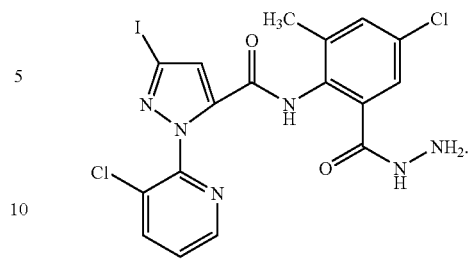

N-[4-chloro-2-(hydrazinocarbonyl)-6-methylphenyl]-1-(3-chloro-2-pyridinyl)-3-iodo-1H-pyrazole-5-carboxamide ¹H-NMR (DMSO-d₆) δ (ppm): 2.13 (3H, s), 4.36 (2H, brs), 7.31 (1H, brs), 7.42 (1H, brs), 7.46 (1H, brs), 7.59 (1H, dd, J=8 Hz, 4 Hz), 8.15 (1H, d, J=8 Hz), 8.49 (1H, dd, J=4 Hz, 1Hz), 9.54 (1H, brs), 10.20 (1H, brs).

REFERENCE PREPARATION EXAMPLE 74-(1)

According to the same manner as that of Reference Preparation Example 22, 4-bromo-1H-pyrazole was used in place of 3-bromo-1H-pyrazole to obtain 2-(4-bromo-1H-pyrazol-1-yl)-3-chloropyridine of the formula:

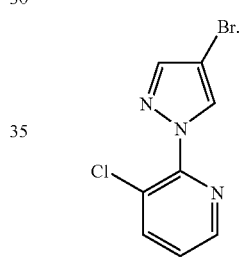

2-(4-Bromo-1H-pyrazol-1-yl)-3-chloropyridine

¹H-NMR (CDCl₃, TMS) δ (ppm): 7.31 (1H, dd, J=8 Hz, 4 Hz), 7.77 (1H, s), 7.92 (1H, dd, J=8 Hz, 1Hz), 8.19 (1H, s), 8.45 (1H, dd, J=4 Hz, 1Hz).

REFERENCE PREPARATION EXAMPLE 74-(2)

According to the same manner as that of Reference Preparation Example 23, 2-(4-bromo-1H-pyrazol-1-yl)-3-chloropyridine was used in place of 2-(3-bromo-1H-pyrazol-1-yl)-3-chloropyridine to obtain 4-bromo-1-(3-chloro-2-pyridinyl)-1H-pyrazole-5-carboxylic acid of the formula:

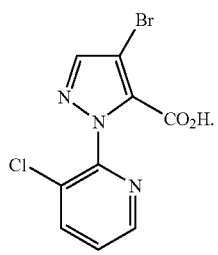

4-Bromo-1-(3-chloro-2-pyridinyl)-1H-pyrazole-5-carboxylic acid $^1$H-NMR (DMSO-$d_6$) δ (ppm): 7.66 (1H, dd, J=8 Hz, 4 Hz), 8.06 (1H, s), 8.23 (1H, dd, J=8 Hz, 1Hz), 8.54 (1H, dd, J=4 Hz, 1Hz).

REFERENCE PREPARATION EXAMPLE 74-(3)

According to the same manner as that of Reference Preparation Example 13, 4-bromo-1-(3-chloro-2-pyridinyl)-1H-pyrazole-5-carboxylic acid was used in place of 1-(3-chloro-2-pyridinyl)-1H-pyrazole-5-carboxylic acid to obtain 2-[4-bromo-1-(3-chloro-2-pyridinyl)-1H-pyrazol-5-yl]-6-chloro-8-methyl-4H-3,1-benzoxazine-4-one of the formula:

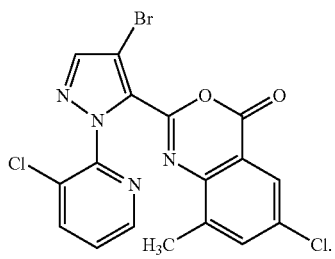

2-[4-Bromo-1-(3-chloro-2-pyridinyl)-1H-pyrazol-5-yl]-6-chloro-8-methyl-4H-3,1-benzoxazine-4-one $^1$H-NMR (CDCl$_3$, TMS) δ (ppm): 2.00 (3H, s), 7.46 (1H, dd, J=8 Hz, 4 Hz), 7.53 (1H, d, J=2 Hz), 7.87 (1H, s), 7.95 (1H, dd, J=8 Hz, 1Hz), 7.98 (1H, d, J=2 Hz), 8.51 (1H, dd, J=4 Hz, 1Hz).

REFERENCE PREPARATION EXAMPLE 74-(4)

According to the same manner as that of Reference Preparation Example 7, 2-[4-bromo-1-(3-chloro-2-pyridinyl)-1H-pyrazol-5-yl]-6-chloro-8-methyl-4H-3,1-benzoxazine-4-one was used in place of 6-chloro-2-[1-(3-chloro-2-pyridinyl)-1H-pyrazol-5-yl]-8-methyl-4H-3,1-benzoxazine-4-one to obtain 4-bromo-N-[4-chloro-2-(hydrazinocarbonyl)-6-methylphenyl]-1-(3-chloro-2-pyridinyl)-1H-pyrazole-5-carboxamide of the formula:

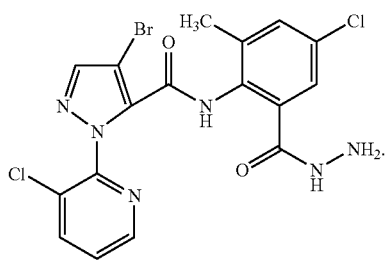

4-Bromo-N-[4-chloro-2-(hydrazinocarbonyl)-6-methylphenyl]-1-(3-chloro-2-pyridinyl)-1H-pyrazole-5-carboxamide $^1$H-NMR (DMSO-$d_6$) δ (ppm): 2.13 (3H, s), 4.47 (2H, brs), 7.37 (1H, s), 7.48 (1H, s), 7.62 (1H, dd, J=8 Hz, 4 Hz), 8.12 (1H, s), 8.19 (1H, d, J=8 Hz), 8.50 (1H, d, J=4 Hz), 9.69 (1H, brs), 10.24 (1H, brs).

REFERENCE PREPARATION EXAMPLE 75-(1)

According to the same manner as that of Reference Preparation Example 22, 3-phenyl-1H-pyrazole was used in place of 3-bromo-1H-pyrazole to obtain 3-chloro-2-(3-phenyl-1H-pyrazol-1-yl)pyridine of the formula:

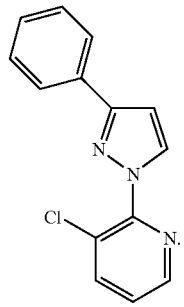

3-Chloro-2-(3-phenyl-1H-pyrazol-1-yl)pyridine $^1$H-NMR (CDCl$_3$, TMS) δ (ppm): 6.82 (1H, d, J=2 Hz), 7.27 (1H, dd, J=8 Hz, 4 Hz), 7.35 (1H, m), 7.43 (2H, m), 7.93 (3H, m), 8.20 (1H, d, J=2 Hz), 8.48 (1H, dd, J=4 Hz, 1Hz).

REFERENCE PREPARATION EXAMPLE 75-(2)

According to the same manner as that of Reference Preparation Example 23, 3-chloro-2-(3-phenyl-1H-pyrazol-1-yl)pyridine was used in place of 2-(3-bromo-1H-pyrazol-1-yl)-3-chloropyridine to obtain 1-(3-chloro-2-pyridinyl)-3-phenyl-1H-pyrazole-5-carboxylic acid of the formula:

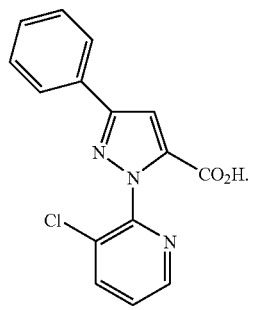

1-(3-Chloro-2-pyridinyl)-3-phenyl-1H-pyrazole-5-carboxylic acid $^1$H-NMR (DMSO-$d_6$) δ (ppm): 7.36-7.45 (3H, m), 7.57 (1H, s), 7.67 (1H, dd, J=8 Hz, 4 Hz), 7.90-7.92 (2H, m), 8.24 (1H, dd, J=8 Hz, 1Hz), 8.57 (1H, dd, J=4 Hz, 1Hz).

REFERENCE PREPARATION EXAMPLE 75-(3)

According to the same manner as that of Reference Preparation Example 13, 1-(3-chloro-2-pyridinyl)-1H-pyrazole-5-carboxylic acid was used in place of 1-(3-chloro-2-pyridinyl)-1H-pyrazole-5-carboxylic acid to obtain 6-chloro-2-[1-(3-chloro-2-pyridinyl)-3-phenyl-1H-pyrazol-5-yl]-8-methyl-4H-3,1-benzoxazine-4-one of the formula:

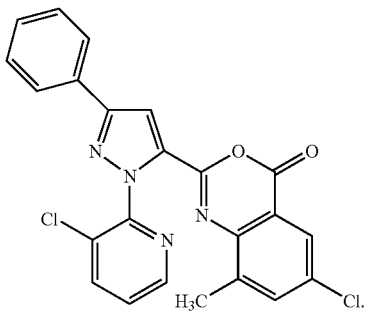

6-Chloro-2-[1-(3-chloro-2-pyridinyl)-3-phenyl-1H-pyrazol-5-yl]-8-methyl-4H-3,1-benzoxazine-4-one $^1$H-NMR (CDCl$_3$, TMS) δ (ppm): 1.83 (3H, s), 7.39-7.52 (5H, m), 7.59 (1H, s), 7.92-8.00 (4H, m), 8.59 (1H, dd, J=4 Hz, 1Hz).

REFERENCE PREPARATION EXAMPLE 75-(4)

According to the same manner as that of Reference Preparation Example 7, 6-chloro-2-[1-(3-chloro-2-pyridinyl)-3-phenyl-1H-pyrazol-5-yl]-8-methyl-4H-3,1-benzoxazine-4-one was used in place of 6-chloro-2-[1-(3-chloro-2-pyridinyl)-1H-pyrazol-5-yl]-8-methyl-4H-3,1-benzoxazine-4-one to obtain N-[4-chloro-2-(hydrazinocarbonyl)-6-methylphenyl]-1-(3-chloro-2-pyridinyl)-3-phenyl-1H-pyrazole-5-carboxamide of the formula:

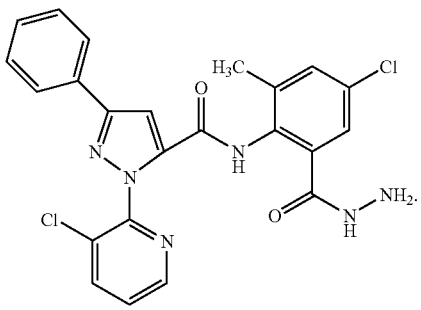

N-[4-chloro-2-(hydrazinocarbonyl)-6-methylphenyl]-1-(3-chloro-2-pyridinyl)-3-phenyl-1H-pyrazole-5-carboxamide $^1$H-NMR (DMSO-d$_6$) δ (ppm): 2.19 (3H, s), 4.40 (2H, brs), 7.33 (1H, d, J=2 Hz), 7.42-7.92 (4H, m), 7.60 (1H, dd, J=8 Hz, 4 Hz), 7.70 (1H, s), 7.88 (2H, d, J=7 Hz), 8.17 (1H, d, J=8 Hz), 8.53 (1H, d, J=4 Hz), 9.58 (1H, brs), 10.27 (1H, brs).

REFERENCE PREPARATION EXAMPLE 76-(1)

To a mixture of 4.0 g of N,N-dimethyl-1H-pyrazole-1-sulfonamide and 45 ml of tetrahydrofuran was added dropwise 15.7 ml of a 1.6M n-butyl lithium solution in hexane at −78° C., and the mixture was stirred at −78° C. for 10 minutes. After 2.3 ml of dimethyl disulfide was added to the mixture, the mixture was stirred for 4 hours while the reaction temperature was gradually returned to room temperature. Water was poured into the reaction mixture, and the mixture was extracted with methyl t-butyl ether three times. The combined organic layer was washed successively with a 1N aqueous sodium hydroxide solution and an aqueous saturated sodium chloride solution, dried over magnesium sulfate, and concentrated under reduced pressure. The resulting residue was subjected to silica gel column chromatography to obtain 4.87 g of N,N-dimethyl-5-methylthio-1H-pyrazole-1-sulfonamide of the formula:

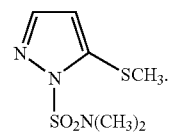

N,N-dimethyl-5-methylthio-1H-pyrazole-1-sulfonamide $^1$H-NMR (CDCl$_3$, TMS) δ (ppm): 2.49 (3H, s), 3.01 (6H, s), 6.10 (1H, d, J=2 Hz), 7.63 (1H, d, J=2 Hz).

REFERENCE PREPARATION EXAMPLE 76-(2)

According to the same manner as that of Reference Preparation Example 21, N,N-dimethyl-5-methylthio-1H-pyrazole-1-sulfonamide was used in place of 5-bromo-N,N-dimethyl-1H-pyrazole-1-sulfonamide to obtain 3-methylthio-1H-pyrazole of the formula:

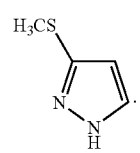

3-Methylthio-1H-pyrazole $^1$H-NMR (CDCl$_3$, TMS) δ (ppm): 2.61 (3H, s), 6.45 (1H, d, J=3 Hz), 8.19 (1H, d, J=3 Hz).

REFERENCE PREPARATION EXAMPLE 76-(3)

According to the same manner as that of Reference Preparation Example 22, 3-methylthio-1H-pyrazole was used in place of 3-bromo-1H-pyrazole to obtain 3-chloro-2-(3-methylthio-1H-pyrazol-1-yl)pyridine of the formula:

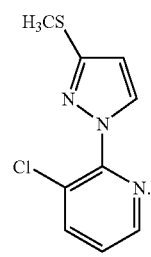

3-Chloro-2-(3-methylthio-1H-pyrazol-1-yl)pyridine $^1$H-NMR (CDCl$_3$, TMS) δ (ppm): 2.61 (3H, s), 6.40 (1H, d, J=2 Hz), 7.25 (1H, dd, J=8 Hz, 4 Hz), 7.89 (1H, dd, J=8 Hz, 1Hz), 8.12 (1H, d, J=2 Hz), 8.43 (1H, dd, J=4 Hz, 1Hz).

REFERENCE PREPARATION EXAMPLE 76-(4)

According to the same manner as that of Reference Preparation Example 23, 3-chloro-2-(3-methylthio-1H-pyrazol-1-yl)pyridine was used in place of 2-(3-bromo-1H-pyrazol-1-yl)-3-chloropyridine to obtain 1-(3-chloro-2-pyridinyl)-3-methylthio-1H-pyrazole-5-carboxylic acid of the formula:

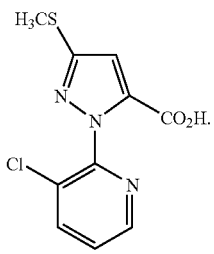

1-(3-Chloro-2-pyridinyl)-3-methylthio-1H-pyrazole-5-carboxylic acid $^1$H-NMR (DMSO-d$_6$) δ (ppm): 2.49 (3H, s), 7.02 (1H, s), 7.62 (1H, dd, J=8 Hz, 4 Hz), 8.19 (1H, dd, J=8 Hz, 1Hz), 8.51 (1H, dd, J=4 Hz, 1Hz).

REFERENCE PREPARATION EXAMPLE 76-(5)

According to the same manner as that of Reference Preparation Example 13, 1-(3-chloro-2-pyridinyl)-3-methylthio-1H-pyrazole-5-carboxylic acid was used in place of 1-(3-chloro-2-pyridinyl)-1H-pyrazole-5-carboxylic acid to obtain 6-chloro-2-[1-(3-chloro-2-pyridinyl)-3-methylthio-1H-pyrazole-5-yl]-8-methyl-4H-3,1-benzoxazine-4-one of the formula:

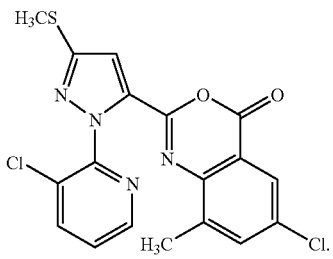

6-Chloro-2-[1-(3-chloro-2-pyridinyl)-3-methylthio-1H-pyrazol-5-yl]-8-methyl-4H-3,1-benzoxazine-4-one $^1$H-NMR (CDCl$_3$, TMS) δ (ppm): 1.81 (3H, s), 2.61 (3H, s), 7.15 (1H, s), 7.45-7.48 (2H, m), 7.94-7.98 (2H, m), 8.56 (1H, d, J=4 Hz).

REFERENCE PREPARATION EXAMPLE 76-(6)

According to the same manner as that of Reference Preparation Example 7, 6-chloro-2-[1-(3-chloro-2-pyridinyl)-3-methylthio-1H-pyrazol-5-yl]-8-methyl-4H-3,1-benzoxazine-4-one was used in place of 6-chloro-2-[1-(3-chloro-2-pyridinyl)-1H-pyrazol-5-yl]-8-methyl-4H-3,1-benzoxazine-4-one to obtain N-[4-chloro-2-(hydrazinocarbonyl)-6-methylphenyl]-1-(3-chloro-2-pyridinyl)-3-methylthio-1H-pyrazole-5-carboxamide of the formula:

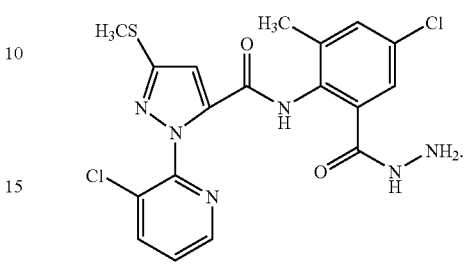

N-[4-chloro-2-(hydrazinocarbonyl)-6-methylphenyl]-1-(3-chloro-2-pyridinyl)-3-methylthio-1H-pyrazole-5-carboxamide $^1$H-NMR (DMSO-d$_6$) δ (ppm): 2.14 (3H, s), 2.53 (3H, s), 4.37 (2H, brs), 7.20 (1H, s), 7.30 (1H, s), 7.46 (1H, s), 7.56 (1H, dd, J=8 Hz, 4 Hz), 8.12 (1H, d, J=8 Hz), 8.47 (1H, d, J=4 Hz), 9.54 (1H, brs), 10.16 (1H, brs).

REFERENCE PREPARATION EXAMPLE 77-(1)

To a mixture of 0.50 g of 1-(3-chloro-2-pyridinyl)-3-methylthio-1H-pyrazole-5-carboxylic acid and 5 ml of trifluoroacetic acid was added 0.4 ml of 30% aqueous hydrogen peroxide, and the resulting mixture was stirred at room temperature for 4 hours. Water was poured into the reaction mixture, and the mixture was extracted with methyl t-butyl ether three times. The combined organic layer was washed with an aqueous saturated sodium chloride solution, dried over anhydrous sodium sulfate, and concentrated under reduced pressure to obtain 0.44 g of 1-(3-chloro-2-pyridinyl)-3-methylsulfonyl-1H-pyrazole-5-carboxylic acid of the formula:

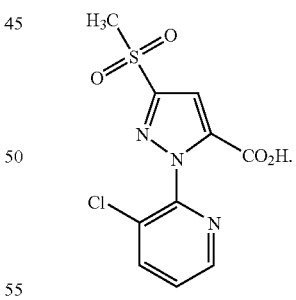

1-(3-Chloro-2-pyridinyl)-3-methylsulfonyl-1H-pyrazole-5-carboxylic acid $^1$H-NMR (DMSO-d$_6$) δ (ppm): 3.39 (3H, s), 7.57 (1H, s), 7.75 (1H, dd, J=8 Hz, 4 Hz), 8.31 (1H, dd, J=8 Hz, 1Hz), 8.61 (1H, dd, J=4 Hz, 1Hz).

REFERENCE PREPARATION EXAMPLE 77-(2)

According to the same manner as that of Reference Preparation Example 13, 1-(3-chloro-2-pyridinyl)-3-methylsulfonyl-1H-pyrazole-5-carboxylic acid was used in place of 1-(3-chloro-2-pyridinyl)-1H-pyrazole-5-carboxylic acid to obtain 6-chloro-2-[1-(3-chloro-2-pyridinyl)-3-methylsulfonyl-1H-pyrazol-5-yl]-8-methyl-4H-3,1-benzoxazine-4-one of the formula:

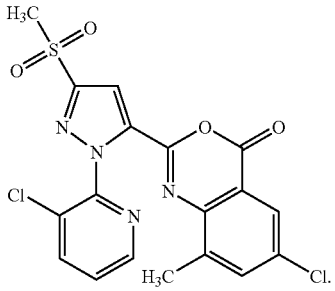

6-Chloro-2-[1-(3-chloro-2-pyridinyl)-3-methylsulfonyl-1H-pyrazol-5-yl]-8-methyl-4H-3,1-benzoxazine-4-one $^1$H-NMR (CDCl$_3$, TMS) δ (ppm): 1.85 (3H, s), 3.30 (3H, s), 7.52-7.57 (2H, m), 7.72 (1H, s), 7.99-8.03 (2H, m), 8.58 (1H, dd, J=4 Hz, 1Hz).

REFERENCE PREPARATION EXAMPLE 78

To a mixture of 0.20 g of 6-chloro-2-[1-(3-chloro-2-pyridinyl)-3-methylthio-1H-pyrazol-5-yl]-8-methyl-4H-3,1-benzoxazine-4-one, 5 ml of dichloromethane and 0.5 ml of water was added 0.18 g of magnesium bis(monoperoxophthalate) hexahydrate (MMPP), and the resulting mixture was stirred at room temperature for 22 hours. Water was added to the reaction mixture, and the mixture was extracted with methyl t-butyl ether. The organic layer was washed with water and an aqueous saturated sodium chloride solution, dried over anhydrous magnesium sulfate, and concentrated under reduced pressure to obtain 0.20 g of 6-chloro-2-[1-(3-chloro-2-pyridinyl)-3-methylsulfinyl-1H-pyrazol-5-yl]-8-methyl-4H-3,1-benzoxazine-4-one of the formula:

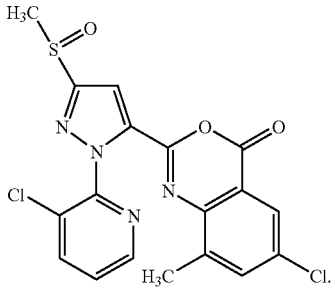

6-Chloro-2-[1-(3-chloro-2-pyridinyl)-3-methylsulfinyl-1H-pyrazol-5-yl]-8-methyl-4H-3,1-benzoxazine-4-one $^1$H-NMR (CDCl$_3$, TMS) δ (ppm): 1.85 (3H, s), 3.04 (3H, s), 7.52-7.55 (2H, m), 7.74 (1H, s), 7.99-8.01 (2H, m), 8.58 (1H, dd, J=4 Hz, 1Hz).

REFERENCE PREPARATION EXAMPLE 79-(1)

A mixture of 2.5 g of ethyl 2,4-dioxovalerate, 1.45 g of O-methylhydroxylamine hydrochloride and 10 ml of ethanol was heated to reflux for 2 hours. The reaction mixture was allowed to cool to room temperature, and partitioned between water and ethyl acetate. The organic layer was washed with water and an aqueous saturated sodium chloride solution, dried over anhydrous magnesium sulfate, and concentrated under reduced pressure. The residue was subjected to silica gel column chromatography to obtain 1.34 g of ethyl 2-methoxyimino-4-oxopentanoate of the formula:

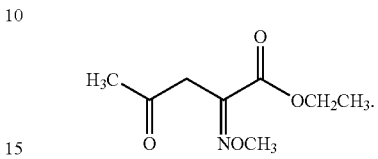

Ethyl 2-methoxyimino-4-oxopentanoate $^1$H-NMR (CDCl$_3$, TMS) δ (ppm): 1.35 (3H, t, J=7 Hz), 2.21 (3H, s), 3.71 (2H, s), 4.07 (3H, s), 4.34 (2H, q, J=7 Hz).

REFERENCE PREPARATION EXAMPLE 79-(2)

A mixture of 1.34 g of ethyl 2-methoxyimino-4-oxopentanoate, 1.23 g of 3-chloro-2-hydrazinopyridine, 25 ml of tetrahydrofuran and 50 ml of acetic acid was heated to reflux for 8 hours. The reaction mixture was concentrated under reduced pressure. Water was poured into the residue, and the mixture was extracted with methyl t-butyl ether two times. The combined organic layer was washed successively with a 1N aqueous sodium hydroxide solution, water and an aqueous saturated sodium chloride solution, dried over anhydrous magnesium sulfate, and concentrated under reduced pressure. The residue was subjected to silica gel column chromatography to obtain 0.30 g of ethyl 1-(3-chloro-2-pyridinyl)-3-methyl-1H-pyrazole-5-carboxylate of the formula:

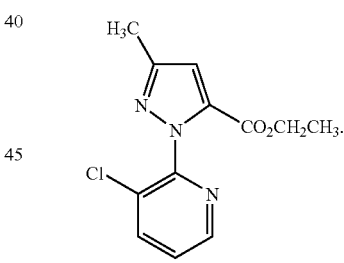

Ethyl 1-(3-chloro-2-pyridinyl)-3-methyl-1H-pyrazole-5-carboxylate $^1$H-NMR (CDCl$_3$, TMS) δ (ppm): 1.20 (3H, t, J=7 Hz), 2.40 (3H, s), 4.20 (2H, q, J=7 Hz), 6.84 (1H, s), 7.40 (1H, dd, J=8 Hz, 4 Hz), 7.88 (1H, d, J=8 Hz), 8.51 (1H, d, J=4 Hz)

REFERENCE PREPARATION EXAMPLE 79-(3)

A mixture of 0.30 g of ethyl 1-(3-chloro-2-pyridinyl)-3-methyl-1H-pyrazole-5-carboxylate, 5 ml of methanol and 5 ml of a 2N aqueous sodium hydroxide solution was heated to reflux for 3 hours. After the reaction mixture was allowed to cool, water was poured and the aqueous layer was washed with methyl t-butyl ether two times. The aqueous layer was adjusted to around pH 3 by an addition of 2N hydrochloric acid, and then extracted with methyl t-butyl ether three times. The combined organic layer was washed with an aqueous saturated sodium chloride solution, dried over anhydrous magnesium sulfate, and concentrated under reduced pressure to obtain 0.24 g of 1-(3-chloro-2-pyridinyl)-3-methyl-1H-pyrazole-5-carboxylic acid of the formula:

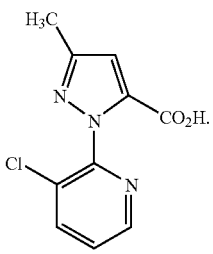

1-(3-Chloro-2-pyridinyl)-3-methyl-1H-pyrazole-5-carboxylic acid $^1$H-NMR (CDCl$_3$, TMS) δ (ppm): 2.40 (3H, s), 6.89 (1H, s), 7.40 (1H, dd, J=8 Hz, 4 Hz), 7.89 (1H, dd, J=8 Hz, 1Hz), 8.49 (1H, dd, J=4 Hz, 1Hz).

REFERENCE PREPARATION EXAMPLE 79-(4)

According to the same manner as that of Reference Preparation Example 13, 1-(3-chloro-2-pyridinyl)-3-methyl-1H-pyrazole-5-carboxylic acid was used in place of 1-(3-chloro-2-pyridinyl)-1H-pyrazole-5-carboxylic acid to obtain 6-chloro-2-[1-(3-chloro-2-pyridinyl)-3-methyl-1H-pyrazol-5-yl]-8-methyl-4H-3,1-benzoxazine-4-one of the formula:

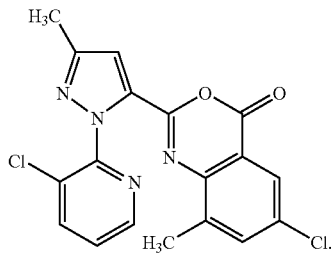

6-Chloro-2-[1-(3-chloro-2-pyridinyl)-3-methyl-1H-pyrazol-5-yl]-8-methyl-4H-3,1-benzoxazine-4-one $^1$H-NMR (CDCl$_3$, TMS) δ (ppm): 1.81 (3H, s), 2.45 (3H, s), 7.07 (1H, s), 7.43-7.47 (2H, m), 7.92-7.98 (2H, m), 8.56 (1H, dd, J=4 Hz, 1Hz).

REFERENCE PREPARATION EXAMPLE 80-(1)

To a mixture of 17.2 g of 3-methyl-2-butanone, 27.1 g of diethyl oxalate and 130 ml of ethanol was added 95 ml of sodium ethoxide (20% ethanol solution), and the resulting mixture was stirred at 60° C. for 5 hours. After allowed to cool to room temperature, a deposited precipitate was collected by filtration and washed with ethanol. The filter cake was partitioned between 2N hydrochloric acid and methyl t-butyl ether. The organic layer was washed with an aqueous saturated sodium chloride solution, dried over anhydrous magnesium sulfate, and concentrated under reduced pressure to obtain 28.8 g of ethyl 4-hydroxy-5-methyl-2-oxo-3-hexenoate of the formula:

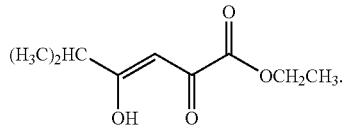

Ethyl 4-hydroxy-5-methyl-2-oxo-3-hexenoate $^1$H-NMR (CDCl$_3$, TMS) δ (ppm): 1.19 (6H, d, J=7 Hz), 1.38 (3H, t, J=7 Hz), 2.66 (1H, hept., J=7 Hz), 4.36 (2H, q, J=7 Hz), 6.41 (1H, s).

REFERENCE PREPARATION EXAMPLE 80-(2)

A mixture of 5.0 g of ethyl 4-hydroxy-5-methyl-2-oxo-3-hexenoate, 2.46 g of O-methylhydroxylamine hydrochloride and 10 ml of ethanol was stirred at room temperature for 6 hours. After ethyl acetate was poured into the reaction mixture, the organic layer was washed with water and an aqueous saturated sodium chloride solution, dried over anhydrous magnesium sulfate, and concentrated under reduced pressure to obtain 5.32 g of ethyl 2-methoxyimino-5-methyl-4-oxo-hexanoate of the formula:

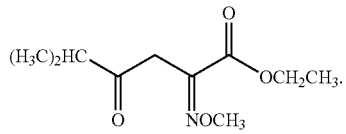

Ethyl 2-methoxyimino-5-methyl-4-oxohexanoate $^1$H-NMR (CDCl$_3$, TMS) δ (ppm): 1.15 (6H, d, J=7 Hz), 1.34 (3H, t, J=7 Hz), 2.68 (1H, hept., J=7 Hz), 3.76 (2H, s), 4.05 (3H, s), 4.33 (2H, q, J=7 Hz).

REFERENCE PREPARATION EXAMPLE 80-(3)

A mixture of 3.0 g of ethyl 2-methoxyimino-5-methyl-4-oxohexanoate, 2.4 g of 3-chloro-2-hydrazinopyridine, 50 ml of tetrahydrofuran and 100 ml of acetic acid was stirred at room temperature for 20 hours, and then heated to reflux for 4 hours. The reaction mixture was concentrated under reduced pressure. Water was poured into the residue, and the mixture was extracted with methyl t-butyl ether two times. The combined organic layer was washed successively with a 1N aqueous sodium hydroxide solution, water and an aqueous saturated chloride solution, dried over anhydrous magnesium sulfate, and concentrated under reduced pressure. The residue was subjected to silica gel column chromatography to obtain 1.07 g of ethyl 1-(3-chloro-2-pyridinyl)-3-isopropyl-1H-pyrazole-5-carboxylate of the formula:

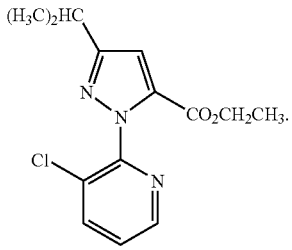

Ethyl 1-(3-chloro-2-pyridinyl)-3-isopropyl-1H-pyrazole-5-carboxylate $^1$H-NMR (CDCl$_3$, TMS) δ (ppm): 1.20 (3H, t, J=7 Hz), 1.34 (6H, d, J=7 Hz), 3.11 (1H, hept., J=7 Hz), 4.20 (2H, q, J=7 Hz), 6.88 (1H, s), 7.40 (1H, dd, J=8 Hz, 4 Hz), 7.88 (1H, d, J=8 Hz), 8.52 (1H, d, J=4 Hz).

REFERENCE PREPARATION EXAMPLE 80-(4)

A mixture of 1.07 g of ethyl 1-(3-chloro-2-pyridinyl)-3-isopropyl-1H-pyrazole-5-carboxylate, 15 ml of methanol and 15 ml of a 2N aqueous sodium hydroxide solution was heated to reflux for 1.5 hours. After the reaction mixture was allowed to cool, water was poured and the mixture was washed with methyl t-butyl ether two times. The aqueous layer was adjusted to around pH 3 by an addition of 2N hydrochloric acid, and then extracted with methyl t-butyl ether three times. The combined organic layer was washed with an aqueous saturated sodium chloride solution, dried over anhydrous magnesium sulfate, and concentrated under reduced pressure to obtain 0.97 g of 1-(3-chloro-2-pyridinyl)-3-isopropyl-1H-pyrazole-5-carboxylic acid of the formula:

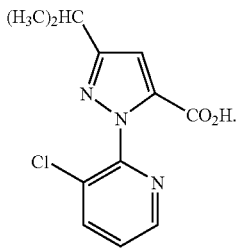

1-(3-Chloro-2-pyridinyl)-3-isopropyl-1H-pyrazole-5-carboxylic acid $^1$H-NMR (CDCl$_3$, TMS) δ (ppm): 1.33 (6H, d, J=7 Hz), 3.10 (1H, hept., J=7 Hz), 6.93 (1H, s), 7.39 (1H, dd, J=8 Hz, 4 Hz), 7.88 (1H, d, J=8 Hz), 8.49 (1H, d, J=4 Hz).

REFERENCE PREPARATION EXAMPLE 80-(5)

According to the same manner as that of Reference Preparation Example 13, 1-(3-chloro-2-pyridinyl)-3-isopropyl-1H-pyrazole-5-carboxylic acid was used in place of 1-(3-chloro-2-pyridinyl)-1H-pyrazole-5-carboxylic acid to obtain 6-chloro-2-[1-(3-chloro-2-pyridinyl)-3-isopropyl-1H-pyrazol-5-yl]-8-methyl-4H-3,1-benzoxazine-4-one of the formula:

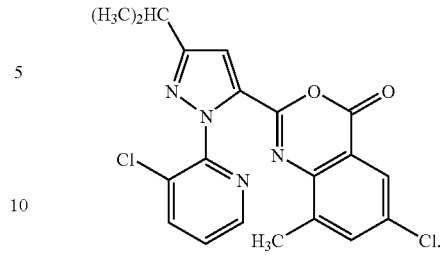

6-Chloro-2-[1-(3-chloro-2-pyridinyl)-3-isopropyl-1H-pyrazol-5-yl]-8-methyl-4H-3,1-benzoxazine-4-one $^1$H-NMR (CDCl$_3$, TMS) δ (ppm): 1.37 (6H, d, J=7 Hz), 1.81 (3H, s), 3.15 (1H, hept., J=7 Hz), 7.12 (1H, s), 7.45 (1H, dd, J=8 Hz, 4 Hz), 7.47 (1H, d, J=1 Hz), 7.93 (1H, dd, J=8 Hz, 1Hz), 7.98 (1H, d, J=1 Hz), 8.56 (1H, dd, J=4 Hz, 1Hz).

REFERENCE PREPARATION EXAMPLE 81

According to the same manner as that of Reference Preparation Example 46, 1-(3-chloro-2-pyridinyl)-3-isopropyl-1H-pyrazole-5-carboxylic acid was used in place of 3-bromo-1-(3-chloro-2-pyridinyl)-1H-pyrazole-5-carboxylic acid to obtain 2-[1-(3-chloro-2-pyridinyl)-3-isopropyl-1H-pyrazol-5-yl]-6,8-dibromo-4H-3,1-benzoxazine-4-one of the formula:

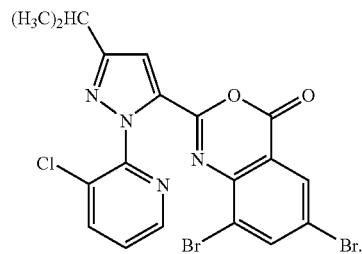

2-[1-(3-Chloro-2-pyridinyl)-3-isopropyl-1H-pyrazol-5-yl]-6,8-dibromo-4H-3,1-benzoxazine-4-one $^1$H-NMR (CDCl$_3$, TMS) δ (ppm): 1.35 (6H, d, J=7 Hz), 3.16 (1H, hept., J=7 Hz), 7.16 (1H, s), 7.43 (1H, dd, J=8 Hz, 4 Hz), 7.94 (1H, dd, J=8 Hz, 1Hz), 8.03 (1H, d, J=2 Hz), 8.25 (1H, d, J=2 Hz), 8.56 (1H, dd, J=4 Hz, 1Hz).

REFERENCE PREPARATION EXAMPLE 82-(1)

A mixture of 23.6 g of pyruvic aldehyde dimethylacetal and 23.8 g of N,N-dimethylformamide dimethylacetal was stirred at 80° C. for 4 hours while produced methanol was distilled off, to obtain 38.8 g (purity: about 80%) of 4-dimethylamino-1,1-dimethoxy-3-butene-2-one of the formula:

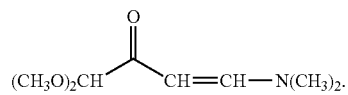

4-Dimethylamino-1,1-dimethoxy-3-butene-2-one

¹H-NMR (CDCl₃, TMS) δ (ppm): 2.87 (3H, s), 3.11 (3H, s), 3.41 (6H, s), 4.58 (1H, s), 5.35 (1H, d, J=12 Hz), 7.74 (1H, d, J=12 Hz).

REFERENCE PREPARATION EXAMPLE 82-(2)

A mixture of 5 g of 4-dimethylamino-1,1-dimethoxy-3-butene-2-one, 1.7 ml of hydrazine monohydrate and 15 ml of methanol was stirred for 8 hours under heat refluxing. The reaction mixture was concentrated under reduced pressure to obtain 4.07 g of 3-(dimethoxymethyl)-1H-pyrazole of the formula:

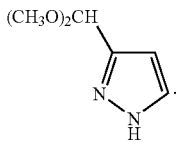

3-(Dimethoxymethyl)-1H-pyrazole

¹H-NMR (CDCl₃, TMS) δ (ppm): 3.37 (6H, s), 5.58 (1H, s), 6.35 (1H, d, J=2 Hz), 7.58 (1H, d, J=2 Hz).

REFERENCE PREPARATION EXAMPLE 82-(3)

According to the same manner as that of Reference Preparation Example 22, 3-(dimethoxymethyl)-1H-pyrazole was used in place of 3-bromo-1H-pyrazole to obtain 3-chloro-2-[3-(dimethoxymethyl)-1H-pyrazol-1-yl]pyridine of the formula:

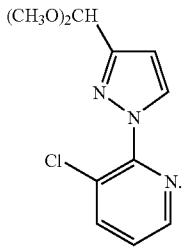

3-Chloro-2-[3-(dimethoxymethyl)-1H-pyrazol-1-yl]pyridine

¹H-NMR (CDCl₃, TMS) δ (ppm): 3.44 (6H, s), 5.58 (1H, s), 6.57 (1H, d, J=2 Hz), 7.29 (1H, dd, J=8 Hz, 5 Hz), 7.90 (1H, dd, J=8 Hz, 2 Hz), 8.07 (1H, d, 2 Hz), 8.47 (1H, dd, 5 Hz, 2 Hz).

REFERENCE PREPARATION EXAMPLE 82-(4)

A mixture of 3.35 g of 3-chloro-2-[3-(dimethoxymethyl)-1H-pyrazol-1-yl]pyridine, 24 ml of formic acid and 6 ml of water was stirred at 60° C. for 1 hour. The reaction mixture was concentrated under reduced pressure. Ice water was poured into the residue, and a precipitated solid was collected by filtration to obtain 2.38 g of 1-(3-chloro-2-pyridinyl)-1H-pyrazole-3-carbaldehyde of the formula:

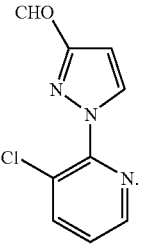

1-(3-Chloro-2-pyridinyl)-1H-pyrazole-3-carbaldehyde

¹H-NMR (CDCl₃, TMS) δ (ppm): 7.01 (1H, d, J=2 Hz), 7.40 (1H, dd, J=8 Hz, 5 Hz), 7.98 (1H, dd, J=8 Hz, 2 Hz), 8.18 (1H, dd, J=3 Hz, 2 Hz), 8.52 (1H, dd, 5 Hz, 2 Hz), 10.14 (1H, d, 2 Hz).

REFERENCE PREPARATION EXAMPLE 82-(5)

A mixture of 2.00 g of 1-(3-chloro-2-pyridinyl)-1H-pyrazole-3-carbaldehyde, 1.21 g of O-methylhydroxylamine hydrochloride and 8 ml of pyridine was heated to reflux for 1 hour. After the reaction mixture was concentrated under reduced pressure, an aqueous saturated sodium hydrogen carbonate solution was poured into the residue and the mixture was extracted with methyl t-butyl ether three times. The organic layers were combined, washed successively with water and an aqueous saturated sodium chloride solution, dried over anhydrous magnesium sulfate, and concentrated under reduced pressure to obtain 2.23 g of 1-(3-chloro-2-pyridinyl)-1H-pyrazole-3-carbaldehyde O-methyloxime of the formula:

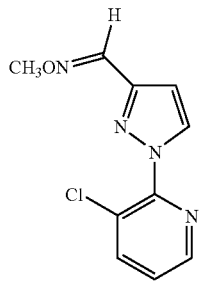

as a mixture of an E isomer and Z isomer (E isomer: Z isomer=3:1).

1-(3-Chloro-2-pyridinyl)-1H-pyrazole-3-carbaldehyde O-methyloxime

¹H-NMR (CDCl₃, TMS) δ (ppm):
E isomer: 3.99 (3H, s), 6.84 (1H, d, J=3 Hz), 7.30 (1H, dd, J=8 Hz, 5 Hz), 7.92 (1H, dd, J=8 Hz, 2 Hz), 8.12 (1H, dd, J=3 Hz, 1Hz), 8.25 (1H, s), 8.48 (1H, dd, J=5 Hz, 2 Hz).
Z isomer: 4.07 (3H, s), 7.18 (1H, d, J=3 Hz), 7.33 (1H, dd, J=8 Hz, 5 Hz), 7.67 (1H, s), 7.93 (1H, dd, J=8 Hz, 2 Hz), 8.14 (1H, dd, J=3 Hz, 1Hz), 8.49 (1H, dd, J=5 Hz, 2 Hz).

REFERENCE PREPARATION EXAMPLE 82-(6)

According to the same manner as that of Reference Preparation Example 23, 1-(3-chloro-2-pyridinyl)-1H-pyrazole-3-carbaldehyde O-methyloxime was used in place of 2-(3-bromo-1H-pyrazol-1-yl)-3-chloropyridine to obtain 1-(3-chloro-2-pyridinyl)-3-methoxyiminomethyl-1H-pyrazole-5-carboxylic acid of the formula:

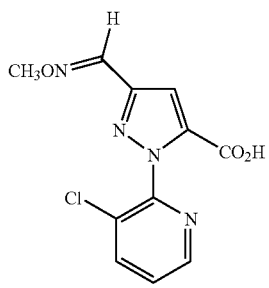

as a mixture of an E isomer and a Z isomer (E isomer: Z isomer=3:1).

1-(3-Chloro-2-pyridinyl)-3-methoxyiminomethyl-1H-pyrazole-5-carboxylic acid $^1$H-NMR (CDCl$_3$, TMS) δ (ppm):
E isomer: 4.00 (3H, s), 7.39 (1H, s), 7.45 (1H, dd, J=8 Hz, 5 Hz), 7.92 (1H, dd, J=8 Hz, 2 Hz), 8.15 (1H, s), 8.51 (1H, dd, J=5 Hz, 2 Hz).
Z isomer: 4.08 (3H, s), 7.38 (1H, s), 7.51 (1H, dd, J=8 Hz, 5 Hz), 7.60 (1H, s), 7.94 (1H, dd, J=8 Hz, 2 Hz), 8.51 (1H, dd, J=5 Hz, 2 Hz).

REFERENCE PREPARATION EXAMPLE 82-(7)

A mixture of 0.70 g of 1-(3-chloro-2-pyridinyl)-3-methoxyiminomethyl-1H-pyrazole-5-carboxylic acid and 0.55 ml of thionyl chloride was heated to reflux for 1 hour. The reaction mixture was allowed to cool to room temperature, and then concentrated under reduced pressure. After the resulting residue was dissolved in 10 ml of acetonitrile, 0.46 g of 2-amino-5-chloro-3-methylbenzoic acid was added and the mixture was stirred at room temperature for 10 minutes. To the mixture was added 0.35 ml of triethylamine, and the mixture was stirred at room temperature for 20 minutes. Further 70 ml of triethylamine was added, and the mixture was stirred at room temperature for 20 minutes. Then 0.21 ml of methanesulfonyl chloride was added, and the mixture was stirred at room temperature for 17 hours. Water was added to the reaction mixture, and the mixture was extracted with chloroform three times. The organic layers were combined, washed with an aqueous saturated sodium chloride solution, dried over anhydrous magnesium sulfate, and concentrated under reduced pressure. The residue was subjected to silica gel column chromatography to obtain 0.16 g of 6-chloro-2-[1-(3-chloro-2-pyridinyl)-3-cyano-1H-pyrazol-5-yl]-8-methyl-4H-3,1-benzoxazine-4-one of the formula:

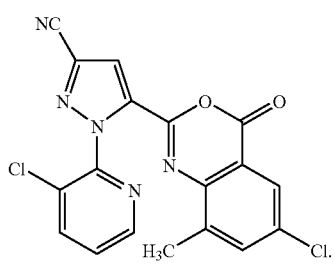

6-Chloro-2-[1-(3-chloro-2-pyridinyl)-3-cyano-1H-pyrazol-5-yl]-8-methyl-4H-3,1-benzoxazine-4-one $^1$H-NMR (CDCl$_3$, TMS) δ (ppm): 1.83 (3H, s), 7.52 (1H, dd, J=2 Hz, 1Hz), 7.56 (1H, dd, 8 Hz, 5 Hz), 7.58 (1H, s), 7.99-8.03 (2H, m), 8.58 (1H, dd, J=5 Hz, 2 Hz).

REFERENCE PREPARATION EXAMPLE 83

To a mixture of 10.6 ml of methylhydrazine, 50 ml of methanol and 8.0 g of sodium hydroxide was added dropwise 15.4 ml of methyl chloroformate under ice-cooling, and the mixture was stirred at room temperature for 1 hour. The reaction mixture was filtered, and the filtrate was concentrated. The residue was distilled under reduced pressure (50 to 80° C./15 mmHg) to obtain 13.4 g of N-methyl-N-methoxycarbonylhydrazine. N-methyl-N-methoxycarbonylhydrazine
$^1$H-NMR (CDCl$_3$, TMS) δ (ppm): 3.11 (3H, s), 3.73 (3H, s), 4.13 (2H, brs).

REFERENCE PREPARATION EXAMPLE 84

A mixture of 1.0 g of 2-[3-bromo-1-(3-chloro-2-pyridinyl)-1H-pyrazol-5-yl]-6-chloro-8-methyl-4H-3,1-benzoxazine-4-one, 0.35 ml of methylhydrazine and 20 ml of tetrahydrofuran was stirred at room temperature for 24 hours. Water was poured into the reaction mixture and the mixture was extracted with ethyl acetate three times. The combined organic layer was washed with an aqueous saturated sodium chloride solution, dried over anhydrous sodium sulfate, and concentrated under reduced pressure. The residue was subjected to silica gel column chromatography to obtain 0.85 g of 3-bromo-N-[4-chloro-2-(N-methylhydrazinocarbonyl)-6-methylphenyl]-1-(3-chloro-2-pyridinyl)-1H-pyrazole-5-carboxamide of the formula:

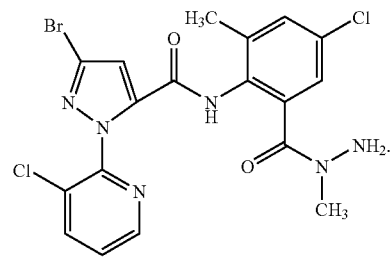

3-Bromo-N-[4-chloro-2-(N-methylhydrazinocarbonyl)-6-methylphenyl]-1-(3-chloro-2-pyridinyl)-1H-pyrazole-5-carboxamide $^1$H-NMR (CDCl$_3$, TMS) δ (ppm): 2.20 (3H, s), 3.21 (3H, s), 3.74 (3H, brs), 7.05 (1H, s), 7.26-7.38 (3H, m), 7.86 (1H, dd, J=8 Hz, 2 Hz), 8.03 (1H, s), 8.42 (1H, dd, J=5 Hz, 2 Hz), 9.47 (1H, s).

REFERENCE PREPARATION EXAMPLE 85-(1)

To a mixture of 0.34 g of 2-amino-4-chloro-3-methylbenzoic acid and 10 ml of N,N-dimethylformamide was added 0.26 g of N-chlorosuccinimide at room temperature, and the mixture was stirred at room temperature for 5 hours. After 30 ml of water was poured into the reaction mixture, the mixture was extracted with ethyl acetate three times. The organic layers were combined, dried over anhydrous sodium sulfate, and concentrated under reduced pressure to obtain 0.22 g of 2-amino-4,5-dichloro-3-methylbenzoic acid of the formula:

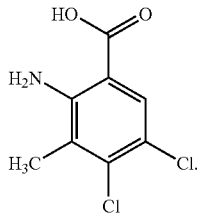

2-Amino-4,5-dichloro-3-methylbenzoic acid $^1$H-NMR (DMSO-$d_6$, TMS) δ: 2.25 (3H, s), 7.76 (1H, s).

REFERENCE PREPARATION EXAMPLE 85-(2)

According to the same manner as that of Reference Preparation Example 46-(1), 2-amino-4,5-dichloro-3-methylbenzoic acid was used in place of 2-amino-3,5-dibromobenzoic acid to obtain 2-[3-bromo-1-(3-chloro-2-pyridinyl)-1H-pyrazol-5-yl]-6,7-dichloro-8-methyl-4H-3,1-benzoxazine-4-one of the formula:

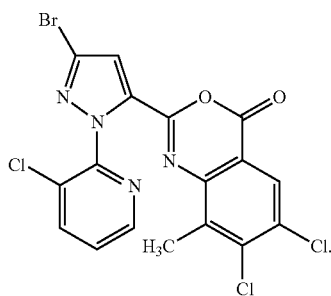

2-[3-Bromo-1-(3-chloro-2-pyridinyl)-1H-pyrazol-5-yl]-6,7-dichloro-8-methyl-4H-3,1-benzoxazine-4-one $^1$H-NMR (DMSO-$d_6$, TMS) δ: 1.82 (3H, s), 7.57 (1H, s), 7.77 (1H, dd, J=8 Hz, 5 Hz), 8.14 (1H, s), 8.36 (1H, d, J=8 Hz), 8.64 (1H, d, J=5 Hz).

REFERENCE PREPARATION EXAMPLE 86-(1)

A mixture of 1.0 g of 2-amino-5-iodo-3-methylbenzoic acid, 0.45 g of copper cyanide and 10 ml of N,N-dimethylformamide was stirred at 150° C. for 9 hours. The reaction mixture was concentrated under reduced pressure. Into the residue, 20 ml of water and 2 ml of ethylenediamine were poured, and the mixture was stirred at room temperature for 1 hour. After the reaction mixture was filtered, the filtrate was adjusted to around pH 5 by an addition of concentrated hydrochloric acid, and then extracted with ethyl acetate three times. The combined organic layer was dried over sodium sulfate, and concentrated under reduced pressure to obtain 0.40 g of 2-amino-5-cyano-3-methylbenzoic acid of the formula:

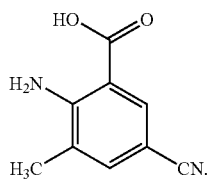

2-Amino-5-cyano-3-methylbenzoic acid $^1$H-NMR (DMSO-$d_6$, TMS) δ: 2.13 (3H, s), 7.34 (2H, brs), 7.51 (1H, d, J=2 Hz), 7.97 (1H, d, J=2 Hz).

REFERENCE PREPARATION EXAMPLE 86-(2)

According to the same manner as that of Reference Preparation Example 46-(1), 2-amino-5-cyano-3-methylbenzoic acid was used in place of 2-amino-3,5-dibromobenzoic acid to obtain 2-[3-bromo-1-(3-chloro-2-pyridinyl)-1H-pyrazol-5-yl]-8-methyl-6-cyano-4H-3,1-benzoxazine-4-one of the formula:

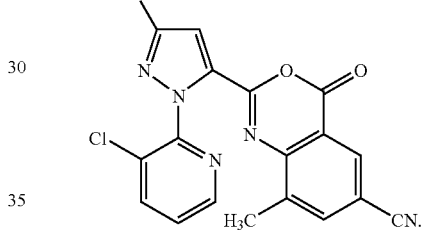

2-[3-Bromo-1-(3-chloro-2-pyridinyl)-1H-pyrazol-5-yl]-8-methyl-6-cyano-4H-3,1-benzoxazine-4-one $^1$H-NMR (DMSO-$d_6$, TMS) δ: 1.73 (3H, s), 7.60 (1H, s), 7.77 (1H, dd, J=8 Hz, 5 Hz), 8.10 (1H, d, J=2 Hz), 8.34-8.39 (2H, m), 8.63 (1H, d, J=5 Hz).

REFERENCE PREPARATION EXAMPLE 87-(1)

To a mixture of 15.1 g of N-methyl anthranilic acid and 300 ml acetic acid was added dropwise 3.2 g of bromine over 15 minutes. The resulting mixture was stirred at room temperature for 5 hours. Further 1.6 g of bromine was added dropwise thereto over 15 minutes, and the mixture was stirred at room temperature for 3 hours. The reaction mixture was filtered, and the resulting solid was washed successively with acetic acid, ethyl acetate and acetone to obtain 23 g of 3,5-dibromo-2-methylaminobenzoic acid of the formula:

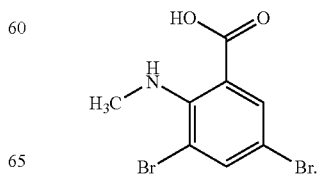

3,5-Dibromo-2-methylaminobenzoic acid $^1$H-NMR (DMSO-d$_6$, TMS) δ: 2.89-2.92 (3H, m), 7.76-7.79 (1H, m), 7.83-7.86 (1H, m).

REFERENCE PREPARATION EXAMPLE 87-(2)

A mixture of 1.0 g of 3-bromo-1-(3-chloro-2-pyridinyl)-1H-pyrazole-5-carboxylic acid, 2 ml of thionyl chloride and one drop of N,N-dimethylformamide was stirred at 80° C. for 1 hour. After the reaction mixture was concentrated under reduced pressure, 10 ml of hexane was added and the mixture was further concentrated under reduced pressure. The resulting residue was mixed with 20 ml of acetonitrile and 0.93 g of 3,5-dibromo-2-methylaminobenzoic acid. After the mixture was stirred at room temperature for 1 hour, 0.6 g of triethylamine was added and the mixture was further stirred at room temperature for 1 hour. The reaction mixture was poured into 30 ml of water, and the mixture was extracted with ethyl acetate three times. The organic layers were combined, washed successively with water and an aqueous saturated sodium chloride solution, dried over anhydrous sodium sulfate, and concentrated under reduced pressure. The residue was washed with methyl t-butyl ether to obtain 1.3 g of 3,5-dibromo-2-{N-[3-bromo-1-(3-chloro-2-pyridinyl)-1H-pyrazole-5-carbonyl]-N-methylamino}benzoic acid of the formula:

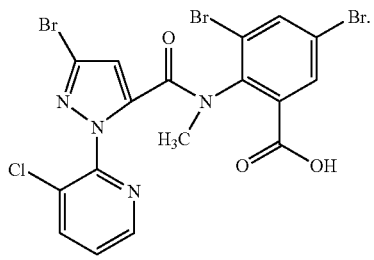

3,5-Dibromo-2-{N-[3-bromo-1-(3-chloro-2-pyridinyl)-1H-pyrazole-5-carbonyl]-N-methylamino}benzoic acid $^1$H-NMR (DMSO-d$_6$, TMS) δ: 2.98-3.34 (3H, m), 5.95 (1H, s), 7.62 (1H, dd, J=8 Hz, 5 Hz), 7.70 (1H, d, J=2 Hz), 7.89 (1H, d, J=2 Hz), 8.18 (1H, d, J=8 Hz), 8.49 (1H, d, J=5 Hz).

REFERENCE PREPARATION EXAMPLE 88

To a mixture of 0.13 g of N,N'-dimethylhydrazine dihydrochloride, 1 ml of water, 0.14 g of potassium carbonate and 10 ml of tetrahydrofuran was added 0.23 g of 2-[3-bromo-1-(3-chloro-2-pyridinyl)-1H-pyrazol-5-yl]-6-chloro-8-methyl-4H-3,1-benzoxazine-4-one, and the resulting mixture was stirred at room temperature for 3 hours. The reaction mixture was poured into 30 ml of water, and the mixture was extracted with ethyl acetate three times. The organic layers were combined, dried over anhydrous sodium sulfate, and concentrated under reduced pressure. The residue was washed with ethyl acetate to obtain 0.35 g of 3-bromo-N-[4-chloro-2-(N,N'-dimethylhydrazinocarbonyl)-6-methylphenyl]-1-(3-chloro-2-pyridinyl)-1H-pyrazole-5-carboxamide of the formula:

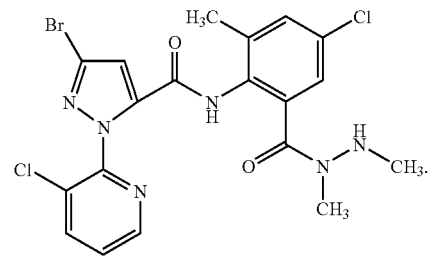

3-Bromo-N-[4-chloro-2-(N,N'-dimethylhydrazinocarbonyl)-6-methylphenyl]-1-(3-chloro-2-pyridinyl)-1H-pyrazole-5-carboxamide $^1$H-NMR (DMSO-d$_6$, TMS) δ: 1.99-2.40 (6H, m), 2.98-3.09 (3H, m), 4.61 (0.7H, brs), 5.68 (0.3H, brs), 7.14-7.51 (3H, m), 7.61 (1H, dd, J=8 Hz, 5 Hz), 8.18 (1H, d, J=5 Hz), 8.50 (1H, d, J=2 Hz), 10.03 (0.6H, brs), 10.39 (0.4H, brs).

REFERENCE PREPARATION EXAMPLE 89-(1)

To a mixture of 0.78 g of 2-amino-5-fluorobenzoic acid and 100 ml of N,N-dimethylformamide was added 1.1 g of N-bromosuccinimide at room temperature, and the mixture was stirred at room temperature for 5 hours. After water was added to the reaction mixture, a deposited precipitate was collected by filtration, and then washed with acetone to obtain 0.43 g of 2-amino-3-bromo-5-fluorobenzoic acid of the formula:

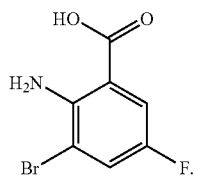

2-Amino-3-bromo-5-fluorobenzoic acid $^1$H-NMR (DMSO-d$_6$, TMS) δ: 7.55 (1H, dd, J=8 Hz, 3 Hz), 7.71 (1H, dd, J=8 Hz, 3 Hz).

REFERENCE PREPARATION EXAMPLE 89-(2)

According to the same manner as that of Reference Preparation Example 46-(1), 2-amino-3-bromo-5-fluorobenzoic acid was used in place of 2-amino-3,5-dibromobenzoic acid to obtain 2-[3-bromo-1-(3-chloro-2-pyridinyl)-1H-pyrazol-5-yl]-8-bromo-6-fluoro-4H-3,1-benzoxazine-4-one of the formula:

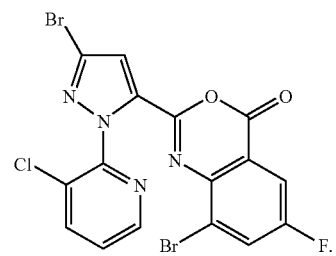

2-[3-Bromo-1-(3-chloro-2-pyridinyl)-1H-pyrazol-5-yl]-8-bromo-6-fluoro-4H-3,1-benzoxazine-4-one ¹H-NMR (DMSO-d₆, TMS) δ: 7.54 (1H, s), 7.72 (1H, dd, J=8 Hz, 5 Hz), 7.92 (1H, dd, J=8 Hz, 3 Hz), 8.15 (1H, dd, J=8 Hz, 3 Hz), 8.32 (1H, dd, J=8 Hz, 1Hz), 8.59 (1H, dd, J=5 Hz, 1Hz).

REFERENCE PREPARATION EXAMPLE 90-(1)

According to the same manner as that of Reference Preparation Example 63-(1), 2-phenylaniline was used in place of 3-chloro-2-methylaniline to obtain N-(biphenyl-2-yl)-2-(hydroxyimino)acetamide of the formula:

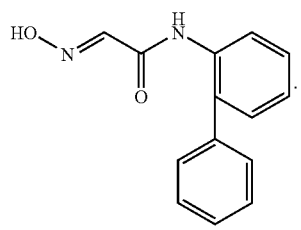

N-(biphenyl-2-yl)-2-(hydroxyimino)acetamide

¹H-NMR (DMSO-d₆, TMS) δ: 7.27-7.48 (9H, m), 7.83 (1H, d, J=8 Hz), 9.18 (1H, s), 12.14 (1H, s).

REFERENCE PREPARATION EXAMPLE 90-(2)

According to the same manner as that of Reference Preparation Example 63-(2), N-(biphenyl-2-yl)-2-(hydroxyimino)acetamide was used in place of N-(3-chloro-2-methylphenyl)-2-(hydroxyimino)acetamide to obtain 7-phenyl-1H-indole-2,3-dione of the formula:

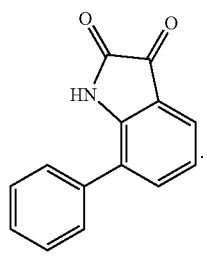

7-Phenyl-1H-indole-2,3-dione

¹H-NMR (DMSO-d₆, TMS) δ: 7.18 (1H, t, J=8 Hz), 7.40-7.63 (7H, m), 10.91 (1H, s).

REFERENCE PREPARATION EXAMPLE 90-(3)

According to the same manner as that of Reference Preparation Example 63-(3), 7-phenyl-1H-indole-2,3-dione was used in place of 6-chloro-7-methyl-1H-indole-2,3-dione to obtain 2-amino-3-phenylbenzoic acid of the formula:

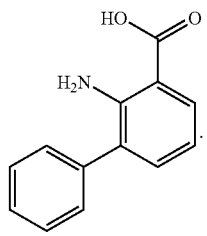

2-Amino-3-phenylbenzoic acid

¹H-NMR (DMSO-d₆, TMS) δ: 6.65 (1H, t, J=8 Hz), 7.17 (1H, d, J=7 Hz), 7.35-7.55 (5H, m), 7.78 (1H, d, J=8 Hz).

REFERENCE PREPARATION EXAMPLE 90-(4)

According to the same manner as that of Reference Preparation Example 46-(1), 2-amino-3-phenylbenzoic acid was used in place of 2-amino-3,5-dibromobenzoic acid to obtain 2-[3-bromo-1-(3-chloro-2-pyridinyl)-1H-pyrazol-5-yl]-8-phenyl-4H-3,1-benzoxazine-4-one of the formula:

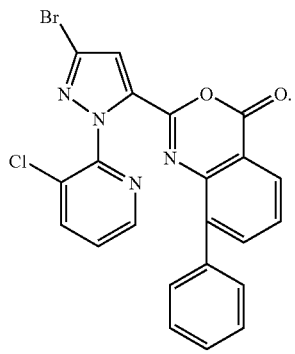

2-[3-Bromo-1-(3-chloro-2-pyridinyl)-1H-pyrazol-5-yl]-8-phenyl-4H-3,1-benzoxazine-4-one ¹H-NMR (DMSO-d₆, TMS) δ: 7.05-7.48 (7H, m), 7.61-7.89 (3H, m), 8.09-8.28 (2H, m)

REFERENCE PREPARATION EXAMPLE 91

According to the same manner as that of Reference Preparation Example 71-(5), 2-amino-3,5-dibromobenzoic acid was used in place of 2-amino-5-chloro-3-methylbenzoic acid to obtain 6,8-dibromo-2-[4-bromo-1-(3-chloro-2-pyridinyl)-1H-pyrrol-2-yl]-4H-3,1-benzoxazine-4-one of the formula:

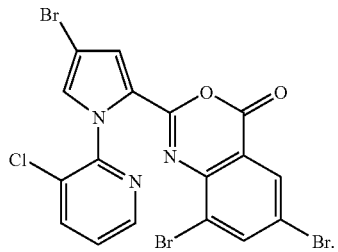

6,8-Dibromo-2-[4-bromo-1-(3-chloro-2-pyridinyl)-1H-pyrrol-2-yl]-4H-3,1-benzoxazine-4-one $^1$H-NMR (CDCl$_3$, TMS) δ (ppm): 7.11 (1H, d, J=2 Hz), 7.37 (1H, d, J=2 Hz), 7.41 (1H, dd, J=8 Hz, 5 Hz), 7.92 (1H, dd, J=8 Hz, 2 Hz), 7.97 (1H, d, J=2 Hz), 8.20 (1H, d, J=2 Hz), 8.51 (1H, dd, J=5 Hz, 2 Hz).

REFERENCE PREPARATION EXAMPLE 92

According to the same manner as that of Reference Preparation Example 71-(5), 2-amino-3-bromo-5-chlorobenzoic acid was used in place of 2-amino-5-chloro-3-methylbenzoic acid to obtain 8-bromo-2-[4-bromo-1-(3-chloro-2-pyridinyl)-1H-pyrrol-2-yl]-6-chloro-4H-3,1-benzoxazine-4-one of the formula:

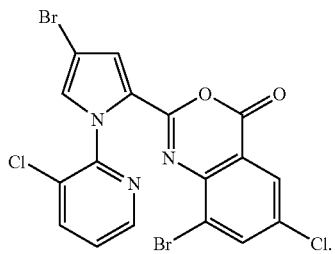

8-Bromo-2-[4-bromo-1-(3-chloro-2-pyridinyl)-1H-pyrrol-2-yl]-6-chloro-4H-3,1-benzoxazine-4-one $^1$H-NMR (CDCl$_3$, TMS) δ (ppm): 7.11 (1H, d, J=2 Hz), 7.37 (1H, d, J=2 Hz), 7.41 (1H, dd, J=8 Hz, 5 Hz), 7.82 (1H, d, J=2 Hz), 7.92 (1H, dd, J=8 Hz, 2 Hz), 8.05 (1H, d, J=2 Hz), 8.51 (1H, dd, J=5 Hz, 2 Hz).

REFERENCE PREPARATION EXAMPLE 93

According to the same manner as that of Reference Preparation Example 71-(5), 2-amino-5-cyano-3-methylbenzoic acid was used in place of 2-amino-5-chloro-3-methylbenzoic acid to obtain 2-[4-bromo-1-(3-chloro-2-pyridinyl)-1H-pyrrol-2-yl]-6-cyano-8-methyl-4H-3,1-benzoxazine-4-one of the formula:

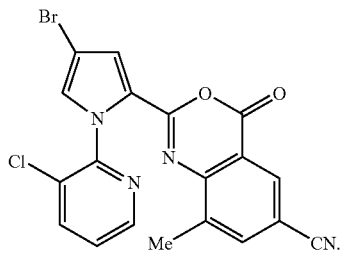

2-[4-Bromo-1-(3-chloro-2-pyridinyl)-1H-pyrrol-2-yl]-6-cyano-8-methyl-4H-3,1-benzoxazine-4-one $^1$H-NMR (DMSO-d$_6$, TMS) δ (ppm): 1.68 (3H, s), 7.35 (1H, d, J=2 Hz), 7.67 (1H, dd, J=8 Hz, 5 Hz), 7.70 (1H, d, J=2 Hz), 7.97 (1H, s), 8.23 (1H, dd, J=8 Hz, 2 Hz), 8.28 (1H, s), 8.57 (1H, dd, J=5 Hz, 2 Hz).

REFERENCE PREPARATION EXAMPLE 94-(1)

According to the same manner as that of Reference Preparation Example 63-(1), 2-ethylaniline was used in place of 3-chloro-2-methylaniline to obtain N-(2-ethylphenyl)-2-(hydroxyimino)acetamide of the formula:

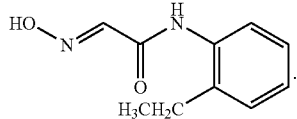

N-(2-ethylphenyl)-2-(hydroxyimino)acetamide $^1$H-NMR (DMSO-d$_6$, TMS) δ:1.12 (3H, t, J=8 Hz), 2.59 (2H, q, J=8 Hz), 7.15-7.27 (3H, m), 7.43 (1H, dd, J=6 Hz, 4 Hz), 7.67 (1H, s), 9.49 (1H, s), 12. 17 (1H, s).

REFERENCE PREPARATION EXAMPLE 94-(2)

According to the same manner as that of Reference Preparation Example 63-(2), N-(2-ethylphenyl)-2-(hydroxyimino)acetamide was used in place of N-(3-chloro-2-methylphenyl)-2-(hydroxyimino)acetamide to obtain crude 7-ethyl-1H-indole-2,3-dione of the formula:

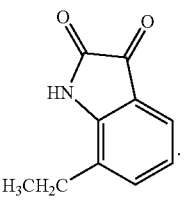

REFERENCE PREPARATION EXAMPLE 94-(3)

A mixture of 1.0 g of crude 7-ethyl-1H-indole-2,3-dione and 3 ml of a 2N aqueous sodium hydroxide solution was added dropwise to 2 g of aqueous hydrogen peroxide (30%) at room temperature, and the resulting mixture was stirred at room temperature for 1 hour. The reaction mixture was adjusted to pH 4 by an addition of 2N hydrochloric acid, and a deposited precipitate was collected by filtration. The resulting filter cake was partitioned between ethyl acetate and a saturated sodium hydrogen carbonate solution. The aqueous layer was adjusted to pH 4 by an addition of 2N hydrochloric acid, and a deposited precipitate was collected by filtration to obtain 0.42 g of 2-amino-3-ethylbenzoic acid of the formula:

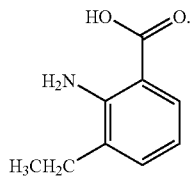

2-Amino-3-ethylbenzoic acid $^1$H-NMR (DMSO-d$_6$, TMS) δ: 1.15 (3H, t, J=7 Hz), 2.44-2.53 (2H, m), 6.50 (1H, dd, J=8 Hz, 7 Hz), 7.15 (1H, d, J=7 Hz), 7.62 (1H, d, J=8 Hz).

REFERENCE PREPARATION EXAMPLE 94-(4)

According to the same manner as that of Reference Preparation Example 46-(1), 2-amino-3-ethylbenzoic acid was used in place of 2-amino-3,5-dibromobenzoic acid to obtain 2-[3-bromo-1-(3-chloro-2-pyridinyl)-1H-pyrazol-5-yl]-8-ethyl-4H-3,1-benzoxazine-4-one of the formula:

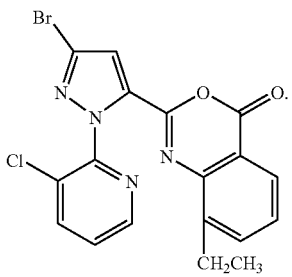

2-[3-Bromo-1-(3-chloro-2-pyridinyl)-1H-pyrazol-5-yl]-8-ethyl-4H-3,1-benzoxazine-4-one $^1$H-NMR (DMSO-d$_6$, TMS) δ: 0.81 (3H, t, J=7 Hz), 2.07 (2H, q, J=7 Hz), 7.47-7.57 (2H, m), 7.70 (1H, d, J=7 Hz), 7.79 (1H, dd, J=8.5 Hz), 7.95 (1H, d, J=7 Hz), 8.37 (1H, d, J=8 Hz), 8.64 (1H, d, J=5 Hz)

REFERENCE PREPARATION EXAMPLE 95-(1)

According to the same manner as that of Reference Preparation Example 67-(1), cyclohexylhydrazine hydrochloride was used in place of tert-butylhydrazine hydrochloride to obtain 1-cyclohexyl-3-trifluoromethyl-1H-pyrazole of the formula:

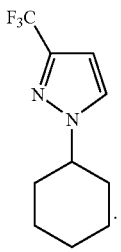

1-Cyclohexyl-3-trifluoromethyl-1H-pyrazole $^1$H-NMR (CDCl$_3$, TMS) δ (ppm): 1.19-1.33 (3H, m), 1.67-1.77 (2H, m), 1.93-1.99 (4H, m), 2.16-2.19 (1H, m), 4.13-4.20 (1H, m), 6.49 (1H, s), 7.45 (1H, s).

REFERENCE PREPARATION EXAMPLE 95-(2)

According to the same manner as that of Reference Preparation Example 15, 1-cyclohexyl-3-trifluoromethyl-1H-pyrazole was used in place of 3-chloro-2-(3-trifluoromethyl-1H-pyrazole-1-yl)pyridine to obtain 1-cyclohexyl-3-trifluoromethyl-1H-pyrazole-5-carboxylic acid of the formula:

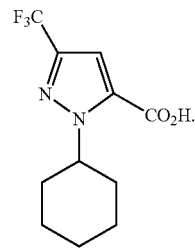

1-Cyclohexyl-3-trifluoromethyl-1H-pyrazole-5-carboxylic acid $^1$H-NMR (CDCl$_3$, TMS) δ (ppm): 1.26-2.00 (10H, m), 5.10-5.18 (1H, m), 7.15 (1H, s).

REFERENCE PREPARATION EXAMPLE 95-(3)

According to the same manner as that of Reference Preparation Example 13, 1-cyclohexyl-3-trifluoromethyl-1H-pyrazole-5-carboxylic acid was used in place of 1-(3-chloro-2-pyridinyl)-1H-pyrazole-5-carboxylic acid to obtain 6-chloro-2-(1-cyclohexyl-3-trifluoromethyl-1H-pyrazol-5-yl)-8-methyl-4H-3,1-benzoxazine-4-one of the formula:

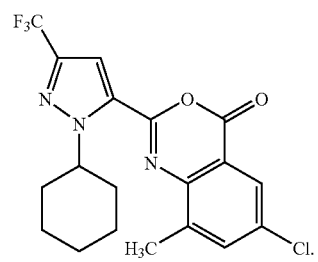

6-Chloro-2-(1-cyclohexyl-3-trifluoromethyl-1H-pyrazol-5-yl)-8-methyl-4H-3,1-benzoxazine-4-one $^1$H-NMR (CDCl$_3$, TMS) δ (ppm): 1.26-1.54 (4H, m), 1.77 (1H, d, J=2 Hz), 1.96-2.62 (5H, m), 2.62 (3H, s), 5.51-5.58 (1H, m), 7.31 (1H, s), 7.69 (1H, d, J=2 Hz), 8.07 (1H, d, J=2 Hz).

REFERENCE PREPARATION EXAMPLE 95-(4)

According to the same manner as that of Reference Preparation Example 1, 6-chloro-2-(1-cyclohexyl-3-trifluoromethyl-1H-pyrazol-5-yl)-8-methyl-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[4-chloro-2-(hydrazinocarbonyl)-6-methylphenyl]-1-cyclohexyl-3-trifluoromethyl-1H-pyrazole-5-carboxamide of the formula:

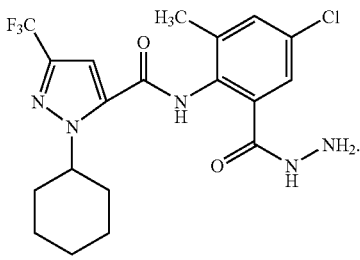

N-[4-chloro-2-(hydrazinocarbonyl)-6-methylphenyl]-1-cyclohexyl-3-trifluoromethyl-1H-pyrazole-5-carboxamide $^1$H-NMR (DMSO-d$_6$, TMS) δ (ppm): 1.20-1.39 (3H, m), 1.66 (1H, d, J=12 Hz), 1.75-1.84 (4H, m), 1.98 (2H, d, J=10 Hz), 2.25 (3H, s), 4.36 (2H, brs), 5.03-5.09 (1H, m), 7.35 (2H, s), 7.52 (1H, s), 9.62 (1H, brs), 10.17 (1H, brs).

REFERENCE PREPARATION EXAMPLE 96-(1)

To a solution of 1.0 g of 3-chloro-2-(2-formyl-1H-pyrrol-1-yl)pyridine in 15 ml of N,N-dimethylformamide, 1.9 g of N-bromosuccinimide was added. The mixture was stirred at room temperature for 3 hours. Water was poured into the reaction mixture, and the mixture was extracted with ethyl acetate three times. The organic layers were combined, washed with an aqueous saturated sodium chloride solution, dried over anhydrous magnesium sulfate, and concentrated under reduced pressure to obtain 1.2 g of 4,5-dibromo-1-(3-chloro-2-pyridinyl)-1H-pyrrole-2-carbaldehyde of the formula:

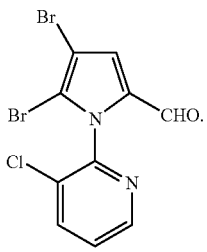

4,5-Dibromo-1-(3-chloro-2-pyridinyl)-1H-pyrrole-2-carbaldehyde $^1$H-NMR (CDCl$_3$, TMS) δ (ppm): 7.14 (1H, s), 7.47 (1H, dd, J=8 Hz, 5 Hz), 7.93 (1H, dd, J=8 Hz, 2 Hz), 8.53 (1H, dd, J=5 Hz, 2 Hz), 9.33 (1H, s).

REFERENCE PREPARATION EXAMPLE 96-(2)

To a mixture of 1.0 g of 4,5-dibromo-1-(3-chloro-2-pyridinyl)-1H-pyrrole-2-carbaldehyde, 15 ml of acetone and 7 ml of water was slowly added 1.3 g of potassium permanganate at 40° C. The resulting mixture was stirred at 60° C. for 2 hours. Precipitates in the reaction mixture were removed by filtration. The resulting filtrate was washed with chloroform two times. The aqueous layer was adjusted to around pH 3 by an addition of 2N hydrochloric acid and then extracted with ethyl acetate three times. The organic layers were combined, washed with an aqueous saturated sodium chloride solution, dried over anhydrous magnesium sulfate, and then concentrated under reduced pressure to obtain 0.69 g of 4,5-dibromo-1-(3-chloro-2-pyridinyl)-1H-pyrrole-2-carboxylic acid of the formula:

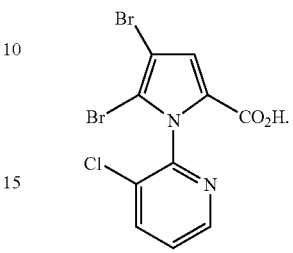

4,5-Dibromo-1-(3-chloro-2-pyridinyl)-1H-pyrrole-2-carboxylic acid $^1$H-NMR (DMSO-d$_6$, TMS) δ (ppm): 7.15 (1H, m), 7.64 (1H, dd, J=8 Hz, 5 Hz), 8.19 (1H, dd, J=8 Hz, 2 Hz), 8.56 (1H, dd, J=5 Hz, 2 Hz).

REFERENCE PREPARATION EXAMPLE 96-(3)

According to the same manner as that of Reference Preparation Example 71-(5), 4,5-dibromo-1-(3-chloro-2-pyridinyl)-1H-pyrrole-2-carboxylic acid was used in place of 4-bromo-1-(3-chloro-2-pyridinyl)-1H-pyrrole-2-carboxylic acid to obtain 2-[4,5-dibromo-1-(3-chloro-2-pyridinyl)-1H-pyrrol-2-yl]-6-chloro-8-methyl-4H-3,1-benzoxazine-4-one of the formula:

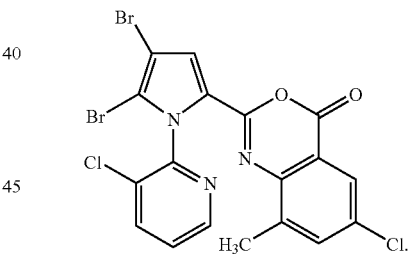

2-[4,5-Dibromo-1-(3-chloro-2-pyridinyl)-1H-pyrrol-2-yl]-6-chloro-8-methyl-4H-3,1-benzoxazine-4-one $^1$H-NMR (CDCl$_3$, TMS) δ (ppm): 1.72 (3H, s), 7.40 (2H, s), 7.48 (1H, dd, J=8 Hz, 5 Hz), 7.92 (1H, s), 7.98 (1H, dd, J=8 Hz, 2 Hz), 8.58 (1H, dd, J=5 Hz, 2 Hz).

REFERENCE PREPARATION EXAMPLE 96-(4)

According to the same manner as that of Reference Preparation Example 71-(6), 2-[4,5-dibromo-1-(3-chloro-2-pyridinyl)-1H-pyrrol-2-yl]-6-chloro-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 4,5-dibromo-N-[4-chloro-2-(hydrazinocarbonyl)-6-methylphenyl]-1-(3-chloro-2-pyridinyl)-1H-pyrrole-2-carboxamide of the formula:

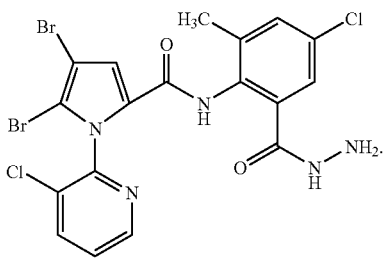

4,5-Dibromo-N-[4-chloro-2-(hydrazinocarbonyl)-6-methylphenyl]-1-(3-chloro-2-pyridinyl)-1H-pyrrole-2-carboxamide $^1$H-NMR (CDCl$_3$, TMS) δ (ppm): 2.15 (3H, s), 4.03 (2H, brs), 7.15 (1H, s), 7.22 (1H, d, J=3 Hz), 7.25 (1H, d, J=3 Hz), 7.37 (1H, dd, J=8 Hz, 5 Hz), 7.70 (1H, brs), 7.86 (1H, dd, J=8 Hz, 2 Hz), 8.47 (1H, dd, J=5 Hz, 2 Hz), 9.50 (1H, brs).

REFERENCE PREPARATION EXAMPLE 97-(1)

To a solution of 1.0 g of 3-chloro-2-(2-formyl-1H-pyrrol-1-yl)pyridine in 15 ml of N,N-dimethylformamide was added 0.68 g of N-chlorosuccinimide. The resulting mixture was stirred at 50° C. for 2 days. Water was poured into the reaction mixture, and the mixture was extracted with ethyl acetate two times. The organic layers were combined, washed successively with water and an aqueous saturated sodium chloride solution, dried over anhydrous magnesium sulfate, and concentrated under reduced pressure. The residue was subjected to silica gel column chromatography to obtain 0.35 g of 4-chloro-1-(3-chloro-2-pyridinyl)-1H-pyrrole-2-carbaldehyde of the formula:

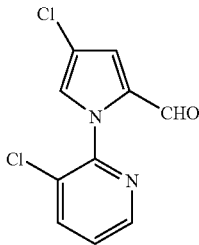

and 0.31 g of 5-chloro-1-(3-chloro-2-pyridinyl)-1H-pyrrole-2-carbaldehyde of the formula:

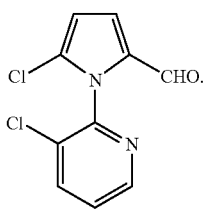

4-Chloro-1-(3-chloro-2-pyridinyl)-1H-pyrrole-2-carbaldehyde $^1$H-NMR (CDCl$_3$, TMS) δ (ppm): 7.04 (1H, d, J=2 Hz), 7.10 (1H, dd, J=2 Hz, 1 Hz), 7.41 (1H, dd, J=8 Hz, 5 Hz), 7.89 (1H, dd, J=8 Hz, 2 Hz), 8.46 (1H, dd, J=5 Hz, 2 Hz), 9.50 (1H, d, J=1 Hz)

5-Chloro-1-(3-chloro-2-pyridinyl)-1H-pyrrole-2-carbaldehyde $^1$H-NMR (CDCl$_3$, TMS) δ (ppm): 6.41 (1H, d, J=4 Hz), 7.08 (1H, d, J=4 Hz), 7.45 (1H, dd, J=8 Hz, 5 Hz), 7.92 (1H, dd, J=8 Hz, 2 Hz), 8.54 (1H, dd, J=5 Hz, 2 Hz), 9.41 (1H, s)

REFERENCE PREPARATION EXAMPLE 97-(2)

According to the same manner as that of Reference Preparation Example 71-(4), 5-chloro-1-(3-chloro-2-pyridinyl)-1H-pyrrole-2-carbaldehyde was used in place of 4-bromo-1-(3-chloro-2-pyridinyl)-1H-pyrrole-2-carbaldehyde to obtain 5-chloro-1-(3-chloro-2-pyridinyl)-1H-pyrrole-2-carboxylic acid of the formula:

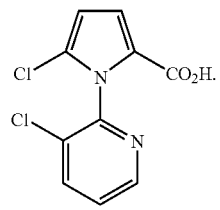

5-Chloro-1-(3-chloro-2-pyridinyl)-1H-pyrrole-2-carboxylic acid $^1$H-NMR (DMSO-d$_6$, TMS) δ (ppm): 6.39 (1H, d, J=4 Hz), 7.01 (1H, d, J=4 Hz), 7.62 (1H, dd, J=8 Hz, 5 Hz), 8.13 (1H, d, J=8 Hz), 8.54 (1H, d, J=5 Hz)

REFERENCE PREPARATION EXAMPLE 97-(3)

According to the same manner as that of Reference Preparation Example 71-(5), 5-chloro-1-(3-chloro-2-pyridinyl)-1H-pyrrole-2-carboxylic acid was used in place of 4-bromo-1-(3-chloro-2-pyridinyl)-1H-pyrrole-2-carboxylic acid to obtain 2-[5-chloro-1-(3-chloro-2-pyridinyl)-1H-pyrrol-2-yl]-6-chloro-8-methyl-4H-3,1-benzoxazine-4-one of the formula:

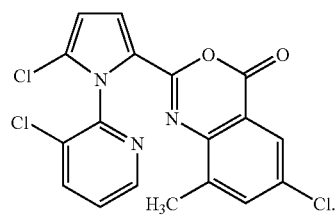

2-[5-Chloro-1-(3-chloro-2-pyridinyl)-1H-pyrrol-2-yl]-6-chloro-8-methyl-4H-3,1-benzoxazine-4-one $^1$H-NMR (CDCl$_3$, TMS) δ (ppm): 1.71 (3H, s), 6.43 (1H, d, J=4 Hz), 7.32 (1H, d, J=4 Hz), 7.38 (1H, d, J=2 Hz), 7.47 (1H, dd, J=8 Hz, 5 Hz), 7.92 (1H, d, J=2 Hz), 7.97 (1H, dd, J=8 Hz, 2 Hz), 8.59 (1H, dd, J=5 Hz, 2 Hz)

REFERENCE PREPARATION EXAMPLE 98-(1)

According to the same manner as that of Reference Preparation Example 71-(4), 1-(3-chloro-2-pyridinyl)-1H-pyrrole- 2-carbaldehyde was used in place of 4-bromo-1-(3-chloro-2-pyridinyl)-1H-pyrrole-2-carbaldehyde to obtain 1-(3-chloro-2-pyridinyl)-1H-pyrrole-2-carboxylic acid of the formula:

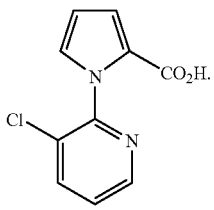

1-(3-Chloro-2-pyridinyl)-1H-pyrrole-2-carboxylic acid

¹H-NMR (DMSO-d$_6$, TMS)$_b$(ppm): 6.33-6.34 (1H, m), 6.97 (1H, d, J=4 Hz), 7.18 (1H, brs), 7.54 (1H, dd, J=8 Hz, 5 Hz), 8.10 (1H, d, J=8 Hz), 8.47-8.49 (1H, m)

REFERENCE PREPARATION EXAMPLE 98-(2)

According to the same manner as that of Reference Preparation Example 71-(5), 1-(3-chloro-2-pyridinyl)-1H-pyrrole-2-carboxylic acid was used in place of 4-bromo-1-(3-chloro-2-pyridinyl)-1H-pyrrole-2-carboxylic acid to obtain 2-[1-(3-chloro-2-pyridinyl)-1H-pyrrol-2-yl]-6-chloro-8-methyl-4H-3,1-benzoxazine-4-one of the formula:

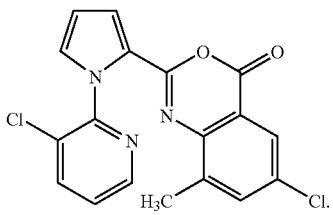

2-[1-(3-Chloro-2-pyridinyl)-1H-pyrrol-2-yl]-6-chloro-8-methyl-4H-3,1-benzoxazine-4-one ¹H-NMR (CDCl$_3$, TMS) δ (ppm): 1.73 (3H, s), 6.50 (1H, dd, J=4 Hz, 3 Hz), 7.09 (1H, dd, J=3 Hz, 2 Hz), 7.36 (1H, dd, J=4 Hz, 2 Hz), 7.39 (1H, s), 7.41 (1H, dd, J=8 Hz, 5 Hz), 7.90 (1H, dd, J=8 Hz, 2 Hz), 7.93 (1H, s), 8.52 (1H, dd, J=5 Hz, 2 Hz)

REFERENCE PREPARATION EXAMPLE 98-(3)

According to the same manner as that of Reference Preparation Example 71-(6), 2-[1-(3-chloro-2-pyridinyl)-1H-pyrrol-2-yl]-6-chloro-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain N-[4-chloro-2-(hydrazinocarbonyl)-6-methylphenyl]-1-(3-chloro-2-pyridinyl)-1H-pyrrole-2-carboxamide of the formula:

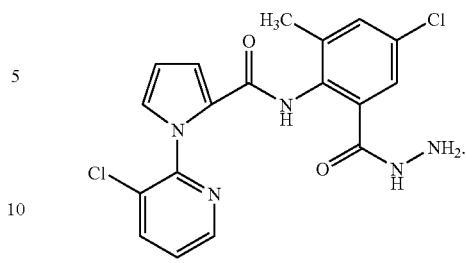

N-[4-chloro-2-(hydrazinocarbonyl)-6-methylphenyl]-1-(3-chloro-2-pyridinyl)-1H-pyrrole-2-carboxamide ¹H-NMR (DMSO-d$_6$, TMS) δ (ppm): 2.16 (3H, s), 4.40 (2H, brs), 6.37 (1H, dd, J=4 Hz, 3 Hz), 7.13-7.16 (2H, m), 7.31 (1H, d, J=2 Hz), 7.41 (1H, brs), 7.47 (1H, dd, J=8 Hz, 5 Hz), 8.02 (1H, d, J=8 Hz), 8.42 (1H, d, J=5 Hz), 9.56 (1H, brs), 9.84 (1H, brs)

REFERENCE PREPARATION EXAMPLE 99

According to the same manner as that of Reference Preparation Example 1, 2-[3-bromo-1-(3-chloro-2-pyridinyl)-1H-pyrazol-5-yl]-6-cyano-8-methyl-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain 3-bromo-1-(3-chloro-2-pyridinyl)-N-[4-cyano-2-(hydrazinocarbonyl)-6-methylphenyl]-1H-pyrazole-5-carboxamide of the formula:

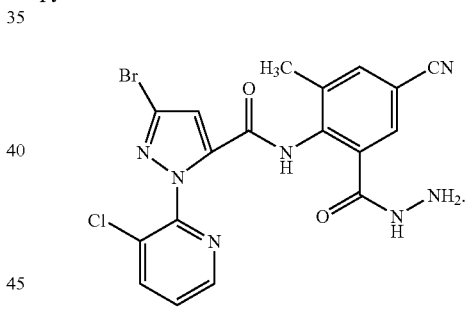

3-Bromo-1-(3-chloro-2-pyridinyl)-N-[4-cyano-2-(hydrazinocarbonyl)-6-methylphenyl]-1H-pyrazole-5-carboxamide ¹H-NMR (DMSO-d$_6$) δ: 2.19 (3H, s), 4.41 (2H, brs), 7.41 (1H, s), 7.61 (1H, dd, J=8 Hz, 5 Hz), 7.72 (1H, s), 7.88 (1H, s), 8.17 (1H, d, J=8 Hz), 8.50 (1H, d, J=5 Hz), 9.65 (1H, brs), 10.52 (1H, brs)

REFERENCE PREPARATION EXAMPLE 100-(1)

To a solution of 3.0 g of 3-chloro-2-(2-formyl-1H-pyrrol-1-yl)pyridine in 10 ml of N,N-dimethylformamide was added 4.5 g of N-chlorosuccinimide. The resulting mixture was stirred at 50° C. for 2 hours. Water was poured into the reaction mixture, and the mixture was extracted with ethyl acetate two times. The organic layers were combined, washed successively with water and an aqueous saturated sodium chloride solution, dried over anhydrous magnesium sulfate, and concentrated under reduced pressure to obtain 3.6 g of 4,5-dichloro-1-(3-chloro-2-pyridinyl)-1H-pyrrole-2-carbaldehyde of the formula:

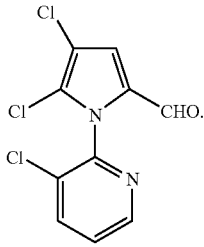

4,5-Dichloro-1-(3-chloro-2-pyridinyl)-1H-pyrrole-2-carbaldehyde $^1$H-NMR (CDCl$_3$, TMS) δ (ppm): 7.06 (1H, s), 7.47 (1H, dd, J=8 Hz, 5 Hz), 7.93 (1H, dd, J=8 Hz, 2 Hz), 8.53 (1H, dd, J=5 Hz, 2 Hz), 9.37 (1H, s)

REFERENCE PREPARATION EXAMPLE 100-(2)

According to the same manner as that of Reference Preparation Example 71-(4), 4,5-dichloro-1-(3-chloro-2-pyridinyl)-1H-pyrrole-2-carbaldehyde was used in place of 4-bromo-1-(3-chloro-2-pyridinyl)-1H-pyrrole-2-carbaldehyde to obtain 4,5-dichloro-1-(3-chloro-2-pyridinyl)-1H-pyrrole-2-carboxylic acid of the formula:

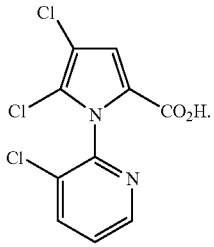

4,5-Dichloro-1-(3-chloro-2-pyridinyl)-1H-pyrrole-2-carboxylic acid $^1$H-NMR (DMSO-d$_6$, TMS) δ (ppm): 7.18 (1H, s), 7.68 (1H, dd, J=8 Hz, 5 Hz), 8.25 (1H, dd, J=8 Hz, 2 Hz), 8.59 (1H, dd, J=5 Hz, 2 Hz)

REFERENCE PREPARATION EXAMPLE 100-(3)

According to the same manner as that of Reference Preparation Example 71-(5), 4,5-dichloro-1-(3-chloro-2-pyridinyl)-1H-pyrrole-2-carboxylic acid was used in place of 4-bromo-1-(3-chloro-2-pyridinyl)-1H-pyrrole-2-carboxylic acid to obtain 2-[4,5-dichloro-1-(3-chloro-2-pyridinyl)-1H-pyrrol-2-yl]-6-chloro-8-methyl-4H-3,1-benzoxazine-4-one of the formula:

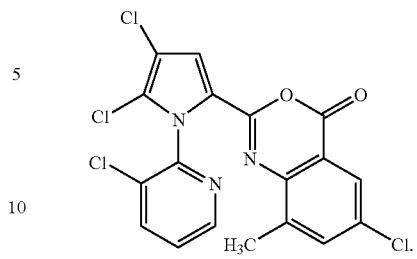

2-[4,5-Dichloro-1-(3-chloro-2-pyridinyl)-1H-pyrrol-2-yl]-6-chloro-8-methyl-4H-3,1-benzoxazine-4-one $^1$H-NMR (CDCl$_3$, TMS) δ (ppm): 1.71 (3H, s), 7.31 (1H, s), 7.40 (1H, s), 7.49 (1H, dd, J=8 Hz, 5 Hz), 7.92 (1H, s), 7.98 (1H, d, J=8 Hz), 8.58 (1H, d, J=5 Hz)

REFERENCE PREPARATION EXAMPLE 100-(4)

According to the same manner as that of Reference Preparation Example 71-(6), 2-[4,5-dichloro-1-(3-chloro-2-pyridinyl)-1H-pyrrole-2-yl]-6-chloro-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 4,5-dichloro-N-[4-chloro-2-(hydrazinocarbonyl)-6-methylphenyl]-1-(3-chloro-2-pyridinyl)-1H-pyrrole-2-carboxamide of the formula:

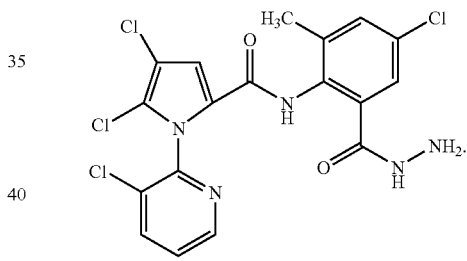

4,5-Dichloro-N-[4-chloro-2-(hydrazinocarbonyl)-6-methylphenyl]-1-(3-chloro-2-pyridinyl)-1H-pyrrole-2-carboxamide $^1$H-NMR (CDCl$_3$, TMS) δ (ppm): 2.01 (3H, s), 4.03 (2H, brs), 7.07 (1H, s), 7.16 (1H, d, J=2 Hz), 7.22 (1H, d, J=2 Hz), 7.37 (1H, dd, J=8 Hz, 5 Hz), 7.47 (1H, brs), 7.86 (1H, dd, J=8 Hz, 2 Hz), 8.47 (1H, dd, J=5 Hz, 2 Hz), 9.41 (1H, brs)

REFERENCE PREPARATION EXAMPLE 101

A mixture of 0.86 g of 2-[4-bromo-1-(3-chloro-2-pyridinyl)-1H-pyrrol-2-yl]-6-chloro-8-methyl-4H-3,1-benzoxazine-4-one, 0.11 g of methylhydrazine and 15 ml of tetrahydrofuran was stirred at room temperature for 2 hours. Water was poured into the reaction mixture, and the mixture was extracted with ethyl acetate. The organic layer was washed with water, dried over sodium sulfate, and concentrated under reduced pressure. The resulting residue was subjected to silica gel chromatography to obtain 0.17 g of 4-bromo-N-[4-chloro-2-(N-methylhydrazinocarbonyl)-6-methylphenyl]-1-(3-chloro-2-pyridinyl)-1H-pyrrole-2-carboxamide of the formula:

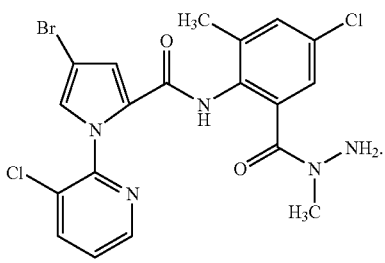

4-Bromo-N-[4-chloro-2-(N-methylhydrazinocarbonyl)-6-methylphenyl]-1-(3-chloro-2-pyridinyl)-1H-pyrrole-2-carboxamide $^1$H-NMR (CDCl$_3$, TMS) δ (ppm): 2.14-2.16 (3H, m), 3.02-3.23 (3H, m), 4.04 (0.7H, brs), 4.60 (1.3H, brs), 7.03 (2H, s), 7.11 (0.5H, s), 7.19 (0.5H, s), 7.31 (1H, dd, J=8 Hz, 4 Hz), 7.80 (1H, d, J=8 Hz), 8.41 (1H, d, J=4 Hz), 8.56 (1H, brs)

REFERENCE PREPARATION EXAMPLE 102

According to the same manner as that of Reference Preparation Example 46-(1), 2-amino-3,5-dichlorobenzoic acid was used in place of 2-amino-3,5-dibromobenzoic acid to obtain 2-[3-bromo-1-(3-chloro-2-pyridinyl)-1H-pyrazol-5-yl]-6,8-dichloro-4H-3,1-benzoxazine-4-one of the formula:

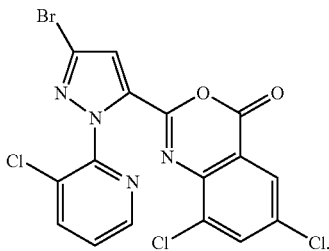

2-[3-Bromo-1-(3-chloro-2-pyridinyl)-1H-pyrazol-5-yl]-6,8-dichloro-4H-3,1-benzoxazine-4-one $^1$H-NMR (DMSO-d$_6$, TMS) δ (ppm): 7.57 (1H, s), 7.73 (1H, dd, J=8 Hz, 5 Hz), 8.03 (1H, d, J=2 Hz), 8.12 (1H, d, J=2 Hz), 8.32 (1H, dd, J=8 Hz, 2 Hz), 8.60 (1H, dd, J=5 Hz, 2 Hz).

REFERENCE PREPARATION EXAMPLE 103

According to the same manner as that of Reference Preparation Example 84, 2-[3-bromo-1-(3-chloro-2-pyridinyl)-1H-pyrazol-5-yl]-6-cyano-8-methyl-4H-3,1-benzoxazine-4-one was used in place of 2-[3-bromo-1-(3-chloro-2-pyridinyl)-1H-pyrazol-5-yl]-6-chloro-8-methyl-4H-3,1-benzoxazine-4-one to obtain 3-bromo-1-(3-chloro-2-pyridinyl)-N-[4-cyano-2-(N-methylhydrazinocarbonyl)-6-methylphenyl]-1H-pyrazole-5-carboxamide of the formula:

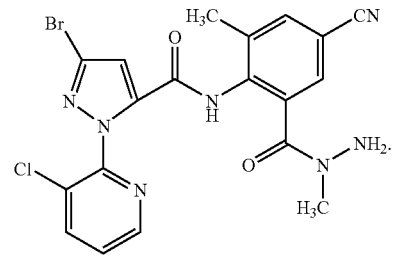

3-Bromo-1-(3-chloro-2-pyridinyl)-N-[4-cyano-2-(N-methylhydrazinocarbonyl)-6-methylphenyl]-1H-pyrazole-5-carboxamide $^1$H-NMR (DMSO-d$_6$, TMS) δ (ppm): 2.22 (3H, s), 2.75-3.10 (3H, m), 4.51-5.03 (2H, m), 7.36 (1H, s), 7.60-7.71 (2H, m), 7.74-7.88 (1H, m), 8.20 (1H, d, J=8 Hz), 8.51 (1H, d, J=4 Hz), 10.27-10.63 (1H, m)

REFERENCE PREPARATION EXAMPLE 104

According to the same manner as that of Reference Preparation Example 101, 2-[4-bromo-1-(3-chloro-2-yridinyl)-1H-pyrrol-2-yl]-6-cyano-8-methyl-4H-3,1-enzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 4-bromo-1-(3-chloro-2-pyridinyl)-N-[4-cyano-2-(N-methylhydrazinocarbonyl)-6-methylphenyl]-1H-pyrrole-2-carboxamide of the formula:

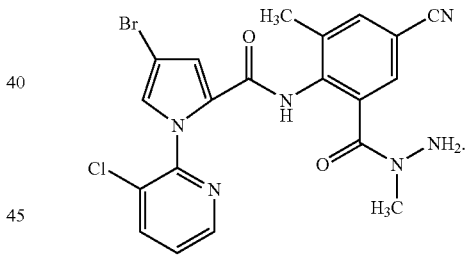

4-Bromo-1-(3-chloro-2-pyridinyl)-N-[4-cyano-2-(N-methylhydrazinocarbonyl)-6-methylphenyl]-1H-pyrrole-2-carboxamide $^1$H-NMR (DMSO-d$_6$, TMS) δ (ppm): 2.21 (3H, s), 2.74-3.10 (3H, m), 4.51-4.99 (2H, m), 7.22-7.28 (1H, m), 7.46-7.56 (2H, m), 7.56-7.65 (1H, m), 7.70-7.84 (1H, m), 8.09 (1H, d, J=8 Hz), 8.44 (1H, d, J=4 Hz), 9.76-10.04 (1H, m)

REFERENCE PREPARATION EXAMPLE 105-(1)

According to the same manner as that of Reference Preparation Example 46-(1), 3-amino-4-bromo-2-naphthoic acid was used in place of 2-amino-3,5-dibromobenzoic acid to obtain 10-bromo-2-[3-bromo-1-(3-chloro-2-pyridinyl)-1H-pyrazol-5-yl]-4H-naphtho[2,3-d][1,3]oxazine-4-one of the formula:

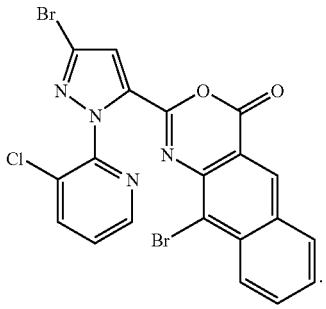

10-Bromo-2-[3-bromo-1-(3-chloro-2-pyridinyl)-1H-pyrazol-5-yl]-4H-naphtho[2,3-d][1,3]oxazine-4-one $^1$H-NMR (DMSO-d$_6$, TMS) δ (ppm): 7.55 (1H, s), 7.72-7.79 (2H, m), 7.89 (1H, t, J=8 Hz), 8.23 (1H, d, J=8 Hz), 8.32 (1H, d, J=8 Hz), 8.37 (1H, dd, J=8 Hz, 1Hz), 8.63 (1H, dd, J=5 Hz, 1Hz), 8.93 (1H, s)

REFERENCE PREPARATION EXAMPLE 105-(2)

According to the same manner as that of Reference Preparation Example 1, 10-bromo-2-[3-bromo-1-(3-chloro-2-pyridinyl)-1H-pyrazol-5-yl]-4H-naphtho[2,3-d][1,3]oxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain 3-bromo-N-[1-bromo-3-(hydrazinocarbonyl)-2-naphthyl]-1-(3-chloro-2-pyridinyl)-1H-pyrazole-5-carboxamide of the formula:

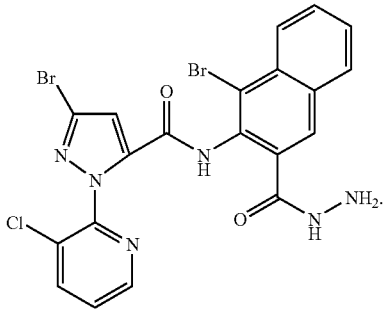

3-Bromo-N-[1-bromo-3-(hydrazinocarbonyl)-2-naphthyl]-1-(3-chloro-2-pyridinyl)-1H-pyrazole-5-carboxamide $^1$H-NMR (DMSO-d$_6$, TMS) δ (ppm): 4.37 (2H, brs), 7.52 (1H, s), 7.59 (1H, dd, J=8 Hz, 4 Hz), 7.69 (1H, t, J=8 Hz), 7.77 (1H, t, J=8 Hz), 8.04-8.09 (2H, m), 8.15 (1H, d, J=8 Hz), 8.21 (1H, d, J=8 Hz), 8.50 (1H, d, J=4 Hz), 9.63 (1H, brs), 10.65 (1H, brs)

REFERENCE PREPARATION EXAMPLE 106-(1)

According to the same manner as that of Reference Preparation Example 71-(5), 3-amino-4-bromo-2-naphthoic acid was used in place of 2-amino-5-chloro-3-methylbenzoic acid to obtain 10-bromo-2-[4-bromo-1-(3-chloro-2-pyridinyl)-1H-pyrrol-2-yl]-4H-naphtho[2,3-d][1,3]oxazine-4-one of the formula:

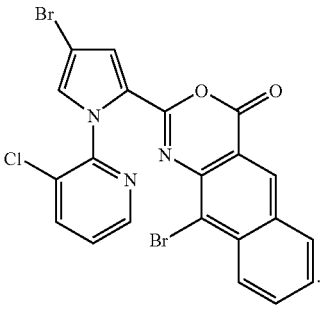

10-Bromo-2-[4-bromo-1-(3-chloro-2-pyridinyl)-1H-pyrrol-2-yl]-4H-naphtho[2,3-d][1,3]oxazine-4-one $^1$H-NMR (DMSO-d$_6$, TMS) δ (ppm): 7.33 (1H, d, J=2 Hz), 7.65-7.75 (3H, m), 7.84 (1H, t, J=8 Hz), 8.17 (1H, d, J=8 Hz), 8.28 (2H, d, J=8 Hz), 8.57-8.61 (1H, m), 8.87 (1H, s)

REFERENCE PREPARATION EXAMPLE 106-(2)

According to the same manner as that of Reference Preparation Example 71-(6), 10-bromo-2-[4-bromo-1-(3-chloro-2-pyridinyl)-1H-pyrrol-2-yl]-4H-naphtho[2,3-d][1,3]oxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 4-bromo-N-[1-bromo-3-(hydrazinocarbonyl)-2-naphthyl]-1-(3-chloro-2-pyridinyl)-1H-pyrrole-2-carboxamide of the formula:

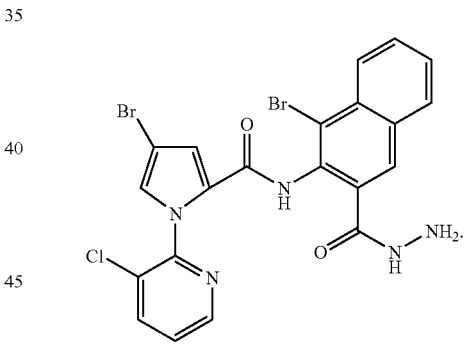

4-Bromo-N-[1-bromo-3-(hydrazinocarbonyl)-2-naphthyl]-1-(3-chloro-2-pyridinyl)-1H-pyrrole-2-carboxamide $^1$H-NMR (DMSO-d$_6$, TMS) δ (ppm): 4.37 (2H, brs), 7.40 (1H, s), 7.43-7.52 (2H, m), 7.66 (1H, t, J=7 Hz), 7.75 (1H, t, J=7 Hz), 8.01-8.08 (3H, m), 8.20 (1H, d, J=8 Hz), 8.43 (1H, d, J=5 Hz), 9.55 (1H, brs), 10.12 (1H, brs)

REFERENCE PREPARATION EXAMPLE 107

According to the same manner as that of Reference Preparation Example 71-(6), 2-[4-bromo-1-(3-chloro-2-pyridinyl)-1H-pyrrol-2-yl]-6-cyano-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 4-bromo-1-(3-chloro-2- pyridinyl)-N-[4-cyano-2-(hydrazinocarbonyl)-6-methylphenyl]-1H-pyrrole-2-carboxamide of the formula:

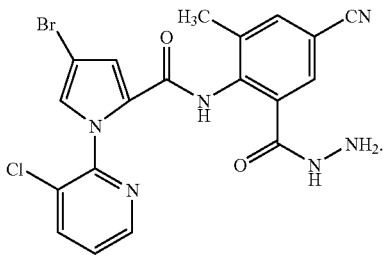

4-Bromo-1-(3-chloro-2-pyridinyl)-N-[4-cyano-2-(hydrazinocarbonyl)-6-methylphenyl]-1H-pyrrole-2-carboxamide $^1$H-NMR (DMSO-d$_6$, TMS) δ (ppm): 2.18 (3H, s), 4.42 (2H, brs), 7.28 (1H, s), 7.45-7.55 (2H, m), 7.71 (1H, s), 7.84 (1H, s), 8.07 (1H, d, J=8 Hz), 8.44 (1H, d, J=4 Hz), 9.68 (1H, brs), 10.16 (1H, brs)

REFERENCE PREPARATION EXAMPLE 108

According to the same manner as that of Reference Preparation Example 88, 2-[4-bromo-1-(3-chloro-2-pyridinyl)-1H-pyrrol-2-yl]-6-cyano-8-methyl-4H-3,1-benzoxazine-4-one was used in place of 2-[3-bromo-1-(3-chloro-2-pyridinyl)-1H-pyrazol-5-yl]-6-chloro-8-methyl-4H-3,1-benzoxazine-4-one to obtain 3-bromo-1-(3-chloro-2-pyridinyl)-N-[4-cyano-2-(N,N'-dimethylhydrazinocarbonyl)-6-methylphenyl]-1H-pyrazole-5-carboxamide of the formula:

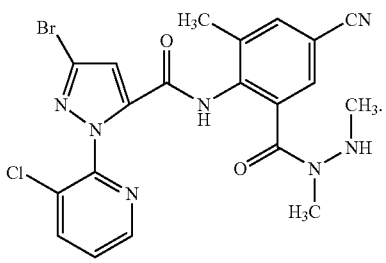

3-Bromo-1-(3-chloro-2-pyridinyl)-N-[4-cyano-2-(N,N'-dimethylhydrazinocarbonyl)-6-methylphenyl]-1H-pyrazole-5-carboxamide $^1$H-NMR (DMSO-d$_6$, TMS) δ (ppm): 2.14-2.33 (6H, m), 2.70-3.09 (3H, m), 4.55-6.05 (1H, m), 7.37 (1H, s), 7.58-7.66 (2H, m), 7.71-7.90 (1H, m), 8.15-8.21 (1H, m), 8.48-8.52 (1H, m), 10.25-10.62 (1H, m)

REFERENCE PREPARATION EXAMPLE 109

To a mixture of 0.29 g of N,N'-dimethylhydrazine dihydrochloride, 1 ml of water, 0.31 g of potassium carbonate and 10 ml of N,N-dimethylformamide was added 1.0 g of 2-[4-bromo-1-(3-chloro-2-pyridinyl)-1H-pyrrol-2-yl]-6-chloro-8-methyl-4H-3,1-benzoxazine-4-one. The resulting mixture was stirred at room temperature for 6 hours. Water was poured into the reaction mixture, and the mixture was extracted with ethyl acetate three times. The organic layers were combined, dried over anhydrous sodium sulfate, and concentrated under reduced pressure. The resulting residue was subjected to silica gel chromatography to obtain 0.26 g of 4-bromo-N-[4-chloro-2-(N,N'-dimethylhydrazinocarbonyl)-6-methylphenyl]-1-(3-chloro-2-pyridinyl)-1H-pyrrole-2-carboxamide of the formula:

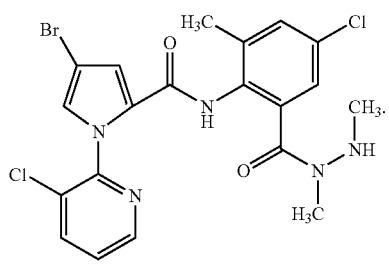

4-Bromo-N-[4-chloro-2-(N,N'-dimethylhydrazinocarbonyl)-6-methylphenyl]-1-(3-chloro-2-pyridinyl)-1H-pyrrole-2-carboxamide $^1$H-NMR (CDCl$_3$, TMS) δ (ppm): 2.16 (3H, s), 2.43 (1H, d, J=6 Hz), 2.61 (2H, d, J=6 Hz), 2.95 (2H, s), 3.19 (1H, s), 3.54 (0.3H, d, J=6 Hz), 5.62 (0.7H, d, J=6 Hz), 7.01-7.07 (3H, m), 7.14-7.18 (1H, m), 7.30 (1H, dd, J=8 Hz, 5 Hz), 7.79 (1H, d, J=8 Hz), 8.40 (1H, d, J=5 Hz), 8.56 (1H, brs)

REFERENCE PREPARATION EXAMPLE 110-(1)

According to the same manner as that of Reference Preparation Example 71-(5), 4,5-dichloro-1-(3-chloro-2-pyridinyl)-1H-pyrrole-2-carboxylic acid and 2-amino-3,5-dibromobenzoic acid were used in place of 4-bromo-1-(3-chloro-2-pyridinyl)-1H-pyrrole-2-carboxylic acid and 2-amino-5-chloro-3-methylbenzoic acid respectively to obtain 6,8-dibromo-2-[4,5-dichloro-1-(3-chloro-2-pyridinyl)-1H-pyrrol-2-yl]-4H-3,1-benzoxazine-4-one of the formula:

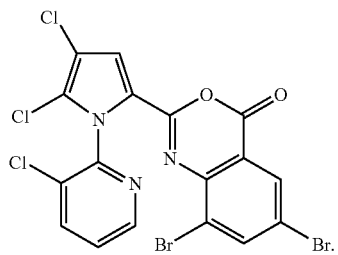

6,8-Dibromo-2-[4,5-dichloro-1-(3-chloro-2-pyridinyl)-1H-pyrrol-2-yl]-4H-3,1-benzoxazine-4-one $^1$H-NMR (CDCl$_3$, TMS) δ (ppm): 7.36 (1H, s), 7.47 (1H, dd, J=8 Hz, 5 Hz), 7.95 (1H, d, J=2 Hz), 7.99 (1H, dd, J=8 Hz, 2 Hz), 8.19 (1H, d, J=2 Hz), 8.57 (1H, dd, J=5 Hz, 2 Hz)

REFERENCE PREPARATION EXAMPLE 110-(2)

According to the same manner as that of Reference Preparation Example 71-(6), 6,8-dibromo-2-[4,5-dichloro-1-(3- chloro-2-pyridinyl)-1H-pyrrol-2-yl]-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain N-[4,6-dibromo-2-(hydrazinocarbonyl)phenyl]-4,5-dichloro-1-(3-chloro-2-pyridinyl)-1H-pyrrole-2-carboxamide of the formula:

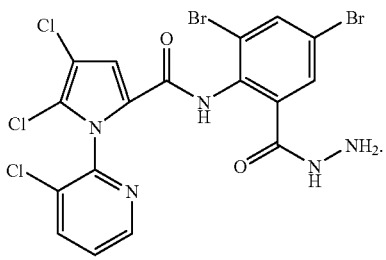

N-[4,6-dibromo-2-(hydrazinocarbonyl)phenyl]-4,5-dichloro-1-(3-chloro-2-pyridinyl)-1H-pyrrole-2-carboxamide $^1$H-NMR (DMSO-$d_6$, TMS) δ (ppm): 4.40 (2H, brs), 6.47 (1H, s), 7.65 (1H, s), 7.75-7.76 (1H, m), 7.89 (1H, s), 8.05-8.06 (1H, m), 8.27-8.28 (1H, m), 9.64 (1H, brs), 10.20 (1H, brs)

REFERENCE PREPARATION EXAMPLE 111

According to the same manner as that of Reference Preparation Example 46-(1), 3-amino-4-chloro-2-naphthoic acid was used in place of 2-amino-3,5-dibromobenzoic acid to obtain 2-[3-bromo-1-(3-chloro-2-pyridinyl)-1H-pyrazol-5-yl]-10-chloro-4H-naphtho[2,3-d][1,3]oxazine-4-one of the formula:

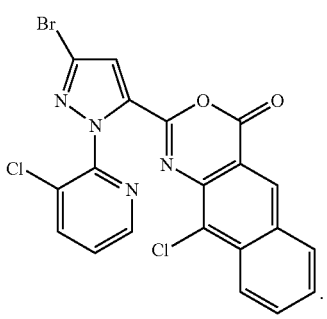

2-[3-Bromo-1-(3-chloro-2-pyridinyl)-1H-pyrazol-5-yl]-10-chloro-4H-naphtho[2,3-d][1,3]oxazine-4-one $^1$H-NMR (DMSO-$d_6$, TMS) δ (ppm): 7.56 (1H, s), 7.73-7.81 (2H, m), 7.89 (1H, t, J=8 Hz), 8.23 (1H, d, J=8 Hz), 8.34 (1H, d, J=8 Hz), 8.37 (1H, dd, J=8 Hz, 1Hz), 8.64 (1H, dd, J=5 Hz, 1Hz), 8.89 (1H, s)

REFERENCE PREPARATION EXAMPLE 112

According to the same manner as that of Reference Preparation Example 71-(5), 3-amino-4-chloro-2-naphthoic acid was used in place of 2-amino-5-chloro-3-methylbenzoic acid to obtain 2-[4-bromo-1-(3-chloro-2-pyridinyl)-1H-pyrrol-2-yl]-10-chloro-4H-naphtho[2,3-d][1,3]oxazine-4-one of the formula:

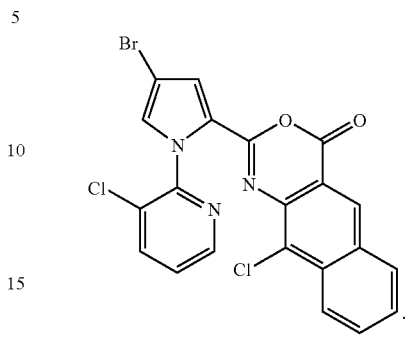

2-[4-Bromo-1-(3-chloro-2-pyridinyl)-1H-pyrrol-2-yl]-10-chloro-4H-naphtho[2,3-d][1,3]oxazine-4-one $^1$H-NMR (DMSO-$d_6$, TMS) δ (ppm): 7.33 (1H, d, J=2 Hz), 7.67-7.73 (2H, m), 7.74 (1H, d, J=2 Hz), 7.82-7.87 (1H, m), 8.17 (1H, d, J=8 Hz), 8.26-8.31 (2H, m), 8.59 (1H, dd, J=5 Hz, 1Hz), 8.84 (1H, s)

REFERENCE PREPARATION EXAMPLE 113-(1)

According to the same manner as that of Reference Preparation Example 71-(4), 4-chloro-1-(3-chloro-2-pyridinyl)-1H-pyrrole-2-carboxamide was used in place of 4-bromo-1-(3-chloro-2-pyridinyl)-1H-pyrrole-2-carbaldehyde to obtain 4-chloro-1-(3-chloro-2-pyridinyl)-1H-pyrrole-2-carboxylic acid of the formula:

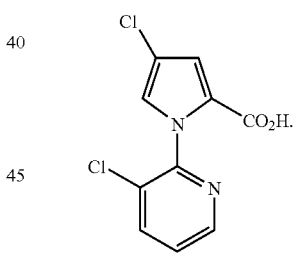

4-Chloro-1-(3-chloro-2-pyridinyl)-1H-pyrrole-2-carboxylic acid $^1$H-NMR (DMSO-$d_6$, TMS) δ (ppm): 6.97 (1H, d, J=2 Hz), 7.48 (1H, d, J=2 Hz), 7.59 (1H, dd, J=8 Hz, 5 Hz), 8.16 (1H, dd, J=8 Hz, 2 Hz), 8.50 (1H, dd, J=5 Hz, 2 Hz)

REFERENCE PREPARATION EXAMPLE 113-(2)

According to the same manner as that of Reference Preparation Example 71-(5), 4-chloro-1-(3-chloro-2-pyridinyl)-1H-pyrrole-2-carboxylic acid was used in place of 4-bromo-1-(3-chloro-2-pyridinyl)-1H-pyrrole-2-carboxylic acid to obtain 2-[4-chloro-1-(3-chloro-2-pyridinyl)-1H-pyrrol-2-yl]-6-chloro-8-methyl-4H-3,1-benzoxazine-4-one of the formula:

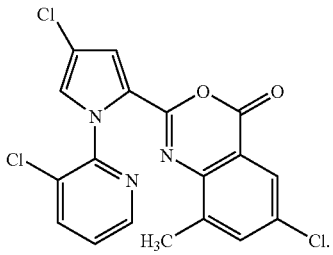

2-[4-Chloro-1-(3-chloro-2-pyridinyl)-1H-pyrrol-2-yl]-6-chloro-8-methyl-4H-3,1-benzoxazine-4-one $^1$H-NMR (CDCl$_3$, TMS) δ (ppm): 1.73 (3H, s), 7.03 (1H, d, J=2 Hz), 7.26 (1H, d, J=2 Hz), 7.41 (1H, d, J=2 Hz), 7.43 (1H, dd, J=8 Hz, 5 Hz), 7.91 (1H, dd, J=8 Hz, 2 Hz), 7.94 (1H, d, J=2 Hz), 8.51 (1H, dd, J=5 Hz, 2 Hz)

REFERENCE PREPARATION EXAMPLE 113-(3)

According to the same manner as that of Reference Preparation Example 71-(6), 2-[4-chloro-1-(3-chloro-2-pyridinyl)-1H-pyrrol-2-yl]-6-chloro-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 4-chloro-N-[4-chloro-2-(hydrazinocarbonyl)-6-methylphenyl]-1-(3-chloro-2-pyridinyl)-1H-pyrrole-2-carboxamide of the formula:

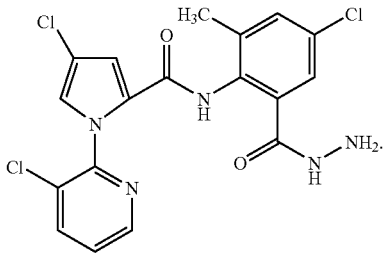

4-Chloro-N-[4-chloro-2-(hydrazinocarbonyl)-6-methylphenyl]-1-(3-chloro-2-pyridinyl)-1H-pyrrole-2-carboxamide $^1$H-NMR (CDCl$_3$, TMS) δ (ppm): 2.19 (3H, s), 6.97 (1H, d, J=2 Hz), 7.00 (1H, d, J=2 Hz), 7.26 (1H, s), 7.30 (1H, dd, J=8 Hz, 5 Hz), 7.48 (1H, s), 7.79 (1H, dd, J=8 Hz, 2 Hz), 8.40 (1H, dd, J=5 Hz, 2 Hz), 9.29 (1H, brs)

REFERENCE PREPARATION EXAMPLE 114

According to the same manner as that of Reference Preparation Example 84, 2-[3-bromo-1-(3-chloro-2-pyridinyl)-1H-pyrazol-5-yl]-6,8-dichloro-4H-3,1-benzoxazine-4-one was used in place of 2-[3-bromo-1-(3-chloro-2-pyridinyl)-1H-pyrazol-5-yl]-6-chloro-8-methyl-4H-3,1-benzoxazine-4-one to obtain 3-bromo-N-[4,6-dichloro-2-(N-methylhydrazinocarbonyl)phenyl]-1-(3-chloro-2-pyridinyl)-1H-pyrazole-5-carboxamide of the formula:

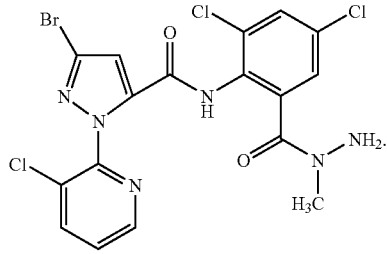

3-Bromo-N-[4,6-dichloro-2-(N-methylhydrazinocarbonyl)phenyl]-1-(3-chloro-2-pyridinyl)-1H-pyrazole-5-carboxamide $^1$H-NMR (DMSO-d$_6$, TMS) δ (ppm): 2.76 (0.6H, s), 3.06 (2.4H, s), 4.55 (1.6H, s), 5.02 (0.4H, s), 7.38-7.46 (2.0H, m), 7.60-7.64 (1.0H, m), 7.71 (0.8H, d, J=2 Hz), 7.83 (0.2H, d, J=2 Hz), 8.17-8.20 (1.0H, m), 8.51 (1.0H, dd, J=5 Hz, 2 Hz), 10.38 (0.8H, s), 10.64 (0.2H, s).

REFERENCE PREPARATION EXAMPLE 115-(1)

To a solution of 3.0 g of 3-chloro-2-(1H-pyrrol-1-yl)pyridine in 30 ml of N,N-dimethylformamide was added 3.1 g of N-bromosuccinimide. The resulting mixture was stirred at room temperature for 6 hours. Water was poured into the reaction mixture, and the mixture was extracted with ethyl acetate two times. The organic layers were combined, washed with an aqueous saturated sodium chloride solution, dried over anhydrous magnesium sulfate, and concentrated under reduced pressure. The residue was subjected to silica gel column chromatography to obtain 1.1 g of 2-(2-bromo-1H-pyrrol-1-yl)-3-chloropyridine of the formula:

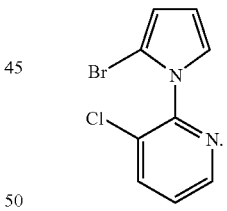

2-(2-Bromo-1H-pyrrol-1-yl)-3-chloropyridine $^1$H-NMR (CDCl$_3$, TMS) δ (ppm): 6.37-6.41 (2H, m), 6.93 (1H, dd, J=3 Hz, 2 Hz), 7.38 (1H, dd, J=8 Hz, 5 Hz), 7.91 (1H, dd, J=8 Hz, 2 Hz), 8.52 (1H, dd, J=5 Hz, 2 Hz)

REFERENCE PREPARATION EXAMPLE 115-(2)

According to the same manner as that of Reference Preparation Example 71-(2), 2-(2-bromo-1H-pyrrol-1-yl)-3-chloropyridine was used in place of 3-chloro-2-(1H-pyrrol-1-yl)pyridine to obtain 5-bromo-1-(3-chloro-2-pyridinyl)-1H-pyrrole-2-carbaldehyde of the formula:

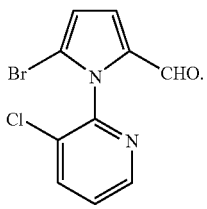

5-Bromo-1-(3-chloro-2-pyridinyl)-1H-pyrrole-2-carbaldehyde $^1$H-NMR (CDCl$_3$, TMS) δ (ppm): 6.53 (1H, d, J=4 Hz), 7.07 (1H, d, J=4 Hz), 7.45 (1H, dd, J=8 Hz, 5 Hz), 7.92 (1H, dd, J=8 Hz, 2 Hz), 8.54 (1H, dd, J=5 Hz, 2 Hz), 9.36 (1H, s)

REFERENCE PREPARATION EXAMPLE 115-(3)

According to the same manner as that of Reference Preparation Example 71-(4), 5-bromo-1-(3-chloro-2-pyridinyl)-1H-pyrrole-2-carbaldehyde was used in place of 4-bromo-1-(3-chloro-2-pyridinyl)-1H-pyrrole-2-carbaldehyde to obtain 5-bromo-1-(3-chloro-2-pyridinyl)-1H-pyrrole-2-carboxylic acid of the formula:

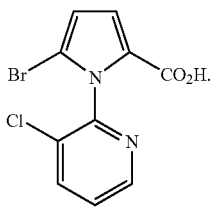

5-Bromo-1-(3-chloro-2-pyridinyl)-1H-pyrrole-2-carboxylic acid $^1$H-NMR (DMSO-d$_6$, TMS) δ (ppm): 6.54 (1H, d, J=4 Hz), 7.02 (1H, d, J=4 Hz), 7.63 (1H, dd, J=8 Hz, 5 Hz), 8.21 (1H, d, J=8 Hz), 8.56 (1H, d, J=5 Hz), 12.54 (1H, brs)

REFERENCE PREPARATION EXAMPLE 115-(4)

According to the same manner as that of Reference Preparation Example 71-(5), 5-bromo-1-(3-chloro-2-pyridinyl) -1H-pyrrole-2-carboxylic acid was used in place of 4-bromo-1-(3-chloro-2-pyridinyl)-1H-pyrrole-2-carboxylic acid to obtain 2-[5-bromo-1-(3-chloro-2-pyridinyl)-1H-pyrrol-2-yl]-6-chloro-8-methyl-4H-3,1-benzoxazine-4-one of the formula:

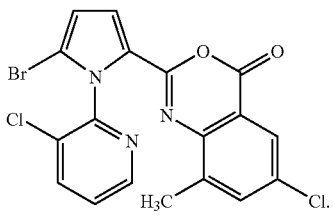

2-[5-Bromo-1-(3-chloro-2-pyridinyl)-1H-pyrrol-2-yl]-6-chloro-8-methyl-4H-3,1-benzoxazine-4-one $^1$H-NMR (CDCl$_3$, TMS) δ (ppm): 1.57 (3H, s), 6.55 (1H, d, J=4 Hz), 7.33 (1H, d, J=4 Hz), 7.38 (1H, d, J=2 Hz), 7.47 (1H, dd, J=8 Hz, 5 Hz), 7.92 (1H, d, J=2 Hz), 7.97 (1H, dd, J=8 Hz, 2 Hz), 8.59 (1H, dd, J=5 Hz, 2 Hz)

REFERENCE PREPARATION EXAMPLE 115-(5)

According to the same manner as that of Reference Preparation Example 71-(6), 2-[5-bromo-1-(3-chloro-2-pyridinyl)-1H-pyrrol-2-yl]-6-chloro-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 5-bromo-N-[4-chloro-2-(hydrazinocarbonyl)-6-methylphenyl]-1-(3-chloro-2-pyridinyl )-1H-pyrrole-2-carboxamide of the formula:

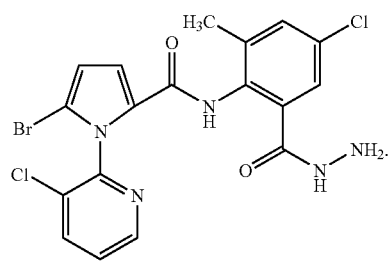

5-Bromo-N-[4-chloro-2-(hydrazinocarbonyl)-6-methylphenyl]-1-(3-chloro-2-pyridinyl)-1H-pyrrole-2-carboxamide $^1$H-NMR (CDCl$_3$, TMS) δ (ppm): 2.17 (3H, s), 4.02 (2H, brs), 6.47 (1H, d, J=4 Hz), 7.03 (1H, d, J=4 Hz), 7.20 (1H, s), 7.27 (1H, s), 7.36 (1H, dd, J=8 Hz, 5 Hz), 7.86 (1H, dd, J=8 Hz, 2 Hz), 8.40 (1H, dd, J=5 Hz, 2 Hz), 9.22 (1H, brs)

REFERENCE PREPARATION EXAMPLE 116-(1)

A mixture of 1.9 g of 2-pyrrolecarbaldehyde, 2.3 g of 2-chloropyrimidine, 7.8 g of cesium carbonate and 20 ml of N-methylpyrrolidone was stirred at 130° C. for 13 hours, and then allowed to cool to room temperature. Water was poured into the reaction mixture, and the mixture was extracted with ethyl acetate two times. The organic layers were combined, washed successively with water and an aqueous saturated sodium chloride solution, dried over anhydrous sodium sulfate, and concentrated under reduced pressure. The resulting residue was subjected to silica gel chromatography to obtain 0.94 g of 1-(2-pyrimidinyl)-1H-pyrrole-2-carbaldehyde of the formula:

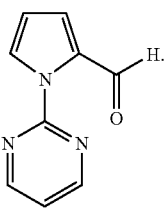

1-(2-Pyrimidinyl)-1H-pyrrole-2-carbaldehyde $^1$H-NMR (CDCl$_3$, TMS) δ (ppm): 6.40-6.41 (1H, m), 7.22 (1H, t, J=5 Hz), 7.29 (1H, dd, J=4 Hz, 2 Hz), 7.96 (1H, dd, J=3 Hz, 2 Hz), 8.73 (2H, d, J=5 Hz), 10.61 (1H, s)

REFERENCE PREPARATION EXAMPLE 116-(2)

To a solution of 0.5 g of 1-(2-pyrimidinyl)-1H-pyrrole-2-carbaldehyde in 10 ml of N,N-dimethylformamide was added 0.6 g of N-bromosuccinimide. The resulting mixture was stirred at room temperature for 1 hour. Water was poured into the reaction mixture, and the mixture was extracted with ethyl acetate two times. The organic layers were combined, washed successively with water and an aqueous saturated sodium chloride solution, dried over anhydrous sodium sulfate, and concentrated under reduced pressure. The resulting residue was subjected to silica gel chromatography to obtain 0.43 g of 5-bromo-1-(2-pyrimidinyl)-1H-pyrrole-2-carbaldehyde of the formula:

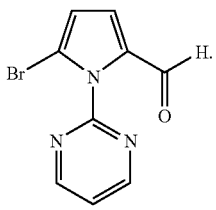

5-Bromo-1-(2-pyrimidinyl)-1H-pyrrole-2-carbaldehyde $^1$H-NMR (DMSO-d$_6$, TMS) δ (ppm): 6.67 (1H, d, J=4 Hz), 7.28 (1H, d, J=4 Hz), 7.75 (1H, t, J=5 Hz), 9.02 (2H, d, J=5 Hz), 9.39 (1H, s)

REFERENCE PREPARATION EXAMPLE 116-(3)

A solution of 2.0 g of potassium permanganate in 10 ml of water was added dropwise to a mixture of 0.76 g of 5-bromo-1-(2-pyrimidinyl)-1H-pyrrole-2-carbaldehyde and 18 ml of acetone while the mixture was maintained at 40° C. The resulting mixture was stirred at 40° C. for 4 hours. A precipitate was filtered off to obtain a filtrate. The filtrate was adjusted to pH 10-12 by an addition of a 2N aqueous sodium hydroxide solution, and then washed with chloroform two times. The aqueous layer was adjusted to around pH 3 by an addition of 2N hydrochloric acid, and then extracted with ethyl acetate two times. The organic layers were combined, washed successively with water and an aqueous saturated sodium chloride solution, dried over anhydrous sodium sulfate, and concentrated under reduced pressure to obtain 0.28 g of 5-bromo-1-(2-pyrimidinyl)-1H-pyrrole-2-carboxylic acid of the formula:

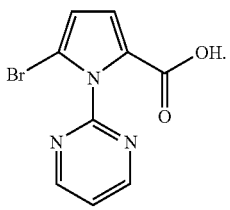

5-Bromo-1-(2-pyrimidinyl)-1H-pyrrole-2-carboxylic acid $^1$H-NMR (DMSO-d$_6$, TMS) (ppm): 6.40-6.51 (1H, m), 6.89-7.16 (1H, m), 7.66-7.75 (1H, m), 8.99 (2H, d, J=5 Hz)

REFERENCE PREPARATION EXAMPLE 116-(4)

According to the same manner as that of Reference Preparation Example 71-(5), 5-bromo-1-(2-pyrimidinyl)-1H-pyrrole-2-carboxylic acid was used in place of 4-bromo-1-(3-chloro-2-pyridinyl)-1H-pyrrole-2-carboxylic acid to obtain 2-[5-bromo-1-(2-pyrimidinyl)-1H-pyrrol-2-yl]-6-chloro-8-methyl-4H-3,1-benzoxazine-4-one of the formula:

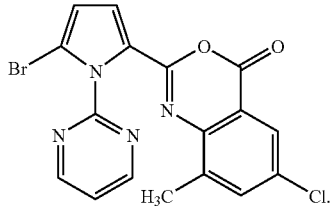

2-[5-Bromo-1-(2-pyrimidinyl)-1H-pyrrol-2-yl]-6-chloro-8-methyl-4H-3,1-benzoxazine-4-one $^1$H-NMR (DMSO-d$_6$, TMS) δ (ppm): 1.67 (3H, s), 6.62 (1H, d, J=4 Hz), 7.20-7.30 (1H, m), 7.67-7.72 (1H, m), 7.77-7.88 (2H, m), 9.06-9.12 (2H, m)

REFERENCE PREPARATION EXAMPLE 116-(5)

According to the same manner as that of Reference Preparation Example 71-(6), 2-[5-bromo-1-(2-pyrimidinyl)-1H-pyrrol-2-yl]-6-chloro-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 5-bromo-N-[4-chloro-2-(hydrazinocarbonyl)-6-methylphenyl]-1-(2-pyrimidinyl)-1H-pyrrole-2-carboxamide of the formula:

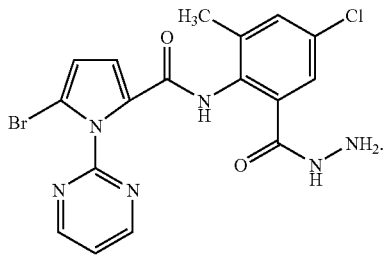

5-Bromo-N-[4-chloro-2-(hydrazinocarbonyl)-6-methylphenyl]-1-(2-pyrimidinyl)-1H-pyrrole-2-carboxamide $^1$H-NMR (DMSO-d$_6$, TMS) δ (ppm): 2.13 (3H, s), 6.45 (1H, d, J=4 Hz), 7.12 (1H, brs), 7.30 (1H, brs), 7.44 (1H, brs), 7.59-7.66 (1H, m), 8.90-8.95 (2H, m), 9.51 (1H, brs), 9.92 (1H, brs)

REFERENCE PREPARATION EXAMPLE 117-(1)

A mixture of 5 g of 2,6-dichloroaniline, 4.5 g of 2,5-dimethoxytetrahydrofuran and 30 ml of acetic acid was heated to reflux for 10 hours. The reaction mixture was allowed to cool, poured into water, and extracted with ethyl acetate two times. The organic layers were combined, washed successively with water and an aqueous saturated sodium chloride solution, dried over anhydrous sodium sulfate, and concentrated under reduced pressure. The resulting residue was subjected to silica gel chromatography to obtain 5.45 g of 1-(2,6-dichlorophenyl)-1H-pyrrole of the formula:

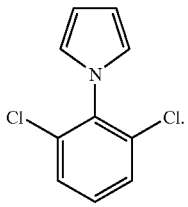

1-(2,6-Dichlorophenyl)-1H-pyrrole $^1$H-NMR (DMSO-$d_6$, TMS) δ (ppm): 6.26 (2H, t, J=2 Hz), 6.82 (2H, t, J=2 Hz), 7.50 (1H, t, J=8 Hz), 7.66 (2H, d, J=8 Hz)

REFERENCE PREPARATION EXAMPLE 117-(2)

Under ice-cooling, 7.67 g of phosphorus oxychloride was added dropwise to 4 g of N,N-dimethylformamide. The mixture was stirred at room temperature for 30 minutes, and 2.1 g of 1-(2,6-dichlorophenyl)-1H-pyrrole was added thereto. The resulting mixture was stirred at 60° C. for 2 hours, allowed to cool to room temperature, and then poured into ice water. The mixture was adjusted to pH 4 by an addition of a 2N aqueous sodium hydroxide solution, and then extracted with ethyl acetate two times. The organic layers were combined, washed successively with water and an aqueous saturated sodium chloride solution, dried over anhydrous sodium sulfate, and concentrated under reduced pressure. The resulting residue was subjected to silica gel chromatography to obtain 0.80 g of 1-(2,6-dichlorophenyl)-1H-pyrrole-2-carbaldehyde of the formula:

and 1.00 g of 1-(2,6-dichlorophenyl)-1H-pyrrole-3-carbaldehyde of the formula:

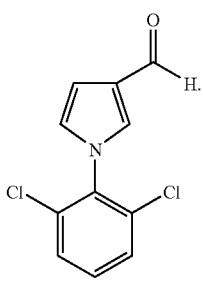

1-(2,6-Dichlorophenyl)-1H-pyrrole-2-carbaldehyde $^1$H-NMR (DMSO-$d_6$, TMS) δ (ppm): 6.54 (1H, dd, J=4 Hz, 3 Hz), 7.29 (1H, dd, J=4 Hz, 2 Hz), 7.35 (1H, ddd, J=3 Hz, 2 Hz, 1Hz), 7.53 (1H, dd, J=9 Hz, 7 Hz), 7.63-7.67 (2H, m), 9.50 (1H, d, J=1 Hz)

1-(2,6-Dichlorophenyl)-1H-pyrrole-3-carbaldehyde $^1$H-NMR (DMSO-$d_6$, TMS) δ (ppm): 6.69 (1H, dd, J=3, 2 Hz), 7.07 (1H, ddd, J=3 Hz, 2 Hz, 1Hz), 7.58 (1H, dd, J=9 Hz, 8 Hz), 7.71-7.75 (2H, m), 7.85 (1H, brs), 9.78 (1H, d, J=1 Hz)

REFERENCE PREPARATION EXAMPLE 117-(3)

In 10 ml of N,N-dimethylformamide was dissolved 0.65 g of 1-(2,6-dichlorophenyl)-1H-pyrrole-2-carbaldehyde, and then 0.53 g of N-bromosuccinimide was added thereto. The mixture was stirred at room temperature for 1 hour. Water was poured into the reaction mixture, a deposited precipitate was collected by filtration to obtain 0.85 g of 4-bromo-1-(2,6-dichlorophenyl)-1H-pyrrole-2-carbaldehyde of the formula:

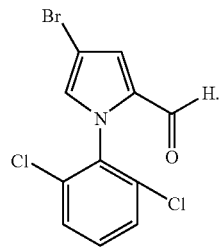

4-Bromo-1-(2,6-dichlorophenyl)-1H-pyrrole-2-carbaldehyde $^1$H-NMR (DMSO-$d_6$, TMS) δ (ppm): 7.43 (1H, d, J=2 Hz), 7.56 (1H, dd, J=9 Hz, 7 Hz), 7.65-7.69 (3H, m), 9.46 (1H, s)

REFERENCE PREPARATION EXAMPLE 117-(4)

A solution of 2.0 g of potassium permanganate in 10 ml of water was added dropwise to a mixture of 0.85 g of 4-bromo-1-(2,6-dichlorophenyl)-1H-pyrrole-2-carbaldehyde and 18 ml of acetone while the mixture was maintained at 40° C. The resulting mixture was stirred at 40° C. for 2 hours. A precipitate was filtered off to obtain a filtrate. The filtrate was adjusted to pH 10-12 by an addition of a 2N aqueous sodium hydroxide solution, and then extracted with chloroform two times. The aqueous layer was adjusted to around pH 3 by an addition of 2N hydrochloric acid, and then extracted with ethyl acetate two times. The organic layers were combined, washed successively with water and an aqueous saturated sodium chloride solution, dried over anhydrous sodium sulfate, and concentrated under reduced pressure to obtain 0.66 g of 4-bromo-1-(2,6-dichlorophenyl)-1H-pyrrole-2-carboxylic acid of the formula:

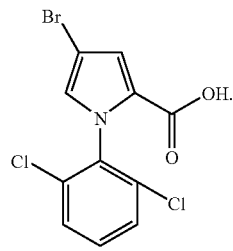

4-Bromo-1-(2,6-dichlorophenyl)-1H-pyrrole-2-car-
boxylic acid $^1$H-NMR (DMSO-d$_6$, TMS) δ (ppm): 7.05 (1H, brs), 7.40 (1H, brs), 7.51 (1H, t, J=8 Hz), 7.60-7.67 (2H, m), 12.65 (1H, s)

REFERENCE PREPARATION EXAMPLE 117-(5)

According to the same manner as that of Reference Preparation Example 71-(5), 4-bromo-1-(2,6-dichlorophenyl)-1H-pyrrole-2-carboxylic acid was used in place of 4-bromo-1-(3-chloro-2-pyridinyl)-1H-pyrrole-2-carboxylic acid to obtain 2-[4-bromo-1-(2,6-dichlorophenyl)-1H-pyrrol-2-yl]-6-chloro-8-methyl-4H-3,1-benzoxazine-4-one of the formula:

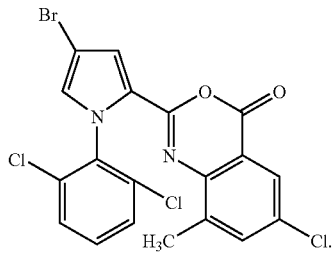

2-[4-Bromo-1-(2,6-dichlorophenyl)-1H-pyrrol-2-yl]-
6-chloro-8-methyl-4H-3,1-benzoxazine-4-one $^1$H-NMR (DMSO-d$_6$, TMS) δ (ppm): 1.68 (3H, s), 7.32 (1H, d, J=1 Hz), 7.54-7.64 (2H, m), 7.67-7.77 (3H, m), 7.83 (1H, d, J=2 Hz)

REFERENCE PREPARATION EXAMPLE 117-(6)

According to the same manner as that of Reference Preparation Example 71-(6), 2-[4-bromo-1-(2,6-dichlorophenyl)-1H-pyrrol-2-yl]-6-chloro-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 4-bromo-N-[4-chloro-2-(hydrazinocarbonyl)-6-methylphenyl]-1-(2,6-dichlorophenyl)-1H-pyrrole-2-carboxamide of the formula:

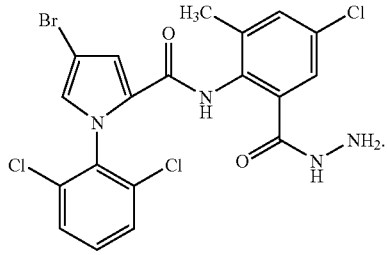

4-Bromo-N-[4-chloro-2-(hydrazinocarbonyl)-6-me-
thylphenyl]-1-(2,6-dichlorophenyl)-1H-pyrrole-2-
carboxamide $^1$H-NMR (DMSO-d$_6$, TMS) δ (ppm): 2.11 (3H, s), 4.38 (2H, brs), 7.27-7.30 (2H, m), 7.34 (1H, d, J=2 Hz), 7.40-7.46 (2H, m), 7.56 (2H, d, J=8 Hz), 9.51 (1H, brs), 9.81 (1H, brs)

REFERENCE PREPARATION EXAMPLE 118-(1)

A mixture of 2.6 g of 2-pyrrolecabaldehyde, 5.0 g of 3,4,5-trichloropyridine, 10.7 g of cesium carbonate and 30 ml of N-methylpyrrolidone was stirred at 100° C. for 2 hours, and then allowed to cool to room temperature. Water was poured into the reaction mixture, and the mixture was extracted with ethyl acetate two times. The organic layers were combined, washed successively water and an aqueous saturated sodium chloride solution, dried over anhydrous sodium sulfate, and concentrated under reduced pressure. The resulting residue was subjected to silica gel chromatography to obtain 2.14 g of 1-(3,5-dichloro-4-pyridinyl)-1H-pyrrole-2-carbaldehyde of the formula:

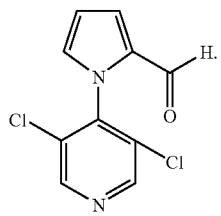

1-(3,5-Dichloro-4-pyridinyl)-1H-pyrrole-2-carbalde-
hyde $^1$H-NMR (DMSO-d$_6$, TMS) δ (ppm): 6.61 (1H, dd, J=4 Hz, 3 Hz), 7.37 (1H, dd, J=4 Hz, 2 Hz), 7.46 (1H, ddd, J=3 Hz, 2 Hz, 1Hz), 8.85 (2H, s), 9.54 (1H, d, J=1 Hz)

REFERENCE PREPARATION EXAMPLE 118-(2)

To a solution of 2.14 g of 1-(3,5-dichloro-4-pyridinyl)-1H-pyrrole-2-carbaldehyde in 10 ml of N,N-dimethylformamide was added 1.7 g of N-bromosuccinimide. The mixture was stirred at room temperature for 2 hours. Water was poured into the reaction mixture, and a deposited precipitate was collected by filtration to obtain 2.9 g of 4-bromo-1-(3,5-dichloro-4-pyridinyl)-1H-pyrrole-2-carbaldehyde of the formula:

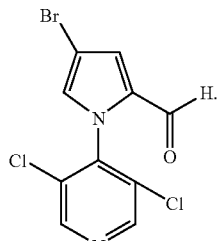

4-Bromo-1-(3,5-dichloro-4-pyridinyl)-1H-pyrrole-2-
carbaldehyde $^1$H-NMR (DMSO-d$_6$, TMS) δ (ppm): 7.52 (1H, d, J=2 Hz), 7.74 (1H, dd, J=2 Hz, 1Hz), 8.88 (2H, s), 9.51 (1H, d, J=1 Hz)

REFERENCE PREPARATION EXAMPLE 118-(3)

A solution of 2.9 g of potassium permanganate in 15 ml of water was added dropwise to a mixture of 2.86 g of 4-bromo- 1-(3,5-dichloro-4-pyridinyl)-1H-pyrrole-2-carbaldehyde and 30 ml of acetone while the mixture was maintained at 40° C. The mixture was stirred at 40° C. for 2 hours. A precipitate was filtered off to obtain a filtrate. The filtrate was adjusted to pH 10-12 by an addition of a 2N aqueous sodium hydroxide solution, and then washed with chloroform two times. The aqueous layer was adjusted to around pH 3 by an addition of 2N hydrochloric acid. A deposited precipitate was collected by filtration to obtain 2.08 g of 4-bromo-1-(3,5-dichloro-4-pyridinyl)-1H-pyrrole-2-carboxylic acid of the formula:

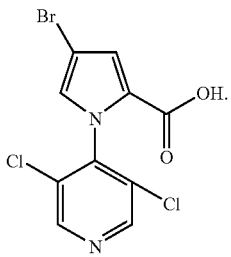

4-Bromo-1-(3,5-dichloro-4-pyridinyl)-1H-pyrrole-2-carboxylic acid $^1$H-NMR (DMSO-$d_6$, TMS) δ (ppm): 7.12 (1H, d, J=2 Hz), 7.51 (1H, d, J=2 Hz), 8.85 (2H, s)

REFERENCE PREPARATION EXAMPLE 118-(4)

According to the same manner as that of Reference Preparation Example 71-(5), 4-bromo-1-(3,5-dichloro-4-pyridinyl)-1H-pyrrole-2-carboxylic acid was used in place of 4-bromo-1-(3-chloro-2-pyridinyl)-1H-pyrrole-2-carboxylic acid to obtain 2-[4-bromo-1-(3,5-dichloro-4-pyridinyl)-1H-pyrrol-2-yl]-6-chloro-8-methyl-4H-3,1-benzoxazine-4-one of the formula:

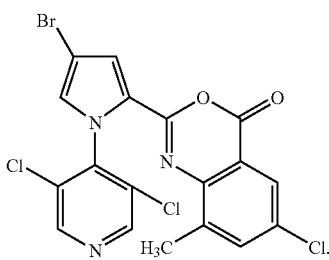

2-[4-Bromo-1-(3,5-dichloro-4-pyridinyl)-1H-pyrrol-2-yl]-6-chloro-8-methyl-4H-3,1-benzoxazine-4-one $^1$H-NMR (DMSO-$d_6$, TMS) δ (ppm): 1.64 (3H, s), 7.39 (1H, brs), 7.72 (2H, s), 7.85 (1H, brs), 8.95 (2H, s)

REFERENCE PREPARATION EXAMPLE 118-(5)

According to the same manner as that of Reference Preparation Example 71-(6), 2-[4-bromo-1-(3,5-dichloro-4-pyridinyl)-1H-pyrrol-2-yl]-6-chloro-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 4-bromo-N-[4-chloro-2-(hydrazinocarbonyl)-6-methylphenyl]-1-(3,5-dichloro-4-pyridinyl)-1H-pyrrole-2-carboxamide of the formula:

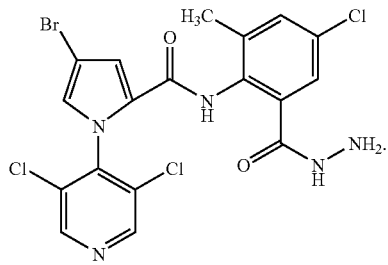

4-Bromo-N-[4-chloro-2-(hydrazinocarbonyl)-6-methylphenyl]-1-(3,5-dichloro-4-pyridinyl)-1H-pyrrole-2-carboxamide $^1$H-NMR (DMSO-$d_6$, TMS) δ (ppm): 2.13 (3H, s), 4.35 (2H, brs), 7.28 (1H, d, J=2 Hz), 7.37 (1H, d, J=2 Hz), 7.43-7.47 (2H, m), 8.76 (2H, s), 9.52 (1H, brs), 9.89 (1H, brs)

REFERENCE PREPARATION EXAMPLE 119-(1)

A solution of 0.9 g of potassium permanganate in 10 ml of water was added dropwise to a mixture of 0.58 g of 1-(2,6-dichlorophenyl)-1H-pyrrole-3-carbaldehyde and 20 ml of acetone while the mixture was maintained at 40° C. The resulting mixture was stirred at 40° C. for 2 hours. A deposited precipitate was filtered off to obtain a filtrate. The filtrate was adjusted to pH 10-12 by an addition of a 2N aqueous sodium hydroxide solution, and then washed with chloroform two times. The aqueous layer was adjusted to around pH 3 by an addition of 2N hydrochloric acid, and then extracted with ethyl acetate two times. The organic layers were combined, washed successively with water and an aqueous saturated sodium chloride solution, dried over anhydrous sodium sulfate, and concentrated under reduced pressure to obtain 0.34 g of 1-(2,6-dichlorophenyl)-1H-pyrrole-3-carboxylic acid of the formula:

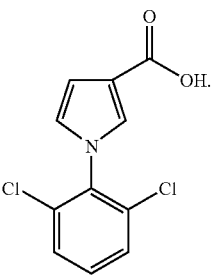

1-(2,6-Dichlorophenyl)-1H-pyrrole-3-carboxylic acid $^1$H-NMR (DMSO-$d_6$, TMS) δ (ppm): 6.60 (1H, dd, J=3 Hz, 2 Hz), 6.92 (1H, dd, J=3 Hz, 1Hz), 7.48 (1H, dd, J=2 Hz, 1Hz), 7.55 (1H, dd, J=8 Hz, 7 Hz), 7.67-7.72 (2H, m), 12.05 (1H, brs)

REFERENCE PREPARATION EXAMPLE 119-(2)

According to the same manner as that of Reference Preparation Example 71-(5), 1-(2,6-dichlorophenyl)-1H-pyrrole- 3-carboxylic acid was used in place of 4-bromo-1-(3-chloro-2-pyridinyl)-1H-pyrrole-2-carboxylic acid to obtain 6-chloro-2-[1-(2,6-dichlorophenyl)-1H-pyrrol-3-yl]-8-methyl-4H-3,1-benzoxazine-4-one of the formula:

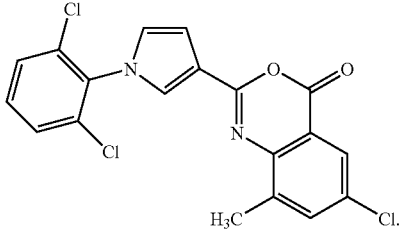

6-Chloro-2-[1-(2,6-dichlorophenyl)-1H-pyrrol-3-yl]-8-methyl-4H-3,1-benzoxazine-4-one $^1$H-NMR (DMSO-d$_6$, TMS) δ (ppm): 2.53 (3H, s), 6.89 (1H, s), 7.10 (1H, s), 7.43-7.64 (2H, m), 7.67-7.77 (2H, m), 7.82-7.91 (2H, m)

REFERENCE PREPARATION EXAMPLE 119-(3)

According to the same manner as that of Reference Preparation Example 71-(6), 6-chloro-2-[1-(2,6-dichlorophenyl)-1H-pyrrol-3-yl]-8-methyl-4H-3,1-benzoxazine -4-one was used in place of 2-[4-bromo-1-(3-chloro-2-pyridinyl)-1H-pyrrol-2-yl]-6-chloro-8-methyl-4H-3,1-benzoxazine-4-one to obtain N-[4-chloro-2-(hydrazinocarbonyl)-6-methylphenyl]-1-(2,6-dichlorophenyl)-1H-pyrrole-3-carboxamide of the formula:

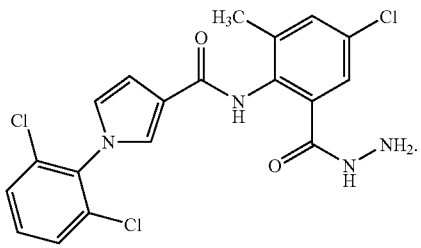

N-[4-chloro-2-(hydrazinocarbonyl)-6-methylphenyl]-1-(2,6-dichlorophenyl)-1H-pyrrole-3-carboxamide $^1$H-NMR (DMSO-d$_6$, TMS) δ (ppm): 2.22 (3H, s), 4.59 (2H, brs), 6.79 (1H, brs), 6.97 (1H, brs), 7.37 (1H, brs), 7.47-7.59 (3H, m), 7.71 (2H, d, J=8 Hz), 9.66 (1H, brs), 9.70 (1H, brs)

REFERENCE PREPARATION EXAMPLE 120

To a mixture of 4.61 g of methylhydrazine, 25 ml of methanol and 4.0 g of sodium hydroxide was added dropwise 10.8 g of N,N-dimethylcarbamoyl chloride under ice-cooling. The mixture was stirred at room temperature for 1 hour. The reaction mixture was filtered, and the filtrate was concentrated under reduced pressure. The residue was distilled under reduced pressure (90 to 99° C./22 mmHg) to obtain 5.70 g of 2,4,4-trimethylsemicarbazide of the formula:

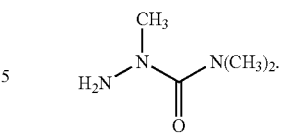

2,4,4-Trimethylsemicarbazide $^1$H-NMR (CDCl$_3$, TMS) δ (ppm): 2.90 (6H, s), 2.95 (3H, s), 3.94 (2H, brs).

REFERENCE PREPARATION EXAMPLE 121

According to the same manner as that of Reference Preparation Example 101, 2-[4,5-dichloro-1-(3-chloro-2-pyridinyl)-1H-pyrrol-2-yl]-6-chloro-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 4,5-dichloro-N-[4-chloro-2-(N-methylhydrazinocarbonyl)-6-methylphenyl]-1-(3-chloro-2-pyridinyl)-1H-pyrrole-2-carboxamide of the formula:

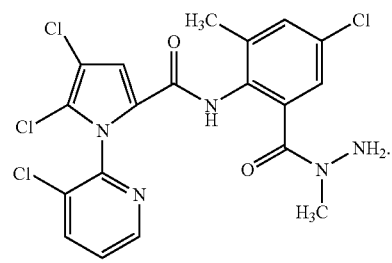

4,5-Dichloro-N-[4-chloro-2-(N-methylhydrazinocarbonyl)-6-methylphenyl]-1-(3-chloro-2-pyridinyl)-1H-pyrrole-2-carboxamide $^1$H-NMR (CDCl$_3$, TMS) δ (ppm): 2.01-2.05 (3H, m), 2.92 (2H, s), 3.21 (1H, s), 4.05 (0.7H, brs), 4.59 (1.3H, brs), 6.95-7.10 (2H, m), 7.19 (0.6H, s), 7.29 (0.4H, s), 7.37 (1H, dd, J=8 Hz, 4 Hz), 7.86 (1H, d, J=8 Hz), 8.48 (1H, d, J=5 Hz), 9.11 (0.6H, brs), 9.42 (0.4H, brs)

REFERENCE PREPARATION EXAMPLE 122-(1)

According to the same manner as that of Reference Preparation Example 13, 1-[(2-fluoro-3-pyridinyl)methyl]-3-trifluoromethyl-1H-pyrazole-5-carboxylic acid was used in place of 1-(3-chloro-2-pyridinyl)-1H-pyrazole-5-carboxylic acid to obtain 6-chloro-2-[1-[(2-fluoro-3-pyridinyl)methyl]-3-trifluoromethyl-1H-pyrazol-5-yl]-8-methyl-4H-3,1-benzoxazine-4-one of the formula:

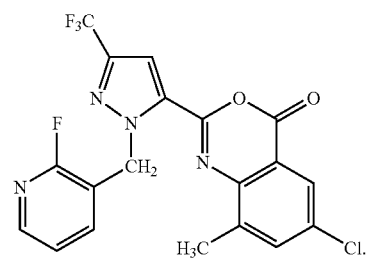

6-Chloro-2-[1-[(2-fluoro-3-pyridinyl)methyl]-3-trifluoromethyl-1H-pyrazol-5-yl]-8-methyl-4H-3,1-benzoxazine-4-one $^1$H-NMR (DMSO-$d_6$, TMS) δ (ppm): 2.25 (3H, s), 6.16 (2H, s), 7.30-7.36 (1H, m), 7.39-7.46 (1H, m), 7.69 (1H, s), 7.90 (1H, d, J=2 Hz), 7.98 (1H, d, J=2 Hz), 8.20 (1H, d, J=4 Hz)

REFERENCE PREPARATION EXAMPLE 122-(2)

According to the same manner as that of Reference Preparation Example 1, 6-chloro-2-[1-[(2-fluoro-3-pyridinyl)methyl]-3-trifluoromethyl-1H-pyrazol-5-yl]-8-methyl-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[4-chloro-2-(hydrazinocarbonyl)-6-methylphenyl]-1-[(2-fluoro-3-pyridinyl)methyl]-3-trifluoromethyl-1H-pyrazole-5-carboxamide of the formula:

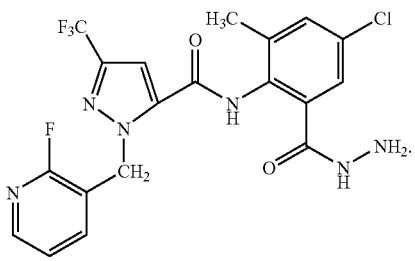

N-[4-chloro-2-(hydrazinocarbonyl)-6-methylphenyl]-1-[(2-fluoro-3-pyridinyl)methyl]-3-trifluoromethyl-1H-pyrazole-5-carboxamide $^1$H-NMR (DMSO-$d_6$, TMS) δ (ppm): 2.13 (3H, s), 4.37 (2H, brs), 5.86 (2H, s), 7.32-7.38 (2H, m), 7.50-7.57 (2H, m), 7.57-7.64 (1H, m), 8.16-8.21 (1H, m), 9.62 (1H, brs), 10.28 (1H, brs)

REFERENCE PREPARATION EXAMPLE 123-(1)

According to the same manner as that of Reference Preparation Example 13, 1-[(3-chloro-2-pyridinyl)methyl]-5-trifluoromethyl-1H-pyrazole-3-carboxylic acid was used in place of 1-(3-chloro-2-pyridinyl)-1H-pyrazole-5-carboxylic acid to obtain 2-[1-[(3-chloro-2-pyridinyl)methyl]-5-trifluoromethyl-1H-pyrazol-3-yl]-6-chloro-8-methyl-4H-3,1-benzoxazine-4-one of the formula:

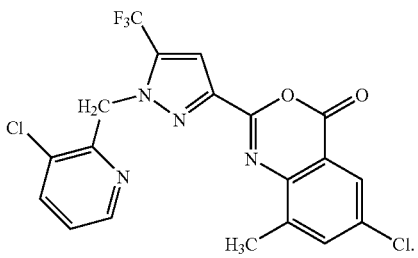

2-[1-[(3-Chloro-2-pyridinyl)methyl]-5-trifluoromethyl-1H-pyrazol-3-yl]-6-chloro-8-methyl-4H-3,1-benzoxazine-4-one $^1$H-NMR (DMSO-$d_6$, TMS) δ (ppm): 2.56 (3H, s), 5.92 (2H, s), 7.44 (1H, dd, J=8 Hz, 5 Hz), 7.67 (1H, s), 7.89-7.95 (2H, m), 8.04 (1H, d, J=8 Hz), 8.42 (1H, d, J=5 Hz)

REFERENCE PREPARATION EXAMPLE 123-(2)

According to the same manner as that of Reference Preparation Example 1, 2-[1-[(3-chloro-2-pyridinyl)methyl]-5-trifluoromethyl-1H-pyrazol-3-yl]-6-chloro-8-methyl-4H-3,1-benzoxazine-4-one was used in place of 6-chloro-2-[1-(3-chloro-2-pyridinyl)-3-trifluoromethyl-1H-pyrazol-5-yl]-8-methyl-4H-3,1-benzoxazine-4-one to obtain N-[4-chloro-2-(hydrazinocarbonyl)-6-methylphenyl]-1-[(3-chloro-2-pyridinyl)methyl]-5-trifluoromethyl-1H-pyrazole-3-carboxamide of the formula:

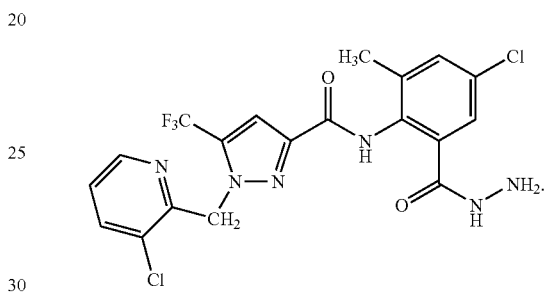

N-[4-chloro-2-(hydrazinocarbonyl)-6-methylphenyl]-1-[(3-chloro-2-pyridinyl)methyl]-5-trifluoromethyl-1H-pyrazole-3-carboxamide $^1$H-NMR (DMSO-$d_6$, TMS) δ (ppm): 2.19 (3H, s), 4.45 (2H, brs), 5.87 (2H, s), 7.37 (1H, brs), 7.41-7.50 (2H, m), 7.52 (1H, brs), 8.04 (1H, d, J=8 Hz), 8.45 (1H, d, J=4 Hz), 9.71 (1H, brs), 10.12 (1H, brs)

REFERENCE PREPARATION EXAMPLE 124-(1)

To a solution of 5.0 g of 3-chloro-2-(2-formyl-1H-pyrrol-1-yl)pyridine in 50 ml of N,N-dimethylformamide was added 5.4 g of N-iodosuccinimide. The resulting mixture was stirred at room temperature for 1 day. Water was poured into the reaction mixture, and the mixture was extracted with ethyl acetate two times. The organic layers were combined, washed with an aqueous saturated sodium chloride solution, dried over anhydrous magnesium sulfate, and concentrated under reduced pressure. The residue was subjected to silica gel column chromatography to obtain 3.2 g of 1-(3-chloro-2-pyridinyl)-4-iodo-1H-pyrrole-2-carbaldehyde of the formula:

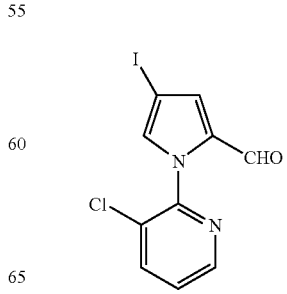

and 0.90 g of 1-(3-chloro-2-pyridinyl)-5-iodo-1H-pyrrole-2-carbaldehyde of the formula:

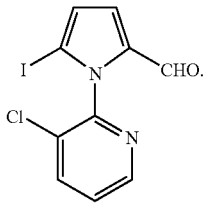

1-(3-Chloro-2-pyridinyl)-4-iodo-1H-pyrrole-2-carbaldehyde $^1$H-NMR (CDCl$_3$, TMS) δ (ppm): 7.19-7.20 (2H, m), 7.38-7.42 (1H, m), 7.89 (1H, d, J=8 Hz), 8.45-8.47 (1H, m), 9.51 (1H, s)

1-(3-Chloro-2-pyridinyl)-5-iodo-1H-pyrrole-2-carbaldehyde $^1$H-NMR (CDCl$_3$, TMS) δ (ppm): 6.72 (1H, d, J=4 Hz), 7.04 (1H, d, J=4 Hz), 7.47 (1H, dd, J=8 Hz, 5 Hz), 7.93 (1H, dd, J=8 Hz, 2 Hz), 8.55 (1H, dd, J=5 Hz, 2 Hz), 9.26 (1H, s)

REFERENCE PREPARATION EXAMPLE 124-(2)

According to the same manner as that of Reference Preparation Example 71-(4), 1-(3-chloro-2-pyridinyl)-4-iodo-1H-pyrrole-2-carbaldehyde was used in place of 4-bromo-1-(3-chloro-2-pyridinyl)-1H-pyrrole-2-carbaldehyde to obtain 1-(3-chloro-2-pyridinyl)-4-iodo-1H-pyrrole-2-carboxylic acid of the formula:

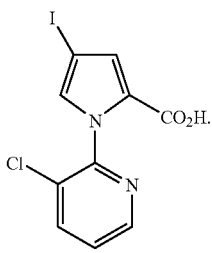

1-(3-Chloro-2-pyridinyl)-4-iodo-1H-pyrrole-2-carboxylic acid $^1$H-NMR (DMSO-d$_6$, TMS)$_δ$(ppm): 7.05 (1H, d, J=2 Hz), 7.45 (1H, d, J=2 Hz), 7.57 (1H, dd, J=8 Hz, 5 Hz), 8.15 (1H, dd, J=8 Hz, 2 Hz), 8.49 (1H, dd, J=5 Hz, 2 Hz), 12.65 (1H, brs)

REFERENCE PREPARATION EXAMPLE 124-(3)

According to the same manner as that of Reference Preparation Example 71-(5), 1-(3-chloro-2-pyridinyl)-4-iodo-1H-pyrrole-2-carboxylic acid was used in place of 4-bromo-1-(3-chloro-2-pyridinyl)-1H-pyrrole-2-carboxylic acid to obtain 6-chloro-2-[1-(3-chloro-2-pyridinyl)-4-iodo-1H-pyrrol-2-yl]-8-methyl-4H-3,1-benzoxazine-4-one of the formula:

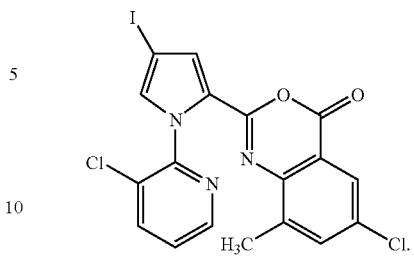

6-Chloro-2-[1-(3-chloro-2-pyridinyl)-4-iodo-1H-pyrrol-2-yl]-8-methyl-4H-3,1-benzoxazine-4-one $^1$H-NMR (CDCl$_3$, TMS) δ (ppm): 1.67 (3H, s), 7.30 (1H, d, J=2 Hz), 7.61 (1H, d, J=2 Hz), 7.63-7.67 (2H, m), 7.82 (1H, d, J=3 Hz), 8.22 (1H, dd, J=8 Hz, 2 Hz), 8.56 (1H, dd, J=5 Hz, 2 Hz)

REFERENCE PREPARATION EXAMPLE 124-(4)

According to the same manner as that of Reference Preparation Example 71-(6), 6-chloro-2-[1-(3-chloro-2-pyridinyl)-4-iodo-1H-pyrrol-2-yl]-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain N-[4-chloro-2-(hydrazinocarbonyl)-6-methylphenyl]-1-(3-chloro-2-pyridinyl)-4-iodo-1H-pyrrole-2-carboxamide of the formula:

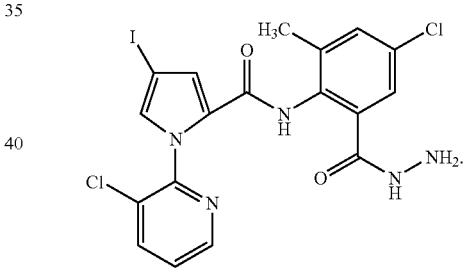

N-[4-chloro-2-(hydrazinocarbonyl)-6-methylphenyl]-1-(3-chloro-2-pyridinyl)-4-iodo-1H-pyrrole-2-carboxamide $^1$H-NMR (DMSO-d$_6$, TMS) δ (ppm): 2.13 (3H, s), 4.39 (2H, brs), 7.26 (1H, s), 7.30 (1H, s), 7.39 (1H, s), 7.42 (1H, s), 7.49 (1H, dd, J=8 Hz, 5 Hz), 8.05 (1H, dd, J=8 Hz, 2 Hz), 8.43 (1H, dd, J=5 Hz, 2 Hz), 9.52 (1H, brs), 9.84 (1H, brs)

REFERENCE PREPARATION EXAMPLE 125

According to the same manner as that of Reference Preparation Example 71-(5), 4,5-dichloro-1-(3-chloro-2-pyridinyl)-1H-pyrrole-2-carboxylic acid and 3-amino-7-bromo-4-chloro-2-naphthoic acid were used in place of 4-bromo-1-(3-chloro-2-pyridinyl)-1H-pyrrole-2-carboxylic acid and 2-amino-5-chloro-3-methylbenzoic acid respectively to obtain 10-chloro-2-[4,5-dichloro-1-(3-chloro-2-pyridinyl)-1H-pyrrol-2-yl]-4H-naphtho[2,3-d][1,3]oxazine-4-one of the formula:

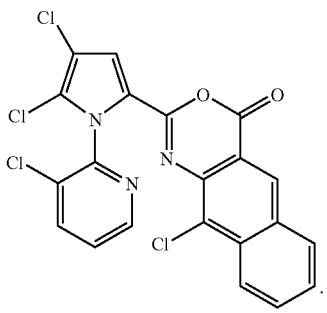

10-Chloro-2-[4,5-dichloro-1-(3-chloro-2-pyridinyl)-1H-pyrrol-2-yl]-4H-naphtho[2,3-d][1,3]oxazine-4-one $^1$H-NMR (DMSO-d$_6$, TMS) δ (ppm): 7.51 (1H, s), 7.70 (1H, t, J=8 Hz), 7.78 (1H, dd, J=8 Hz, 5 Hz), 7.84 (1H, t, J=8 Hz), 8.16 (1H, d, J=8 Hz), 8.28 (1H, d, J=8 Hz), 8.40 (1H, dd, J=8 Hz, 2 Hz), 8.68 (1H, dd, J=5 Hz, 2 Hz), 8.82 (1H, s)

REFERENCE PREPARATION EXAMPLE 126-(1)

To 30 ml of acetic acid were added 5.0 g of 2-chloro-3-pyridinylamine and 5.6 g of 2,5-dimethoxytetrahydrofuran, and the mixture was heated to reflux for 2 hours. The reaction mixture was allowed to cool to room temperature, poured into water, and then extracted with ethyl acetate two times. The organic layers were combined, washed successively with water and an aqueous saturated sodium chloride solution, dried over anhydrous sodium sulfate, and concentrated under reduced pressure. The resulting residue was subjected to silica gel chromatography to obtain 6.5 g of 1-(2-chloro-3-pyridinyl)-1H-pyrrole of the formula:

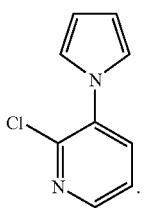

1-(2-Chloro-3-pyridinyl)-1H-pyrrole $^1$H-NMR (DMSO-d$_6$, TMS) δ (ppm): 6.29 (2H, t, J=2 Hz), 7.09 (2H, t, J=2 Hz), 7.58 (1H, dd, J=8H, 5 Hz), 7.95 (1H, dd, J=8H, 2 Hz), 8.45 (1H, dd, J=5H, 2 Hz) Reference Preparation Example 126-(2)

To 14.6 g of N,N-dimethylformamide was added dropwise 8.3 g of phosphorus oxychloride under ice-cooling. The mixture was stirred at room temperature for 30 minutes. Thereto 6.5 g of 1-(2-chloro-3-pyridinyl)-1H-pyrrole was added, and the resulting mixture was stirred at 60° C. for 2 hours. The reaction mixture was allowed to cool to room temperature, and added to ice water. The mixture was adjusted to pH 4 by an addition of a 2N aqueous sodium hydroxide solution, and then extracted with ethyl acetate two times. The organic layers were combined, washed successively with water and an aqueous saturated sodium chloride solution, dried over anhydrous sodium sulfate, and concentrated under reduced pressure. The resulting residue was subjected to silica gel chromatography to obtain 6.05 g of 1-(2-chloro-3-pyridinyl)-1H-pyrrole-2-carbaldehyde of the formula:

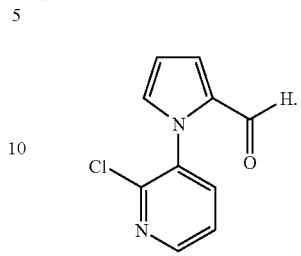

1-(2-Chloro-3-pyridinyl)-1H-pyrrole-2-carbaldehyde $^1$H-NMR (DMSO-d$_6$, TMS) δ (ppm): 6.53 (1H, t, J=2 Hz), 7.30 (1H, d, J=2 Hz), 7.43 (1H, brs), 7.59 (1H, dd, J=8H, 5 Hz), 8.00 (1H, d, J=8 Hz), 8.52 (1H, d, J=5 Hz), 9.51 (1H, s)

REFERENCE PREPARATION EXAMPLE 126-(3)

To a solution of 6.05 g of 1-(2-chloro-3-pyridinyl)-1H-pyrrole-2-carbaldehyde in 20 ml of N,N-dimethylformamide was added 5.72 g of N-bromosuccinimide. The resulting mixture was stirred at room temperature for 1 hour. Water was poured into the reaction mixture, and a deposited precipitate was collected by filtration to obtain 4.22 g of 4-bromo-1-(2-chloro-3-pyridinyl)-1H-pyrrole-2-carbaldehyde of the formula:

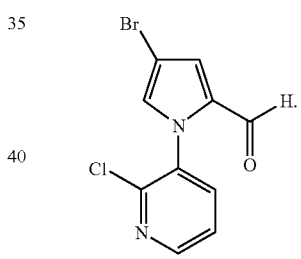

4-Bromo-1-(2-chloro-3-pyridinyl)-1H-pyrrole-2-carbaldehyde $^1$H-NMR (DMSO-d$_6$, TMS) δ (ppm): 7.42 (1H, d, J=2 Hz), 7.60 (1H, dd, J=8H, 5 Hz), 7.70 (1H, dd, J=2H, 1Hz), 8.06 (1H, dd, J=8H, 2 Hz), 8.54 (1H, dd, J=5H, 2 Hz), 9.47 (1H, d, J=1 Hz)

REFERENCE PREPARATION EXAMPLE 126-(4)

A solution of 4.43 g of potassium permanganate in 15 ml of water was added dropwise to a mixture of 4.22 g of 4-bromo-1-(2-chloro-3-pyridinyl)-1H-pyrrole-2-carbaldehyde and 30 ml of acetone while the mixture was maintained at 40° C. The resulting mixture was stirred at 40° C. for 2 hours. A precipitate was filtered off to obtain a filtrate. The filtrate was adjusted to pH 10-12 by an addition of a 2N aqueous sodium hydroxide solution, and then washed with chloroform two times. The aqueous layer was adjusted to around pH 3 by an addition of 2N hydrochloric acid, and then extracted with ethyl acetate two times. The organic layers were combined, washed successively with water and an aqueous saturated sodium chloride solution, dried over anhydrous sodium sulfate, and concentrated under reduced pressure to obtain 3.02 g of 4-bromo-1-(2-chloro-3-pyridinyl)-1H-pyrrole-2-carboxylic acid of the formula:

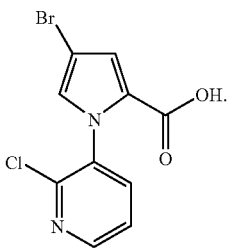

4-Bromo-1-(2-chloro-3-pyridinyl)-1H-pyrrole-2-carboxylic acid

¹H-NMR (DMSO-d₆, TMS) δ (ppm): 7.05 (1H, s), 7.46 (1H, s), 7.57 (1H, dd, J=8H, 4 Hz), 8.02 (1H, d, J=8 Hz), 8.49 (1H, d, J=4 Hz), 12.70 (1H, brs)

REFERENCE PREPARATION EXAMPLE 126-(5)

According to the same manner as that of Reference Preparation Example 71-(5), 4-bromo-1-(2-chloro-3-pyridinyl)-1H-pyrrole-2-carboxylic acid was used in place of 4-bromo-1-(3-chloro-2-pyridinyl)-1H-pyrrole-2-carboxylic acid to obtain 2-[4-bromo-1-(2-chloro-3-pyridinyl)-1H-pyrrol-2-yl]-6-chloro-8-methyl-4H-3,1-benzoxazine-4-one of the formula:

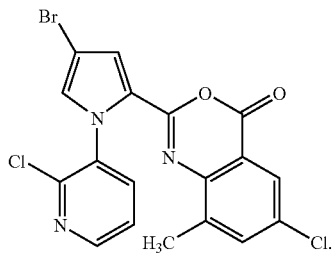

2-[4-Bromo-1-(2-chloro-3-pyridinyl)-1H-pyrrol-2-yl]-6-chloro-8-methyl-4H-3,1-benzoxazine-4-one ¹H-NMR (DMSO-d₆, TMS) δ (ppm): 1.65 (3H, s), 7.31 (1H, s), 7.62-7.73 (3H, m), 7.84 (1H, s), 8.10 (1H, d, J=6 Hz), 8.57 (1H, s)

REFERENCE PREPARATION EXAMPLE 126-(6)

According to the same manner as that of Reference Preparation Example 71-(6), 2-[4-bromo-1-(2-chloro-3-pyridinyl)-1H-pyrrol-2-yl]-6-chloro-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 4-bromo-N-[4-chloro-2-(hydrazinocarbonyl)-6-methylphenyl]-1-(2-chloro-3-pyridinyl)-1H-pyrrole-2-carboxamide of the formula:

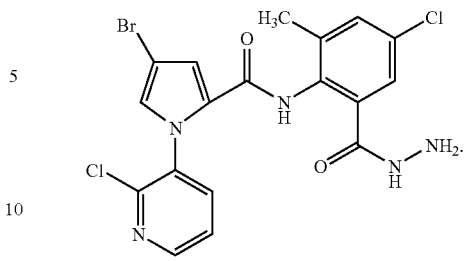

4-Bromo-N-[4-chloro-2-(hydrazinocarbonyl)-6-methylphenyl]-1-(2-chloro-3-pyridinyl)-1H-pyrrole-2-carboxamide ¹H-NMR (DMSO-d₆, TMS) δ (ppm): 2.14 (3H, s), 4.37 (2H, brs), 7.28 (2H, s), 7.40-7.46 (2H, m), 7.52 (1H, dd, J=8H, 4 Hz), 7.95 (1H, d, J=8Hz), 8.42 (1H, d, J=4 Hz), 9.51 (1H, brs), 9.82 (1H, brs)

REFERENCE PREPARATION EXAMPLE 127-(1)

To a mixture of 0.56 g of 3-amino-4-chloro-2-naphthoic acid and 20 ml of acetic acid was added dropwise 0.4 g of bromine at room temperature. The resulting mixture was stirred at room temperature for 1 hour. A deposited precipitate was collected by filtration, and the resulting solid was washed successively with acetic acid and ethyl acetate to obtain 0.36 g of 3-amino-7-bromo-4-chloro-2-naphthoic acid of the formula:

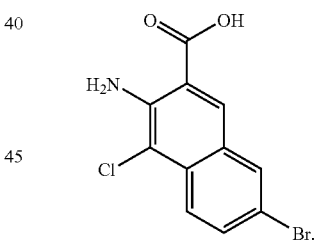

3-Amino-7-bromo-4-chloro-2-naphthoic acid

¹H-NMR (DMSO-d₆, TMS) δ (ppm): 7.70 (1H, d, J=9 Hz), 7.81 (1H, d, J=9 Hz), 8.24 (1H, s), 8.53 (1H, s)

REFERENCE PREPARATION EXAMPLE 127-(2)

According to the same manner as that of Reference Preparation Example 46-(1), 3-amino-7-bromo-4-chloro-2-naphthoic acid was used in place of 2-amino-3,5-dibromobenzoic acid to obtain 7-bromo-2-[3-bromo-1-(3-chloro-2-pyridinyl)-1H-pyrazol-5-yl]-10-chloro-4H-naphtho[2,3-d][1,3]oxazine-4-one of the formula:

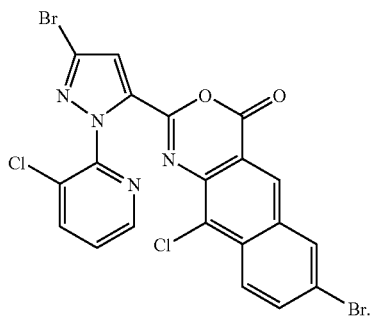

7-Bromo-2-[3-bromo-1-(3-chloro-2-pyridinyl)-1H-pyrazol-5-yl]-10-chloro-4H-naphtho[2,3-d][1,3]oxazine-4-one $^1$H-NMR (DMSO-d$_6$, TMS) δ (ppm): 7.56 (1H, s), 7.75-7.81 (1H, m), 7.99 (1H, d, J=10 Hz), 8.14 (1H, d, J=10 Hz), 8.37 (1H, d, J=8 Hz), 8.61-8.68 (2H, m), 8.85 (1H, brs)

REFERENCE PREPARATION EXAMPLE 128-(1)

To a mixture of 0.47 g of 3-amino-2-naphthoic acid and 20 ml of acetic acid was added dropwise 0.8 g of bromine at room temperature. The resulting mixture was stirred at room temperature for 1 hour. A deposited precipitate was collected by filtration, and the resulting solid was washed successively with acetic acid and ethyl acetate to obtain 0.61 g of 3-amino-4,7-dibromo-2-naphthoic acid of the formula:

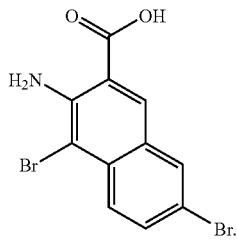

3-Amino-4,7-dibromo-2-naphthoic acid $^1$H-NMR (DMSO-d$_6$, TMS) δ (ppm): 7.70 (1H, dd, J=9, 2 Hz), 7.80 (1H, d, J=9 Hz), 8.22 (1H, d, J=2 Hz), 8.57 (1H, s)

REFERENCE PREPARATION EXAMPLE 128-(2)

According to the same manner as that of Reference Preparation Example 46-(1), 3-amino-4,7-dibromo-2-naphthoic acid was used in place of 2-amino-3,5-dibromobenzoic acid to obtain 7,10-dibromo-2-[3-bromo-1-(3-chloro-2-pyridinyl)-1H-pyrazol-5-yl]-4H-naphtho[2,3-d][1,3]oxazine-4-one of the formula:

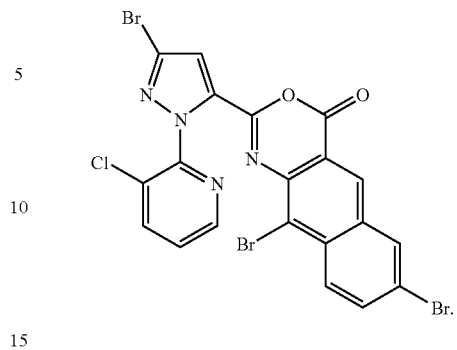

7,10-Dibromo-2-[3-bromo-1-(3-chloro-2-pyridinyl)-1H-pyrazol-5-yl]-4H-naphtho[2,3-d][1,3]oxazine-4-one $^1$H-NMR (DMSO-d$_6$, TMS) δ (ppm): 7.56 (1H, s), 7.76 (1H, dd, J=8 Hz, 5 Hz), 7.99 (1H, d, J=9 Hz), 8.14 (1H, d, J=9 Hz), 8.37 (1H, d, J=8 Hz), 8.61-8.67 (2H, m), 8.90 (1H, brs)

REFERENCE PREPARATION EXAMPLE 129-(1)

A mixture of 10 g of 2-pyrrolecarbaldehyde, 10 g of 2-fluoropyridine, 24 g of cesium carbonate and 100 ml of N-methylpyrrolidone was stirred at 120° C. for 1 day. The reaction mixture was allowed to cool to room temperature. Water was poured into the mixture, and the mixture was extracted with ethyl acetate two times. The organic layers were combined, washed successively with water and an aqueous saturated sodium chloride solution, dried over magnesium sulfate, and concentrated under reduced pressure. The resulting residue was subjected to silica gel chromatography to obtain 7.7 g of 1-(2-pyridinyl)-1H-pyrrole-2-carbaldehyde of the formula:

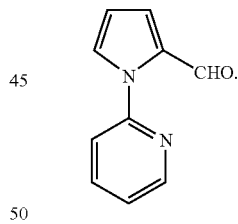

1-(2-Pyridinyl)-1H-pyrrole-2-carbaldehyde $^1$H-NMR (CDCl$_3$, TMS) δ (ppm): 6.44 (1H, dd, J=4 Hz, 3 Hz), 7.21 (1H, dd, J=4 Hz, 2 Hz), 7.30-7.33 (1H, m), 7.44-7.47 (2H, m), 7.81-7.86 (1H, m), 8.53 (1H, dd, J=5 Hz, 2 Hz), 9.77 (1H, s)

REFERENCE PREPARATION EXAMPLE 129-(2)

According to the same manner as that of Reference Preparation Example 97-(1), 1-(2-pyridinyl)-1H-pyrrole-2-carbaldehyde was used in place of 3-chloro-2-(2-formyl-1H-pyrrole-1-yl)pyridine to obtain 5-chloro-1-(2-pyridinyl)-1H-pyrrole-2-carbaldehyde of the formula:

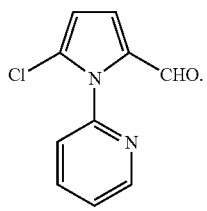

5-Chloro-1-(2-pyridinyl)-1H-pyrrole-2-carbaldehyde $^1$H-NMR (CDCl$_3$, TMS) δ (ppm): 6.36 (1H, d, J=4 Hz), 7.07 (1H, d, J=4 Hz), 7.38 (1H, d, J=8 Hz), 7.44 (1H, dd, J=8 Hz, 5 Hz), 7.87-7.91 (1H, m), 8.6.1 (1H, d, J=5 Hz), 9.41 (1H, s)

REFERENCE PREPARATION EXAMPLE 129-(3)

According to the same manner as that of Reference Preparation Example 71-(4), 5-chloro-1-(2-pyridinyl)-1H-pyrrole-2-carbaldehyde was used in place of 4-bromo-1-(3-chloro-2-pyridinyl)-1H-pyrrole-2-carbaldehyde to obtain 5-chloro-1-(2-pyridinyl)-1H-pyrrole-2-carboxylic acid of the formula:

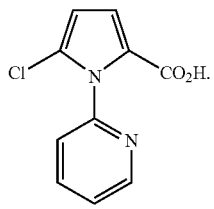

5-Chloro-1-(2-pyridinyl)-1H-pyrrole-2-carboxylic acid $^1$H-NMR (DMSO-d$_6$, TMS) δ (ppm): 6.36 (1H, d, J=4 Hz), 6.98 (1H, d, J=4 Hz), 7.45 (1H, d, J=8 Hz), 7.50-7.53 (1H, m), 7.97-8.00 (1H, m), 8.56 (1H, d, J=5 Hz), 12.34 (1H, brs)

REFERENCE PREPARATION EXAMPLE 129-(4)

According to the same manner as that of Reference Preparation Example 71-(5), 5-chloro-1-(2-pyridinyl)-1H-pyrrole-2-carboxylic acid was used in place of 4-bromo-1-(3-chloro-2-pyridinyl)-1H-pyrrole-2-carboxylic acid to obtain 2-[5-chloro-1-(2-pyridinyl)-1H-pyrrol-2-yl]-6-chloro-8-methyl-4H-3,1-benzoxazine-4-one of the formula:

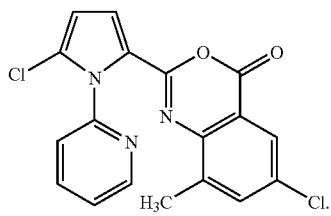

2-[5-Chloro-1-(2-pyridinyl)-1H-pyrrol-2-yl]-6-chloro-8-methyl-4H-3,1-benzoxazine-4-one $^1$H-NMR (CDCl$_3$, TMS) δ (ppm): 1.70 (3H, s), 6.38 (1H, d, J=4 Hz), 7.29 (1H, d, J=4 Hz), 7.38 (1H, s), 7.41-7.49 (2H, m), 7.91-7.94 (2H, m), 8.66 (1H, brs)

REFERENCE PREPARATION EXAMPLE 129-(5)

According to the same manner as that of Reference Preparation Example 71-(6), 2-[5-chloro-1-(2-pyridinyl)-1H-pyrrol-2-yl]-6-chloro-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 5-chloro-N-[4-chloro-2-(hydrazinocarbonyl)-6-methylphenyl]-1-(2-pyridinyl)-1H-pyrrole-2-carboxamide of the formula:

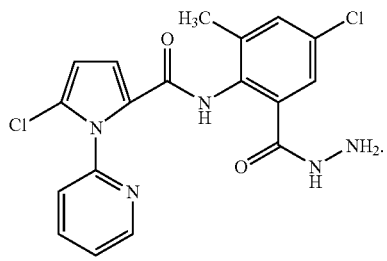

5-Chloro-N-[4-chloro-2-(hydrazinocarbonyl)-6-methylphenyl]-1-(2-pyridinyl)-1H-pyrrole-2-carboxamide $^1$H-NMR (DMSO-d$_6$, TMS) δ (ppm): 2.13 (3H, s), 4.43 (2H, brs), 6.40 (1H, d, J=4 Hz), 7.11 (1H, d, J=4 Hz), 7.30 (1H, d, J=2 Hz), 7.40-7.47 (3H, m), 7.94 (1H, td, J=7 Hz, 2 Hz), 8.51 (1H, dd, J=5 Hz, 2 Hz), 9.51 (1H, brs), 9.85 (1H, brs)

REFERENCE PREPARATION EXAMPLE 130

According to the same manner as that of Reference Preparation Example 101, 8-bromo-2-[4-bromo-1-(3-chloro-2-pyridinyl)-1H-pyrrol-2-yl]-6-chloro-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 4-bromo-N-[6-bromo-4-chloro-2-(N-methylhydrazinocarbonyl)phenyl]-1-(3-chloro-2-pyridinyl)-1H-pyrrole-2-carboxamide of the formula:

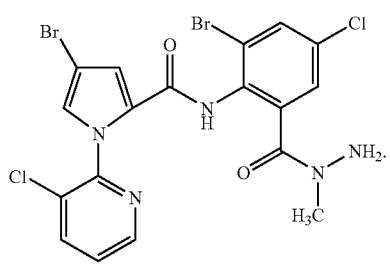

4-Bromo-N-[6-bromo-4-chloro-2-(N-methylhydrazinocarbonyl) phenyl]-1-(3-chlolo-2-pyridinyl)-1H-pyrrole-2-carboxamide $^1$H-NMR (CDCl$_3$, TMS) δ (ppm): 2.96 (1.5H, s), 3.15 (1.5H, s), 4.05 (1H, brs), 4.49 (1H, brs), 7.03 (1H, d, J=2 Hz), 7.16 (1H, dd, J=7 Hz, 4 Hz), 7.20 (1H, d, J=2 Hz), 7.29-7.34 (1H, m), 7.47 (0.5H, d, J=2 Hz), 7.53 (0.5H, d, J=2 Hz), 7.83-7.79 (1H, m), 8.40-8.43 (1H, m), 8.67 (0.5H, brs), 8.77 (0.5H, brs)

REFERENCE PREPARATION EXAMPLE 131-(1)

According to the same manner as that of Reference Preparation Example 129-(1), 2-chloro-3-cyanopyridine was used in place of 2-fluoropyridine to obtain 2-(2-formyl-1H-pyrrol-1-yl)-3-cyanopyridine of the formula:

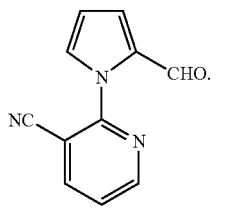

2-(2-Formyl-1H-pyrrol-1-yl)-3-cyanopyridine $^1$H-NMR (CDCl$_3$, TMS) δ (ppm): 6.53 (1H, dd, J=4 Hz, 3 Hz), 7.22 (1H, dd, J=4 Hz, 2 Hz), 7.29-7.31 (1H, m), 7.51 (1H, dd, J=8 Hz, 5 Hz), 8.12 (1H, dd, J=8 Hz, 2 Hz), 8.74 (1H, dd, J=5 Hz, 2 Hz) 9.65 (1H, s)

REFERENCE PREPARATION EXAMPLE 131-(2)

According to the same manner as that of Reference Preparation Example 71-(3), 2-(2-formyl-1H-pyrrol-yl)-3-cyanopyridine was used in place of 3-chloro-2-(2-formyl-1H-pyrrol-1-yl)pyridine to obtain 2-(4-bromo-2-formyl-1H-pyrrol-1-yl)-3-cyanopyridine of the formula:

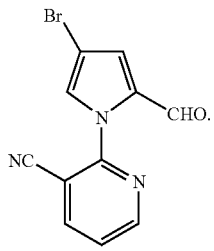

2-(4-Bromo-2-formyl-1H-pyrrol-1-yl)-3-cyanopyridine $^1$H-NMR (CDCl$_3$, TMS) δ (ppm): 7.18 (1H, d, J=2 Hz), 7.29 (1H, d, J=2 Hz), 7.54 (1H, dd, J=8 Hz, 5 Hz), 8.13 (1H, dd, J=8 Hz, 2 Hz), 8.74 (1H, dd, J=5 Hz, 2 Hz), 9.59 (1H, s)

REFERENCE PREPARATION EXAMPLE 131-(3)

According to the same manner as that of Reference Preparation Example 71-(4), 2-(4-bromo-2-formyl-1H-pyrrol-1-yl)-3-cyanopyridine was used in place of 4-bromo-1-(3-chloro-2-pyridinyl)-1H-pyrrole-2-carbaldehyde to obtain 4-bromo-1-(3-cyano-2-pyridinyl)-1H-pyrrole-2-carboxylic acid of the formula:

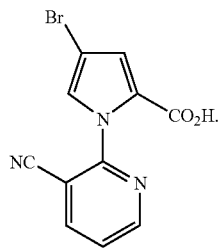

4-Bromo-1-(3-cyano-2-pyridinyl)-1H-pyrrole-2-carboxylic acid $^1$H-NMR (DMSO-d$_6$, TMS) δ (ppm): 7.10 (1H, d, J=2 Hz), 7.65 (1H, d, J=2 Hz), 7.75 (1H, dd, J=8 Hz, 5 Hz), 8.55 (1H, dd, J=8 Hz, 2 Hz), 8.82 (1H, dd, J=5H z, 2 Hz)

REFERENCE PREPARATION EXAMPLE 131-(4)

According to the same manner as that of Reference Preparation Example 71-(5), 4-bromo-1-(3-cyano-2-pyridinyl)-1H-pyrrole-2-carboxylic acid and 2-amino-3,5-dibromobenzoic acid were used in place of 4-bromo-1-(3-chloro-2-pyridinyl)-1H-pyrrole-2-carboxylic acid and 2-amino-5-chloro-3-methylbenzoic acid respectively to obtain 6,8-dibromo-2-[4-bromo-1-(3-cyano-2-pyridinyl)-1H-pyrrol-2-yl]-4H-3,1-benzoxazine-4-one of the formula:

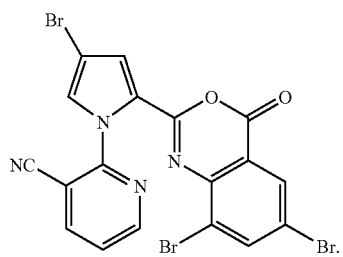

6,8-Dibromo-2-[4-bromo-1-(3-cyano-2-pyridinyl)-1H-pyrrol-2-yl]-4H-3,1-benzoxazine-4-one $^1$H-NMR (DMSO-d$_6$, TMS) δ (ppm): 7.39 (1H, d, J=2 Hz), 7.77 (1H, dd, J=8 Hz, 5 Hz), 7.81 (1H, d, J=2 Hz), 8.14 (1H, d, J=2 Hz), 8.21 (1H, d, J=2 Hz), 8.58 (1H, dd, J=8 Hz, 2 Hz), 8.83 (1H, dd, J=5 Hz, 2 Hz)

REFERENCE PREPARATION EXAMPLE 132-(1)

According to the same manner as that of Reference Preparation Example 129-(1), 2-chloro-3-trifluoromethylpyridine was used in place of 2-fluoropyridine to obtain 1-(3-trifluoromethyl-2-pyridinyl)-1H-pyrrole-2-carbaldehyde of the formula:

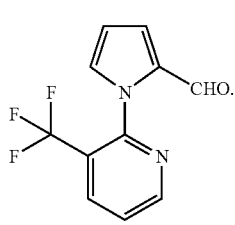

1-(3-Trifluoromethyl-2-pyridinyl)-1H-pyrrole-2-carbaldehyde $^1$H-NMR (CDCl$_3$, TMS) δ (ppm): 6.47 (1H, dd, J=4 Hz, 3 Hz), 7.12-7.14 (2H, m), 7.59 (1H, dd, J=8 Hz, 5 Hz), 8.18 (1H, d, J=8 Hz), 8.75 (1H, d, J=5 Hz), 9.54 (1H, d, J=1 Hz)

REFERENCE PREPARATION EXAMPLE 132-(2)

According to the same manner as that of Reference Preparation Example 71-(3), 1-(3-trifluoromethyl-2-pyridinyl)-1H-pyrrole-2-carbaldehyde was used in place of 3-chloro-2-(2-formyl-1H-pyrrol-1-yl)pyridine to obtain 4-bromo-1-(3-trifluoromethyl-2-pyridinyl)-1H-pyrrole-2-carbaldehyde of the formula:

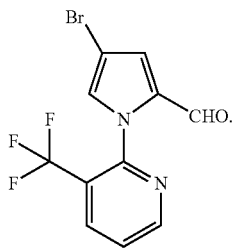

4-Bromo-1-(3-trifluoromethyl-2-pyridinyl)-1H-pyrrole-2-carbaldehyde $^1$H-NMR (CDCl$_3$, TMS) δ (ppm): 7.11 (2H, s), 7.62 (1H, dd, J=8 Hz, 5 Hz), 8.18 (1H, d, J=8 Hz), 8.74 (1H, d, J=5 Hz), 9.47 (1H, s)

REFERENCE PREPARATION EXAMPLE 132-(3)

According to the same manner as that of Reference Preparation Example 71-(4), 4-bromo-1-(3-trifluoromethyl-2-pyridinyl)-1H-pyrrole-2-carbaldehyde was used in place of 4-bromo-1-(3-chloro-2-pyridinyl)-1H-pyrrole-2-carbaldehyde to obtain 4-bromo-1-(3-trifluoromethyl-2-pyridinyl)-1H-pyrrole-2-carboxylic acid of the formula:

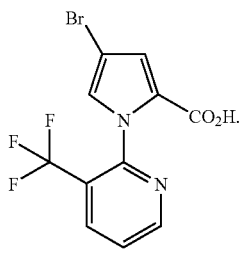

4-Bromo-1-(3-trifluoromethyl-2-pyridinyl)-1H-pyrrole-2-carboxylic acid $^1$H-NMR (DMSO-d$_6$, TMS) δ (ppm): 7.02 (1H, d, J=2 Hz), 7.56 (1H, d, J=2 Hz), 7.80 (1H, dd, J=7 Hz, 5 Hz), 8.42 (1H, d, J=7 Hz), 8.82 (1H, d, J=5 Hz), 12.66 (1H, brs)

REFERENCE PREPARATION EXAMPLE 132-(4)

According to the same manner as that of Reference Preparation Example 71-(5), 4-bromo-1-(3-trifluoromethyl-2-pyridinyl)-1H-pyrrole-2-carboxylic acid and 2-amino-3,5-dibromobenzoic acid were used in place of 4-bromo-1-(3-chloro-2-pyridinyl)-1H-pyrrole-2-carboxylic acid and 2-amino-5-chloro-3-methylbenzoic acid respectively to obtain 6,8-dibromo-2-[4-bromo-1-(3-trifluoromethyl-2-pyridinyl)-1H-pyrrol-2-yl]-4H-3,1-benzoxazine-4-one of the formula:

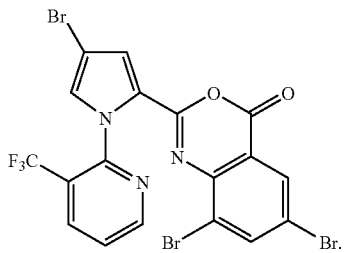

6,8-Dibromo-2-[4-bromo-1-(3-trifluoromethyl-2-pyridinyl)-1H-pyrrol-2-yl]-4H-3,1-benzoxazine-4-one $^1$H-NMR (DMSO-d$_6$, TMS) δ (ppm): 7.34 (1H, s), 7.71 (1H, s), 7.83 (1H, dd, J=8 Hz, 5 Hz), 8.10 (1H, d, J=2 Hz), 8.19 (1H, d, J=2 Hz), 8.48 (1H, d, J=8 Hz), 8.84 (1H, d, J=5 Hz)

REFERENCE PREPARATION EXAMPLE 133-(1)

According to the same manner as that of Reference Preparation Example 71-(4), 1-(3-chloro-2-pyridinyl)-5-iodo-1H-pyrrole-2-carbaldehyde was used in place of 4-bromo-1-(3-chloro-2-pyridinyl)-1H-pyrrole-2-carbaldehyde to obtain 1-(3-chloro-2-pyridinyl)-5-iodo-1H-pyrrole-2-carboxylic acid of the formula:

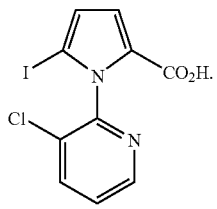

1-(3-Chloro-2-pyridinyl)-5-iodo-1H-pyrrole-2-carboxylic acid $^1$H-NMR (DMSO-d$_6$, TMS) δ (ppm): 6.63 (1H, d, J=4 Hz), 6.97 (1H, d, J=4 Hz), 7.62 (1H, dd, J=8 Hz, 5 Hz), 8.20 (1H, d, J=8 Hz), 8.56 (1H, d, J=5 Hz), 12.43 (1H, brs)

REFERENCE PREPARATION EXAMPLE 133-(2)

According to the same manner as that of Reference Preparation Example 71-(5), 1-(3-chloro-2-pyridinyl)-5-iodo-1H-pyrrole-2-carboxylic acid was used in place of 4-bromo-1-(3-chloro-2-pyridinyl)-1H-pyrrole-2-carboxylic acid to obtain 6-chloro-2-[1-(3-chloro-2-pyridinyl)-5-iodo-1H-pyrrol-2-yl]-8-methyl-4H-3,1-benzoxazine-4-one of the formula:

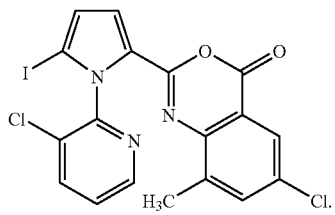

6-Chloro-2-[1-(3-chloro-2-pyridinyl)-5-iodo-1H-pyrrol-2-yl]-8-methyl-4H-3,1-benzoxazine-4-one $^1$H-NMR (DMSO-d$_6$, TMS) δ (ppm): 1.65 (3H, s), 6.82 (1H, d, J=3 Hz), 7.23 (1H, d, J=3 Hz), 7.67 (1H, s), 7.71 (1H, dd, J=8 Hz, 5 Hz), 7.81 (1H, s), 8.32 (1H, d, J=8 Hz), 8.65 (1H, d, J=5 Hz)

REFERENCE PREPARATION EXAMPLE 133-(3)

According to the same manner as that of Reference Preparation Example 71-(6), 6-chloro-2-[1-(3-chloro-2-pyridinyl)-5-iodo-1H-pyrrol-2-yl]-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain N-[4-chloro-2-(hydrazinocarbonyl)-6-methylphenyl]-1-(3-chloro-2-pyridinyl)-5-iodo-1H-pyrrole-2-carboxamide of the formula:

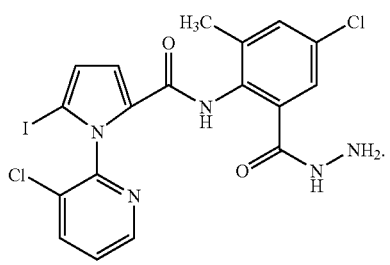

N-[4-chloro-2-(hydrazinocarbonyl)-6-methylphenyl]-1-(3-chloro-2-pyridinyl)-5-iodo-1H-pyrrole-2-carboxamide $^1$H-NMR (CDCl$_3$, TMS) δ (ppm): 2.16 (3H, s), 4.02 (2H, brs), 6.66 (1H, s), 7.05 (1H, s), 7.19 (1H, s), 7.24 (1H, s), 7.37 (1H, dd, J=8 Hz, 5 Hz), 7.50 (1H, brs), 7.86 (1H, d, J=8 Hz), 8.49 (1H, d, J=5 Hz), 9.28 (1H, brs)

REFERENCE PREPARATION EXAMPLE 134-(1)

A mixture of 1.51 g of 2-amino-3-methylbenzoic acid, 1.0 g of acetic anhydride and 20 ml of tetrahydrofuran was stirred at 80° C. for 13 hours. The reaction mixture was allowed to cool to room temperature, poured into water, and extracted with ethyl acetate two times. The organic layers were combined, washed successively with water and an aqueous saturated sodium chloride solution, dried over anhydrous sodium sulfate, and concentrated under reduced pressure. The resulting residue was washed with ethyl acetate to obtain 0.72 g of 2-acetylamino-3-methylbenzoic acid of the formula:

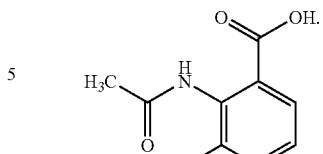

2-Acetylamino-3-methylbenzoic acid $^1$H-NMR (DMSO-d$_6$, TMS) δ (ppm): 2.00 (3H, s), 2.19 (3H, s), 7.21 (1H, t, J=8 Hz), 7.41 (1H, d, J=8 Hz), 7.58 (1H, d, J=8 Hz), 9.47 (1H, brs)

REFERENCE PREPARATION EXAMPLE 134-(2)

To a mixture of 0.72 g of 2-acetylamino-3-methylbenzoic acid and 8 ml of concentrated sulfuric acid was added dropwise 1.6 g of fuming nitric acid at room temperature. The resulting mixture was stirred at room temperature for 2 hours. The reaction mixture was poured into ice water. A deposited precipitate was collected by filtration to obtain 0.45 g of 2-acetylamino-3-methyl-5-nitrobenzoic acid of the formula:

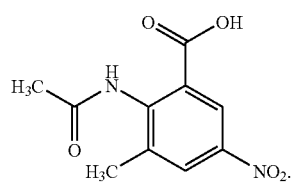

2-Acetylamino-3-methyl-5-nitrobenzoic acid $^1$H-NMR (DMSO-d$_6$, TMS) δ (ppm): 2.06 (3H, s), 2.34 (3H, s), 8.31 (2H, s), 9.93 (1H, brs)

REFERENCE PREPARATION EXAMPLE 134-(3)

A mixture of 0.45 g of 2-acetylamino-3-methyl-5-nitrobenzoic acid, 0.45 g of potassium hydroxide, 5 ml of methanol and 20 ml of water was heated to reflux at 80° C. for 2 hours. The reaction mixture was allowed to cool to room temperature, and water was poured into the mixture. The mixture was adjusted to pH 3 by an addition of 2N hydrochloric acid. A deposited precipitate was collected by filtration to obtain 0.28 g of 2-amino-3-methyl-5-nitrobenzoic acid of the formula:

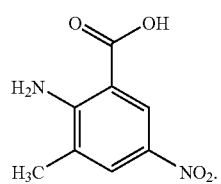

2-Amino-3-methyl-5-nitrobenzoic acid $^1$H-NMR (DMSO-d$_6$, TMS) δ (ppm): 2.19 (3H, s), 7.99 (1H, s), 8.56 (1H, s)

REFERENCE PREPARATION EXAMPLE 134-(4)

According to the same manner as that of Reference Preparation Example 46-(1), 2-amino-3-methyl-5-nitrobenzoic acid was used in place of 2-amino-3,5-dibromobenzoic acid to obtain 2-[3-bromo-1-(3-chloro-2-pyridinyl)-1H-pyrazol-5-yl]-8-methyl-6-nitro-4H-3,1-benzoxazine-4-one of the formula:

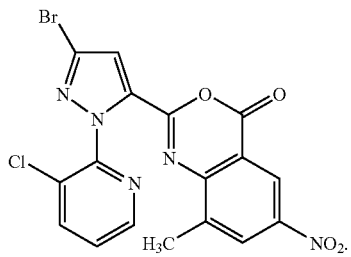

2-[3-Bromo-1-(3-chloro-2-pyridinyl)-1H-pyrazol-5-yl]-8-methyl-6-nitro-4H-3,1-benzoxazine-4-one $^1$H-NMR (DMSO-d$_6$, TMS) δ (ppm): 1.81 (3H, s), 7.64 (1H, s), 7.79 (1H, dd, J=8 Hz, 4 Hz), 8.38 (1H, d, J=8 Hz), 8.48 (1H, s), 8.55 (1H, s), 8.64 (1H, d, J=4 Hz)

REFERENCE PREPARATION EXAMPLE 135-(1)

According to the same manner as that of Reference Preparation Example 129-(1), 2-chloro-3-nitropyridine was used in place of 2-fluoropyridine to obtain 1-(3-nitro-2-pyridinyl)-1H-pyrrole-2-carbaldehyde of the formula:

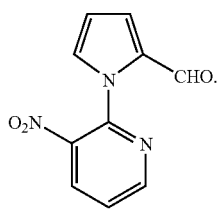

1-(3-Nitro-2-pyridinyl)-1H-pyrrole-2-carbaldehyde $^1$H-NMR (CDCl$_3$, TMS) δ (ppm): 6.54 (1H, dd, J=4 Hz, 3 Hz), 7.18 (1H, dd, J=4 Hz, 2 Hz), 7.34-7.35 (1H, m), 7.60 (1H, dd, J=8 Hz, 5 Hz), 8.51 (1H, dd, J=8 Hz, 2 Hz), 8.75 (1H, dd, J=5 Hz, 2 Hz), 9.48 (1H, d, J=1 Hz)

REFERENCE PREPARATION EXAMPLE 135-(2)

According to the same manner as that of Reference Preparation Example 71-(3), 1-(3-nitro-2-pyridinyl)-1H-pyrrole-2-carbaldehyde was used in place of 3-chloro-2-(2-formyl-1H-pyrrol-1-yl)pyridine to obtain 4-bromo-1-(3-nitro-2-pyridinyl)-1H-pyrrole-2-carbaldehyde of the formula:

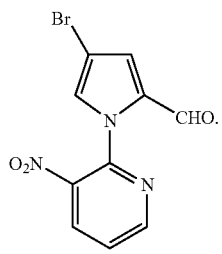

4-Bromo-1-(3-nitro-2-pyridinyl)-1H-pyrrole-2-carbaldehyde $^1$H-NMR (CDCl$_3$, TMS) δ (ppm): 7.14 (1H, d, J=2 Hz), 7.33 (1H, d, J=2 Hz), 7.63 (1H, dd, J=8 Hz, 5 Hz), 8.53 (1H, dd, J=8 Hz, 2 Hz), 8.75 (1H, dd, J=5 Hz, 2 Hz), 9.42 (1H, s)

REFERENCE PREPARATION EXAMPLE 135-(3)

According to the same manner as that of Reference Preparation Example 71-(4), 4-bromo-1-(3-nitro-2-pyridinyl)-1H-pyrrole-2-carbaldehyde was used in place of 4-bromo-1-(3-chloro-2-pyridinyl)-1H-pyrrole-2-carbaldehyde to obtain 4-bromo-1-(3-nitro-2-pyridinyl)-1H-pyrrole-2-carboxylic acid of the formula:

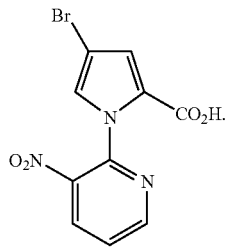

4-Bromo-1-(3-nitro-2-pyridinyl)-1H-pyrrole-2-carboxylic acid $^1$H-NMR (DMSO-d$_6$, TMS) δ (ppm): 7.05 (1H, d, J=2 Hz), 7.60 (1H, d, J=2 Hz), 7.84 (1H, dd, J=8 Hz, 5 Hz), 8.68 (1H, d, J=8 Hz, 2 Hz), 8.84 (1H, d, J=5 Hz, 2 Hz)

REFERENCE PREPARATION EXAMPLE 135-(4)

According to the same manner as that of Reference Preparation Example 71-(5), 4-bromo-1-(3-nitro-2-pyridinyl)-1H-pyrrole-2-carboxylic acid and 2-amino-3,5-dibromobenzoic acid were used in place of 4-bromo-1-(3-chloro-2-pyridinyl)-1H-pyrrole-2-carboxylic acid and 2-amino-5-chloro-3-methylbenzoic acid respectively to obtain 6,8-dibromo-2-[4-bromo-1-(3-nitro-2-pyridinyl)-1H-pyrrol-2-yl]-4H-3,1-benzoxazine-4-one of the formula:

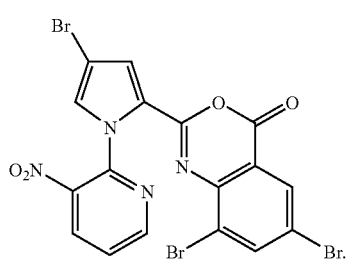

6,8-Dibromo-2-[4-bromo-1-(3-nitro-2-pyridinyl)-1H-pyrrol-2-yl]-4H-3,1-benzoxazine-4-one $^1$H-NMR (DMSO-d$_6$, TMS) δ (ppm): 7.38 (1H, d, J=2 Hz), 7.80 (1H, d, J=2 Hz), 7.92 (1H, dd, J=8 Hz, 5 Hz), 8.11 (1H, d, J=2 Hz), 8.26 (1H, d, J=2 Hz), 8.84 (1H, d, J=8 Hz), 8.65 (1H, d, J=5 Hz)

REFERENCE PREPARATION EXAMPLE 136-(1)

According to the same manner as that of Reference Preparation Example 129-(1), 3-bromo-2-chloropyridine was used in place of 2-fluoropyridine to obtain 1-(3-bromo-2-pyridinyl)-1H-pyrrole-2-carbaldehyde of the formula:

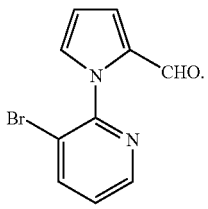

1-(3-Bromo-2-pyridinyl)-1H-pyrrole-2-carbaldehyde $^1$H-NMR (CDCl$_3$, TMS) δ (ppm): 6.48 (1H, dd, J=4 Hz, 3 Hz), 7.10-7.17 (2H, m), 7.31 (1H, dd, J=8 Hz, 5 Hz), 8.05 (1H, dd, J=8 Hz, 2 Hz), 8.51 (1H, dd, J=5 Hz, 2 Hz), 9.57 (1H, s)

REFERENCE PREPARATION EXAMPLE 136-(2)

According to the same manner as that of Reference Preparation Example 71-(3), 1-(3-bromo-2-pyridinyl)-1H-pyrrole-2-carbaldehyde was used in place of 3-chloro-2-(2-formyl-1H-pyrrol-1-yl)pyridine to obtain 4-bromo-1-(3-bromo-2-pyridinyl)-1H-pyrrole-2-carbaldehyde of the formula:

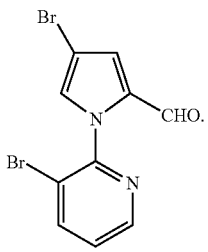

4-Bromo-1-(3-bromo-2-pyridinyl)-1H-pyrrole-2-carbaldehyde $^1$H-NMR (CDCl$_3$, TMS) δ (ppm): 7.11-7.14 (2H, m), 7.33 (1H, dd, J=8 Hz, 5 Hz), 8.06 (1H, dd, J=8 Hz, 2 Hz), 8.50 (1H, dd, J=5 Hz, 2 Hz), 9.50 (1H, d, J=1 Hz)

REFERENCE PREPARATION EXAMPLE 136-(3)

According to the same manner as that of Reference Preparation Example 71-(4), 4-bromo-1-(3-bromo-2-pyridinyl)-1H-pyrrole-2-carbaldehyde was used in place of 4-bromo-1-(3-chloro-2-pyridinyl)-1H-pyrrole-2-carbaldehyde to obtain 4-bromo-1-(3-bromo-2-pyridinyl)-1H-pyrrole-2-carboxylic acid of the formula:

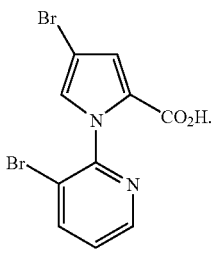

4-Bromo-1-(3-bromo-2-pyridinyl)-1H-pyrrole-2-carboxylic acid $^1$H-NMR (DMSO-d$_6$, TMS) δ (ppm): 7.01 (1H, s), 7.48-7.51 (2H, m), 8.28 (1H, d, J=8 Hz), 8.52 (1H, d, J=5 Hz), 12.67 (1H, brs)

REFERENCE PREPARATION EXAMPLE 136-(4)

According to the same manner as that of Reference Preparation Example 71-(5), 4-bromo-1-(3-bromo-2-pyridinyl)-1H-pyrrole-2-carboxylic acid and 2-amino-3,5-dibromobenzoic acid were used in place of 4-bromo-1-(3-chloro-2-pyridinyl)-1H-pyrrole-2-carboxylic acid and 2-amino-5-chloro-3-methylbenzoic acid respectively to obtain 6,8-dibromo-2-[4-bromo-1-(3-bromo-2-pyridinyl)-1H-pyrrol-2-yl]-4H-3,1-benzoxazine-4-one of the formula:

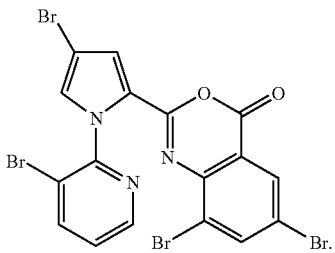

6,8-Dibromo-2-[4-bromo-1-(3-bromo-2-pyridinyl)-1H-pyrrol-2-yl]-4H-3,1-benzoxazine-4-one $^1$H-NMR (DMSO-d$_6$, TMS) δ (ppm): 7.33 (1H, s), 7.53 (1H, dd, J=8 Hz, 5 Hz), 7.72 (1H, s), 8.12 (1H, d, J=2 Hz), 8.27 (1H, d, J=2 Hz), 8.36 (1H, d, J=8 Hz), 8.57 (1H, d, J=5 Hz)

REFERENCE PREPARATION EXAMPLE 137-(1)

A mixture of 2.0 g of 2-pyrrole carbaldehyde, 3.0 g of 3,4-dichloropyridine, 8.0 g of cesium carbonate and 30 ml of N-methylpyrrolidone was stirred at 120° C. for 25 hours. The reaction mixture was allowed to cool room temperature, and water was poured into the mixture. The mixture was extracted with ethyl acetate two times. The organic layers were combined, washed successively with water and an aqueous saturated sodium chloride solution, dried over anhydrous sodium sulfate, and concentrated under reduced pressure. The resulting residue was subjected to silica gel chromatography to obtain 2.95 g of 1-(3-chloro-4-pyridinyl)-1H-pyrrole-2-carbaldehyde of the formula:

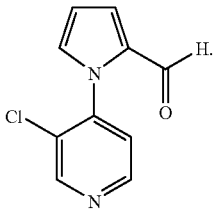

1-(3-Chloro-4-pyridinyl)-1H-pyrrole-2-carbaldehyde $^1$H-NMR (DMSO-$d_6$, TMS) δ (ppm): 6.55 (1H, dd, J=4 Hz, 3 Hz), 7.33 (1H, dd, J=4 Hz, 2 Hz), 7.44 (1H, ddd, J=3 Hz, 2 Hz, 1Hz), 7.60 (1H, d, J=5 Hz), 8.66 (1H, d, J=5 Hz), 8.83 (1H, s), 9.52 (1H, d, J=1 Hz)

REFERENCE PREPARATION EXAMPLE 137-(2)

To a solution of 2.95 g of 1-(3-chloro-4-pyridinyl)-1H-pyrrole-2-carbaldehyde in 20 ml of N,N-dimethylformamide was added 2.66 g of N-bromosuccinimide. The resulting mixture was stirred at room temperature for 10 hours. Water was poured into the reaction mixture, and a deposited precipitate was collected by filtration to obtain 1.2 g of 4-bromo-1-(3-chloro-4-pyridinyl)-1H-pyrrole-2-carbaldehyde of the formula:

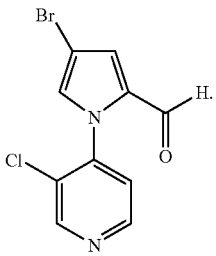

4-Bromo-1-(3-chloro-4-pyridinyl)-1H-pyrrole-2-carbaldehyde $^1$H-NMR (DMSO-$d_6$, TMS) δ (ppm): 7.44-7.46 (1H, m), 7.66 (1H, d, J=5 Hz), 7.69-7.72 (1H, m), 8.68 (1H, d, J=5 Hz), 8.85 (1H, s), 9.47 (1H, s)

REFERENCE PREPARATION EXAMPLE 137-(3)

A solution of 2.0 g of potassium permanganate in 10 ml of water was added dropwise to a mixture of 1.2 g of 4-bromo-1-(3-chloro-4-pyridinyl)-1H-pyrrole-2-carbaldehyde and 30 ml of acetone while the mixture was maintained at 40° C. The resulting mixture was stirred at 60° C. for 1 hour. A precipitate was filtered off to obtain a filtrate. The filtrate was adjusted to pH 10-12 by an addition of a 2N aqueous sodium hydroxide solution, and then washed with chloroform two times. The aqueous layer was adjusted to around pH 3 by an addition of 2N hydrochloric acid, and then extracted with ethyl acetate two times. The organic layers were combined, washed successively with water and an aqueous saturated sodium chloride solution, dried over anhydrous sodium sulfate, and concentrated under reduced pressure to obtain 0.43 g of 4-bromo-1-(3-chloro-4-pyridinyl)-1H-pyrrole-2-carboxylic acid of the formula:

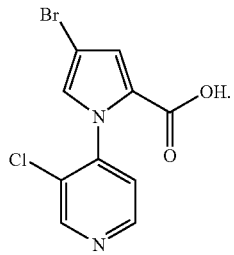

4-Bromo-1-(3-chloro-4-pyridinyl)-1H-pyrrole-2-carboxylic acid $^1$H-NMR (DMSO-$d_6$, TMS) δ (ppm): 7.07 (1H, d, J=2 Hz), 7.47 (1H, d, J=2 Hz), 7.63 (1H, d, J=5 Hz), 8.65 (1H, d, J=5 Hz), 8.81 (1H, s)

REFERENCE PREPARATION EXAMPLE 137-(4)

According to the same manner as that of Reference Preparation Example 71-(5), 4-bromo-1-(3-chloro-4-pyridinyl)-1H-pyrrole-2-carboxylic acid was used in place of 4-bromo-1-(3-chloro-2-pyridinyl)-1H-pyrrole-2-carboxylic acid to obtain 2-[4-bromo-1-(3-chloro-4-pyridinyl)-1H-pyrrol-2-yl]-6-chloro-8-methyl-4H-3,1-benzoxazine-4-one of the formula:

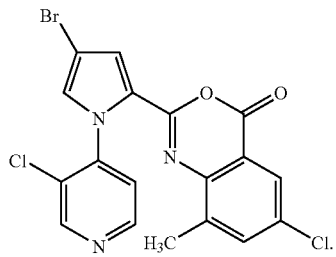

2-[4-Bromo-1-(3-chloro-4-pyridinyl)-1H-pyrrol-2-yl]-6-chloro-8-methyl-4H-3,1-benzoxazine-4-one $^1$H-NMR (DMSO-$d_6$, TMS) δ (ppm): 1.63 (3H, s), 7.33 (1H, d, J=2 Hz), 7.68-7.74 (3H, m), 7.85 (1H, d, J=2 Hz), 8.73 (1H, d, J=5 Hz), 8.91 (1H, s)

REFERENCE PREPARATION EXAMPLE 137-(5)

According to the same manner as that of Reference Preparation Example 71-(6), 2-[4-bromo-1-(3-chloro-4-pyridinyl)-1H-pyrrol-2-yl]-6-chloro-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 4-bromo-N-[4-chloro-2-(hydrazinocarbonyl)-6-methylphenyl]-1-(3-chloro-4-pyridinyl)-1H-pyrrole-2-carboxamide of the formula:

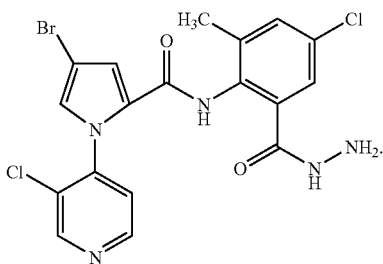

4-Bromo-N-[4-chloro-2-(hydrazinocarbonyl)-6-methylphenyl]-1-(3-chloro-4-pyridinyl)-1H-pyrrole-2-carboxamide $^1$H-NMR (DMSO-d$_6$, TMS) δ (ppm): 2.15 (3H, s), 4.39 (2H, brs), 7.27-7.31 (2H, m), 7.42-7.46 (2H, m), 7.56 (1H, d, J=5 Hz), 8.60 (1H, d, J=5 Hz), 8.72 (1H, s), 9.54 (1H, brs), 9.87 (1H, brs)

REFERENCE PREPARATION EXAMPLE 138-(1)

According to the same manner as that of Reference Preparation Example 46-(1), 2-amino-5-chloro-benzoic acid was used in place of 2-amino-3,5-dibromobenzoic acid to obtain 2-[3-bromo-1-(3-chloro-2-pyridinyl)-1H-pyrazole-5-yl]-6-chloro-4H-3,1-benzoxazine-4-one of the formula:

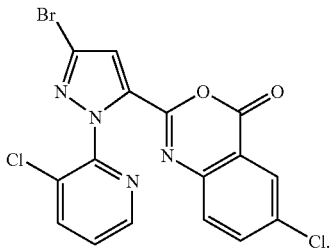

2-[3-Bromo-1-(3-chloro-2-pyridinyl)-1H-pyrazole-5-yl]-6-chloro-4H-3,1-benzoxazine-4-one $^1$H-NMR (DMSO-d$_6$, TMS) δ (ppm): 7.01 (1H, d, J=9 Hz), 7.53 (1H, s), 7.78 (1H, dd, J=8 Hz, 5 Hz), 7.88 (1H, dd, J=9 Hz, 3 Hz), 8.06 (1H, d, J=3 Hz), 8.32 (1H, dd, J=8 Hz, 1Hz), 8.60 (1H, dd, J=5 Hz, 1Hz).

REFERENCE PREPARATION EXAMPLE 139

According to the same manner as that of Reference Preparation Example 84, 2-[3-bromo-1-(3-chloro-2-pyridinyl)-1H-pyrazol-5-yl]-6-chloro-4H-3,1-benzoxazine-4-one was used in place of 2-[3-bromo-1-(3-chloro-2-pyridinyl)-1H-pyrazol-5-yl]-6-chloro-8-methyl-4H-3,1-benzoxazine-4-one to obtain 3-bromo-N-[4-chloro-2-(N-methylhydrazinocarbonyl)phenyl]-1-(3-chloro-2-pyridinyl)-1H-pyrazole-5-carboxamide of the formula:

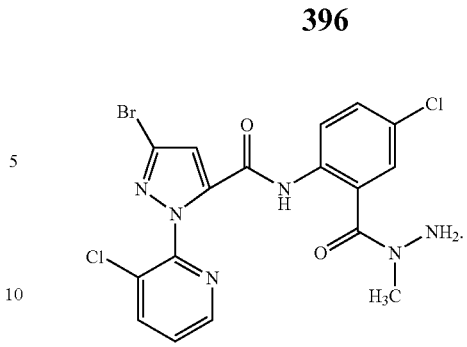

3-Bromo-N-[4-chloro-2-(N-methylhydrazinocarbonyl)phenyl]-1-(3-chloro-2-pyridinyl)-1H-pyrazole-5-carboxamide $^1$H-NMR (DMSO-d$_6$, TMS) δ (ppm): 2.88 (0.6H, s), 3.10 (2.4H, s), 4.71 (1.6H, s), 5.01 (0.4H, s), 7.29-7.34 (1.0H, brm), 7.38-7.52 (3.0H, m), 7.65 (1.0H, dd, J=8 Hz, 5 Hz), 8.22 (1.0H, dd, J=8 Hz, 2 Hz), 8.52 (1.0H, dd, J=5 Hz, 2 Hz), 10.40-10.50 (1.0H, brm).

REFERENCE PREPARATION EXAMPLE 140

According to the same manner as that of Reference Preparation Example 88, 2-[3-bromo-1-(3-chloro-2-pyridinyl)-1H-pyrazol-5-yl]-6-chloro-4H-3,1-benzoxazine-4-one was used in place of 2-[3-bromo-1-(3-chloro-2-pyridinyl)-1H-pyrazol-5-yl]-6-chloro-8-methyl-4H-3,1-benzoxazine-4-one to obtain 3-bromo-N-[4-chloro-2-(N,N'-dimethylhydrazinocarbonyl)phenyl]-1-(3-chloro-2-pyridinyl)-1H-pyrazole-5-carboxamide of the formula:

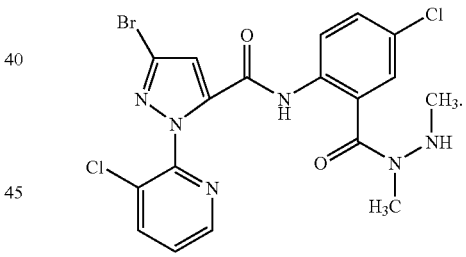

3-Bromo-N-[4-chloro-2-(N,N'-dimethylhydrazinocarbonyl)phenyl]-1-(3-chloro-2-pyridinyl)-1H-pyrazole-5-carboxamide $^1$H-NMR (CDCl$_3$, TMS) δ (ppm): 2.69 (3H, brs), 3.28 (3H, s), 6.92 (1H, s), 7.30-7.46 (3H, m), 7.91 (1H, dd, J=8 Hz, 2 Hz), 8.17 (1H, d, J=9 Hz), 8.49 (1H, dd, J=5 Hz, 2 Hz), 10.29 (1H, brs).

REFERENCE PREPARATION EXAMPLE 141-(1)

According to the same manner as that of Reference Preparation Example Preparation Example 100-(1), 2-(2-FORMYL-1H-pyrrol-1-yl)pyridine was used in place of 3-chloro-2-(2-formyl-1H-pyrrol-1-yl)pyridine to obtain 4,5-dichloro-1-(2-pyridinyl)-1H-pyrrole-2-carbaldehyde of the formula:

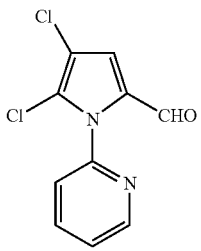

and 3,5-dichloro-1-(2-pyridinyl)-1H-pyrrole-2-carbaldehyde of the formula:

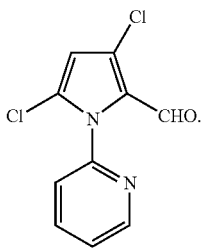

4,5-Dichloro-1-(2-pyridinyl)-1H-pyrrole-2-carbaldehyde $^1$H-NMR (CDCl$_3$, TMS) δ (ppm): 7.08 (1H, s), 7.38-7.41 (1H, m), 7.47-7.50 (1H, m), 7.91-7.95 (1H, m), 8.63-8.65 (1H, m), 9.40 (1H, s)

3,5-Dichloro-1-(2-pyridinyl)-1H-pyrrole-2-carbaldehyde $^1$H-NMR (CDCl$_3$, TMS) δ (ppm): 6.35 (1H, s), 7.33-7.36 (1H, m), 7.45-7.48 (1H, m), 7.89-7.93 (1H, m), 8.61-8.62 (1H, m), 9.64 (1H, s)

REFERENCE PREPARATION EXAMPLE 141-(2)

According to the same manner as that of Reference Preparation Example 71-(4), 4,5-dichloro-1-(2-pyridinyl)-1H-pyrrole-2-carbaldehyde was used in place of 4-bromo-1-(3-chloro-2-pyridinyl)-1H-pyrrole-2-carbaldehyde to obtain 4,5-dichloro-1-(2-pyridinyl)-1H-pyrrole-2-carboxylic acid of the formula:

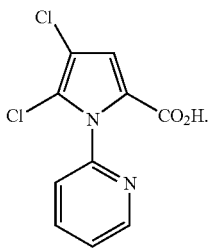

4,5-Dichloro-1-(2-pyridinyl)-1H-pyrrole-2-carboxylic acid $^1$H-NMR (DMSO-d$_6$, TMS) δ (ppm): 7.11 (1H, s), 7.56-7.58 (2H, m), 8.03 (1H, td, J=8 Hz, 2 Hz), 8.58 (1H, dd, J=4 Hz, 2 Hz)

REFERENCE PREPARATION EXAMPLE 141-(3)

According to the same manner as that of Reference Preparation Example 71-(5), 4,5-dichloro-1-(2-pyridinyl)-1H-pyrrole-2-carboxylic acid was used in place of 4-bromo-1-(3-chloro-2-pyridinyl)-1H-pyrrole-2-carboxylic acid to obtain 6-chloro-2-[4,5-dichloro-1-(2-pyridinyl)-1H-pyrrol-2-yl]-8-methyl-4H-3,1-benzoxazine-4-one of the formula:

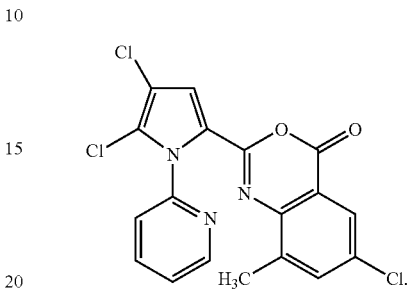

6-Chloro-2-[4,5-dichloro-1-(2-pyridinyl)-1H-pyrrol-2-yl]-8-methyl-4H-3,1-benzoxazine-4-one $^1$H-NMR (DMSO-d$_6$, TMS) δ (ppm): 2.07 (3H, s), 7.35 (1H, s), 7.62-7.67 (3H, m), 7.81 (1H, s), 8.11 (1H, t, J=8 Hz), 8.65 (1H, d, J=5 Hz)

REFERENCE PREPARATION EXAMPLE 141-(4)

According to the same manner as that of Reference Preparation Example 71-(6), 6-chloro-2-[4,5-dichloro-1-(2-pyridinyl)-1H-pyrrol-2-yl]-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 4,5-dichloro-N-[4-chloro-2-(hydrazinocarbonyl)-6-methylphenyl]-1-(2-pyridinyl)-1H-pyrrole-2-carboxamide of the formula:

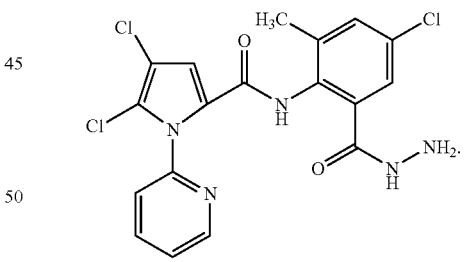

4,5-Dichloro-N-[4-chloro-2-(hydrazinocarbonyl)-6-methylphenyl]-1-(2-pyridinyl)-1H-pyrrole-2-carboxamide $^1$H-NMR (CDCl$_3$, TMS) δ (ppm): 2.16 (3H, s), 7.01 (1H, s), 7.25 (2H, s), 7.36-7.41 (2H, m), 7.87 (1H, td, J=8 Hz, 2 Hz), 7.95 (1H, brs), 8.55-8.57 (1H, m), 9.42 (1H, brs)

REFERENCE PREPARATION EXAMPLE 142-(1)

According to the same manner as that of Reference Preparation Example 71-(4), 3,5-dichloro-1-(2-pyridinyl)-1H-pyrrole-2-carbaldehyde was used in place of 4-bromo-1-(3-chloro-2-pyridinyl)-1H-pyrrole-2-carbaldehyde to obtain 3,5-dichloro-1-(2-pyridinyl)-1H-pyrrole-2-carboxylic acid of the formula:

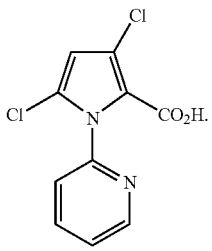

3,5-Dichloro-1-(2-pyridinyl)-1H-pyrrole-2-carboxylic acid $^1$H-NMR (DMSO-d$_6$, TMS) δ (ppm): 6.64 (1H, s), 7.53-7.57 (2H, m), 8.02 (1H, td, J=8 Hz, 2 Hz), 8.55-8.57 (1H, m)

REFERENCE PREPARATION EXAMPLE 142-(2)

According to the same manner as that of Reference Preparation Example 71-(5), 3,5-dichloro-1-(2-pyridinyl)-1H-pyrrole-2-carboxylic acid was used in place of 4-bromo-1-(3-chloro-2-pyridinyl)-1H-pyrrole-2-carboxylic acid to obtain 6-chloro-2-[3,5-dichloro-1-(2-pyridinyl)-1H-pyrrol-2-yl]-8-methyl-4H-3,1-benzoxazine-4-one of the formula:

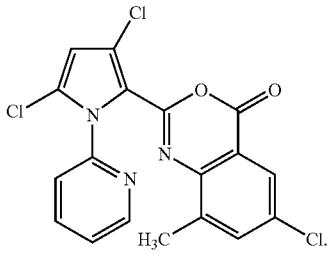

6-Chloro-2-[3,5-dichloro-1-(2-pyridinyl)-1H-pyrrol-2-yl]-8-methyl-4H-3,1-benzoxazine-4-one $^1$H-NMR (DMSO-d$_6$, TMS) δ (ppm): 1.82 (3H, s), 6.97 (1H, s), 7.60-7.70 (3H, m), 7.81-7.83 (1H, m), 8.04-8.12 (1H, m), 8.58 (1H, d, J=6 Hz)

REFERENCE PREPARATION EXAMPLE 142-(3)

According to the same manner as that of Reference Preparation Example 71-(6), 6-chloro-2-[3,5-dichloro-1-(2-pyridinyl)-1H-pyrrol-2-yl]-8-methyl-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 3,5-dichloro-N-[4-chloro-2-(hydrazinocarbonyl)-6-methylphenyl]-1-(2-pyridinyl)-1H-pyrrole-2-carboxamide of the formula:

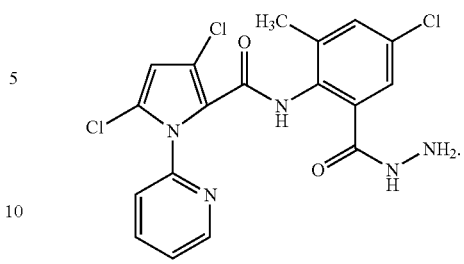

3,5-D-chloro-N-[4-chloro-2-(hydrazinocarbonyl)-6-methylphenyl]-1-(2-pyridinyl)-1H-pyrrole-2-carboxamide $^1$H-NMR (CDCl$_3$, TMS) δ (ppm): 2.14 (3H, s), 6.26 (1H, s), 7.20-7.23 (2H, s), 7.28-7.34 (2H, m), 7.61-7.65 (1H, m), 7.76-7.81 (1H, m), 8.49 (1H, brs), 8.79 (1H, brs)

REFERENCE PREPARATION EXAMPLE 143-(1)

To a solution of 3.0 g of 3-chloro-2-(4-bromo-2-formyl-1H-pyrrol-1-yl)-pyridine in 30 ml of tetrahydrofuran was added 1.5 g of N-chlorosuccinimide. The resulting mixture was stirred at room temperature for 2 days. Water was poured into the reaction mixture, and the mixture was extracted with ethyl acetate two times. The organic layers were combined, washed with an aqueous saturated sodium chloride solution, dried over anhydrous magnesium sulfate, and concentrated under reduced pressure. The residue was subjected to silica gel column chromatography to obtain 2.5 g of 4-bromo-5-chloro-1-(3-chloro-2-pyridinyl)-1H-pyrrole-2-carbaldehyde of the formula:

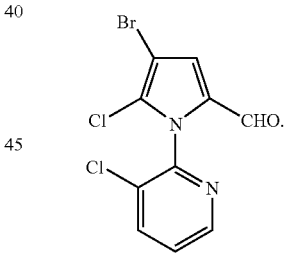

4-Bromo-5-chloro-1-(3-chloro-2-pyridinyl)-1H-pyrrole-2-carbaldehyde $^1$H-NMR (CDCl$_3$, TMS) δ (ppm): 7.12 (1H, s), 7.47 (1H, dd, J=8 Hz, 5 Hz), 7.94 (1H, dd, J=8 Hz, 2 Hz), 8.53 (1H, dd, J=5 Hz, 2 Hz), 9.38 (1H, s)

REFERENCE PREPARATION EXAMPLE 143-(2)

According to the same manner as that of Reference Preparation Example 71-(4), 4-bromo-5-chloro-1-(3-chloro-2-pyridinyl)-1H-pyrrole-2-carbaldehyde was used in place of 4-bromo-1-(3-chloro-2-pyridinyl)-1H-pyrrole-2-carbaldehyde to obtain 4-bromo-5-chloro-1-(3-chloro-2-pyridinyl)-1H-pyrrole-2-carboxylic acid of the formula:

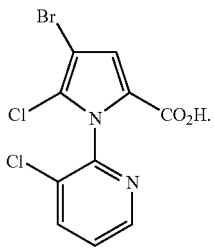

4-Bromo-5-chloro-1-(3-chloro-2-pyridinyl)-1H-pyrrole-2-carboxylic acid $^1$H-NMR (DMSO-$d_6$, TMS) δ (ppm): 7.20 (1H, s), 7.67 (1H, dd, J=8 Hz, 5 Hz), 8.25 (1H, dd, J=8 Hz, 2 Hz), 8.58 (1H, dd, J=5 Hz, 2 Hz), 12.99 (1H, brs)

REFERENCE PREPARATION EXAMPLE 143-(3)

According to the same manner as that of Reference Preparation Example 71-(5), 4-bromo-5-chloro-1-(3-chloro-2-pyridinyl)-1H-pyrrole-2-carboxylic acid and 2-amino-3,5-dibromobenzoic acid were used in place of 4-bromo-1-(3-chloro-2-pyridinyl)-1H-pyrrole-2-carboxylic acid and 2-amino-5-chloro-3-methylbenzoic acid respectively to obtain 2-[4-bromo-5-chloro-1-(3-chloro-2-pyridinyl)-1H-pyrrol-2-yl]-6,8-dibromo-4H-3,1-benzoxazine-4-one of the formula:

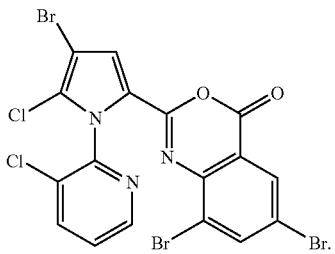

2-[4-Bromo-5-chloro-1-(3-chloro-2-pyridinyl)-1H-pyrrol-2-yl]-6,8-dibromo-4H-3,1-benzoxazine-4-one $^1$H-NMR (CDCl$_3$, TMS) δ (ppm): 7.49 (1H, s), 7.71 (1H, dd, J=8 Hz, 5 Hz), 8.11 (1H, d, J=2 Hz), 8.26 (1H, d, J=2 Hz), 8.34 (1H, dd, J=8 Hz, 1Hz), 8.63 (1H, dd, J=5 Hz, 1Hz)

REFERENCE PREPARATION EXAMPLE 143-(4)

According to the same manner as that of Reference Preparation Example 71-(6), 2-[4-bromo-5-chloro-1-(3-chloro-2-pyridinyl)-1H-pyrrol-2-yl]-6,8-dibromo-4H-3,1-benzoxazine-4-one was used in place of 2-[4-bromo-1-(3-chloro-2-pyridinyl)-1H-pyrrol-2-yl]-6-chloro-8-methyl-4H-3,1-benzoxazine-4-one to obtain 4-bromo-N-[4,6-dibromo-2-(hydrazinocarbonyl)phenyl]-5-chloro-1-(3-chloro-2-pyridinyl)-1H-pyrrole-2-carboxamide of the formula:

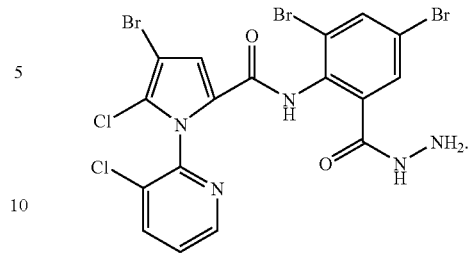

4-Bromo-N-[4,6-dibromo-2-(hydrazinocarbonyl)phenyl]-5-chloro-1-(3-chloro-2-pyridinyl)-1H-pyrrole-2-carboxamide $^1$H-NMR (CDCl$_3$, TMS) δ (ppm): 7.21 (1H, s), 7.39 (1H, dd, J=8 Hz, 5 Hz), 7.42 (1H, d, J=2 Hz), 7.70 (1H, d, J=2 Hz), 7.88 (1H, dd, J=8 Hz, 2 Hz), 8.49 (1H, dd, J=5 Hz, 2 Hz), 8.71 (1H, s)

REFERENCE PREPARATION EXAMPLE 144

Under ice-cooling, 8.42 g of 2-[3-bromo-1-(3-chloro-2-pyridinyl)-1H-pyrazol-5-yl]-6,8-dibromo-4H-3,1-benzoxazine-4-one, 3.0 g of hydrazine monohydrate and 60 ml of tetrahydrofuran were mixed, and the mixture was stirred at room temperature for 3 hours. A deposited precipitate was collected by filtration, and washed successively with tetrahydrofuran and methyl t-butyl ether to obtain 4.85 g of 3-bromo-N-[4,6-dibromo-2-(hydrazinocarbonyl)phenyl]-1-(3-chloro-2-pyridinyl)-1H-pyrazole-5-carboxamide of the formula:

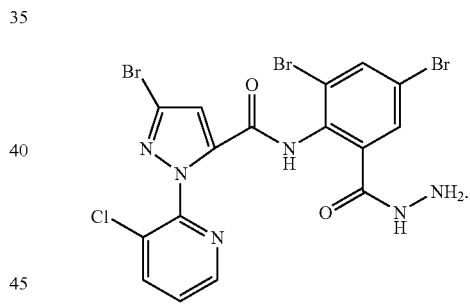

3-Bromo-N-[4,6-dibromo-2-(hydrazinocarbonyl)phenyl]-1-(3-chloro-2-pyridinyl)-1H-pyrazole-5-carboxamide $^1$H-NMR (DMSO-$d_6$, TMS) δ (ppm): 4.35 (2H, brs), 7.42 (1H, s), 7.58-7.62 (2H, m), 8.07 (1H, d, J=2 Hz), 8.16 (1H, dd, J=8 Hz, 2 Hz), 8.50 (1H, dd, J=5 Hz, 2 Hz), 9.61 (1H, brs)

REFERENCE PREPARATION EXAMPLE 145

A mixture of 0.50 g of 6,8-dibromo-2-[4-bromo-1-(3-chloro-2-pyridinyl)-1H-pyrrol-2-yl]-4H-3,1-benzoxazine-4-one, 0.15 ml of methylhydrazine and 8 ml of tetrahydrofuran was stirred at room temperature for 20 hours. Water was poured into the reaction mixture, and the mixture was extracted with ethyl acetate. The organic layer was washed successively with water and an aqueous saturated sodium chloride solution, dried over anhydrous magnesium sulfate, and concentrated under reduced pressure. The resulting residue was subjected to silica gel chromatography to obtain 0.39 g of 4-bromo-N-[4,6-dibromo-2-(N-methylhydrazinocarbonyl)phenyl]-1-(3-chloro-2-pyridinyl)-1H-pyrrole-2-carboxamide of the formula:

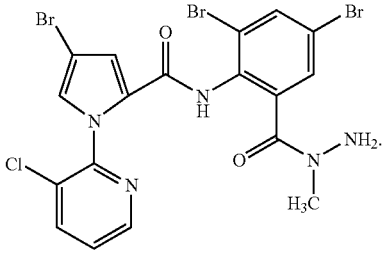

4-Bromo-N-[4,6-dibromo-2-(N-methylhydrazinocarbonyl)phenyl]-1-(3-chloro-2-pyridinyl)-1H-pyrrole-2-carboxamide $^1$H-NMR (CDCl$_3$, TMS) δ (ppm): 2.96 (1.5H, s), 3.15 (1.5H, s), 4.05 (1.0H, s), 4.48 (1.0H, s), 7.03 (1.0H, d, J=2 Hz), 7.18 (0.5H, d, J=2 Hz), 7.21 (0.5H, d, J=2 Hz), 7.29-7.34 (2.0H, m), 7.63 (0.5H, d, J=2 Hz), 7.68 (0.5H, d, J=2 Hz), 7.79-7.83 (1.0H, m), 8.40-8.44 (1.0H, m), 8.67 (0.5H, s), 8.77 (0.5H, s)

REFERENCE PREPARATION EXAMPLE 146

A mixture of 1.0 g of 2-[3-bromo-1-(3-chloro-2-pyridinyl)-1H-pyrazol-5-yl]-6,8-dibromo-4H-3,1-benzoxazine-4-one, 0.28 ml of methylhydrazine and 16 ml of tetrahydrofuran was stirred at room temperature for 19 hours. Water was poured into the reaction mixture, and the mixture was extracted with ethyl acetate. The organic layer was washed successively with water and an aqueous saturated sodium chloride solution, dried over anhydrous magnesium sulfate, and concentrated under reduced pressure. The resulting residue was subjected to silica gel chromatography to obtain 0.97 g of 3-bromo-N-[4,6-dibromo-2-(N-methylhydrazinocarbonyl)phenyl]-1-(3-chloro-2-pyridinyl)-1H-pyrazole-5-carboxamide of the formula:

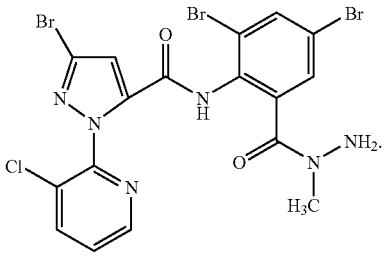

3-Bromo-N-[4,6-dibromo-2-(N-methylhydrazinocarbonyl)phenyl]-1-(3-chloro-2-pyridinyl)-1H-pyrazole-5-carboxamide $^1$H-NMR (CDCl$_3$, TMS) δ (ppm): 2.97 (1.5H, s), 3.17 (1.5H, s), 3.99 (1.0H, s), 4.51 (1.0H, s), 7.31 (1.0H, d, J=2 Hz), 7.35-7.41 (2.0H, m), 7.61 (0.5H, d, J=2 Hz), 7.67 (0.5H, d, J=2 Hz), 7.84-7.89 (1.0H, m), 8.45-8.50 (1.0H, m), 9.32 (0.5H, s), 9.45 (0.5H, s)

REFERENCE PREPARATION EXAMPLE 147

To a mixture of 0.42 g of N,N'-dimethylhydrazine dihydrochloride, five drops of water, 0.87 g of potassium carbonate and 10 ml of tetrahydrofuran was added 0.60 g of 2-[3-bromo-1-(3-chloro-2-pyridinyl)-1H-pyrazol-5-yl]-6,8-dibromo-4H-3,1-benzoxazine-4-one. The resulting mixture was stirred at room temperature for 19 hours. Water was poured into the reaction mixture, and the mixture was extracted with ethyl acetate. The organic layer was washed successively with water and an aqueous saturated sodium chloride solution, dried over anhydrous magnesium sulfate, and concentrated under reduced pressure. The resulting residue was subjected to silica gel chromatography to obtain 0.51 g of 3-bromo-N-[4,6-dibromo-2-(N,N'-dimethylhydrazinocarbonyl)phenyl]-1-(3-chloro-2-pyridinyl)-1H-pyrazole-5-carboxamide of the formula:

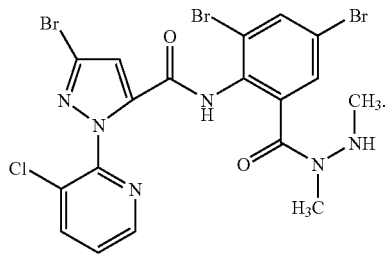

3-Bromo-N-[4,6-dibromo-2-(N,N'-dimethylhydrazinocarbonyl)phenyl]-1-(3-chloro-2-pyridinyl)-1H-pyrazole-5-carboxamide $^1$H-NMR (CDCl$_3$, TMS) δ (ppm): 2.49 (1.5H, d, J=6 Hz), 2.58 (1.5H, d, J=6 Hz), 2.92 (1.5H, s), 3.11 (1.5H, s), 3.52 (0.5H, q, J=6 Hz), 5.43 (0.5H, q, J=6 Hz), 7.21 (0.5H, s), 7.24 (0.5H, s), 7.30 (0.5H, d, J=2 Hz), 7.32 (0.5H, d, J=2 Hz), 7.35-7.39 (1.0H, m), 7.61 (0.5H, d, J=2 Hz), 7.67 (0.5H, d, J=2 Hz), 7.83-7.87 (1.0H, m), 8.44-8.47 (1.0H, m), 9.24 (0.5H, s), 9.42 (0.5H, s)

REFERENCE PREPARATION EXAMPLE 148

To a mixture of 0.42 g of N,N'-dimethylhydrazine dihydrochloride, five drops of water, 0.87 g of potassium carbonate and 10 ml of tetrahydrofuran was added 0.59 g of 6,8-dibromo-2-[4-bromo-1-(3-chloro-2-pyridinyl)-1H-pyrrol-2-yl]-4H-3,1-benzoxazine-4-one. The resulting mixture was stirred at room temperature for 2 hours. Water was poured into the reaction mixture, and the mixture was extracted with ethyl acetate. The organic layer was washed successively with water and an aqueous saturated sodium chloride solution, dried over anhydrous magnesium sulfate, and concentrated under reduced pressure. The resulting residue was subjected to silica gel chromatography to obtain 0.52 g of 4-bromo-N-[4,6-dibromo-2-(N,N'-dimethylhydrazinocarbonyl)phenyl]-1-(3-chloro-2-pyridinyl)-1H-pyrrole-2-carboxamide of the formula:

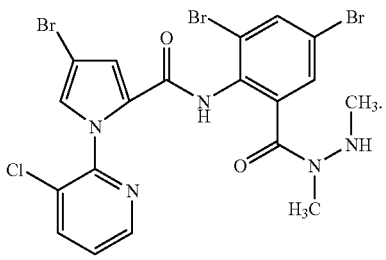

4-Bromo-N-[4,6-dibromo-2-(N,N'-dimethylhydrazinocarbonyl)phenyl]-1-(3-chloro-2-pyridinyl)-1H-pyrrole-2-carboxamide $^1$H-NMR (CDCl$_3$) δ:2.47 (1.5H, d, J=6 Hz), 2.55 (1.5H, brs), 2.91 (1.5H, s), 3.08 (1.5H, s), 3.54 (0.5H, q, J=6 Hz), 5.46 (0.5H, brs), 7.03 (1.0H, d, J=2 Hz), 7.10 (0.5H, d, J=2 Hz), 7.15 (0.5H, d, J=2 Hz), 7.28-7.32 (2.0H, m), 7.65 (0.5H, d, J=2 Hz), 7.69 (0.5H, d, J=2 Hz), 7.77-7.81 (1.0H, m), 8.39-8.41 (1.5H, m), 8.62 (0.5H, s).

REFERENCE PREPARATION EXAMPLE 149-(1)

To 10 ml of methanol were added 1.0 g of 3-chloro-2-(2-formyl-1H-pyrrol-1-yl)pyridine and 1.4 g of sodium thiocyanate. A solution of 1.0 g of bromine in 5 ml of saturated sodium bromide-methanol was added dropwise thereto at −20° C. The resulting mixture was stirred at the same temperature for 2 hours. The reaction mixture was added to 100 ml of ice water, and extracted with chloroform two times. The organic layers were combined, washed with an aqueous saturated sodium chloride solution, dried over anhydrous magnesium sulfate, and concentrated under reduced pressure to obtain 1.6 g of 1-(3-chloro-2-pyridinyl)-5-thiocyanato-1H-pyrrole-2-carbaldehyde of the formula:

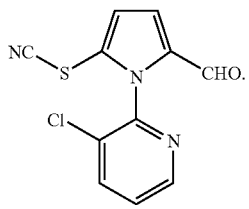

1-(3-Chloro-2-pyridinyl)-5-thiocyanato-1H-pyrrole-2-carbaldehyde $^1$H-NMR (CDCl$_3$, TMS) δ (ppm): 6.95 (1H, d, J=4 Hz), 7.16 (1H, d, J=4 Hz), 7.52 (1H, dd, J=8 Hz, 5 Hz), 7.97 (1H, dd, J=8 Hz, 2 Hz), 8.57 (1H, dd, J=5 Hz, 2 Hz), 9.58 (1H, s)

REFERENCE PREPARATION EXAMPLE 149-(2)

According to the same manner as that of Reference Preparation Example 71-(4), 1-(3-chloro-2-pyridinyl)-5-thiocyanato-1H-pyrrole-2-carbaldehyde was used in place of 4-bromo-1-(3-chloro-2-pyridinyl)-1H-pyrrole-2-carbaldehyde to obtain 1-(3-chloro-2-pyridinyl)-5-thiocyanato-1H-pyrrole-2-carboxylic acid of the formula:

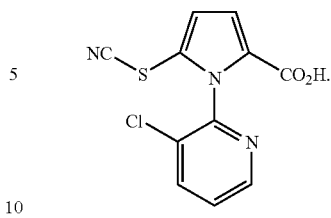

1-(3-Chloro-2-pyridinyl)-5-thiocyanato-1H-pyrrole-2-carboxylic acid $^1$H-NMR (DMSO-d$_6$, TMS) δ (ppm): 7.07 (1H, d, J=4 Hz), 7.11 (1H, d, J=4 Hz), 7.69 (1H, dd, J=8 Hz, 5 Hz), 8.27 (1H, d, J=8 Hz), 8.62 (1H, d, J=5 Hz)

REFERENCE PREPARATION EXAMPLE 149-(3)

According to the same manner as that of Reference Preparation Example 71-(5), 1-(3-chloro-2-pyridinyl)-5-thiocyanato-1H-pyrrole-2-carboxylic acid and 2-amino-3,5-dibromobenzoic acid were used in place of 4-bromo-1-(3-chloro-2-pyridinyl)-1H-pyrrole-2-carboxylic acid and 2-amino-5-chloro-3-methylbenzoic acid respectively to obtain 6,8-dibromo-2-[1-(3-chloro-2-pyridinyl)-5-thiocyanato-1H-pyrrol-2-yl]-4H-3,1-benzoxazine-4-one of the formula:

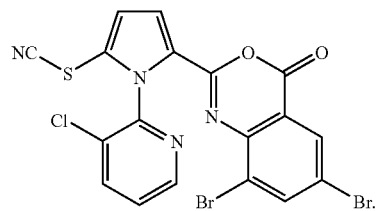

6,8-Dibromo-2-[1-(3-chloro-2-pyridinyl)-5-thiocyanato-1H-pyrrol-2-yl]-4H-3,1-benzoxazine-4-one $^1$H-NMR (DMSO-d$_6$, TMS) δ (ppm): 7.23 (1H, d, J=4 Hz), 7.41 (1H, d, J=4 Hz), 7.72 (1H, dd, J=8 Hz, 5 Hz), 8.14 (1H, d, J=2 Hz), 8.29 (1H, d, J=2 Hz), 7.34 (1H, d, J=8 Hz), 8.66 (1H, d, J=5 Hz)

REFERENCE PREPARATION EXAMPLE 150

Under ice-cooling, 0.569 g of 6,8-dibromo-2-[4-bromo-1-(3-chloro-2-pyridinyl)-1H-pyrrol-2-yl]-4H-3,1-benzoxazine-4-one, 0.20 g of hydrazine monohydrate and 2 ml of tetrahydrofuran were mixed, and the mixture was stirred at room temperature for 1 hour. Water was poured into the reaction mixture, and the mixture was extracted with ethyl acetate. The organic layer was washed with water, dried over sodium sulfate, and concentrated under reduced pressure to obtain 0.53 g of 4-bromo-N-[4,6-dibromo-2-(hydrazinocarbonyl)phenyl]-1-(3-chloro-2-pyridinyl)-1H-pyrrole-2-carboxamide of the formula:

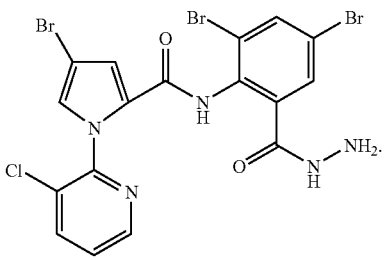

REFERENCE PREPARATION EXAMPLE 151-(1)

A mixture of 1.0 g of 4-bromoimidazole, 1.3 g of 3-chloro-2-(methanesulfonyl)pyridine, 2.7 g of cesium carbonate and 10 ml of N,N-dimethylformamide was stirred at 100° C. for 6 hours. The reaction mixture was allowed to cool to room temperature, and water was poured into the mixture. A deposited precipitate was collected by filtration to obtain 1.7 g of 2-(4-bromo-1H-imidazol-1-yl)-3-chloropyridine of the formula:

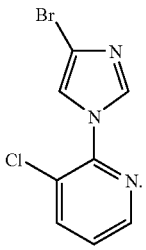

2-(4-Bromo-1H-imidazol-1-yl)-3-chloropyridine $^1$H-NMR (CDCl$_3$, TMS) δ (ppm): 7.33 (1H, dd, J=8 Hz, 5 Hz), 7.63 (1H, s), 7.93 (1H, dd, J=8 Hz, 2 Hz), 8.13 (1H, s), 8.45-8.46 (1H, m)

REFERENCE PREPARATION EXAMPLE 151-(2)

To a solution of 1.0 g of 2-(4-bromo-1H-imidazol-1-yl)-3-chloropyridine in 5 ml of dichloromethane was added dropwise a solution of 0.45 ml of trichloroacetyl chloride in 5 ml of dichloromethane at room temperature. The resulting mixture was stirred at room temperature for 1 day. Thereto 0.57 ml of triethylamine was added, and the resulting mixture was stirred at room temperature for 2 hours. The reaction mixture was concentrated under reduced pressure, and the resulting residue was subjected to silica gel chromatography to obtain 1.0 g of 1-[4-bromo-1-(3-chloro-2-pyridinyl)-1H-imidazol-2-yl]-2,2,2-trichloroethanone of the formula:

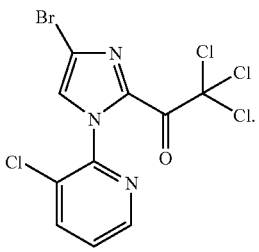

1-[4-Bromo-1-(3-chloro-2-pyridinyl)-1H-imidazol-2-yl]-2,2,2-trichloroethanone $^1$H-NMR (CDCl$_3$, TMS) δ (ppm): 7.35 (1H, s), 7.49 (1H, dd, J=8 Hz, 5 Hz), 7.95 (1H, dd, J=8 Hz, 2 Hz), 8.51 (1H, dd, J=5 Hz, 2 Hz)

REFERENCE PREPARATION EXAMPLE 151-(3)

To a solution of 0.50 g of 1-[4-bromo-1-(3-chloro-2-pyridinyl)-1H-imidazol-2-yl]-2,2,2-trichloroethanone and 0.37 g of 2-amino-3,5-dibromobenzoic acid in 10 ml of acetonitrile was added 0.43 ml of triethylamine. The resulting mixture was stirred at room temperature for 1 day. Thereto 0.12 ml of methanesulfonyl chloride was added, and the mixture was stirred at room temperature for 3 hours. Water was poured into the reaction mixture, and the mixture was extracted with ethyl acetate three times. The organic layers were combined, washed with an aqueous saturated sodium chloride solution, dried over anhydrous magnesium sulfate, and concentrated under reduced pressure. The residue was subjected to silica gel column chromatography to obtain 0.29 g of 2-[4-bromo-1-(3-chloro-2-pyridinyl)-1H-imidazol-2-yl]-6,8-dibromo-4H-3,1-benzoxazine-4-one of the formula:

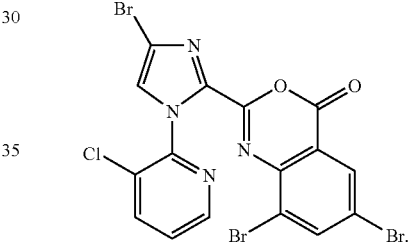

2-[4-Bromo-1-(3-chloro-2-pyridinyl)-1H-imidazol-2-yl]-6,8-dibromo-4H-3,1-benzoxazine-4-one $^1$H-NMR (DMSO-d$_6$, TMS) δ (ppm): 7.70 (1H, dd, J=8 Hz, 5 Hz), 8.18 (1H, d, J=3 Hz), 8.18 (1H, s), 8.31 (1H, dd, J=8 Hz, 1Hz), 8.33 (1H, d, J=3 Hz), 8.59 (1H, dd, J=5 Hz, 1Hz)

REFERENCE PREPARATION EXAMPLE 152-(1)

A mixture of 0.70 g of 1-(3-chloro-2-pyridinyl)-5-thiocyanato-1H-pyrrole-2-carbaldehyde, 0.64 g of sodium sulfide nonahydrate and 10 ml of water was stirred for 1 hour under heat refluxing. The reaction mixture was allowed to cool to room temperature, adjusted to pH 5 by an addition of acetic acid, and then extracted with ethyl acetate two times. The organic layers were combined, washed with an aqueous saturated sodium chloride solution, dried over anhydrous magnesium sulfate, and concentrated under reduced pressure. The residue was washed with methyl tert-butyl ether to obtain 0.50 g of 1-(3-chloro-2-pyridinyl)-5-mercapto-1H-pyrrole-2-carbaldehyde of the formula:

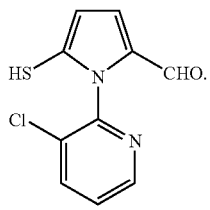

1-(3-Chloro-2-pyridinyl)-5-mercapto-1H-pyrrole-2-carbaldehyde $^1$H-NMR (CDCl$_3$, TMS) δ (ppm): 6.56 (1H, d, J=4 Hz), 7.07 (1H, d, J=4 Hz), 7.46 (1H, dd, J=8 Hz, 5 Hz), 7.93 (1H, dd, J=8 Hz, 2 Hz), 8.54 (1H, dd, J=5 Hz, 2 Hz), 9.42 (1H, s)

REFERENCE PREPARATION EXAMPLE 152-(2)

A mixture of 0.50 g of 1-(3-chloro-2-pyridinyl)-5-mercapto-1H-pyrrole-2-carbaldehyde, 0.36 g of methyl iodide, 0.43 g of potassium carbonate and 50 ml of N,N-dimethylformamide was stirred at room temperature for 1 day Water was poured into the reaction mixture, and the mixture was extracted with ethyl acetate three times. The organic layers were combined, washed successively with water and an aqueous saturated sodium chloride solution, dried over anhydrous magnesium sulfate, and concentrated under reduced pressure. The residue was subjected to silica gel column chromatography to obtain 0.34 g of 1-(3-chloro-2-pyridinyl)-5-methylthio-1H-pyrrole-2-carbaldehyde of the formula:

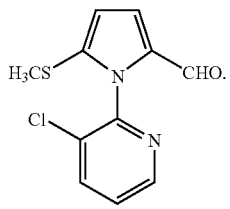

1-(3-Chloro-2-pyridinyl)-5-methylthio-1H-pyrrole-2-carbaldehyde $^1$H-NMR (CDCl$_3$, TMS) δ (ppm): 2.39 (3H, s), 6.45 (1H, d, J=4 Hz), 7.10 (1H, d, J=4 Hz), 7.43 (1H, dd, J=8 Hz, 5 Hz), 7.90 (1H, dd, J=8 Hz, 2 Hz), 8.52 (1H, dd, J=5 Hz, 2 Hz), 9.41 (1H, s)

REFERENCE PREPARATION EXAMPLE 152-(3)

To a mixture of 0.38 g of 1-(3-chloro-2-pyridinyl)-5-methylthio-1H-pyrrole-2-carbaldehyde, 5 ml of acetone and 3 ml of water was added 0.38 g of potassium permanganate at 40° C. The resulting mixture was stirred at 50° C. for 4 hours. The reaction mixture was allowed to cool to room temperature, and filtered. The filtrate was washed with chloroform two times, and then adjusted to around pH 3 by an addition of 2N hydrochloric acid. A deposited crystal was collected by filtration to obtain 0.38 g of a mixture of 1-(3-chloro-2-pyridinyl) 75-methylsulfonyl-1H-pyrrole-2-carboxylic acid and 1-(3-chloro-2-pyridinyl)-5-methylthio-1H-pyrrole-2-carboxylic acid.

A mixture of the resulting mixture and 0.29 ml of thionyl chloride was heated to reflux in 10 ml of acetonitrile for 1 hour. The reaction mixture was allowed to cool to room temperature, and concentrated under reduced pressure. The resulting residue was dissolved in 10 ml of acetonitrile. Thereto 0.39 g of 2-amino-3,5-dibromobenzoic acid and 0.65 ml of triethylamine were added, and the mixture was stirred at room temperature for 6 hours. Thereto 0.13 ml of methanesulfonyl chloride was added, and the mixture was stirred at room temperature for 1 hour. Water was poured into the reaction mixture, and the mixture was extracted with ethyl acetate three times. The organic layers were combined, washed with an aqueous saturated sodium chloride solution, dried over anhydrous magnesium sulfate, and concentrated under reduced pressure. The residue was subjected to silica gel column chromatography to obtain 0.05 g of 6,8-dibromo-2-[1-(3-chloro-2-pyridinyl)-5-methylsulfonyl-1H-pyrrol-2-yl]-4H-3,1-benzoxazine-4-one of the formula:

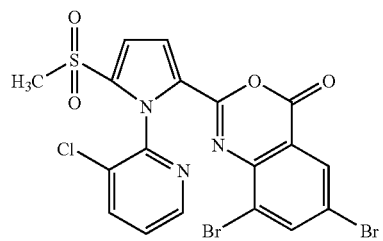

and 0.05 g of 6,8-dibromo-2-[1-(3-chloro-2-pyridinyl)-5-methylthio-1H-pyrrol-2-yl]-4H-3,1-benzoxazine-4-one of the formula:

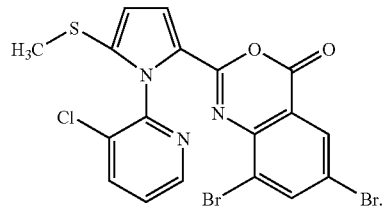

6,8-Dibromo-2-[1-(3-chloro-2-pyridinyl)-5-methylsulfonyl-1H-pyrrol-2-yl]-4H-3,1-benzoxazine-4-one $^1$H-NMR (CDCl$_3$, TMS) δ (ppm): 3.23 (3H, s), 7.21 (1H, d, J=4 Hz), 7.41 (1H, d, J=4 Hz), 7.50 (1H, dd, J=8 Hz, 4 Hz), 7.95 (1H, d, J=8 Hz), 8.02 (1H, d, J=2 Hz), 8.24 (1H, d, J=2 Hz), 8.56 (1H, d, J=4 Hz)

6,8-Dibromo-2-[1-(3-chloro-2-pyridinyl)-5-methylthio-1H-pyrrol-2-yl]-4H-3,1-benzoxazine-4-one $^1$H-NMR (CDCl$_3$, TMS) δ (ppm): 2.39 (3H, s), 6.63 (1H, d, J=4 Hz), 7.35 (1H, d, J=4 Hz), 7.63 (1H, dd, J=8 Hz, 5 Hz), 8.08 (1H, d, J=2 Hz), 8.22 (1H, d, J=2 Hz), 8.25 (1H, dd, J=8 Hz, 2 Hz), 8.58 (1H, dd, J=5 Hz, 2 Hz)

REFERENCE PREPARATION EXAMPLE 153-(1)

To a mixture of 20 g of 3-chloro-2-hydrazinopyridine, 56 ml of sodium ethoxide (a 21% solution in ethanol) and 75 ml of ethanol was added dropwise 27 ml of diethyl maleate. The resulting mixture was heated to reflux for 10 minutes. The reaction mixture was allowed to cool to 65° C., and 15 ml of acetic acid was poured into the mixture. The reaction mixture was allowed to cool to room temperature. After 190 ml of water was poured into the reaction mixture, the mixture was adjusted to pH 2 by an addition of 6N hydrochloric acid and then extracted with methyl tert-butyl ether three times. The organic layers were combined, washed with an aqueous saturated sodium chloride solution, dried over anhydrous magnesium sulfate, and concentrated under reduced pressure. Diethyl ether was added to the resulting residue, and a solid was collected by filtration to obtain 4.28 g of ethyl 2-(3-chloro-2-pyridinyl)-5-oxo-3-pyrazolidinecarboxylate of the formula:

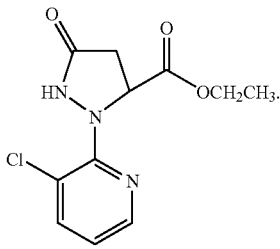

Ethyl 2-(3-chloro-2-pyridinyl)-5-oxo-3-pyrazolidinecarboxylate $^1$H-NMR (DMSO-$d_6$, TMS) δ (ppm): 1.22 (3H, t, J=7 Hz), 2.36 (1H, d, J=17 Hz), 2.92 (1H, dd, J=17 Hz, 10 Hz), 4.20 (2H, q, J=7 Hz), 4.83 (1H, d, J=10 Hz), 7.20 (1H, dd, J=8 Hz, 5 Hz), 7.93 (1H, d, J=8 Hz), 8.27 (1H, d, J=5 Hz), 10.17 (1H, s)

REFERENCE PREPARATION EXAMPLE 153-(2)

To a mixture of 12.0 g of ethyl 2-(3-chloro-2-pyridinyl)-5-oxo-3-pyrazolidinecarboxylate, 90 ml of acetonitrile and 4.8 ml of sulfuric acid was added 14.5 g of potassium persulfate. The resulting mixture was heated to reflux for 3.5 hours. The reaction mixture was allowed to cool to room temperature, and filtered. Water was poured into the filtrate, and the mixture was extracted with methyl tert-butyl ether three times. The organic layers were combined, washed with an aqueous saturated sodium chloride solution, dried over anhydrous magnesium sulfate, and concentrated under reduced pressure. The resulting residue was subjected to silica gel chromatography to obtain 7.23 g of ethyl 1-(3-chloro-2-pyridinyl)-3-hydroxy-1H-pyrazole-5-carboxylate of the formula:

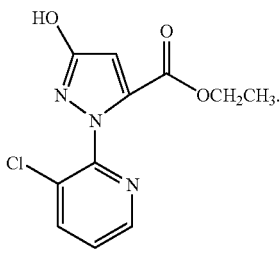

Ethyl 1-(3-chloro-2-pyridinyl)-3-hydroxy-1H-pyrazole-5-carboxylate $^1$H-NMR (DMSO-$d_6$, TMS) δ (ppm): 1.06 (3H, t, J=7 Hz), 4.11 (2H, q, J=7 Hz), 6.34 (1H, s), 7.59-7.63 (1H, m), 8.17-8.23 (1H, m), 8.50-8.52 (1H, m), 10.65 (1H, s)

REFERENCE PREPARATION EXAMPLE 153-(3)

Trifluoromethyl trifluorovinyl ether was blown into a mixture of 1.0 g of ethyl 1-(3-chloro-2-pyridinyl)-3-hydroxy-1H-pyrazole-5-carboxylate, 0.042 g of potassium hydroxide, 10 ml of methanol and 10 ml of dimethyl sulfoxide under ice-cooling. The resulting mixture was stirred at room temperature for 4 days. Water was poured into the reaction mixture, and the mixture was extracted with diethyl ether two times. The organic layers were combined, washed with water and an aqueous saturated sodium chloride solution, dried over anhydrous magnesium sulfate, and concentrated under reduced pressure. The resulting residue was subjected to silica gel chromatography to obtain 1.32 g of methyl 1-(3-chloro-2-pyridinyl)-3-[1,1,2-trifluoro-2-(trifluoromethoxy)ethoxy]-1H-pyrazole-5-carboxylate of the formula:

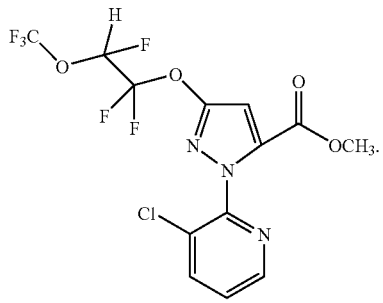

Methyl 1-(3-chloro-2-pyridinyl)-3-[1,1,2-trifluoro-2-(trifluoromethoxy)ethoxy]-1H-pyrazole-5-carboxylate $^1$H-NMR (CDCl$_3$, TMS) δ (ppm): 3.80 (3H, s), 6.04 (1H, dt, J=54 Hz, 3 Hz), 6.80 (1H, s), 7.45 (1H, dd, J=8 Hz, 5 Hz), 7.92 (1H, dd, J=8 Hz, 2 Hz), 8.51 (1H, dd, J=5 Hz, 2 Hz)

REFERENCE PREPARATION EXAMPLE 153-(4)

To a mixture of 1.32 g of methyl 1-(3-chloro-2-pyridinyl)-3-[1,1,2-trifluoro-2-(trifluoromethoxy)ethoxy]-1H-pyrazole-5-carboxylate and 15 ml of methanol was added 5 ml of a 2N aqueous sodium hydroxide solution. The resulting mixture was stirred at room temperature for 3 hours. Water was poured into the reaction mixture, and the mixture was washed with methyl tert-butyl ether. The aqueous layer was adjusted to pH 2 by an addition of 6N hydrochloric acid and then extracted with methyl tert-butyl ether two times. The organic layers were combined, washed with an aqueous saturated sodium chloride solution, dried over anhydrous magnesium sulfate, and concentrated under reduced pressure to obtain 1.18 g of 1-(3-chloro-2-pyridinyl)-3-[1,1,2-trifluoro-2-(trifluoromethoxy)ethoxy]-1H-pyrazole-5-carboxylic acid of the formula:

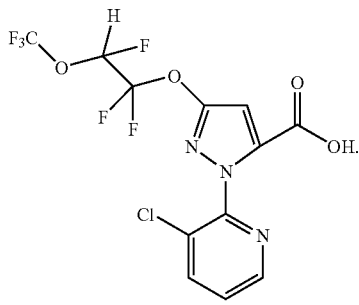

1-(3-Chloro-2-pyridinyl)-3-[1,1,2-trifluoro-2-(trifluoromethoxy)ethoxy]-1H-pyrazole-5-carboxylic acid $^1$H-NMR (CDCl$_3$, TMS) δ (ppm): 6.04 (1H, dt, J=54 Hz, 3 Hz), 6.84 (1H, s), 7.46 (1H, dd, J=8 Hz, 5 Hz), 7.93 (1H, dd, J=8 Hz, 2 Hz), 8.50 (1H, dd, J=5 Hz, 2 Hz)

REFERENCE PREPARATION EXAMPLE 153-(5)

According to the same manner as that of Reference Preparation Example 13, 1-(3-chloro-2-pyridinyl)-3-[1,1,2-trifluoro-2-(trifluoromethoxy)ethoxy]-1H-pyrazole-5-carboxylic acid was used in place of 1-(3-chloro-2-pyridinyl)-1H-pyrazole-5-carboxylic acid to obtain 6-chloro-2-{1-(3-chloro-2-pyridinyl)-3-[1,1,2-trifluoro-2-(trifluoromethoxy)ethoxy]-1H-pyrazol-5-yl}-8-methyl-4H-3,1-benzoxazine-4-one of the formula:

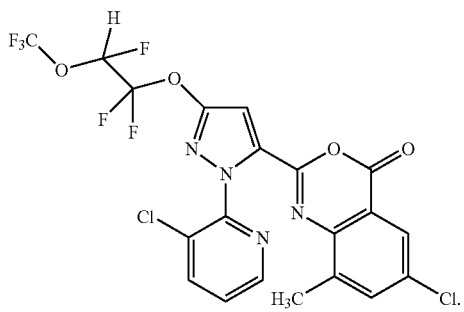

6-Chloro-2-{1-(3-chloro-2-pyridinyl)-3-[1,1,2-trifluoro-2-(trifluoromethoxy)ethoxy]-1H-pyrazol-5-yl}-8-methyl-4H-3,1-benzoxazin-4-one $^1$H-NMR (CDCl$_3$, TMS) δ (ppm): 1.83 (3H, s), 6.06 (1H, dt, J=54 Hz, 3 Hz), 7.04 (1H, s), 7.48-7.51 (2H, m), 7.96-8.00 (2H, m), 8.55 (1H, dd, J=5 Hz, 2 Hz)

REFERENCE PREPARATION EXAMPLE 154-(1)

To a mixture of 4.0 g of N,N-dimethyl-1H-pyrazole-1-sulfonamide and 50 ml of tetrahydrofuran was added dropwise 15.7 ml of a 1.6M solution of N-butyl lithium in hexane at −78° C. The resulting mixture was stirred at −78° C. for 10 minutes. A mixture of 1.46 g of sulfur and 20 ml of tetrahydrofuran was added to the mixture. The mixture was stirred at −78° C. for 1 hour, and further stirred for 1.5 hours while the reaction temperature was gradually raised to room temperature. A deposited solid was collected by filtration, and washed with diethyl ether. The solid was dissolved in water. The resulting aqueous solution was adjusted to around pH 3 by an addition of 6N hydrochloric acid, and then extracted with methyl t-butyl ether three times. The organic layers were combined, washed with an aqueous saturated sodium chloride solution, dried over magnesium sulfate, and concentrated under reduced pressure to obtain 3.92 g of N,N-dimethyl-5-mercapto-1H-pyrazole-1-sulfonamide of the formula:

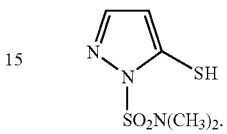

N,N-Dimethyl-5-mercapto-1H-pyrazole-1-sulfonamide $^1$H-NMR (CDCl$_3$, TMS) δ (ppm): 3.03 (6H, s), 4.39 (1H, s), 6.27 (1H, d, J=2 Hz), 7.59 (1H, d, J=2 Hz)

REFERENCE PREPARATION EXAMPLE 154-(2)

A mixture of 1.0 g of N,N-dimethyl-5-mercapto-1H-pyrazole-1-sulfonamide, 0.30 g of sodium hydride (50% in oil) and 25 ml of tetrahydrofuran was stirred at room temperature for 0.5 hour, and then cooled to −60° C. Thereto 1.94 g of S-(trifluoromethyl)dibenzothiophenium trifluoromethanesulphonate was added. The resulting mixture was stirred at −60° C. for 0.5 hour, and further stirred at room temperature for 2 hours. Water was poured into the reaction mixture, and the mixture was extracted with ethyl acetate three times. The organic layers were combined, washed with an aqueous saturated sodium chloride solution, dried over magnesium sulfate, and concentrated under reduced pressure. The resulting residue was subjected to silica gel chromatography to obtain 1.30 g of N,N-dimethyl-5-(triflioromethylthio)-1H-pyrazole-1-sulfonamide of the formula:

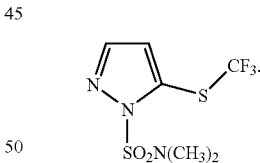

N,N-Dimethyl-5-(triflioromethylthio)-1H-pyrazole-1-sulfonamide $^1$H-NMR (CDCl$_3$, TMS) δ (ppm): 3.08 (6H, s), 6.73 (1H, s), 7.73 (1H, s)

REFERENCE PREPARATION EXAMPLE 154-(3)

According to the same manner as that of Reference Preparation Example 21, N,N-dimethyl-5-(trifluoromethylthio)-1H-pyrazole-1-sulfonamide was used in place of 5-bromo-N,N-dimethyl-1H-pyrazole-1-sulfonamide to obtain 3-(trifluoromethylthio)-1H-pyrazole of the formula:

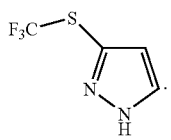

3-(Trifluoromethylthio)-1H-pyrazole

¹H-NMR (CDCl₃, TMS) δ (ppm): 6.70 (1H, d, J=3 Hz), 7.74 (1H, d, J=3 Hz), 12.47 (1H, brs)

REFERENCE PREPARATION EXAMPLE 154-(4)

According to the same manner as that of Reference Preparation Example 22, 3-(trifluoromethylthio)-1H-pyrazole was used in place of 3-bromo-1H-pyrazole to obtain 3-chloro-2-[3-(trifluoromethylthio)-1H-pyrazol-1-yl]pyridine of the formula:

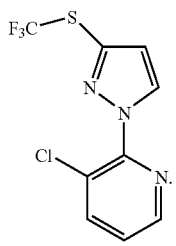

3-Chloro-2-[3-(trifluoromethylthio)-1H-pyrazol-1-yl]pyridine

¹H-NMR (CDCl₃, TMS) δ (ppm): 6.78 (1H, d, J=3 Hz), 7.35 (1H, dd, J=8 Hz, 5 Hz), 7.94 (1H, dd, J=8 Hz, 2 Hz), 8.17 (1H, d, J=3 Hz), 8.47 (1H, dd, J=5 Hz, 2 Hz)

REFERENCE PREPARATION EXAMPLE 154-(5)

According to the same manner as that of Reference Preparation Example 23, 3-chloro-2-[3-(trifluoromethylthio)-1H-pyrazol-1-yl]pyridine was used in place of 2-(3-bromo-1H-pyrazol-1-yl)-3-chloropyridine to obtain 1-(3-chloro-2-pyridinyl)-3-(trifluoromethylthio)-1H-pyrazole-5-carboxylic acid of the formula:

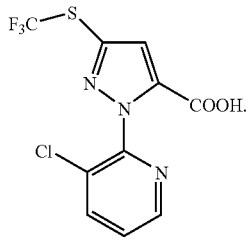

1-(3-Chloro-2-pyridinyl)-3-(trifluoromethylthio)-1H-pyrazole-5-carboxylic acid

¹H-NMR (CDCl₃, TMS) δ (ppm): 7.35 (1H, s), 7.47 (1H, dd, J=8 Hz, 5 Hz), 7.94 (1H, d, J=8 Hz), 8.52 (1H, d, J=5 Hz)

REFERENCE PREPARATION EXAMPLE 154-(6)

According to the same manner as that of Reference Preparation Example 13, 1-(3-chloro-2-pyridinyl)-3-(trifluoromethylthio)-1H-pyrazole-5-carboxylic acid was used in place of 1-(3-chloro-2-pyridinyl)-1H-pyrazole-5-carboxylic acid to obtain 6-chloro-2-[1-(3-chloro-2-pyridinyl)-3-(trifluoromethylthio)-1H-pyrazol-5-yl]-8-methyl-4H-3,1-benzoxazine-4-one of the formula:

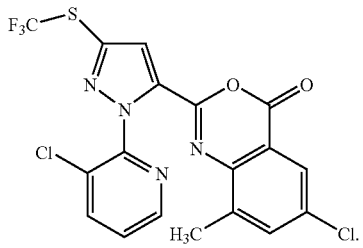

6-Chloro-2-[1-(3-chloro-2-pyridinyl)-3-(trifluoromethylthio)-1H-pyrazol-5-yl]-8-methyl-4H-3,1-benzoxazin-4-one ¹H-NMR (CDCl₃, TMS) δ (ppm): 1.82 (3H, s), 7.50-7.54 (3H, m), 7.98-8.00 (2H, m), 8.57 (1H, dd, J=5 Hz, 2 Hz)

REFERENCE PREPARATION EXAMPLE 155

According to the same manner as that of Reference Preparation Example 147, 2-[3-bromo-1-(3-chloro-2-pyridinyl)-1H-pyrazol-5-yl]-6,8-dichloro-4H-3,1-benzoxazin-4-one was used in place of 2-[3-bromo-1-(3-chloro-2-pyridinyl)-1H-pyrazol-5-yl]-6,8-dibromo-4H-3,1-benzoxazin-4-one to obtain 3-bromo-N-[4,6-dichloro-2-(N,N'-dimethylhydrazinocarbonyl)phenyl]-1-(3-chloro-2-pyridinyl)-1H-pyrazole-5-carboxamide of the formula:

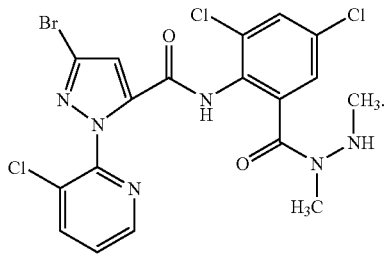

3-Bromo-N-[4,6-dichloro-2-(N,N'-dimethylhydrazinocarbonyl)phenyl]-1-(3-chloro-2-pyridinyl)-1H-pyrazole-5-carboxamide ¹H-NMR (DMSO-d₆, TMS) δ (ppm): 2.20 (2.4H, d, J=5 Hz), 2.39 (0.6H, d, J=6 Hz), 2.72 (0.6H, s), 3.02 (2.4H, s), 4.59 (0.8H, q, J=5 Hz), 5.68 (0.2H, q, J=6 Hz), 7.38 (0.8H, d, J=2 Hz), 7.40 (1.0H, s), 7.53 (0.2H, d, J=2 Hz), 7.60-7.64 (1.0H, m), 7.70 (0.8H, d, J=2 Hz), 7.84 (0.2H, d, J=2 Hz), 8.16-8.19 (1.0H, m), 8.49-8.50 (1.0H, m), 10.34 (0.8H, s), 10.65 (0.2H, s)

Then, Formulation Examples will be shown. All parts are by weight.

FORMULATION EXAMPLE 1

Into a mixture of 35 parts of xylene and 35 parts of N,N-dimethylformamide, 10 parts of any one of the present compounds (1) to (231) is dissolved, and then 14 parts of polyoxyethylene styrylphenyl ether and 6 parts of calcium dodecylbenzenesulfonate are added. The mixture is stirred thoroughly to obtain a 10% emulsion.

FORMULATION EXAMPLE 2

To a mixture of 4 parts of sodium laurylsulfate, 2 parts of calcium ligninsulfonate, 20 parts of synthetic hydrous silicon oxide fine powder and 54 parts of diatomaceous earth, 20 parts of any one of the present compounds (1) to (231) is added. The mixture is stirred thoroughly to obtain a 20% wettable agent.

FORMULATION EXAMPLE 3

To 2 parts of anyone of the present compounds (1) to (231), 1 part of synthetic hydrous silicon oxide fine powder, 2 parts of calcium ligninsulfonate, 30 parts of bentonite and 65 parts of kaolin clay are added, and then stirred thoroughly. Then, an appropriate amount of water is added to the mixture. The mixture is further stirred, granulated with a granulator, and forced-air dried to obtain a 2% granule.

FORMULATION EXAMPLE 4

Into an appropriate amount of acetone, 1 part of any one of the present compounds (1) to (231) is dissolved, and then 5 parts of synthetic hydrous silicon oxide fine powder, 0.3 part of PAP and 93.7 parts of fubasami clay are added. The mixture is stirred thoroughly. Then, acetone is removed from the mixture by evaporation to obtain a 1% powder.

FORMULATION EXAMPLE 5

A mixture of 10 parts of any one of the present compounds (1) to (231); 35 parts of white carbon containing 50 parts of polyoxyethylene alkyl ether sulfate ammonium salt; and 55 parts of water is finely ground by a wet grinding method to obtain a 10% flowable agent.

FORMULATION EXAMPLE 6

In 5 parts of xylene and 5 parts of trichloroethane, 0.1 part of any one of the present compounds (1) to (231) is dissolved. The solution is mixed with 89.9 parts of deodorized kerosene to obtain a 0.1% oil.

FORMULATION EXAMPLE 7

In 0.5 ml of acetone, 10 mg of any one of the present compounds (1) to (231) is dissolved. The solution is mixed uniformly with 5 g of a solid feed powder for an animal (solid feed powder for rearing and breeding CE-2, manufactured by CLEA Japan, Inc.), and then dried by evaporation of acetone to obtain poison bait.

Then, it will be shown by Test Examples that the present compound is effective in controlling harmful arthropods.

TEST EXAMPLE 1

Preparations of the present compounds (1), (4) to (53), (55) to (74), (76) to (83), (85) to (120), (122) to (156), (158) to (167), (170) to (171), (173), (175) to (176), (178), (181) to (184), (188) to (190), (195) to (197), (200) to (216), (218) to (219), (221) to (223) and (231) obtained in Formulation Example 5 were diluted with water so that the active ingredient concentration became 500 ppm, to prepare test spray solutions.

At the same time, cabbage was planted in a polyethylene cup, and grown until the third true leaf or the fourth true leaf was developed. The test spray solution as described above was sprayed in an amount of 20 ml/cup on the cabbage.

After the drug solution sprayed on the cabbage was dried, 10 third-instar larvae of diamondback moths were put on the cabbage. After 5 days, the number of diamondback moths was counted, and a controlling value was calculated by the following equation:

$$\text{Controlling value}(\%) = \{1 - (Cb \times Tai)/(Cai \times Tb)\} \times 100$$

wherein, $Cb$: the number of worms in a non-treated section before treatment $Cai$: the number of worms in a non-treated section on observation $Tb$: the number of worms in a treated-section before treatment $Tai$: the number of worms in a treated-section on observation.

As a result, the test spray solutions of the present compounds (1), (4) to (53), (55) to (74), (76) to (83), (85) to (120), (122) to (156), (158) to (167), (170) to (171), (173), (175) to (176), (178), (181) to (184), (188) to (190), (195) to (197), (200) to (216), (218) to (219), (221) to (223) and (231) each exhibited a controlling value of 80% or more.

TEST EXAMPLE 2

Preparations of the present compounds (4) to (7), (9) to (12), (17) to (23), (27), (29), (32) to (44), (48) to (51), (56) to (61), (65) to (68), (70) to (72), (74) to (75), (78) to (81), (83) to (85), (87) to (88), (91) to (97), (99) to (102), (104) to (120), (122) to (125), (127) to (135), (137) to (144), (147) to (149), (151) to (161), (164), (166) to (168), (171) to (173), (175) to (184), (186) to (188), (191), (193) to (205), (208) to (209), (213) to (215), (218) to (224), (226) to (230) and (231) obtained in Formulation Example 5 was diluted with water so that the active ingredient concentration became 500 ppm to prepare test spray solutions.

At the same time, cucumber was planted in a polyethylene cup, and was grown until the first true leaf was developed. About 30 cotton aphids were put on the cucumber. One day after, the test spray solution as described above was sprayed in an amount of 20 ml/cup on the cucumber. Six days after spraying, the number of cotton aphids was counted, and a controlling value was calculated by the following equation:

$$\text{Controlling value}(\%) = \{1 - (Cb \times Tai)/(Cai \times Tb)\} \times 100$$

wherein, $Cb$: the number of insects in a non-treated section before treatment $Cai$: the number of insects in a non-treated section on observation $Tb$: the number of insects in a treated-section before treatment $Tai$: the number of insects in a treated-section on observation.

As a result, the test spray solutions of the present compounds (4) to (7), (9) to (12), (17) to (23), (27), (29) (32) to (44), (48) to (51), (56) to (61), (65) to (68), (70) to (72), (74)

to (75), (78) to (81), (83) to (85), (87) to (88), (91) to (97), (99) to (102), (104) to (120), (122) to (125), (127) to (135), (137) to (144), (147) to (149), (151) to (161), (164), (166) to (168), (171) to (173), (175) to (184), (186) to (188), (191), (193) to (205), (208) to (209), (213) to (215), (218) to (224), (226) to (230) and (231) each exhibited a controlling value of 90% or more.

Furthermore, the same way as Test Example 2, test spray solution of the comparative compound of the formula:

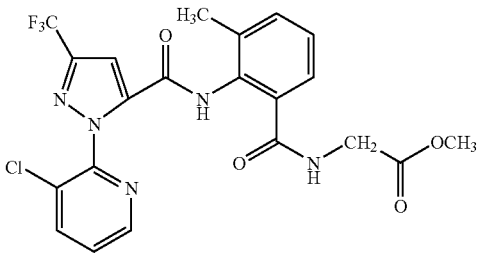

(disclosed in WO2003/015518A page 109 Compound 354) exhibited a controlling value of less than 30%.

TEST EXAMPLE 3

Preparations of the present compounds (4) to (13), (15) to (23), (25) to (44), (48) to (51), (56) to (58), (61), (65) to (74), (80) to (81), (85) to (97), (100), (102), (104) to (120), (122) to (125), (127) to (137), (139) to (156), (158) to (167), (170) to (171), (173), (175) to (176), (178), (181) to (184), (188) to (190), (195) to (197), (200) to (208), (210) to (216), (218) to (219), (221) to (224) and (231) obtained in Formulation Example 5 was diluted with water so that the active ingredient concentration became 500 ppm to prepare test spray solutions.

At the same time, cabbage was planted in a polyethylene cup, and grown until the third true leaf or the fourth true leaf was developed. The test spray solution as described above was sprayed in an amount of 20 ml/cup on the cabbage. After the drug solution sprayed on the cabbage was dried, 10 fourth-instar larvae of *Spodoptera litura* were put on the cabbage. After 4 days, the number of *Spodoptera litura* surviving on the cabbage leaves was counted, and a controlling value was calculated by the following equation:

Controlling value(%)={1−($Cb \times Tai$)/($Cai \times Tb$)}×100 wherein,

Cb: the number of worms in a non-treated section before treatment

Cai: the number of worms in a non-treated section on observation

Tb: the number of worms in a treated-section before treatment

Tai: the number of worms in a treated-section on observation.

As a result, the test spray solutions of the present compounds (4) to (13), (15) to (23), (25) to (44), (48) to (51), (56) to (58), (61), (65) to (74), (80) to (81), (85) to (97), (100), (102), (104) to (120), (122) to (125), (127) to (137), (139) to (156), (158) to (167), (170) to (171), (173), (175) to (176), (178), (181) to (184), (188) to (190), (195) to (197), (200) to (208), (210) to (216), (218) to (219), (221) to (224) and (231) each exhibited a controlling value of 80% or more.

TEST EXAMPLE 4

Preparations of the present compounds) (4) to (13), (15) to (23), (25) to (45), (47) to (51), (53), (55) to (61), (65) to (72), (74), (78) to (81), (83), (85) to (102), (104) to (105), (107) to (117), (119) to (120), (122) to (125), (127) to (156), (158) to (164), (166) to (167), (171), (173), (175) to (176), (178), (181) to (184), (188) to (190), (195) to (197), (200) to (211), (213) to (216), (218) to (219), (221) to (224) and (231) obtained in Formulation Example 5 was diluted with water so that the active ingredient concentration became 500 ppm to prepare test spray solutions.

At the same time, 20 ml of the test spray solution as described above was sprayed to an apple seedling (28 day-old seeding, tree height: about 15 cm) planted in a plastic cup. The apple seedling was air-dried to such an extent that the drug solution sprayed on the apple seedling was dried, about 30 first-instar larvae of *Adoxophyes orana fasciata* were released. Seven days after spraying, the number of worms surviving on the apple seedling was counted, and a controlling value was calculated by the following equation:

Controlling value(%)={1−($Cb \times Tai$)/($Cai \times Tb$)}×100 wherein,

Cb: the number of worms in a non-treated section before treatment

Cai: the number of worms in a non-treated section on observation

Tb: the number of worms in a treated-section before treatment

Tai: the number of worms in a treated-section on observation.

As a result, the test spray solutions of the present compounds (4) to (13), (15) to (23), (25) to (45), (47) to (51), (53), (55) to (61), (65) to (72), (74), (78) to (81), (83), (85) to (102), (104) to (105), (107) to (117), (119) to (120), (122) to (125), (127) to (156), (158) to (164), (166) to (167), (171), (173), (175) to (176), (178), (181) to (184), (188) to (190), (195) to (197), (200) to (211), (213) to (216), (218) to (219), (221) to (224) and (231) each exhibited a controlling value of 90% or more.

TEST EXAMPLE 5

Preparations of the present compounds (4) to (5), (9) to (10), (17), (19) to (22), (27), (29), (32) to (44), (48) to (51), (56) to (61), (66) to (68), (70) to (72), (74) to (75), (79), (81), (85), (88), (91) to (92), (94) to (95), (99), (101) to (102), (104) to (120), (122) to (124), (127) to (129), (131) to (132), (135) to (136), (140), (142) to (145), (147) to (151), (153) to (157), (159), (163) to (164), (167), (171) to (172), (175) to (176), (183), (187), (193) to (194), (196) to (204), (206), (208) to (209), (213) to (221), (226), (227) and (231) obtained in Formulation Example 5 was diluted with water so that the active ingredient concentration became 500 ppm to prepare test spray solutions.

At the same time, cucumber was planted in a polyethylene cup, and was grown until the first true leaf was developed. The test spray solution as described above was sprayed in an amount of 20 ml/cup on the cucumber. After the drug solution sprayed on the cucumber was dried, the first true leaf was cut and then placed on a filter paper (diameter: 70 mm) containing water in a polyethylene cup (diameter: 110 mm). On the cucumber leaf, 20 larvae of *Frankliniella occidentalis* were released, and the polyethylene cup was capped. Seven days after spraying, the number of insects surviving on the cucumber leaf was counted, and a controlling value was calculated by the following equation:

Controlling value(%)={1−(Cb×Tai)/(Cai×Tb)}×100 wherein,

Cb: the number of insects in a non-treated section before treatment

Cai: the number of insects in a non-treated section on observation

Tb: the number of insects in a treated-section before treatment

Tai: the number of insects in a treated-section on observation.

As a result, the test spray solutions of the present compounds (4) to (5), (9) to (10), (17), (19) to (22), (27), (29), (32) to (44), (48) to (51), (56) to (61), (66) to (68), (70) to (72), (74) to (75), (79), (81), (85), (88), (91) to (92), (94) to (95), (99), (101) to (102), (104) to (120), (122) to (124), (127) to (129), (131) to (132), (135) to (136), (140), (142) to (145), (147) to (151), (153) to (157), (159), (163) to (164), (167), (171) to (172), (175) to (176), (183), (187), (193) to (194), (196) to (204), (206), (208) to (209), (213) to (221), (226), (227) and (231) each exhibited a controlling value of 90% or more.

TEST EXAMPLE 6

Preparations of the present compounds (5), (32), (34), (43) to (44), (49) to (50), (56), (59), (93), (95) to (96), (107), (111) to (112), (114), (119), (127), (129), (132) to (133), (144), (147) to (148), (153), (158), (167) to (168), (171) to (172), (177) to (178), (182) to (184), (186) to (187), (193) to (194), (197) to (199), (201), (204), (209), (213), (215), (219) to (220), (221), (223), (226) and (231) obtained in Formulation Example 5 was diluted with water so that the active ingredient concentration became 500 ppm to prepare test spray solutions.

At the same time, cabbage was planted in a polyethylene cup, and grown until the first true leaf was developed. All leaves excluding the first true leaf were cut off. On the first true leaf, imagoes of silver leaf whitefly were released and allowed to lay eggs for about 24 hours. The cabbage was retained in a greenhouse for 8 days. When larvae hatched from the laid eggs, the test spray solution as described above was sprayed in an amount of 20 ml/cup to the cabbage. Seven days after spraying, the number of larvae surviving on the cabbage was counted, and a controlling value was calculated by the following equation:

Controlling value(%)={1−(Cb×Tai)/(Cai×Tb)}×100 wherein,

Cb: the number of worms in a non-treated section before treatment

Cai: the number of worms in a non-treated section on observation

Tb: the number of worms in a treated-section before treatment

Tai: the number of worms in a treated-section on observation.

As a result, the test spray solutions of the present compounds (5), (32), (34), (43) to (44), (49) to (50), (56) (59), (93), (95) to (96), (107), (111) to (112), (114), (119), (127), (129), (132) to (133), (144), (147) to (148), (153), (158), (167) to (168), (171) to (172), (177) to (178), (182) to (184), (186) to (187), (193) to (194), (197) to (199), (201), (204), (209), (213), (215), (219) to (220), (221), (223), (226) and (231) each exhibited a controlling value of 90% or more.

INDUSTRIAL APPLICABILITY

According to the present invention, since the hydrazide compound of the present invention has excellent efficacy of controlling pests, it is useful as an active ingredient of a pesticide.

The invention claimed is:

1. A hydrazide compound represented by the formula (1):

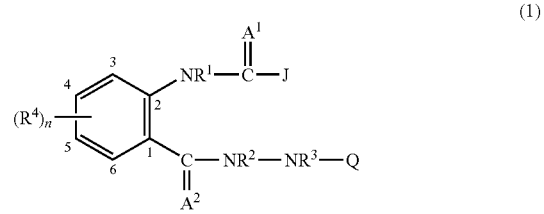

wherein, $R^1$ represents a hydrogen atom, a C1-C6 alkyl group optionally substituted with at least one halogen atom, a C2-C6 cyanoalkyl group, a C2-C6 alkoxyalkyl group optionally substituted with at least one halogen atom, a C2-C6 alkenyl group optionally substituted with at least one halogen atom, a C3-C6 alkynyl group optionally substituted with at least one halogen atom, or a C7-C9 phenyl alkyl group whose benzene ring moiety may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^2$ and $R^3$ independently represent a hydrogen atom, a C1-C6 alkyl group optionally substituted with at least one halogen atom, a C1-C6 acyl group, a C2-C6 alkoxycarbonyl group, a C3-C7 N,N-dialkylcarbamoyl group, or a phenyl group optionally substituted with 1 to 5 independent substituents selected from the group consisting of (1) a halogen atom, (2) a cyano group, (3) a nitro group and (4) a C1-C6 alkyl group optionally substituted with at least one halogen atom, $R^4$ represents a halogen atom, a cyano group, a nitro group, a C1-C6 alkyl group optionally substituted with at least one halogen atom, a C1-C6 alkoxy group optionally substituted with at least one halogen atom, a phenyl group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, or two $R^4$ groups which are bound to the adjacent carbon atoms are bound at their terminal ends to each other to form a group T1 or T2

T1: —CR$^{41}$=CR$^{42}$—CR$^{43}$=CR$^{44}$—

T2: —(CR$^{45}$R$^{46}$)$_n$—

(wherein $R^{41}$, $R^{42}$, $R^{43}$ and $R^{44}$ independently represent a hydrogen atom, a halogen atom, a cyano group, a nitro group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, $R^{45}$ and $R^{46}$ independently represent a hydrogen atom, or a C1-C6 alkyl group optionally substituted with at least one halogen atom, and h represents an integer of 3 or 4), n represents an integer of 0 to 4 (provided that, when n is an integer of 2 or more, $R^4$'s may be the same or different), Q represents a group selected from Q1 to Q6:

Q1: —C(=$A^{31}$)-$R^5$
Q2: —C(=$A^{32}$)-O$R^6$
Q3: —C(=$A^{33}$)-S$R^7$
Q4: —C(=$A^{34}$)-N$R^8R^9$
Q5: —S(O)$_2$—$R^{10}$
Q6: —S(O)$_2$—N$R^{11}R^{12}$ (wherein $A^{31}$, $A^{32}$, $A^{33}$ and $A^{34}$ represent an oxygen atom or a sulfur atom, $R^5$ represents a hydrogen atom; a C2-C6 alkenyl group optionally substituted with at least one halogen atom; a C2-C6 alkynyl group optionally substituted with at least one halogen atom;

a C1-C6 alkyl group optionally substituted with one or more independent substituents selected from the group consisting of (1) a halogen atom, (2) a C1-C6 alkoxy group, (3) a C1-C6 alkylthio group, (4) a C1-C6 alkylsulfinyl group, (5) a C1-C6 alkylsulfonyl group, (6) a C2-C6 dialkylamino group and (7) a C3-C6 cycloalkyl group; a C3-C6 cycloalkyl group optionally substituted with one or more independent substituents selected from the group consisting of (1) a halogen atom and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom; a naphthyl group optionally substituted with 1 to 9 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; a 5- to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; a 3- to 8-membered non-aromatic heterocyclic group optionally substituted with one or more independent substituents selected from the group consisting of (1) a halogen atom and (2) a C1-C6 alkyl group; a C7-C9 phenylalkyl group whose benzene ring moiety may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or a C7-C9 phenoxyalkyl group whose benzene ring moiety may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^6$ and $R^7$ represent a C1-C6 alkyl group optionally substituted with at least one halogen atom; a C3-C6 alkoxyalkyl group optionally substituted with at least one halogen atom; a C2-C6 alkenyl group optionally substituted with at least one halogen atom; a C3-C6 alkynyl group optionally substituted with at least one halogen atom; a C3-C6 cycloalkyl group optionally substituted with one or more independent substituents selected from the group consisting of (1) a halogen atom and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom; a 5- to 6-membered heteroaryl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or a C7-C9 phenylalkyl group whose benzene ring moiety may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^8$ and $R^9$ independently represent a hydrogen atom; a C1-C6 alkyl group optionally substituted with at least one halogen atom; a C2-C6 alkoxyalkyl group optionally substituted with at least one halogen atom; a C2-C6 alkenyl group optionally substituted with at least one halogen atom; a C3-C6 alkynyl group optionally substituted with at least one halogen atom; a C3-C6 cycloalkyl group optionally substituted with one or more independent substituents selected from the group consisting of (1) a halogen atom and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom; a 5- to 6-membered heteroaryl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or a C7-C9 phenylalkyl group whose benzene ring moiety may be substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or $R^8$ and $R^9$ are taken together with the nitrogen atom to which they are bound to form a 3- to 8-membered non-aromatic heterocyclic group, the 3 to 8-membered non-aromatic heterocyclic group may contain, in the ring, one or more independent groups selected from the group consisting of (1) an oxygen atom, (2) a sulfur group and (3) a —$NR^a$— group (wherein $R^a$ represents a C1-C6 alkyl group optionally substituted with at least one halogen atom, a C2-C6 alkoxycarbonyl group optionally substituted with at least one halogen atom, or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom), or carbon atom(s) in the ring may be substituted with one or more independent substituents selected from the group consisting of (1) a halogen atom, (2) a C1-C6 alkyl group optionally substituted with at least one halogen atom and (3) a C2-C6 alkoxycarbonyl group optionally substituted with at least one halogen atom, $R^{10}$ represents a C1-C6 alkyl group optionally substituted with at least one halogen atom; a C3-C6 cycloalkyl group optionally substituted with one or more independent substituents selected from the group consisting of (1) a halogen atom and (2) a C1-C6 alkyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, and $R^{11}$ and $R^{12}$ independently represent a C1-C6 alkyl group optionally substituted with at least one halogen atom; a C3-C6 cycloalkyl group optionally substituted with one or more independent substituents selected from the group consisting of (1) a halogen atom and (2) a C1-C6 alkyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or $R^{11}$ and $R^{12}$ are taken together with the nitrogen atom to which they are bound to form a 3- to 8-membered non-aromatic heterocyclic group, the 3- to 8-membered non-aromatic heterocyclic group may contain, in the ring, one or more independent groups selected from the group consisting of (1) an oxygen atom, (2) a sulfur atom and (3) a —$NR^b$-group (wherein $R^b$ represents a C1-C6 alkyl group optionally substituted with at least one halogen atom, a C2-C6 alkoxycarbonyl group optionally substituted with at least one halogen atom, or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom), and carbon atom(s) in the ring may be substituted with one or more independent substituents selected from the group consisting of (1) a halogen atom, (2) a C1-C6 alkyl group optionally substituted with at least one halogen atom and (3) a C2-C6 alkoxycarbonyl group optionally substituted with at least one halogen atom), J represents a group represented by J1 or J2:

J1:

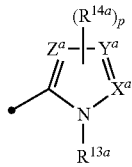

J2:

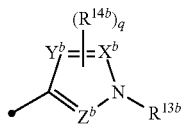

(wherein $X^a$, $Y^a$, $Z^a$, $X^b$, $Y^b$ and $Z^b$ independently represent CH or a nitrogen atom, $R^{13a}$ and $R^{13b}$ represent a C1-C6 alkyl group optionally substituted with at least one halogen atom; a C2-C6 cyanoalkyl group; a C2-C6 alkoxyalkyl group optionally substituted with at least one halogen atom; a C2-C6 alkenyl group optionally substituted with at least one halogen atom; a C2-C6 alkynyl group optionally substituted with at least one halogen atom; a C3-C6 cycloalkyl group optionally substituted with one or more independent substituents selected from the group consisting of (1) a halogen atom and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom and (8) a C1-C6 alkylsulfonyl group optionally substituted with at least one halogen atom;

a 5- to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; a C7-C9 phenylalkyl group in whose benzene ring moiety may be substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or a C7-C9 pyridinylalkyl group whose pyridine ring moiety may be substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^{14a}$ and $R^{14b}$ represent a halogen atom; a cyano group; a nitro group; an isocyanato group; a C1-C6 alkyl group optionally substituted with at least one halogen atom; a C1-C6 alkoxy group optionally substituted with at least one halogen atom; a C2-C6 cyanoalkyloxy group; a C3-C6 alkoxyalkyloxy group optionally substituted with at least one halogen atom; a C3-C6 alkenyloxy group optionally substituted with at least one halogen atom; a C3-C6 alkynyloxy group optionally substituted with at least one halogen atom; a C1-C6 alkylthio group optionally substituted with at least one halogen atom; a C1-C6 alkylsulfinyl group optionally substituted with at least one halogen atom; a C1-C6 alkylsulfonyl group optionally substituted with at least one halogen atom; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; a 5- to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or a phenoxy group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, p represents an integer of 0 to 3, and q represents an integer of 0 to 3 (provided that, when p is an integer of 2 or 3, two or more $R^{14a}$'s may be the same or different and, when q is an integer of 2 or 3, two or more $R^{14b}$'s may be the same or different), and $A^1$ and $A^2$ independently represent an oxygen atom or a sulfur atom.

2. The compound according to claim 1, wherein n is an integer of 0 to 3.

3. The compound according to claim 2, wherein $R^4$ is a halogen atom, a cyano group, a C1-C6 alkyl group optionally substituted with at least one halogen atom, a C1-C6 alkoxy group optionally substituted with at least one halogen atom, or a phenyl group optionally substituted with at least one halogen atom, or two $R^4$ groups which are bound to the adjacent carbon atoms are bound at their terminal ends to form a group T1: —CR$^{41}$=CR$^{42}$—CR$^{43}$=CR$^{44}$—
(wherein $R^{41}$, $R^{42}$, $R^{43}$ and $R^{44}$ represent a hydrogen atom).

4. The compound according to claim 3, wherein $R^4$ is a fluorine atom, a chlorine atom, a bromine atom, an iodine atom, a cyano group, a methyl group, an ethyl group, a trifluoromethyl group, a methoxy group, a phenyl group, or two $R^4$ groups which are bound to the adjacent carbon atoms are bound at their terminal end to form a group T1: —CR$^{41}$=CR$^{42}$—CR$^{43}$=CR$^{44}$—
(wherein $R^{41}$, $R^{42}$, $R^{43}$ and $R^{44}$ represent a hydrogen atom).

5. The compound according to claim 1, wherein

J is J1, $Y^a$ is CH, $R^{13a}$ is a C1-C6 alkyl group optionally substituted with at least one halogen atom; a C3-C6 cycloalkyl group optionally substituted with one or more independent substituents selected from the group consisting of (1) a halogen atom and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom and (8) a C1-C6 alkylsulfonyl group optionally substituted with at least one halogen atom; or a 5 to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^{14a}$ is a halogen atom; a cyano group; a C1-C6 alkyl group optionally substituted with at least one halogen atom; a C1-C6 alkylthio group optionally substituted with at least one halogen atom; a C1-C6 alkylsulfinyl group optionally substituted with at least one halogen atom; a C1-C6 alkylsulfonyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, and p is an integer of 0 to 2.

6. The compound according to claim 1, wherein

J is J2, $Y^b$ is CH, $R^{13b}$ is a C1-C6 alkyl group optionally substituted with at least one halogen atom, $R^{14b}$ is a C1-C6 alkyl group optionally substituted with at least one halogen atom, or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, and q is 1.

7. The compound according to claim 1, wherein $A^1$ and $A^2$ are an oxygen atom, and $R^1$ is a hydrogen atom or a methyl group.

8. The compound according to claim 1, wherein
Q is Q1,
$A^{31}$ is an oxygen atom, and
$R^5$ is a hydrogen atom; a C1-C6 alkyl group optionally substituted with one or more independent substituents selected from the group consisting of (1) a halogen atom, (2) a C1-C6 alkoxy group, (3) a C1-C6 alkylthio group, (4) a C1-C6 alkylsulfinyl group, (5) a C1-C6 alkylsulfonyl group, (6) a C2-C6 dialkylamino group and (7) a C3-C6 cycloalkyl group; a C3-C6 cycloalkyl group optionally substituted with one or more independent substituents selected from the group consisting of (1) a halogen and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom, a 5- to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, or a 3- to 8-membered non-aromatic heterocyclic group optionally substituted with one or more independent groups selected from the group consisting of (1) a halogen atom and (2) a C1-C6 alkyl group.

9. The compound according to claim 8, wherein $R^5$ is a hydrogen atom, a methyl group, an ethyl group, a tert-butyl group, a cyclopropyl group, a phenyl group, a 3-methylphenyl group, a 4-methoxyphenyl group, a 2-pyridinyl group, or a morpholino group.

10. The compound according to claim 1, wherein
Q is Q2,
$A^{32}$ is an oxygen atom, and
$R^6$ is a C1-C6 alkyl group optionally substituted with at least one halogen atom; a C2-C6 alkenyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxy carbonyl group optionally substituted with at least one halogen atom.

11. The compound according to claim 10, wherein $R^6$ is a methyl group, an ethyl group, a propyl group, an isopropyl group, a butyl group, a sec-butyl group, a 2-propenyl group, or a phenyl group.

12. The compound according to claim 1, wherein
Q is Q4,
$A^{34}$ is an oxygen atom, and
$R^8$ and $R^9$ independently represent a hydrogen atom; a C1-C6 alkyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxy carbonyl group optionally substituted with at least one halogen atom.

13. The compound according to claim 12, wherein $R^8$ and $R^9$ independently represent a hydrogen atom, a methyl group, an ethyl group, or a phenyl group.

14. The compound according to claim 1, wherein $R^2$ is a hydrogen atom or a methyl group, and $R^3$ is a hydrogen atom, a methyl group, an isopropyl group, or a methoxycarbonyl group.

15. The compound according to claim 1, wherein
$R^1$ is a hydrogen atom, or a C1-C6 alkyl group optionally substituted with at least one halogen atom,
$R^2$ is a hydrogen atom, or a C1-C6 alkyl group optionally substituted with at least one halogen atom,
$R^3$ is a hydrogen atom, a C1-C6 alkyl group optionally substituted with at least one halogen atom, or a C2-C6 alkoxycarbonyl group,
$R^4$ is a halogen atom, a cyano group, a C1-C6 alkyl group optionally substituted with at least one halogen atom, a C1-C6 alkoxy group optionally substituted with at least one halogen atom, a phenyl group optionally substituted with at least one halogen atom, or
two $R^4$ groups which are bound to the adjacent carbon atoms are bound at their terminal ends to form a group T1: —$CR^{41}$=$CR^{42}$—$CR^{43}$=$CR^{44}$—
(wherein $R^{41}$, $R^{42}$, $R^{43}$ and $R^{44}$ represent a hydrogen atom),
n is an integer of 0 to 3,
Q is a group selected from Q1 to Q6:
Q1: —C(=$A^{31}$)-$R^5$
Q2: —C(=$A^{32}$)-$OR^6$
Q3: —C(=$A^{33}$)-$SR^7$
Q4: —C(=$A^{34}$)-$NR^8R^9$
Q5: —S(O)$_2$—$R^{10}$
Q6: —S(O)$_2$—$NR^{11}R^{12}$
(wherein $A^{31}$, $A^{32}$ and $A^{33}$ are an oxygen atom, $A^{34}$ is an oxygen atom or a sulfur atom,
$R^5$ is a hydrogen atom; a C1-C6 alkyl group optionally substituted with one or more independent substituents selected from the group consisting of (1) a halogen atom, (2) a C1-C6 alkoxy group, (3) a C1-C6 alkylthio group, (4) a C1-C6 alkylsulfinyl group, (5) a C1-C6 alkylsulfonyl group, (6) a C2-C6 dialkylamino group and (7) a C3-C6 cycloalkyl group optionally substituted with one or more independent substituents selected from the group consisting of (1) a halogen atom and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom; a 5- to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom; or a 3- to 8-membered non-aromatic heterocyclic group optionally substituted with one or more independent substituents selected from the group consisting of (1) a halogen atom and (2) a C1-C6 alkyl group, $R^6$ is a C1-C6 alkyl group optionally substituted with at least one halogen atom; a C2-C6 alkenyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom, $R^7$ is a C1-C6 alkyl group optionally substituted with at least one halogen atom, $R^8$ and $R^9$ independently represent a hydrogen atom; a C1-C6 alkyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom, (8) a C1-C6 alkylsulfonyl group optionally substituted with at least one halogen atom, (9) a C2-C6 dialkylamino group optionally substituted with at least one halogen atom and (10) a C2-C6 alkoxycarbonyl group optionally substituted with at least one halogen atom, $R^{10}$ is a C1-C6 alkyl group optionally substituted with at least one halogen atom, and $R^{11}$ and $R^{12}$ independently represent a C1-C6 alkyl group optionally substituted with at least one halogen atom), J is a group represented by J1 or J2:

J1:

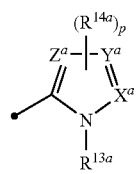

J2:

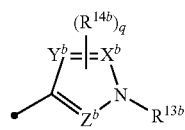

(wherein $X^a$ is CH or a nitrogen atom, $Y^a$ is CH, $Z^a$ is CH or a nitrogen atom, $X^b$ is CH or a nitrogen atom, $Y^b$ is CH, and $Z^b$ is CH or a nitrogen atom, $R^{13a}$ is a C1-C6 alkyl group optionally substituted with at least one halogen atom; a C3-C6 cycloalkyl group optionally substituted with one or more independent substituents selected from the group consisting of (1) a halogen atom and (2) a C1-C6 alkyl group; a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom, (5) a C1-C6 alkoxy group optionally substituted with at least one halogen atom, (6) a C1-C6 alkylthio group optionally substituted with at least one halogen atom, (7) a C1-C6 alkylsulfinyl group optionally substituted with at least one halogen atom and (8) a C1-C6 alkylsulfonyl group optionally substituted with at least one halogen atom; or a 5 to 6-membered heteroaryl group optionally substituted with one or more independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^{13b}$ is a C1-C6 alkyl group optionally substituted with at least one halogen atom, $R^{14a}$ is a halogen atom; a cyano group; a C1-C6 alkyl group optionally substituted with at least one halogen atom; a C1-C6 alkylthio group optionally substituted with at least one halogen atom; a C1-C6 alkylsulfinyl group optionally substituted with at least one halogen atom; a C1-C6 alkylsulfonyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, $R^{14b}$ is a C1-C6 alkyl group optionally substituted with at least one halogen atom; or a phenyl group optionally substituted with 1 to 5 independent substituents selected from the group consisting of (1) a halogen atom, (2) a cyano group, (3) a nitro group, (4) a C1-C6 alkyl group optionally substituted with at least one halogen atom and (5) a C1-C6 alkoxy group optionally substituted with at least one halogen atom, p is an integer of 0 to 2, and q is 1, (provided that, when p is 2, two $R^{14a}$s may be the same or different)), and $A^1$ and $A^2$ are an oxygen atom.

16. A hydrazide compound represented by the formula (1-1):

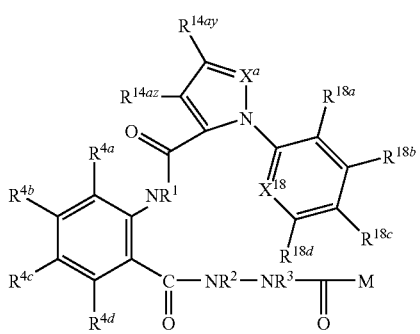

(1-1)

wherein $R^1$ is a hydrogen atom, or a C1-C6 alkyl group optionally substituted with at least one halogen atom, $R^2$ is a C1-C6 alkyl group optionally substituted with at least one halogen atom, $R^3$ is a hydrogen atom, a C1-C6 alkyl group optionally substituted with at least one halogen atom, or a C2-C6 alkoxycarbonyl group, $R^{4a}$ is a hydrogen atom, a halogen atom, a C1-C6 alkyl group optionally substituted with at least one halogen atom, a C1-C6 alkoxy group optionally substituted with at least one halogen atom, or a phenyl group optionally substituted with at least one halogen atom, $R^{4b}$, $R^{4c}$ and $R^{4d}$ independently are a hydrogen atom, a halogen atom, a cyano group, or a C1-C6 alkyl group optionally substituted with at least one halogen atom, or $R^{4b}$ and $R^{4c}$ are bound to each other at their terminal ends to form a group: $-CR^{41}=CR^{42}-CR^{43}=CR^{44}-$ (wherein $R^{41}$, $R^{42}$, $R^4$ and $R^{44}$ represent a hydrogen atom), M is $OR^6$, $SR^7$ or $NR^8R^9$ (wherein $R^6$ and $R^7$ are independently a C1-C6 alkyl group optionally substituted with at least one halogen atom, a C3-C6 alkoxyalkyl group optionally substituted with at least one halogen atom, a C2-C6 alkenyl group optionally substituted with at least one halogen atom, or a C3-C6 alkynyl group optionally substituted with at least one halogen atom, $R^8$ and $R^9$ are independently a hydrogen atom, a C1-C6 alkyl group optionally substituted with at least one halogen atom, a C2-C6 alkenyl group optionally substituted with at least one halogen atom, a C3-C6 alkynyl group optionally substituted with at least one halogen atom, or $R^8$ and $R^9$ are taken together with the nitrogen atom to which they are bound to form a pyrrolidin-1-yl group, a piperidino group, a hexamethyleneimin-1-yl group, a heptamethyleneimin-1-yl group, a morpholino group, a thiomorpholin-4-yl group, or a 4-phenylpiperazin-1-yl group), $X^a$ is a nitrogen atom or $CR^{14ax}$ (wherein $R^{14ax}$ represents a hydrogen atom, a halogen atom, a cyano group, a C1-C6 alkyl group optionally substituted with at least one halogen atom, a C1-C6 alkylthio group optionally substituted with at least one halogen atom, or a C1-C6 alkylsulfinyl group optionally substituted with at least one halogen atom), $R^{14ay}$ is a hydrogen atom, a halogen atom, a cyano group, a C1-C6 alkyl group optionally substituted with at least one halogen atom, a C1-C6 alkylthio group optionally substituted with at least one halogen atom, a C1-C6 alkylsulfinyl group optionally substituted with at least one halogen atom, a C1-C6 alkylsulfonyl group optionally substituted with at least one halogen atom, or a phenyl group, $R^{14az}$ is a hydrogen atom, $X^{18}$ is a nitrogen atom or $CR^{18e}$ (wherein $R^{18e}$ is a hydrogen atom or a halogen atom), and $R^{18a}$, $R^{18b}$, $R^{18c}$ and $R^{18d}$ are independently a hydrogen atom or a halogen atom.

17. A hydrazide compound represented by the formula (1-1):

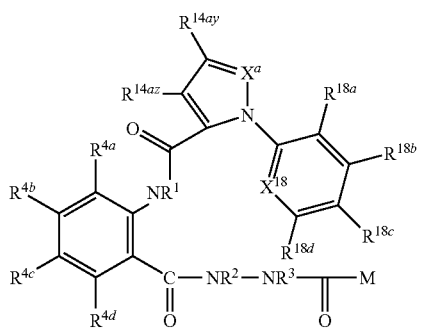

(1-1)

wherein $R^1$ is a hydrogen atom, or a C1-C6 alkyl group optionally substituted with at least one halogen atom, $R^2$ is a hydrogen atom, or a C1-C6 alkyl group optionally substituted with at least one halogen atom, $R^3$ is a hydrogen atom, a C1-C6 alkyl group optionally substituted with at least one halogen atom, or a C2-C6 alkoxycarbonyl group, $R^{4a}$ is a hydrogen atom, a halogen atom, a C1-C6 alkyl group optionally substituted with at least one halogen atom, a C1-C6 alkoxy group optionally substituted with at least one halogen atom, or a phenyl group optionally substituted with at least one halogen atom, $R^{4b}$, $R^{4c}$ and $R^{4d}$ are independently a hydrogen atom, a halogen atom, a cyano group, a C1-C6 alkyl group optionally substituted with at least one halogen atom, or $R^{4b}$ and $R^{4c}$ are bound to each other at their terminal ends to form a group: $-CR^{41}=CR^{42}-CR^{43}=CR^{44}-$ (wherein $R^{41}$, $R^{42}$, $R^{43}$ and $R^{44}$ represent a hydrogen atom), M is a hydrogen atom, $X^a$ is a nitrogen atom or $CR^{14ax}$ (wherein $R^{14ax}$ is a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom), $R^{14ay}$ is a hydrogen atom, a halogen atom, a cyano group, a C1-C6 alkyl group optionally substituted with at least one halogen atom, a C1-C6 alkylthio group optionally substituted with at least one halogen atom, a C1-C6 alkylsulfinyl group optionally substituted with at least one halogen atom, a C1-C6 alkylsulfonyl group optionally substituted with at least one halogen atom, or a phenyl group, $R^{14az}$ is a hydrogen atom, $X^{18}$ is a nitrogen atom or $CR^{18e}$ (wherein $R^{18e}$ is a hydrogen atom or a halogen atom), and $R^{18a}$, $R^{18b}$, $R^{18c}$ and $R^{18d}$, each, independently, are a hydrogen atom or a halogen atom.

18. A hydrazide compound represented by the formula (II):

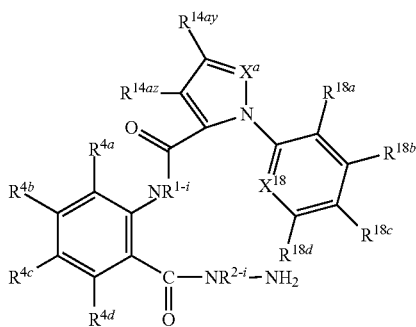

wherein $R^{1-i}$ represents a hydrogen atom, or a C1-C6 alkyl group optionally substituted with at least one halogen atom, $R^{2-i}$ represents a hydrogen atom or a methyl group, $R^{4a}$ represents a halogen atom, or a C1-C6 alkyl group optionally substituted with at least one halogen atom, $R^{4b}$, $R^{4c}$ and $R^{4d}$ independently represent a hydrogen atom, a halogen atom, a cyano group, a C1-C6 alkyl group optionally substituted with at least one halogen atom, or $R^{4b}$ and $R^{4c}$ are bound to each other at their terminal ends to form T1: —$CR^{41}$=$CR^{42}$—$CR^{43}$=$CR^{44}$—

(wherein $R^{41}$, $R^{42}$, $R^{43}$ and $R^{44}$ independently represent a hydrogen atom, a halogen atom, a cyano group, or a C1-C6 alkyl group optionally substituted with at least one halogen atom), $X^a$ represents a nitrogen atom or $CR^{14ax}$ (wherein $R^{14ax}$ represents a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom), $R^{14ay}$ and $R^{14az}$, each, independently, represent a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, $X^{18}$ represents a nitrogen atom or $CR^{18e}$, (wherein $R^{18e}$ represents a hydrogen atom, a halogen atom, or a C1-C6 alkyl group optionally substituted with at least one halogen atom)

$R^{18a}$ represents a halogen atom, or a C1-C6 alkyl group optionally substituted with at least one halogen atom, and $R^{18b}$, $R^{18c}$ and $R^{18d}$ independently represent a hydrogen atom, a halogen atom, or a C1-C6 alkyl group optionally substituted with at least one halogen atom.

19. The compound according to claim 18, wherein $R^{2-i}$ is a methyl group.

20. A pesticide comprising the compound according to claim 1 as an active ingredient.

21. A method of controlling a pest which comprises applying the compound according to claim 1 directly to a pest, or to a place where a pest inhabits.

* * * * *